(12) United States Patent
Glunz et al.

(10) Patent No.: US 7,576,098 B2
(45) Date of Patent: Aug. 18, 2009

(54) HETEROCYCLIC COMPOUNDS AS INHIBITORS OF FACTOR VIIA

(75) Inventors: Peter W. Glunz, Yardley, PA (US); Nicolas Wurtz, Plainsboro, NJ (US); Xuhong Cheng, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 562 days.

(21) Appl. No.: 11/295,961

(22) Filed: Dec. 7, 2005

(65) Prior Publication Data

US 2006/0211720 A1 Sep. 21, 2006

Related U.S. Application Data

(60) Provisional application No. 60/634,290, filed on Dec. 8, 2004, provisional application No. 60/732,926, filed on Nov. 2, 2005.

(51) Int. Cl.
*C07D 401/02* (2006.01)
*A61K 31/44* (2006.01)

(52) U.S. Cl. .................. 514/307; 514/311; 514/314; 514/352; 514/381; 514/383; 514/394; 514/397; 514/406; 546/139; 546/148; 546/152; 546/268.1; 546/304; 548/254; 548/262.2; 548/302.7; 548/335.1

(58) Field of Classification Search .................. None
See application file for complete search history.

(56) References Cited

U.S. PATENT DOCUMENTS

| | | | |
|---|---|---|---|
| 5,023,236 | A | 6/1991 | Edgington et al. |
| 5,843,442 | A | 12/1998 | Soule et al. |
| 5,866,542 | A | 2/1999 | Vlasuk et al. |
| 6,140,353 | A | 10/2000 | Ackermann et al. |
| 6,242,644 | B1 | 6/2001 | Ackermann et al. |
| 6,271,237 | B1 | 8/2001 | Galemmo, Jr. et al. |
| 6,632,815 | B2 | 10/2003 | Zhu et al. |
| 6,642,252 | B2 | 11/2003 | Bisacchi et al. |
| 6,713,467 | B2 | 3/2004 | Bisacchi et al. |
| 6,906,084 | B2 | 6/2005 | Nazaré et al. |
| 6,953,802 | B2 | 10/2005 | Konradi et al. |
| 2002/0151534 | A1 | 10/2002 | Ries et al. |
| 2004/0006065 | A1 | 1/2004 | Glunz |
| 2004/0176375 | A1 | 9/2004 | Bisacchi et al. |
| 2004/0204412 | A1 | 10/2004 | Glunz et al. |
| 2005/0009895 | A1 | 1/2005 | Priestley et al. |
| 2005/0038030 | A1 | 2/2005 | Zhang |
| 2005/0043336 | A1 | 2/2005 | Hennequin et al. |
| 2005/0054662 | A1 | 3/2005 | Hennequin et al. |
| 2006/0166997 | A1 | 7/2006 | Zhang et al. |
| 2007/0003539 | A1 | 1/2007 | Zhang et al. |

FOREIGN PATENT DOCUMENTS

| | | |
|---|---|---|
| WO | WO 02/00651 | 1/2002 |
| WO | WO 02/062778 | 8/2002 |
| WO | WO 02/064578 | 8/2002 |
| WO | WO 02/064598 | 8/2002 |
| WO | WO 02/064599 | 8/2002 |
| WO | WO2003/047512 A | 6/2003 |
| WO | WO2004/000214 A | 12/2003 |
| WO | WO2004/002406 A | 1/2004 |
| WO | WO2004/072101 A | 8/2004 |
| WO | WO2004/110374 A | 12/2004 |

OTHER PUBLICATIONS

West, Anthony R., Solid State Chemistry and Its Applications, Wiley, New York, 1988, pp. 358 & 365.*
U.S. Appl. No. 11/328,479, filed Jan. 9, 2006, Zhang et al.
Carson, S.D. et al., "The role of tissue factor in the production of thrombin", Blood Coagulation and Fibrinolysis, vol. 4, pp. 281-292 (1993).
Colman, R. W., Chapter 6: "Contact Activation Pathway: Inflammatory, Fibrinolytic, Anticoagulant, Antiadhesive, and Antiangiogenic Activities", Hemostasis and Thrombosis: Basic Principles and Clinical Practice, $4^{th}$ Ed., Lippincott Williams & Wilkins, publ., Colman, R.W. et al., eds., pp. 103-121 (2001).
Girard, T.J. et al., "The role of tissue factor/factor VIIa in the pathophysiology of acute thrombotic formation", Current Opinion in Pharmacology, vol. 1, pp. 159-163 (2001).
Goodnight, S.H. et al., Chapter 4: "Screening Tests of Hemostasis", Disorders of Hemostasis and Thrombosis: A Clinical Guide, The McGraw-Hill Companies, publ., pp. 41-51 (2001).
Schmaier, A.H., Chapter 5: "Contact Activation", Hemostasis and Thrombosis: Basic Principles and Clinical Practice, $4^{th}$ Ed., Lippincott Williams & Wilkins, publ., Colman, R.W. et al., eds., pp. 105-127 (2001).

* cited by examiner

*Primary Examiner*—Zinna N Davis
(74) *Attorney, Agent, or Firm*—Jing G. Sun

(57) ABSTRACT

The present invention relates generally to compounds that inhibit serine proteases. In particular it is directed to novel heterocyclic compounds, or a stereoisomer or pharmaceutically acceptable salt, solvate, or prodrug form thereof, which are useful as selective inhibitors of serine protease enzymes of the coagulation cascade; for example thrombin, factor VIIa, factor Xa, factor XIa, factor IXa, and/or plasma kallikrein. In particular, it relates to compounds that are factor VIIa inhibitors. This invention also relates to pharmaceutical compositions comprising these compounds and methods of using the same.

24 Claims, No Drawings

HETEROCYCLIC COMPOUNDS AS INHIBITORS OF FACTOR VIIA

CROSS-REFERENCE TO RELATED APPLICATIONS

The present application claims the priority benefit of U.S. Provisional Application No. 60/634,290, filed Dec. 8, 2004 and the priority benefit of U.S. Provisional Application No. 60/732,926, filed Nov. 2, 2005, all of which are expressly incorporated fully herein by reference.

FIELD OF THE INVENTION

The present invention provides novel heterocyclic compounds, and analogues thereof, which are selective inhibitors of serine protease enzymes of the coagulation cascade and/or contact activation system; for example thrombin, factor VIIa, factor Xa, factor XIa, factor IXa, and/or plasma kallikrein. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the initiation of the coagulation cascade. It binds with high affinity to tissue factor in the presence of calcium ions to form a complex with enhanced proteolytic activity (Carson, S. D. and Brozna, J. P. *Blood Coag. Fibrinol.* 1993, 4, 281-292). The tissue factor/factor VIIa complex initiates blood coagulation by proteolytic cleavage of factor X to factor Xa, factor IX to factor IXa and additional factor VII to VIIa. Ultimately, the activity of factor VIIa induces the conversion of prothrombin to thrombin. Thrombin coverts fibrinogin to fibrin, which forms a clot through polymerization.

While blood coagulation is essential to the regulation of an organism's hemostasis, it is also involved in many pathological conditions. For instance, thrombosis, or formation of a clot which obstructs circulation, plays a key role in unstable angina, myocardial infarction, ischemic stroke, deep vein thrombosis, peripheral occlusive arterial disease, pulmonary embolism, and other diseases.

Because of its key role in the coagulation cascade, researchers have postulated that inhibition of factor VIIa could be used to treat or prevent thrombotic disease. (Girard, T. J.; Nicholson, N. S. *Curr. Opin. Pharmacol.* 2001, 1, 159-163). Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Plasma kallikrein is a zymogen of a trypsin-like serine protease and is present in plasma at 35 to 50 µg/mL. The gene structure is similar to that of factor XI, overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Separate from the compounds reported herein, some benzamidine and benzylamine compounds have been reported in WO 02/62778 as antithrombotic compounds; and in WO 02/64578, WO 02/64598, and WO 02/64599 as matrix metalloproteinase inhibitors. The scope of the present invention is considered not to be exemplified nor suggested by the above references.

While a number of factor VIIa inhibitors have been discussed in the art, improved inhibitors, especially non-peptide inhibitors, of serine proteases for the treatment of thromboembolic disorders are always desirable. The present invention discloses novel heterocyclic compounds, and analogues thereof, as inhibitors of coagulation Factor VIIa and as such are useful in the treatment of thromboembolic disorders.

In addition, it is also desirable to find new compounds with improved pharmacological characteristics compared with known serine protease inhibitors. For example, it is preferred to find new compounds with improved factor VIIa inhibitory activity and selectivity for factor VIIa versus other serine proteases. Also, it is preferred to find new compounds with improved plasma kallikrein inhibitory activity and selectivity for plasma kallikrein versus other serine proteases. Also, it is preferred to find new compounds with improved activity in in vitro clotting assays, such as the prothrombin time (PT) assay or activated partial thromboplastin time assay (APTT) (for a description of the PT and APTT assays see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51). It is also desirable and preferable to find compounds with advantageous and improved characteristics in one or more of the following categories, but are not limited to: (a) pharmaceutical properties, including oral bioavailability; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

The present invention provides novel heterocyclic compounds, which are useful as selective inhibitors of serine protease enzymes, especially factor VIIa The present invention also provides processes and intermediates for making the compounds of the present invention or a stereoisomer, tautomer, pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a stereoisomer, tautomer, pharmaceutically acceptable salt, solvate, or prodrug form thereof.

The present invention also provides a method for modulation of the coagulation cascade and/or the contact activation system comprising administering to a host in need of such treatment a therapeutically effective amount of at least one of the compounds of the present invention or a stereoisomer, tautomer, pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a stereoisomer, tautomer, pharmaceutically acceptable salt, solvate, or prodrug form thereof.

The present invention also provides a method for treating inflammatory diseases disorders comprising administering to a host in need of such treatment a therapeutically effective amount of at least one of the compounds of the present invention or a stereoisomer, tautomer, pharmaceutically acceptable salt or prodrug form thereof.

The present invention also provides novel heterocyclic compounds for use in therapy.

The present invention also provides the use of novel heterocyclic compounds for the manufacture of a medicament for the treatment of a thromboembolic disorder.

The present invention also provides the use of novel heterocyclic compounds for the manufacture of a medicament for the treatment of an inflammatory disorder.

These and other features of the invention will be set forth in the expanded form as the disclosure continues.

DETAILED DESCRIPTION OF THE INVENTION

In a first aspect, the present invention provides, inter alia, compounds of Formula (I):

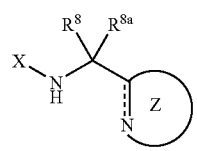

or a stereoisomer, tautomer, pharmaceutically acceptable salt, solvate, or prodrug form thereof, wherein:

X is selected from:

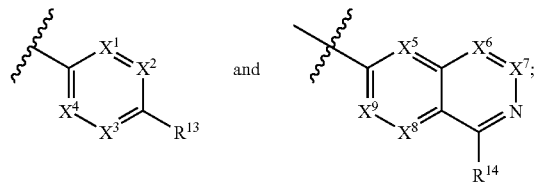

wherein $X^1$, $X^2$, $X^3$, $X^4$, $X^5$, $X^6$, $X^7$, $X^8$, and $X^9$ are independently $CR^6$ or N, provided that X does not contain more than three ring nitrogen atoms;

$R^6$ is, independently at each occurrence, H, —$(CH_2)_r$—$OR^a$, F, Cl, Br, $OCF_3$, CN, $NO_2$, —$NR^bR^c$, —$(CF_2)_r$ $CF_3$, or $C_{1-6}$ alkyl substituted with 0-2 $R^e$;

$R^8$ is phenyl substituted with 0-5 $R^{8b}$, or a 5- to 6-membered heteroaryl comprising: carbon atoms and 1-4 heteroatoms selected from N, O, and S, wherein said heteroaryl is substituted with 0-5 $R^{8b}$;

$R^{8a}$ is H or $C_{1-4}$ alkyl;

$R^{8b}$ is, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^c R^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-7}$ cycloalkyl substituted with 0-2 $R^e$, —$(CH_2)_r$—$C_{3-7}$ cycloalkenyl substituted with 0-2 $R^e$, —$(CH_2)_r$-phenyl substituted with 0-4 $R^f$, —$(CH_2)_r$-5- to 6-membered heteroaryl comprising: carbon atoms and 1-4 heteroatoms selected from N, O, and $S(O)_p$, or —$(CH_2)_r$-4- to 7-membered heterocycle comprising: carbon atoms and 1-4 heteroatoms selected from N, O, and $S(O)_p$, wherein said heteroaryl and heterocycle are substituted with 0-4 $R^f$;

alternatively, two $R^{8b}$ groups on two adjacent carbon atoms may be taken together with the carbon atoms to which they are attached, to form a 5- to 7-membered carbocycle or heterocycle comprising: carbon atoms and 0-4 heteroatoms selected from N, O, and $S(O)_p$, wherein said carbocycle and heterocycle are substituted with 0-3 $R^f$;

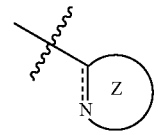

is a 5- to 6-membered heteroaryl including the nitrogen atom shown in the ring, comprising: carbon atoms and additional 0-3 heteroatoms selected from N, $NR^{11}$, $NR^{11a}$, O, and S, and ring Z is substituted with 0-1 $R^{12}$ and 0-3 $R^{12a}$; provided that: all three valences of the nitrogen atom shown in ring Z are satisfied by ring bonds;

optionally, ring Z is fused to a 5- to 10-membered carbocycle or heterocycle comprising: carbon atoms and additional 0-4 heteroatoms selected from N, $NR^{11}$, $NR^{11a}$, O, and $S(O)_p$, wherein said carbocycle and heterocycle are fully unsaturated or partially saturated and are substituted with 0-1 $R^{12}$ and 0-3 $R^{12a}$;

$R^{11}$ and $R^{11a}$ are, independently at each occurrence, H, $C_{1-6}$ alkyl substituted with 0-4 $R^e$, —($C_{0-4}$ alkyl)-($C_{6-10}$ aryl), —($C_{0-4}$ alkyl)-(5- to 10-membered heteroaryl comprising: carbon atoms and 1-4 heteroatoms selected from N, O, and $S(O)_p$); wherein said aryl and heteroaryl are substituted with 0-4 $R^f$;

$R^{12}$ and $R^{12a}$ are, independently at each occurrence, H, —$(CH_2)_r$—$OR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-7}$ cycloalkyl substituted with 0-2 $R^e$, —$(CH_2)_r$—$C_{3-7}$ cycloalkenyl substituted with 0-2 $R^e$, —$(CH_2)_r$-phenyl substituted with 0-4 $R^f$, —$(CH_2)_r$-naphthyl substituted with 0-4 $R^f$, —$(CH_2)_r$-5- to 10-membered heteroaryl comprising: carbon atoms and 1-4 heteroatoms selected from N, O, and $S(O)_p$, or —$(CH_2)_r$-4- to 8-membered heterocycle comprising: carbon atoms and 1-4 heteroatoms selected from N, O, and $S(O)_p$; wherein said heteroaryl and heterocycle are substituted with 0-4 $R^f$;

$R^{13}$ is —$C(=NR^h)NR^bR^c$ or —$CR^aR^aNR^bR^c$;

$R^{14}$ is —$NR^bR^c$, H, or $C_{1-4}$ alkyl;

$R^{a1}$ is, independently at each occurrence, $C_{1-6}$ alkyl substituted with 0-4 $R^j$, —$(CH_2)_r$—$C_{3-7}$ cycloalkyl substituted with 0-4 $R^f$, —$(CH_2)_r$—$C_{6-10}$ aryl, or —$(CH_2)_r$-5- to 10-membered heteroaryl comprising: carbon atoms and 1-4 heteroatoms selected from $NR^b$, O, and $S(O)_p$; wherein said aryl and heterocycle are optionally substituted with 0-4 $R^f$;

$R^a$ is, independently at each occurrence, H or $R^{a1}$;

$R^b$ is, independently at each occurrence, H, $C_{1-6}$ alkyl, —$(CH_2)_n$-phenyl, ($C_{1-6}$ alkyl)$C(O)$—, ($C_{3-6}$ cycloalkyl)-$C_{0-4}$alkyl-$C(O)$—, ($C_{6-10}$ aryl)-($C_{0-4}$alkyl)-$C(O)$—, (5- to 10-membered heteroaryl)-$C_{0-4}$ alkyl-$C(O)$—, ($C_{1-6}$ alkyl)-$NHC(O)$—, ($C_{1-6}$ alkyl)$_2$-$NHC(O)$—, ($C_{6-10}$ aryl)-$C_{0-4}$ alkyl-$NHC(O)$—, (5- to 10-membered heteroaryl)-$C_{0-4}$ alkyl-$NHC(O)$—, ($C_{1-6}$ alkyl)-$S(O)_2$—, ($C_{6-10}$ aryl)-$C_{0-4}$ alkyl-$S(O)_2$—, or (5- to 10-membered heteroaryl)-$C_{0-4}$ alkyl-$S(O)_2$—, wherein said phenyl, aryl and heteroaryl are substituted with 0-2 $R^f$; said heteroaryl comprises: carbon atoms and 1-4 heteroatoms selected from N, O, and $S(O)_p$;

$R^c$ is, independently at each occurrence, H, $C_{1-6}$ alkyl substituted with 0-3 $R^j$, or —$(CH_2)_n$-phenyl substituted with 0-3 $R^j$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^e$ is, independently at each occurrence, =O, $OR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

$R^f$ is, independently at each occurrence, H, =O, —$(CH_2)_r$$OR^g$, F, Cl, Br, I, CN, $NO_2$, —$OCF_3$, —$NR^cR^c$, —$C(O)R^g$, —$C(O)OR^g$, —$NR^cC(O)R^g$, —$C(O)NR^cR^c$, —$SO_2NR^cR^c$, —$NR^cSO_2NR^cR^c$, —$NR^cSO_2$—$C_{1-4}$ alkyl, —$NR^cSO_2CF_3$, —$NR^cSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, —$(CH_2)_r$—$C_{3-10}$ carbocycle substituted with 0-3 $R^j$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^j$;

$R^g$ is, independently at each occurrence, H, $C_{1-6}$ alkyl, or —$(CH_2)_n$-phenyl;

$R^h$ is, independently at each occurrence, H, OH, $C_{1-6}$ alkyl, $C_{1-4}$ alkoxy, ($C_{6-10}$ aryl)-$C_{1-4}$ alkoxy, —$(CH_2)_n$-phenyl, ($C_{1-6}$ alkyl)$C(O)$—, ($C_{6-10}$ aryl)-$C_{0-4}$ alkyl-$C(O)$—, ($C_{3-6}$ cycloalkyl)-$C_{0-4}$ alkyl-$C(O)$—, (5-10 membered heteroaryl)-$C_{0-4}$ alkyl-$C(O)$—, ($C_{1-4}$ alkyl)$OC(O)$—, ($C_{6-10}$ aryl)-$C_{1-4}$ alkyl-$OC(O)$—, ($C_{1-4}$ alkyl)-$C(O)O$—($C_{1-4}$ alkyl)-$OC(O)$—, ($C_{6-10}$ aryl)-$C(O)O$—($C_{1-4}$ alkyl)-$OC(O)$—, (5-10 membered heteroaryl)-$C_{0-4}$ alkyl-$OC(O)$—, $C_{1-4}$ alkoxy, ($C_{1-4}$ alkyl)$C(O)O$—, or ($C_{6-10}$ aryl)-($C_{0-4}$ alkyl)-$C(O)O$—; wherein said phenyl, aryl and heteroaryl are substituted with 0-2 $R^f$; said heteroaryl comprises: carbon atoms and 1-4 heteroatoms selected from N, O, and $S(O)_p$;

$R^i$ is, independently at each occurrence, $OR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2$—$C_{1-4}$ alkyl, —$NR^cSO_2CF_3$, —$NR^cSO_2$-phenyl, —$S(O)_2CF_3$, —$S(O)_p$—$C_{1-4}$ alkyl, —$S(O)_p$-phenyl, —$(CF_2)_rCF_3$, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

$R^j$ is, independently at each occurrence, H, =O, —$(CH_2)_r$$OR^g$, F, Cl, Br, I, CN, $NO_2$, —$OCF_3$, —$NR^gR^g$, —$C(O)R^g$, —$C(O)OR^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, ($C_{1-6}$ alkyl)$C(O)$—, ($C_{3-6}$ cycloalkyl)-$C_{0-4}$ alkyl-$C(O)$—, ($C_{6-10}$ aryl)-($C_{0-4}$ alkyl)-$C(O)$—, (5-10 membered heteroaryl)-$C_{0-4}$ alkyl-$C(O)$—, ($C_{1-6}$ alkyl)-$NHC(O)$—, ($C_{1-6}$ alkyl)$_2$-$NHC(O)$—, ($C_{6-10}$ aryl)-$C_{0-4}$ alkyl-$NHC(O)$—, (5-10 membered heteroaryl)-$C_{0-4}$ alkyl-$NHC(O)$—, ($C_{1-6}$ alkyl)-$S(O)_2$—, ($C_{6-10}$ aryl)-$C_{0-4}$ alkyl-$S(O)_2$—, (5-10 membered heteroaryl)-$C_{0-4}$ alkyl-$S(O)_2$—, —$(CH_2)_r$—$C_{3-10}$ carbocycle, or a —$(CH_2)_r$-5- to 12-membered heterocycle comprising: carbon atoms and 1-4 heteroatoms selected from N, O, and $S(O)_p$; wherein said heteroaryl comprises: carbon atoms and 1-4 heteroatoms selected from N, O, and $S(O)_p$, n, at each occurrence, is selected from 0, 1, 2, 3, and 4;

p, at each occurrence, is selected from 0, 1, and 2; and r, at each occurrence, is selected from 0, 1, 2, 3, and 4.

In a second aspect, the present invention provides compounds of Formula (Ia):

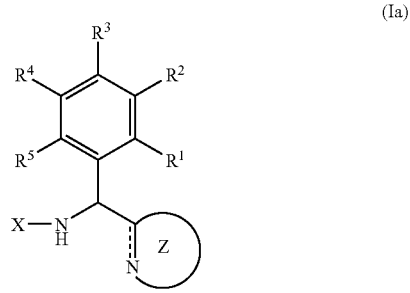

(Ia)

or a stereoisomer, tautomer, pharmaceutically acceptable salt, solvate, or prodrug form thereof, wherein:

$R^1$, $R^2$, $R^3$, $R^4$, and $R^5$ are, independently at each occurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-7}$ cycloalkyl substituted with 0-2 $R^e$, —$(CH_2)_r$—$C_{3-7}$ cycloalkenyl substituted with 0-2 $R^e$, —$(CH_2)_r$-phenyl substituted with 0-4 $R^f$, —$(CH_2)_r$-5- to 6-membered heteroaryl comprising: carbon atoms and 1-4 heteroatoms selected from N, O, and $S(O)_p$, or —$(CH_2)_r$-4- to 7-membered heterocycle comprising: carbon atoms and 1-4 heteroatoms selected from N, O, and $S(O)_p$, wherein said heteroaryl and heterocycle are substituted with 0-4 $R^f$;

alternatively, $R^2$ and $R^3$, $R^3$ and $R^4$, or $R^4$ and $R^5$ may be taken together with the carbon atoms to which they are attached, to form a 5- to 7-membered carbocycle or heterocycle comprising: carbon atoms and 0-4 heteroatoms selected from N, O, and $S(O)_p$, wherein said carbocycle and heterocycle are substituted with 0-3 $R^f$;

X is selected from:

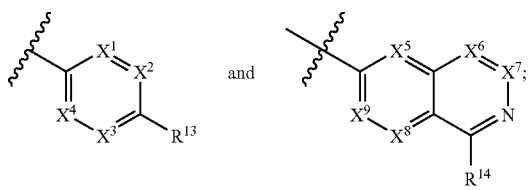

wherein $X^1$, $X^2$, $X^3$, $X^4$, $X^5$, $X^6$, $X^7$, $X^8$, and $X^9$ are independently $CR^6$ or N, provided that X does not contain more than three ring nitrogen atoms;

$R^6$ is, independently at each occurrence, H, —$(CH_2)_r$—$OR^a$, F, Cl, Br, $OCF_3$, CN, $NO_2$, —$NR^bR^c$, —$(CF_2)_rCF_3$, or $C_{1-6}$ alkyl substituted with 0-2 $R^e$;

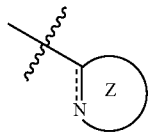

is a 5- to 6-membered heteroaryl including the nitrogen atom shown in the ring, comprising: carbon atoms and additional 0-3 heteroatoms selected from N, $NR^{11}$, $NR^{11a}$, O, and S, and ring Z is substituted with 0-1 $R^{12}$ and 0-3 $R^{12a}$; provided that: all three valences of the nitrogen atom shown in ring Z are satisfied by ring bonds;

optionally, ring Z is fused to a 5- to 7-membered carbocycle or heterocycle comprising: carbon atoms and additional 0-4 heteroatoms selected from N, $NR^{11}$, $NR^{11a}$, O, and $S(O)_p$, wherein said carbocycle and heterocycle are fully unsaturated or partially saturated and substituted with 0-1 $R^{12}$ and 0-3 $R^{12a}$;

$R^{11}$ and $R^{11a}$ are, independently at each occurrence, H, $C_{1-6}$ alkyl substituted with 0-4 $R^e$, —$(C_{0-4}$ alkyl)-$(C_{6-10}$ aryl), —$(C_{0-4}$ alkyl)-(5- to 10-membered heteroaryl comprising: carbon atoms and 1-4 heteroatoms selected from N, O, and $S(O)_p$); wherein said aryl and heteroaryl are substituted with 0-4 $R^f$;

$R^{12}$ and $R^{12a}$ are, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-7}$ cycloalkyl substituted with 0-2 $R^e$, —$(CH_2)_r$—$C_{3-7}$ cycloalkenyl substituted with 0-2 $R^e$, —$(CH_2)_r$-phenyl substituted with 0-4 $R^f$, —$(CH_2)_r$-naphthyl substituted with 0-4 $R^f$, —$(CH_2)_r$-5- to 10-membered heteroaryl comprising: carbon atoms and 1-4 heteroatoms selected from N, O, and $S(O)_p$, or —$(CH_2)_r$-4- to 8-membered heterocycle comprising: carbon atoms and 1-4 heteroatoms selected from N, O, and $S(O)_p$; wherein said heteroaryl and heterocycle are substituted with 0-4 $R^f$;

$R^{13}$ is —$C(=NR^h)NR^bR^c$ or —$CR^aR^aNR^bR^c$;

$R^{14}$ is —$NR^bR^c$, H, or $C_{1-4}$ alkyl;

$R^{a1}$ is, independently at each occurrence, $C_{1-6}$ alkyl substituted with 0-4 $R^f$, —$(CH_2)_r$—$C_{3-7}$ cycloalkyl substituted with 0-4 $R^f$, —$(CH_2)_r$—$C_{6-10}$ aryl, or —$(CH_2)_r$-5- to 10-membered heterocycle comprising: carbon atoms and 1-4 heteroatoms selected from $NR^b$, O, and $S(O)_p$; wherein said aryl and heterocycle are optionally substituted with 0-4 $R^f$;

$R^a$ is, independently at each occurrence, H or $R^{a1}$;

$R^b$ is, independently at each occurrence, H, $C_{1-6}$ alkyl, —$(CH_2)_n$-phenyl, $(C_{1-6}$ alkyl)C(O)—, $(C_{3-6}$ cycloalkyl)-$C_{0-4}$ alkyl-C(O)—, $(C_{6-10}$ aryl)-$(C_{0-4}$ alkyl)-C(O)—, (5- to 10-membered heteroaryl)-$C_{0-4}$ alkyl-C(O)—, $(C_{1-6}$ alkyl)-NHC(O)—, $(C_{1-6}$ alkyl)$_2$—NHC(O)—, $(C_{6-10}$ aryl)-$C_{0-4}$ alkyl-NHC(O)—, (5- to 10-membered heteroaryl)-$C_{0-4}$ alkyl-NHC(O)—, $(C_{1-6}$ alkyl)-$S(O)_2$—, $(C_{6-10}$ aryl)-$C_{0-4}$ alkyl-$S(O)_2$—, or (5- to 10-membered heteroaryl)-$C_{0-4}$ alkyl-$S(O)_2$—, wherein said phenyl, aryl and heteroaryl are substituted with 0-2 $R^f$; said heteroaryl comprises: carbon atoms and 1-4 heteroatoms selected from N, O, and $S(O)_p$;

$R^c$ is, independently at each occurrence, H, $C_{1-6}$ alkyl substituted with 0-3 $R^j$, or —$(CH_2)_n$-phenyl substituted with 0-3 $R^j$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^e$ is, independently at each occurrence, =O, $OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

$R^f$ is, independently at each occurrence, H, =O, —$(CH_2)_r$ $OR^g$, $SR^g$, F, Cl, Br, I, CN, $NO_2$, —$OCF_3$, —$NR^cR^c$, —$C(O)R^g$, —$C(O)OR^g$, —$NR^cC(O)R^g$, —$C(O)NR^cR^c$, —$SO_2NR^cR^c$, —$NR^cSO_2NR^cR^c$, —$NR^cSO_2$—$C_{1-4}$ alkyl, —$NR^cSO_2CF_3$, —$NR^cSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, —$(CH_2)_r$—$C_{3-10}$ carbocycle substituted with 0-3 $R^j$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^j$;

$R^g$ is, independently at each occurrence, H, $C_{1-6}$ alkyl, or —$(CH_2)_n$-phenyl;

$R^h$ is, independently at each occurrence, H, OH, $C_{1-6}$ alkyl, $C_{1-4}$ alkoxy, $(C_{6-10}$ aryl)-$C_{1-4}$ alkoxy, —$(CH_2)_n$-phenyl, $(C_{1-6}$ alkyl)C(O)—, $(C_{6-10}$ aryl)-$C_{0-4}$ alkyl-C(O)—, $(C_{3-6}$ cycloalkyl)-$C_{0-4}$ alkyl-C(O)—, (5-10 membered heteroaryl)-$C_{0-4}$ alkyl-C(O)—, $(C_{1-4}$ alkyl)OC(O)—, $(C_{6-10}$ aryl)-$C_{1-4}$ alkyl-OC(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, (5-10 membered heteroaryl)-$C_{0-4}$ alkyl-OC(O)—, $C_{1-4}$ alkoxy, $(C_{1-4}$ alkyl)C(O)O—, or $(C_{6-0}$ aryl)-$(C_{0-4}$ alkyl)-C(O)O—; wherein said phenyl, aryl and heteroaryl are substituted with 0-2 $R^f$; wherein said heteroaryl comprises: carbon atoms and 1-4 heteroatoms selected from N, O, and $S(O)_p$;

$R^j$ is, independently at each occurrence, H, =O, —$(CH_2)_r$ $OR^g$, $SR^g$, F, Cl, Br, I, CN, $NO_2$, —$OCF_3$, —$NR^gR^g$, —$C(O)R^g$, —$C(O)OR^g$, —$NR^gC(O)R^g$, —$C(O)NR^g$ $R^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2$ $CF_3$, —$S(O)_p$—$C_{1-4}$ alkyl, —$S(O)_p$-phenyl, —$(CF_2)_r$ $CF_3$, $C_{1-6}$ alkyl, $C_{2-6}$ alkenyl, $C_{2-6}$ alkynyl, $(C_{1-6}$ alkyl) C(O)—, $(C_{3-6}$ cycloalkyl)-$C_{0-4}$ alkyl-C(O)—, $(C_{6-10}$ aryl)-$(C_{0-4}$ alkyl)-C(O)—, (5-10 membered heteroaryl)-$C_{0-4}$ alkyl-C(O)—, $(C_{1-6}$ alkyl)-NHC(O)—, $(C_{1-6}$ alkyl)$_2$-NHC(O)—, $(C_{6-10}$ aryl)-$C_{0-4}$ alkyl-NHC(O)—, (5-10 membered heteroaryl)-$C_{0-4}$ alkyl-NHC(O)—, $(C_{1-6}$ alkyl)-$S(O)_2$—, $(C_{6-10}$ aryl)-$C_{0-4}$ alkyl-$S(O)_2$—, (5-10 membered heteroaryl)-$C_{0-4}$ alkyl-$S(O)_2$—, —$(CH_2)_r$—$C_{3-10}$ carbocycle, or a —$(CH_2)_r$-5- to 12-membered heterocycle comprising: carbon atoms and 1-4 heteroatoms selected from N, O, and $S(O)_p$; wherein said heteroaryl comprises: carbon atoms and 1-4 heteroatoms selected from N, O, and $S(O)_p$;

n, at each occurrence, is selected from 0, 1, 2, 3, and 4;

p, at each occurrence, is selected from 0, 1, and 2; and r, at each occurrence, is selected from 0, 1, 2, 3, and 4.

In a third aspect, the present invention includes the compounds of Formula (Ia), within the scope of the second aspect, wherein:

$R^1$ is H;

$R^2$ is H, F, Br, Cl, $C_{2-4}$ alkenyl, $C_{2-4}$ alkynyl, $C_{3-6}$ cycloalkyl, —O—$C_{1-4}$ alkyl, —O—$C_{3-6}$ cycloalkyl, or $C_{1-4}$ alkyl substituted with 0-1 OH;

$R^3$, $R^4$, and $R^5$ are, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2$ $R^{a1}$, —$S(O)R^{a1}$, —$(CF_2)_rCF_3$, $C_{1-6}$ alkyl, $C_{2-6}$ alkenyl, $C_{2-6}$ alkynyl, tetrahydrofuran-3-yloxy, 1-pyrrolidinyl, N-morpholinyl, 1-Me-piperidin-4-yloxy, or 3-(dimethylamino)-2,2-dimethylpropoxy, phenyl substituted with 0-2 $R^f$, or benzyl substituted with 0-2 $R^f$;

alternatively, $R^2$ and $R^3$, $R^3$ and $R^4$, or $R^4$ and $R^5$ may be taken together with the carbon atoms to which they are attached, to form a 5- to 6-membered carbocycle or heterocycle comprising: carbon atoms and 0-4 heteroatoms selected from N, O, and $S(O)_p$, wherein said carbocycle and heterocycle are substituted with 0-3 $R^f$; and $R^6$ is, independently at each occurrence, —$(CH_2)_r$—$OR^a$, F, Cl, Br, $OCF_3$, CN, $NO_2$, —$NR^bR^c$, or —$(CF_2)_rCF_3$.

In a fourth aspect, the present invention includes the compounds of Formula (Ia), within the scope of the second aspect, wherein:

$R^3$, $R^4$, and $R^5$ are, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2$ $R^{a1}$, —$S(O)R^{a1}$, —$(CF_2)_rCF_3$, $C_{1-6}$ alkyl, $C_{2-6}$ alkenyl, $C_{2-6}$ alkynyl, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-methyl-2-oxoimidazolidin-1-yl or 3-(dimethylamino)-2,2-dimethylpropoxy, phenyl substituted with 0-2 $R^f$, or benzyl substituted with 0-2 $R^f$;

alternatively, $R^2$ and $R^3$, $R^3$ and $R^4$, or $R^4$ and $R^5$ may be taken together with the carbon atoms to which they are attached, to form a 5- to 6-membered carbocycle or heterocycle comprising: carbon atoms and 0-3 heteroatoms selected from N, O, and $S(O)_p$, wherein said carbocycle and heterocycle are substituted with 0-3 $R^f$;

X is 4-C(=NH)$NH_2$-phenyl, 4-C(=NOH)$NH_2$-phenyl, 4-$CH_2NH_2$-phenyl, isoquinolin-6-yl, 1-$NH_2$-isoquinolin-6-yl, quinazolin-7-yl, 4-$NH_2$-quinazolin-7-yl, phthalazin-6-yl, or 1-$NH_2$-phthalazin-6-yl; and X is substituted with 0-2 $R^6$;

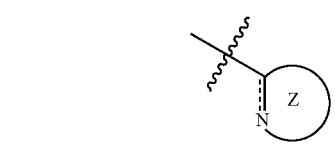

is substituted with 0-1 R$^{12}$ and 0-3 R$^{12a}$ and is selected from:

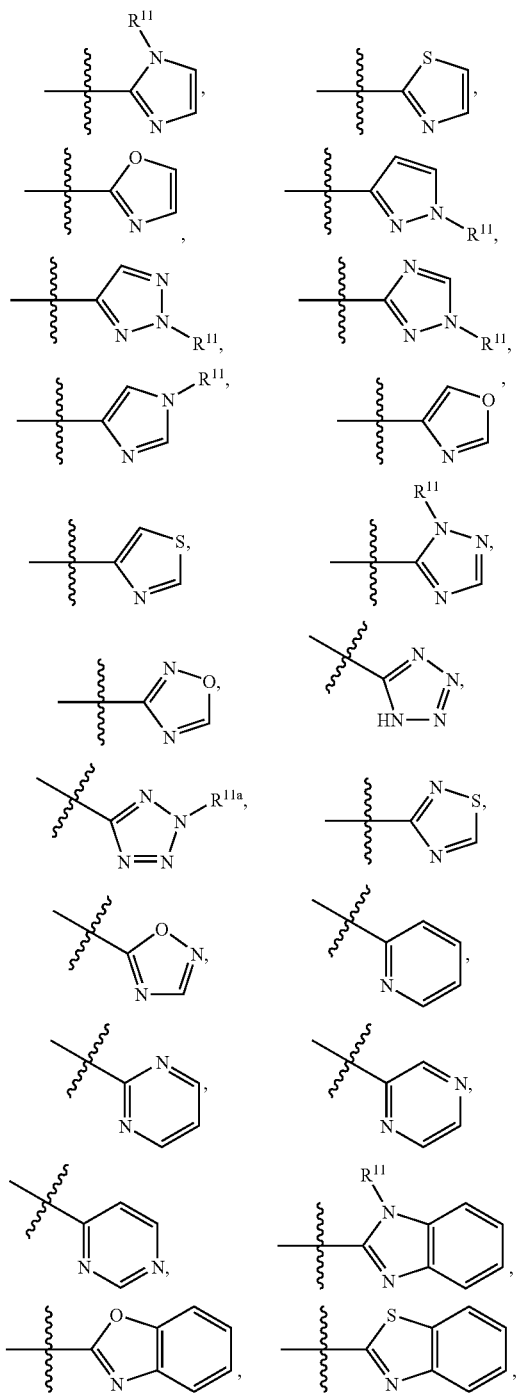

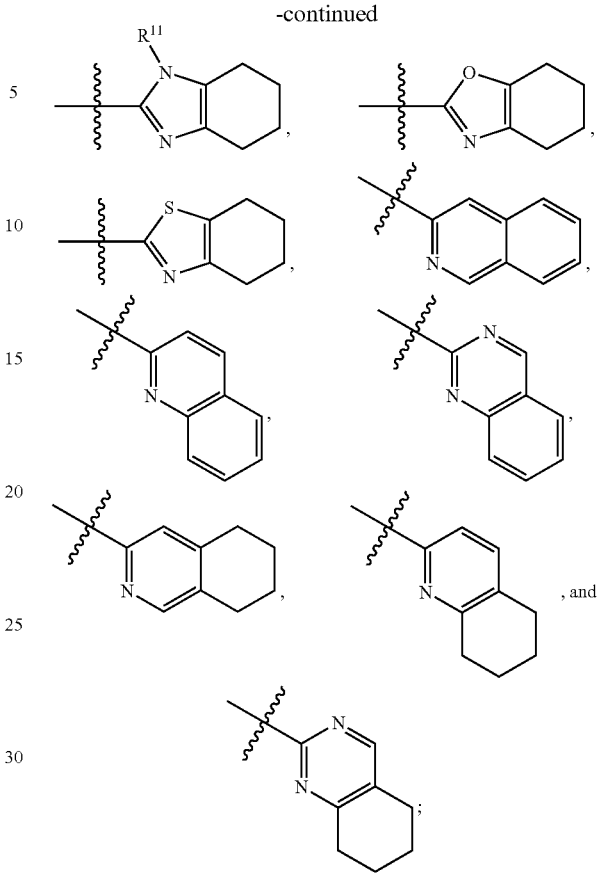

R$^{12}$ and R$^{12a}$ are, independently at each ocurrence, H, —(CH$_2$)$_r$—OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-7}$ cycloalkyl substituted with 0-3 R$^f$, —(CH$_2$)$_r$-phenyl substituted with 0-4 R$^f$, —(CH$_2$)$_r$-naphthyl substituted with 0-4 R$^f$, or —(CH$_2$)$_r$-5- to 10-membered heterocycle comprising: carbon atoms and 1-4 heteroatoms selected from N, O, and S(O)$_p$, wherein said heteroaryl is substituted with 0-4 R$^f$;

R$^{a1}$ is, independently at each occurrence, H, C$_{1-4}$ alkyl substituted with 0-2 R$^j$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said cycloalkyl, aryl and heteroaryl groups are optionally substituted with 0-2 R$^f$;

R$^c$ is, independently at each occurrence, H, C$_{1-6}$ alkyl substituted with 0-2 R$^j$, or —(CH$_2$)$_n$-phenyl substituted with 0-2 R$^j$;

R$^d$ is, independently at each occurrence, H, C$_{1-6}$ alkyl, —(CH$_2$)$_r$—C$_{3-10}$ carbocycle substituted with 0-3 R$^f$, or a —(CH$_2$)$_r$-5- to 12-membered heterocycle comprising: carbon atoms and 1-4 heteroatoms selected from N, O, and S(O)$_p$, wherein said heterocycle is substituted with 0-3 R$^f$;

alternatively, R$^c$ and R$^d$, when attached to the same nitrogen atom, may be taken together with the nitrogen atom to form a 4- to 10-membered heterocycle comprising:

carbon atoms and 1-4 heteroatoms selected from N, O, and $S(O)_p$, wherein said heterocycle is substituted with 0-2 $R^f$;

$R^e$ is, independently at each occurrence, =O, $OR^a$, $SR^a$, F, Cl, Br, I, CN, $NO_2$, $-OCF_3$, $-NR^bR^c$, $-C(O)R^a$, $-C(O)OR^a$, $-NR^dC(O)R^a$, $-C(O)NR^cR^d$, $-SO_2NR^cR^d$, $-NR^cSO_2NR^cR^d$, $-NR^cSO_2R^{a1}$, $-NR^cSO_2CF_3$, $-S(O)_2CF_3$, $-S(O)_2R^{a1}$, $-S(O)R^{a1}$, or $-(CF_2)_rCF_3$; and $R^j$ is, independently at each occurrence, H, =O, $-(CH_2)_r$-$OR^g$, $SR^g$, F, Cl, Br, I, CN, $NO_2$, $-OCF_3$, $-NR^gR^g$, $-C(O)R^g$, $-C(O)OR^g$, $-NR^gC(O)R^g$, $-C(O)NR^g$-$R^g$, $-SO_2NR^gR^g$, $-NR^gSO_2NR^gR^g$, $-NR^gSO_2$-$C_{1-4}$ alkyl, $-NR^gSO_2CF_3$, $-NR^gSO_2$-phenyl, $-S(O)_2$-$CF_3$, $-S(O)_p$-$C_{1-4}$ alkyl, $-S(O)_p$-phenyl, $-(CF_2)_r$-$CF_3$, or $C_{1-6}$ alkyl.

In a fifth aspect, the present invention includes the compounds of Formula (Ia):

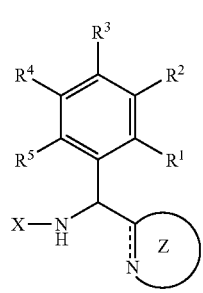

(Ia)

or a stereoisomer, tautomer, pharmaceutically acceptable salt, solvate, or prodrug form thereof, wherein:

$R^1$ is H;

$R^2$ is H, Me, Et, i-Pr, vinyl, ethynyl, prop-1-en-2-yl, —CH(OH)Me, OMe, or OEt;

$R^3$ is H, F, Cl, OMe, OEt, O(i-Pr), or OBn;

$R^4$ is H, OMe, OEt, OPr, O(i-Pr), O(i-Bu), —O(CH$_2$OMe), —OCH$_2$C(Me)$_2$CH$_2$NMe$_2$, cyclopentoxy, cyclohexoxy, cyclopropylmethoxy, Ph, 3-Me-Ph, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-Me-2-oxoimidazolidin-1-yl or 3-(dimethylamino)-2,2-dimethylpropoxy;

$R^5$ is H or F;

alternatively,

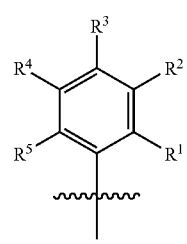

is selected from:

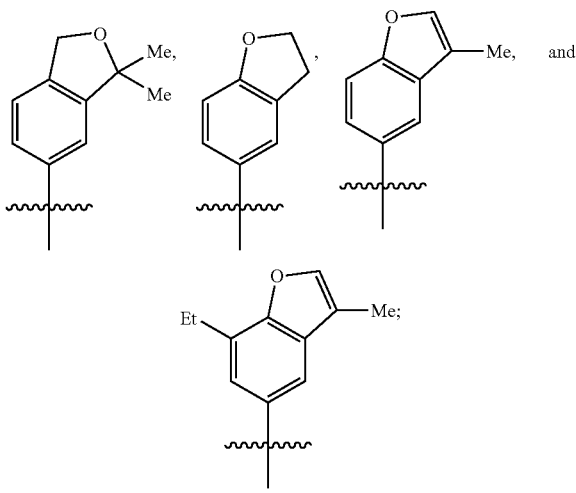

X is 4-C(=NH)NH$_2$-Ph, 2-F-4-C(=NH)NH$_2$-Ph, 3-F-4-C(=NH)NH$_2$-Ph, 2,5-diF-4-C(=NH)NH$_2$-Ph, 2,6-diF-4-C(=NH)NH$_2$-Ph, 4-C(=NOH)NH$_2$-Ph, 2,5-diF-4-C(=NOH)NH$_2$-Ph, 4-CH$_2$NH$_2$-Ph, isoquinolin-6-yl, 1-NH$_2$-isoquinolin-6-yl, quinazolin-7-yl, 4-NH$_2$-quinazolin-7-yl, phthalazin-6-yl, or 1-NH$_2$-phthalazin-6-yl;

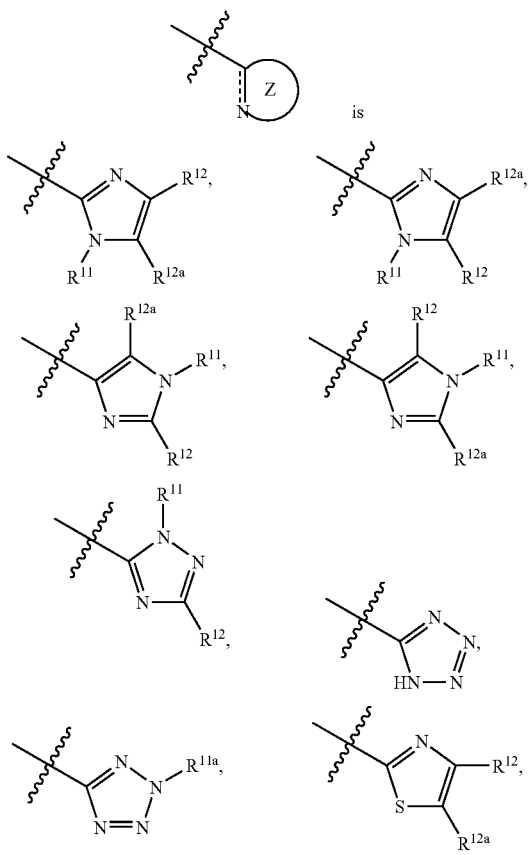

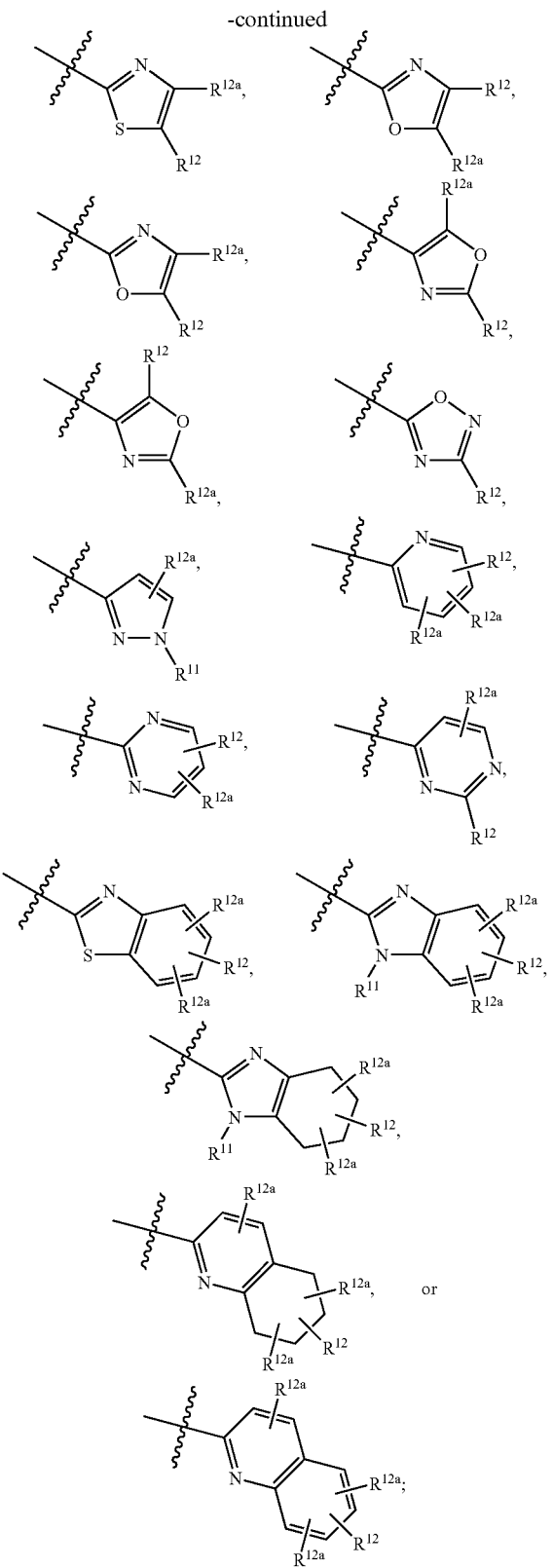

-continued

—CH$_2$CONHEt, —CH$_2$CONH(i-Pr), —CH$_2$CONH (CH$_2$CH$_2$OH), —CH$_2$CONH(CH$_2$CONH$_2$), —CH$_2$CONH(CH$_2$CF$_3$), —CH$_2$CONH(cyclopropyl), —CH$_2$CONH(cyclobutyl), —CH$_2$CONHPh, —CH$_2$CONMe$_2$, —CH$_2$CH$_2$CONMe$_2$, —CH$_2$CON (Me)Et, —CH$_2$OBn, —CH$_2$CO(1-pyrrolidinyl)

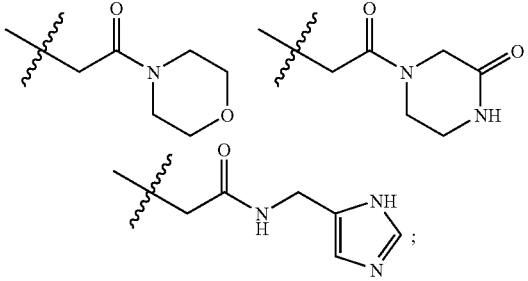

$R^{11a}$ is, independently at each occurrence, Ph or Bn;

$R^{12}$ is, independently at each occurrence, H, F, Cl, Br, CF$_3$, C$_{1-4}$ alkyl, OR$^a$, SR$^a$, —OCF$_3$, —NR$^b$R$^c$, C$_{3-7}$ cycloalkyl, 2-(2-Me-1,3-dioxolan-2-yl)-phenyl, 3-(2-Me-1,3-dioxolan-2-yl)-phenyl, 4-(2-Me-1,3-dioxolan-2-yl)-phenyl, phenyl substituted with 0-3 R$^f$, naphthyl substituted with 0-3 R$^f$, or a heterocycle substituted with 0-3 R$^f$, wherein said heterocycle is selected from: furanyl, thienyl, pyrazolyl, pyrrolidinyl, pyridyl, pyrimidinyl, tetrahydropyrimidinyl, morpholinyl, piperidinyl, indolinyl, benzofuryl, dihydrobenzofuranyl, and methylenedioxyphenyl;

$R^{12a}$ is, independently at each occurrence, H, F, Cl, Br, C$_{1-4}$ alkyl, C$_{1-4}$ alkoxy, NH$_2$, or Ph;

$R^a$ is, independently at each occurrence, H, C$_{1-6}$ alkyl, or C$_{3-7}$ cycloalkyl;

$R^b$ is, independently at each occurrence, H, C$_{1-6}$ alkyl, —(CH$_2$)$_n$-phenyl, or (C$_{1-6}$ alkyl)C(O)—;

$R^c$ is, independently at each occurrence, H, C$_{1-6}$ alkyl substituted with 0-2 R$^j$, or —(CH$_2$)$_n$-phenyl substituted with 0-2 R$^j$;

$R^f$ is, independently at each occurrence, C$_{1-4}$ alkyl, C$_{1-4}$ alkoxy, OH, SMe, —CH$_2$OH, —CH(Me)OH, —CH$_2$OMe, F, Cl, Br, CF$_3$, OCF$_3$, CN, COMe, COEt, CO$_2$H, CO$_2$Me, CO$_2$Et, NH$_2$, NMe$_2$, —CH$_2$NMe$_2$, CONH$_2$, CONHMe, CONMe$_2$, CONHEt, —CONHCH$_2$CH$_2$OH, —NHCOMe-Ph, —NHCOEt-Ph, SO$_2$Me, SO$_2$Et, —NHSO$_2$Me, SO$_2$NH$_2$, Ph, OPh, OBn, furanyl, or thienyl.

In a sixth aspect, the present invention includes the compounds of Formula (Ia), within the scope of the fifth aspect, wherein:

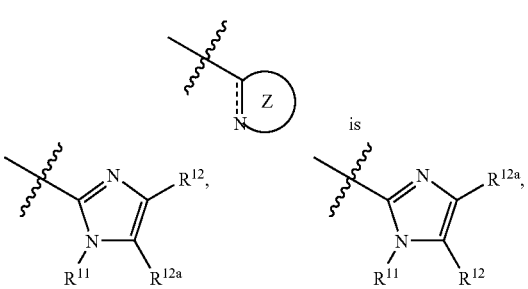

$R^{11}$ is, independently at each occurrence, H, C$_{1-4}$ alkyl, C$_{2-4}$ alkenyl, —CH$_2$CH$_2$OH, Ph, 2-CONH$_2$-Ph, —CH$_2$CO$_2$H, —CH$_2$CH$_2$CO$_2$H, —CH(Me)CO$_2$H, —C(Me)$_2$CO$_2$H, —CH$_2$CONH$_2$, —CH$_2$CONHMe,

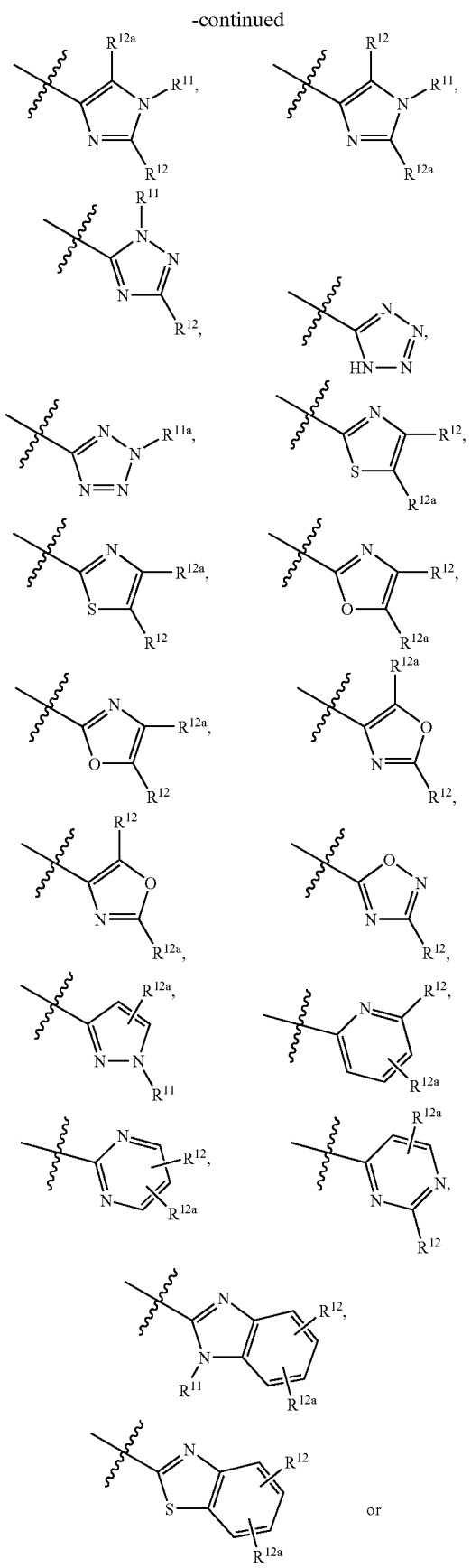

R$^{12}$ is, independently at each occurrence, H, Me, Et, Bu, F, Cl, Br, CF$_3$, OMe, OEt, OPr, O(i-Pr), O(i-Bu), SMe, NHMe, NMe$_2$, —N(Me)COMe, cyclopropyl, cyclopentyl, cyclohexyl, cyclobutoxy, cyclopentoxy, Ph, 2-Me-Ph, 3-Me-Ph, 4-Me-Ph, 2-Et-Ph, 3-Et-Ph, 3-Pr-Ph, 2-i-Pr-Ph, 2-OH-Ph, 3-OH-Ph, 4-OH-Ph, 2-CH$_2$OH-Ph, 3-CH$_2$OH-Ph, 4-CH$_2$OH-Ph, 2-CH(Me)OH-Ph, 2-CH$_2$OMe-Ph, 2-OMe-Ph, 3-OMe-Ph, 4-OMe-Ph, 2-OEt-Ph, 3-OEt-Ph, 2-OPr-Ph, 2-O(i-Pr)-Ph, 3-O(i-Pr)-Ph, 2-SMe-Ph, 2-OCF$_3$-Ph, 3-OCF$_3$-Ph, 2-F-Ph, 3-F-Ph, 4-F-Ph, 2-Cl-Ph, 3-Cl-Ph, 4-Cl-Ph, 2-Br-Ph, 2-CF$_3$-Ph, 3-CF$_3$-Ph, 4-CF$_3$-Ph, 2-CN-Ph, 3-CN-Ph, 2-COMe-Ph, 3-COMe-Ph, 2-COEt-Ph, 2-CO$_2$H-Ph, 3-CO$_2$H-Ph, 2-CO$_2$Me-Ph, 3-CO$_2$Me-Ph, 4-CO$_2$Me-Ph, 2-CO$_2$Et-Ph, 2-NMe$_2$-Ph, 4-NMe$_2$-Ph, 2-CH$_2$NMe$_2$-Ph, 3-CH$_2$NMe$_2$-Ph, 2-CONH$_2$-Ph, 3-CONH$_2$-Ph, 4-CONH$_2$-Ph, 2-CONHMe-Ph, 3-CONHMe-Ph, 4-CONHMe-Ph, 2-CONHEt-Ph, 2-CONMe$_2$-Ph, 3-CONH(CH$_2$)$_2$OH-Ph, 2-CONH(CH$_2$)$_3$OH-Ph, 2-CONHCH$_2$CO$_2$H-Ph, 2-CONHCH$_2$CO$_2$(t-Bu)-Ph, 2-NHCOMe-Ph, 3-NHCOMe-Ph, 4-NHCOMe-Ph, 2-NHCOEt-Ph, 2-SO$_2$Me-Ph, 3-SO$_2$Me-Ph, 2-SO$_2$Et-Ph, 2-NHSO$_2$Me-Ph, 3-NHSO$_2$Me-Ph, 2-SO$_2$NH$_2$-Ph, 2-Ph-Ph, 3-Ph-Ph, 4-Ph-Ph, 2-OPh-Ph, 2-OBn-Ph, 3-OBn-Ph, 2-(2-Me-1,3-dioxolan-2-yl)-Ph, 2-(1-pyrrolidinyl)-Ph, 2-(3-OH-pyrrolidin-1-yl)-Ph, 2,5-diMe-Ph, 2,6-diMe-Ph, 2,3-diF-Ph, 2,3-diCl-Ph, 2,4-diCl-Ph, 3,5-diCl-Ph, 2-OMe-5-Cl-Ph, 2-CO$_2$H-5-Me-Ph, 2-CO$_2$H-6-Me-Ph, 2-CO$_2$H-3-F-Ph, 2-CO$_2$H-4-Cl-Ph, 2-CO$_2$Me-3-Me-Ph, 2-CO$_2$Me-5-Me-Ph, 2-CO$_2$Me-6-Me-Ph, 2-CO$_2$Me-3-F-Ph, 2-CONH$_2$-3-Me-Ph, 2-CONH$_2$-5-Me-Ph, 2-CONH$_2$-6-Me-Ph, 2-CONH$_2$-3-F-Ph, 2-CONH$_2$-4-Cl-Ph, 2-CONHMe-3-F-Ph, 2-(3-furanyl)-Ph, 1-naphthyl, 2-naphthyl, 2-furanyl, 3-furanyl, 5-Me-furan-2-yl, 3-thienyl, 4-pyrazolyl, 1-Me-pyrazol-4-yl, 1-Et-pyrazol-4-yl, 1,4,5,6-tetrahydropyrimidin-5-yl, 1-pyrrolidinyl, 2-CH$_2$OH-pyrrolidin-1-yl, 2-CH$_2$OMe-pyrrolidin-1-yl, 2-CONH$_2$-pyrrolidin-1-yl, N-morpholinyl, 1-piperidinyl, 3-pyridyl, 4-pyridyl, 4-Me-pyrid-3-yl, 2-F-pyrid-3-yl, 2-OMe-pyrid-3-yl, 4-OMe-pyrid-3-yl, 5-OMe-pyrid-3-yl, 5-pyrimidinyl, 3,4-methylenedioxyphenyl, 2-benzofuranyl, 5-indolyl, or dihydrobenzofuran-5-yl; and R$^{12a}$ is, independently at each occurrence, H, F, Cl, Me, OMe, NH$_2$, or Ph.

In a seventh aspect, the present invention includes the compounds of Formula (Ia), within the scope of the fifth aspect, wherein:

R$^2$ is H, Me, Et, i-Pr, vinyl, prop-1-en-2-yl, —CH(OH)Me, OMe, or OEt;

R$^3$ is H or F;

R$^4$ is H, OMe, OEt, OPr, O(i-Pr), O(i-Bu), —O(CH$_2$OMe), cyclohexoxy, cyclopropylmethoxy, Ph, 3-Me-Ph, tetrahydrofuran-3-yloxy, tetrahydro-2-H-pyran-4-yloxy, 1-pyrrolidinyl, N-morpholinyl, 1-Me-piperidin-4-yloxy, or 3-(dimethylamino)-2,2-dimethylpropoxy;

X is 4-C(=NH)NH$_2$-Ph, or 1-NH$_2$-isoquinolin-6-yl;

alternatively,

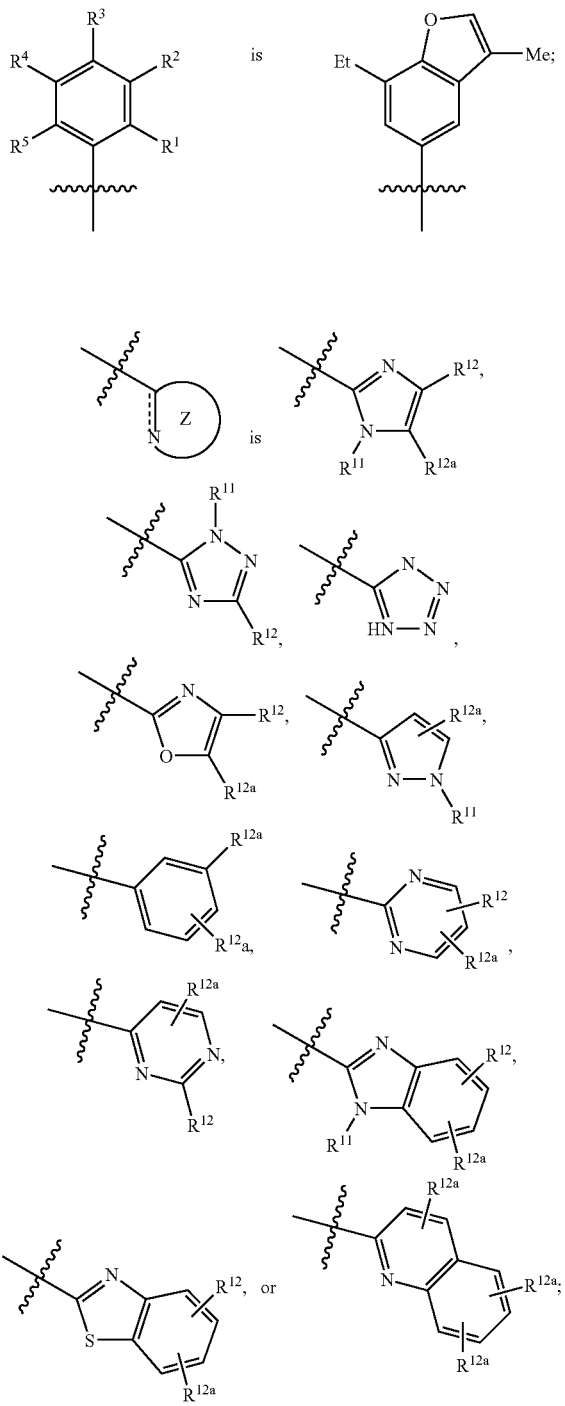

R$^{12}$ is, independently at each occurrence, H, Me, Et, Bu, Br, CF$_3$, OMe, OEt, OPr, O(i-Pr), O(i-Bu), SMe, cyclopropyl, cyclopentyl, Ph, 2-Me-Ph, 3-Me-Ph, 2-Et-Ph, 2-i-Pr-Ph, 2-OH-Ph, 3-OH-Ph, 4-OH-Ph, 2-CH$_2$OH-Ph, 3-CH$_2$OH-Ph, 2-CH(Me)OH-Ph, 2-CH$_2$OMe-Pb, 2-OMe-Ph, 2-OEt-Ph, 2-OPr-Ph, 2-SMe-Ph, 3-OCF$_3$-Ph, 2-F-Ph, 3-F-Ph, 4-F-Ph, 3-Cl-Ph, 2-Br-Ph, 2-CF$_3$-Ph, 2-CN-Ph, 3-CN-Ph, 2-COMe-Ph, 2-COEt-Ph, 2-CO$_2$H-Ph, 2-CO$_2$Me-Ph, 2-CO$_2$Et-Ph, 2-CONH$_2$-Ph, 3-CONH$_2$-Ph, 2-CONHMe-Ph, 3-CONHMe-Ph, 2-CONHEt-Ph, 2-CONMe$_2$-Ph, 2-CONH(CH$_2$)$_3$OH-Ph, 2-CONHCH$_2$CO$_2$H-Ph, 2-CONHCH$_2$CO$_2$(t-Bu)-Ph, 2-NHCOMe-Ph, 2-SO$_2$Me-Ph, 2-NHSO$_2$Me-Ph, 2-SO$_2$NH$_2$-Ph, 2-(2-Me-1,3-dioxolan-2-yl)-Ph, 2-(1-pyrrolidinyl)-Ph, 2-(3-OH-pyrrolidin-1-yl)-Ph, 2,5-diMe-Ph, 2,6-diMe-Ph, 2-CO$_2$H-3-F-Ph, 2-CO$_2$Me-3-Me-Ph, 2-CO$_2$Me-6-Me-Ph, 2-CO$_2$Me-3-F-Ph, 2-CONH$_2$-3-Me-Ph, 2-CONH$_2$-6-Me-Ph, 2-CONH$_2$-3-F-Ph, 1-naphthyl, 2-furanyl, 3-furanyl, 3-thienyl, 4-pyrazolyl, or 3-pyridyl; and R$^{12a}$ is, independently at each occurrence, H, Me, NH$_2$, or Ph.

In an eighth aspect, the present invention includes the compounds of Formula (Ia), within the scope of the sixth aspect, wherein:

X is 1-NH$_2$-isoquinolin-6-yl;

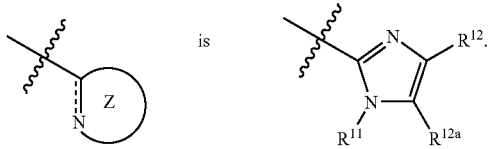

In a ninth aspect, the present invention includes the compounds of Formula (Ia), within the scope of the sixth aspect, wherein:

X is 1-NH$_2$-isoquinolin-6-yl;

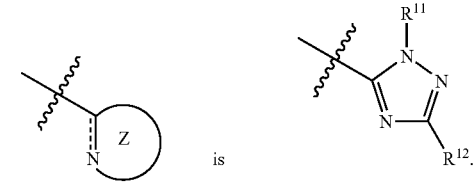

In a tenth aspect, the present invention includes the compounds of Formula (Ia):

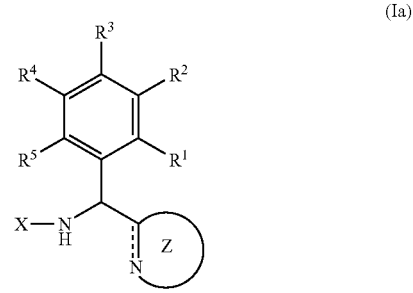

(Ia)

or a stereoisomer or pharmaceutically acceptable salt, solvate, or prodrug form thereof, wherein:

R$^1$ is H;

R$^2$ is H, F, Br, Cl, C$_{2-4}$ alkenyl, C$_{2-4}$ alkynyl, C$_{3-6}$ cycloalkyl, —O—C$_{1-4}$ alkyl, —O—C$_{3-6}$ cycloalkyl, or C$_{1-4}$ alkyl substituted with 0-1 OH;

$R^3$, $R^4$, and $R^5$ are, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl, $C_{2-6}$ alkenyl, $C_{2-6}$ alkynyl, tetrahydrofuran-3-yloxy, tetrahydro-2-H-pyran-4-yloxy, 1-pyrrolidinyl, N-morpholinyl, 1-Me-piperidin-4-yloxy, or 3-(dimethylamino)-2,2-dimethyl-propoxy, phenyl substituted with 0-2 $R^f$, or benzyl substituted with 0-2 $R^f$;

alternatively,

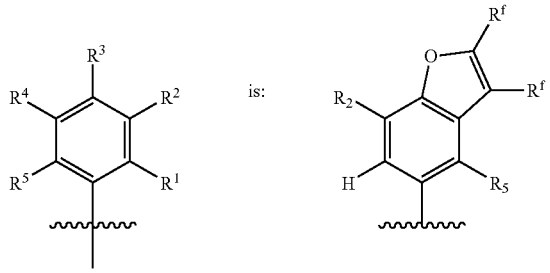

is:

X is 4-C(=NH)$NH_2$-Ph, 4-C(=NOH)$NH_2$-Ph, 4-$CH_2NH_2$-Ph, isoquinolin-6-yl, 1-$NH_2$-isoquinolin-6-yl, quinazolin-7-yl, 4-$NH_2$-quinazolin-7-yl, phthalazin-6-yl, or 1-$NH_2$-phthalazin-6-yl; and X is substituted with 0-1 $R^6$;

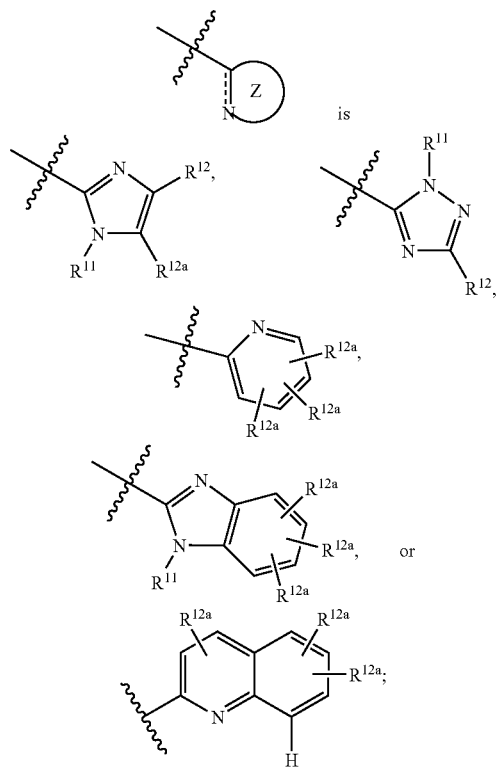

$R^6$ is, independently at each occurrence, —$(CH_2)_r$—$OR^a$, F, Cl, Br, $OCF_3$, CN, $NO_2$, $NR^bR^c$, or —$(CF_2)_rCF_3$;

$R^{11}$ is, independently at each occurrence, H, $C_{1-6}$ alkyl substituted with 0-4 $R^e$, $C_{2-6}$ alkyl substituted with 0-4 $R^e$, —$(C_{0-4}$ alkyl)-$(C_{6-10}$ aryl), —$(C_{0-4}$ alkyl)-(5- to 10-membered heteroaryl comprising: carbon atoms and 1-4 heteroatoms selected from N, O, and S; wherein said aryl and heteroaryl are substituted with 0-4 $R^f$;

$R^{12}$ is, independently at each occurrence, phenyl substituted with 0-3 $R^f$, furanyl substituted with 0-3 $R^f$, or pyridyl substituted with 0-3 $R^f$;

$R^{12a}$ is, independently at each occurrence, H, F, Cl, Br, $C_{1-4}$ alkyl, $C_{1-4}$ alkoxy, $NH_2$, or Ph;

$R^a$ is, independently at each occurrence, H, $C_{1-6}$ alkyl, or $C_{3-7}$ cycloalkyl;

$R^{a1}$ is, independently at each occurrence, H, $C_{1-4}$ alkyl substituted with 0-2 $R^f$, —$(CH_2)_r$—$C_{3-7}$ cycloalkyl, —$(CH_2)_r$—$C_{6-10}$ aryl, or —$(CH_2)_r$-5-10 membered heteroaryl, wherein said cycloalkyl, aryl and heteroaryl groups are optionally substituted with 0-2 $R^f$;

$R^b$ is, independently at each occurrence, H, $C_{1-6}$ alkyl, —$(CH_2)_n$-phenyl, $(C_{1-6}$ alkyl)C(O)—, phenyl-$(C_{0-2}$ alkyl)-C(O)—, (5- to 6-membered heteroaryl)-$C_{0-2}$ alkyl-C(O)—, $(C_{1-6}$ alkyl)-NHC(O)—, $(C_{1-6}$ alkyl)$_2$-NHC(O)—, phenyl-$C_{0-2}$ alkyl-NHC(O)—, (5- to 6-membered heteroaryl)-$C_{0-2}$ alkyl-NHC(O)—, $(C_{1-6}$ alkyl)-$S(O)_2$—, phenyl-$C_{0-2}$ alkyl-$S(O)_2$—, or (5- to 6-membered heteroaryl)-$C_{0-2}$ alkyl-$S(O)_2$—, wherein said phenyl and heteroaryl are substituted with 0-2 $R^f$; said heteroaryl comprises: carbon atoms and 1-4 heteroatoms selected from N, O, and $S(O)_p$;

$R^c$ is, independently at each occurrence, H, $C_{1-6}$ alkyl substituted with 0-2 $R^j$, or —$(CH_2)_n$-phenyl substituted with 0-2 $R^j$;

alternatively, $R^b$ and $R^c$, when attached to the same nitrogen atom, may be taken together with the nitrogen atom to form a 5- to 6-membered heterocycle comprising: carbon atoms and 1-2 heteroatoms selected from N, O, and $S(O)_p$, wherein said heterocycle is substituted with 0-2 $R^f$;

$R^d$ is, independently at each occurrence, H, $C_{1-6}$ alkyl, —$(CH_2)_r$—$C_{3-7}$ cycloalkyl substituted with 0-2 $R^f$, —$(CH_2)_r$-phenyl substituted with 0-2 $R^f$, or a —$(CH_2)_r$-5- to 6-membered heterocycle comprising: carbon atoms and 1-4 heteroatoms selected from N, O, and $S(O)_p$, wherein said heterocycle is substituted with 0-2 $R^f$;

alternatively, $R^c$ and $R^d$, when attached to the same nitrogen atom, may be taken together with the nitrogen atom to form a 4- to 7-membered heterocycle comprising: carbon atoms and 1-4 heteroatoms selected from N, O, and $S(O)_p$, wherein said heterocycle is substituted with 0-2 $R^f$;

$R^e$ is, independently at each occurrence, =O, $OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, or —$(CF_2)_rCF_3$;

$R^f$ is, independently at each occurrence, H, $C_{1-4}$ alkyl, $C_{1-4}$ alkoxy, OH, SMe, —$CH_2OH$, —CH(Me)OH, —$CH_2OMe$, F, Cl, Br, $CF_3$, $OCF_3$, CN, COMe, COEt, $CO_2H$, $CO_2Me$, $CO_2Et$, $NH_2$, $NMe_2$, —$CH_2NMe_2$, $CONH_2$, CONHMe, $CONMe_2$, CONHEt, —$CONHCH_2CH_2OH$, —NHCOMe-Ph, —NHCOEt-Ph, $SO_2Me$, $SO_2Et$, —$NHSO_2Me$, $SO_2NH_2$, Ph, OPh, OBn, furanyl, or thienyl;

$R^g$ is, independently at each occurrence, H, $C_{1-6}$ alkyl, or —$(CH_2)_n$-phenyl;

$R^j$ is, independently at each occurrence, H, =O, —$(CH_2)_r$ $OR^g$, $SR^g$, F, Cl, Br, I, CN, $NO_2$, —$OCF_3$, —$NR^gR^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, or C$_{1-6}$ alkyl;

n, at each occurrence, is selected from 0, 1, 2, and 3;
p, at each occurrence, is selected from 0, 1, and 2; and
r, at each occurrence, is selected from 0, 1, 2, and 3.

In another aspect, the present invention includes the compounds of Formula (Ia) or a stereoisomer, tautomer, pharmaceutically acceptable salt, solvate, or prodrug form thereof, wherein:

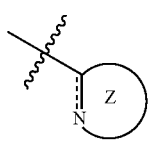

is selected from:

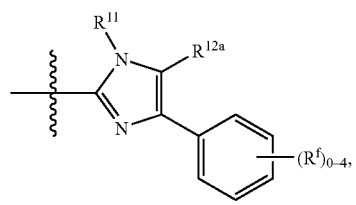

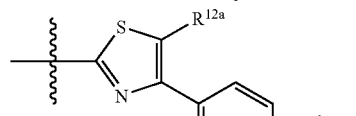

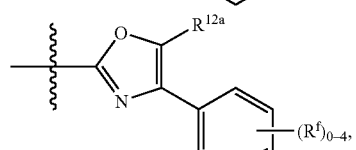

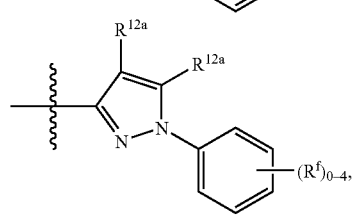

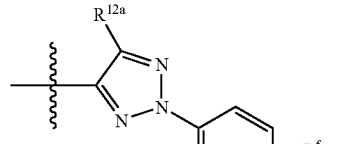

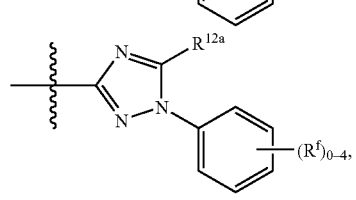

-continued

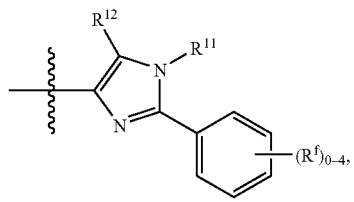

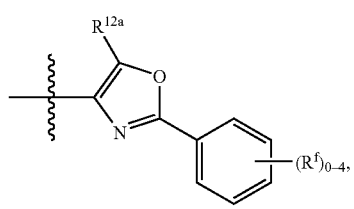

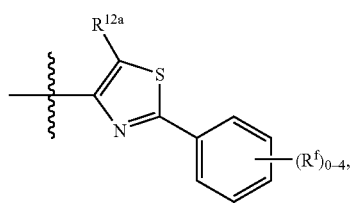

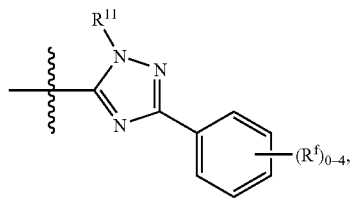

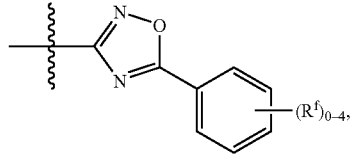

and alternatively,

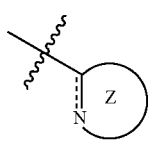

c is substituted with 0-4 $R^{12a}$ and selected from:

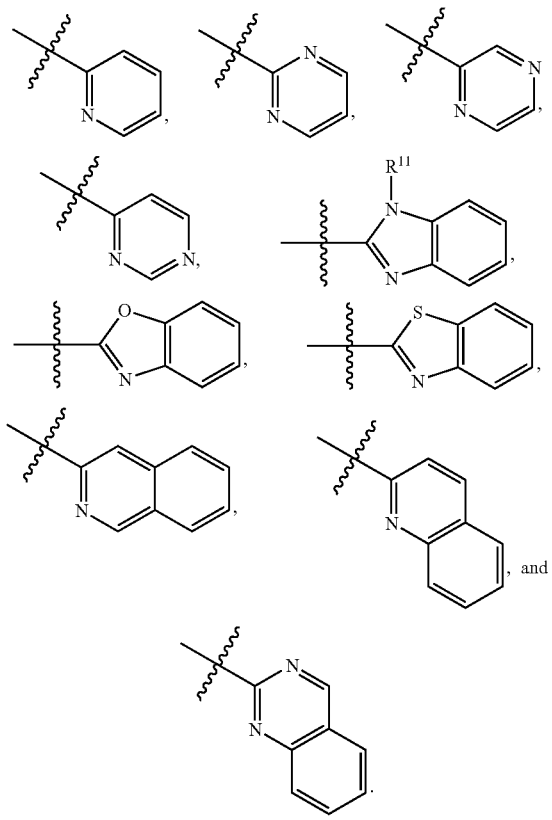

In another aspect, the present invention includes the compounds of Formula (Ia) or a stereoisomer, tautomer, pharmaceutically acceptable salt, solvate, or prodrug form thereof, wherein:

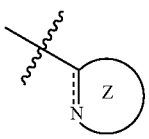

is selected from:

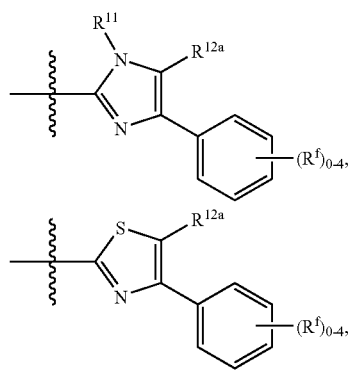

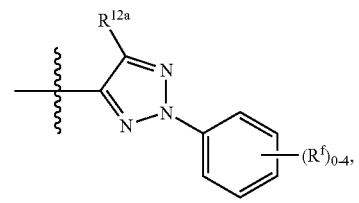

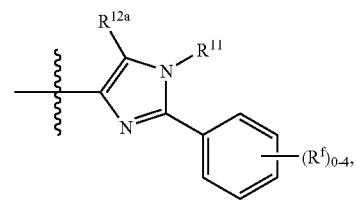

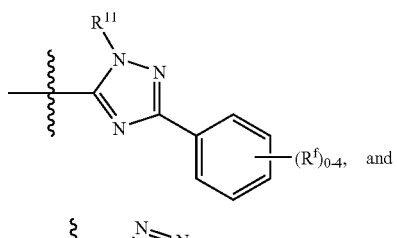

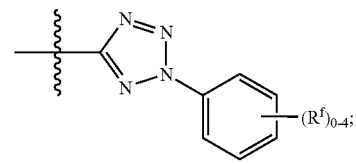

alternatively,

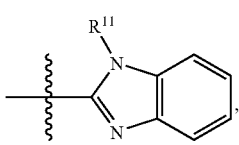

is substituted with 0-1 $R^{12}$ and 0-3 $R^{12a}$ and is selected from:

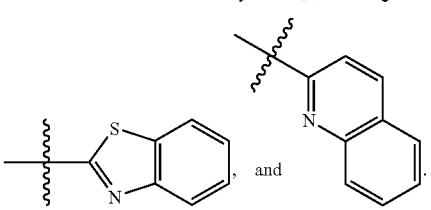

In another aspect, the present invention includes the compounds of Formula (Ia) or a stereoisomer, tautomer, pharmaceutically acceptable salt, solvate, or prodrug form thereof, wherein: Z is

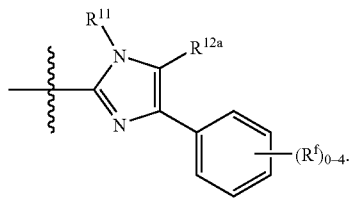

In another aspect, the present invention includes the compounds of Formula (Ia) or a stereoisomer, tautomer, pharmaceutically acceptable salt, solvate, or prodrug form thereof, wherein: Z is

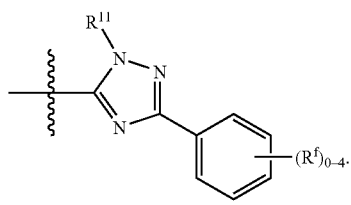

In another aspect, the present invention includes the compounds of Formula (Ia) or a stereoisomer, tautomer, pharmaceutically acceptable salt, solvate, or prodrug form thereof, wherein: Z is

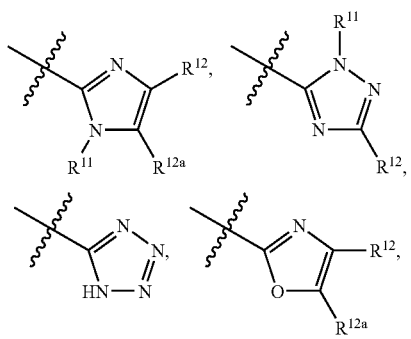

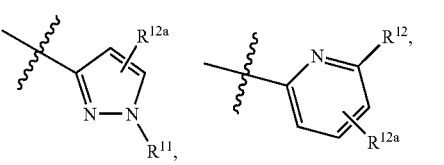

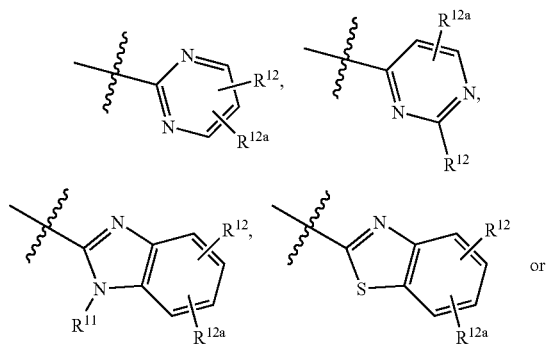

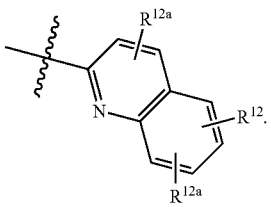

In another aspect, the present invention includes the compounds of Formula (Ia) or a stereoisomer, tautomer, pharmaceutically acceptable salt, solvate, or prodrug form thereof, wherein: Z is

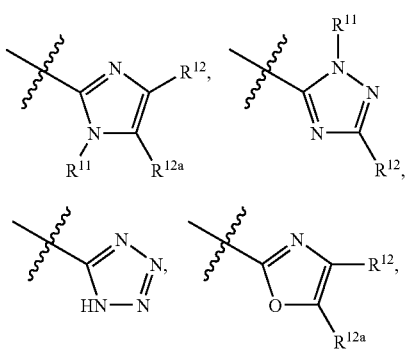

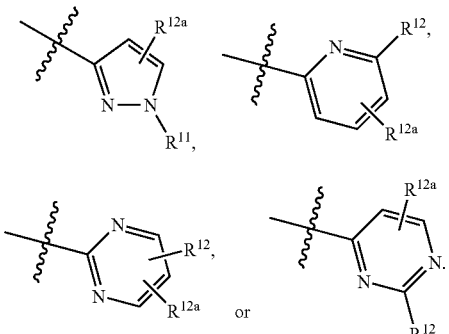

In another aspect, the present invention includes the compounds of Formula (Ia) or a stereoisomer, tautomer, pharmaceutically acceptable salt, solvate, or prodrug form thereof, wherein: Z is

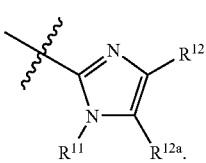

In another aspect, the present invention includes the compounds of Formula (Ia) or a stereoisomer, tautomer, pharmaceutically acceptable salt, solvate, or prodrug form thereof, wherein: Z is

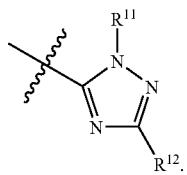

In another aspect, the present invention includes the compounds of Formula (Ia) or a stereoisomer, tautomer, pharmaceutically acceptable salt, solvate, or prodrug form thereof, wherein: Z is

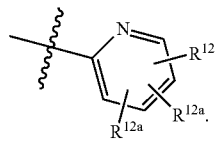

In another aspect, the present invention includes the compounds of Formula (Ia) or a stereoisomer, tautomer, pharmaceutically acceptable salt, solvate, or prodrug form thereof, wherein: Z is

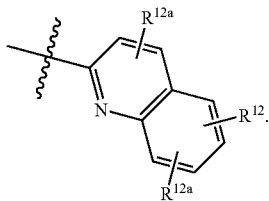

In another aspect, the present invention includes the compounds of Formula (Ia) or a stereoisomer, tautomer, pharmaceutically acceptable salt, solvate, or prodrug form thereof, wherein:
$R^2$ is H, Me, Et, vinyl, ethynyl, i-Pr, —CH(OH)Me, OMe, or OEt;
$R^3$ is H, F, Cl, OMe, OEt, O(i-Pr), or OBn;
$R^4$ is H, OMe, OEt, OPr, O(i-Pr), O(i-Bu), —O(CH$_2$OMe), cyclopentoxy, cyclohexoxy, cyclopropylmethoxy, Ph, 3-Me-Ph, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-Me-2-oxoimidazolidin-1-yl or 3-(dimethylamino)-2,2-dimethylpropoxy; and
$R^5$ is H or F.

In another aspect, the present invention includes the compounds of Formula (Ia) or a stereoisomer, tautomer, pharmaceutically acceptable salt, solvate, or prodrug form thereof, wherein:
$R^2$ is OEt;
$R^3$ is H; and
$R^4$ is O(i-Pr).

In another aspect, the present invention includes the compounds of Formula (Ia) or a stereoisomer, tautomer, pharmaceutically acceptable salt, solvate, or prodrug form thereof, wherein:
$R^2$ is Et;
$R^3$ is H; and
$R^4$ is OEt.

In another aspect, the present invention includes the compounds of Formula (Ia) or a stereoisomer, tautomer, pharmaceutically acceptable salt, solvate, or prodrug form thereof, wherein: $R^2$ is H, Me, Et, vinyl, ethynyl, i-Pr, —CH(OH)Me, OMe, or OEt.

In another aspect, the present invention includes the compounds of Formula (Ia) or a stereoisomer, tautomer, pharmaceutically acceptable salt, solvate, or prodrug form thereof, wherein: $R^3$ is H, F, Cl, OMe, OEt, O(i-Pr), or OBn.

In another aspect, the present invention includes the compounds of Formula (Ia) or a stereoisomer, tautomer, pharmaceutically acceptable salt, solvate, or prodrug form thereof, wherein: $R^4$ is H, OMe, OEt, OPr, O(i-Pr), O(i-Bu), —O(CH$_2$OMe), cyclopentoxy, cyclohexoxy, cyclopropylmethoxy, Ph, 3-Me-Ph, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-Me-2-oxoimidazolidin-1-yl or 3-(dimethylamino)-2,2-dimethylpropoxy.

In another aspect, the present invention includes the compounds of Formula (Ia) or a stereoisomer, tautomer, pharmaceutically acceptable salt, solvate, or prodrug form thereof, wherein: $R^4$ is H, OMe, OEt, OPr, O(i-Pr), or O(i-Bu).

In another aspect, the present invention includes the compounds of Formula (Ia) or a stereoisomer, tautomer, pharmaceutically acceptable salt, solvate, or prodrug form thereof, wherein: $R^5$ is H or F.

In another aspect, the present invention includes the compounds of Formula (Ia) or a stereoisomer, tautomer, pharmaceutically acceptable salt, solvate, or prodrug form thereof, wherein: $R^5$ is H.

In another aspect, the present invention provides compounds of Formula (Ia) or a stereoisomer, tautomer, pharmaceutically acceptable salt, solvate, or prodrug form thereof, wherein: X is 4-C(=NH)NH$_2$-phenyl.

In another aspect, the present invention provides compounds of Formula (Ia) or a stereoisomer, tautomer, pharmaceutically acceptable salt, solvate, or prodrug form thereof, wherein: X is isoquinolin-6-yl or 1-NH$_2$-isoquinolin-6-yl.

In another aspect, the present invention provides compounds of Formula (Ia) or a stereoisomer, tautomer, pharmaceutically acceptable salt, solvate, or prodrug form thereof, wherein: X is 1-NH$_2$-isoquinolin-6-yl.

In an eleventh aspect, the present invention provides a compound selected from the exemplified examples or a stereoisomer, tautomer, pharmaceutically acceptable salt, solvate, or prodrug form thereof.

In another embodiment the present invention provides a pharmaceutical composition comprising a pharmaceutically acceptable carrier and a therapeutically effective amount of at least one of the compounds of the present invention or a pharmaceutically acceptable salt, solvate, or prodrug form thereof.

In another embodiment, the present invention provides a novel process for making a compound of the present invention or a stereoisomer, tautomer, pharmaceutically acceptable salt, solvate or prodrug form thereof.

In another embodiment, the present invention provides a novel intermediate for making a compound of the present invention or a stereoisomer, tautomer, pharmaceutically acceptable salt, solvate or prodrug form thereof.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, pharmaceutically acceptable salt, solvate, or prodrug form thereof.

In another embodiment the present invention provides a method for treating thromboembolic disorders comprising: administering to a patient in need of such treatment a therapeutically effective amount of at least one of the compounds of the present invention or a stereoisomer, tautomer, pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, pharmaceutically acceptable salt, solvate, or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug form thereof in an amount effective to treat a thromboembolic disorder.

In another embodiment, the present invention provides a method of treating a patient in need of inflammatory disorder treatment, comprising: administering a compound of the present invention or a stereoisomer, tautomer, pharmaceutically acceptable salt, solvate, or prodrug form thereof in an amount effective to treat an inflammatory disorder.

In another embodiment, the present invention provides a method, comprising: administering a compound of the present invention or a a stereoisomer, tautomer, pharmaceutically acceptable salt, solvate, or prodrug form thereof in an amount effective to treat a thromboembolic and/or inflammatory disorder.

In another embodiment, the present invention provides a pharmaceutical composition further comprising at least one additional therapeutic agent selected from one or more of potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, anti-osteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In a preferred embodiment, the present invention provides a pharmaceutical composition wherein the at least one additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor VIIa inhibitors, other plasma kallikrein inhibitors, factor VIIa inhibitors and factor Xa inhibitors, and antiplatelet agents selected from GPIIb/IIIa blockers, $P2Y_1$ and $P2Y_{12}$ antagonists, thromboxane receptor antagonists, and aspirin.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a novel method, comprising: administering a compound of the present invention or a stereoisomer, tautomer, pharmaceutically acceptable salt, solvate, or prodrug form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising:
 (a) a first container;
 (b) a pharmaceutical composition located within the first container, wherein the composition, comprises: a first therapeutic agent, comprising: a compound of the present invention or a stereoisomer, tautomer, pharmaceutically acceptable salt form thereof, and
 (c) a package insert stating that the pharmaceutical composition can be used for the treatment of a thromboembolic disorder.

In another preferred embodiment, the present invention provides a novel article of manufacture, further comprising:
 (d) a second container;

wherein components (a) and (b) are located within the second container and component (c) is located within or outside of the second container.

In another embodiment, the present invention provides a novel article of manufacture, comprising:
 (a) a first container;
 (b) a pharmaceutical composition located within the first container, wherein the composition, comprises: a first therapeutic agent, comprising: a compound of the present invention or a stereoisomer, tautomer, pharmaceutically acceptable salt form thereof; and (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. When the term "carbocycle" is used, it is intended to include "aryl".

As used herein, the term "heterocycle" or "heterocyclic group" is intended to mean a stable 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include "heteroaryl".

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. Heteroaryl groups can be substituted or unsubstituted.

The term "counterion" is used to represent a small, negatively charged species such as chloride, bromide, hydroxide, acetate, and sulfate.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided, herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor VIIa and/or plasma kallikrein. "Therapeutically effective amount" is also intended to include an amount of the combination of compounds claimed that is effective to inhibit factor VIIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor VIIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds of Formula (I) may be prepared according to Scheme 1. An optionally protected heterocycle is metallated via deprotonation or lithium-halogen exchange with a strong base such as n-BuLi. This species is then reacted with a ketone or aldehyde ($R^{8a}$=H) to afford an alcohol. The $R^8$ and the heterocycle may optionally be functionalized. The alcohol functionality is then converted to a leaving group by treatment with reagents such as methanesulfonyl chloride/TEA or $CCl_4/PPh_3$. The resultant product is reacted with optionally protected amine $X$—$NH_2$. If necessary, protecting groups are removed and X, $R^8$, $R^{8a}$ and Z may be further modified to provide desired compound 1.

Scheme 1

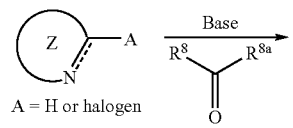

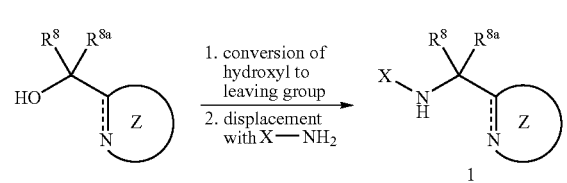

Alternatively, compounds of Formula (I) may be prepared according to Scheme 2. A ketone or aldehyde is dehydrated with X—$NH_2$ to afford an imine. This imine is then reacted with an anion formed from an optionally protected heterocycle via deprotonation or lithium-halogen exchange with a strong base such as n-BuLi. If necessary, protecting groups are removed and X, $R^8$, $R^{8a}$ and Z may be further modified to provide desired compound 1.

Scheme 2

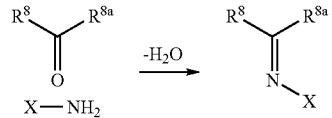

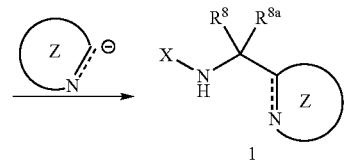

Alternatively, compounds of Formula (I) may be prepared according to Scheme 3. An anion derived from $R^8$-A, via lithium-halogen exchange or deprotonation with a strong base such as BuLi, is added to an optionally protected heterocyclic aldehyde. This aldehyde, if not commercially available, may be prepared via lithium-halogen exchange or deprotonation of an optionally protected heterocycle Z with a strong base followed by quenching with dimethylformamide, or by other means known to one skilled in the arts. The resultant alcohol functionality is then converted to a leaving group by treatment with reagents such as methanesulfonyl chloride/TEA or $CCl_4/PPh_3$. The resultant product is reacted with optionally protected amine $X$—$NH_2$. If necessary, protecting groups are removed and X, $R^8$, $R^{8a}$ and Z may be further modified to provide desired compound 1.

Scheme 3

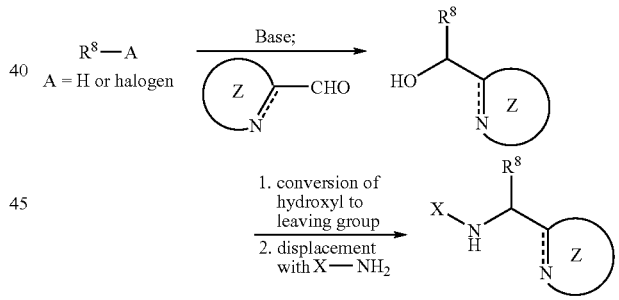

Alternatively, compounds of Formula (I) may be prepared according to Scheme 4. An optionally protected heterocyclic aldehyde is dehydrated with X—$NH_2$ to afford an imine. This imine is then reacted with an anion formed from an optionally protected group $R^8$-A via deprotonation or lithium-halogen exchange with a strong base such as n-BuLi. If necessary, protecting groups are removed and X, $R^8$, $R^{8a}$ and Z may be further modified to provide desired compound 1.

Scheme 4

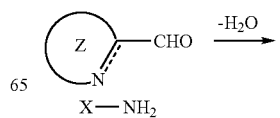

-continued

R⁸—A

A = H or halogen

|Base

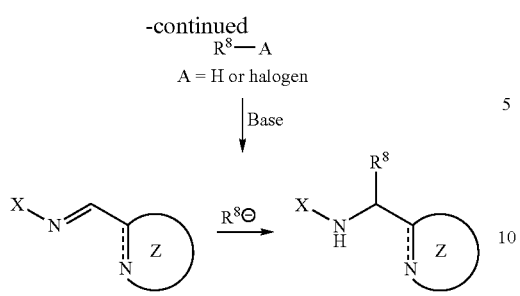

Alternatively, compounds of Formula (I) may be prepared according to Scheme 5. An amino acid, either commercially available or prepared according to WO2004/072101, which is incorporated herein by reference, or by other methods known to one skilled in the art, is subjected to heterocycle-forming reactions according methods described in "*Comprehensive Heterocyclic Chemistry II*" Vol. 2-7, Katritzky, Rees and Scriven; 1996, Pergamon. One example of such heterocycle formations includes conversion of the acid to a keto ester upon treatment with an x-haloketone followed by cyclization with upon heating with ammonium acetate to afford an imidazol-2-yl group. Another example of a heterocycle-forming strategy is the coupling of the amino acid with a 2-nitroaniline, followed by reduction of the nitro to an amine, cyclization and dehydration. If necessary, protecting groups are removed and X, $R^8$, $R^{8a}$ and Z may be further modified to provide desired compound 1.

Scheme 5

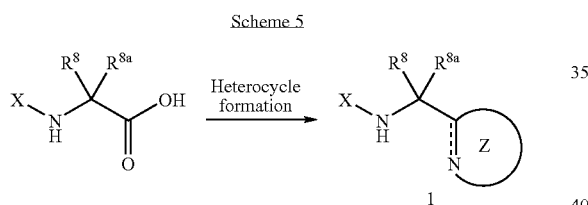

EXAMPLES

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Alternatively, flash chromatography was carried out on an ISCO CombiFlash™ System Sq16x using prepacked $SiO_2$ cartridges eluted with gradients of the specified solvents. Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "rt" for room temperature, "atm" for atmosphere, "psi" for pounds per square inch, "RT" for retention time, "MS" for mass spectrometry, "ESI" for electrospray ionization mass spectroscopy, "HR" for high resolution, "LCMS" for liquid chromatography mass spectrometry, "HPLC" for high pressure liquid chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

As used throughout the specification, the following abbreviations for chemical reagents apply:

ACN is acetonitrile,
AIBN is azo-bis-isobutyrlnitrile,
BINAP is 2,2'-bis(diphenylphosphino)-1,1'-binaphthalene,
Bn is benzyl,
Boc is tert-butyl oxycarbonyl,
BOM is benzyloxymethyl,
BOP is benzotriazol-1-yloxy-tris(dimethylamino)phosphonium hexafluorophosphate,
Bu is butyl,
iBu or i-Bu is isobutyl,
t-Bu is tert-butyl,
Cbz is carbonylbenzyloxy,
m-CPBA is meta-chloroperbenzoic acid,
DCE is 1,2-dichloroethane,
DCM is dichloromethane,
DIBAH is diisobutylaluminum hydride,
DIC is 1,3-diisopropylcarbodiimide,
DIEA is diethylpropyl amine,
DMAP is dimethylaminopyridine,
DME is dimethyl ether,
DMF is dimethylformamide,
DMSO is dimethyl sulfoxide,
DPPA is diphenylphosphoryl azide,
EDCI is 1-(3-dimethylaminopropyl)-3-ethylcarbodiimide hydrochloride,
Et is ethyl,
EtOAc is ethyl acetate,
HOAc or AcOH is acetic acid,
HOAt or HOAT is 1-hydroxy-7-azabenzotriazole,
LAH is lithium aluminum hydride
LDA is lithium diisopropylamide,
LiHMDS is bis(trimethylsilyl)amide,
Me is methyl,
MsCl is methanesulfonyl chloride,
NaOAc is sodium actetate,
NBS is N-bromosuccinamide,
OAc is acetate,
$Pd_2(dba)_3$ is tris(dibenzylideneacetone)dipalladium(0),
$Pd(PPh_3)_4$ is tetraks (triphenylphosphine) palladium,
Ph is phenyl,
PMDTA is N,N,N',N',N"-pentamethyldiethylenetriamine,
Pr is propyl,
iPr or i-Pr is isopropyl,
TBAF is tetrabutylammoniumfluoride,
TBAI is tetrabutylammonium iodide,
TBS is tert-butyldimethylsilyl,
TBSCl is tert-butyldimethylsilyl chloride,
TEA is triethylamine,
TFA is trifluoroacetic acid,
TFAA is trifluoroacetic anhydride,
THF is tetrahydrofuran,
TrCl is trityl chloride,
Trt is trityl,
Xantpos is 4,5-bis(diphenylphosphino)-9,9-dimethylxanthene.

The following Examples have been prepared, isolated and characterized using the methods disclosed herein. The following Examples demonstrate a partial scope of the invention and are not meant to be limiting of the scope of the invention.

Example 1

4-((3-ethoxy-4-isopropoxyphenyl)(1H-imidazol-2-yl)methylamino)benzamidine bis-triluoroacetic acid salt

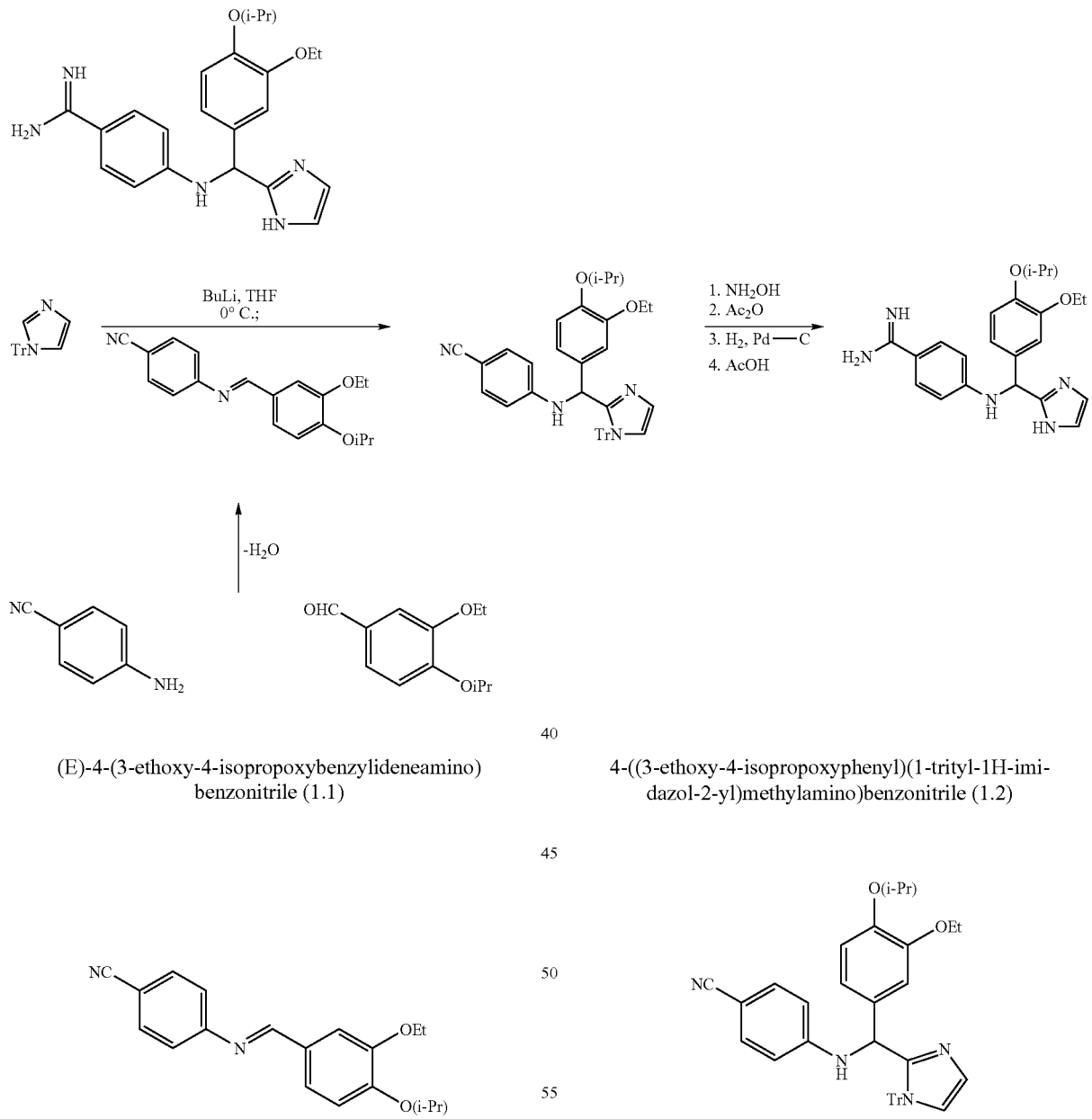

(E)-4-(3-ethoxy-4-isopropoxybenzylideneamino)benzonitrile (1.1)

4-((3-ethoxy-4-isopropoxyphenyl)(1-trityl-1H-imidazol-2-yl)methylamino)benzonitrile (1.2)

A mixture of 3-ethoxy-4-isopropoxybenzaldehyde (1.78 g, 8.55 mmol), 4-aminobenzonitrile (1.01 g, 8.55 mmol), and 5 g 4 Å molecular sieves in 20 mL toluene was refluxed with azeotropic removal of water for 2 h. The mixture was filtered and concentrated to afford 2.29 g of Intermediate 1.1 as a pale yellow solid.

To a solution of N-tritylimidazole (100 mg, 0.322 mmol) in 4 mL THF at 0° C., was added BuLi (1.6 M in hexanes, 221 µL, 0.354 mmol). The mixture was stirred at 0° C. for 15 min, rt for 15 min, then recooled to 0° C. To this mixture was added a solution of Intermediate 1.1 (109 mg, 0.354 mmol) in 600 µL THF. The mixture was stirred at 0° C. for 30 min, then quenched with sat. NH$_4$Cl. The mixture was diluted with EtOAc, washed with H$_2$O and brine, dried (Na$_2$SO$_4$) and concentrated. The crude product was purified by flash chromatography (30 to 35 to 40% EtOAc/hexanes, stepwise gradient) to afford 121 mg of Intermediate 1.2 as a white solid.

Example 1

To a solution of hydroxylamine hydrochloride (193.5 mg, 3.0 mmol) in 1 mL DMSO, was added TEA (418 µL, 3.0 mmol). The mixture was stirred for 10 min, diluted with 1 mL THF. The suspension was filtered, rinsed with 0.5 mL THF and the volatile THF was removed from the filtrate by rotary evaporation to afford a DMSO solution of $NH_2OH$. To this solution was added Intermediate 1.2 (88 mg). The mixture was stirred at 60° C. for 3 h, then was diluted with EtOAc. The organic phase was washed with $H_2O$ (2×) and brine, dried ($Na_2SO_4$) and concentrated to afford 84 mg of the amide oxime intermediate as a white solid.

To a suspension of the amide oxime in 2 mL $CH_2Cl_2$, was added acetic anhydride. The clear solution was stirred at rt for 15 min, then concentrated. The acylated intermediate was dissolved in 4 mL MeOH and hydrogenated over 10% Pd—C (~20 mg) with a balloon of $H_2$ for 1.5 h. The reaction was filtered and concentrated to afford the amidine intermediate.

A solution of this intermediate in 3 mL 90% aq. acetic acid was stirred at 60° C. for 3 h, then concentrated. The crude residue was purified by preparative HPLC to afford 19 mg of Example 1. LCMS (4 min gradient) RT=1.84 min, 391.41 $(M+H)^+$; $^1$H NMR (400 MHz, $D_2O$) δ ppm 1.29-1.35 (m, 6 H) 4.06 (q, J=7.0 Hz, 2H) 4.62-4.67 (m, 1 H) 6.15 (s, 1 H) 6.80 (d, J=8.8 Hz, 2 H) 6.96 (dd, J=8.4, 2.2 Hz, 1H) 7.05 (d, J=2.2 Hz, 1H) 7.09 (d, J=8.4 Hz, 1H) 7.40 (s, 2 H) 7.61 (d, J=2.2 Hz, 2 H).

Example 2

4-((3-ethoxy-4-isopropoxyphenyl)(thiazol-2-yl)methylamino)benzamidine trifluoroacetic acid salt

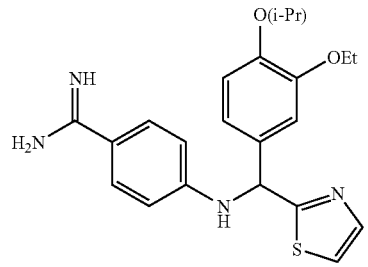

4-((3-ethoxy-4-isopropoxyphenyl)(thiazol-2-yl)methylamino)benzonitrile (2.1)

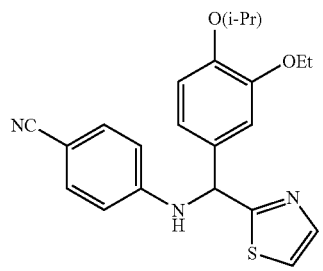

To a solution of thiazole (60 mg, 0.705 mmol) in 3 mL THF at −78° C., was added BuLi (1.6 M in hexanes, 484 µL, 0.775 mmol). The pale yellow suspension was allowed to slowly warm to −45° C. over 30 min, then a solution of Intermediate 1.1 (239 mg, 0.775 mmol) in 2 mL THF was added. The mixture was allowed to warm slowly from −45° C. to 0° C. over 45 min, then was quenched with sat. $NH_4Cl$. The mixture was diluted with EtOAc, washed with $H_2O$ and brine, dried ($Na_2SO_4$) and concentrated. The crude product was purified by flash chromatography (30 to 35 to 40% EtOAc/hexanes, stepwise gradient) to afford 146 mg of Intermediate 2.1 as a yellow glass.

Example 2

A solution of Intermediate 2.1 (135 mg, 0.343 mmol) in 1 mL 3 M $NH_2OH$ in DMSO was converted to the amide oxime, acylated and hydrogenated as in Example 1 to afford after HPLC purification 124 mg of Example 2. LCMS (4 min gradient) RT=3.08 min, 411.26 $(M+H)^+$; $^1$H NMR (400 MHz, $CD_3OD$) δ ppm 1.28 (d, J=5.7 Hz, 6 H) 1.36 (t, J=7.0 Hz, 3 H), 4.02 (q, J=7.0 Hz, 2 H) 4.48-4.57 (m, 1H) 5.98 (s, 1 H), 6.81 (d, J=8.8 Hz, 2 H) 6.93 (s, 2H), 7.05 (s, 1 H) 7.54 (d, J=2.2 Hz, 1 H), 7.58 (d, J=8.8 Hz, 2 H) 7.77 (d, J=2.2 Hz, 1 H).

Example 3

4-(benzo[d]thiazol-2-yl(3-ethoxy-4-isopropoxyphenyl)methylamino)benzamidine trifluoroacetic acid salt

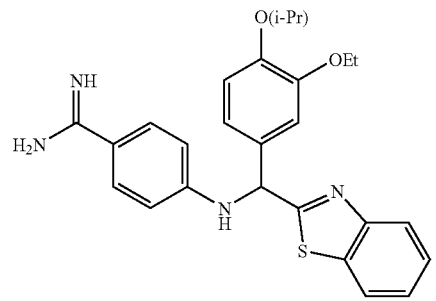

4-(benzo[d]thiazol-2-yl(3-ethoxy-4-isopropoxyphenyl)methylamino)benzonitrile (3.1)

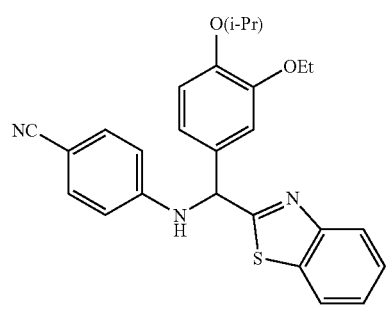

According to the procedure for Intermediate 2.1, benzothiazole (61.9 mg, 0.458 mmol) afforded 40 mg of Intermediate 3.1.

Example 3

A solution of Intermediate 3.1 (36 mg, 0.0812 mmol) in 1 mL 3 M NH$_2$OH in DMSO was converted to the amide oxime, acylated and hydrogenated as in Example 1 to afford after HPLC purification 32 mg of Example 3. LCMS (4 min gradient) RT=3.35 min, 461.24 (M+H)$^+$; $^1$H NMR (400 MHz, CD$_3$OD) δ ppm 1.27 (d, J=5.7 Hz, 6 H) 1.36 (t, J=7.0 Hz, 3 H), 3.98-4.07 (m, 2 H) 4.48-4.56 (m, 1 H) 6.07 (s, 1 H), 6.86 (d, J=8.8 Hz, 2 H) 6.95-7.07 (m, 2 H), 7.14 (d, 1 H), 7.37-7.44 (m, 1 H) 7.50 (t, 1 H) 7.59 (d, J=8.8 Hz, 2 H) 7.92-7-97 (m, 1 H).

Example 4

4-((3-ethoxy-4-isopropoxyphenyl)(pyridin-2-yl)methylamino)benzamidine bis-trifluoroacetic acid salt

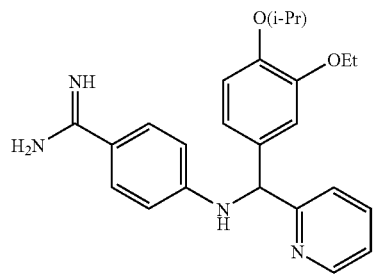

4-((3-ethoxy-4-isopropoxyphenyl)(pyridin-2-yl)methylamino)benzonitrile (4.1)

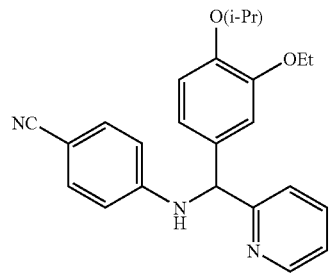

According to the procedure for Intermediate 2.1, 2-bromopyridine (100 mg, 0.633 mmol) afforded 177 mg of Intermediate 4.1.

Example 4

A solution of Intermediate 4.1 (155 mg, 0.400 mmol) in 1 mL 3 M NH$_2$OH in DMSO was converted to the amide oxime, acylated and hydrogenated as in Example 1 to afford after HPLC purification 156 mg of Example 4. LCMS (4 min gradient) RT=2.11 min, 405.36 (M+H)$^+$; $^1$H NMR (400 MHz, CD$_3$OD) δ ppm 1.27 (d, J=6.2 Hz, 6 H) 1.35 (t, J=7.0 Hz, 3 H), 4.01 (q, J=7.0 Hz, 2 H) 4.47-4.53 (m, 1H) 5.89 (s, 1 H), 6.79 (d, J=9.2 Hz, 2 H) 6.88-6.95 (m, 2 H), 7.02 (d, J=1.7 Hz, 1H), 7.58-7.62 (m, 3 H) 7.72 (d, J=8.0 Hz, 1 H) 8.13 (t, J=7.5 Hz, 1 H) 8.64 (d, J=5.2 Hz, 1 H).

Example 7

4-(benzo[d]thiazol-2-yl(5-ethoxy-2-fluoro-3-isopropoxyphenyl)methylamino)benzamidine trifluoroacetic acid salt

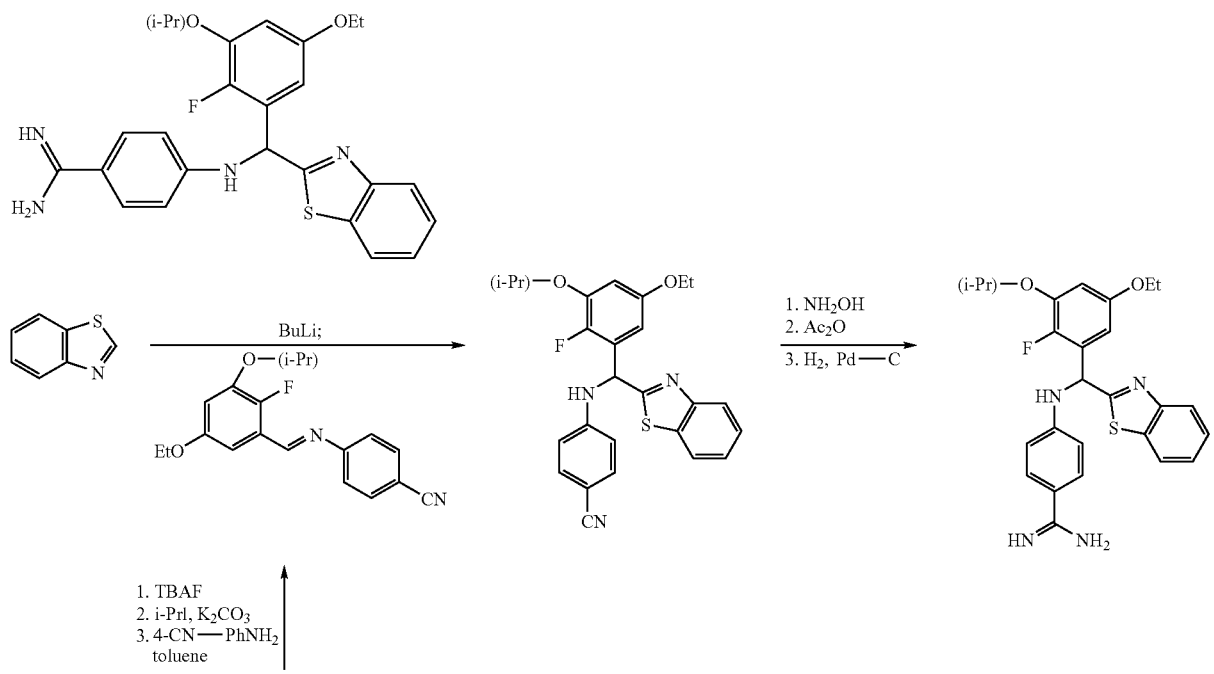

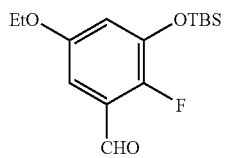

5-ethoxy-2-fluoro-3-hydroxybenzaldehyde (7.1)

To a solution of 3-(tert-butyldimethylsilyloxy)-5-ethoxy-2-fluorobenzaldehyde (7.25 g, 24.3 mmol), prepared according to WO2003066588 A1, which is incorporated herein by reference, in 50 mL THF at 0° C., was added a 1 M solution of TBAF in THF (24.3 mL, 24.3 mmol). The mixture was stirred for 30 min, then was diluted with EtOAc, washed with $H_2O$ (2×) and brine, dried ($Na_2SO_4$) and concentrated. The crude product was purified by flash chromatography (0 to 50% EtOAc/hexanes gradient) to afford Intermediate 7.1, contaminated with tetrabutylammonium salts.

5-ethoxy-2-fluoro-3-isopropoxybenzaldehyde (7.2)

To a solution of Intermediate 7.1 (assumed 24.3 mmol) in 50 mL DMF, was added $K_2CO_3$ (4.03 g, 29.2 mmol) and 2-iodopropane (4.86 mL, 48.6 mmol). The mixture was stirred at 50° C. for 16 h, then was diluted with EtOAc/hexanes (1:1). The organic phase was washed with $H_2O$ (3×) and brine, dried ($Na_2SO_4$) and concentrated. The crude product was purified by flash chromatography (0 to 30% EtOAc/hexanes gradient) to afford 3.94 g of Intermediate 7.2 as a white solid.

(E)-4-(5-ethoxy-2-fluoro-3-isopropoxybenzylideneamino)benzonitrile (7.3)

According to the procedure for Intermediate 1.1, Intermediate 7.2 (3.13 g, 13.8 mmol) and 4-aminobenzonitrile (1.63 g, 13.8 mmol) afforded 4.45 g of Intermediate 7.3 as a yellow solid.

4-(benzo[d]thiazol-2-yl(5-ethoxy-2-fluoro-3-isopropoxyphenyl)methylamino)benzonitrile (7.4)

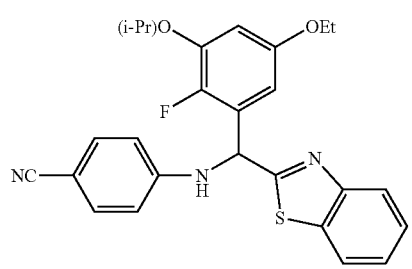

To a solution of benzothiazole (61.9 mg, 0.458 mmol) in 2 mL THF at −78° C. was added 1.6 M solution of BuLi in THF (315 μL, 0.504 mmol). The mixture was stirred at −78° C. for 45 min, then a solution of Intermediate 7.3 (149 mg, 0.458 mmol) in 0.5 mL THF was added dropwise. The mixture was stirred and allowed to warm to rt overnight, then was quenched with sat. $NH_4Cl$. The mixture was diluted with EtOAc, washed with $H_2O$ and brine, dried ($Na_2SO_4$) and concentrated. The crude product was purified by flash chromatography (0 to 50% EtOAc/hexanes gradient) to afford 90 mg of Intermediate 7.4 as a white solid.

Example 7

A solution of Intermediate 7.4 (80 mg, 0.173 mmol) in 1 mL 3 M $NH_2OH$ in DMSO was converted to the amide oxime, acylated and hydrogenated as in Example 1 to afford after HPLC purification 20 mg of Example 7 as a white powder. LCMS (4 min gradient) RT=3.56 min, 479.23 (M+H)$^+$; $^1$H NMR (400 MHz, METHANOL-D3) δ ppm 1.29 (t, J=7.03 Hz, 3 H) 1.33 (d, J=6.15 Hz, 6 H) 3.87-3.94 (m, 2 H) 4.59 (dq, J=6.15, 6.01 Hz, 1 H) 6.39 (s, 1 H) 6.51 (dd, J=4.83, 3.08 Hz, 1 H) 6.63 (dd, J=6.81, 2.86 Hz, 1 H) 6.89 (d, J=8.79 Hz, 2 H) 7.41-7.45 (m, 1 H) 7.49-7.54 (m, 1 H) 7.63 (d, J=8.79 Hz, 2 H) 7.96 (d, J=8.35 Hz, 2 H).

Example 8

4-((5-ethoxy-2-fluoro-3-isopropoxyphenyl)(4-phenyl-1H-imidazol-2-yl)methylamino)benzamidine bis-trifluoroacetic acid salt

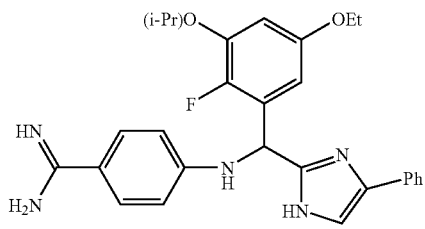

4-phenyl-1-trityl-1H-imidazole (8.1)

To a solution of 4-phenylimidazole (500 mg, 3.47 mmol) in 5 mL DMF, were added TEA (508 μL, 3.64 mmol) and trityl chloride (1.06 g, 3.82 mmol). The mixture was stirred at rt for 15 h, then was poured into 50 mL $H_2O$. The precipitate was collected by filtration and sucked dry, then was suspended in 20 mL $Et_2O$. The suspension was filtered, rinsed with 5 mL $Et_2O$, then vacuum dried to afford 974 mg of Intermediate 8.1 as a white solid.

4-((5-ethoxy-2-fluoro-3-isopropoxyphenyl)(4-phenyl-1-trityl-1H-imidazol-2-yl)methylamino)benzonitrile (8.2)

To a solution of Intermediate 8.1 (100 mg, 0.259 mmol) in 2 mL THF at 0° C., was added BuLi (1.6 M in THF, 178 μL, 0.285 mmol). The mixture was stirred at 0° C. for 20 min, then a solution of Intermediate 7.3 (84 mg, 0.259 mmol) in 0.5 mL THF was added dropwise. The mixture was stirred at 0° C. for 30 min, then was quenched with sat. NH₄Cl. The mixture was diluted with EtOAc, washed with H₂O and brine, dried (Na₂SO₄) and concentrated. The crude product was purified by flash chromatography (0 to 40% EtOAc/hexanes gradient) to afford 141 mg of Intermediate 8.2 as a white solid.

Example 8

A solution of Intermediate 8.2 (130 mg, 0.182 mmol) in 1 mL 3 M NH₂OH in DMSO was converted to the amide oxime, acylated, hydrogenated and then deprotected as in Example 1 to afford after HPLC purification 88.0 mg of Example 8 as a white powder. LCMS (4 min gradient) RT=2.94 min, 488.26 (M+H)⁺; ¹H NMR (400 MHz, METHANOL-D3) δ ppm 1.30-1.35 (m, 9 H) 3.95 (q, J=7.03 Hz, 2 H) 4.62 (ddd, J=12.19, 6.04, 5.93 Hz, 1 H) 6.36 (s, 1 H) 6.48 (dd, J=4.61, 2.86 Hz, 1 H) 6.72 (dd, J=6.81, 2.86 Hz, 1 H) 6.88 (d, J=8.79 Hz, 2 H) 7.41-7.51 (m, 3 H) 7.66-7.73 (m, 4 H) 7.78 (s, 1 H).

Example 9

4-((5-ethoxy-2-fluoro-3-isopropoxyphenyl)(1-methyl-1H-benzo[d]imidazol-2-yl)methylamino)benzamidine bis-trifluoroacetic acid salt

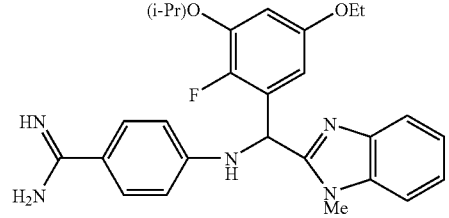

4-((5-ethoxy-2-fluoro-3-isopropoxyphenyl)(1-methyl-1H-benzo[d]imidazol-2-yl)methylamino)benzonitrile (9.1)

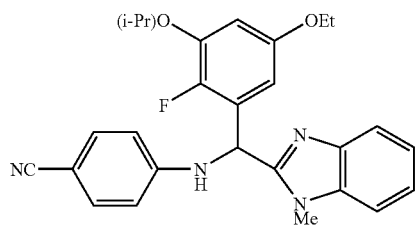

To a solution of N-methyl benzimidazole (50.0 mg, 0.378 mmol) in 2 mL THF at −78° C. was added 1.6 M solution of BuLi in THF (260 μL, 0.416 mmol). The mixture was stirred at −78° C. for 30 min, then a solution of Intermediate 7.3 (123 mg, 0.378 mmol) in 0.6 mL THF was added dropwise. The mixture was stirred and allowed to warm to rt over 3 h, then was quenched with sat. NH₄Cl. The mixture was diluted with EtOAc, washed with H₂O and brine, dried (Na₂SO₄) and concentrated. The crude product was purified by flash chromatography (0 to 50% EtOAc/hexanes gradient) to afford 109 mg of Intermediate 9.1 as a white solid.

Example 9

A solution of Intermediate 9.1 (98 mg, 0.214 mmol) in 1 mL 3 M NH₂OH in DMSO was converted to the amide oxime, acylated and hydrogenated as in Example 1 to afford after HPLC purification 107 mg of Example 9 as a white powder. LCMS (4 min gradient) RT=2.67 min, 476.28 (M+H)⁺; ¹H NMR (400 MHz, METHANOL-D3) δ ppm 1.26-1.35 (m, 9 H) 3.93 (q, J=7.03 Hz, 2 H) 3.94 (s, 3 H) 4.62 (qd, J=6.08, 5.93 Hz, 1 H) 6.48 (dd, J=4.83, 3.08 Hz, 1 H) 6.55 (s, 1 H) 6.73 (dd, J=6.81, 2.86 Hz, 1 H) 6.92 (d, J=9.23 Hz, 2 H) 7.51-7.60 (m, 2 H) 7.67 (d, J=8.79 Hz, 2 H) 7.72 (d, J=7.47 Hz, 1 H) 7.79 (d, J=7.91 Hz, 1 H).

Example 10

4-((1-(benzyloxymethyl)-1H-benzo[d]imidazol-2-yl)(5-ethoxy-2-fluoro-3-isopropoxyphenyl)methylamino)benzamidine bis-trifluoroacetic acid salt

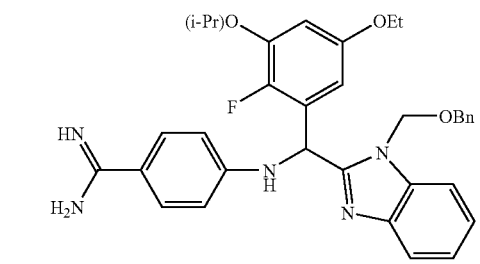

1-(benzyloxymethyl)-1H-benzo[d]imidazole (10.1)

To a solution of benzimidazole (500 mg, 4.23 mmol) in 10 mL DMF at 0° C., was added NaH (60%, 169 mg, 4.23 mmol). The mixture was stirred for 20 min, then BOM-Cl (802 μL, 4.65 mmol) was added. The mixture was stirred at rt for 4 h, then was diluted with EtOAc. The organic phase was washed with H₂O (3×) and brine, dried (Na₂SO₄), filtered through 1" SiO₂ (eluting with EtOAc). The crude product was purified by flash chromatography (30 to 100% EtOAc/hexanes gradient) to afford 453 mg of Intermediate 10.1 as a white crystalline solid.

4-((1-(benzyloxymethyl)-1H-benzo[d]imidazol-2-yl)(5-ethoxy-2-fluoro-3-isopropoxyphenyl)methylamino)benzonitrile (10.2)

To a solution of Intermediate 10.1 (50.0 mg, 0.210 mmol) in 2 mL THF at −78° C. was added 1.6 M solution of BuLi in THF (144 μL, 0.231 mmol). The mixture was stirred at −78° C. for 15 min, then a solution of Intermediate 7.3 (69 mg, 0.210 mmol) in 0.6 mL THF was added dropwise. The mixture was stirred at −78° C. for 30 min, was allowed to warm to rt over 1 h, then was quenched with sat. NH₄Cl. The mixture was diluted with EtOAc, washed with H₂O and brine, dried (Na₂SO₄) and concentrated. The crude product was purified by flash chromatography (0 to 40% EtOAc/hexanes gradient) to afford 95 mg of Intermediate 10.2 as a pale yellow oil.

Example 10

A solution of Intermediate 10.2 (89 mg, 0.158 mmol) in 1 mL 3 M NH$_2$OH in DMSO was converted to the amide oxime, acylated and hydrogenated as in Example 1 to afford after HPLC purification 81 mg of Example 10 as a white powder. LCMS (4 min gradient) RT=3.42 min, 582.23 (M+H)$^+$; $^1$H NMR (400 MHz, METHANOL-D3) δ ppm 1.25-1.31 (m, 11H) 3.87 (q, J=6.88 Hz, 2H) 4.47 (s, 2H) 4.55 (qd, J=6.08, 5.93 Hz, 1 H) 5.73-5.77 (m, 1 H) 5.82-5.86 (m, 1 H) 6.46-6.49 (m, 2 H) 6.62 (dd, J=6.81, 2.86 Hz, 1 H) 6.80 (d, J=8.79 Hz, 2 H) 7.16-7.20 (m, 2H) 7.25-7.29 (m, 3 H) 7.36-7.45 (m, 2 H) 7.58 (d, J=8.79 Hz, 2 H) 7.68 (d, J=7.47 Hz, 2 H).

Example 11

4-((1H-benzo[d]imidazol-2-yl)(5-ethoxy-2-fluoro-3-isopropoxyphenyl)methylamino)benzamidine bis-trifluoroacetic acid salt

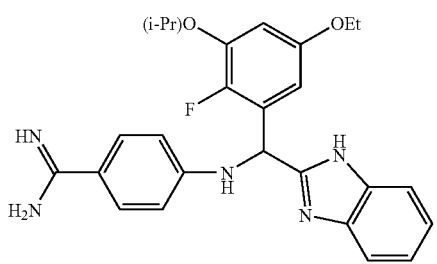

To a solution of Example 10 (59 mg) in 3 mL MeOH with 3 drops conc. HCl, was added 30 mg 10% Pd—C. The mixture was evacuated and flushed with H$_2$ (3×), then was stirred under an atmosphere of H$_2$ for 20 h. The reaction was filtered and concentrated and the resultant crude product was purified by preparative HPLC to afford 40.6 mg of Example 11. LCMS (4 min gradient) RT=2.84 min, 462.27 (M+H)$^+$; $^1$H NMR (400 MHz, METHANOL-D3) δ ppm 1.28-1.34 (m, 9 H) 3.94 (q, J=7.03 Hz, 2 H) 4.61 (qd, J=6.08, 5.93 Hz, 1 H) 6.45 (s, 1 H) 6.51 (dd, J=4.61, 2.86 Hz, 1 H) 6.70 (dd, J=7.03, 2.64 Hz, 1 H) 6.91 (d, J=8.79 Hz, 2 H) 7.45 (dd, J=6.15, 3.08 Hz, 2 H) 7.64-7.68 (m, 4 H).

Example 12

4-((5-ethoxy-2-fluoro-3-isopropoxyphenyl)(1H-tetrazol-5-yl)methylamino)benzamidine trifluoroacetic acid salt

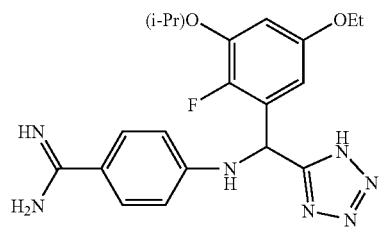

1-(benzyloxymethyl)-1H-tetrazole (12.1)

To a mixture of tetrazole (500 mg, 7.13 mmol) in 14 mL DMF at 0° C. was added NaH (60%, 286 mg, 7.13 mmol). The mixture was stirred at 0° C. for 20 min, then was treated with BOM-Cl (80%, 1.35 mL, 7.84 mmol). The mixture was stirred at rt for 2 h, then was diluted with EtOAc. The organic phase was washed with H$_2$O (3×) and brine, dried (Na$_2$SO$_4$), filtered through 1″ SiO$_2$ and concentrated. The crude product was purified by flash chromatography (0 to 50% EtOAc/hexanes gradient) to afford 483 mg of Intermediate 12.1 as a colorless oil.

4-((1-(benzyloxymethyl)-1H-tetrazol-5-yl)(5-ethoxy-2-fluoro-3-isopropoxyphenyl)methylamino)benzonitrile (12.2)

To a solution of Intermediate 12.1 (50.0 mg, 0.263 mmol) in 2 mL THF at −78° C. was added 1.6 M solution of BuLi in THF (181 μL, 0.289 mmol). The mixture was stirred at −78° C. for 2 min, then a solution of Intermediate 7.3 (86 mg, 0.263 mmol) in 0.6 mL THF was added dropwise. The mixture was stirred at −78° C. for 30 min, was allowed to warm to rt over 1 h, then was quenched with sat. NH$_4$Cl. The mixture was diluted with EtOAc, washed with H$_2$O and brine, dried (Na$_2$SO$_4$) and concentrated. The crude product was purified by flash chromatography (25 to 30% EtOAc/hexanes, stepwise gradient) to afford 33 mg of Intermediate 12.2 as yellow residue.

Example 12

A solution of Intermediate 12.2 (30 mg, 0.058 mmol) in 1 mL 3 M NH$_2$OH in DMSO was converted to the amide oxime, acylated and hydrogenated as in Example 1 to afford after HPLC purification 17 mg of Example 12 as a white powder. LCMS (4 min gradient) RT=2.64 min, 414.29 (M+H)$^+$; $^1$H NMR (400 MHz, METHANOL-D3) δ ppm 1.29-1.33 (m, 9 H) 3.92 (q, J=7.03 Hz, 2 H) 4.58 (qd, J=6.08, 5.93 Hz, 1 H) 6.40 (s, 1 H) 6.49 (dd, J=4.83, 2.64 Hz, 1 H) 6.63 (dd, J=7.03, 3.08 Hz, 1 H) 6.82 (d, J=9.23 Hz, 2 H) 7.62 (d, J=8.79 Hz, 2 H).

Example 13

4-((5-ethoxy-2-fluoro-3-isopropoxyphenyl)(1-methyl-4-phenyl-1H-imidazol-2-yl)methylamino)benzamidine bis-trifluoroacetic acid salt

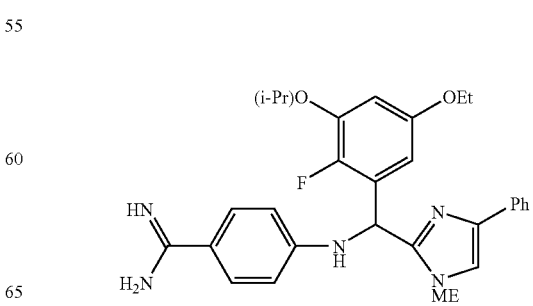

1-methyl-4-phenyl-1H-imidazole (13.1)

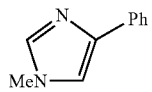

and 1-methyl-5-phenyl-1H-imidazole (13.2)

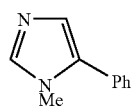

To a solution of 4-phenylimidazole (500 mg, 3.47 mmol) in 10 mL THF at rt, was added 60% NaH (146 mg, 3.64 mmol). The mixture was stirred at rt for 5 min, then iodomethane (238 μL, 3.82 mmol) was added. The mixture was stirred at rt for 30 min, then was diluted with EtOAc. The organic phase was washed with $H_2O$ and brine, dried ($Na_2SO_4$) and concentrated. The crude residue was purified by flash chromatography (column #1: 0 to 10% MeOH/$CH_2Cl_2$ gradient, column #2: 1 to 2 to 5% MeOH/EtOAc, stepwise gradient) to afford 352 mg of Intermediate 13.1 and 166 mg of Intermediate 13.2.

4-((5-ethoxy-2-fluoro-3-isopropoxyphenyl)(1-methyl-4-phenyl-1H-imidazol-2-yl)methylamino)benzonitrile (13.3)

To a solution of Intermediate 13.1 (100 mg, 0.632 mmol) in 3 mL THF at 0° C., was added BuLi (1.6 M in THF, 435 μL, 0.695 mmol). The mixture was stirred at 0° C. for 20 min, then a solution of Intermediate 7.3 (206 mg, 0.632 mmol) in 0.8 mL THF was added dropwise. The mixture was stirred at 0° C. for 30 min and rt for 30 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 40% EtOAc/hexanes gradient) to afford 228 mg of Intermediate 13.3 as a white solid.

Example 13

A solution of Intermediate 13.3 (200 mg, 0.413 mmol) in 1.5 mL 3 M $NH_2OH$ in DMSO was converted to the amide oxime, acylated and hydrogenated as in Example 1 to afford after HPLC purification 137 mg of Example 13 as a pale yellow powder. LCMS (4 min gradient) RT=2.60 min, 502.32 (M+H)$^+$; $^1$H NMR (400 MHz, METHANOL-D3) δ ppm 1.29-1.35 (m, 9 H) 3.83 (s, 3 H) 3.95 (q, J=6.74 Hz, 2 H) 4.62 (dq, J=6.15, 6.01 Hz, 1 H) 6.39-6.40 (m, 1 H) 6.50 (dd, J=4.83, 2.64 Hz, 1 H) 6.73 (dd, J=6.81, 2.86 Hz, 1 H) 6.90 (d, J=8.79 Hz, 2 H) 7.42-7.49 (m, 3H) 7.63-7.72 (m, 4 H) 7.82 (s, 1 H).

Example 14

4-((5-ethoxy-2-fluoro-3-isopropoxyphenyl)(1-methyl-5-phenyl-1H-imidazol-2-yl)methylamino)benzamidine bis-trifluoroacetic acid salt

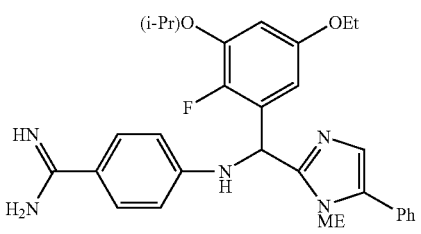

4-((5-ethoxy-2-fluoro-3-isopropoxyphenyl)(1-methyl-5-phenyl-1H-imidazol-2-yl)methylamino)benzonitrile (14.1)

To a solution of Intermediate 13.2 (100 mg, 0.632 mmol) in 3 mL THF at 0° C., was added BuLi (1.6 M in THF, 435 μL, 0.695 mmol). The mixture was stirred at 0° C. for 20 min, then a solution of Intermediate 7.3 (206 mg, 0.632 mmol) in 0.8 mL THF was added dropwise. The mixture was stirred at 0° C. for 30 min and rt 30 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 50% EtOAc/hexanes gradient) to afford 236 mg of Intermediate 14.1 as a white solid.

Example 14

A solution of Intermediate 14.1 (200 mg, 0.413 mmol) in 1.5 mL 3 M $NH_2OH$ in DMSO was converted to the amide oxime, acylated and hydrogenated as in Example 1 to afford after HPLC purification 141 mg of Example 14 as a pale yellow powder. LCMS (4 min gradient) RT=2.48 min, 502.32 (M+H)$^+$; $^1$H NMR (400 MHz, METHANOL-D3) δ ppm 1.32-1.36 (m, 9 H) 3.73 (s, 3 H) 3.94-4.01 (m, 2 H) 4.64 (ddd, J=11.97, 6.15, 6.04 Hz, 1 H) 6.44 (s, 1 H) 6.49 (dd, J=4.61, 2.86 Hz, 1 H) 6.76 (dd, J=7.03, 2.64 Hz, 1 H) 6.92 (d, J=8.79 Hz, 2 H) 7.54-7.59 (m, 6 H) 7.70 (d, J=8.79 Hz, 2 H).

Example 15

4-((5-ethoxy-2-fluoro-3-isopropoxyphenyl)(2-phenyl-1H-imidazol-4-yl)methylamino)benzamidine bis-trifluoroacetic acid salt

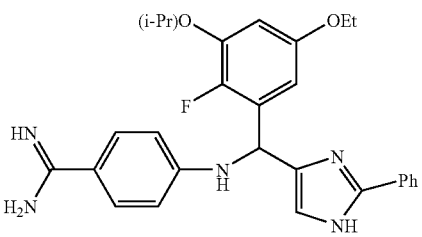

1-(benzyloxymethyl)-2-phenyl-1H-imidazole (15.1)

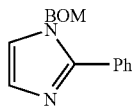

To 2-phenylimidazole (500 mg, 3.47 mmol) in 10 mL THF at 0° C., was added 60% NaH (146 mg, 3.64 mmol). The mixture was stirred at 0° C. for 15 min, then BOM-Cl (80%, 656 µL, 3.82 mmol) was added. The mixture was stirred at rt for 1 h, then was diluted with EtOAc. The organic phase was washed with $H_2O$ and brine, dried ($Na_2SO_4$) and concentrated. The crude product was purified by flash chromatography (0 to 100% EtOAc/hexanes gradient) to afford 630 mg of Intermediate 15.1 as a colorless oil.

4-((1-(benzyloxymethyl)-2-phenyl-1H-imidazol-5-yl)(5-ethoxy-2-fluoro-3-isopropoxyphenyl)methylamino)benzonitrile (15.2)

To a solution of Intermediate 15.1 (100 mg, 0.378 mmol) in 2 mL THF at 0° C., was added sec-BuLi (0.81 M in cyclohexane, 514 µL, 0.416 mmol). The mixture was stirred at 0° C. for 10 min, then a solution of Intermediate 7.3 (123 mg, 0.378 mmol) in 0.6 mL THF was added dropwise. The mixture was stirred at 0° C. for 30 min and rt 1 h, then was quenched with sat. $NH_4Cl$. The mixture was diluted with EtOAc, washed with $H_2O$ and brine, dried ($Na_2SO_4$) and concentrated. The crude product was purified by flash chromatography (0 to 75% EtOAc/hexanes gradient) followed by preparative HPLC purification to afford 53.7 mg of Intermediate 15.2.

Example 15

A solution of Intermediate 15.2 (52 mg) in 1 mL 3 M $NH_2OH$ in DMSO was converted to the amide oxime, acylated and hydrogenated over Pd—C as in Example 1 followed by hydrogenation over $Pd(OH)_2$ to afford after HPLC purification 16.1 mg of Example 15 as an off-white powder. LCMS (4 min gradient) RT=3.15 min, 488.11 (M+H)+; 1H NMR (400 MHz, METHANOL-D3) δ ppm 1.28-1.35 (m, 9 H) 3.89-3.98 (m, 2 H) 4.57-4.64 (m, J=6.15, 6.15, 6.15, 6.15 Hz, 1 H) 6.22 (s, 1 H) 6.55 (dd, J=4.83, 2.64 Hz, 1 H) 6.66 (dd, J=6.81, 2.86 Hz, 1H) 6.85 (d, J=9.23 Hz, 2 H) 7.24 (s, 1 H) 7.62-7.71 (m, 6H) 7.92 (d, J=6.59 Hz, 2 H).

Example 16

4-((5-ethoxy-2-fluoro-3-isopropoxyphenyl)(4-phenylthiazol-2-yl)methylamino)benzamidine trifluoroacetic acid salt

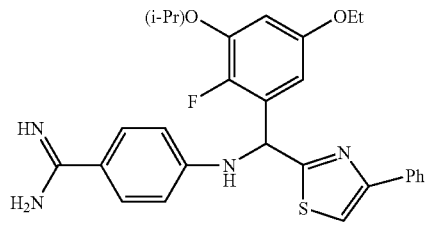

4-((4-bromothiazol-2-yl)(5-ethoxy-2-fluoro-3-isopropoxyphenyl)methylamino)benzonitrile (16.1)

To a solution of 2,4-dibromothiazole (100 mg, 0.412 mmol) in 2 mL THF was added BuLi (1.6 M in THF, 283 µL, 0.453 mmol). The mixture was stirred at −78° C. for 15 min, then a solution of Intermediate 7.3 (134 mg, 0.412 mmol) in 0.6 mL THF was added dropwise. The mixture was stirred at −78° C. for 30 min, was allowed to warm to rt, then was quenched with sat. $NH_4Cl$. The mixture was diluted with EtOAc, washed with $H_2O$ and brine, dried ($Na_2SO_4$) and concentrated. The crude product was purified by flash chromatography (0 to 40% EtOAc/hexanes gradient) followed by preparative HPLC purification to afford 39 mg of Intermediate 16.1.

4-((5-ethoxy-2-fluoro-3-isopropoxyphenyl)(4-phenylthiazol-2-yl)methylamino)benzonitrile (16.2)

To a degassed mixture of Intermediate 16.1 (35 mg, 0.071 mmol), phenylboronic acid (10.4 mg, 0.086 mmol), tri-ortho-tolylphosphine (4.4 mg, 0.014 mmol) and $NaHCO_3$ (24.6 mg, 0.293 mmol) in 2 mL $DME/H_2O$ (3:1), was added $Pd(OAc)_2$. The mixture was stirred at 80° C. for 1 h, then was diluted with EtOAc, washed with $H_2O$ and brine, dried ($Na_2SO_4$) and concentrated. The crude product was purified by flash chromatography to afford 27 mg of Intermediate 16.2 as an oily residue. LCMS (4 min gradient) RT=4.15 min, 488.23 (M+H)+.

Example 16

A solution of Intermediate 16.2 (25 mg) in 1 mL 3 M $NH_2OH$ in DMSO was converted to the amide oxime, acylated and hydrogenated as in Example 1 to afford after HPLC purification 23 mg of Example 16 as a white powder. LCMS (2 min gradient) RT=1.79 min, 505.21 (M+H)+; 1H NMR (400 MHz, METHANOL-D3) δ ppm 1.30 (t, J=7.03 Hz, 3 H) 1.33 (d, J=6.15 Hz, 6 H) 3.91 (q, 2H) 4.59 (dq, J=6.15, 6.01 Hz, 1 H) 6.33 (s, 1H) 6.50 (dd, J=4.61, 2.86 Hz, 1 H) 6.63 (dd, J=6.81, 2.86 Hz, 1 H) 6.87 (d, J=9.23 Hz, 2 H) 7.32 (t, J=7.25 Hz, 1 H) 7.40 (t, J=7.47 Hz, 2 H) 7.63 (d, J=8.79 Hz, 2 H) 7.78 (s, 1 H) 7.90 (d, J=7.03 Hz, 2 H).

Example 17

4-((5-ethoxy-2-fluoro-3-isopropoxyphenyl)(5-phenyl-2H-1,2,4-triazol-3-yl)methylamino)benzamidine trifluoroacetic acid salt

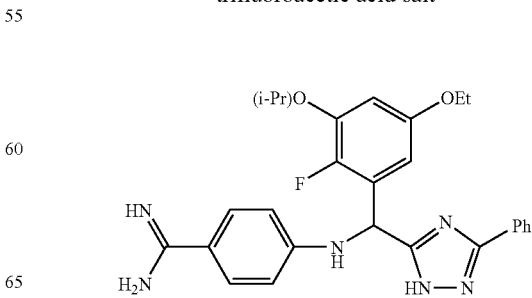

3-phenyl-1H-1,2,4-triazole (17.1)

3-phenyl-1,2,4-triazole-5-thiol (1.80 g, 10.2 mmol) and Raney Ni (rinsed with EtOH 3×, 3 g) in 30 mL EtOH was refluxed for 1.5 h. The mixture was filtered and concentrated. The crude yellow oil was redissolved in EtOAc and filtered through 1" $SiO_2$, then concentrated to afford 1.32 g of Intermediate 17.1 as a white crystalline solid.

1-(benzyloxymethyl)-5-phenyl-1H-1,2,4-triazole (isomer #1) and 1-(benzyloxymethyl)-3-phenyl-1H-1,2,4-triazole (isomer #2, 17.2)

To a solution of Intermediate 17.1 (500 mg, 3.44 mmol) in 10 mL THF at 0° C., was added NaH (60%, 145 mg, 3.62 mmol). The mixture was stirred at 0° C. for 15 min, then was treated with BOM-Cl (80%, 520 µL, 3.78 mmol). The mixture was stirred at rt overnight, then was diluted with EtOAc. The organic phase was washed with $H_2O$ and brine, dried ($Na_2SO_4$) and concentrated. The crude reaction mixture was purified by flash chromatography (0 to 50% EtOAc/hexanes gradient) to afford BOM-protected isomer #1 (117 mg) followed by BOM-protected isomer #2 (199 mg, Intermediate 17.2).

4-((2-(benzyloxymethyl)-5-phenyl-2H-1,2,4-triazol-3-yl)(5-ethoxy-2-fluoro-3-isopropoxyphenyl)methylamino)benzonitrile (17.3)

To a solution of Intermediate 17.2 (50.0 mg, 0.188 mmol) in 2 mL THF at –78° C. was added 1.6 M solution of BuLi in THF (148 µL, 0.207 mmol). The mixture was stirred at –78° C. for 20 min, then a solution of Intermediate 7.3 (61 mg, 0.188 mmol) in 0.5 mL THF was added dropwise. The mixture was stirred and allowed to warm to rt over 30 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 30% EtOAc/hexanes gradient) to afford 72.2 mg of Intermediate 17.3 as a colorless oil.

Example 17

A solution of Intermediate 17.3 (66 mg) in 1 mL 3 M $NH_2OH$ in DMSO was converted to the amide oxime, acylated and hydrogenated as in Example 1 to afford after HPLC purification 45 mg of Example 17 as a white powder. LCMS (2 min gradient) RT=1.83 min, 489.27 (M+H)+; 1H NMR (400 MHz, METHANOL-D3) δ ppm 1.25-1.37 (m, 9 H) 3.92 (q, J=6.74 Hz, 2 H) 4.57 (qd, J=6.08, 5.93 Hz, 1 H) 6.16 (s, 1 H) 6.59 (d, J=6.15 Hz, 2 H) 6.82 (d, J=8.79 Hz, 2 H) 7.47-7.51 (m, 3 H) 7.61 (d, J=8.79 Hz, 2 H) 7.93-8.02 (m, 2 H).

Example 18

4-((5-ethoxy-2-fluoro-3-isopropoxyphenyl)(quinolin-2-yl)methylamino)benzamidine bis-trifluoroacetic acid salt

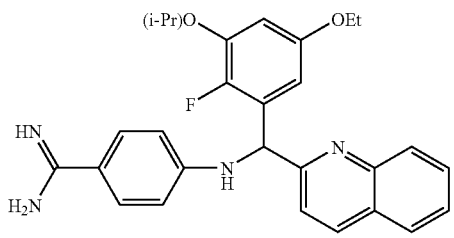

4-((5-ethoxy-2-fluoro-3-isopropoxyphenyl)(quinolin-2-yl)methylamino)benzonitrile (18.1)

To 2-bromoquinoline (50.0 mg, 0.240 mmol) in 2 mL THF at –78° C. was added 1.4 M solution of BuLi in THF (189 µL, 0.264 mmol). The mixture was stirred at –78° C. for 15 min, then a solution of Intermediate 7.3 (78 mg, 0.240 mmol) in 0.5 mL THF was added dropwise. The mixture was stirred –78° C. for 15 min, allowed to warm to rt over 30 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 30% EtOAc/hexanes gradient) to afford 85 mg of Intermediate 18.1 as a white solid.

Example 18

A solution of Intermediate 18.1 (79 mg) in 1 mL 3 M $NH_2OH$ in DMSO was converted to the amide oxime, acylated and hydrogenated as in Example 1 to afford after HPLC purification 75.0 mg of Example 18 as a pale yellow powder. LCMS (2 min gradient) RT=1.78 min, 473.31 (M+H)+; 1H NMR (400 MHz, METHANOL-D3) δ ppm 1.24 (t, J=7.03 Hz, 3 H) 1.32 (dd, J=6.15, 4.39 Hz, 6 H) 3.80-3.87 (m, J=7.03, 6.92, 6.92, 1.98 Hz, 2 H) 4.52-4.59 (m, J=6.15, 6.15, 6.15, 6.15 Hz, 1 H) 6.23 (s, 1 H) 6.43 (dd, J=4.83, 3.08 Hz, 1 H) 6.54 (dd, J=6.81, 2.86 Hz, 1 H) 6.85 (d, J=8.79 Hz, 2 H) 7.54 (d, J=8.79 Hz, 1H) 7.58-7.62 (m, 3H) 7.77-7.81 (m, 1H) 7.92 (d, J=7.91 Hz, 1H) 8.12 (d, J=8.79 Hz, 1 H) 8.31 (d, J=8.35 Hz, 1 H).

Example 19

4-((4,5-diphenyl-1H-imidazol-2-yl)(5-ethoxy-2-fluoro-3-isopropoxyphenyl)methylamino)benzamidine bis-trifluoroacetic acid salt

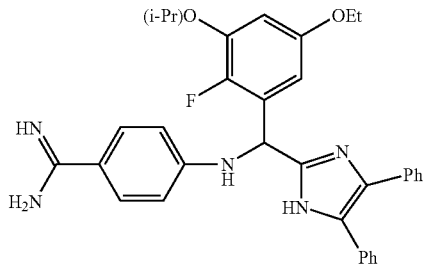

4,5-diphenyl-1-trityl-1H-imidazole (19.1)

To a suspension of 4,5-diphenylimidazole (500 mg, 2.27 mmol) in 5 mL CH$_2$Cl$_2$ at rt were added TEA (348 µL, 2.50 mmol) and trityl chloride (664 mg, 2.38 mmol). The mixture was stirred at rt for 18 h, then was diluted with EtOAc, washed with H$_2$O and brine, dried (Na$_2$SO$_4$) and concentrated. The crude product was purified by flash chromatography (0 to 30% EtOAc/hexanes gradient) to afford 692 mg of Intermediate 19.1 as a pale green solid.

4-((4,5-diphenyl-1-trityl-1H-imidazol-2-yl)(5-ethoxy-2-fluoro-3-isopropoxyphenyl)methylamino)benzonitrile (19.2)

To a solution of Intermediate 19.1 (100 mg, 0.216 mmol) in 3 mL THF at 0° C., was added BuLi (1.4 M in THF, 170 µL, 0.238 mmol). The mixture was stirred at 0° C. for 20 min, then a solution of Intermediate 7.3 (70.5 mg, 0.216 mmol) in 0.5 mL THF was added dropwise. The mixture was stirred at rt for 30 min, then was quenched with sat. NH$_4$Cl. The mixture was diluted with EtOAc, washed with H$_2$O and brine, dried (Na$_2$SO$_4$) and concentrated. The crude product was purified by flash chromatography (0 to 30% EtOAc/hexanes gradient) to afford 96 mg of Intermediate 19.2 as a white solid.

Example 19

A solution of Intermediate 19.2 (84 mg) in 1 mL 3 M NH$_2$OH in DMSO was converted to the amide oxime, acylated, hydrogenated and deprotected as in Example 1 to afford after HPLC purification 19.5 mg of Example 19 as a white powder. LCMS (2 min gradient) RT=1.72 min, 564.25 (M+H)$^+$; $^1$H NMR (400 MHz, METHANOL-D3) δ ppm 1.29-1.36 (m, 9 H) 3.97 (qd, J=6.88, 1.76 Hz, 2 H) 4.62 (qd, J=6.08, 5.93 Hz, 1 H) 6.36 (s, 1 H) 6.57 (dd, J=4.83, 3.08 Hz, 1 H) 6.71 (dd, J=6.81, 2.86 Hz, 1 H) 6.90 (d, J=9.23 Hz, 2 H) 7.41 (s, 10 H) 7.69 (d, J=8.79 Hz, 2 H).

Example 20

4-((5-ethoxy-2-fluoro-3-isopropoxyphenyl)(5-methyl-4-phenyl-1H-imidazol-2-yl)methylamino)benzamidine bis-trifluoroacetic acid salt

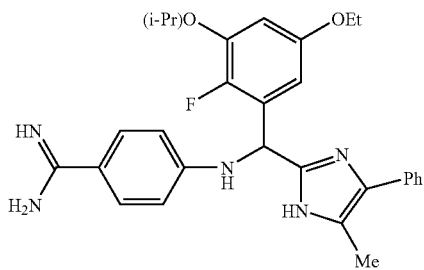

5-methyl-4-phenyl-1-trityl-1H-imidazole (20.1)

To a solution of 4-methyl-5-phenylimidazole (250 mg, 1.58 mmol) in 5 mL DMF at rt, were added TEA (242 µL, 1.74 mmol) and TrCl (485 mg, 1.74 mmol). The mixture was stirred at rt for 20 h, then was diluted with EtOAc, washed with H$_2$O (2×) and brine, dried (Na$_2$SO$_4$) and concentrated. The crude product was purified by flash chromatography (0 to 50% EtOAc/hexanes gradient) to afford 504 mg of Intermediate 20.1 as a white solid.

4-((5-ethoxy-2-fluoro-3-isopropoxyphenyl)(5-methyl-4-phenyl-1-trityl-1H-imidazol-2-yl)methylamino)benzonitrile (20.2)

To a solution of Intermediate 20.1 (100 mg, 0.250 mmol) in 3 mL THF at 0° C., was added BuLi (1.6 M in THF, 172 µL, 0.275 mmol). The mixture was stirred at 0° C. for 20 min, then a solution of Intermediate 7.3 (70.5 mg, 0.216 mmol) in 0.5 mL THF was added dropwise. The mixture was stirred at rt for 30 min, then was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 144 mg of Intermediate 20.2 as an off-white foam.

Example 20

A solution of Intermediate 20.2 (134 mg) in 1 mL 3 M NH$_2$OH in DMSO was converted to the amide oxime, acylated, hydrogenated and deprotected as in Example 1 to afford after HPLC purification 91.4 mg of Example 20 as a white powder. LCMS (2 min gradient) R=1.47 min, 502.27 (M+H)$^+$; $^1$H NMR (400 MHz, METHANOL-D3) δ ppm 1.30-1.36 (m, 9 H) 2.42 (s, 3 H) 3.96 (q, J=6.74 Hz, 2 H) 4.62 (dq, J=6.15, 6.01 Hz, 1 H) 6.33 (s, 1 H) 6.50 (dd, J=4.83, 2.64 Hz, 1 H) 6.72 (dd, J=7.03, 2.64 Hz, 1 H) 6.89 (d, J=8.79 Hz, 2 H) 7.46-7.55 (m, 5 H) 7.69 (d, J=8.79 Hz, 2 H).

Example 21

4-((5-ethoxy-2-fluoro-3-isopropoxyphenyl)(2-phenyl-2H-tetrazol-5-yl)methylamino)benzamidine trifluoroacetic acid salt

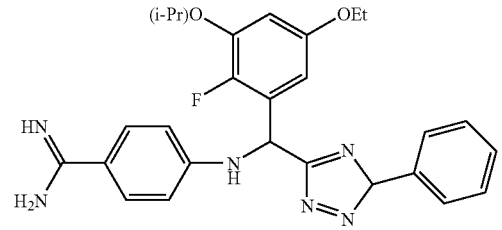

4-((5-ethoxy-2-fluoro-3-isopropoxyphenyl)(2-phenyl-2H-tetrazol-5-yl)methylamino)benzonitrile (21.1)

To a solution of 2-phenyltetrazole (prepared according to the method of Huisgen, R. et al. *Chem. Ber.* 1983, 116, 3027-3038) (50 mg, 0.342 mmol) in 2 mL THF at −78° C. was added 1.4 M solution of BuLi in THF (269 µL, 0.376 mmol). The mixture was stirred at −78° C. for 15 min, then a solution of Intermediate 7.3 (112 mg, 0.342 mmol) in 0.5 mL THF was added dropwise. The mixture was stirred −78° C. for 5 min, allowed to warm to rt over 20 min, then was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 108.5 mg of Intermediate 21.1 as a orange solid.

Example 21

A solution of Intermediate 21.1 (100 mg) in 2 mL 3 M NH$_2$OH in DMSO was converted to the amide oxime, acylated and hydrogenated as in Example 1 to afford after HPLC purification 114 mg of Example 21 as a white powder. LCMS (2 min gradient) RT=1.87 min, 490.3 (M+H)$^+$; $^1$H NMR (400 MHz, METHANOL-D3) δ ppm 1.27-1.35 (m, 9 H) 3.93 (q, J=7.03 Hz, 2 H) 4.57 (qd, J=6.08, 5.93 Hz, 1 H) 6.46 (s, 1 H) 6.60 (dd, J=6.81, 2.86 Hz, 1 H) 6.66 (dd, J=4.83, 3.08 Hz, 1 H) 6.88 (d, J=9.23 Hz, 2 H) 7.54-7.64 (m, 5 H) 8.11 (d, J=8.35 Hz, 2 H) 8.23 (s, 1 H) 8.78 (s, 1 H).

Example 25

N-((5-ethoxy-2-fluoro-3-isopropoxyphenyl)(4-phenyl-1H-imidazol-2-yl)methyl)isoquinolin-6-amine bis-trifluoroacetic acid salt

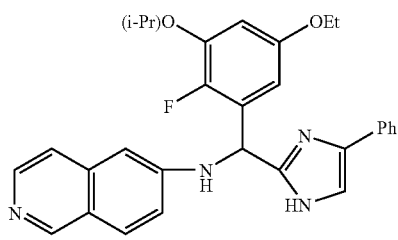

(5-ethoxy-2-fluoro-3-isopropoxyphenyl)(4-phenyl-1-trityl-1H-imidazol-2-yl)methanol (25.1)

To a solution of Intermediate 8.1 (200 mg, 0.517 mmol) in 3 mL THF at 0° C., was added BuLi (1.4 M in THF, 0.406 mL, 0.569 mmol). The mixture was stirred at 0° C. for 25 min, then a solution of Intermediate 7.2 (117 mg, 0.517 mmol) in 1 mL THF was added dropwise. The mixture was stirred at 0° C. for 30 min, then was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 240 mg of Intermediate 25.1 as a colorless solid.

2-(chloro(5-ethoxy-2-fluoro-3-isopropoxyphenyl)methyl)-4-phenyl-1-trityl-1H-imidazole (25.2)

To a solution of Intermediate 25.1 (100 mg, 0.163 mmol) in 2 mL CH$_2$Cl$_2$, were added DMAP (2 mg, cat.), TEA (27 μL, 0.20 mmol) and MsCl (15.2 μL, 0.196 mmol). The mixture was stirred at rt for 30 min, then TEA (27 μL, 0.20 mmol) and MsCl (15.2 μL, 0.196 mmol) were added. The mixture was stirred at rt for 30 min, then was diluted with EtOAc, washed with H$_2$O and brine, dried (Na$_2$SO$_4$) and concentrated. to afford 125 mg of Intermediate 25.2 as a yellow solid, which was used in the following step without further purification.

N-((5-ethoxy-2-fluoro-3-isopropoxyphenyl)(4-phenyl-1-trityl-1H-imidazol-2-yl)methyl)isoquinolin-6-amine (25.3)

To a mixture of Intermediate 25.2 (0.054 mmol) in 1 mL CH$_3$CN at rt, were added DIEA (14 μL, 0.082 mmol) and 6-aminoisoquinoline (15.7 mg, 0.109 mmol). The mixture was stirred at rt for 2 h, then was diluted with EtOAc, washed with H$_2$O and brine, dried (Na$_2$SO$_4$) and concentrated. The crude product was purified by flash chromatography (0 to 100% EtOAc/hexanes gradient) to afford 22.5 mg of Intermediate 25.3 as a yellow solid.

Example 25

A solution of Intermediate 25.3 (22.5 mg) in 1 mL 90% aq. acetic acid was stirred at 60° C. for 0.5 h, then concentrated. The crude residue was purified by preparative HPLC to afford 14.5 mg of Example 25. LCMS (2 min gradient) RT=1.42 min, 497.28 (M+H)$^+$; $^1$H NMR (400 MHz, METHANOL-D3) δ ppm 1.30-1.35 (m, 9 H) 3.96 (q, J=7.03 Hz, 2 H) 4.63 (dq, J=6.15, 6.01 Hz, 1 H) 6.48 (s, 1 H) 6.48-6.50 (m, 1 H) 6.73 (dd, J=7.03, 3.08 Hz, 1 H) 7.03 (d, J=1.76 Hz, 1 H) 7.38 (t, J=7.47 Hz, 1 H) 7.45 (t, J=7.47 Hz, 2 H) 7.54 (dd, J=9.23, 2.20 Hz, 1 H) 7.69 (s, 1 H) 7.71 (d, J=7.03 Hz, 2 H) 7.89 (d, J=7.03 Hz, 1 H) 8.16 (dd, 2 H) 9.17 (s, 1 H).

Example 27

N$^6$-((5-ethoxy-2-fluoro-3-isopropoxyphenyl)(4-phenyl-1H-imidazol-2-yl)methyl)isoquinoline-1,6-diamine bis-trifluoroacetic acid salt

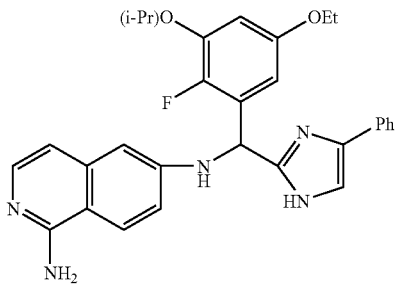

N$^1$-di-(tert-butoxycarbonyl)-N$^6$-((5-ethoxy-2-fluoro-3-isopropoxyphenyl)(4-phenyl-1-trityl-1H-imidazol-2-yl)methyl)isoquinoline-1,6-diamine (27.1)

To a mixture of Intermediate 25.2 (0.065 mmol) in 1 mL CH$_3$CN at rt, were added DIEA (17 μL, 0.098 mmol) and 6-amino-1-di-(tert-butoxycarbonyl)aminoisoquinoline (prepared by heating 1,6-diaminoisoquinoline (WO2004/072101, which is incorporated herein by reference) in neat Boc$_2$O at 130° C.) (47 mg, 0.131 mmol). The mixture was stirred at rt for 14 h, then was diluted with EtOAc, washed with H$_2$O and brine, dried (Na$_2$SO$_4$) and concentrated. The crude product was purified by flash chromatography (0 to 50% EtOAc/hexanes gradient) to afford 45.5 mg of Intermediate 27.1 as a yellow solid. LCMS (2 min gradient) RT=2.30 min, 712.21 (M-CPh$_3$)$^+$.

Alternate procedure of making di-tert-butyl (6-aminoisoquinolin-1-yl)imidodicarbonate

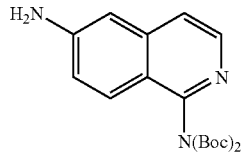

A mixture of 2-methyl-4-nitrobenzonitrile (Aldrich, 5.0 g, 31 mmol) and 1-(1,1-dimethylethoxy)-N,N,N',N'-tetramethyl-methanediamine (Aldrich, 12.2 mL, 59 mmol) in dry DMF (8 mL) was stirred at 70° C. for 2 h under $N_2$. After cooling to rt, DMF was removed in vacuo and the crude product was triturated with hexanes/ethyl acetate (5:1). The solid was collected by filtration and washed with hexane to give (E)-2-(2-(dimethylamino)vinyl)-4-nitrobenzonitrile (6.5 g, 97% yield) as a black solid. $^1$H NMR (400 MHz, $CDCl_3$) δ ppm 2.97 (s, 6 H) 5.36 (d, J=13.18 Hz, 1 H) 7.16 (d, J=13.62 Hz, 1 H) 7.52 (d, J=8.79 Hz, 1 H) 7.60 (m, 1 H) 8.11 (d, J=1.76 Hz, 1 H).

(E)-2-(2-(Dimethylamino)vinyl)-4-nitrobenzonitrile (4.6 g, 21.2 mmol) and 2,4-dimethoxylbenzylamine (4.0 mL, 1.25 equiv) in DMPU (10 mL) were heated at 140° C. for 3 h. The solvent was removed by vacuum distillation and residue was treated with hexanes/ethyl acetate (1:1). The solid was collected by filtration and washed with hexane to give 2-(2,4-dimethoxybenzyl)-6-nitroisoquinolin-1 (2H)-imine (4.6 g). $^1$H NMR (400 MHz, DMSO-$d_6$) δ ppm 3.72 (s, 3 H) 3.81 (s, 3 H) 4.96 (s, 1 H) 6.28 (d, J=6.59 Hz, 1 H) 6.46 (d, J=7.47 Hz, 1 H) 6.58 (d, J=1.76 Hz, 1 H) 7.03 (d, J=8.79 Hz, 1 H) 7.27 (d, J=6.15 Hz, 1 H) 8.02 (dd, J=9.01, 2.42 Hz, 1 H) 8.31 (d, J=2.20 Hz, 1 H) 8.43 (d, J=8.35 Hz, 1 H).

To a solution of 2-(2,4-dimethoxybenzyl)-6-nitroisoquinolin-1(2H)-imine (11.9 g, 35 mmol) in anisole (24 mL) was added TFA (24 mL). The reaction mixture was stirred at 90° C. for 6 h and the solvent was removed under reduced pressure. The residue was suspended in MeOH (30 mL) and then treated with NaOH (1.0 N, 38 mL). The mixture was stirred at rt for 10 min and pH was checked to be 9-10. The precipitate was collected by filtration and washed with water to afford 6-nitroisoquinolin-1-amine (6.0 g). $^1$H NMR (400 MHz, DMSO-$d_6$) δ ppm 7.20 (d, J=5.72 1 H) 7.36 (s, 2 H) 7.95 (d, J=5.72 Hz, 1 H) 8.15 (d, J=9.24, 2.64 Hz, 1 H) 8.43 (d, J=9.24 Hz, 1 H) 8.67 (d, J=2.64 Hz, 1 H).

A solution of 6-nitroisoquinolin-1-amine (25.00 g, 0.132 mol), di-tert-butyl dicarbonate (63.45 g, 0.29 mol) and DMAP (750 mg, catalyst) in DMPU (125 ml) was stirred at 70° C. for 30 min. The reaction was quenched with water (300 ml). The reaction mixture was diluted with ethyl acetate (500 ml) and washed with water. The organic layer was separated and the solvent removed under vacuum. The residue was recrystallized from methanol to give 54.05 g (95.02%) of di-tert-butyl (6-nitroisoquinolin-1-yl)imidodicarbonate as a solid. $^1$H NMR (400 MHz, $CDCl_3$) δ ppm 1.33 (s, 18 H) 7.86 (d, J=5.27 Hz, 1 H) 8.15 (d, J=9.23 Hz, 1 H) 8.39 (dd, J=9.23, 2.20 Hz, 1 H) 8.62 (d, J=5.71 Hz, 1 H) 8.82 (d, J=2.20 Hz, 1 H). LC-MS: 801 (2M+Na)$^+$.

di-tert-butyl (6-nitroisoquinolin-1-yl)imidodicarbonate (75.00 g, 0.193 mol) in methanol/THF (500 ml/500 ml) was hydrogenated with a hydrogen balloon in the presence of Pd/C (5%, 5 g) for 2.0 h. Filtration of the Pd/C and concentration gave a solid, which was recrystallized from methanol to give 65.72 g (94.97%) of di-tert-butyl (6-aminoisoquinolin-1-yl)imidodicarbonate as a white solid. $^1$H NMR (400 MHz, $CDCl_3$) δ ppm 1.33 (m, 18 H) 4.18 (s, 2 H) 6.89 (d, J=2.20 Hz, 1 H) 6.99 (dd, J=9.01, 2.42 Hz, 1 H) 7.35 (d, J=6.59 Hz, 1 H) 7.75 (d, J=8.79 Hz, 1 H) 8.22 (d, J=5.71 Hz, 1 H). LC-MS: 741 (2M+Na)$^+$.

Example 27

A mixture of Intermediate 27.1 (44 mg) in 1 mL EtOAc and 1 mL 4 N HCl/dioxane was stirred at rt for 15 h. The mixture was concentrated, then was purified by preparative HPLC to afford 24.5 mg of Example 27 as a white powder. LCMS (2 min gradient) RT=1.45 min, 512.29 (M+H)$^+$; $^1$H NMR (400 MHz, METHANOL-D3) δ ppm 1.30-1.35 (m, J=6.37, 6.37 Hz, 9 H) 3.96 (q, J=7.03 Hz, 2 H) 4.63 (dq, J=6.15, 6.01 Hz, 1 H) 6.43 (s, 1 H) 6.49 (dd, J=4.83, 3.08 Hz, 1 H) 6.73 (dd, J=7.03, 2.64 Hz, 1 H) 6.87 (d, J=2.20 Hz, 1 H) 6.93 (d, J=7.03 Hz, 1 H) 7.26 (dd, J=9.01, 2.42 Hz, 1 H) 7.36 (d, J=7.03 Hz, 1 H) 7.40-7.50 (m, 3 H) 7.71 (d, J=7.03 Hz, 2 H) 7.76 (s, 1 H) 8.19 (d, J=9.23 Hz, 1 H).

Example 28

4-((5-ethoxy-2-fluoro-3-isopropoxyphenyl)(4-m-tolyl-1H-imidazol-2-yl)methylamino)benzamidine bis-trifluoroacetic acid salt

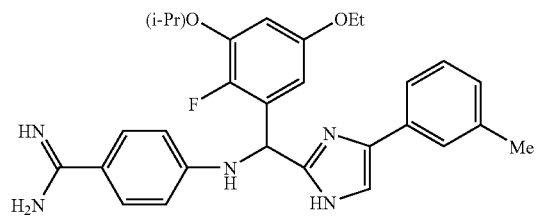

4-((4-bromo-1-trityl-1H-imidazol-2-yl)(5-ethoxy-2-fluoro-3-isopropoxyphenyl)methylamino)benzonitrile (28.1)

To a mixture of 4-bromo-1-triphenylmethyl-imidazole (101 mg, 0.259 mmol) in 3 mL THF at 0° C., was added BuLi (1.6 M in THF, 0.178 mL, 0.285 mmol). The mixture was stirred at 0° C. for 30 min, then a solution of Intermediate 7.2 (84.5 mg, 0.259 mmol) in 0.6 mL THF was added dropwise. The mixture was stirred at 0° C. for 30 min and at rt for 1.5 h, then was quenched with sat. $NH_4Cl$. The mixture was diluted with EtOAc, washed with $H_2O$ and brine, dried ($Na_2SO_4$) and concentrated. The crude product was purified by flash chromatography (0 to 30% EtOAc/hexanes gradient) to afford 91 mg of Intermediate 28.1 as a colorless solid.

4-((5-ethoxy-2-fluoro-3-isopropoxyphenyl)(4-m-tolyl-1-trityl-1H-imidazol-2-yl)methylamino)benzonitrile (28.2)

To a degassed mixture of Intermediate 28.1 (41 mg, 0.057 mmol), m-tolylboronic acid (10.3 mg, 0.0755 mmol), tri-ortho-tolylphosphine (3.8 mg, 0.0.13 mmol) and $NaHCO_3$ (21.7 mg, 0.258 mmol) in 1 mL DME/$H_2O$ (3:1), was added $Pd(OAc)_2$ (1.41 mg, 0.0063 mmol). The mixture was stirred at 80° C. for 1.5 h, then was diluted with EtOAc, washed with H₂O and brine, dried (Na₂SO₄), filtered through a 1" pad of SiO₂ and concentrated to afford 28 mg of Intermediate 28.2 as a colorless solid.

Example 28

A solution of Intermediate 28.2 (27 mg) in 1 mL 3 M NH₂OH in DMSO was converted to the amide oxime, acylated, hydrogenated and deprotected as in Example 1 to afford after HPLC purification 14.5 mg of Example 28 as a white powder. LCMS (4 min gradient) RT=2.88 min, 502.32 (M+H)⁺; ¹H NMR (400 MHz, METHANOL-D3) δ ppm 1.30-1.35 (m, 9 H) 2.39 (s, 3 H) 3.95 (q, J=7.03 Hz, 2 H) 4.62 (dq, J=6.15, 6.01 Hz, 1 H) 6.34 (s, 1 H) 6.48 (dd, J=4.83, 3.08 Hz, 1 H) 6.71 (dd, J=6.81, 2.86 Hz, 1 H) 6.87 (d, J=9.23 Hz, 2 H) 7.25 (d, J=7.47 Hz, 1 H) 7.36 (t, J=7.69 Hz, 1 H) 7.49 (d, J=7.47 Hz, 1 H) 7.54 (s, 1 H) 7.68 (d, J=8.79 Hz, 2 H) 7.74 (s, 1 H).

Example 29

4-((4-bromo-1H-imidazol-2-yl)(5-ethoxy-2-fluoro-3-isopropoxyphenyl)methylamino)benzamidine bis-trifluoroacetic acid salt

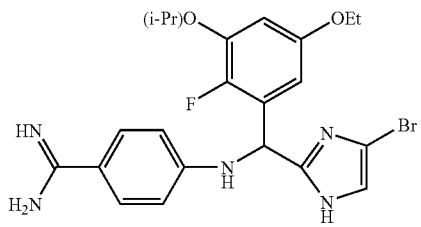

A solution of Intermediate 28.1 (15 mg) in 1 mL 3 M NH₂OH in DMSO was converted to the amide oxime, acylated, hydrogenated and deprotected as in Example 1 to afford after HPLC purification 11 mg of Example 29 as a white powder. LCMS (4 min gradient) RT=2.45 min, 492.17 (M+H)⁺.

Example 53

4-((5-ethoxy-2-fluorophenyl)(4-phenyl-1H-imidazol-2-yl)methylamino)benzamidine bis-trifluoroacetic acid salt

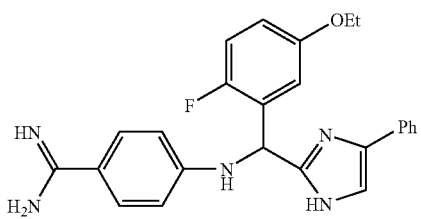

5-ethoxy-2-fluorobenzaldehyde (53.1)

To a solution of 1-ethoxy-4-fluorobenzene (1.1 g, 7.9 mmol) and pentamethyl diethylene triamine (2 mL) in anhydrous THF (6 mL) was added BuLi dropwise (1.38 M, 5.98 mL, 8.3 mmol) at −78° C. After addition, the reaction mixture was warmed up to −40° C. and stirred for 30 min, the reaction mixture was then cooled to −78° C. and DMF (0.7 mL) was added. The solution was warmed to rt, and stirred for 1 h. The reaction mixture was then partitioned between EtOAc and sat. NH₄Cl, the organic layer was dried over (Na₂SO₄), filtered and concentrated. The residue was subjected to chromatographic purification (0-10% EtOAc/hexanes gradient), 600 mg (55%) of Intermediate 53.1 was obtained. ¹H NMR (CDCl₃) δ 1.40 (t, 3H), 4.08 (q, 2H), 6.81 (m, 1H), 7.15 (m, 1H), 7.29 (m, 1H), 10.33 (s, 1H).

(E)-4-(5-ethoxy-2-fluorobenzylideneamino)benzonitrile (53.2)

A mixture of 53.1 (600 mg, 3.6 mmol) and 4-aminobenzonitrile (421 mg, 3.6 mmol) in toluene (50 mL) was refluxed in a Dean-stark apparatus for 4 h. The reaction mixture was the concentrated and the resulted solid was washed with hexane to obtained Intermediate 53.2 (700 mg, 80%). ¹H NMR (CDCl₃) δ 1.42 (t, 3H), 4.08 (q, 2H), 7.05 (m, 2H), 7.27 (d, J=8 Hz, 2H), 7.70 (d, J=8 Hz, 2H), 8.69 (s, 1H).

4-((5-ethoxy-2-fluorophenyl)(4-phenyl-1-trityl-1H-imidazol-2-yl)methylamino)benzonitrile (53.3)

To a solution of 4-phenyl-1-trityl-1H-imidazole (87 mg, 0.2 mmol) in THF was added BuLi (1.38 M, 0.18 mL, 0.3 mmol) at 0° C., the reaction mixture was stirred at 0° C. for 20 min, then a solution of imine Intermediate 53.2 (50 mg, 0.18 mmol) was added, the reaction mixture was stirred at 0° C. for 30 min, then warmed up to rt for 1 h. The reaction mixture was then partitioned between EtOAc and sat. NH₄Cl, the organic layer was dried over (Na₂SO₄), filtered and concentrated. The residue was subject to chromatographic purification (0-40% EtOAc/hexanes gradient), 50 mg (46%) of Intermediate 53.3 was obtained. ¹H NMR (CDCl₃) δ 1.38 (t, 3H), 3.98 (q, 2H), 5.31 (m, 2H), 6.10 (d, J=12 Hz, 2H), 6.99 (s, 1H), 7.05-7.60 (Ar—Hs, 22H), 7.78 (d, J=8 Hz, 2H).

Example 53

According to the procedure for Example 1, Intermediate 53.3 was subjected to amide oxime formation, acylation, hydrogenation and deprotection to afford after HPLC purification 11.3 mg of Example 53. LCMS (2 min gradient) RT=1.30 min, 430.12 (M+H)⁺, ¹H NMR (400 MHz, CD₃OD) δ 1.24 (t, J=7.2 Hz, 3H), 3.89 (q, 2H), 6.27 (s, 1H), 6.79 (d, J=8.8 Hz, 2H), 6.90 (m, 2H), 7.07 (t, J=9.2 Hz, 1H), 7.37 (m, 3H), 7.60 (m, 4H), 7.67 (s, 1H).

Example 54

4-((5-ethoxy-2-fluoro-3-isopropoxyphenyl)(6-phenylpyridin-2-yl)methylamino)benzamidine bis-trifluoroacetic acid salt

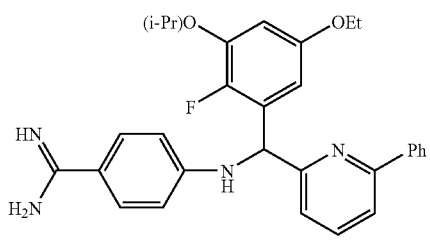

4-((5-ethoxy-2-fluoro-3-isopropoxyphenyl)(6-phenylpyridin-2-yl)methylamino)benzonitrile (54.1)

To a solution of 2-bromo-6-phenylpyridine (32 mg, 0.13 mmol) in anhydrous THF (1.5 mL) was added BuLi dropwise (1.38 M, 0.1 mL, 0.1 mmol) at −78° C. The reaction mixture was stirred at −78° C. for 20 min, then a solution of Intermediate 7.3 (50 mg, 0.13 mmol) was added, and the solution was slowly warmed up to rt over 1 h. The reaction mixture was then partitioned between EtOAc and sat. NH$_4$Cl, the organic layer was dried over (Na$_2$SO$_4$), filtered and concentrated. The residue was subject to chromatographic purification (0-60% EtOAc/hexanes gradient), 40 mg (70%) of Intermediate 54.1 was obtained. $^1$H NMR (CDCl$_3$) δ 1.28 (t, 3H), 1.39 (m, 6H), 3.84 (q, 2H), 4.53 (m, 1H), 6.03 (d, J=4 Hz, 1H), 6.42 (m, 2H), 6.50 (d, J=8 Hz, 1H), 6.68 (d, J=8 Hz, 2H), 6.90 (d, J=8 Hz, 1H), 7.22-7.70 (Ar—Hs, 7H), 8.05 (d, J=8 Hz, 2H).

Example 54

According to the procedure for Example 1, Intermediate 54.1 was subjected to amide oxime formation, acylation and hydrogenation to afford after HPLC purification 5.7 mg of Example 54. LCMS (2 min gradient) RT=1.84 min, 499.19 (M+H)$^+$, $^1$H NMR (400 MHz, CD$_3$OD) δ 1.23 (m, 9H), 3.78 (q, 2H), 4.44 (m, 1H), 6.04 (s, 1H), 6.42 (d, J=5.6 Hz, 1H), 6.74 (d, J=9.2 Hz, 2H), 7.45 (m, 4H), 7.51 (d, J=9.2 Hz, 1H), 7.75 (m, 2H), 7.95 (d, J=7.2 Hz, 2H).

Example 55

4-((4,6-dichlorobenzo[d]thiazol-2-yl)(5-ethoxy-2-fluoro-3-isopropoxyphenyl)methylamino)benzamidine trifluoroacetic acid salt

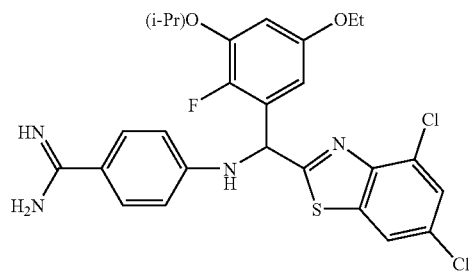

According to the procedure for Example 3, 4,6-dichlorobenzo[d]thiazole afforded after HPLC purification Example 55. LCMS (2 min gradient) RT=1.97 min, 547.01 (M+H)$^+$, $^1$H NMR (400 MHz, CD$_3$OD) δ 1.23 (m, 9H), 3.80 (q, 2H), 4.50 (m, 1H), 6.30 (s, 1H), 6.41 (m, 1H), 6.52 (m, 1H), 6.82 (d, J=8.8 Hz, 1H), 7.55 (m, 3H), 7.88 (s, 1H).

Example 66

4-((5-ethoxy-2-fluoro-3-isopropoxyphenyl)(4-(3-(methylsulfonyl)phenyl)-1H-imidazol-2-yl)methylamino)benzamidine bis-trifluoroacetic acid salt

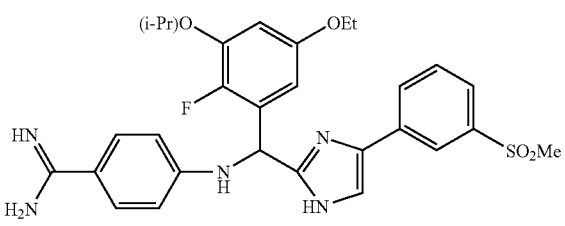

4-((4-bromo-1-trityl-1H-imidazol-2-yl)(5-ethoxy-2-fluoro-3-isopropoxyphenyl)methylamino)-N'-hydroxybenzamidine (66.1)

To a solution of Intermediate 28.1 (2.00 g, 2.8 mmol) in 3M NH$_2$OH in DMSO (6 mL) (prepared according to example 1) was heated at 60° C. for 3 h. The reaction mixture was poured into water and the resultant precipitate was collected by filtration and dried in vacuo to afford Intermediate 66.1, which was used in the following step without purification.

4-((4-bromo-1-trityl-1H-imidazol-2-yl)(5-ethoxy-2-fluoro-3-isopropoxyphenyl)methylamino)-N'-acetoxybenzamidine (66.2)

To a suspension of Intermediate 66.1 in 20 mL EtOAc, was added 0.5 mL Ac$_2$O. The reaction mixture was stirred at rt for 1 h, then was treated with 1 mL MeOH and evaporated to afford Intermediate 66.2, which was used in the following step without further purification.

N-((4-bromo-1-trityl-1H-imidazol-2-yl)(5-ethoxy-2-fluoro-3-isopropoxyphenyl)methyl)-4-(5-methyl-1,2,4-oxadiazol-3-yl)benzenamine (66.3)

To a solution of Intermediate 66.2 in 20 mL THF, was added 1 M TBAF in THF (3 ML). The mixture was stirred at rt for 3 h, then was diluted with EtOAc and washed with water. The organic phase was dried (Na$_2$SO$_4$) and concentrated. The crude product was purified by flash chromatography (0 to 50% EtOAc/hexanes, gradient) to afford Intermediate 66.3. $^1$H NMR (400 MHz, CDCl$_3$) 1.30 (d, J=6.0, 6H), 1.37 (t, J=7.0, 3H), 2.57 (s, 3H), 3.95 (m, 2H), 4.30 (m, 1H), 5.05 (d, J=8.4, 1H), 5.32 (d, J=8.4, 1H), 6.16 (d, J=8.8, 2H), 6.27 (m, 1H), 6.64 (s, 1H), 6.92 (m, 1H), 7.06-7.19 (m, 15H), 7.60 (d, J=8.8, 2H).

N-((5-ethoxy-2-fluoro-3-isopropoxyphenyl)(4-(3-(methylsulfonyl)phenyl)-1-trityl-1H-imidazol-2-yl)methyl)-4-(5-methyl-1,2,4-oxadiazol-3-yl)benzenamine (66.4)

To a degassed mixture of Intermediate 66.3 (48 mg, 0.063 mmol), 3-(methylsulfonyl)phenylboronic acid (16 mg, 0.0755 mmol), tri-ortho-tolylphosphine (3.8 mg, 0.0.13 mmol) and NaHCO₃ (21.7 mg, 0.258 mmol) in 2 mL DME/H2O (3:1), was added Pd(OAc)₂ (1.4 mg, 0.0063 mmol). The mixture was stirred at 80° C. for 1.5 h, then was diluted with EtOAc, washed with H₂O and brine, dried (Na₂SO₄), and concentrated. The crude mixture was purified by flash chromatography (0 to 100% EtOAc/hexanes gradient) to afford 8 mg of Intermediate 66.4 as a colorless solid.

4-((5-ethoxy-2-fluoro-3-isopropoxyphenyl)(4-(3-(methylsulfonyl)phenyl)-1-trityl-1H-imidazol-2-yl)methylamino)benzamidine (66.5)

To a solution of Intermediate 66.4 (8 mg) in 2 mL MeOH/TEA (8:1), was added 10% Pd—C (10 mg). The mixture was degassed and stirred under an atmosphere of H₂ overnight. The mixture was filtered, then concentrated to afford Intermediate 66.5, which was used in the following step without further purification.

Example 66

A mixture of Intermediate 66.5 in 1 mL 90% aq. AcOH was stirred at 60° C. for 1.5 h, then concentrated. The crude material was purified by HPLC to afford after HPLC purification 1.2 mg of Example 66. LCMS (2 min gradient) RT=1.57 min, 566.4(M+H)⁺, ¹H NMR (400 MHz, CD₃OD) δ 1.22 (m, 9H), 3.08 (s, 1H), 3.85 (q, 2H), 4.51 (m, 1H), 6.13 (s, 1H), 6.38 (m, 1H), 6.58 (m, 1H), 6.75 (d, J=8.8 Hz, 2H), 7.57 (m, 3H), 7.67 (s, 1H), 7.80 (d, J=6.6 Hz, 1H), 7.97 (d, J=7.2 Hz, 1H), 8.22 (s, 1H).

Example 68

4-((5-ethoxy-2-fluoro-3-isopropoxyphenyl)(5,6,7,8-tetrahydroquinolin-2-yl)methylamino)benzamidine bis-trifluoroacetic acid salt

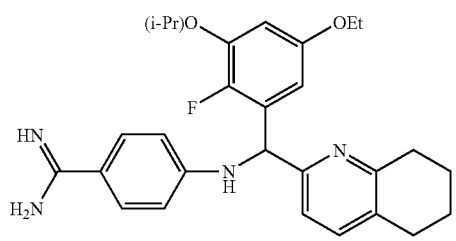

2-bromo-5,6,7,8-tetrahydroquinoline (68.1)

A mixture of 5,6,7,8-tetrahydro-2(1H)-quinolinone (100 mg, 0.670 mmol), P₂O₅ (228 mg, 1.61 mmol) and tetrabutylammonium bromide (259 mg, 0.804 mmol) in 4 mL xylene, was irradiated in a microwave reactor at 220° C. for 1000 s. The mixture was decanted and the rinsed with EtOAc (2×). The combined organic phase was washed with sat. NaHCO₃ and brine, dried (Na₂SO₄) and concentrated to afford 91.6 mg (64%) of Intermediate 68.1 as a light brown oil, which was used without further purification.

4-((5-ethoxy-2-fluoro-3-isopropoxyphenyl)(5,6,7,8-tetrahydroquinolin-2-yl)methylamino)benzonitrile (68.2)

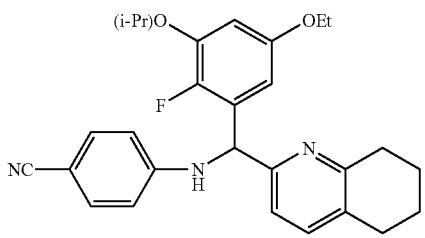

To a solution of 68.1 (91.6 mg, 0.432 mmol) in 2 mL THF at −78° C., was added BuLi (1.4 M in hexanes, 339 μL, 0.475 mmol). The mixture was stirred at −78° C. for 15 min, then a solution of Intermediate 7.3 (141 mg, 0.432 mmol) in 0.6 mL THF was added. The mixture was stirred 5 min at −78° C., allowed to warm to rt over 1 h, then was quenched with sat. NH₄Cl and diluted with EtOAc. The organic phase was washed with H₂O and brine, dried (Na₂SO₄) and concentrated. The crude product was purified by flash chromatography (0 to 30% EtOAc/hexanes gradient) to afford 163.5 mg (70%) of Intermediate 68.2 as a yellow oil.

Example 68

A solution of Intermediate 68.2 (153 mg, 0.333 mmol) in 1 mL 3 M NH₂OH in DMSO was converted to the amide oxime, acylated and hydrogenated as in Example 1 to afford after HPLC purification 37.1 mg of Example 68 as a white powder. LCMS (2 min gradient) RT=1.42 min, 477.4 (M+H)⁺; ¹H NMR (400 MHz, METHANOL-D3) δ ppm 1.27-1.33 (m, 9H) 1.85-1.91 (m, 2H) 1.93-1.99 (m, 2H) 2.89 (t, J=6.15 Hz, 2H) 3.05 (t, J=6.15 Hz, 2H) 3.90 (qd, J=6.96, 2.42 Hz, 2H) 4.58 (dq, J=6.15, 6.01 Hz, 1H) 6.14 (s, 1H) 6.35 (dd, J=4.61, 2.86 Hz, 1H) 6.63 (dd, J=6.81, 2.86 Hz, 1H) 6.80 (d, J=8.79 Hz, 2H) 7.42 (d, J=8.35 Hz, 1H) 7.62 (d, J=9.23 Hz, 2H) 7.93 (d, J=7.91 Hz, 1H).

Example 69

4-((5-ethoxy-2-fluoro-3-isopropoxyphenyl)(4,5,6,7-tetrahydro-1H-benzo[d]imidazol-2-yl)methylamino)benzamidine bis-trifluoroacetic acid salt

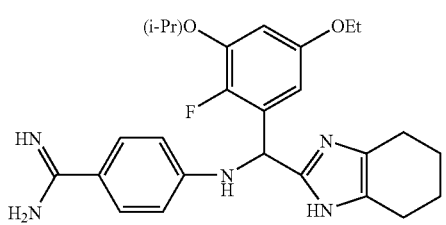

1-trityl-4,5,6,7-tetrahydro-1H-benzo[d]imidazole (69.1)

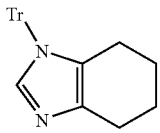

A mixture of 2-chlorocyclohexanone (5.00 g, 37.7 mmol) in 40 mL formamide was stirred at 180° C. for 2.5 h. The mixture was diluted with 150 mL 0.1 N HCl, then was extracted with $CH_2Cl_2$ (3×). The aqueous phase was saturated with $K_2CO_3$(s), then was extracted with THF (5×). The combined organic extract was washed with brine, dried ($Na_2SO_4$) and concentrated to afford a brown oil composed of 4,5,6,7-tetrahydro-1H-benzo[d]imidazole and formamide. The crude product was diluted with 15 mL DMF and treated with triphenylmethylchloride (10.5 g, 37.8 mmol) and TEA (5.52 mL, 39.6 mmol). The mixture was stirred at rt 15 h, then diluted with EtOAc. The organic phase was washed with $H_2O$ (2×) and brine, dried ($Na_2SO_4$) and concentrated. The crude residue was suspended in 30 mL hexanes/$Et_2O$ (3:1), filtered and sucked dry to afford 10.1 g of ~70% pure material. A 2 g portion of this material was purifed by flash chromatography (0-75% EtOAc/hexanes gradient) to afford 1.28 g of Intermediate 69.1.

4-((5-ethoxy-2-fluoro-3-isopropoxyphenyl)(1-trityl-4,5,6,7-tetrahydro-1H-benzo[d]imidazol-2-yl)methylamino)benzonitrile (69.2)

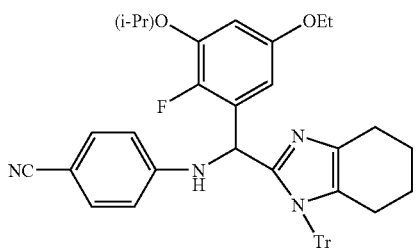

To a solution of Intermediate 69.1 (100 mg, 0.274 mmol) in 2 mL THF at 0° C., was added BuLi (1.4 M in hexanes, 216 μL, 0.302 mmol). The mixture was stirred at 0° C. for 20 min, then a solution of Intermediate 7.3 (89 mg, 0.274 mmol) in 0.6 mL THF was added. The mixture was stirred at rt for 20 min, then was quenched with sat. $NH_4Cl$ and diluted with EtOAc. The organic phase was washed with $H_2O$ and brine, dried ($Na_2SO_4$) and concentrated. The crude product was purified by flash chromatography (0 to 50% EtOAc/hexanes gradient) to afford 110 mg of Intermediate 69.2 as a yellow oil.

Example 69

A solution of Intermediate 69.2 (105 mg, 0.152 mmol) in 1 mL 3 M $NH_2OH$ in DMSO was converted to the amide oxime, acylated, hydrogenated and then deprotected as in Example 1 to afford after HPLC purification 48.3 mg of Example 69 as a white powder. LCMS (2 min gradient) RT=1.37 min, 466.4 (M+H)$^+$; $^1$H NMR (400 MHz, METHANOL-D3) δ ppm 1.30-1.35 (m, 9 H) 1.88 (s, 4 H) 2.61 (s, 4 H) 3.95 (q, J=6.88 Hz, 2 H) 4.58-4.65 (m, J=6.15, 6.15, 6.15, 6.15 Hz, 1 H) 6.29 (s, 1 H) 6.46 (dd, J=4.83, 3.08 Hz, 1 H) 6.71 (dd, J=7.03, 2.64 Hz, 1 H) 6.87 (d, J=8.79 Hz, 2 H) 7.67 (d, J=8.79 Hz, 2 H).

Example 75

4-((5-ethoxy-2-fluoro-3-isopropoxyphenyl)(4-(furan-2-yl)-1H-imidazol-2-yl)methylamino)benzamidine bis-trifluoroacetic acid salt

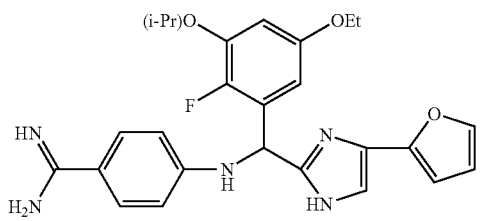

N-((5-ethoxy-2-fluoro-3-isopropoxyphenyl)(4-(furan-2-yl)-1-trityl-1H-imidazol-2yl)methyl)-4-(5-methyl-1,2,4-oxadiazol-3-yl)benzenamine (75.1)

To a mixture of Intermediate 28.1 (30 mg, mmol) and tributyl(furan-2-yl)stannane (30 mg) in 1 mL xylene (degassed) was added $PdCl_2(PPh_3)_2$ (15 mg). The mixture was stirred at reflux for 3 h. The mixture was diluted with EtOAc, washed with $H_2O$ and brine, dried ($Na_2SO_4$) and concentrated to afford Intermediate 75.1.

Example 75

Intermediate 75.1 was subjected to amide oxime formation, acylation, hydrogenation and deprotection as in Example 1 to afford after HPLC purification Example 75. LCMS (2 min gradient) RT=1.33 min, 478.4 (M+H)$^+$, $^1$H NMR (400 MHz, $CD_3OD$) δ 1.32 (m, 9 H), 3.95 (q, 2H), 4.60 (m, 1 H), 6.37 (s, 1H), 6.48 (m, 1H), 6.59 (m, 1H), 6.88 (m, 3H), 7.69 (m, 4H).

Example 76

4-((4-(benzofuran-2-yl)-1H-imidazol-2-yl)(5-ethoxy-2-fluoro-3-isopropoxyphenyl)methylamino)benzamidine bis-trifluoroacetic acid salt

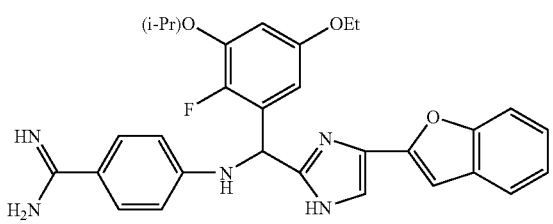

According to the procedure for Example 75, coupling of Intermediate 28.1 with tributyl(benzofuran-3-yl)stannane, followed by amide oxime formation, acylation, hydrogenation and deprotection as in Example 1 to afford after HPLC purification Example 76. LCMS (2 min gradient) RT=1.62 min, 528.3 (M+H)$^+$, $^1$H NMR (400 MHz, $CD_3OD$) δ 1.32 (m, 9H), 3.94 (q, 2H), 4.60 (m, 1H), 6.26 (s, 1H), 6.50 (m, 1H), 6.68 (m, 1H), 6.87 (d, J=8.8 Hz, 2H), 7.13 (s, 1H), 7.22 (t, J=5.6 Hz, 1H), 7.30 (t, J=5.6 Hz, 1H), 7.50 (d, J=7.2 Hz, 1H), 7.60 (d, J=6.8 Hz, 1H), 7.65 (d, J=8.8 Hz, 2H), 7.71 (s, 1H).

Example 77

4-((5-ethoxy-2-fluoro-3-isopropoxyphenyl)(4-(2-(trifluoromethyl)phenyl)-1H-imidazol-2-yl)methylamino)benzamidine bis-trifluoroacetic acid salt

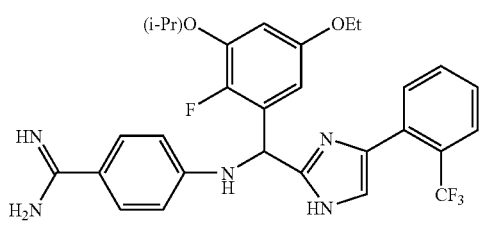

N-((5-ethoxy-2-fluoro-3-isopropoxyphenyl)(4-(2-(trifluoromethyl)phenyl)-1-trityl-1H-imidazol-2-yl)methyl)-4-(5-methyl-1,2,4-oxadiazol-3-yl)benzenamine (77.1)

To a degassed mixture of Intermediate 66.3 (48 mg, 0.062 mmol), 2-trifluoromethylphenylboronic acid (18 mg, 0.093 mmol) and Na₂CO₃ (28 mg, 0.24 mmol) was added Pd(PPh₃)₄ (36 mg, 0.031 mmol). The mixture was stirred at 150° C. for 5 min in a microwave oven, then was diluted with EtOAc, washed with water and brine, dried (Na₂SO₄) and concentrated to afford Intermediate 77.1.

Example 77

Intermediate 77.1 was hydrogenated and then deprotected with aq. AcOH according to the procedure for Example 66 to afford after HPLC purification Example 77. LCMS (2 min gradient) RT=1.42 min, 556.3 (M+H)⁺, ¹H NMR (400 MHz, CD₃OD) δ 1.33 (m, 9H), 3.96 (q, 2H), 4.61 (m, 1H), 6.43 (s, 1H), 6.47 (m, 1H), 6.73 (m, 1H), 6.91 (d, J=8.8 Hz, 2H), 7.61 (m, 2H), 7.69 (d, J=8.8 Hz, 2H), 7.75 (m, 2H), 7.90 (d, J=6.6 Hz, 1H).

The following examples were prepared according to the procedure described in Example 28. Coupling of Intermediate 28.1 with the respective acid indicated in each example, followed by amide oxime formation, acylation, hydrogenation and deprotection as in Example 1 afforded after HPLC purification product.

Example 30

4-((5-ethoxy-2-fluoro-3-isopropoxyphenyl)(4-p-tolyl-1H-imidazol-2-yl)methylamino)benzamidine bis-trifluoroacetic acid salt

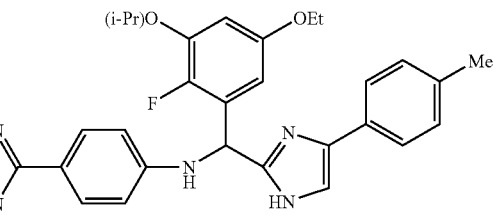

p-tolylboronic acid; LCMS (4 min gradient) RT=2.87 min, 502.32 (M+H)⁺; ¹H NMR (400 MHz, METHANOL-D3) δ ppm 1.30-1.34 (m, 9 H) 2.38 (s, 3H) 3.95 (q, J=7.03 Hz, 2 H) 4.62 (qd, J=6.08, 5.93 Hz, 1H) 6.33 (s, 1 H) 6.47 (dd, J=4.83, 2.64 Hz, 1 H) 6.71 (dd, J=7.03, 3.08 Hz, 1 H) 6.87 (d, J=8.79 Hz, 2 H) 7.30 (d, J=7.91 Hz, 2 H) 7.58 (d, J=8.35 Hz, 2 H) 7.65-7.71 (m, 3 H).

Example 31

4-((5-ethoxy-2-fluoro-3-isopropoxyphenyl)(4-o-tolyl-1H-imidazol-2-yl)methylamino)benzamidine bis-trifluoroacetic acid salt

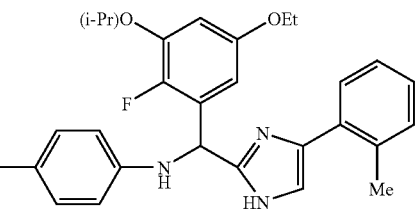

o-tolylboronic acid; LCMS (4 min gradient) RT=2.74 min, 502.27 (M+H)⁺; ¹H NMR (400 MHz, METHANOL-D3) δ ppm 1.30-1.37 (m, 9 H) 2.35 (s, 3H) 3.96 (q, J=7.03 Hz, 2 H) 4.62 (dq, J=6.15, 6.01 Hz, 1 H) 6.38 (s, 1 H) 6.50 (dd, J=4.83, 3.08 Hz, 1 H) 6.72 (dd, J=7.03, 2.64 Hz, 1 H) 6.89 (d, J=8.79 Hz, 2 H) 7.28-7.32 (m, 1 H) 7.34-7.42 (m, 3 H) 7.54 (s, 1 H) 7.69 (d, J=8.79 Hz, 2 H).

Example 32

4-((4-(2,5-dimethylphenyl)-1H-imidazol-2-yl)(5-ethoxy-2-fluoro-3-isopropoxyphenyl)methylamino)benzamidine bis-trifluoroacetic acid salt

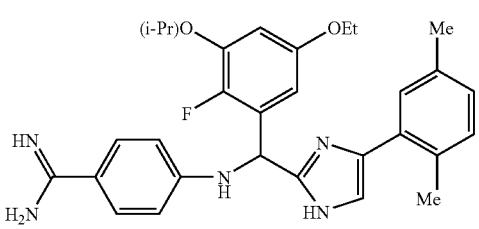

2,5-dimethylphenylboronic acid; LCMS (4 min gradient) RT=2.92 min, 516.27 (M+H)+; 1H NMR (400 MHz, METHANOL-D3) δ ppm 1.30-1.36 (m, 9 H) 2.30 (s, 3 H) 2.33 (s, 3 H) 3.96 (q, J=6.74 Hz, 2 H) 4.62 (dq, J=6.15, 6.01 Hz, 1 H) 6.38 (s, 1 H) 6.48-6.51 (m, 1 H) 6.72 (dd, J=7.03, 2.64 Hz, 1 H) 6.89 (d, J=9.23 Hz, 2 H) 7.19-7.25 (m, 3 H) 7.53 (s, 1 H) 7.69 (d, J=8.79 Hz, 2 H).

Example 33

4-((4-(2-chlorophenyl)-1H-imidazol-2-yl)(5-ethoxy-2-fluoro-3-isopropoxyphenyl)methylamino)benzamidine bis-trifluoroacetic acid salt

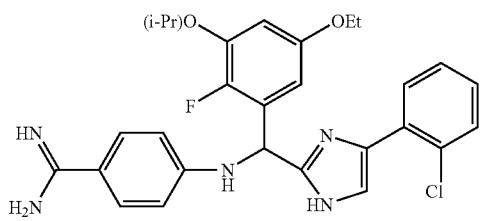

2-chlorophenylboronic acid; LCMS (2 min gradient) RT=1.52 min, 522.04 (M+H)+; 1H NMR (400 MHz, CD3OD) δ 1.22 (m, 9H), 3.85 (q, 2H), 4.52 (m, 1H), 6.23 (s, 1H), 6.40 (m, 1H), 6.60 (m, 1H), 6.80 (d, 2H), 7.30-7.60 (m, 7H).

Example 34

4-((4-(3-chlorophenyl)-1H-imidazol-2-yl)(5-ethoxy-2-fluoro-3-isopropoxyphenyl)methylamino)benzamidine bis-trifluoroacetic acid salt

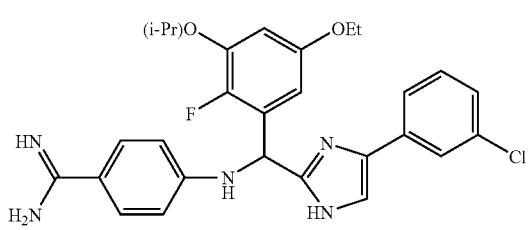

3-chlorophenylboronic acid; LCMS (2 min gradient) RT=1.63 min, 522.11 (M+H)+; 1H NMR (400 MHz, CD3OD) δ 1.22 (m, 9H), 3.85 (q, 2H), 4.51 (m, 1H), 6.21 (s, 1H), 6.40 (m, 1H), 6.60 (m, 1H), 6.78 (d, 2H), 7.30 (m, 2H), 7.50 (m, 3H), 7.70 (d, J=7.0 Hz, 2H).

Example 35

4-((4-(4-chlorophenyl)-1H-imidazol-2-yl)(5-ethoxy-2-fluoro-3-isopropoxyphenyl)methylamino)benzamidine bis-trifluoroacetic acid salt

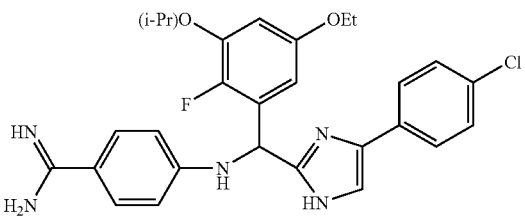

4-chlorophenylboronic acid; LCMS (2 min gradient) RT=1.62 min, 522.07 (M+H)+; 1H NMR (400 MHz, CD3OD) δ 1.22 (m, 9H), 3.85 (q, 2H), 4.51 (m, 1H), 6.20 (s, 1H), 6.38 (m, 1H), 6.78 (d, J=9.0 Hz, 2H), 7.38 (d, J=8.8 Hz, 2H), 7.60 (m, 4H).

Example 36

4-((5-ethoxy-2-fluoro-3-isopropoxyphenyl)(4-(2-methoxyphenyl)-1H-imidazol-2-yl)methylamino) benzamidine bis-trifluoroacetic acid salt

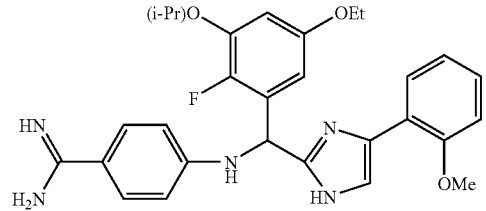

2-methoxyphenylboronic acid; LCMS (2 min gradient) RT=1.44 min, 518.27 (M+H)+; 1H NMR (400 MHz, CD3OD) δ 1.23 (m, 9H), 3.84 (s, 3H), 3.85 (q, 2H), 4.52 (m, 1H), 6.31 (s, 1H), 6.36 (m, 1H), 6.63 (m, 1H), 6.78 (d, J=8.8 Hz, 2H), 6.98 (dd, J=7.4, 8.4 Hz, 1H), 7.09 (d, J=8.4 Hz, 1H), 7.35 (dd, J=7.4, 8.8 Hz, 1H), 7.58 (m, 3H), 7.66 (s, 1H).

Example 37

4-((5-ethoxy-2-fluoro-3-isopropoxyphenyl)(4-(3-methoxyphenyl)-1H-imidazol-2-yl)methylamino) benzamidine bis-trifluoroacetic acid salt

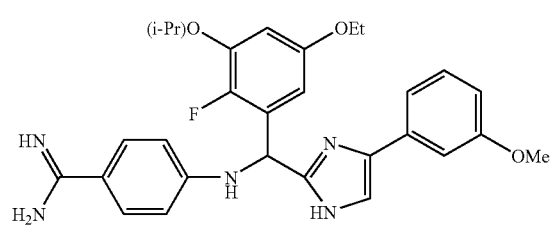

3-methoxyphenylboronic acid; LCMS (2 min gradient) RT=1.45 min, 518.26 (M+H)+; 1H NMR (400 MHz, CD3OD) δ 1.23 (m, 9H), 3.75 (s, 3H), 3.86 (q, 2H), 4.51 (m, 1H), 6.24 (s, 1H), 6.39 (m, 1H), 6.62 (m, 1H), 6.78 (d, J=8.8 Hz, 2H), 6.90 (d, J=8.8 Hz, 1H), 7.18 (d, J=7.9 Hz, 1H), 7.19 (s, 1H), 7.28 (t, J=7.9 Hz, 1H), 7.57 (d, J=8.8 Hz, 1H), 7.66 (s, 1H).

Example 38

4-((5-ethoxy-2-fluoro-3-isopropoxyphenyl)(4-(4-methoxyphenyl)-1H-imidazol-2-yl)methylamino)benzamidine bis-trifluoroacetic acid salt

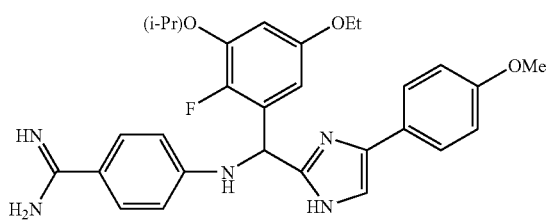

4-methoxyphenylboronic acid; LCMS (2 min gradient) RT=1.42 min, 518.27 (M+H)+; 1H NMR (400 MHz, CD3OD) δ 1.23 (m, 9H), 3.74 (s, 3H), 3.86 (q, 2H), 4.51 (m, 1H), 6.25 (s, 1H), 6.38 (m, 1H), 6.62 (m, 1H), 6.78 (d, J=9.2 Hz, 2H), 6.93 (d, J=9.2 Hz, 2H), 7.55 (m, 4H).

Example 39

4-((5-ethoxy-2-fluoro-3-isopropoxyphenyl)(4-(3-(trifluoromethyl)phenyl)-1H-imidazol-2-yl)methylamino)benzamidine bis-trifluoroacetic acid salt

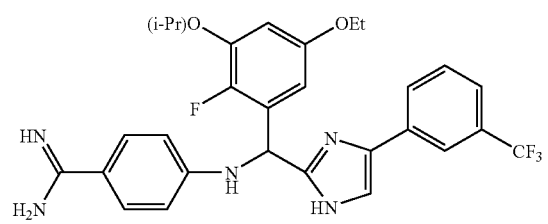

3-trifluorophenylboronic acid; LCMS (2 min gradient) RT=1.60 min, 556.23 (M+H)+; 1H NMR (400 MHz, CD3OD) δ 1.24 (m, 9H), 3.85 (q, 2H), 4.52 (m, 1H), 6.23 (s, 1H), 6.41 (m, 1H), 6.60 (m, 1H), 6.78 (d, J=8.8 Hz, 2H), 7.57 (m, 4H), 7.60 (s, 1H), 7.89 (d, J=7.2 Hz, 1H), 7.99 (s, 1H).

Example 40

4-((5-ethoxy-2-fluoro-3-isopropoxyphenyl)(4-(3-hydroxyphenyl)-1H-imidazol-2-yl)methylamino)benzamidine bis-trifluoroacetic acid salt

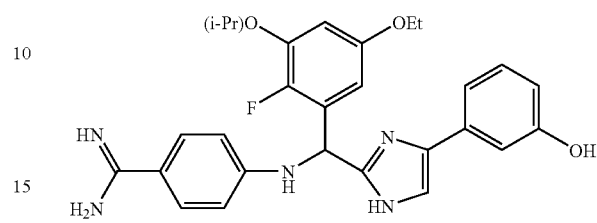

3-hydroxyphenylboronic acid; LCMS (2 min gradient) RT=1.31 min, 504.25 (M+H)+; 1H NMR (400 MHz, CD3OD) δ 1.24 (m, 9H), 3.84 (q, 2H), 4.52 (m, 1H), 6.23 (s, 1H), 6.40 (m, 1H), 6.61 (m, 1H), 6.78 (d, J=9.2 Hz, 2H), 7.50 (t, J=8.0 Hz, 1H), 7.57 (t, J=9.2 Hz, 2H), 7.71 (s, 1H), 7.86 (d, J=7.2 Hz, 1H), 7.95 (d, J=7.2 Hz, 1H), 8.29 (s, 1H).

Example 41

4-((4-(1H-indol-5-yl)-1H-imidazol-2-yl)(5-ethoxy-2-fluoro-3-isopropoxyphenyl)methylamino)benzamidine tris-trifluoroacetic acid salt

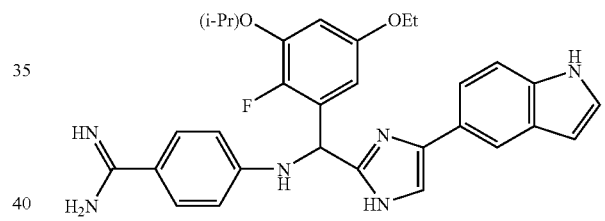

1H-indol-5-ylboronic acid; LCMS (2 min gradient) RT=1.39 min, 527.29 (M+H)+; 1H NMR (400 MHz, CD3OD) δ 1.24 (m, 9H), 3.87 (q, 2H), 4.52 (m, 1H), 6.30 (s, 1H), 6.41 (m, 2H), 6.63 (m, 1H), 6.80 (d, J=8.8 Hz, 2H), 7.23 (d, J=3.0 Hz, 1H), 7.31, 7.40 (d, J=9.2 Hz, 2H), 7.59 (s, 1H), 7.61 (d, J=8.8 Hz, 2H), 7.82 (s, 1H).

Example 42 methyl 3-(2-((4-carbamimidoylphenylamino)(5-ethoxy-2-fluoro-3-isopropoxyphenyl)methyl)-1H-imidazol-4-yl)benzoate bis-trifluoroacetic acid salt

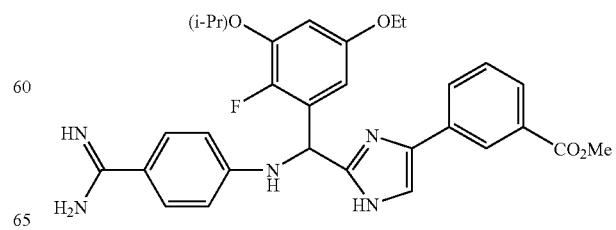

3-(methoxycarbonyl)phenylboronic acid; LCMS (2 min gradient) RT=1.46 min, 546.25 (M+H)+; $^1$H NMR (400 MHz, CD$_3$OD) δ 1.24 (m, 9H), 3.83 (s, 3H), 3.85 (q, 2H), 4.52 (m, 1H), 6.23 (s, 1H), 6.40 (m, 1H), 6.61 (m, 1H), 6.78 (d, J=8.8 Hz, 2H), 7.50 (t, J=8.0 Hz, 1H), 7.58 (d, J=8.8 Hz, 2H), 7.72 (s, 1H), 7.87, 7.94 (d, J=8.0 Hz, 2H), 8.29 (s, 1H).

Example 43 methyl 4-(2-((4-carbamimidoylphenylamino)(5-ethoxy-2-fluoro-3-isopropoxyphenyl)methyl)-1H-imidazol-4-yl)benzoate bis-trifluoroacetic acid salt

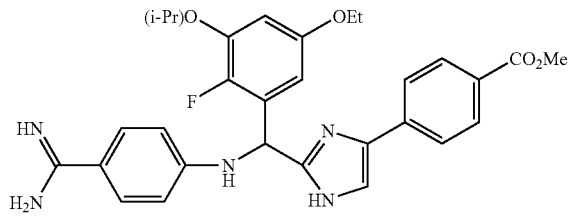

4-(methoxycarbonyl)phenylboronic acid; LCMS (2 min gradient) RT=1.46 min, 546.22 (M+H)+; $^1$H NMR (400 MHz, CD$_3$OD) δ 1.22 (m, 9H), 3.80 (s, 3H), 3.85 (q, 2H), 4.52 (m, 1H), 6.20 (s, 1H), 6.40 (m, 1H), 6.59 (m, 1H), 6.77, 7.57 (d, J=8.8 Hz, 4H), 7.73 (s, 1H), 7.75 (d, J=9.6 Hz, 1H), 7.98 (d, J=9.6 Hz, 2H), 7.72 (s, 1H), 7.87, 7.94 (d, J=8.0 Hz, 2H), 8.00 (s, 1H).

Example 44

4-((5-ethoxy-2-fluoro-3-isopropoxyphenyl)(4-(3-fluorophenyl)-1H-imidazol-2-yl)methylamino)benzamidine bis-trifluoroacetic acid salt

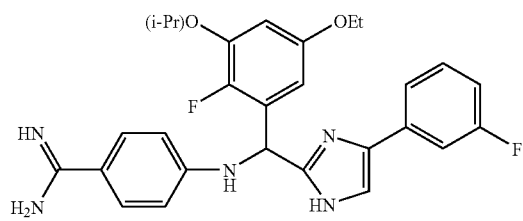

3-fluorophenylboronic acid; LCMS (2 min gradient) RT=1.49 min, 506.25 (M+H)+; $^1$H NMR (400 MHz, CD$_3$OD) δ 1.23 (m, 9H), 3.85 (q, 2H), 4.52 (m, 1H), 6.23 (s, 1H), 6.40 (m, 1H), 6.59 (m, 1H), 6.78, (d, J=8.8 Hz, 2H), 7.03 (dd, J=7.2, 8.0 Hz, 1H), 7.42 (m, 3H), 7.57 (d, J=8.8 Hz, 1H), 7.70 (s, 1H).

Example 45

4-((5-ethoxy-2-fluoro-3-isopropoxyphenyl)(4-(4-fluorophenyl)-1H-imidazol-2-yl)methylamino)benzamidine bis-trifluoroacetic acid salt

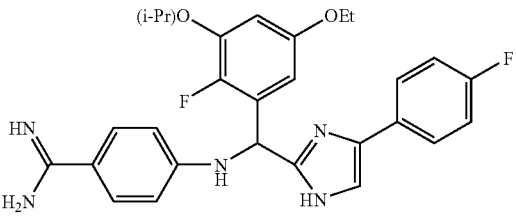

4-fluorophenylboronic acid; LCMS (2 min gradient) RT=1.46 min, 506.25 (M+H)+; $^1$H NMR (400 MHz, CD$_3$OD) δ 1.23 (m, 9H), 3.87 (q, 2H), 4.52 (m, 1H), 6.28 (s, 1H), 6.40 (m, 1H), 6.66 (m, 1H), 6.80 (d, J=8.8 Hz, 2H), 7.15 (t, J=8.8 Hz, 2H), 7.51 (d, J=8.8 Hz, 2H), 7.60 (m, 2H), 7.66 (s, 1H).

Example 46

4-((4-(2,3-dihydrobenzofuran-5-yl)-1H-imidazol-2-yl)(5-ethoxy-2-fluoro-3-isopropoxyphenyl)methylamino)benzamidine bis-trifluoroacetic acid salt

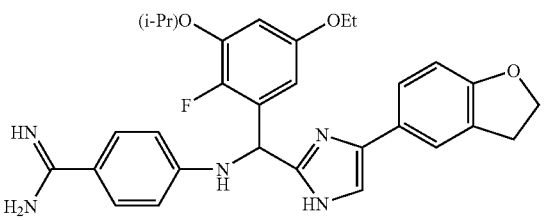

2,3-dihydrobenzofuran-5-ylboronic acid; LCMS (2 min gradient) RT=1.47 min, 530.24 (M+H)+; $^1$H NMR (400 MHz, CD$_3$OD) δ 1.23 (m, 9H), 3.15 (t, J=5.6 Hz, 2H), 3.87 (q, 2H), 4.51 (m, 3H), 6.24 (s, 1H), 6.38 (m, 1H), 6.62 (m, 1H), 6.72 (d, J=8.0 Hz, 1H), 6.78 (d, J=9.2 Hz, 2H), 7.31 (d, J=8.8 Hz, 1H), 7.45, 7.52 (s, 2H), 7.58 (d, J=8.8 Hz, 2H).

Example 47

4-((5-ethoxy-2-fluoro-3-isopropoxyphenyl)(4-(2-hydroxyphenyl)-1H-imidazol-2-yl)methylamino)benzamidine bis-trifluoroacetic acid salt

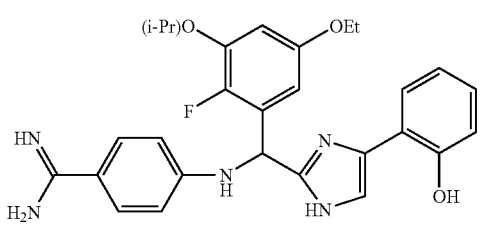

2-hydroxyphenylboronic acid; LCMS (2 min gradient) RT=1.45 min, 504.11 (M+H)+; 1H NMR (400 MHz, CD3OD) δ 1.23 (m, 9H), 3.87 (q, 2H), 4.51 (m, 1H), 6.30 (s, 1H), 6.36 (m, 1H), 6.63 (m, 1H), 6.78 (d, J=8.8 Hz, 2H), 6.86 (m, 2H), 7.18 (t, J=7.0 Hz, 1H), 7.50 (dd, J=7.0, 3.2 Hz, 1H), 7.60 (d, J=8.8 Hz, 2H), 7.70 (s, 1H).

Example 48

4-((5-ethoxy-2-fluoro-3-isopropoxyphenyl)(4-(4-hydroxyphenyl)-1H-imidazol-2-yl)methylamino)benzamidine bis-trifluoroacetic acid salt

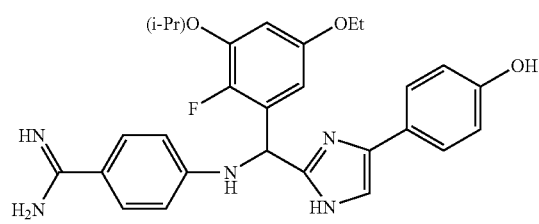

4-hydroxyphenylboronic acid; LCMS (2 min gradient) RT=1.38 min, 504.18 (M+H)+; 1H NMR (400 MHz, CD3OD) δ 1.23 (m, 9H), 3.85 (q, 2H), 4.53 (m, 1H), 6.26 (s, 1H), 6.38 (m, 1H), 6.63 (m, 1H), 6.78 (m, 4H), 7.43 (d, J=8.8 Hz, 1H), 7.54 (s, 1H), 7.58 (d, J=8.8 Hz, 2H).

Example 49

4-(2-((4-carbamimidoylphenylamino)(5-ethoxy-2-fluoro-3-isopropoxyphenyl)methyl)-1H-imidazol-4-yl)benzamide bis-trifluoroacetic acid salt

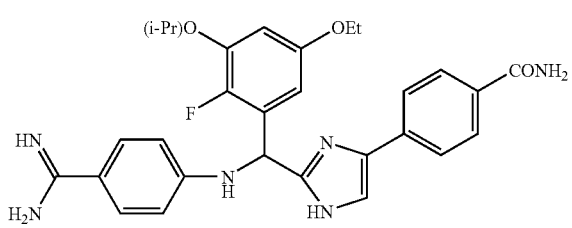

4-carbamoylphenylboronic acid; LCMS (2 min gradient) RT=1.24 min, 531.25 (M+H)+; 1H NMR (400 MHz, CD3OD) δ 1.23 (m, 9H), 3.85 (q, 2H), 4.51 (m, 1H), 6.29 (s, 1H), 6.41 (m, 1H), 6.62 (m, 1H), 6.80, 7.58 (d, J=8.8 Hz, 2H), 7.51, 7.88 (d, J=8.8 Hz, 4H), 7.80 (s, 1H).

Example 50

4-(2-((4-carbamimidoylphenylamino)(5-ethoxy-2-fluoro-3-isopropoxyphenyl)methyl)-1H-imidazol-4-yl)-N-methylbenzamide bis-trifluoroacetic acid salt

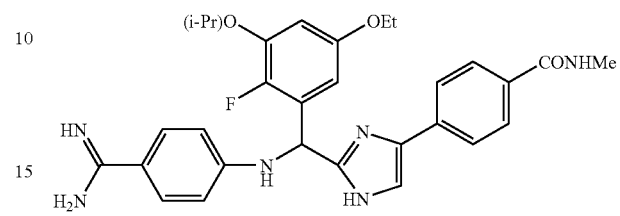

4-(methylcarbamoyl)phenylboronic acid; LCMS (2 min gradient) RT=1.30 min, 545.24 (M+H)+; 1H NMR (400 MHz, CD3OD) δ 1.23 (m, 9H), 2.83 (s, 3H), 3.86 (q, 2H), 4.51 (m, 1H), 6.28 (s, 1H), 6.41 (m, 1H), 6.62 (m, 1H), 6.79, 7.58 (d, J=8.8 Hz, 4H), 7.41, 7.79 (d, J=8.0 Hz, 4H), 7.78 (s, 1H).

Example 51

3-(2-((4-carbamimidoylphenylamino)(5-ethoxy-2-fluoro-3-isopropoxyphenyl)methyl)-1H-imidazol-4-yl)benzamide bis-trifluoroacetic acid salt

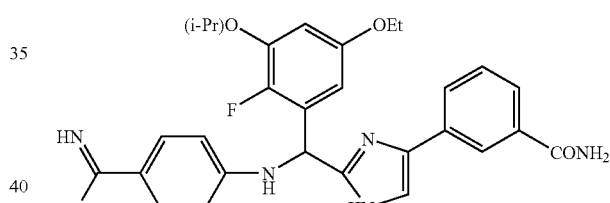

3-carbamoylphenylboronic acid; LCMS (2 min gradient) RT=1.27 min, 531.24 (M+H)+; 1H NMR (400 MHz, CD3OD) δ 1.23 (m, 9H), 3.86 (q, 2H), 4.51 (m, 1H), 6.31 (s, 1H), 6.41 (m, 1H), 6.62 (m, 1H), 6.80, 7.59 (d, J=8.8 Hz, 4H), 7.50 (t, J=5.6 Hz, 1H), 7.78 (s, 1H), 7.81 (m, 2H), 8.15 (s, 1H).

Example 52

3-(2-((4-carbamimidoylphenylamino)(5-ethoxy-2-fluoro-3-isopropoxyphenyl)methyl)-1H-imidazol-4-yl)-N-methylbenzamide bis-trifluoroacetic acid salt

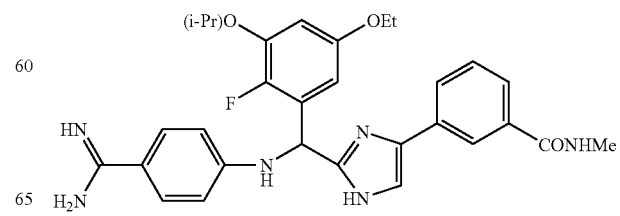

3-(methylcarbamoyl)phenylboronic acid; LCMS (2 min gradient) RT=1.32 min, 545.25 (M+H)+; 1H NMR (400 MHz, CD3OD) δ 1.23 (m, 9H), 2.84 (s, 3H), 3.86 (q, 2H), 4.51 (m, 1H), 6.30 (s, 1H), 6.41 (m, 1H), 6.62 (m, 1H), 6.80, 6.59 (d, J=8.8 Hz, 4H), 7.49 (t, J=5.6 Hz, 1H), 7.76 (m, 3H), 8.09 (s, 1H).

Example 56

N-(3-(2-((4-carbamimidoylphenylamino)(5-ethoxy-2-fluoro-3-isopropoxyphenyl)methyl)-1H-imidazol-4-yl)phenyl)acetamide bis-trifluoroacetic acid salt

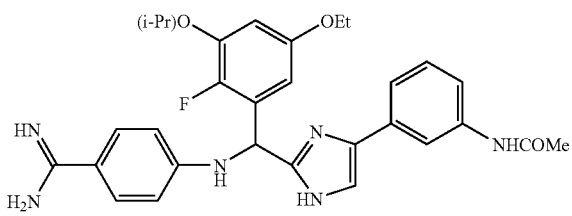

3-acetamidophenylboronic acid; LCMS (5 min gradient) RT=2.51 min, 545.15 (M+H)+; 1H NMR (400 MHz, CD3OD) δ 1.23 (m, 9H), 3.68 (s, 3H), 3.98 (q, 2H), 3.65 (m, 1H), 6.42 (s, 1H), 6.52 (m, 1H), 6.76 (m, 1H), 6.91 (d, J=8.8 Hz, 2H), 7.47 (m, 3H), 7.70 (d, J=8.8 Hz, 2H), 7.80 (s, 1H), 8.13 (s, 1H).

Example 57

4-((4-(2-(benzyloxy)phenyl)-1H-imidazol-2-yl)(5-ethoxy-2-fluoro-3-isopropoxyphenyl)methylamino)benzamidine bis-trifluoroacetic acid salt

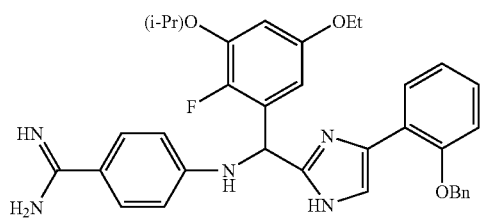

2-benzyloxyphenylboronic acid; LCMS (2 min gradient) RT=1.71 min, 594.31 (M+H)+; 1H NMR (400 MHz, CD3OD) δ 1.22 (m, 9H), 3.84 (q, 2H), 4.52 (m, 1H), 5.14 (s, 2H), 6.26 (s, 1H), 6.52 (m, 1H), 6.61 (m, 1H), 6.75 (d, J=8.8 Hz, 2H), 6.98 (t, J=6.0 Hz, 1H), 7.12-7.60 (m, Ar—H's, 11H).

Example 58

4-((4-(3-(benzyloxy)phenyl)-1H-imidazol-2-yl)(5-ethoxy-2-fluoro-3-isopropoxyphenyl)methylamino)benzamidine bis-trifluoroacetic acid salt

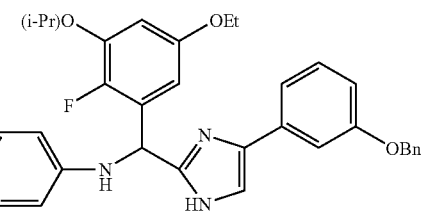

3-benzyloxyphenylboronic acid; LCMS (2 min gradient) RT=1.76 min, 594.31 (M+H)+; 1H NMR (400 MHz, CD3OD) δ 1.22 (m, 9H), 3.97 (q, 2H), 4.62 (m, 1H), 5.15 (s, 2H), 6.42 (s, 1H), 6.52 (m, 1H), 6.71 (m, 1H), 6.92 (d, J=8.8 Hz, 2H), 7.10 (dd, J=6.0, 2.8 Hz, 1H), 7.30-7.50 (m, Ar—H's, 8H), 7.70 (d, J=8.8 Hz, 2H), 7.84 (s, 1H).

Example 59

4-((5-ethoxy-2-fluoro-3-isopropoxyphenyl)(4-(furan-3-yl)-1H-imidazol-2-yl)methylamino)benzamidine bis-trifluoroacetic acid salt

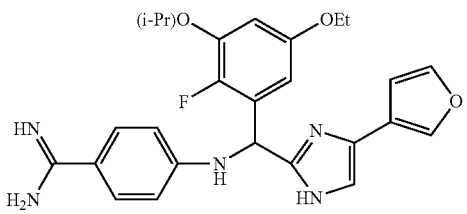

furan-3-ylboronic acid; LCMS (4 min gradient) RT=2.48 min, 478.13 (M+H)+, 1H NMR (400 MHz, CD3OD) δ 1.23 (m, 9H), 3.91 (q, 2H), 4.58 (m, 1H), 6.32 (s, 1H), 6.40 (m, 1H), 6.70 (m, 1H), 6.78 (s, 1H), 6.85, 7.66 (d, J=8.8 Hz, 4H), 7.60 (m, 2H), 7.97 (s, 1H).

Example 61

4-((5-ethoxy-2-fluoro-3-isopropoxyphenyl)(4-(2-(methoxymethyl)phenyl)-1H-imidazol-2-yl)methylamino)benzamidine bis-trifluoroacetic acid salt

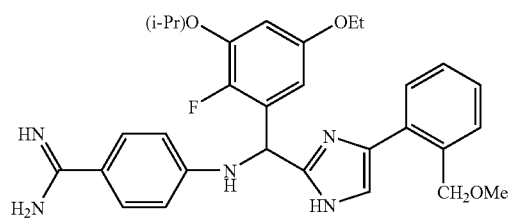

2-(methoxymethyl)phenylboronic acid; LCMS (4 min gradient) RT=2.59 min, 532.15 (M+H)+; 1H NMR (400 MHz, CD3OD) δ 1.23 (m, 9H), 3.80 (q, 2H), 4.36 (s, 3H), 4.50 (m, 1H), 6.26 (s, 1H), 6.30 (m, 1H), 6.60 (m, 1H), 6.78 (d, J=8.8 Hz, 2H), 6.96 (t, J=6.0 Hz, 1H), 7.05 (d, J=6.0 Hz, 1H), 7.30 (t, J=5.6 Hz, 1H), 7.54 (d, J=6.0 Hz, 2H), 7.60 (d, J=8.8 Hz, 1H), 7.63 (s, 1H).

Example 62

4-((5-ethoxy-2-fluoro-3-isopropoxyphenyl)(4-(naphthalen-1-yl)-1H-imidazol-2-yl)methylamino)benzamidine bis-trifluoroacetic acid salt

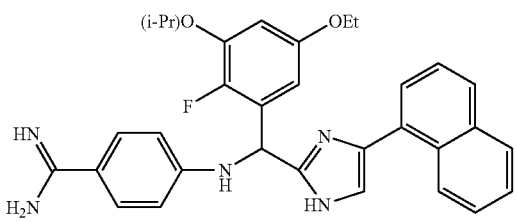

1-naphthylboronic acid; LCMS (2 min gradient) RT=1.58 min, 538.3 (M+H)+; 1H NMR (400 MHz, CD3OD) δ 1.25 (m, 9H), 3.88 (q, 2H), 4.52 (m, 1H), 6.38 (s, 1H), 6.47 (m, 1H), 6.65 (m, 1H), 6.85 (d, J=8.8 Hz, 2H), 7.40-7.60 (m, 4H), 7.60 (s, 1H), 7.61 (d, J=4.4 Hz, 2H), 7.80 (d, J=8.0 Hz, 1H), 7.90 (m, 2H).

Example 63

4-((5-ethoxy-2-fluoro-3-isopropoxyphenyl)(4-(naphthalen-2-yl)-1H-imidazol-2-yl)methylamino)benzamidine bis-trifluoroacetic acid salt

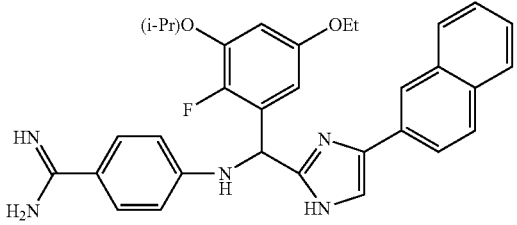

2-naphthylboronic acid; LCMS (2 min gradient) RT=1.67 min, 538.3 (M+H)+; 1H NMR (400 MHz, CD3OD) δ 1.24 (m, 9H), 3.87 (q, 2H), 4.52 (m, 1H), 6.33 (s, 1H), 6.44 (m, 1H), 6.64 (m, 1H), 6.82 (d, J=8.8 Hz, 2H), 7.45 (m, 2H), 7.60 (d, J=8.8 Hz, 2H), 7.70 (d, J=6.6 Hz, 1H), 7.80 (m, 4H), 8.16 (s, 1H).

Example 64

N-(2-(2-((4-carbamimidoylphenylamino)(5-ethoxy-2-fluoro-3-isopropoxyphenyl)methyl)-1H-imidazol-4-yl)phenyl)acetamide bis-trifluoroacetic acid salt

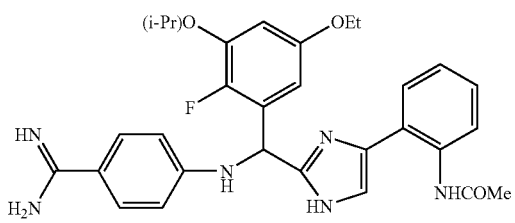

2-acetamidophenylboronic acid; LCMS (2 min gradient) RT=1.35 min, 545.22 (M+H)+; 1H NMR (400 MHz, CD3OD) δ 1.24 (m, 9H), 1.85 (s, 3H), 3.86 (q, 2H), 4.50 (m, 1H), 6.22 (s, 1H), 6.42 (m, 1H), 6.62 (m, 1H), 6.77 (d, J=8.8 Hz, 2H), 7.18 (t, J=5.6 Hz, 1H), 7.30 (t, J=5.6 Hz, 1H), 7.46 (m, 2H), 7.57 (m, 3H).

Example 65

4-((5-ethoxy-2-fluoro-3-isopropoxyphenyl)(4-(2-phenoxyphenyl)-1H-imidazol-2-yl)methylamino)benzamidine bis-trifluoroacetic acid salt

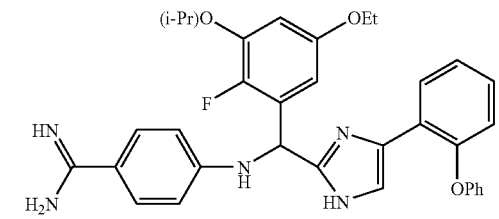

1-phenyloxyphenylboronic acid; LCMS (2 min gradient) RT=1.63 min, 580.3 (M+H)+; 1H NMR (400 MHz, CD3OD) δ 1.22 (m, 9H), 3.82 (q, 2H), 4.50 (m, 1H), 6.23 (s, 1H), 6.30 (m, 1H), 6.60 (m, 1H), 6.74 (d, J=8.8 Hz, 2H), 6.87 (m, 2H), 7.00-7.38 (m, 6H), 7.54 (s, 1H), 7.56 (d, J=4.4 Hz, 1H).

Example 67

4-((5-ethoxy-2-fluoro-3-isopropoxyphenyl)(4-(thiophen-3-yl)-1H-imidazol-2-yl)methylamino)benzamidine bis-trifluoroacetic acid salt

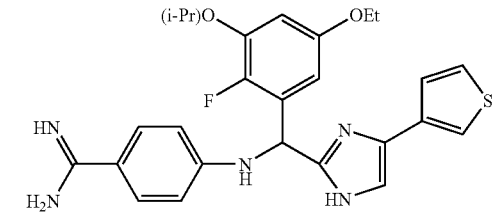

3-thiophenylboronic acid; LCMS (2 min gradient) RT=1.38 min, 494.3 (M+H)+; 1H NMR (400 MHz, CD3OD) δ 1.32 (m, 9H), 3.96 (q, 2H), 4.60 (m, 1H), 6.38 (s, 1H), 6.49 (m, 1H), 6.70 (m, 1H), 6.88 (d, J=8.8 Hz, 4H), 7.46 (m, 1H), 7.60 (m, 1H), 7.67 (d, J=8.8 Hz, 4H), 7.72 (s, 1H), 7.85 (m, 1H).

Example 70

4-((5-ethoxy-2-fluoro-3-isopropoxyphenyl)(4-(biphen-1-yl)-1H-imidazol-2-yl)methylamino)benzamidine bis-trifluoroacetic acid salt

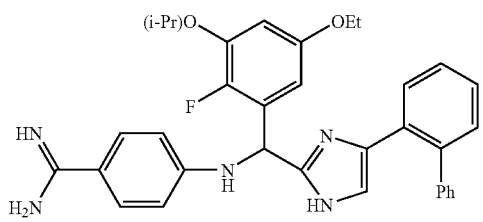

2-biphenylboronic acid; LCMS (2 min gradient) RT=1.62 min, 564.13 (M+H)+; 1H NMR (400 MHz, CD3OD) δ 1.25 (m, 9H), 3.86 (q, 2H), 4.51 (m, 1H), 6.07 (s, 1H), 6.22 (m, 1H), 6.62 (m, 1H), 6.69 (d, J=9.2 Hz, 2H), 6.93 (s, 1H), 7.10 (m, 2H), 7.21 (m, 3H), 7.40 (m, 2H), 7.48 (m, 2H), 7.58 (d, J=8.8 Hz, 2H).

Example 71

4-((5-ethoxy-2-fluoro-3-isopropoxyphenyl)(4-(biphen-2-yl)-1H-imidazol-2-yl)methylamino)benzamidine bis-trifluoroacetic acid salt

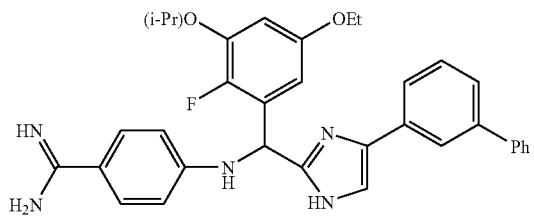

3-biphenylboronic acid; LCMS (2 min gradient) RT=1.71 min, 564.17 (M+H)+; 1H NMR (400 MHz, CD3OD) δ 1.24 (m, 9H), 3.86 (q, 2H), 4.50 (m, 1H), 6.26 (s, 1H), 6.40 (m, 1H), 6.60 (m, 1H), 6.79 (d, J=8.8 Hz, 2H), 7.28 (t, J=5.6 Hz, 1H), 7.36 (m, 2H), 7.46 (t, J=6.0 Hz, 1H), 7.58 (m, 6H), 7.74 (s, 1H), 7.91 (s, 1H).

Example 72

4-((5-ethoxy-2-fluoro-3-isopropoxyphenyl)(4-(2-ethoxyphenyl)-1H-imidazol-2-yl)methylamino)benzamidine bis-trifluoroacetic acid salt

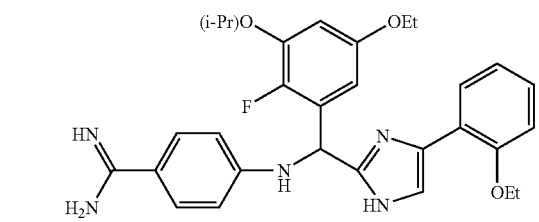

2-ethoxyphenylboronic acid; LCMS (2 min gradient) RT=1.50 min, 532.4 (M+H)+; 1H NMR (400 MHz, CD3OD) δ 1.25 (m, 12H), 3.86 (q, 2H), 4.07 (q, 2H), 4.52 (m, 1H), 6.27 (s, 1H), 6.38 (m, 1H), 6.62 (m, 1H), 6.78 (d, J=8.8 Hz, 2H), 6.96 (t, J=6.0 Hz, 1H), 7.05 (d, J=6.0 Hz, 1H), 7.30 (t, J=6.0 Hz, 1H), 7.54 (d, J=6.0 Hz, 2H), 7.60 (d, J=8.8 Hz, 1H), 7.63 (s, 1H).

Example 73

4-((5-ethoxy-2-fluoro-3-isopropoxyphenyl)(4-(3-ethoxyphenyl)-1H-imidazol-2-yl)methylamino)benzamidine bis-trifluoroacetic acid salt

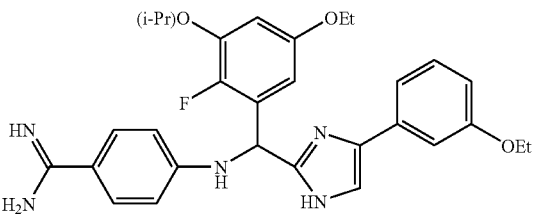

3-ethoxyphenylboronic acid; LCMS (2 min gradient) RT=1.59 min, 532.25 (M+H)+; 1H NMR (400 MHz, CD3OD) δ 1.22 (m, 9H), 1.30 (t, J=6.4 Hz, 3H), 3.85 (q, 2H), 3.99 (q, 2H), 4.51 (m, 1H), 6.25 (s, 1H), 6.38 (m, 1H), 6.63 (m, 1H), 6.78 (d, J=8.8 Hz, 2H), 6.88 (m, 1H), 7.18 (m, 2H), 7.28 (t, J=6.6 Hz, 1H), 7.58 (d, J=8.8 Hz, 1H), 7.68 (d, J=8.8 Hz, 1H).

Example 74

N-(4-(2-((4-carbamimidoylphenylamino)(5-ethoxy-2-fluoro-3-isopropoxyphenyl)methyl)-1H-imidazol-4-yl)phenyl)acetamide bis-trifluoroacetic acid salt

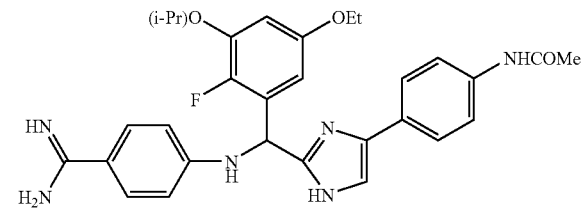

4-acetamidophenylboronic acid; LCMS (2 min gradient) RT=1.35 min, 545.15 (M+H)⁺; ¹H NMR (400 MHz, CD₃OD) δ 1.23 (m, 9H), 2.04 (s, 3H), 3.86 (q, 2H), 4.53 (m, 1H), 6.25 (s, 1H), 6.38 (m, 1H), 6.62 (m, 1H), 6.78 (d, J=8.8 Hz, 2H), 7.50-7.70 (m, 5H).

Example 79

4-((5-ethoxy-2-fluoro-3-isopropoxyphenyl)(4-(3-ethylphenyl)-1H-imidazol-2-yl)methylamino)benzamidine bis-trifluoroacetic acid salt

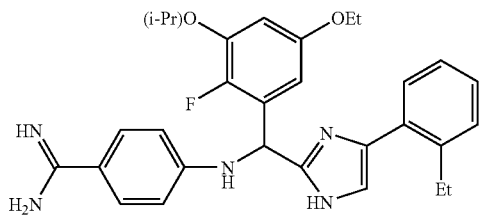

2-ethylphenylboronic acid; LCMS (2 min gradient) RT=1.45 min, 516.4 (M+H)⁺; ¹H NMR (400 MHz, CD₃OD) δ 1.11 (t, J=6.6 Hz, 3H), 1.34 (m, 9H), 2.66 (q, 2H), 3.94 (q, 2H), 4.62 (m, 1H), 6.41 (s, 1H), 6.49 (m, 1H), 6.72 (m, 1H), 6.91 (d, J=8.8 Hz, 2H), 7.38 (m, 4H), 7.55 (s, 1H), 7.70 (d, J=8.8 Hz, 2H).

The following examples were prepared according to the procedure described in Example 77. Coupling of Intermediate 66.3 with the respective acid indicated in each example, followed by hydrogenation and deprotection as in Example 66 afforded after HPLC purification product.

Example 78

4-((5-ethoxy-2-fluoro-3-isopropoxyphenyl)(4-(3-(methylsulfonamido)phenyl)-1H-imidazol-2-yl)methylamino)benzamidine bis-trifluoroacetic acid salt

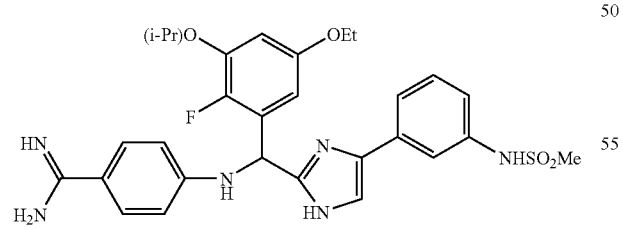

3-(methylsulfonamido)phenylboronic acid; LCMS (2 min gradient) RT=1.30 min, 581.4 (M+H)⁺; ¹H NMR (400 MHz, CD₃OD) δ 1.32 (m, 9H), 3.29 (s, 1H), 3.94 (q, 2H), 4.61 (m, 1H), 6.27 (s, 1H), 6.47 (m, 1H), 6.68 (m, 1H), 6.85 (d, J=8.8 Hz, 2H), 7.22 (m, 1H), 7.45 (m, 2H), 7.70 (m, 2H), 7.66 (d, J=8.8 Hz, 2H).

Example 81

4-((4-(2-(dimethylamino)phenyl)-1H-imidazol-2-yl)(5-ethoxy-2-fluoro-3-isopropoxyphenyl)methylamino)benzamidine tris-trifluoroacetic acid salt

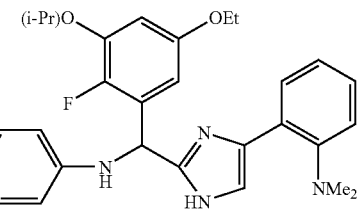

2-(dimethylamino)phenylboronic acid; LCMS (4 min gradient) RT=2.36 min, 531.5 (M+H)⁺; ¹H NMR (400 MHz, CD₃OD) δ 1.32 (t, J=6.81 Hz, 3 H) 1.36 (dd, J=6.15, 2.64 Hz, 6 H) 3.02 (s, 6 H) 3.94 (m, J=7.03, 7.03 Hz, 2 H) 4.66 (m, 1 H) 6.28 (s, 1 H) 6.55 (dd, J=4.83, 2.64 Hz, 1 H) 6.72 (dd, J=6.59, 2.64 Hz, 1 H) 6.89 (d, J=8.79 Hz, 2 H) 7.48 (m, 2 H) 7.66 (d, J=8.79 Hz, 2 H) 7.75 (d, J=7.91 Hz, 1 H) 7.88 (m, 2 H).

Example 82

4-((5-ethoxy-2-fluoro-3-isopropoxyphenyl)(4-(2-(hydroxymethyl)phenyl)-1H-imidazol-2-yl)methylamino)benzamidine bis-trifluoroacetic acid salt

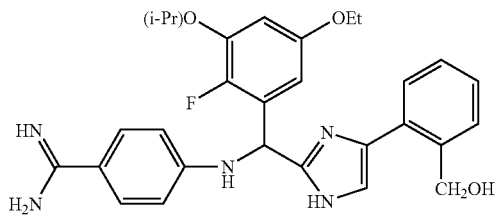

2-(hydroxymethyl)phenylboronic acid; LCMS (2 min gradient) RT=1.30 min, 518.4 (M+H)⁺; ¹H NMR (400 MHz, CD₃OD) δ 1.33 (m, 9 H) 3.97 (q, J=7.03 Hz, 2 H) 4.55 (d, J=2.64 Hz, 2 H) 4.62 (m, 1 H) 6.42 (s, 1 H) 6.52 (dd, J=4.61, 2.86 Hz, 1 H) 6.72 (dd, J=7.03, 2.64 Hz, 1 H) 6.91 (d, J=8.79 Hz, 2 H) 7.47 (m, 3 H) 7.59 (m, 1 H) 7.69 (d, J=8.79 Hz, 2 H) 7.75 (s, 1 H).

Example 83

4-((5-ethoxy-2-fluoro-3-isopropoxyphenyl)(4-(4-(hydroxymethyl)phenyl)-1H-imidazol-2-yl)methylamino)benzamidine bis-trifluoroacetic acid salt

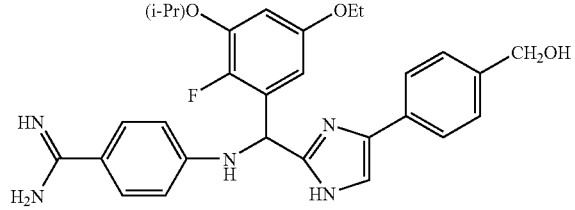

4-(hydroxymethyl)phenylboronic acid; LCMS (2 min gradient) RT=1.55 min, 518.5 (M+H)⁺; ¹H NMR (400 MHz, CD₃OD) δ 1.32 (t, J=5.71 Hz, 9 H) 3.96 (q, J=7.03 Hz, 2 H) 4.63 (m, 3 H) 6.34 (s, 1 H) 6.48 (dd, J=4.61, 2.86 Hz, 1 H) 6.71 (dd, J=6.81, 2.86 Hz, 1 H) 6.88 (d, J=8.79 Hz, 2 H) 7.49 (m, 2 H) 7.70 (m, 5 H).

Example 84

4-((4-(2,6-dimethylphenyl)-1H-imidazol-2-yl)(5-ethoxy-2-fluoro-3-isopropoxyphenyl)methylamino)benzamidine bis-trifluoroacetic acid salt

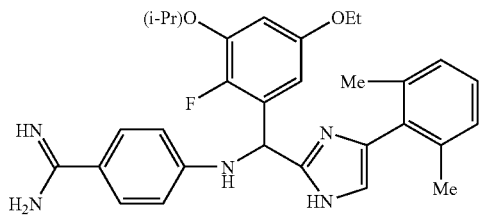

2,6-dimethylphenylboronic acid; LCMS (2 min gradient) RT=1.38 min, 516.5 (M+H)⁺; ¹H NMR (400 MHz, CD₃OD) δ 1.34 (m, 9 H) 2.14 (s, 6 H) 3.96 (q, J=7.03 Hz, 2 H) 4.63 (m, 1 H) 6.41 (s, 1 H) 6.49 (dd, J=4.61, 2.86 Hz, 1 H) 6.73 (dd, J=6.81, 2.86 Hz, 1 H) 6.91 (d, J=9.23 Hz, 2 H) 7.17 (d, J=7.91 Hz, 2 H) 7.29 (m, 1 H) 7.48 (s, 1 H) 7.70 (d, J=8.79 Hz, 2 H).

Example 85

4-((5-ethoxy-2-fluoro-3-isopropoxyphenyl)(4-(3-isopropoxyphenyl)-1H-imidazol-2-yl)methylamino)benzamidine bis-trifluoroacetic acid salt

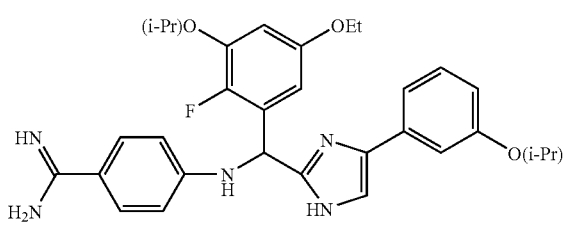

3-isopropoxyphenylboronic acid; LCMS (4 min gradient) RT=3.13 min, 546.4 (M+H)⁺; ¹H NMR (400 MHz, CD₃OD) δ 1.05 (t, J=7.47 Hz, 6 H) 1.33 (m, 6 H) 1.81 (m, 3 H) 3.97 (m, 3 H) 4.62 (m, 1 H) 6.38 (s, 1 H) 6.49 (dd, J=4.61, 2.86 Hz, 1 H) 6.72 (dd, J=6.81, 2.86 Hz, 1 H) 6.89 (d, J=9.23 Hz, 2 H) 7.00 (dd, J=8.35, 2.20 Hz, 1 H) 7.28 (m, 2 H) 7.39 (t, J=7.91 Hz, 1 H) 7.82 (s, 1 H).

Example 86

4-((5-ethoxy-2-fluoro-3-isopropoxyphenyl)(4-(2-isopropoxyphenyl)-1H-imidazol-2-yl)methylamino)benzamidine bis-trifluoroacetic acid salt

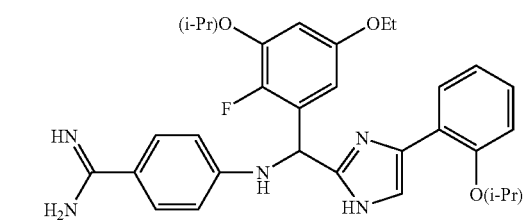

2-isopropoxyphenylboronic acid; LCMS (4 min gradient) RT=2.85 min, 546.4 (M+H)⁺; ¹H NMR (400 MHz, CD₃OD) δ 1.34 (m, 15 H) 3.95 (q, J=6.88 Hz, 2 H) 4.65 (m, 2 H) 6.37 (s, 1 H) 6.49 (s, 1 H) 6.70 (d, J=3.95 Hz, 1 H) 6.88 (d, J=8.79 Hz, 2 H) 6.95 (d, J=8.35 Hz, 1 H) 7.25 (d, J=8.35 Hz, 2 H) 7.36 (t, J=7.69 Hz, 1 H) 7.70 (m, 3 H).

Example 87

4-((5-ethoxy-2-fluoro-3-isopropoxyphenyl)(4-(3-(trifluoromethoxy)phenyl)-1H-imidazol-2-yl)methylamino)benzamidine bis-trifluoroacetic acid salt

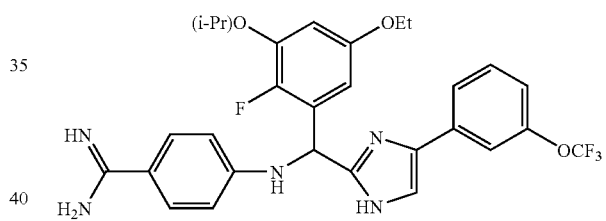

3-(trifluoromethoxy)phenylboronic acid; LCMS (4 min gradient) RT=3.13 min, 572.4 (M+H)⁺; ¹H NMR (400 MHz, CD₃OD) δ 1.32 (m, 9 H) 3.96 (q, J=7.03 Hz, 2 H) 4.62 (m, 1 H) 6.37 (s, 1 H) 6.50 (dd, J=4.83, 3.08 Hz, 1 H) 6.72 (dd, J=6.81, 2.86 Hz, 1 H) 6.89 (d, J=8.79 Hz, 2 H) 7.36 (d, J=8.35 Hz, 1 H) 7.59 (t, J=7.91 Hz, 1 H) 7.71 (m, 4 H) 7.90 (s, 1 H).

Example 88

4-((4-(2-cyanophenyl)-1H-imidazol-2-yl)(5-ethoxy-2-fluoro-3-isopropoxyphenyl)methylamino)benzamidine bis-trifluoroacetic acid salt

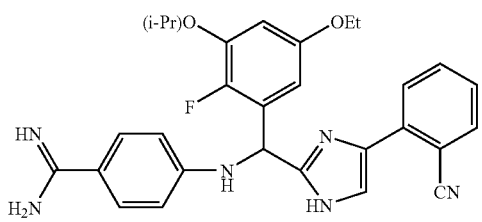

2-cyanophenylboronic acid; LCMS (2 min gradient) RT=1.38 min, 513.5 (M+H)+; 1H NMR (400 MHz, CD3OD) δ 1.35 (m, 9 H) 3.96 (m, 2 H) 4.59 (m, 1 H) 6.17 (s, 1 H) 6.49 (dd, J=4.83, 3.08 Hz, 1 H) 6.63 (dd, J=6.81, 2.86 Hz, 1 H) 6.82 (d, J=8.79 Hz, 2 H) 7.63 (m, 2 H) 7.74 (m, 3 H) 7.92 (m, 2 H).

Example 89

4-((5-ethoxy-2-fluoro-3-isopropoxyphenyl)(4-(2-isopropylphenyl)-1H-imidazol-2-yl)methylamino)benzamidine bis-trifluoroacetic acid salt

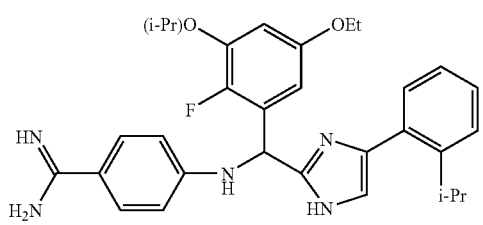

2-isopropylphenylboronic acid; LCMS (2 min gradient) RT=1.46 min, 530.4 (M+H)+; 1H NMR (400 MHz, CD3OD) δ 1.18 (dd, J=14.94, 7.03 Hz, 6 H) 1.35 (m, 9 H) 3.03 (t, J=7.03 Hz, 1 H) 3.96 (q, J=7.03 Hz, 2 H) 4.62 (m, 1 H) 6.35 (s, 1 H) 6.49 (dd, J=4.61, 2.86 Hz, 1 H) 6.71 (dd, J=6.81, 2.86 Hz, 1 H) 6.89 (d, J=8.79 Hz, 2 H) 7.29 (m, 2 H) 7.41 (s, 1 H) 7.47 (m, 2 H) 7.69 (d, J=8.79 Hz, 2 H).

Example 90

4-((6-chloroquinolin-2-yl)(5-ethoxy-2-fluoro-3-isopropoxyphenyl)methylamino)benzamidine bis-trifluoroacetic acid salt

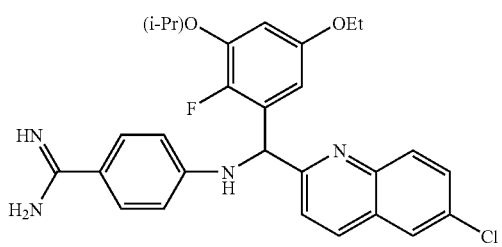

2-bromo-6-chloroquinoline (90.1)

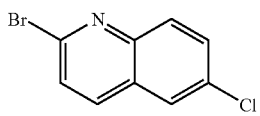

A mixture of 6-chloro-2-hydroxyquinolinone (200 mg, 1.11 mmol), P2O5 (383 mg, 2.67 mmol) and tetrabutylammonium bromide (429 mg, 1.33 mmol) in 4 mL xylene, was irradiated in a microwave reactor at 220° C. for 1000 s. The mixture was decanted and the rinsed with EtOAc (2×). The combined organic phase was washed with sat. NaHCO3 and brine, dried (Na2SO4), filtered through a 1" pad of silica gel and concentrated to afford 225 mg (83%) of Intermediate 90.1 as an off-white solid, which was used without further purification.

4-((6-chloroquinolin-2-yl)(5-ethoxy-2-fluoro-3-isopropoxyphenyl)methylamino)benzonitrile (90.2)

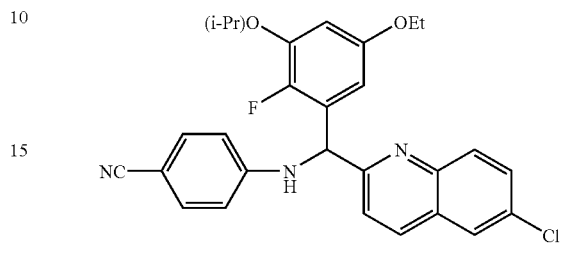

To a solution of Intermediate 90.1 (100 mg, 0.412 mmol) in 2 mL THF at −78° C., was added BuLi (1.4 M in hexanes, 324 µL, 0.454 mmol). The mixture was stirred at −78° C. for 10 min, then a solution of Intermediate 7.3 (134 mg, 0.412 mmol) in 0.7 mL THF was added. The mixture was stirred 15 min at −78° C., allowed to warm to rt over 30 min, then was quenched with sat. NH4Cl and diluted with EtOAc. The organic phase was washed with H2O and brine, dried (Na2SO4) and concentrated. The crude product was purified by flash chromatography (0 to 30% EtOAc/hexanes gradient) to afford 112 mg of Intermediate 90.2 as a pale orange solid.

Example 90

A solution of Intermediate 90.2 (100 mg, 0.204 mmol) in 1 mL 3 M NH2OH in DMSO was converted to the amide oxime, acylated and hydrogenated as in Example 1 to afford after HPLC purification 58.5 mg of Example 90 as a yellow powder. LCMS (2 min gradient) RT=1.89 min, 507.4 (M+H)+; 1H NMR (400 MHz, METHANOL-D3) δ ppm 1.25 (t, J=7.03 Hz, 3 H) 1.30-1.34 (m, 6 H) 3.84 (q, J=7.03 Hz, 2 H) 4.55 (dq, J=6.15, 6.01 Hz, 1 H) 6.22 (s, 1 H) 6.43 (dd, J=4.61, 2.86 Hz, 1 H) 6.53 (dd, J=6.81, 2.86 Hz, 1 H) 6.85 (d, J=8.79 Hz, 2 H) 7.56-7.62 (m, 3 H) 7.75 (dd, J=9.01, 2.42 Hz, 1 H) 7.96 (d, J=2.64 Hz, 1 H) 8.11 (d, J=9.23 Hz, 1 H) 8.26 (d, J=8.79 Hz, 1 H).

Example 91

4-((8-chloroquinolin-2-yl)(5-ethoxy-2-fluoro-3-isopropoxyphenyl)methylamino)benzamidine bis-trifluoroacetic acid salt

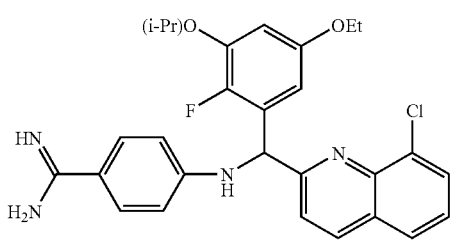

2-bromo-8-chloroquinoline (91.1)

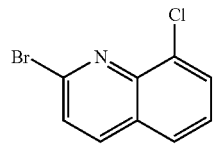

A mixture of 8-chloro-2-hydroxyquinolinone (200 mg, 1.11 mmol), P₂O₅ (383 mg, 2.67 mmol) and tetrabutylammonium bromide (429 mg, 1.33 mmol) in 4 mL xylene, was irradiated in a microwave reactor at 220° C. for 1000 s. The mixture was decanted and the rinsed with EtOAc (2×). The combined organic phase was washed with sat. NaHCO₃ and brine, dried (Na₂SO₄), filtered through a 1" pad of silica gel and concentrated to afford 229 mg (85%) of Intermediate 91.1 as an off-white solid, which was used without further purification.

4-((8-chloroquinolin-2-yl)(5-ethoxy-2-fluoro-3-isopropoxyphenyl)methylamino)benzonitrile (91.2)

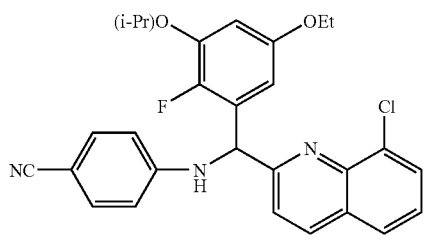

According to the procedure for Intermediate 90.2, Intermediate 91.1 (100 mg, 0.412 mmol) afforded 165 mg of Intermediate 91.2 as an off-white solid.

Example 91

A solution of Intermediate 91.2 (155 mg, 0.316 mmol) in 1.5 mL 3 M NH₂OH in DMSO was converted to the amide oxime, acylated and hydrogenated as in Example 1 to afford after HPLC purification 101.7 mg of Example 91 as an off-white powder. LCMS (2 min gradient) RT=1.87 min, 507.4 (M+H)⁺; ¹H NMR (400 MHz, METHANOL-D3) δ ppm 1.24 (t, J=6.81 Hz, 3 H) 1.33 (dd, J=6.15, 3.96 Hz, 6H) 3.79-3.87 (m, 2 H) 4.53-4.59 (m, J=6.15, 6.15, 6.15, 6.15 Hz, 1 H) 6.30 (s, 1 H) 6.46 (dd, J=4.83, 3.08 Hz, 1 H) 6.52 (dd, J=7.03, 3.08 Hz, 1 H) 6.86 (d, J=8.79 Hz, 2H) 7.53-7.59 (m, 2 H) 7.62 (d, J=9.23 Hz, 2 H) 7.87 (d, J=8.35 Hz, 1 H) 7.92 (d, J=7.47 Hz, 1 H) 8.33 (d, J=8.79 Hz, 1 H).

Example 92

4-((4,8-dimethylquinolin-2-yl)(5-ethoxy-2-fluoro-3-isopropoxyphenyl)methylamino)benzamidine bis-trifluoroacetic acid salt

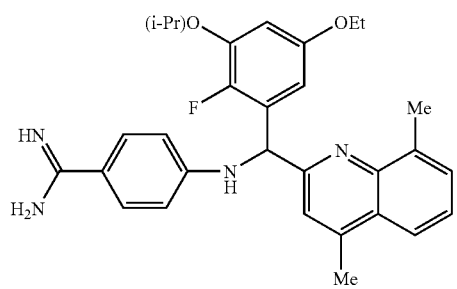

2-bromo-4,8-dimethylquinoline (92.1)

A mixture of 4,8-dimethyl-2-hydroxyquinolinone (200 mg, 1.15 mmol), P₂O₅ (393 mg, 2.77 mmol) and tetrabutylammonium bromide (445 mg, 1.38 mmol) in 4 mL xylene, was irradiated in a microwave reactor at 220° C. for 1000 s. The mixture was decanted and the rinsed with EtOAc (2×). The combined organic phase was washed with sat. NaHCO₃ and brine, dried (Na₂SO₄), filtered through a 1" pad of silica gel and concentrated to afford 224 mg (82%) of Intermediate 92.1 as an off-white solid, which was used without further purification.

4-((4,8-dimethylquinolin-2-yl)(5-ethoxy-2-fluoro-3-isopropoxyphenyl)methylamino)benzonitrile (92.2)

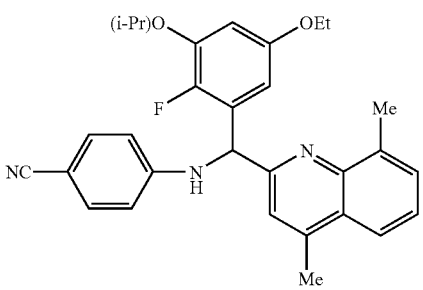

According to the procedure for Intermediate 90.2, Intermediate 92.1 (100 mg, 0.424 mmol) afforded 97 mg of Intermediate 92.2 as an off-white solid.

Example 92

A solution of Intermediate 92.2 (90 mg, 0.186 mmol) in 1.5 mL 3 M NH$_2$OH in DMSO was converted to the amide oxime, acylated and hydrogenated as in Example 1 to afford after HPLC purification 82.0 mg of Example 92 as a yellow powder. LCMS (2 min gradient) RT=1.97 min, 501.4 (M+H)$^+$; $^1$H NMR (400 MHz, METHANOL-D3) δ ppm 1.24 (t, J=6.81 Hz, 3 H) 1.33 (dd, J=6.15, 3.96 Hz, 6H) 3.79-3.87 (m, J=6.87, 6.87, 6.70, 4.17 Hz, 2 H) 4.56 (dt, J=12.30, 6.15 Hz, 1 H) 6.30 (s, 1 H) 6.46 (dd, J=4.83, 3.08 Hz, 1 H) 6.52 (dd, J=7.03, 3.08 Hz, 1 H) 6.86 (d, J=8.79 Hz, 2 H) 7.52-7.60 (m, 2 H) 7.62 (d, J=9.23 Hz, 2 H) 7.87 (d, J=8.35 Hz, 1 H) 7.92 (dd, J=7.69, 1.10 Hz, 1 H) 8.33 (d, J=8.79 Hz, 1 H).

Example 93

4-((5-ethoxy-2-fluoro-3-isopropoxyphenyl)(4-(2-(methylsulfonyl)phenyl)-1H-imidazol-2-yl)methylamino)benzamidine bis-trifluoroacetic acid salt

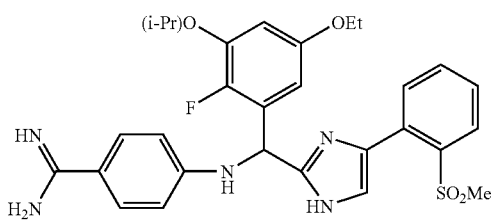

N-((5-ethoxy-2-fluoro-3-isopropoxyphenyl)(4-(2-(methylthio)phenyl)-1-trityl-1H-imidazol-2-yl)methyl)-4-(5-methyl-1,2,4-oxadiazol-3-yl)benzenamine (93.1)

A suspension of 66.3 (48 mg, 0.06 mmol), 2-(methylthio)phenylboronic acid (12.5 mg, 0.2 mmol), Na$_2$CO$_3$ (28 mg, 0.24 mmol) in 3:1 DME/H$_2$O (2 mL) was degassed and then added in Pd(PPh$_3$)$_4$ (10 mg). The reaction mixture was heated to 150° C. for 5 min in microwave. The reaction mixture was then partionated between EtOAc and sat. NaCl, the organic layer was collected and dried over (Na$_2$SO$_4$), filtered and concentrated. The crude product of Intermediate 93.1 used as is for the next step. LCMS (4 min gradient) RT=4.87 min, 816.3 (M+H).

N-((5-ethoxy-2-fluoro-3-isopropoxyphenyl)(4-(2-(methylsulfonyl)phenyl)-1-trityl-1H-imidazol-2-yl) methyl)-4-(5-methyl-1,2,4-oxadiazol-3-yl)benzenamine (93.2)

A solution of Intermediate 93.1 and m-CPBA (20 mg, 0.12 mmol) in anhydrous CH$_2$Cl$_2$ (1 mL) was stirred under N$_2$ atmosphere at rt for 30 min. The reaction mixture was then partionated between EtOAc and sat. NaCl, the organic layer was collected and dried over (Na$_2$SO$_4$), filtered and concentrated. The crude material of Intermediate 93.2 was used as is in the next step. LCMS 848.4 (M+H), RT 2.23 min/2 min gradient.

Example 93

A mixture of Intermediate 93.2 and 10% Pd—C (10 mg) in MeOH/Et$_3$N (10:1, 3 mL) was stirred under H$_2$ (1 atm) for 15 h, the reaction mixture was then filtered and concentrated. The crude product was stirred in 1 mL 90% aq. AcOH at 60° C. for 30 min, then concentrated. The residue was purified by preparative HPLC to obtained 12 mg of Example 93. (34% for 3 steps) LCMS (2 min gradient) RT=1.25 min, 566.4 (M+H); $^1$H NMR (400 MHz, CD$_3$OD) δ 1.33 (m, 9 H) 3.00 (s, 3 H) 3.97 (m, 2 H) 4.61 (m, 1 H) 6.27 (s, 1 H) 6.50 (dd, J=4.83, 3.08 Hz, 1 H) 6.67 (dd, J=6.81, 2.86 Hz, 1 H) 6.87 (d, J=8.79 Hz, 2 H) 7.69 (m, 5 H) 8.18 (d, J=7.91 Hz, 2 H).

Example 94

4-((5-ethoxy-2-fluoro-3-isopropoxyphenyl)(4-(2-(trifluoromethoxy)phenyl)-1H-imidazol-2-yl)methylamino)benzamidine bis-trifluoroacetic acid salt

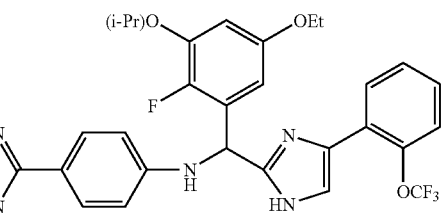

A suspension of Intermediate 66.3 (48 mg, 0.06 mmol), 2-(trifluoromethoxy)phenylboronic acid (16 mg, 0.2 mmol), Na$_2$CO$_3$ (28 mg, 0.24 mmol) in 3:1 DME/H$_2$O (2 mL) was degassed and then added in Pd(PPh$_3$)$_4$ (10 mg). The reaction mixture was heated to 150° C. for 5 min in a microwave reactor. The reaction mixture was then partitioned between EtOAc and sat. NaCl, the organic layer was collected and dried over (Na$_2$SO$_4$), filtered and concentrated. The residue was purified by flash chromatography (0-40% EA/hexanes, gradient). LCMS 854.3 (M+H), RT 4.5/5 mins. This product was hydrogenated as in Example 93 to afford after HPLC purification 1.2 mg of Example 94. LCMS (2 min gradient) RT=1.54 min, 572.3 (M+H)$^+$, $^1$H NMR (400 MHz, CD$_3$OD) 1.31 (m, 9 H) 3.93 (q, 2 H) 4.60 (m, 1 H) 6.23 (s, 1 H) 6.46 (d, J=1.76 Hz, 1 H) 6.66 (m, 1 H) 6.84 (d, J=8.79 Hz, 2 H) 7.44 (m, 4 H) 7.53 (s, 1 H) 7.65 (d, J=8.79 Hz, 2 H).

Example 101

4-((5-ethoxy-2-fluoro-3-isopropoxyphenyl)(4-(pyrimidin-2-yl)-1H-imidazol-2-yl)methylamino)benzamidine bis-trifluoroacetic acid salt

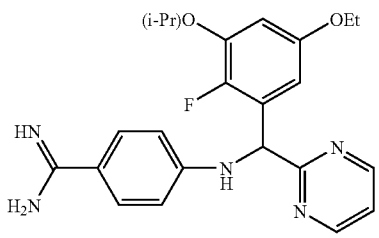

N-((5-ethoxy-2-fluoro-3-isopropoxyphenyl)(4-(pyrimidin-2-yl)-1-trityl-1H-imidazol-2-yl)methyl)-4-(5-methyl-1,2,4-oxadiazol-3-yl)benzenamine (101.1)

To 2-tributyl stannyl pyrimidine (93 mg, 0.25 mmol) in 1 mL THF at −78° C., was added BuLi (1.38 M, 0.19 mL, 0.25 mmol). When TLC showed the disappearance of starting material, a solution of Intermediate 7.3 (117 mg, 0.3 mmol) in THF. The mixture was allowed to warm to rt and was stirred at that temperature for 1 h. The reaction was quenched with sat. NH$_4$Cl and partitioned with EtOAc. The organic phase was dried (Na$_2$SO$_4$) and concentrated. The crude product was purified by flash chromatography (0 to 75% EtOAc/hexanes, gradient) to afford Intermediate 101.1, which was used in the following step. MS 407.4 (M+H)$^+$.

Example 101

Intermediate 101.1 was converted to the amide oxime, acylated and hydrogenated as in Example 1 to afford after HPLC purification 10.6 mg Example 101. LCMS (2 min gradient) RT=1.39 min, 424.4 (M+H)$^+$; $^1$H NMR (400 MHz, CD$_3$OD) 1.29 (m, 9 H) 3.87 (m, 2 H) 4.53 (m, 1 H) 6.15 (s, 1 H) 6.50 (m, 2 H) 6.84 (d, J=8.79 Hz, 2 H) 7.39 (t, J=5.05 Hz, 1 H) 7.60 (d, J=8.79 Hz, 2 H) 8.80 (d, J=4.83 Hz, 2 H).

The following examples were prepared according to the procedure described in Example 94. Coupling of Intermediate 66.3 with the respective acid indicated in each example, followed by hydrogenation and deprotection as in Example 66 afforded after HPLC purification product.

Example 95

4-((5-ethoxy-2-fluoro-3-isopropoxyphenyl)(4-(4-methoxypyridin-3-yl)-1H-imidazol-2-yl)methylamino)benzamidine tris-trifluoroacetic acid salt

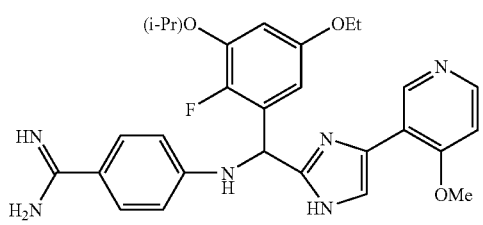

4-methoxypyridin-3-ylboronic acid; LCMS (2 min gradient) RT=1.19 min, 519.4 (M+H)$^+$; $^1$H NMR (400 MHz, CD$_3$OD) δ 1.31 (m, 9 H) 3.92 (m, J=7.03 Hz, 2 H) 4.29 (s, 3 H) 4.58 (m, 1 H) 6.12 (s, 1 H) 6.49 (s, 1 H) 6.61 (d, J=7.03 Hz, 1H) 6.81 (d, J=8.79 Hz, 2 H) 7.64 (m, 3 H) 7.81 (s, 1 H) 8.55 (s, 1 H) 9.14 (s, 1 H).

Examples 96

4-((4-(2-acetylphenyl)-1H-imidazol-2-yl)(5-ethoxy-2-fluoro-3-isopropoxyphenyl)methylamino)benzamidine bis-trifluoroacetic acid salt

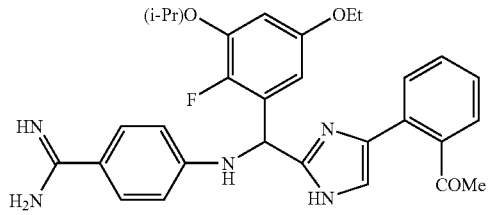

Example 97

4-((5-ethoxy-2-fluoro-3-isopropoxyphenyl)(4-(2-(2-methyl-1,3-dioxolan-2-yl)phenyl)-1H-imidazol-2-yl)methylamino)benzamidine bis-trifluoroacetic acid salt

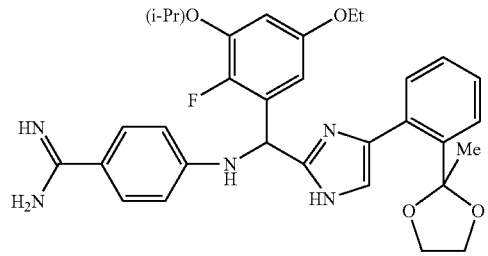

2-(2-methyl-1,3-dioxolan-2-yl)phenylboronic acid; Example 96: LCMS (4 min gradient) RT=2.97 min, 530.4 (M+H)$^+$; $^1$H NMR (400 MHz, CD$_3$OD) δ 1.34 (m, 9 H) 2.49 (s, 3 H) 4.01 (m, 2 H) 4.62 (m, 1 H) 6.32 (s, 1 H) 6.49 (dd, J=4.61, 2.86 Hz, 1 H) 6.71 (dd, J=7.03, 2.64 Hz, 1 H) 6.88 (d, J=8.79 Hz, 2 H) 7.44 (s, 1 H) 7.54 (m, 1 H) 7.63 (m, 2 H) 7.69 (d, J=9.23 Hz, 2 H) 7.96 (s, 1 H). Example 97: LCMS (2 min gradient) RT=1.39 min, 574.4 (M+H)$^+$; $^1$H NMR (400 MHz, CD$_3$OD) δ 1.33 (m, 9 H) 2.48 (s, 3 H) 4.00 (m, 6 H) 4.63 (m, 1 H) 6.31 (m, 1H) 6.50 (m, 1 H) 6.71 (m, 1 H) 6.89 (d, J=8.79 Hz, 2 H) 7.44 (d, J=8.79 Hz, 2 H) 7.54 (m, 1 H) 7.64 (m, 1 H) 7.71 (m, 2 H) 7.96 (s, 1 H).

Example 98

4-((5-ethoxy-2-fluoro-3-isopropoxyphenyl)(4-(2-propoxyphenyl)-1H-imidazol-2-yl)methylamino)benzamidine bis-trifluoroacetic acid salt

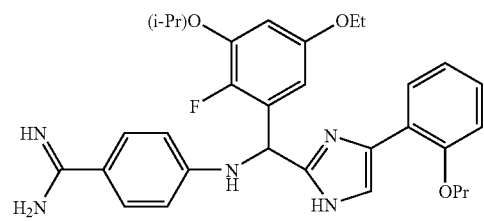

2-(propyloxy)phenylboronic acid; LCMS (2 min gradient) RT=1.56 min, 546.4 (M+H)$^+$; $^1$H NMR (400 MHz, CD$_3$OD) δ 0.98 (t, J=7.47 Hz, 3 H) 1.33 (m, 9 H) 1.78 (q, J=7.03 Hz, 2 H) 3.96 (q, J=7.03 Hz, 2 H) 4.06 (m, 2 H) 4.63 (m, 1 H) 6.37 (d, J=5.71 Hz, 1 H) 6.47 (d, J=3.95 Hz, 1 H) 6.73 (dd, J=6.81, 2.86 Hz, 1 H) 6.88 (d, J=8.79 Hz, 2 H) 7.06 (t, J=7.69 Hz, 1 H) 7.14 (d, J=8.35 Hz, 1 H) 7.42 (m, 1 H) 7.64 (d, J=6.59 Hz, 1 H) 7.70 (m, 3 H).

Example 99

4-((4-(2-((dimethylamino)metenyl)-1H-imidazol-2-yl)(5-ethoxy-2-fluoro-3-isopropoxyphenyl)methylamino)benzamidine tris-trifluoroacetic acid salt

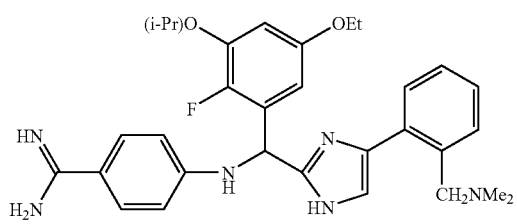

2-((dimethylamino)methyl)phenylboronic acid; LCMS (2 min gradient) RT=1.57 min, 545.4 (M+H)$^+$; $^1$H NMR (400 MHz, CD$_3$OD) 2.51 (m, 15 H) 3.84 (m, J=7.03, 7.03 Hz, 2 H) 4.05 (m, 2 H) 4.53 (m, 1 H) 6.13 (s, 1 H) 6.42 (s, 1 H) 6.58 (s, 1 H) 6.74 (d, J=7.91 Hz, 2 H) 7.29 (t, J=7.47 Hz, 1 H) 7.36 (m, 1 H) 7.42 (t, J=7.47 Hz, 1 H) 7.50 (s, 1 H) 7.56 (d, J=7.91 Hz, 2 H) 7.62 (d, J=7.91 Hz, 1 H).

Example 100

4-((5-ethoxy-2-fluoro-3-isopropoxyphenyl)(4-(2-(methylsulfonamido)phenyl)-1H-imidazol-2-yl)methylamino)benzamidine bis-trifluoroacetic acid salt

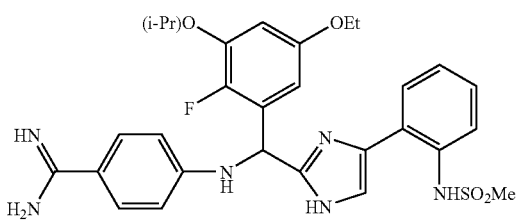

2-(methylsulfonamido)phenylboronic acid; LCMS (4 min gradient) RT=3.15 min, 581.47 (M+H)$^+$; $^1$H NMR (400 MHz, CD$_3$OD) 1.23 (m, 9 H) 2.66 (s, 3 H) 3.85 (m, 2 H) 4.49 (m, 1 H) 6.13 (s, 1 H) 6.41 (dd, J=4.83, 2.64 Hz, 1 H) 6.54 (dd, J=6.81, 2.86 Hz, 1 H) 6.76 (d, J=8.79 Hz, 2 H) 7.17 (t, J=7.47 Hz, 1 H) 7.25 (t, J=7.25 Hz, 1 H) 7.42 (d, J=7.91 Hz, 1 H) 7.54 (m, 4 H).

Example 102

4-((5-ethoxy-2-fluoro-3-isopropoxyphenyl)(4-(2-fluorophenyl)-1H-imidazol-2-yl)methylamino)benzamidine bis-trifluoroacetic acid salt

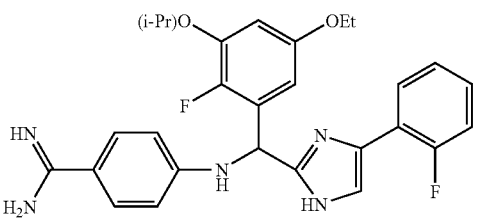

2-fluorophenylboronic acid; LCMS (2 min gradient) RT=1.44 min, 506.3 (M+H)$^+$; $^1$H NMR (400 MHz, CD$_3$OD) 1.23 (m, 9 H) 4.06 (m, 2 H) 4.52 (m, 1H) 6.31 (s, 1 H) 6.40 (dd, J=4.83, 3.08 Hz, 1 H) 6.62 (dd, J=6.81, 2.86 Hz, 1 H) 6.80 (d, J=8.79 Hz, 2 H) 7.21 (m, 2 H) 7.39 (m, 1 H) 7.59 (d, J=8.79 Hz, 2 H) 7.68 (m, 2H).

Example 106

2-(2-((4-carbamimidoylphenylamino)(5-ethoxy-2-fluoro-3-isopropoxyphenyl)methyl)-1H-imidazol-4-yl)benzoic acid bis-trifluoroacetic acid salt

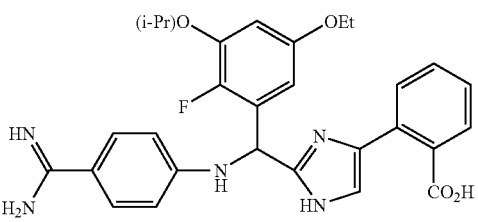

2-boronobenzoic acid; LCMS (2 min gradient) RT=1.29 min, 532.4 (M+H)$^+$; $^1$H NMR (400 MHz, CD$_3$OD) 1.34 (m, 9 H) 3.96 (m, 2 H) 4.59 (m, J=12.08, 5.93 Hz, 1 H) 6.29 (m, 1 H) 6.48 (m, 1 H) 6.67 (m, J=7.03, 2.64 Hz, 1 H) 6.86 (d, J=8.13 Hz, 2 H) 7.45 (d, J=8.35 Hz, 1 H) 7.59 (m, 2 H) 7.65 (d, J=8.79 Hz, 2 H) 7.71 (m, 1 H) 8.03 (d, J=7.47 Hz, 1 H).

Example 107 methyl 2-(2-((4-carbamimidoylphenylamino)(5-ethoxy-2-fluoro-3-isopropoxyphenyl)methyl)-1H-imidazol-4-yl)benzoate bis-trifluoroacetic acid salt

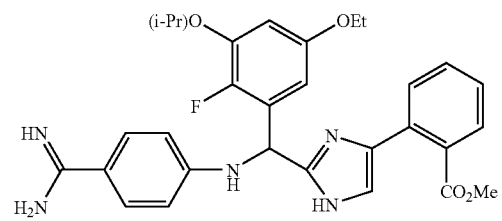

2-(methoxycarbonyl)phenylboronic acid; LCMS (2 min gradient) RT=1.38 min, 546.3 (M+H)⁺; ¹H NMR (400 MHz, CD₃OD) 1.24 (m, 9 H) 3.89 (m, 2 H) 4.02 (s, 3 H) 4.52 (m, 1 H) 6.22 (s, 1 H) 6.40 (dd, J=4.83, 3.08 Hz, 1 H) 6.60 (dd, J=6.81, 2.86 Hz, 1 H) 6.78 (d, J=8.79 Hz, 2 H) 7.36 (s, 1 H) 7.55 (m, 5 H) 7.92 (d, J=7.47 Hz, 1 H).

Example 109

4-((5-ethoxy-2-fluoro-3-isopropoxyphenyl)(4-(2-(ethylsulfonyl)phenyl)-1H-imidazol-2-yl)methylamino)benzamidine bis-trifluoroacetic acid salt

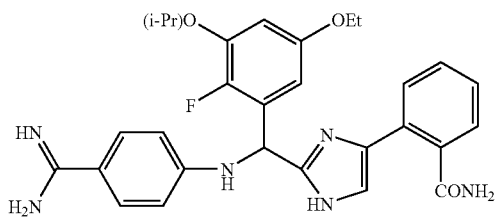

2-carbamoylphenylboronic acid; LCMS (2 min gradient) RT=1.19 min, 531.4 (M+H)⁺; ¹H NMR (400 MHz, CD₃OD) 1.33 (m, 9 H) 3.98 (m, 2 H) 4.62 (m, 1 H) 6.41 (s, 1 H) 6.49 (dd, J=4.83, 3.08 Hz, 1 H) 6.72 (dd, J=6.81, 2.86 Hz, 1 H) 6.90 (d, J=8.79 Hz, 2 H) 7.59 (m, 4 H) 7.71 (m, 3 H).

Example 110 ethyl 2-(2-((4-carbamimidoylphenylamino)(5-ethoxy-2-fluoro-3-isopropoxyphenyl)methyl)-1H-imidazol-4-yl)benzoate bis-trifluoroacetic acid salt

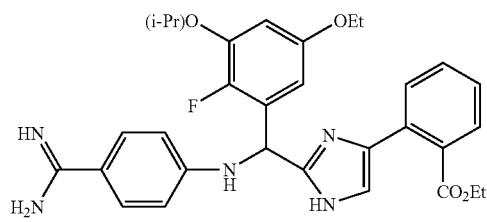

2-(ethoxycarbonyl)phenylboronic acid; LCMS (2 min gradient) RT=1.40 min, 560.4 (M+H)⁺; ¹H NMR (400 MHz, CD₃OD) 1.31 (m, 12 H) 4.00 (m, 2 H) 4.23 (q, J=7.18 Hz, 2 H) 4.61 (m, 1 H) 6.38 (s, 1 H) 6.50 (dd, J=4.61, 2.86 Hz, 1 H) 6.72 (m, 1 H) 6.90 (d, J=9.23 Hz, 2 H) 7.53 (m, 2 H) 7.69 (m, 3 H) 8.14 (m, 2 H).

Example 112

4-((5-ethoxy-2-fluoro-3-isopropoxyphenyl)(4-(1,4,5,6-tetrahydropyrimidin-5-yl)-1H-imidazol-2-yl)methylamino)benzamidine tris-trifluoroacetic acid salt

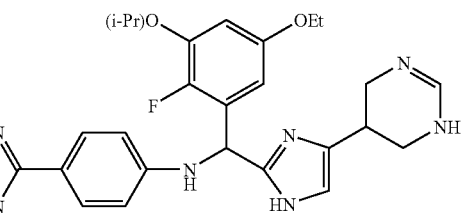

pyrimidin-5-ylboronic acid; LCMS (2 min gradient) RT=1.04 min, 494.4 (M+H)⁺; ¹H NMR (400 MHz, CD₃OD) 1.31 (m, 9 H) 3.53 (m, 2 H) 3.77 (m, 1 H) 3.95 (m, 2 H) 4.59 (dd, J=11.86, 6.15 Hz, 1 H) 6.32 (s, 1 H) 6.49 (dd, J=4.61, 2.86 Hz, 1 H) 6.68 (dd, J=6.81, 2.86 Hz, 1 H) 6.86 (d, J=8.79 Hz, 2 H) 7.25 (m, 1 H) 7.40 (m, 1 H) 7.66 (d, J=8.79 Hz, 2 H) 8.12 (s, 1 H).

Example 119

4-((4-cyclohexyl-1H-imidazol-2-yl)(5-ethoxy-2-fluoro-3-isopropoxyphenyl)methylamino)benzamidine bis-trifluoroacetic acid salt

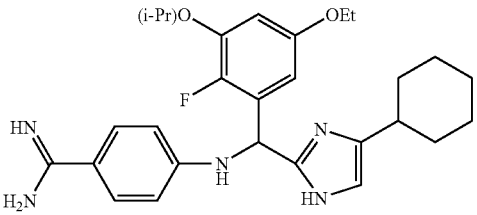

cyclohexenylboronic acid; LCMS (2 min gradient) RT=1.46 min, 494.4 (M+H)⁺; ¹H NMR (400 MHz, CD₃OD 1.33 (m, 9 H) 1.40 (m, 4 H) 1.79 (m, 4 H) 2.00 (m, 2 H) 2.69 (m, 1 H) 3.94 (q, J=7.03 Hz, 2 H) 4.61 (m, 1 H) 6.32 (s, 1 H) 6.43 (dd, J=4.83, 2.64 Hz, 1 H) 6.71 (dd, J=6.81, 2.86 Hz, 2 H) 6.71 (dd, J=6.81, 2.86 Hz, 1 H) 6.85 (d, J=9.23 Hz, 2 H) 7.22 (s, 1 H) 7.67 (d, J=8.79 Hz, 2 H).

Example 120

4-((4-cyclopentyl-1H-imidazol-2-yl)(5-ethoxy-2-fluoro-3-isopropoxyphenyl)methylamino)benzamidine bis-trifluoroacetic acid salt

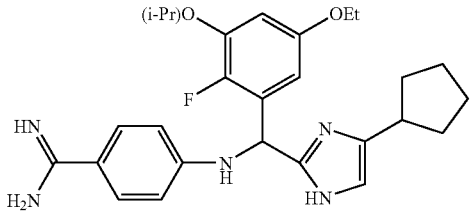

cyclopentenylboronic acid; LCMS (2 min gradient) RT=1.41 min, 480.4 (M+H)+; 1H NMR (400 MHz, CD3OD) δ 1.33 (t, J=5.49 Hz, 9 H) 1.70 (m, 6 H) 2.11 (m, J=7.69, 4.17 Hz, 2 H) 3.12 (m, 1 H) 3.95 (q, J=7.03 Hz, 2 H) 4.62 (m, 1 H) 6.32 (s, 1 H) 6.43 (dd, J=4.83, 3.08 Hz, 1 H) 6.72 (dd, J=7.03, 2.64 Hz, 1 H) 6.87 (d, J=8.79 Hz, 2 H) 7.25 (s, 1 H) 7.68 (d, J=9.23 Hz, 2 H).

Example 121

4-({(5-Ethoxy-2-fluoro-3-isopropoxy-phenyl)-[4-(2-sulfamoyl-phenyl)-1H-imidazol-2-yl]-methyl}-amino)-benzamidine bis-trifluoroacetic acid salt

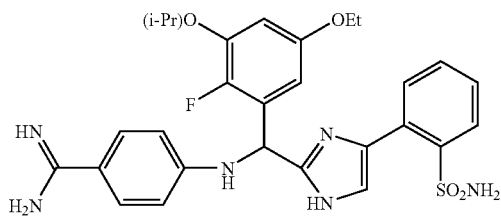

2-boronobenzenesulfonamide; LCMS (2 min gradient) RT=1.22 min, 567.35 (M+H)+; 1H NMR (400 MHz, CD3OD) δ 1.34 (m, J=5.49, 5.49 Hz, 9 H) 3.97 (m, 2 H) 4.61 (m, 1 H) 6.32 (s, 1 H) 6.49 (dd, J=4.61, 2.86 Hz, 1 H) 6.68 (dd, J=7.03, 2.64 Hz, 1 H) 6.87 (d, J=9.23 Hz, 2 H) 7.62 (m, 6 H) 8.12 (m, 1 H).

Example 108

4-((5-ethoxy-2-fluoro-3-isopropoxyphenyl)(4-(2-(ethylsulfonyl)phenyl)-1H-imidazol-2-yl)methylamino)benzamidine bis-trifluoroacetic acid salt

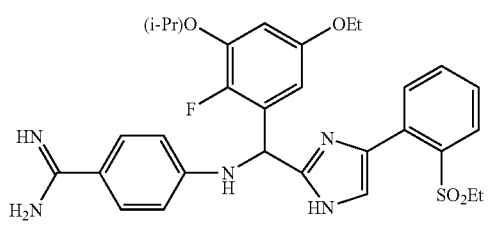

According to the procedure for Example 93, coupling of Intermediate 93.3 and 2-(ethylthio)phenylboronic acid, followed by oxidation and hydrogenation afforded Example 108. LCMS (2 min gradient) RT=1.29 min, 580.3 (M+H)+, 1H NMR (400 MHz, CD3OD) 1.12 (t, J=7.25 Hz, 3 H) 1.33 (m, 9 H) 3.06 (q, J=7.47 Hz, 2 H) 3.98 (m, 2 H) 4.61 (m, 1 H) 6.36 (s, 1 H) 6.49 (dd, A4.61, 2.86 Hz, 1 H) 6.70 (dd, J=6.81, 2.86 Hz, 1 H) 6.90 (d, J=9.23 Hz, 2 H) 7.67 (m, 4 H) 7.81 (m, 2 H) 8.16 (m, 1 H).

Example 111

4-((5-ethoxy-2-fluoro-3-isopropoxyphenyl)(4-(2-(1-hydroxyethyl)phenyl)-1H-imidazol-2-yl)methylamino)benzamidine bis-trifluoroacetic acid salt

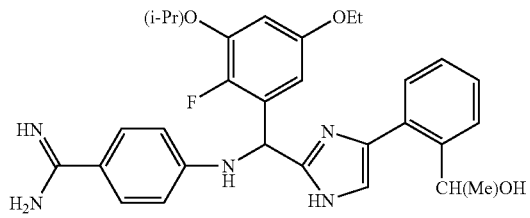

1-(2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)phenyl)ethanone (111.1)

According to the procedure for Intermediate 93.4, Intermediate 66.3 was coupled with 2-acetylphenylboronic acid to afford Intermediate 111.1.

1-(2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)phenyl)ethanol (111.2)

A solution of Intermediate 111.1 (40 mg, 0.05 mmol) and NaBH4 (5 mg) in 1 mL MeOH was stirred for 0.5 h at rt. The reaction mixture was partitioned between EtOAc and H2O, the organic layer was collected, dried (Na2SO4), filtered and concentrated to afford 30 mg of Intermediate 111.2. LCMS (2 min gradient) RT=1.49 min, 814.4 (M+H).

Example 111

According to the procedure for Example 93, Intermediate 111.2 was hydrogenated and purified by preparative HPLC to afford Example 111. LCMS (2 min gradient) RT=1.32 min, 532.4 (M+H)+; 1H NMR (400 MHz, CD3OD) 1.36 (m, 12 H) 3.96 (q, J=7.03 Hz, 2 H) 4.62 (m, 1 H) 4.82 (m, 1 H) 6.43 (s, 1 H) 6.51 (s, 1 H) 6.73 (dd, J=7.03, 3.08 Hz, 1 H) 6.91 (dd, J=8.79, 3.95 Hz, 2 H) 7.40 (t, J=7.47 Hz, 1 H) 7.49 (m, 2 H) 7.62 (d, J=7.91 Hz, 1 H) 7.68 (m, 3 H).

Example 113

4-((5-ethoxy-2-fluoro-3-(1-methylpiperidin-4-yloxy)phenyl)(4-phenyl-1H-imidazol-2-yl)methylamino)benzamidine tris-trifluoroacetic acid salt

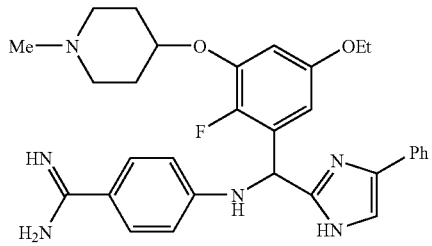

(E)-4-(3-(tert-butyldimethylsilyloxy)-5-ethoxy-2-fluorobenzylideneamino)benzamidine (113.1)

A mixture of 3-(tert-butyldimethylsilyloxy)-5-ethoxy-2-fluorobenzaldehyde, prepared according to WO2003066588 A1, which is incorporated herein by reference, (1.00 g, 3.35 mmol), 4-aminobenzonitrile (396 mg, 3.35 mmol) and 4 A molecular sieves in 10 mL toluene was refluxed for 5 h with azeotropic removal of water. The mixture was filtered and concentrated to afford 1.15 g of Intermediate 113.1 as a yellow solid.

4-((3-(tert-butyldimethylsilyloxy)-5-ethoxy-2-fluorophenyl)(4-phenyl-1-trityl-1H-imidazol-2-yl)methylamino)benzonitrile (113.2)

To a solution of Intermediate 8.1 (533 mg, 1.38 mmol) in 10 mL THF at 0° C., was added BuLi (1.4 M, 1.08 mL, 1.52 mmol). The mixture was stirred 30 min, then a solution of Intermediate 113.1 (550 mg, 1.38 mmol) in 1 mL THF was added dropwise. The mixture was stirred at 0° C. for 1 h, then was quenched with sat. NH$_4$Cl and diluted with EtOAc. The organic phase was washed with H$_2$O and brine, dried (Na$_2$SO$_4$) and concentrated. The crude product was purified by flash chromatography (0 to 30% EtOAc/hexanes, gradient) to afford 628 mg (58%) of Intermediate 113.2.

4-((5-ethoxy-2-fluoro-3-hydroxyphenyl)(4-phenyl-1-trityl-1H-imidazol-2-yl)methylamino)benzonitrile (113.3)

To a solution of Intermediate 113.2 (620 mg, 0.790 mmol) in 5 mL THF at rt, was added TBAF (1M, 0.79 mL, 0.790 mmol). The mixture was stirred at rt for 1 h, then was diluted with EtOAc. The organic phase was washed with sat. NH$_4$Cl (2×), H$_2$O (2×) and brine, dried (Na$_2$SO) and concentrated. The crude product was purified by flash chromatography (0 to 50% EtOAc/hexanes, gradient) to afford 530 mg (100%) of Intermediate 113.3 as a colorless solid.

4-((5-ethoxy-2-fluoro-3-(1-methylpiperidin-4-yloxy)phenyl)(4-phenyl-1-trityl-1H-imidazol-2-yl)methylamino)benzonitrile (113.4)

To triphenylphosphine (117 mg, 0.447 mmol) in THF (2 mL) at 0° C., was added diethylazodicarboxylate (71 μL, 0.447 mmol). The mixture was stirred at 0° C. for 30 min, then a solution of Intermediate 113.3 (100 mg, 0.149 mmol) and 4-hydroxy-1-methylpiperidine (34 mg, 0.298 mmol) in 1 mL THF. The mixture was allowed to warm to rt and stir 15 h, then was concentrated. The crude mixture was purified by flash chromatography (0 to 10% MeOH/CH$_2$Cl$_2$, gradient) to afford 77 mg of Intermediate 113.4.

Example 113

A solution of Intermediate 113.4 was converted to the amide oxime, acylated, hydrogenated and then deprotected as in Example 1 to afford after HPLC purification 27.1 mg of Example 113 as an off-white powder. LCMS (2 min gradient) RT=1.01 min, 543.4 (M+H)$^+$; $^1$H NMR (400 MHz, METHANOL-D3) δ ppm 1.32 (t, J=7.03 Hz, 3 H) 1.85-1.96 (m, 1 H) 2.03-2.15 (m, 2 H) 2.20-2.28 (m, 2 H) 2.37 (d, J=14.06 Hz, 1 H) 2.90 (s, 3 H) 3.09-3.20 (m, 1 H) 3.38-3.46 (m, 1 H) 3.60 (d, J=13.18 Hz, 1 H) 3.97 (q, J=7.03 Hz, 2 H) 4.59 (s, 1 H) 4.77 (s, 1 H) 6.36 (s, 1 H) 6.58-6.64 (m, 1 H) 6.84 (dd, J=6.59, 3.08 Hz, 1 H) 6.88 (d, J=8.79 Hz, 2 H) 7.40 (t, J=7.25 Hz, 1 H) 7.47 (t, J=7.25 Hz, 2 H) 7.65-7.75 (m, 5 H).

The following examples were prepared according to the procedure described in Example 113 using the respective alcohol indicated in each example.

Example 114

4-((5-ethoxy-2-fluoro-3-((R)-tetrahydrofuran-3-yloxy)phenyl)(4-phenyl-1H-imidazol-2-yl)methylamino)benzamidine bis-trifluoroacetic acid salt

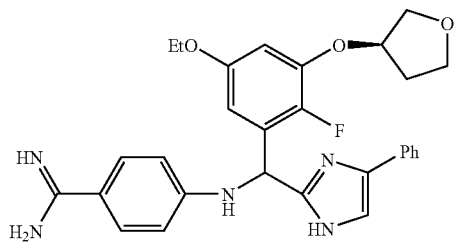

(S)-3-hydroxytetrahydrofuran; LCMS (2 min gradient) RT=1.22 min, 516.4 (M+H)$^+$; $^1$H NMR (400 MHz, METHANOL-D3) δ ppm 1.33 (t, J=7.03 Hz, 3 H) 2.09-2.15 (m, 1 H) 2.22-2.31 (m, J=13.73, 8.35, 8.24, 5.71 Hz, 1 H) 3.87 (td, J=8.35, 4.39 Hz, 1 H) 3.92-3.99 (m, J=7.25, 7.25, 7.25, 7.25 Hz, 5 H) 5.06-5.10 (m, J=3.08 Hz, 1 H) 6.38 (s, 1 H) 6.53 (dd, J=4.61, 2.86 Hz, 1 H) 6.70 (dd, J=6.81, 2.86 Hz, 1 H) 6.89 (d, J=9.23 Hz, 2 H) 7.42-7.51 (m, 3 H) 7.66-7.73 (m, 4 H) 7.78 (s, 1 H).

Example 115

4-((5-ethoxy-2-fluoro-3-((S)-tetrahydrofuran-3-yloxy)phenyl)(4-phenyl-1H-imidazol-2-yl)methylamino)benzamidine bis-trifluoroacetic acid salt

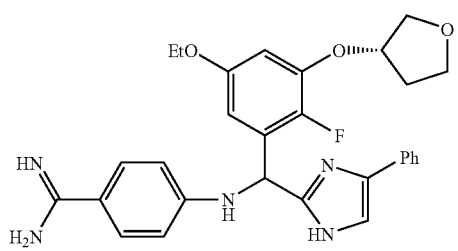

(R)-3-hydroxytetrahydrofuran; LCMS (2 min gradient) RT=1.23 min, 516.4 (M+H)$^+$; $^1$H NMR (400 MHz, METHANOL-D3) δ ppm 1.33 (t, J=6.81 Hz, 3 H) 2.09-2.15 (m, 1 H) 2.22-2.31 (m, 1 H) 3.87 (td, J=8.35, 4.39 Hz, 1 H) 3.96 (qd, J=7.40, 7.25 Hz, 5 H) 5.08 (d, J=3.08 Hz, 1 H) 6.37-6.40 (m, 1 H) 6.52-6.55 (m, 1 H) 6.71 (dd, J=7.03, 2.64 Hz, 1 H) 6.88 (d, J=1.76 Hz, 1 H) 6.90 (d, J=1.76 Hz, 1 H) 7.42-7.51 (m, 3 H) 7.67-7.73 (m, 4 H) 7.78-7.81 (m, 1 H).

Example 116

4-((3-(cyclohexyloxy)-5-ethoxy-2-fluorophenyl)(4-phenyl-1H-imidazol-2-yl)methylamino)benzamidine bis-trifluoroacetic acid salt

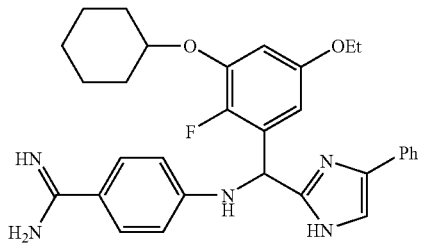

cyclohexanol; LCMS (2 min gradient) RT=1.62 min, 528.4 (M+H)+; 1H NMR (400 MHz, METHANOL-D3) δ ppm 1.32 (t, J=7.03 Hz, 3 H) 1.36-1.47 (m, 3 H) 1.50-1.60 (m, 3 H) 1.75-1.83 (m, 2 H) 1.92-1.99 (m, 2 H) 3.95 (q, J=7.03 Hz, 2 H) 4.35 (ddd, J=12.19, 8.46, 3.52 Hz, 1 H) 6.36 (s, 1 H) 6.47-6.49 (m, 1 H) 6.71 (dd, J=6.81, 2.86 Hz, 1 H) 6.88 (d, J=8.79 Hz, 2 H) 7.41-7.51 (m, J=14.12, 7.11, 7.11, 6.81 Hz, 3 H) 7.66-7.73 (m, 4 H) 7.78 (s, 1 H).

Example 117

4-((3-(3-(dimethylamino)-2,2-dimethylpropoxy)-5-ethoxy-2-fluorophenyl)(4-phenyl-1H-imidazol-2-yl)methylamino)benzamidine tris-trifluoroacetic acid salt

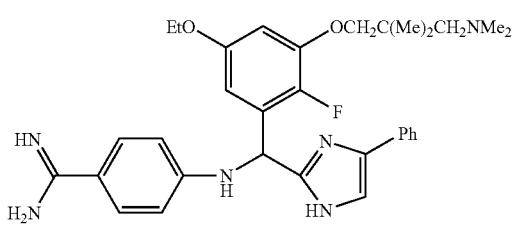

3-dimethylamino-2,2-dimethyl-1-propanol; LCMS (2 min gradient) RT=1.13 min, 559.5 (M+H)+; 1H NMR (400 MHz, METHANOL-D3) δ ppm 1.23 (d, J=3.95 Hz, 6 H) 1.33 (t, J=6.81 Hz, 3 H) 2.98 (s, 6 H) 3.91-4.00 (m, 4 H) 4.11-4.18 (m, 1 H) 6.32-6.39 (m, 1 H) 6.58 (s, 1 H) 6.76-6.79 (m, 1 H) 6.85-6.90 (m, 2 H) 7.38-7.49 (m, 3 H) 7.65-7.76 (m, 5 H).

Example 122

4-((5-ethoxy-2-fluoro-3-isopropoxyphenyl)(4-(2-propionylphenyl)-1H-imidazol-2-yl)methylamino)benzamidine bis-trifluoroacetic acid salt

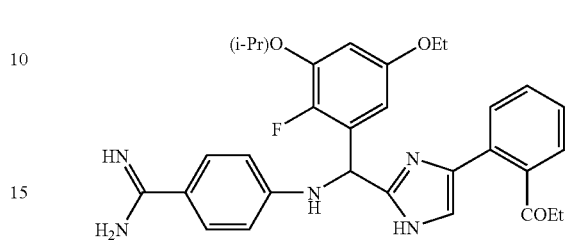

2-(2-(((5-ethoxy-2-fluoro-3-isopropoxyphenyl)(4-(5-methyl-1,2,4-oxadiazol-3-yl)phenylamino)methyl)-1-trityl-1H-imidazol-4-yl)benzaldehyde (122.1)

A suspension of Intermediate 66.3 (100 mg, 0.13 mmol), 2-formyl phenylboronic acid (30 mg, 0.2 mmol), Na2CO3 (56 mg, 0.52 mmol) in 3:1 DME/H2O (4 mL) was degassed and then added in Pd(PPh3)4 (10 mg). The reaction mixture was heated to 150° C. for 8 min in microwave. The reaction mixture was then partionated between EtOAc and sat. NaCl, the organic layer was collected and dried over (Na2SO4), filtered and concentrated. The residue was subject to chromatographic purification (0-30% EtOAc/hexanes gradient), 100 mg (65%) of Intermediate 122.1 was obtained. LCMS (2 min gradient) RT 2.35 min, 798.3 (M+H).

1-(2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)phenyl)propan-1-ol (122.2)

To a solution of Intermediate 122.1 (50 mg, 0.06 mmol) in THF (1 mL) was added EtMgBr dropwise at 0° C. under N2 atmosphere, the reaction mixture was stirred at 0° C. for 30 min. The reaction mixture was then partionated between EtOAc and sat. NaCl, the organic layer was collected and dried over (Na2SO4), filtered and concentrated. The crude material Intermediate 122.2 was used as is in the following step. LCMS (2 min gradient) RT=2.23 min, 828.4 (M+H).

1-(2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)phenyl)propan-1-one (122.3)

A mixture of Intermediate 122.2 and Dess-Martin periodinate (60 mg, 0.12 mmol) in anhydrous CH2Cl2 (2 mL) was stirred at rt for 20 min. The reaction mixture was then partionated between EtOAc and 1 N NaOH, the organic layer was collected and dried over (Na2SO4), filtered and concentrated to afford Intermediate 122.3, which was used in the following step without further purification. LCMS (2 min gradient) RT=2.27 min, 826.4 (M+H).

Example 122

According to the procedure for Example 94, Intermediate 122.3 was hydrogentated and purifed by HPLC to afford Example 122. LCMS (2 min gradient) RT=1.39 min, 546.4 (M+H)+; $^1$H NMR (400 MHz, CD$_3$OD) δ 0.75 (q, 2 H) 0.83 (t, J=7.25 Hz, 3 H) 1.34 (m, 9 H) 3.96 (m, 2 H) 4.63 (m, 1 H) 6.42 (s, 1 H) 6.51 (m, 1 H) 6.73 (dd, J=6.81, 2.86 Hz, 1 H) 6.91 (m, 3 H) 7.48 (m, 3 H) 7.69 (m, 3 H).

Example 123

N$^6$-((5-ethoxy-2-fluoro-3-(1-methylpiperidin-4-yloxy)phenyl)(4-phenyl-1H-imidazol-2-yl)methyl)isoquinoline-1,6-diamine tris-trifluoroacetic acid salt

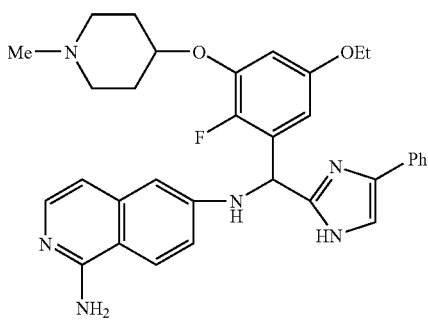

(3-(tert-butyldimethylsilyloxy)-5-ethoxy-2-fluorophenyl)(4-phenyl-1-trityl-1H-imidazol-2-yl)methanol (123.1)

To a solution of intermediate 8.1 (1.00 g, 2.59 mmol) in 20 mL THF at 0° C., was added BuLi (1.4 M, 2.03 mL, 2.85 mmol). The mixture was stirred for 30 min at 0° C., then a solution of 3-(tert-butyldimethylsilyloxy)-5-ethoxy-2-fluorobenzaldehyde (773 mg, 2.59 mmol) in 2 mL THF was added dropwise. The mixture was stirred at 0° C. for 30 min, quenched with sat. NH$_4$Cl and diluted with EtOAc. The organic phase was washed with H$_2$O and brine, dried (Na$_2$SO$_4$) and concentrated. The crude product was purified by flash chromatography (0 to 30% EtOAc/hexanes, gradient) to afford 1.50 g (80%) of Intermediate 123.1 as a pale yellow solid.

N$^6$-((3-(tert-butyldimethylsilyloxy)-5-ethoxy-2-fluorophenyl)(4-phenyl-1-trityl-1H-imidazol-2-yl)methyl)-N$^1$,N$^1$-di-(tert-butoxycarbonyl)isoquinoline-1,6-diamine (123.2)

To a solution of Intermediate 123.1 (400 mg, 0.584 mmol), TEA (122 μL, 0.876 mmol), and DMAP (~5 mg, cat.) in 4 mL CH$_2$Cl$_2$ at rt, was added methanesulfonyl chloride (68 μL, 0.876 mmol). The mixture was stirred for 1 h, then diluted with EtOAc. The aqueous phase washed with ice water and brine, dried (Na$_2$SO$_4$) and concentrated to afford the chloro intermediate. To a suspension of this intermediate in 8 mL CH$_3$CN at rt, were added DIEA (153 μL, 0.876 mmol) and 1-(di-(tert-butyloxycarbonyl)amino)-6-aminoisoquinoline (231 mg, 0.642 mmol). The mixture was stirred at rt for 16 h and at 50° C. for 4 h, then was diluted with EtOAc. The organic phase was washed with water and brine, dried (Na$_2$SO$_4$) and concentrated. The crude residue was purified by flash chromatography (0 to 50% EtOAc/hexanes, gradient) to afford 527 mg (88%) of Intermediate 123.2 as a yellow solid.

3-((1-(di-tert-butoxycarbonylamino)isoquinolin-6-ylamino)(4-phenyl-1-trityl-1H-imidazol-2-yl)methyl)-5-ethoxy-2-fluorophenol (123.3)

To a solution of Intermediate 123.2 (635 mg, 0.619 mmol) in 5 mL THF, was added TBAF (1 M, 0.619 mL, 0.619 mmol). The mixture was stirred at rt for 30 min, then was diluted with EtOAc. The organic phase was washed with 0.1 N HCl, water (2×) and brine; dried (Na$_2$SO$_4$) and concentrated. The crude product was purified by flash chromatography (0 to 75% EtOAc/hexanes) to afford 509 mg (90%) of Intermediate 123.3 as a pale yellow solid.

N$^6$-((5-ethoxy-2-fluoro-3-(1-methylpiperidin-4-yloxy)phenyl)(4-phenyl-1-trityl-1H-imidazol-2-yl)methyl)-N$^1$,N$^1$-(di-tert-butoxycarbonyl)-isoquinoline-1,6-diamine (123.4)

To triphenylphosphine (69 mg, 0.263 mmol) in THF (2 mL) at 0° C., was added diethylazodicarboxylate (41.6 μL, 0.263 mmol). The mixture was stirred at 0° C. for 30 min, then a solution of Intermediate 123.3 (80 mg, 0.088 mmol) and 4-hydroxy-1-methylpiperidine (20.2 mg, 0.175 mmol) in 1 mL THF. The mixture was allowed to warm to rt and stir 15 h, then was concentrated. The crude mixture was purified by flash chromatography (0 to 10% MeOH/CH$_2$Cl$_2$, gradient) to afford 83 mg of Intermediate 123.4.

Example 123

Intermediate 123.4 (78 mg) was treated with 1 mL TFA and 2 drops water. The mixture was stirred at rt for 20 min, then concentrated. The crude product was purified by preparative HPLC to afford 39.8 mg Example 123 as a white powder. LCMS (2 min gradient) RT=1.01 min, 543.4 (M+H)+; $^1$H NMR (400 MHz, METHANOL-D3) δ ppm 1.32 (t, J=7.0 Hz, 3 H) 1.85-1.95 (m, 1 H) 2.05-2.15 (m, 1 H) 2.23-2.28 (m, 1 H) 2.37 (d, J=14 Hz, 1 H) 2.90 (s, 3 H) 3.11-3.18 (m, 1 H) 3.30-3.35 (m, 1 H) 3.41-3.46 (m, 1 H) 3.60 (d, J=13 Hz, 1 H) 3.97 (q, J=7.0 Hz, 2 H) 4.60 (m, 1 H) 6.47 (d, J=4.8 Hz, 1 H) 6.59-6.63 (m, 1 H) 6.84-6.88 (m, 2 H) 6.92 (d, J=7.0 Hz, 1 H) 7.24-7.27 (m, 1 H) 7.36 (d, J=7.0 Hz, 1 H) 7.40-7.49 (m, 3 H) 7.72 (d, J=7.4 Hz, 2 H) 7.77 (s, 1 H) 8.19 (d, J=9.2 Hz, 1 H).

The following examples were prepared according to the procedure described in Example 123 using the respective alcohol indicated in each example.

Example 124

N$^6$-((5-ethoxy-2-fluoro-3-((R)-tetrahydrofuran-3-yloxy)phenyl)(4-phenyl-1H-imidazol-2-yl)methyl)isoquinoline-1,6-diamine bis-trifluoroacetic acid salt

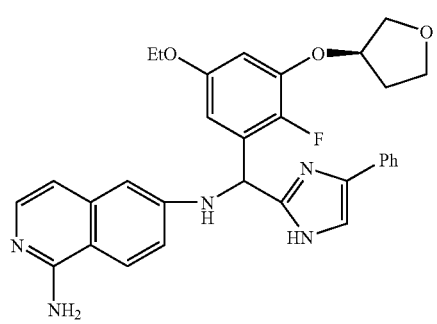

(S)-3-hydroxytetrahydrofuran; LCMS (2 min gradient) RT=1.22 min, 516.4 (M+H)+; 1H NMR (400 MHz, METHANOL-D3) δ ppm 1.34 (t, J=7.0 Hz, 3 H) 2.10-2.05 (m, 1 H) 2.23-2.32 (m, 1 H) 3.85-3.92 (m, 1 H) 3.94-4.01 (m, 5 H) 5.08-5.11 (m, 1 H) 6.47 (s, 1 H) 6.56 (dd, J=4.4, 2.6 Hz, 1 H) 6.73 (dd, J=7.0, 2.6 Hz, 1 H) 6.89 (d, J=2.2 Hz, 1 H) 6.94 (d, J=7.0 Hz, 1 H) 7.24-7.27 (m, 1 H) 7.37 (d, J=7.0 Hz, 1 H) 7.42-7.51 (m, 3 H) 7.72 (d, J=7.4 Hz, 2 H) 7.79 (s, 1 H) 8.20 (d, J=8.8 Hz, 1 H).

Example 125

N6-((5-ethoxy-2-fluoro-3-((S)-tetrahydrofuran-3-yloxy)phenyl)(4-phenyl-1H-imidazol-2-yl)methyl)isoquinoline-1,6-diamine bis-trifluoroacetic acid salt

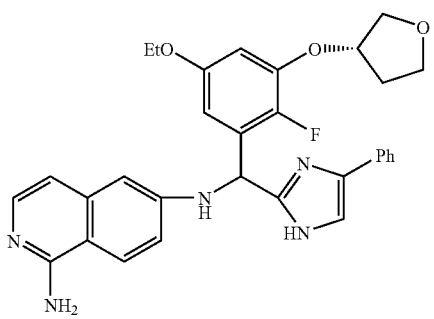

(R)-3-hydroxytetrahydrofuran; LCMS (2 min gradient) RT=1.23 min, 516.4 (M+H)+; 1H NMR (400 MHz, METHANOL-D3) δ ppm 1.34 (t, J=7.0 Hz, 3 H) 2.10-2.05 (m, 1 H) 2.23-2.32 (m, 1 H) 3.85-3.92 (m, 1 H) 3.94-4.01 (m, 5 H) 5.08-5.11 (m, 1 H) 6.47 (s, 1 H) 6.56 (dd, J=4.4, 2.6 Hz, 1 H) 6.73 (dd, J=7.0, 2.6 Hz, 1 H) 6.89 (d, J=2.2 Hz, 1 H) 6.94 (d, J=7.0 Hz, 1 H) 7.24-7.27 (m, 1 H) 7.37 (d, J=7.0 Hz, 1 H) 7.42-7.51 (m, 3 H) 7.72 (d, J=7.4 Hz, 2 H) 7.79 (s, 1 H) 8.20 (d, J=8.8 Hz, 1 H).

Example 126

N6-((3-(cyclohexyloxy)-5-ethoxy-2-fluorophenyl)(4-phenyl-1H-imidazol-2-yl)methyl)isoquinoline-1,6-diamine bis-trifluoroacetic acid salt

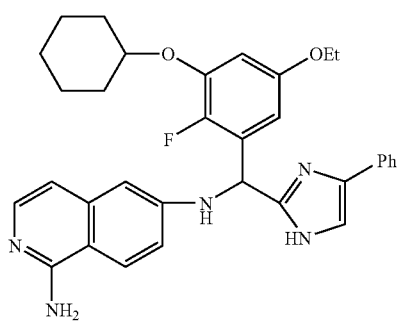

cyclohexanol; LCMS (2 min gradient) RT=1.62 min, 528.4 (M+H)+; 1H NMR (400 MHz, METHANOL-D3) δ ppm 1.32 (t, J=7.0 Hz, 3 H) 1.37-1.43 (m, 2 H) 1.51-1.58 (m, 2 H) 1.76-1.82 (m, 2 H) 1.93-1.98 (m, 2 H) 3.95 (q, J=7.0 Hz, 2 H) 4.33-4.38 (m, 1 H) 6.44 (s, 1 H) 6.49 (dd, J=4.4, 2.6 Hz, 1 H) 6.73 (dd, J=7.0, 3.1 Hz, 1 H) 6.88 (d, J=2.2 Hz, 1 H) 6.93 (d, J=7.0 Hz, 1 H) 7.24-7.27 (m, 1 H) 7.36 (d, J=7.0 Hz, 1 H) 7.42-7.51 (m, 3 H) 7.71 (d, J=7.4 Hz, 2 H) 7.77 (s, 1 H) 8.19 (d, J=9.2 Hz, 1 H).

Example 127

N6-((3-(3-(dimethylamino)-2,2-dimethylpropoxy)-5-ethoxy-2-fluorophenyl)(4-phenyl-1H-imidazol-2-yl)methyl)isoquinoline-1,6-diamine tris-trifluoroacetic acid salt

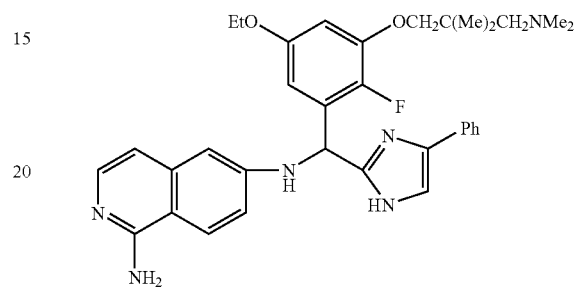

3-dimethylamino-2,2-dimethyl-1-propanol; LCMS (2 min gradient) RT=1.13 min, 559.5 (M+H)+; 1H NMR (400 MHz, METHANOL-D3) δ ppm 1.23 (t, J=2.6, 6 H) 1.32 (t, J=7.0 Hz, 3 H) 2.98 (s, 6 H) 3.96-4.02 (m, 4 H) 6.47 (s, 1 H) 6.59 (dd, J=4.4, 2.6 Hz, 1 H) 6.79 (dd, J=7.0, 3.1. Hz, 1 H) 6.87 (d, J=2.2 Hz, 1 H) 6.91 (d, J=7.0 Hz, 1 H) 7.24-7.27 (m, 1 H) 7.36 (d, J=7.0 Hz, 1 H) 7.38-7.49 (m, 3 H) 7.71 (d, J=7.4 Hz, 2 H) 7.74 (s, 1 H) 8.19 (d, J=9.2 Hz, 1 H).

Example 133

2-(2-((4-carbamimidoylphenylamino)(5-ethoxy-2-fluoro-3-isopropoxyphenyl)methyl)-1H-imidazol-4-yl)-N-ethylbenzamide bis-trifluoroacetic acid salt

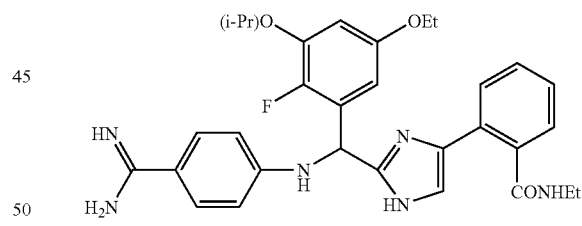

2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)benzoic acid (133.1)

A suspension of 66.3 (100 mg, 0.13 mmol), 2-carboxyl phenylboronic acid (30 mg, 0.2 mmol), Na2CO3 (56 mg, 0.52 mmol) in 3:1 DME/H2O (3 mL) was degassed and then added in Pd(PPh3)4 (10 mg). The reaction mixture was heated to 170° C. for 15 mins in microwave. The reaction mixture was adjust to PH ~4-5, then partitioned between EtOAc and sat. NaCl, the organic layer was collected and dried over (Na2SO4), filtered and concentrated to afford Intermediate 133.1. The crude material was used in the next step without further purification. LCMS (2 min grad.) RT=2.13 min, 814.3 (M+H).

2-(2-((5-ethoxy-2-fluoro-3-isopropoxyphenyl)(4-(5-methyl-1,2,4-oxadiazol-3-yl)phenylamino)methyl)-1-trityl-1H-imidazol-4-yl)-N-ethylbenzamide (133.2)

A mixture of Intermediate 133.1 (crude, ~30 mg), NH₂Et.HCl (7 mg, 0.13 mmol), HOAt (41 mg, 0.3 mmol), EDCI (58 mg, 0.3 mmol), NaHCO₃ (50 mg, 0.6 mmol) in 4:1 CH₂Cl₂/DMF (2 mL) was stirred at rt for 2 h. The reaction mixture was then partitioned between EtOAc and sat. NaHCO₃, the organic layer was then washed by NH₄Cl, and sat. NaCl, the organic layer was collected and dried over (Na₂SO₄), filtered and concentrated to afford Intermediate 133.2. The crude material was used without further purification in the following step.

Example 133

A mixture of Intermediate 133.2 and 10 mg of 10% Pd/C in MeOH (2 mL) was stirred under H₂ atmosphere for 4 h. The reaction mixture was filtered, concentrated, and purified by preparative HPLC to afford 4 mg of Example 133 (10% for three steps). LCMS (2 min gradient) RT=1.29 min, 559.4 (M+H)⁺; ¹H NMR (400 MHz, CD₃OD) δ 1.32 (m, 12 H) 2.65 (m, 2 H) 3.96 (m, 2 H) 4.63 (m, 1 H) 6.35 (s, 1 H) 6.45 (m, 1 H) 6.73 (dd, J=6.82, 2.86 Hz, 1 H) 7.02 (d, J=8.79 Hz, 2 H) 7.55 (s, 1 H), 7.60 (m, 3 H) 7.69 (m, 3 H).

The following examples were prepared according to the procedure described in Example 133 by amide coupling Intermediate 133.1 with the respective amine indicated in each example.

Example 134

2-(2-((4-carbamimidoylphenylamino)(5-ethoxy-2-fluoro-3-isopropoxyphenyl)methyl)-1H-imidazol-4-yl)-N,N-dimethylbenzamide bis-trifluoroacetic acid salt

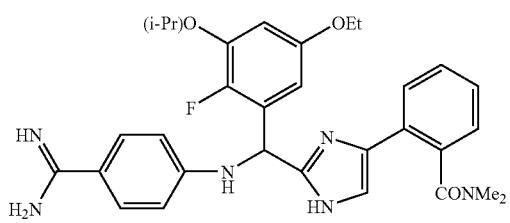

dimethylamine hydrochloride; LCMS (2 min gradient) RT=1.22 min, 559.4 (M+H)⁺; ¹H NMR (400 MHz, CD₃OD) δ 1.32 (m, 12 H) 2.65 (m, 2 H) 2.68 (s, 3 H), 2.98 (s, 3 H) 3.95 (m, 2 H) 4.60 (m, 1 H) 6.25 (s, 1 H) 6.46 (m, 1 H) 6.67 (dd, J=6.82, 2.86 Hz, 1 H) 6.85 (d, J=8.79 Hz, 2 H) 7.28 (s, 1 H), 7.60 (m, 3 H) 7.66 (m, 3 H).

Example 135

2-(2-((4-carbamimidoylphenylamino)(5-ethoxy-2-fluoro-3-isopropoxyphenyl)methyl)-1H-imidazol-4-yl)-N-methylbenzamide

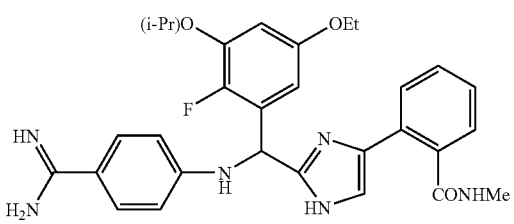

methylamine hydrochloride; LCMS (2 min gradient) RT=1.25 min, 545.3 (M+H)⁺; ¹H NMR (400 MHz, CD₃OD) δ 1.32 (m, 12H) 2.65 (m, 2H) 3.30 (s, 3H) 3.95 (m, 2 H) 4.60 (m, 1 H) 6.25 (s, 1 H) 6.46 (m, 1 H) 6.67 (dd, J=6.82, 2.86 Hz, 1 H) 6.82 (d, J=8.79 Hz, 2 H) 7.28 (s, 1H), 7.60 (m, 3 H) 7.76 (m, 3 H).

Example 136

2-(2-((4-carbamimidoylphenylamino)(5-ethoxy-2-fluoro-3-((5)-tetrahydrofuran-3-yloxy)phenyl)methyl)-1H-imidazol-4-yl)benzamide

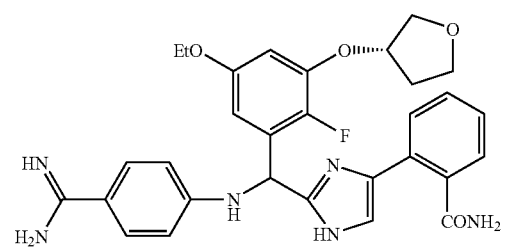

4-((3-(tert-butyldimethylsilyloxy)-5-ethoxy-2-fluorophenyl)(1-trityl-1H-imidazol-2-yl)methylamino)benzonitrile (136.1)

To a solution of N-trityl-imidazole (200 mg, 0.644 mmol) in 6 mL THF at 0° C., was added BuLi (1.4 M in hexanes, 0.506 mL, 0.708 mmol). The mixture was stirred at rt for 15 min, then was re-cooled to 0° C. To this mixture was added a solution of Intermediate 113.1 (257 mg, 0.644 mmol) in 1 mL THF. The mixture was stirred at 0° C. for 15 min and at rt for 1 h, then was quenched with sat. NH₄Cl. The mixture was diluted with EtOAc, washed with H₂O and brine, dried (Na₂SO₄) and concentrated. The crude product was purified by flash chromatography (0 to 50% EtOAc/hexanes gradient) to afford 367 mg (80%) of Intermediate 136.1 as a white solid.

4-((4-bromo-1-trityl-1H-imidazol-2-yl)(3-(tert-butyldimethylsilyloxy)-5-ethoxy-2-fluorophenyl)methylamino)benzonitrile (136.2)

To a suspension of 136.1 (303 mg, 0.427 mmol) in DMF (5 mL) at rt, was added NBS (79.9 mg, 0.449 mmol). The mixture was stirred at rt for 17 h, then was diluted with EtOAc, washed with H₂O (2×) and brine, dried (Na₂SO₄) and concentrated. The crude product was purified by flash chromatography (0 to 25% EtOAc/hexanes gradient) to afford 177 mg of Intermediate 136.2 (~50% purity, use as is in the following step.)

2-(2-((4-cyanophenylamino)(5-ethoxy-2-fluoro-3-hydroxyphenyl)methyl)-1-trityl-1H-imidazol-4-yl)benzamide (136.3)

To a mixture of 136.2 (170 mg, 0.216 mmol), 2-carbamoylphenylboronic acid (53.4 mg, 0.324 mmol) and Na₂CO₃ (91.6 mg, 0.864 mmol) in 4 mL DME/H₂O (3:1) was degassed via vacuum/Argon flush (4×). Pd(PPh₃)₄ (25 mg, 0.0216 mmol) was added and the mixture was reacted in a microwave for 400 sec at 150° C. The reaction mixture was diluted with EtOAc, washed with H₂O (2×) and brine, dried (Na₂SO₄) and concentrated. The crude product was purified by flash chromatography (0 to 75% EtOAc/hexanes gradient) to afford 32.2 mg of Intermediate 136.3. LCMS (2 min gradient) RT=1.90 min, 714.2 (M+H)⁺.

2-(2-((4-cyanophenylamino)(5-ethoxy-2-fluoro-3-((S)-tetrahydrofuran-3-yloxy)phenyl)methyl)-1-trityl-1H-imindazol-4-yl)benzamide (136.4)

To PPh₃ (34.2 mg, 0.130 mmol) in 1 mL THF at 0° C. was added diethylazodicarboxylate (20.6 µL, 0.130 mmol) dropwise. The mixture was stirred at 0° C. for 30 min, then a solution of Intermediate 136.3 (31 mg, 0.434 mmol) and (R)-tetrahydrofuran-3-ol in 1 mL THF, dropwise. The mixture was stirred at 0° C. for 3 min and 2 h at rt, then was concentrated. The crude mixture was purified by flash chromatography (0 to 75% EtOAc/hexanes gradient) to afford 16 mg of 136.4.

Example 136

A solution of Intermediate 136.4 (16 mg) in 1 mL 3M NH₂OH in DMSO was converted to the amide oxime, acylated, hydrogenated and deprotected as in Example 1 to afford after HPLC purification 2.2 mg of Example 136 as a white powder. LCMS (2 min gradient) RT=1.14 min, 559.53 (M+H)⁺; ¹H NMR (400 MHz, METHANOL-D3) δ ppm 1.34 (t, J=6.81 Hz, 3 H) 2.09-2.15 (m, 1 H) 2.22-2.31 (m, 1 H) 3.87 (td, J=8.35, 4.39 Hz, 1 H) 3.93-4.01 (m, 5 H) 5.08 (d, J=6.15 Hz, 1 H) 6.41 (d, J=2.20 Hz, 1 H) 6.51-6.54 (m, 1 H) 6.71 (dd, J=6.81, 2.86 Hz, 1 H) 6.90 (d, J=8.79 Hz, 3 H) 7.56-7.62 (m, 4 H) 7.67-7.73 (m, 3 H).

Example 137

4-((5-ethoxy-2-fluoro-3-isopropoxyphenyl)(6-methoxypyridin-2-yl)methylamino)benzamidine bis-trifluoroacetic acid salt

4-((5-ethoxy-2-fluoro-3-isopropoxyphenyl)(6-methoxypyridin-2-yl)methylamino)benzonitrile (137.1)

To a solution of 2-bromo-6-methoxypyridine (50 mg, 0.266 mmol) in 1 mL THF at −78° C., was added BuLi (1.6 M in hexanes, 0.183 mL, 0.293 mmol). The mixture was stirred at −78° C. for 10 min. To this mixture was added a solution of Intermediate 113.1 (78 mg, 0.239 mmol) in 0.5 mL THF. The mixture was stirred at −78° C. for 20 min, then the cooling bath was removed and the reaction was stirred for 15 min. The reaction was quenched with sat. NH₄Cl, diluted with EtOAc, washed with H₂O and brine, dried (Na₂SO₄) and concentrated. The crude product was purified by flash chromatography (0 to 40% EtOAc/hexanes gradient) to afford 89 mg (76%) of Intermediate 137.1 as a white solid. LCMS (2 min gradient) RT 2.03 min, 436.3 (M+H)⁺.

Example 137

A solution of Intermediate 137.1 (79 mg, 0.181 mmol) in 2 mL 3 M NH₂OH in DMSO was converted to the amide oxime, acylated and hydrogenated as in Example 1 to afford after HPLC purification 77.3 mg of Example 137. LCMS (2 min gradient) RT=1.68 min, 453.3 (M+H)⁺; LCMS (2 min gradient) RT=1.68 min, 453.3 (M+H)⁺; ¹H NMR (400 MHz, METHANOL-D3) δ ppm 1.28 (t, J=7.03, 3 H) 1.30 (d, J=6.59 Hz, 3 H) 1.31 (d, J=6.59 Hz, 3 H) 3.87 (q, J=7.03 Hz, 2 H) 3.93 (s, 3 H) 4.54 (ddd, J=11.97, 6.15, 6.04 Hz, 1 H) 5.95 (s, 1 H) 6.46-6.49 (m, 1 H) 6.52 (dd, J=7.03, 3.08 Hz, 1 H) 6.68 (d, J=7.91 Hz, 1 H) 6.79 (d, J=8.79 Hz, 2 H) 6.98 (d, J=7.47 Hz, 1 H) 7.59 (d, J=9.23 Hz, 2 H) 7.62 (t, J=7.47 Hz, 1 H).

Example 138

4-((5-ethoxy-2-fluoro-3-isopropoxyphenyl)(6-(furan-3-yl)pyridin-2-yl)methylamino)benzamidine bis-trifluoroacetic acid salt

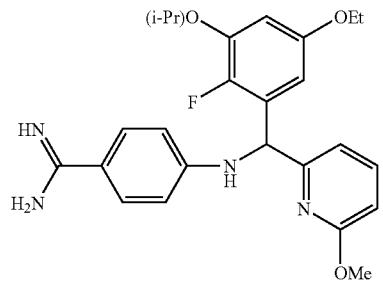

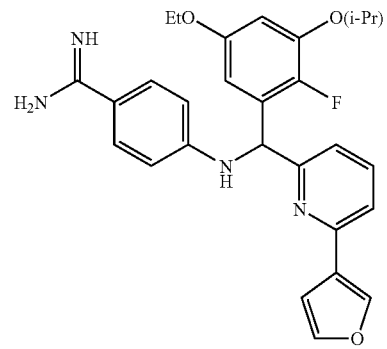

4-((6-bromopyridin-2-yl)(5-ethoxy-2-fluoro-3-isopropoxyphenyl)methylamino)benzonitrile (138.1)

To a mixture of 2,6-dibromopyridine (100 mg, 0.422 mmol) in 2 mL THF at −78° C., was added BuLi (1.6 M in THF, 0.290 mL, 0.464 mmol). The mixture was stirred at −78° C. for 5 min, then a solution of Intermediate 7.2 (138 mg, 0.422 mmol) in 0.6 mL THF was added. dropwise. The mixture was stirred at −78° C. for 30 min and at rt for 15 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 40% EtOAc/hexanes gradient) to afford 139 mg of Intermediate 138.1 as a colorless solid. LCMS (2 min gradient) RT=2.02 min, 484.2 $(M+H)^+$.

4-((5-ethoxy-2-fluoro-3-isopropoxyphenyl)(6-(furan-3-yl)pyridin-2-yl)methylamino)benzonitrile (138.2)

To a degassed mixture of Intermediate 138.1 (48 mg, 0.062 mmol), 3-furanylboronic acid (13.9 mg, 0.124 mmol) and $Na_2CO_3$ (35 mg, 0.33 mmol) in 2 mL $DME/H_2O$ (3:1) was added $Pd(PPh_3)_4$ (10 mg, 0.0083 mmol). The mixture was stirred at 150° C. for 5 min in a microwave oven, then was diluted with EtOAc, washed with water and brine, dried ($Na_2SO_4$) and concentrated. The crude product was purified by flash chromatography (0 to 40% EtOAc/hexanes gradient) to afford 37.5 mg of Intermediate 138.2. LCMS (2 min gradient) RT=2.07 min, 472.3 $(M+H)^+$.

Example 138

A solution of Intermediate 138.2 (37.5 mg) in 1 mL 3 M $NH_2OH$ in DMSO was converted to the amide oxime, acylated and hydrogenated as in Example 1 to afford after HPLC purification 43.7 mg of Example 138. LCMS (2 min gradient) RT=1.77 min, 489.23 $(M+H)^+$; $^1H$ NMR (400 MHz, METHANOL-D3) δ ppm 1.26 (t, J=7.03 Hz, 3 H) 1.29-1.34 (m, 6 H) 3.86 (q, J=6.74 Hz, 2 H) 4.52-4.58 (m, J=6.15, 6.15, 6.15, 6.15 Hz, 1 H) 6.07 (s, 1 H) 6.46 (dd, J=4.83, 2.64 Hz, 1 H) 6.52 (dd, J=6.81, 2.86 Hz, 1 H) 6.83 (d, J=8.79 Hz, 2 H) 7.02 (s, 1 H) 7.25 (d, J=7.91 Hz, 1 H) 7.54 (d, J=7.47 Hz, 1 H) 7.57-7.64 (m, 3 H) 7.75 (t, J=7.91 Hz, 1 H) 8.19 (s, 1 H) 8.21 (s, 1 H) 8.73 (s, 1 H).

Example 139

4-((5-ethoxy-2-fluoro-3-isopropoxyphenyl)(6-(pyrrolidin-1-yl)pyridin-2-yl)methylamino)benzamidine bis-trifluoracetic acid salt

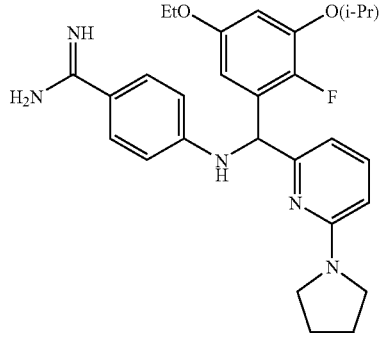

4-((5-ethoxy-2-fluoro-3-isopropoxyphenyl)(6-(pyrrolidin-1-yl)pyridin-2-yl)methylamino)benzonitrile (139.1)

To a solution of intermediate 138.1 (35.7 mg, 0.0737) in 0.6 mL DMSO, was added pyrrolidine (0.031 mL, 0.37 mmol). The mixture was stirred 2 h at 60° C. and 5 h at 100° C. The mixture was diluted with EtOAc, washed with $H_2O$ and brine, dried ($Na_2SO_4$) and concentrated. The crude product was purified by flash chromatography (0 to 40% EtOAc/hexanes gradient) to afford 30.8 mg of Intermediate 139.1 as a pale yellow solid. LCMS (2 min gradient) RT=1.59 min, 475.4 $(M+H)^+$.

Example 139

A solution of Intermediate 139.1 (37.5 mg) in 1 mL 3 M $NH_2OH$ in DMSO was converted to the amide oxime, acylated and hydrogenated as in Example 1 to afford after HPLC purification 24.8 mg of Example 139. LCMS (2 min gradient) RT=1.35 min, 492.44 $(M+H)^+$; $^1H$ NMR (400 MHz, METHANOL-D3) δ ppm 1.26-1.35 (m, 9 H) 2.09-2.15 (m, 4 H) 3.55-3.64 (m, 4 H) 3.85-3.93 (m, 2 H) 4.54-4.63 (m, J=6.08, 6.08, 6.08, 6.08, 6.08, 6.08 Hz, 1 H) 6.19 (s, 1 H) 6.34 (dd, J=4.83, 3.08 Hz, 1 H) 6.63 (dd, J=6.81, 2.86 Hz, 1 H) 6.66 (d, J=7.03 Hz, 1 H) 6.79 (d, J=8.79 Hz, 2 H) 6.91 (d, J=8.79 Hz, 1 H) 7.63 (d, J=8.79 Hz, 2 H) 7.75-7.80 (m, 1 H).

Example 140

4-((5-ethoxy-2-fluoro-3-isopropoxyphenyl)(6-morpholinopyridin-2-yl)methylamino)benzamidine bis-trifluoroacetic acid salt

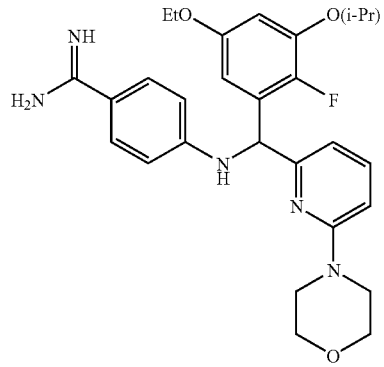

According to the procedure for the preparation of Example 139, reaction of Intermediate 138.1 with morpholine at 110° C. for 15 h and 130° C. for 5 h, followed by conversion to the amide oxime, acylation and hydrogenation as in Example 1 afforded after HPLC purification Example 140. LCMS (2 min gradient) RT=1.63 min, 508.44 $(M+H)^+$; $^1H$ NMR (400 MHz, METHANOL-D3) δ ppm 1.27 (t, J=7.03 Hz, 3 H) 1.31 (dd, J=6.15, 3.95 Hz, 6 H) 3.47-3.57 (m, 4 H) 3.79 (t, J=4.83 Hz, 4 H) 3.86 (q, J=7.03 Hz, 2 H) 4.53 (qd, J=6.08, 5.93 Hz, 1 H) 5.89 (s, 1 H) 6.45 (dd, J=4.83, 3.08 Hz, 1 H) 6.50 (dd, J=6.81, 2.86 Hz, 1 H) 6.72 (dd, J=10.55, 7.91 Hz, 2 H) 6.78 (d, J=9.23 Hz, 2 H) 7.53 (dd, J=8.35, 7.47 Hz, 1 H) 7.58 (d, J=9.23 Hz, 2 H).

Examples 141 and 142

(2R)-1-(6-((4-carbamimidoylphenylamino)(5-ethoxy-2-fluoro-3-isopropoxyphenyl)methyl)pyridin-2-yl)pyrrolidine-2-carboxamide bis-trifuoroacetic acid salt, diastereomers

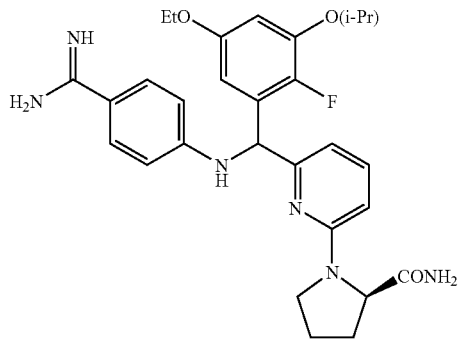

According to the procedure for the preparation of Example 139, reaction of Intermediate 138.1 with (R)-pyrrolidine-2-carboxamide at 150° C. for 20 h, followed by conversion to the amide oxime, acylation and hydrogenation as in Example 1 afforded after HPLC purification diastereomeric Examples 141 and 142. Example 141: LCMS (2 min gradient) RT=1.43 min, 535.3 (M+H)$^+$; $^1$H NMR (400 MHz, METHANOL-D3) δ ppm 1.25 (t, J=7.03 Hz, 3 H) 1.31 (dd, J=5.93, 3.74 Hz, 6H) 2.07-2.19 (m, 2 H) 2.34-2.40 (m, 1 H) 3.38-3.44 (m, 1 H) 3.69-3.74 (m, 1 H) 3.80-3.88 (m, 2 H) 4.44 (dd, J=8.79, 3.52 Hz, 1 H) 4.53 (dq, J=6.15, 6.01 Hz, 1 H) 5.90 (s, 1 H) 6.34 (dd, J=4.83, 3.08 Hz, 1 H) 6.45 (dd, J=6.81, 2.86 Hz, 1 H) 6.48 (d, J=8.35 Hz, 1 H) 6.62 (d, J=7.03 Hz, 1 H) 6.82 (d, J=8.79 Hz, 2 H) 7.48-7.52 (m, 1H) 7.58 (d, J=9.23 Hz, 2 H). Example 142: LCMS (2 min gradient) RT=1.52 min, 535.3 (M+H)$^+$; $^1$H NMR (400 MHz, METHANOL-D3) δ ppm 1.25 (t, J=6.81 Hz, 3 H) 1.31 (t, J=5.93 Hz, 6 H) 2.07-2.19 (m, 2 H) 2.35-2.43 (m, 1 H) 3.38-3.44 (m, 1 H) 3.70-3.75 (m, 1 H) 3.84 (qd, J=7.03, 2.20 Hz, 2 H) 4.43 (dd, J=8.57, 4.17 Hz, 1 H) 4.49-4.55 (m, J=6.15, 6.15, 6.15, 6.15 Hz, 1 H) 5.89 (s, 1 H) 6.41-6.47 (m, 2 H) 6.49 (d, J=8.35 Hz, 2 H) 6.69 (d, J=7.47 Hz, 1 H) 6.81 (d, J=8.79 Hz, 2 H) 7.49-7.53 (m, 1 H) 7.57 (d, J=9.23 Hz, 2 H).

Examples 145 and 146

(2S)-1-(6-((4-carbamimidoylphenylamino)(5-ethoxy-2-fluoro-3-isopropoxyphenyl)methyl)pyridin-2-yl)pyrrolidine-2-carboxamide bis-trifuoroacetic acid salt, diastereomers

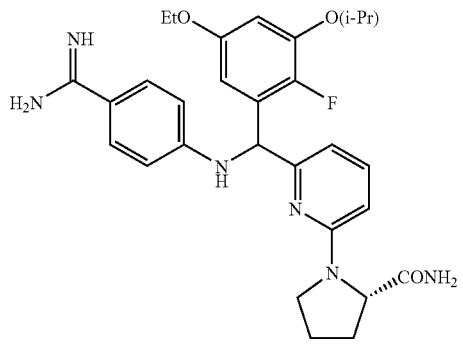

According to the procedure for the preparation of Example 139, reaction of Intermediate 138.1 with (S)-pyrrolidine-2-carboxamide at 150° C. for 20 h, followed by conversion to the amide oxime, acylation and hydrogenation as in Example 1 afforded after HPLC purification diastereomeric Examples 145 and 146. Example 145: LCMS (2 min gradient) RT=1.46 min, 535.3 (M+H)$^+$; $^1$H NMR (400 MHz, METHANOL-D3) δ ppm 1.25 (t, J=7.03 Hz, 3 H) 1.31 (dd, J=5.93, 3.74 Hz, 6H) 2.07-2.19 (m, 3 H) 2.34-2.41 (m, 1 H) 3.38-3.44 (m, 1 H) 3.69-3.75 (m, 1 H) 3.80-3.88 (m, 2 H) 4.45 (dd, J=8.57, 3.30 Hz, 1 H) 4.53 (qd, J=6.08, 5.93 Hz, 1 H) 5.90 (s, 1 H) 6.34 (dd, J=4.61, 2.86 Hz, 1 H) 6.45 (dd, J=6.81, 2.86 Hz, 1 H) 6.48 (d, J=8.35 Hz, 1 H) 6.62 (d, J=7.47 Hz, 1 H) 6.82 (d, J=8.79 Hz, 2 H) 7.50 (t, J=7.91 Hz, 1 H) 7.58 (d, J=9.23 Hz, 2 H). Example 146: LCMS (2 min gradient) RT=1.51 min, 535.3 (M+H)$^+$; $^1$H NMR (400 MHz, METHANOL-D3) δ ppm 1.25 (t, J=6.81 Hz, 3 H) 1.31 (t, J=5.93 Hz, 6 H) 2.07-2.19 (m, 2 H) 2.35-2.43 (m, 1 H) 3.38-3.44 (m, 1 H) 3.70-3.75 (m, 1 H) 3.84 (qd, J=7.03, 1.76 Hz, 2 H) 4.43 (dd, J=8.79, 3.96 Hz, 1 H) 4.52 (qd, J=6.08, 5.93 Hz, 1 H) 5.89 (s, 1 H) 6.43-6.50 (m, 3 H) 6.69 (d, J=7.03 Hz, 1 H) 6.81 (d, J=8.79 Hz, 2 H) 7.51 (t, J=7.91 Hz, 1 H) 7.57 (d, J=9.23 Hz, 2 H).

Example 147

4-((5-ethoxy-2-fluoro-3-isopropoxyphenyl)(6-(piperidin-1-yl)pyridin-2-yl)methylamino)benzamidine bis-trifuoroacetic acid salt

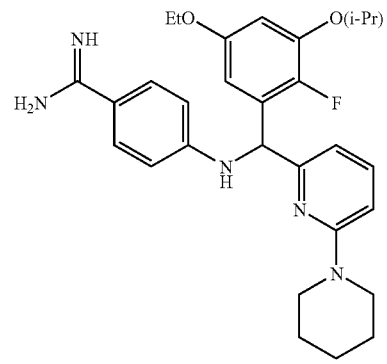

According to the procedure for the preparation of Example 139, reaction of Intermediate 138.1 with piperidine at 130° C. for 2 h and 150° C. for 1 h, followed by conversion to the amide oxime, acylation and hydrogenation as in Example 1 afforded after HPLC purification Example 147. LCMS (2 min gradient) RT=1.52 min, 506.4 (M+H)$^+$; $^1$H NMR (400 MHz, METHANOL-D3) δ ppm 1.28 (t, J=7.03 Hz, 3 H) 1.31 (dd, J=5.93, 3.74 Hz, 6 H) 1.61-1.72 (m, 6 H) 3.61 (d, J=5.71 Hz, 4 H) 3.87 (q, J=6.74 Hz, 2 H) 4.54 (qd, J=6.08, 5.93 Hz, 1 H) 5.94 (s, 1 H) 6.42-6.45 (m, 1 H) 6.52 (dd, J=6.81, 2.86 Hz, 1 H) 6.64 (d, J=7.03 Hz, 1 H) 6.79 (t, J=9.45 Hz, 3 H) 7.55 (t, J=8.13 Hz, 1 H) 7.59 (d, J=8.79 Hz, 2 H).

Example 148

4-((5-ethoxy-2-fluoro-3-isopropoxyphenyl)(6-((S)-2-(hydroxymethyl)pyrrolidin-1-yl)pyridin-2-yl)methylamino)benzamidine bis-trifluoroacetic acid salt

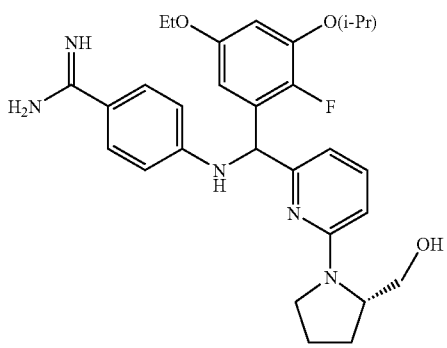

According to the procedure for the preparation of Example 139, reaction of Intermediate 138.1 with (S)-pyrrolidin-2-ylmethanol at 130° C. for 2 h and 150° C. for 1 h, followed by conversion to the amide oxime, acylation and hydrogenation as in Example 1 afforded after HPLC purification Example 148 as a 1:1 diastereomeric mixture. LCMS (2 min gradient) RT=1.20 min, 522.3 (M+H)+; $^1$H NMR (400 MHz, METHANOL-D3) δ ppm 1.26-1.35 (m, 12 H) 1.90-1.97 (m, 0.5 H) 2.05-2.17 (m, 0.5 H) 3.49-3.57 (m, 1 H) 3.61-3.73 (m, 3 H) 3.91 (q, J=7.03 Hz, 2 H) 4.05 (s, 1 H) 4.18-4.28 (m, 1 H) 4.58 (qd, J=6.08, 5.93 Hz, 1 H) 6.04 (d, J=2.64 Hz, 1 H) 6.43 (dd, J=4.83, 3.08 Hz, 1 H) 6.62 (dd, J=6.81, 2.86 Hz, 1 H) 6.74 (d, J=7.47 Hz, 0.5 H) 6.81 (t, J=7.25 Hz, 2.5 H) 6.90 (s, 1 H) 7.63 (dd, J=9.01, 2.86 Hz, 2 H) 7.78-7.83 (m, 1 H).

Example 149

4-((5-ethoxy-2-fluoro-3-isopropoxyphenyl)(6-((R)-2-(hydroxymethyl)pyrrolidin-1-yl)pyridin-2-yl)methylamino)benzamidine bis-trifluoroacetic acid salt

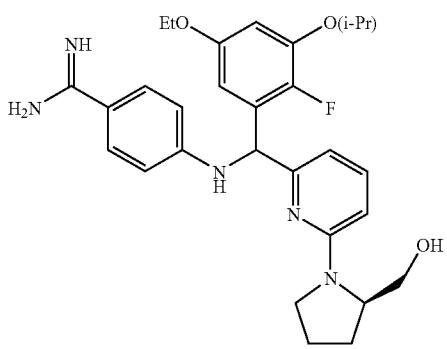

According to the procedure for the preparation of Example 139, reaction of Intermediate 138.1 with (R)-pyrrolidin-2-ylmethanol at 130° C. for 2 h and 150° C. for 1 h, followed by conversion to the amide oxime, acylation and hydrogenation as in Example 1 afforded after HPLC purification Example 149 as a 1:1 diastereomeric mixture. LCMS (2 min gradient) RT=1.21 min, 522.3 (M+H)+; $^1$H NMR (400 MHz, METHANOL-D3) δ ppm −0.29--0.22 (m, 12 H) 0.34-0.42 (m, 1 H) 0.49-0.61 (m, 3 H) 1.94-2.01 (m, 1 H) 2.06-2.12 (m, 2 H) 2.14 (t, J=5.27 Hz, 2 H) 2.36 (q, J=7.03 Hz, 2 H) 2.50 (m, 0.5 H) 2.67 (m, 0.5 H) 2.99-3.06 (m, J=6.04, 6.04, 5.93, 5.71 Hz, 1 H) 4.48 (s, 1 H) 4.86-4.89 (m, 1 H) 5.06 (dd, J=7.03, 2.64 Hz, 1 H) 5.19 (d, J=7.47 Hz, 0.5 H) 5.23-5.28 (m, 2.5 H) 5.35 (d, J=9.23 Hz, 1 H) 6.07 (dd, J=9.01, 2.86 Hz, 2 H) 6.21-6.27 (m, 1 H).

Example 150

4-((6-cyclopentylpyridin-2-yl)(5-ethoxy-2-fluoro-3-isopropoxyphenyl)methylamino)benzamidine bis-trifluoroacetic acid salt

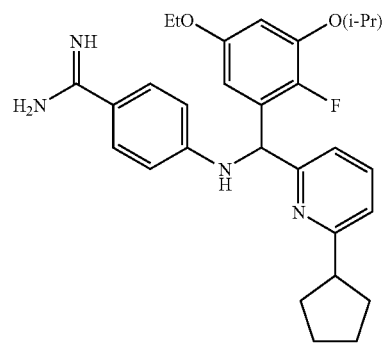

According to the procedure for the preparation of Example 138, Intermediate 138.1 coupled with cyclopentenylboronic acid, followed by conversion to the amide oxime, acylation and hydrogenation as in Example 1 afforded after HPLC purification Example 150. LCMS (2 min gradient) RT=1.64 min, 491.4 (M+H)+; $^1$H NMR (400 MHz, METHANOL-D3) δ ppm 1.27 (t, J=7.03 Hz, 3 H) 1.30-1.33 (m, 6 H) 1.69-1.93 (m, 6 H) 2.06-2.14 (m, J=8.79, 2.64 Hz, 2 H) 3.24-3.28 (m, 1 H) 3.86 (q, J=7.03 Hz, 2 H) 4.52-4.58 (m, J=6.15, 6.15, 6.15, 6.15 Hz, 1 H) 6.06 (s, 1 H) 6.38 (dd, J=4.83, 3.08 Hz, 1 H) 6.53 (dd, J=6.81, 2.86 Hz, 1 H) 6.78 (d, J=8.79 Hz, 2 H) 7.25 (d, J=7.47 Hz, 1 H) 7.30 (d, J=7.91 Hz, 1 H) 7.60 (d, J=8.79 Hz, 2 H) 7.76 (t, J=7.91 Hz, 1 H).

Example 151

4-((5-ethoxy-2-fluoro-3-isopropoxyphenyl)(6-((R)-2-(methoxymethyl)pyrrolidin-1-yl)pyridin-2-yl)methylamino)benzamidine bis trifluoroacetic acid salt

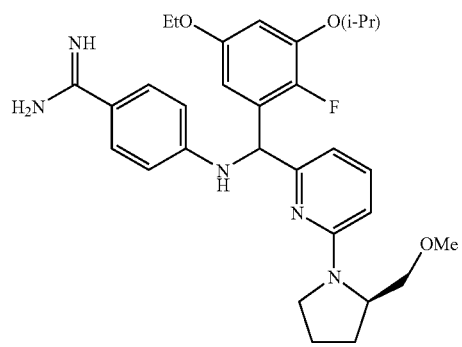

According to the procedure for the preparation of Example 139, reaction of Intermediate 138.1 with (R)-2-(methoxymethyl)pyrrolidine at 150° C. for 20 h, followed by conversion to the amide oxime, acylation and hydrogenation as in Example 1 afforded after HPLC purification Example 151 as a 1:1 diastereomeric mixture. LCMS (2 min gradient) RT=1.26 min, 536.3 (M+H)+; $^1$H NMR (400 MHz, METHANOL-D3) δ ppm 1.25-1.33 (m, 9 H) 1.98 (t, J=7.69 Hz, 1 H) 2.04-2.15 (m, 3 H) 3.10-3.18 (m, 1 H) 3.38 (s, 2 H) 3.44-3.56 (m, 2 H) 3.59-3.67 (m, 1 H) 3.85-3.93 (m, 2 H) 4.13-4.23 (m, 0.5 H) 4.33-4.41 (m, 0.5 H) 4.54-4.61 (m, 1 H) 6.02-6.11 (m, 0.5 H) 6.33-6.39 (m, 0.5 H) 6.45 (dd, J=4.83, 3.08 Hz, 0.5 H) 6.59-6.63 (m, 1 H) 6.66 (d, J=7.47 Hz, 0.5 H) 6.76-6.86 (m, 3 H) 7.60-7.67 (m, 2 H).

Example 152

4-((5-ethoxy-2-fluoro-3-isopropoxyphenyl)(6-((S)-2-(methoxymethyl)pyrrolidin-1-yl)pyridin-2-yl)methylamino)benzamidine bis trifluoroacetic acid salt

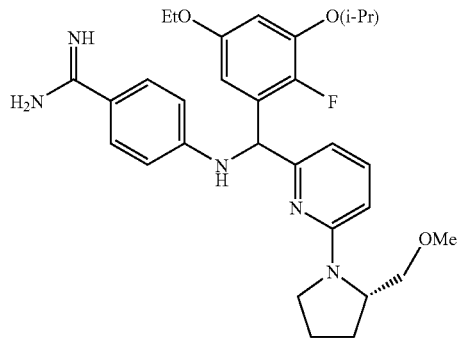

According to the procedure for the preparation of Example 139, reaction of Intermediate 138.1 with (S)-2-(methoxymethyl)pyrrolidine at 150° C. for 20 h, followed by conversion to the amide oxime, acylation and hydrogenation as in Example 1 afforded after HPLC purification Example 152 as a 1:1 diastereomeric mixture. LCMS (2 min gradient) RT=1.26 min, 536.3 (M+H)+; $^1$H NMR (400 MHz, METHANOL-D3) δ ppm 1.25-1.33 (m, 9 H) 1.98 (t, J=7.69 Hz, 1 H) 2.04-2.15 (m, 3 H) 3.10-3.18 (m, 1 H) 3.38 (s, 2 H) 3.44-3.56 (m, 2 H) 3.59-3.67 (m, 1 H) 3.85-3.93 (m, 2 H) 4.13-4.23 (m, 0.5 H) 4.33-4.41 (m, 0.5 H) 4.54-4.61 (m, 1 H) 6.02-6.11 (m, 0.5 H) 6.33-6.39 (m, 0.5 H) 6.45 (dd, J=4.83, 3.08 Hz, 0.5 H) 6.59-6.63 (m, 1 H) 6.66 (d, J=7.47 Hz, 0.5 H) 6.76-6.86 (m, 3 H) 7.60-7.67 (m, 2 H).

Example 154

4-((5-ethoxy-2-fluoro-3-isopropoxyphenyl)(6-methylpyridin-2-yl)methylamino)benzamidine bis-trifluoracetic acid salt

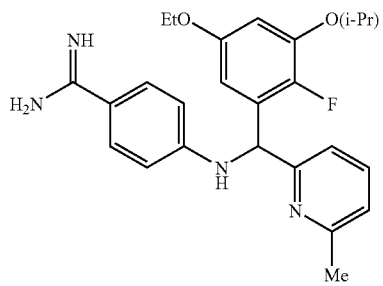

According to the procedure for the preparation of Example 153, 2-bromo-6-methylpyridine afforded Example 154. LCMS (2 min gradient) RT=1.25 min, 437.3 (M+H)+; $^1$H NMR (400 MHz, METHANOL-D3) δ ppm 1.28 (t, J=7.03, 3 H) 1.30 (d, J=6.59 Hz, 3H) 1.31 (d, J=6.59 Hz, 3H) 2.67 (s, 3 H) 3.88 (q, J=7.03 Hz, 2 H) 4.57 (ddd, J=11.97, 6.15, 6.04 Hz, 1 H) 6.13 (s, 1 H) 6.36 (dd, J=4.83, 2.64 Hz, 1 H) 6.60 (dd, J=6.81, 2.86 Hz, 1 H) 6.80 (d, J=8.79 Hz, 2 H) 7.42 (d, J=7.91 Hz, 1 H) 7.48 (d, J=7.91 Hz, 1 H) 7.62 (d, J=8.79 Hz, 2 H) 7.99 (t, J=7.91 Hz, 1 H).

Example 155

4-((5-ethoxy-2-fluoro-3-isopropoxyphenyl)(6-(trifluoromethyl)pyridin-2-yl)methylamino)benzamidine bis-trifluoracetic acid salt

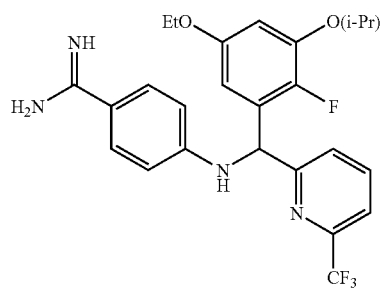

According to the procedure for the preparation of Example 153, 2-bromo-6-(trifluoromethyl)pyridine afforded Example 155. LCMS (2 min gradient) RT=1.66 min, 491.3 (M+H)+; $^1$H NMR (400 MHz, METHANOL-D3) δ ppm 1.28 (t, J=7.03, 3 H) 1.30 (d, J=6.59 Hz, 3H) 1.31 (d, J=6.59 Hz, 3H) 3.88 (q, J=7.03 Hz, 2 H) 4.55 (qd, J=6.08, 5.93 Hz, 1 H) 6.16 (s, 1 H) 6.45 (dd, J=4.61, 2.86 Hz, 1 H) 6.54 (dd, J=6.81, 2.86 Hz, 1 H) 6.82 (d, J=8.79 Hz, 2 H) 7.60 (d, J=8.79 Hz, 2 H) 7.69 (d, J=7.91 Hz, 1 H) 7.73 (d, J=7.91 Hz, 1 H) 8.01 (t, J=7.69 Hz, 1 H).

Example 156

4-((5-ethoxy-2-fluoro-3-isopropoxyphenyl)(6-ethoxypyridin-2-yl)methylamino)benzamidine bis-trifluoroacetic acid salt

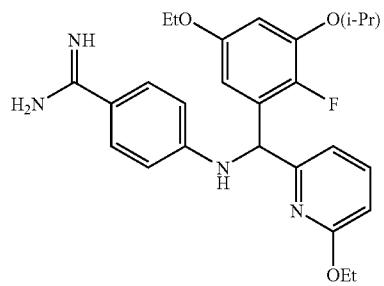

2-bromo-6-ethoxypyridine (156.1)

To a sodium ethoxide solution, prepared by addition of sodium (36 mg, 1.58 mmol) to ethanol (2 mL), was added 2,6-dibromopyridine (250 mg, 1.06 mmol). The mixture was stirred at 90° C. for 2.5 h, then was diluted with EtOAc. The organic phase was washed with water (2×) and brine, dried (Na$_2$SO$_4$) and concentrated. The crude material was purified by flash chromatography (0 to 10% EtOAc/hexanes gradient) to afford 163 mg of 156.1 as a colorless oil. LCMS (2 min gradient) RT=1.68 min, 202.1 (M+H)$^+$.

Example 156

According to the procedure for the preparation of Example 153, Intermediate 156.1 afforded Example 156. LCMS (2 min gradient) RT=1.73 min, 467.3 (M+H)$^+$; $^1$H NMR (400 MHz, METHANOL-D3) δ ppm 1.28-1.38 (m, 12 H) 3.88 (q, J=7.0 Hz, 2 H) 4.37 (q, J=7.0 Hz, 2 H) 4.53-4.60 (m, 1 H) 5.97 (s, 1 H) 6.48-6.51 (m, 1 H) 6.53 (dd, J=7.0, 3.1 Hz, 1 H) 6.68 (d, J=7.9 Hz, 1 H) 6.80 (d, J=8.8 Hz, 2 H) 6.99 (d, J=7.5 Hz, 1 H) 7.60-7.67 (m, 3 H).

Example 157

4-((5-ethoxy-2-fluoro-3-isopropoxyphenyl)(6-isopropoxypyridin-2-yl)methylamino)benzamidine bis-trifluoroacetic acid salt

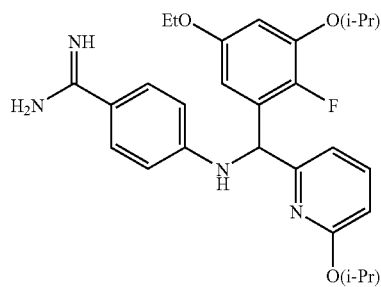

2-bromo-6-ethoxypyridine (157.1)

According to the procedure for the preparation of 156.1, reaction of sodium isopropoxide (1.58 mmol) in isopropanol with 2,6-dibromopyridine (250 mg, 1.06 mmol) afforded 109 mg of intermediate 157.1 as a colorless oil. LCMS (2 min gradient) RT=1.81 min, 216.13 (M+H)$^+$.

Example 157

According to the procedure for the preparation of Example 153, Intermediate 157.1 afforded Example 157. LCMS (2 min gradient) RT=1.80 min, 481.3 (M+H)$^+$; $^1$H NMR (400 MHz, METHANOL-D3) δ ppm 1.25-1.33 (m, 15 H) 3.87 (q, J=7.03 Hz, 2 H) 4.54 (qd, J=6.08, 5.93 Hz, 1 H) 5.25-5.31 (m, J=6.15, 6.15, 6.15, 6.15 Hz, 1 H) 5.94 (s, 1 H) 6.46 (dd, J=4.83, 2.64 Hz, 1 H) 6.51 (dd, J=6.81, 2.86 Hz, 1 H) 6.59 (d, J=7.91 Hz, 1 H) 6.79 (d, J=9.23 Hz, 2 H) 6.95 (d, J=7.03 Hz, 1 H) 7.56-7.62 (m, 3 H).

Example 158

4-((6-cyclobutoxypyridin-2-yl)(5-ethoxy-2-fluoro-3-isopropoxyphenyl)methylamino)benzamidine bis-trifluoroacetic acid salt

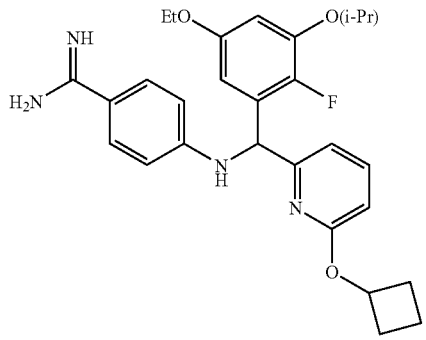

2-bromo-6-cyclobutoxypyridine (158.1)

To cyclobutanol (1 mL), was added sodium (36 mg, 1.56 mmol). When the sodium was consumed, the mixture was diluted with 1 mL THF and 2,6-dibromopyridine (250 mg, 1.06 mmol). The mixture was stirred at 90° C. for 3 h, then was diluted with EtOAc. The organic phase was washed with water (2×) and brine, dried (Na$_2$SO$_4$) and concentrated. The crude material was purified by flash chromatography (0 to 10% EtOAc/hexanes gradient) to afford 106 mg of 158.1 as a colorless oil. LCMS (2 min gradient) RT=1.87 min, 228.17 (M+H)$^+$.

Example 158

According to the procedure for the preparation of Example 153, Intermediate 158.1 afforded Example 158. LCMS (2 min gradient) RT=1.84 min, 493.3 (M+H)$^+$; $^1$H NMR (400 MHz, METHANOL-D3) δ ppm 1.24-1.35 (m, 9 H) 1.65-1.73 (m, 1 H) 1.82 (q, J=10.11 Hz, 1 H) 2.02-2.12 (m, 2 H) 2.35-2.46 (m, 2H) 3.87 (q, J=6.88 Hz, 2 H) 4.54 (qd, J=6.08, 5.93 Hz, 1 H) 5.10-5.18 (m, 1 H) 5.93 (s, 1 H) 6.45 (dd, J=4.83, 3.08 Hz, 1 H) 6.51 (dd, J=6.81, 2.86 Hz, 1 H) 6.62 (d, J=8.35 Hz, 1 H) 6.78 (d, J=9.23 Hz, 2 H) 6.98 (d, J=7.03 Hz, 1 H) 7.57-7.64 (m, 3 H).

Example 159

4-((6-(cyclopentyloxy)pyridin-2-yl)(5-ethoxy-2-fluoro-3-isopropoxyphenyl)methylamino)benzamidine bis-trifluoroacetic acid salt

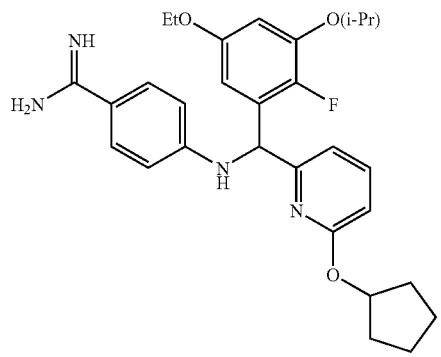

2-bromo-6-(cyclopentyloxy)pyridine (159.1)

To cyclopentanol (1 mL), was added sodium (36 mg, 1.56 mmol). When the sodium was consumed, the mixture was diluted with 1 mL THF and 2,6-dibromopyridine (250 mg, 1.06 mmol). The mixture was stirred at 90° C. for 3 h, sodium hydride (20 mg) was added and the mixture was stirred an additional 1 h at 90° C. The reaction was diluted with EtOAc. The organic phase was washed with water (2×) and brine, dried (Na$_2$SO$_4$) and concentrated. The crude material was purified by flash chromatography (0 to 10% EtOAc/hexanes gradient) to afford 222 mg of 159.1 as a colorless oil. LCMS (2 min gradient) RT=2.01 min, 242.15 (M+H)$^+$.

Example 159

According to the procedure for the preparation of Example 153, Intermediate 159.1 afforded Example 159. LCMS (2 min gradient) RT=1.90 min, 507.3 (M+H)$^+$; $^1$H NMR (400 MHz, METHANOL-D3) δ ppm 1.26-1.33 (m, 9 H) 1.58-1.67 (m, 2 H) 1.70-1.80 (m, 4 H) 1.89-1.99 (m, 2 H) 3.87 (q, J=7.03 Hz, 2 H) 4.54 (qd, J=6.08, 5.93 Hz, 1 H) 5.37 (ddd, J=5.93, 3.30, 3.08 Hz, 1 H) 5.94 (s, 1 H) 6.47 (dd, J=4.83, 3.08 Hz, 1 H) 6.51 (dd, J=6.81, 2.86 Hz, 1 H) 6.62 (d, J=7.91 Hz, 1 H) 6.79 (d, J=8.79 Hz, 2 H) 6.96 (d, J=7.47 Hz, 1 H) 7.57-7.62 (m, 3 H).

Example 160

4-((5-ethoxy-2-fluoro-3-isopropoxyphenyl)(pyridin-2-yl)methylamino)benzamidine bis-trifluoroacetic acid salt

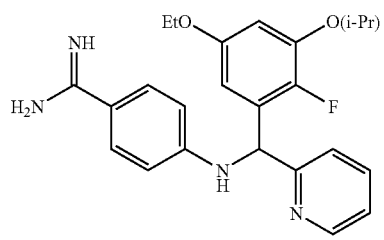

According to the procedure for the preparation of Example 153, 2-bromopyridine afforded Example 160. LCMS (2 min gradient) RT=1.31 min, 423.3 (M+H)$^+$; $^1$H NMR (400 MHz, METHANOL-D3) δ ppm 1.25-1.33 (m, 9 H) 3.87 (q, J=7.03 Hz, 2 H) 4.55 (qd, J=6.08, 5.93 Hz, 1 H) 6.06 (s, 1 H) 6.39 (dd, J=4.61, 2.86 Hz, 1 H) 6.54 (dd, J=6.81, 2.86 Hz, 1 H) 6.78 (d, J=8.79 Hz, 2 H) 7.38 (dd, J=7.69, 5.05 Hz, 1 H) 7.49 (d, J=7.91 Hz, 1 H) 7.59 (d, J=9.23 Hz, 2 H) 7.84-7.88 (m, 1 H) 8.57 (d, J=4.83 Hz, 1 H).

Example 161

4-((5-ethoxy-2-fluoro-3-isopropoxyphenyl)(6-propoxypyridin-2-yl)methylamino)benzamidine bis-trifluoroacetic acid salt

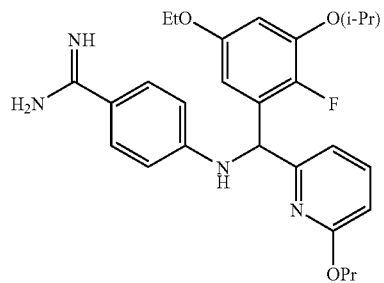

2-bromo-6-propoxypyridine (161.1)

To a sodium propan-1-olate solution, prepared by addition of sodium (36 mg, 1.58 mmol) to propanol (1 mL), was added 2,6-dibromopyridine (250 mg, 1.06 mmol). The mixture was stirred at 90° C. for 2 h, then was diluted with EtOAc. The organic phase was washed with water (2×) and brine, dried (Na$_2$SO$_4$) and concentrated. The crude material was purified by flash chromatography (0 to 10% EtOAc/hexanes gradient) to afford 189 mg of Intermediate 161.1 as a colorless oil. LCMS (2 min gradient) RT=1.82 min, 216.1 (M+H)$^+$.

Example 161

According to the procedure for the preparation of Example 153, Intermediate 161.1 afforded Example 156. LCMS (2 min gradient) RT=1.84 min, 481.3 (M+H)$^+$; $^1$H NMR (400 MHz, METHANOL-D3) δ ppm 0.99 (t, J=7.47 Hz, 3 H) 1.26-1.33 (m, 9 H) 1.70-1.79 (m, J=7.14, 7.14, 7.14, 7.14, 7.03 Hz, 2 H) 3.87 (q, J=7.03 Hz, 2 H) 4.26 (td, J=6.70, 1.54 Hz, 2 H) 4.54 (qd, J=6.08, 5.93 Hz, 1 H) 5.94 (s, 1 H) 6.47 (dd, J=4.83, 3.08 Hz, 1 H) 6.51 (dd, J=6.59, 3.08 Hz, 1 H) 6.66 (d, J=8.35 Hz, 1 H) 6.78 (d, J=9.23 Hz, 2 H) 6.97 (d, J=7.47 Hz, 1 H) 7.57-7.64 (m, 3 H).

Example 162

4-((5-ethoxy-2-fluoro-3-isopropoxyphenyl)(6-isobutoxypyridin-2-yl)methylamino)benzamidine bis-trifluoroacetic acid salt

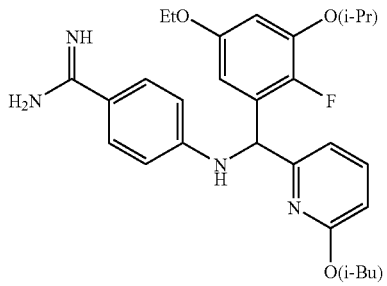

2-bromo-6-isobutoxypyridine (162.1)

To 2-methylpropan-1-ol (1 mL), was added sodium (36 mg, 1.56 mmol). The mixture was stirred at 70° C. until sodium was ~75% consumed, then 1 mL THF and the mixture was stirred an additional 15 min. To this mixture, 2,6-dibromopyridine (250 mg, 1.06 mmol). The mixture was stirred at 90° C. for 2 h, then was diluted with EtOAc. The organic phase was washed with water (2×) and brine, dried ($Na_2SO_4$) and concentrated. The crude material was purified by flash chromatography (0 to 10% EtOAc/hexanes gradient) to afford 185 mg of Intermediate 162.1 as a colorless oil. LCMS (2 min gradient) RT=1.98 min, 230.2 $(M+H)^+$.

Example 162

According to the procedure for the preparation of Example 153, Intermediate 162.1 afforded Example 162. LCMS (2 min gradient) RT=1.91 min, 495.2 $(M+H)^+$; $^1H$ NMR (400 MHz, METHANOL-D3) δ ppm 0.98 (d, J=7.03 Hz, 6 H) 1.25-1.34 (m, 9 H) 1.97-2.08 (m, 1 H) 3.87 (q, J=7.03 Hz, 2 H) 4.07 (ddd, J=12.74, 10.55, 6.59 Hz, 2 H) 4.50-4.57 (m, J=6.15, 6.15, 6.15, 6.15 Hz, 1 H) 5.94 (s, 1 H) 6.46-6.48 (m, 1 H) 6.52 (dd, J=6.81, 2.86 Hz, 1 H) 6.67 (d, J=8.35 Hz, 1 H) 6.78 (d, J=8.79 Hz, 2 H) 6.97 (d, J=7.47 Hz, 1 H) 7.59 (d, J=9.23 Hz, 2 H) 7.63 (d, J=8.35 Hz, 1 H).

Example 163

4-((5-ethoxy-2-fluoro-3-isopropoxyphenyl)(6-ethylpyridin-2-yl)methylamino)benzamidine bis-trifluoroacetic acid salt

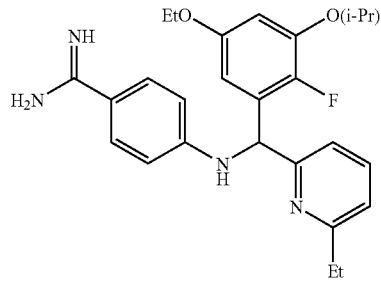

2-bromo-6-ethylpyridine (163.1)

To a solution of 2-bromo-6-methylpyridine (302 mg, 1.76 mmol) an 10 mL THF at −78° C., was added a solution of lithium diisopropylamide (1.8 M in heptane/THF/ethylbenzene, 1.07 mL, 1.93 mmol). The bright orange/red mixture was treated with iodomethane (0.20 mL, 3.2 mmol). The mixture was stirred at −78° C. for 10 min, then was removed from the ice bath and stirred 30 min. The reaction was quenched with sat. $NH_4Cl$, then was diluted with EtOAc. The organic phase was washed with water (2×) and brine, dried ($Na_2SO_4$) and concentrated. The crude residue was purified by flash chromatography (0 to 20% EtOAc/hexanes gradient) to afford 157 mg of Intermediate 163.1 as a colorless oil. LCMS (2 min gradient) RT=1.26 min, 186.0 $(M+H)^+$.

Example 163

According to the procedure for the preparation of Example 153, Intermediate 163.1 afforded Example 163. LCMS (2 min gradient) RT=1.38 min, 451.2 $(M+H)^+$; $^1H$ NMR (400 MHz, METHANOL-D3) δ ppm 1.25-1.34 (m, 12 H) 2.88 (q, J=7.76 Hz, 2 H) 3.86 (q, J=6.88 Hz, 2 H) 4.55 (qd, J=6.08, 5.93 Hz, 1 H) 6.05 (s, 1 H) 6.37 (dd, J=4.83, 2.64 Hz, 1 H) 6.55 (dd, J=6.81, 2.86 Hz, 1 H) 6.78 (d, J=8.79 Hz, 2 H) 7.28 (dd, J=9.23, 8.35 Hz, 2 H) 7.59 (d, J=8.79 Hz, 2 H) 7.78 (t, J=7.69 Hz, 1 H).

Example 164

4-((6-(dimethylamino)pyridin-2-yl)(5-ethoxy-2-fluoro-3-isopropoxyphenyl)methylamino)benzamidine bis-trifluoroacetic acid salt

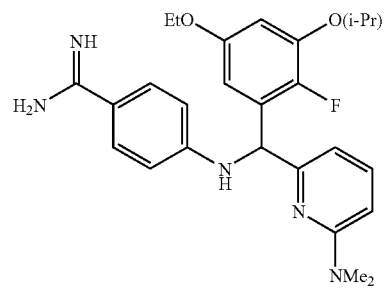

4-((6-(dimethylamino)pyridin-2-yl)(5-ethoxy-2-fluoro-3-isopropoxyphenyl)methylamino)benzonitrile (164.1)

A mixture of Intermediate 138.1 (30 mg, 0.124 mmol) and diethanolamine (32.6 mg, 0.31 mmol) in DMF (0.5 mL) was stirred at 130° C. for 5 h, then 140° C. for 15 h. The mixture was diluted with EtOAc, washed with water (2×) and brine, dried ($Na_2SO_4$), filtered through a 1" pad of silica gel, then was concentrated. The crude residue was used in the following step without further purification.

Example 164

A solution of Intermediate 164.1 (28.5 mg) in 1.5 mL 3 M $NH_2OH$ in DMSO was converted to the amide oxime, acylated and hydrogenated as in Example 1 to afford after HPLC purification 25.6 mg of Example 164. LCMS (2 min gradient) RT=1.27 min, 466.2 $(M+H)^+$; $^1H$ NMR (400 MHz, METHANOL-D3) δ ppm 1.28 (t, J=7.03 Hz, 3 H) 1.31 (dd, J=5.93, 4.17 Hz, 6 H) 3.19 (s, 6 H) 3.87 (q, J=7.03 Hz, 2 H) 4.56 (dq, J=6.15, 6.01 Hz, 1 H) 6.03 (s, 1 H) 6.41 (dd, J=4.61, 2.86 Hz, 1 H) 6.56 (dd, J=6.81, 2.86 Hz, 1 H) 6.64 (d, J=7.03 Hz, 1 H) 6.76-6.81 (m, 3 H) 7.58-7.65 (m, 3 H).

Example 165

4-((5-ethoxy-2-fluoro-3-isopropoxyphenyl)(6-(methylthio)pyridin-2-yl)methylamino)benzamidine bis-trifluoroacetic acid salt

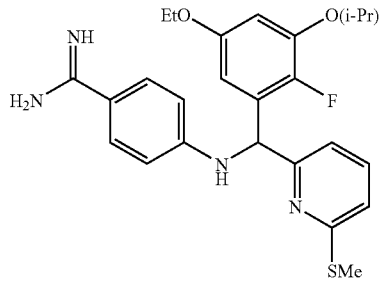

2-bromo-6-(methylthio)pyridine (165.1)

To a solution of 2,6-dibromopyridine (200 mg, 0.844 mmol) in DMF (2 mL), was added sodium methanethiolate (65.1 mg, 0.929 mmol). The mixture was stirred at rt for 16 h, then was diluted with EtOAc. The organic phase was washed with water (2×) and brine, dried ($Na_2SO_4$) and concentrated. The crude residue was purified by flash chromatography (0 to 20% EtOAc/hexanes gradient) to afford Intermediate 165.1.

Example 165

According to the procedure for the preparation of Example 153, Intermediate 165.1 afforded Example 165. LCMS (2 min gradient) RT=1.73 min, 469.2 (M+H)$^+$; $^1$H NMR (400 MHz, METHANOL-D3) δ ppm 1.28 (t, J=7.03 Hz, 3H) 1.31 (d, J=6.2 Hz, 3 H) 1.32 (d, J=6.2 Hz, 3 H) 2.53 (s, 3 H) 3.87 (q, J=7.03 Hz, 2 H) 4.54 (dq, J=6.15, 6.01 Hz, 1 H) 6.00 (s, 1 H) 6.45 (dd, J=4.83, 3.08 Hz, 1 H) 6.52 (dd, J=6.81, 2.86 Hz, 1 H) 6.79 (d, J=9.23 Hz, 2 H) 7.09 (d, J=7.47 Hz, 1 H) 7.15 (d, J=7.91 Hz, 1 H) 7.54-7.61 (m, 3 H).

Examples 166 and 167

4-((5-ethoxy-2-fluoro-3-isopropoxyphenyl)(6-(methylamino)pyridin-2-yl)methylamino)benzamidine (166)

N-(6-((4-carbamimidoylphenylamino)(5-ethoxy-2-fluoro-3-isopropoxyphenyl)methyl)pyridin-2-yl)-N-methylacetamide (167)

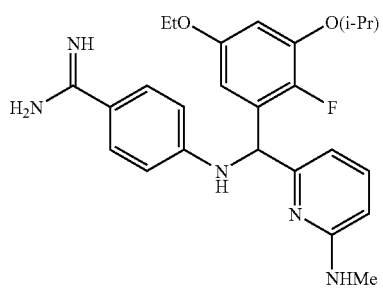

Example 166

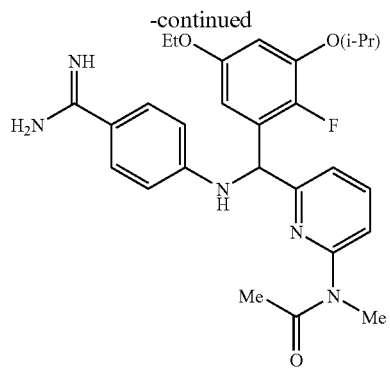

Example 167

4-((5-ethoxy-2-fluoro-3-isopropoxyphenyl)(6-(methylamino)pyridin-2-yl)methylamino)benzonitrile (166.1)

A mixture of Intermediate 138.1 (30 mg, 0.124 mmol) and diethanolamine (32.6 mg, 0.31 mmol) in N-methylformamide (0.5 mL) was stirred at 130° C. for 5 h, 140° C. for 7 h, and 140° C. for 16 h. The mixture was diluted with EtOAc, washed with water (2×) and brine, dried ($Na_2SO_4$), filtered through a 0.5" pad of silica gel, then was concentrated to afford 28 mg of 166.1 as a yellow residue. LCMS (2 min gradient) RT=1.50 min, 435.3 (M+H)$^+$.

Examples 166 and 167

A solution of Intermediate 166.1 (28 mg) in 1.5 mL 3 M $NH_2OH$ in DMSO was converted to the amide oxime, acylated and hydrogenated as in Example 1 to afford after HPLC purification 9.8 mg of Example 166 and 7.1 mg of Example 167. Example 166: LCMS (2 min gradient) RT=1.22 min, 452.3 (M+H)$^+$; $^1$H NMR (400 MHz, METHANOL-D3) δ ppm 1.28-1.33 (m, 12 H) 3.02 (s, 3 H) 3.90 (qd, J=6.96, 2.42 Hz, 2 H) 4.56-4.62 (m, J=6.15, 6.15, 6.15, 6.15 Hz, 1 H) 6.09 (s, 1 H) 6.37 (dd, J=4.83, 3.08 Hz, 1 H) 6.63-6.68 (m, 2 H) 6.81 (d, J=8.79 Hz, 2 H) 6.91 (d, J=8.79 Hz, 1 H) 7.64 (d, J=8.79 Hz, 2 H) 7.80 (t, J=8.13 Hz, 1 H). Example 167: LCMS (2 min gradient) RT=1.42 min, 494.3 (M+H)$^+$; $^1$H NMR (400 MHz, METHANOL-D3) δ ppm 1.26-1.32 (m, 12 H) 1.96 (s, 3 H) 3.34 (s, 3 H) 3.87 (q, J=6.74 Hz, 2 H) 4.54 (qd, J=6.08, 5.93 Hz, 1 H) 6.07 (s, 1 H) 6.46 (dd, J=4.83, 3.08 Hz, 1 H) 6.53 (dd, J=6.81, 2.86 Hz, 1 H) 6.82 (d, J=9.23 Hz, 2 H) 7.35 (d, J=7.91 Hz, 1 H) 7.40 (d, J=7.91 Hz, 1 H) 7.59 (d, J=9.23 Hz, 2 H) 7.88 (t, J=7.69 Hz, 1 H).

Example 168

4-((6-amino-2-(methylthio)pyrimidin-4-yl)(5-ethoxy-2-fluoro-3-isopropoxyphenyl)methylamino)benzamidine tris-trifluoroacetic acid salt

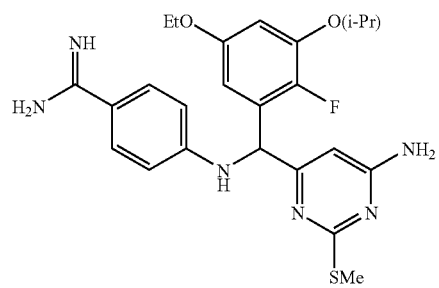

4-((6-chloro-2-(methylthio)pyrimidin-4-yl)(5-ethoxy-2-fluoro-3-isopropoxyphenyl)methylamino)benzonitrile (168.1)

To THF (6 mL) at −40° C., was added a solution of BuLi (1.6 M in hexanes, 0.428 mL, 0.685 mmol). To this solution was added 2,2,6,6-tetramethylpiperidine (0.121 mL, 0.715 mmol). The mixture was stirred 5 min at −40° C., then was cooled to −78° C. To this solution was added 4-chloro-2-(methylthio)pyrimidine (50 mg, 0.311 mmol) in 0.5 mL THF, dropwise. The dark brown mixture was stirred at −78° C. for 30 min, then a solution of Intermediate 7.2 (102 mg, 0.311 mmol) in 0.6 mL THF was added dropwise. The mixture was stirred at −78° C. for 15 min, then was allowed to warm to −50° C. over 30 min. The reaction was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 24 mg of Intermediate 168.1 as a colorless solid. LCMS (4 min gradient, A=95% H$_2$O/5% CH$_3$CN/0.1% TFA, B=5% H$_2$O/95% CH$_3$CN/0.1% TFA) RT=4.00 min, 487.6 (M+H)$^+$.

Example 168

A solution of Intermediate 168.1 (24 mg) in 1.5 mL 3 M NH$_2$OH in DMSO was converted to the amide oxime, acylated and hydrogenated as in Example 1 to afford after HPLC purification 17.8 mg of Example 168. LCMS (2 min gradient) RT=1.31 min, 485.2 (M+H)$^+$; $^1$H NMR (400 MHz, METHANOL-D3) δ ppm 1.28-1.34 (m, 12 H) 2.57 (s, 3 H) 3.91 (qd, J=6.96, 1.98 Hz, 2 H) 4.59 (dq, J=6.15, 6.01 Hz, 1 H) 5.80 (s, 1 H) 6.25 (s, 1 H) 6.39 (dd, J=4.61, 2.86 Hz, 1 H) 6.64 (dd, J=6.81, 2.86 Hz, 1 H) 6.79 (d, J=8.79 Hz, 2 H) 7.63 (d, J=8.79 Hz, 2 H).

Example 169

4-((5-ethoxy-2-fluoro-3-isopropoxyphenyl)(2-methoxypyrimidin-4-yl)methylamino)benzamidine bis-trifluoroacetic acid salt

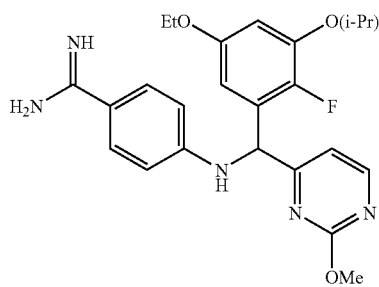

4-((5-ethoxy-2-fluoro-3-isopropoxyphenyl)(2-methoxypyrimidin-4-yl)methylamino)benzonitrile (169.1)

To a solution of 2,2,6,6-tetramethylpiperidine (0.135 mL, 0.799 mmol) in 3 mL THF at −30° C., was added BuLi (1.6 M in hexanes, 0.455 mL, 0.728 mmol). The mixture was stirred 5 min at −30° C., then was cooled to −78° C. To this solution was added 2-methoxypyrimidine (20 mg, 0.182 mmol) in 0.5 mL THF, dropwise. The mixture was stirred at −78° C. for 5 min, then a solution of Intermediate 7.2 (59.4 mg, 0.182 mmol) in 0.5 mL THF was added dropwise. The mixture was stirred at −78° C. for 1.5 h, then was quenched with sat. NH$_4$Cl. The mixture was diluted with EtOAc, washed with H$_2$O and brine, dried (Na$_2$SO$_4$) and concentrated. The crude product was purified by flash chromatography (0 to 50% EtOAc/hexanes gradient) to afford 30.2 mg of Intermediate 169.1 as a colorless solid. LCMS (2 min gradient) RT=1.95 min, 437.2 (M+H)$^+$.

Example 169

A solution of Intermediate 169.1 (24 mg) in 1.5 mL 3 M NH$_2$OH in DMSO was converted to the amide oxime, acylated and hydrogenated as in Example 1 to afford after HPLC purification 18.7 mg of Example 169. LCMS (2 min gradient) RT=1.52 min, 454.2 (M+H)$^+$; $^1$H NMR (400 MHz, METHANOL-D3) δ ppm 1.24-1.36 (m, 12 H) 3.89 (q, J=7.03 Hz, 2 H) 4.00 (s, 3 H) 4.56 (qd, J=6.08, 5.93 Hz, 1 H) 5.98 (s, 1 H) 6.44 (dd, J=4.83, 2.64 Hz, 1 H) 6.57 (dd, J=6.81, 2.86 Hz, 1 H) 6.81 (d, J=8.79 Hz, 2 H) 7.15 (d, J=5.27 Hz, 1 H) 7.60 (d, J=8.79 Hz, 2 H) 8.51 (d, J=5.27 Hz, 1 H).

Example 170

4-((5-ethoxy-2-fluoro-3-isopropoxyphenyl)(2-(methylthio)pyrimidin-4-yl)methylamino)benzamidine bis-trifluoroacetic acid salt

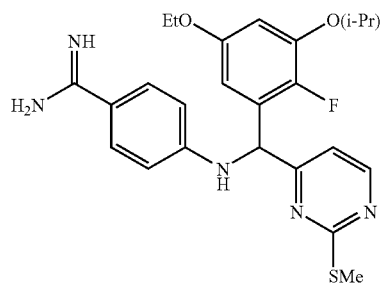

4-((5-ethoxy-2-fluoro-3-isopropoxyphenyl)(2-(methylthio)pyrimidin-4-yl)methylamino)benzonitrile (170.1)

To a solution of 2,2,6,6-tetramethylpiperidine (0.092 mL, 0.547 mmol) in 2 mL THF at −30° C., was added BuLi (1.6M in hexanes, 0.327 mL, 0.728 mmol). The mixture was stirred 5 min at −30° C., then was cooled to −78° C. To this solution was added 2-(methylthio)pyrimidine (30 mg, 0.238 mmol) in 0.5 mL THF, dropwise. The mixture was stirred at −78° C. for 5 min, then a solution of Intermediate 7.2 (78 mg, 0.238 mmol) in 0.5 mL THF was added dropwise. The mixture was stirred at −78° C. for 0.5 h, then was quenched with sat. NH$_4$Cl. The mixture was diluted with EtOAc, washed with H$_2$O and brine, dried (Na$_2$SO$_4$) and concentrated. The crude product was purified by flash chromatography (0 to 50% EtOAc/hexanes gradient) to afford 40.0 mg of Intermediate 170.1. LCMS (2 min gradient) RT=2.05 min, 453.2 (M+H)$^+$.

Example 170

A solution of Intermediate 170.1 (35 mg) in 2 mL 3M NH$_2$OH in DMSO was converted to the amide oxime, acylated and hydrogenated as in Example 1 to afford after HPLC purification 29.0 mg of Example 170. LCMS (2 min gradient) RT=1.65 min, 470.2 (M+H)+; $^1$H NMR (400 MHz, METHANOL-D3) δ ppm 1.30-1.34 (m, 12 H) 2.53 (s, 3 H) 3.90 (q, J=7.0 Hz, 2 H) 4.54-4.59 (m, 1 H) 5.99 (s, 1 H) 6.45 (dd, J=4.8, 3.0 Hz, 1 H) 6.57 (dd, J=6.6, 3.0 Hz, 1 H) 6.82 (d, J=8.8 Hz, 2 H) 7.17 (d, J=5.3 Hz, 1 H) 7.61 (d, J=8.8 Hz, 2 H) 8.61 (d, J=5.2 Hz, 1 H).

Example 171

4-((5-ethoxy-2-fluoro-3-isopropoxyphenyl)(4-methyl-1H-benzo[d]imidazol-2-yl)methylamino)benzamidine bis-trifluoroacetic acid salt

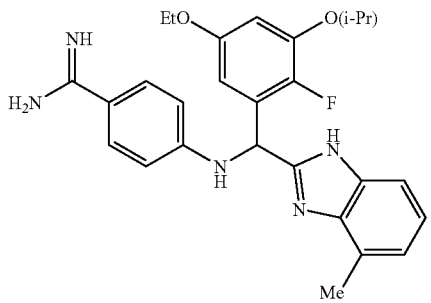

4-methyl-1H-benzo[d]imidazole (171.1)

A solution of 3-methylbenzene-1,2-diamine (170 mg) in formic acid (2 mL) was heated at 140° C. for 5 min in a microwave reactor. The mixture was diluted with water, neutralized with sat. NaHCO$_3$, then extracted with EtOAc. The organic phase was washed with water and brine, dried (Na$_2$SO$_4$), filtered through a 1" pad of silica gel and concentrated to afford 122 mg of Intermediate 171.1 as a tan solid.

1-(benzyloxymethyl)-4-methyl-1H-benzo[d]imidazole (171.2)

To a solution of Intermediate 171.1 (130 mg, 0.984 mmol) in 3 mL THF at rt, was added sodium hydride (60%, 43 mg, 1.1 mmol). The mixture was stirred 5 min, then BOM-Cl (80%, 0.204 mL, 1.18 mmol) was added. The mixture was stirred at rt for 2 h, then was diluted with EtOAc, washed with H$_2$O (2×) and brine, dried (Na$_2$SO$_4$) and concentrated. The crude product was purified by flash chromatography (0 to 100% EtOAc/hexanes gradient) to afford 60 mg of Intermediate 171.2.

4-((1-(benzyloxymethyl)-4-methyl-1H-benzo[d]imidazol-2-yl)(5-ethoxy-2-fluoro-3-isopropoxyphenyl) methylamino)benzonitrile (171.3)

To a mixture of Intermediate 171.2 (47 mg, 0.186 mmol) in 1 mL THF at −78° C., was added BuLi (1.6 M in THF, 0.128 mL, 0.205 mmol). The mixture was stirred at −78° C. for 15 min, then a solution of Intermediate 7.2 (61 mg, 0.186 mmol) in 0.5 mL THF was added dropwise. The mixture was stirred at −78° C. for 20 min and at rt for 30 min., then was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 68.5 mg of Intermediate 171.3 as a colorless solid. LCMS (2 min gradient) RT=2.09 min, 579.1 (M+H)+.

Example 171

A solution of Intermediate 171.3 (68 mg) in 2 mL 3M NH$_2$OH in DMSO was converted to the amide oxime, acylated and hydrogenated (24 h) as in Example 1 to afford after HPLC purification 27.8 mg of Example 171. LCMS (2 min gradient) RT=1.65 min, 470.2 (M+H)+; $^1$H NMR (400 MHz, METHANOL-D3) δ ppm 1.26-1.35 (m, 9 H) 2.61 (s, 3 H) 3.94 (q, J=6.74 Hz, 2 H) 4.62 (qd, J=5.86, 5.71 Hz, 1 H) 6.48 (s, 1 H) 6.49-6.52 (m, 1 H) 6.72 (dd, J=6.81, 2.86 Hz, 1 H) 6.91 (d, J=8.79 Hz, 2 H) 7.31 (d, J=7.03 Hz, 1 H) 7.36-7.42 (m, 1 H) 7.50 (d, J=8.35 Hz, 1 H) 7.67 (d, J=8.79 Hz, 2 H).

Example 172

4-((5,6-dimethyl-1H-benzo[d]imidazol-2-yl)(5-ethoxy-2-fluoro-3-isopropoxyphenyl)methylamino) benzamidine bis-trifluoroacetic acid salt

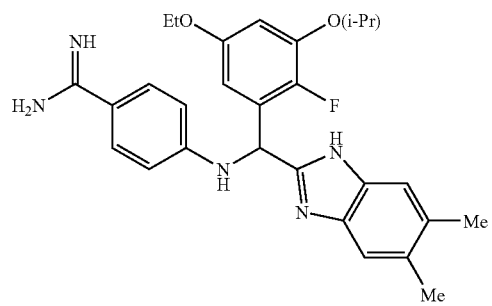

According to the procedure for the preparation of Example 171, 5,6-dimethyl-1H-benzo[d]imidazole was converted to Example 172. LCMS (2 min gradient) RT=1.48 min, 490.1 (M+H)+; $^1$H NMR (400 MHz, METHANOL-D3) δ ppm 1.28-1.35 (m, 9 H) 2.42 (s, 6 H) 3.94 (q, J=6.74 Hz, 2 H) 4.62 (dq, J=5.93, 5.79 Hz, 1 H) 6.51 (s, 2 H) 6.73 (d, J=6.15 Hz, 1 H) 6.93 (d, J=7.47 Hz, 2 H) 7.47 (s, 2 H) 7.68 (d, J=7.47 Hz, 2 H).

Example 173

4-((5-ethoxy-2-fluoro-3-isopropoxyphenyl)(5-methyl-1H-benzo[d]imidazol-2-yl)methylamino)benzamidine bis-trifluoroacetic acid salt

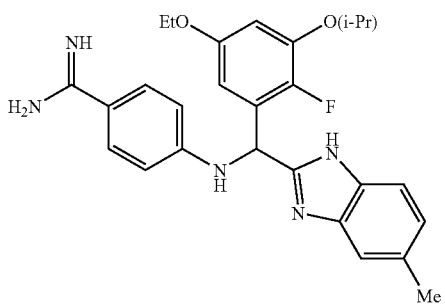

According to the procedure for the preparation of Example 171, 5-methyl-1H-benzo[d]imidazole was converted to Example 173. LCMS (2 min gradient) RT=1.42 min, 476.1 (M+H)+; 1H NMR (400 MHz, METHANOL-D3) δ ppm 1.28-1.35 (m, 9 H) 2.51 (s, 3 H) 3.91-3.98 (m, 2 H) 4.58-4.65 (m, J=5.93, 5.66, 5.66, 5.66, 5.66 Hz, 1 H) 6.52 (s, 2 H) 6.73 (dd, J=6.59, 2.64 Hz, 1 H) 6.93 (d, J=8.79 Hz, 2 H) 7.38 (d, J=8.35 Hz, 1 H) 7.50 (s, 1 H) 7.56-7.60 (m, 1 H) 7.68 (d, J=8.79 Hz, 2 H).

Example 174

4-((5-ethoxy-2-fluoro-3-isopropoxyphenyl)(5-methoxy-1H-benzo[d]imidazol-2-yl)methylamino)benzamidine bis-trifluoroacetic acid salt

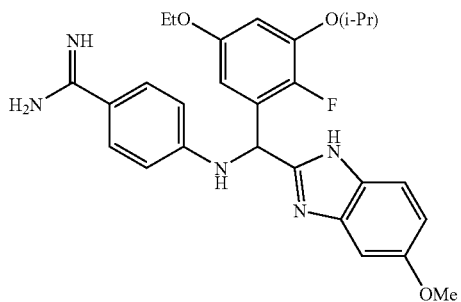

According to the procedure for the preparation of Example 171, 5-methoxy-1H-benzo[d]imidazole was converted to Example 174. LCMS (2 min gradient) RT=1.40 min, 492.1 (M+H)+; 1H NMR (400 MHz, METHANOL-D3) δ ppm 1.31 (none, 21 H) 3.84-3.89 (m, 3 H) 3.91-3.98 (m, 2 H) 4.59-4.65 (m, J=5.82, 5.82, 5.71, 5.49 Hz, 1 H) 6.49 (s, 1 H) 6.50-6.53 (m, J=2.64 Hz, 1 H) 6.70-6.74 (m, 1 H) 6.92 (d, J=8.79 Hz, 2 H) 7.11-7.16 (m, 2 H) 7.55-7.59 (m, 1 H) 7.68 (d, J=8.79 Hz, 2 H).

Example 175

(Z)-2-(2-((4-(N-hydroxycarbamimidoyl)phenylamino)(3-ethylphenyl)methyl)-1H-imidazol-4-yl)benzamide trifluoroacetic acid salt

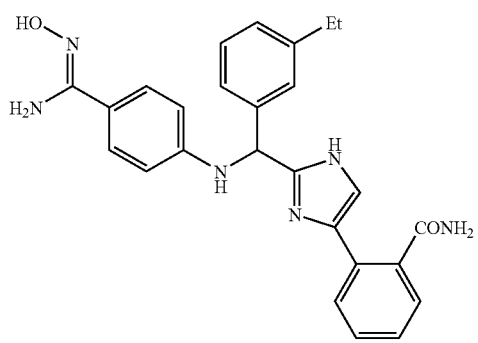

4-bromo-1-trityl-1H-imidazole-2-carbaldehyde (175.1)

To 4-bromo-1-trityl-1H-imidazole (2.00 g, 5.14 mmol) in 30 mL THF at 0° C., was added a solution of BuLi (1.6M in hexanes, 3.85 mL, 6.17 mmol). The mixture was stirred at 0° C. for 1.25 h, then DMF (0.80 mL, 10.3 mmol) was added. The mixture was stirred for 1 h at 0° C. and 1 h at rt, then was quenched with sat. NH4Cl. The mixture was diluted with EtOAc, washed with H2O and brine, dried (Na2SO4), filtered through a 1" pad of SiO2 and concentrated. The crude product was purified by flash chromatography (0 to 40% EtOAc/hexanes gradient) to afford 1.24 g of Intermediate 175.1 as a colorless solid.

(4-bromo-1-trityl-1H-imidazol-2-yl)(3-ethylphenyl)methanol (175.2)

To a solution of 1-bromo-3-ethylbenzene (266 mg, 1.44 mmol) in 7 mL THF at −78° C., was added BuLi (1.6 M in hexanes, 0.99 mL, 1.58 mmol). The mixture was stirred at −78° C. for 10 min, then a solution of Intermediate 175.1 (600 mg, 1.44 mmol) in 3 mL THF was added. The mixture was stirred at −78° C. for 1 h, then was removed from the cooling bath and stirred 20 min. The reaction was quenched with sat. NH4Cl, then was diluted with EtOAc. The organic phase was washed with H2O and brine, dried (Na2SO4) and concentrated. The crude product was purified by flash chromatography (0 to 40% EtOAc/hexanes gradient) to afford 585 mg of Intermediate 175.2 as a colorless solid. LCMS (4 min gradient, 50 to 100% B, A=95% H2O/5% CH3CN/0.1% TFA, B=95% CH3CN/5% H2O/0.1% TFA) RT=3.65 min, 523.10 (M+H)+.

4-((4-bromo-1-trityl-1H-imidazol-2-yl)(3-ethylphenyl)methylamino)benzonitrile (175.3)

To a solution of Intermediate 175.2 (200 mg, 0.382 mmol) and TEA (0.16 mL, 1.15 mmol) in 5 mL CH2Cl2 at 0° C., was added MsCl (0.074 mL, 0.955 mmol). The mixture was stirred at 0° C. for 1 h, then was diluted with EtOAc. The mixture was washed with ice water and brine, dried (Na2SO4) and concentrated to afford 228 mg of the chloro intermediate (4-bromo-2-(chloro(3-ethylphenyl)methyl)-1-trityl-1H-imidazole), which was used without further purification.

To a suspension of the chloro intermediate (0.382 mmol) in 3 mL CH3CN at rt, was added DIEA (0.133 mL, 0.764 mmol), 4-aminobenzonitrile (67.7 mg, 0.573 mmol) and 1 mL CH2Cl2. The mixture was stirred at 50° C. for 3 h, then was diluted with EtOAc. The organic phase was washed with H2O and brine, dried (Na2SO4) and concentrated. The crude product was purified by flash chromatography (O to 50% EtOAc/hexanes gradient) to afford 225 mg of Intermediate 175.3 as a colorless oil. LCMS (4 min gradient, 50 to 100% B, A=95% H2O/5% CH3CN/0.1% TFA, B=95% CH3CN/5% H2O/0.1% TFA) RT=5.20 min, 623.13 (M+H)+.

2-(2-((4-cyanophenylamino)(3-ethylphenyl)methyl)-1-trityl-1H-imidazol-4-yl)benzamide (175.4)

To a degassed mixture of Intermediate 175.3 (100 mg, 0.16 mmol), 2-carbamoylphenylboronic acid (34.4 mg, 0.208 mmol) and Na2CO3 (68 mg, 0.64 mmol) was added Pd(PPh3)4 (18.4 mg, 0.016 mmol). The mixture was stirred at 150° C. for 6 min in a microwave oven, then was diluted with EtOAc, washed with water and brine, dried (Na2SO4) and concentrated. The crude product was purified by flash chromatography (0 to 75% EtOAc/hexanes gradient) to afford 73 mg of Intermediate 175.4. LCMS (4 min gradient, 0 to 100% B, A=95% H2O/5% CH3CN/0.1% TFA, B 95% CH3CN/5% H2O/0.1% TFA) RT=5.34 min, 664.37 (M+H)+.

Example 175

A solution of Intermediate 175.4 (70 mg) in 2 mL 3 M NH$_2$OH in DMSO (prepared as in Example 1) was stirred 1.5 h at 70° C. The mixture was diluted with EtOAc and washed with water (2×) and brine, dried (Na$_2$SO$_4$) and concentrated. The crude material was purified by flash chromatography (50 to 100% EtOAc/hexanes gradient) to afford 52.5 mg of the amide oxime as an off-white solid. This material was dissolved in 1 mL TFA with 2 drops water, then concentrated and purified by HPLC to afford 33.1 mg of Example 175 as a white powder. LCMS (2 min gradient) RT=1.11 min, 455.2 (M+H)$^+$; $^1$H NMR (400 MHz, CD$_3$OD) δ ppm 1.23 (t, J=7.69 Hz, 3 H) 2.68 (q, J=7.47 Hz, 2 H) 6.11 (s, 1 H) 6.85 (d, J=8.79 Hz, 2 H) 7.28 (t, J=7.03 Hz, 2 H) 7.34 (s, 1 H) 7.38 (t, J=7.69 Hz, 1 H) 7.51-7.60 (m, 6 H) 7.69 (d, J=7.03 Hz, 1 H).

Example 176

4-((5-ethoxy-2-fluoro-3-isopropoxyphenyl)(4-methoxy-1H-benzo[d]imidazol-2-yl)methylamino)benzamidine bis-trifluoroacetic acid salt

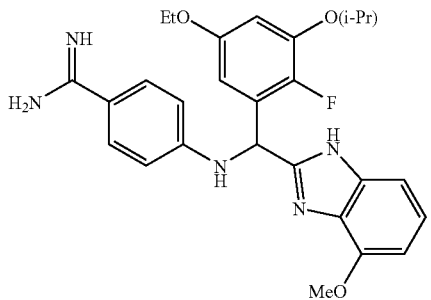

According to the procedure for the preparation of Example 171, 3-methoxybenzene-1,2-diamine (Lumma, W. C., Jr., et al. *J. Med. Chem.* 1981, 24, 93-101) was converted to Example 176. LCMS (2 min gradient) RT=1.39 min, 492.2 (M+H)$^+$; $^1$H NMR (400 MHz, METHANOL-D3) δ ppm 1.28-1.35 (m, 9 H) 3.94 (q, J=6.74 Hz, 2 H) 4.02 (s, 3 H) 4.61 (dq, J=6.15, 6.01 Hz, 1 H) 6.45 (s, 1 H) 6.50 (dd, J=4.83, 3.08 Hz, 1 H) 6.71 (dd, J=6.81, 2.86 Hz, 1 H) 6.89 (d, J=8.79 Hz, 2 H) 7.04 (d, J=7.91 Hz, 1 H) 7.24 (d, J=8.35 Hz, 1 H) 7.44 (t, J=8.13 Hz, 1 H) 7.66 (d, J=8.79 Hz, 2 H).

Example 177

4-((5-chloro-1H-benzo[d]imidazol-2-yl)(5-ethoxy-2-fluoro-3-isopropoxyphenyl)methylamino)benzamidine bis-trifluorocaetic acid salt

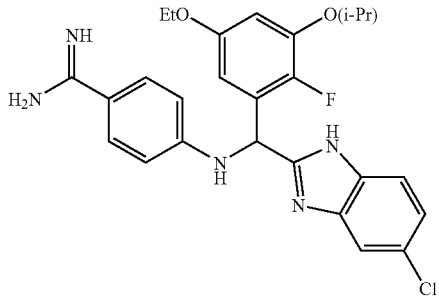

6-chloro-1-trityl-1H-benzo[d]imidazole (177.1)

To a solution of 5-chloro-1H-benzo[d]imidazole (500 mg, 3.28 mmol) in 5 mL DMF, were added TEA (0.502 mL, 3.60 mmol) and TrCl (1.00 g, 3.60 mmol). The mixture was stirred at rt for 3 h, then was diluted with EtOAc. The organic phase was washed with H$_2$O (2×) and brine, dried (Na$_2$SO$_4$) and concentrated. The crude product was purified by flash chromatography (0 to 75% EtOAc/hexanes gradient) to afford 580 mg of 5-chloro-1-trityl-1H-benzo[d]imidazole, followed by 225 mg of 6-chloro-1-trityl-1H-benzo[d]imidazole (177.1) as a white solid.

4-((6-chloro-1-trityl-1H-benzo[d]imidazol-2-yl)(5-ethoxy-2-fluoro-3-isopropoxyphenyl)methylamino)benzonitrile (177.2)

To a mixture of 177.1 (50 mg, 0.127 mmol) in 3 mL THF at 0° C., was added BuLi (1.6 M in THF, 0.087 mL, 0.139 mmol). The mixture was stirred at 0° C. for 20 min to give a colorless suspension, then a solution of Intermediate 7.2 (41.4 mg, 0.127 mmol) in 0.5 mL THF was added dropwise. The mixture was stirred at 0° C. for 5 min and at rt for 1 h, then was quenched with sat. NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) to afford 73.7 mg of Intermediate 177.2 as a colorless glass. (4 min gradient, 50 to 100% B, A=95% H$_2$O/5% CH$_3$CN/0.1% TFA, B=95% CH$_3$CN/5% H$_2$O/0.1% TFA) RT=1.39 min, 479.1 (M−Tr+2H)$^+$.

Example 177

A solution of Intermediate 177.2 (73 mg) in 2 mL 3 M NH$_2$OH in DMSO was converted to the amide oxime, acylated and hydrogenated as in Example 1. The resultant material was taken up in 1 mL TFA with 2 drops water, then immediately concentrated to afford after HPLC purification 42.8 mg of Example 177. LCMS (2 min gradient) RT=1.60 min, 496.1 (M+H)$^+$; $^1$H NMR (400 MHz, METHANOL-D3) δ ppm 1.28-1.35 (m, 9 H) 3.94 (q, J=6.74 Hz, 2 H) 4.02 (s, 3 H) 4.61 (dq, J=6.15, 6.01 Hz, 1 H) 6.45 (s, 1 H) 6.50 (dd, J=4.83, 3.08 Hz, 1 H) 6.71 (dd, J=6.81, 2.86 Hz, 1 H) 6.89 (d, J=8.79 Hz, 2 H) 7.04 (d, J=7.91 Hz, 1 H) 7.24 (d, J=8.35 Hz, 1 H) 7.44 (t, J=8.13 Hz, 1 H) 7.66 (d, J=8.79 Hz, 2 H).

Example 178

4-((4,5-dimethyl-1H-benzo[d]imidazol-2-yl)(5-ethoxy-2-fluoro-3-isopropoxyphenyl)methylamino)benzamidine bis-trifluoroacetic acid salt

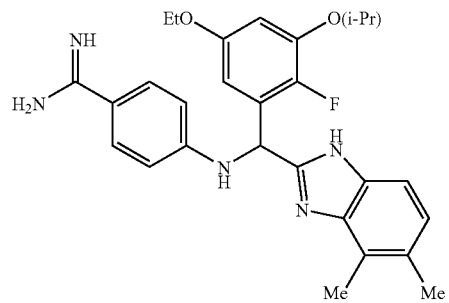

4,5-dimethyl-1H-benzo[d]imidazole (178.1)

3,4-dimethylbenzene-1,2-diamine (300 mg) in 3 mL formic acid was irradiated in a microwave reactor at 150° C. for 5 min. The mixture was diluted with water, neutralized with sat. NaHCO₃, then extracted with EtOAc (3×). The organic phase was washed with water and brine, dried (Na₂SO₄), filtered through a 1" pad of silica gel and concentrated to afford 320 mg of Intermediate 178.1 as a tan solid. LCMS (2 min gradient) RT=0.90 min, 147.0 (M+H)⁺.

Example 178

According to the procedure for the preparation of Example 177, Intermediate 178.1 was converted to Example 178. LCMS (2 min gradient) RT=1.49 min, 490.2 (M+H)⁺; ¹H NMR (400 MHz, METHANOL-D3) δ ppm 1.29-1.35 (m, 9 H) 2.45 (s, 3 H) 2.53 (s, 3 H) 3.95 (q, J=7.03 Hz, 2 H) 4.62 (ddd, J=11.97, 6.15, 6.04 Hz, 1 H) 6.48-6.50 (m, 2 H) 6.74 (dd, J=6.81, 2.86 Hz, 1 H) 6.91 (d, J=8.79 Hz, 2 H) 7.36-7.44 (m, 2 H) 7.68 (d, J=8.79 Hz, 2 H).

Example 179

4-((4,6-dimethyl-1H-benzo[d]imidazol-2-yl)(5-ethoxy-2-fluoro-3-isopropoxyphenyl)methylamino)benzamidine bis-trifluoroacetic acid salt

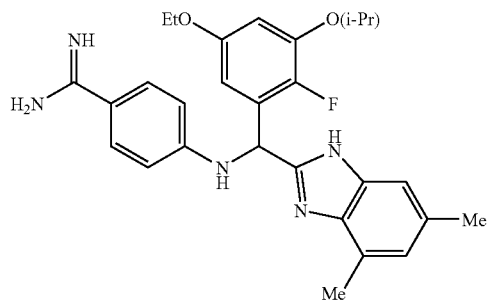

3,5-dimethylbenzene-1,2-diamine (179.1)

To a solution of 4,6-dimethyl-2-nitroaniline (312 mg) in 5 mL MeOH, was added 10% Pd/C (50 mg). The mixture evacuated and flushed with H₂ (3×), then was stirred under an atmosphere of H₂ for 6 h. Conc. HCl (2 drops) was added and the mixture was stirred under H₂ for an additional 18 h, then was filtered and concentrated to afford 280 mg of Intermediate 179.1, which was used without further purification.

4,6-dimethyl-1H-benzo[d]imidazole (179.2)

Intermediate 179.1 (275 mg) in 3 mL formic acid was irradiated in a microwave reactor at 150° C. for 5 min. The mixture was diluted with water, neutralized with sat. NaHCO₃, then extracted with EtOAc (3×). The organic phase was washed with water and brine, dried (Na₂SO₄) and concentrated to afford 245 mg of Intermediate 179.2 as an orange solid.

Example 179

According to the procedure for the preparation of Example 177, Intermediate 179.2 was converted to Example 179. LCMS (2 min gradient) RT=1.55 min, 490.1 (M+H)⁺; ¹H NMR (400 MHz, CD₃OD) δ ppm 1.29-1.35 (m, 9 H) 2.47 (s, 3 H) 2.57 (s, 3 H) 3.95 (q, J=7.03 Hz, 2 H) 4.58-4.67 (m, J=6.08, 6.08, 6.08, 6.08, 6.08, 6.08 Hz, 1 H) 6.49-6.51 (m, 2 H) 6.74 (dd, J=7.03, 3.08 Hz, 1 H) 6.91 (d, J=8.79 Hz, 2 H) 7.22 (s, 1 H) 7.32 (s, 1 H) 7.68 (d, J=8.79 Hz, 2 H).

Example 180

4-((5-ethoxy-2-fluoro-3-isopropoxyphenyl)(5-ethyl-1H-benzo[d]imidazol-2-yl)methylamino)benzamidine bis-trifluoroacetic acid salt

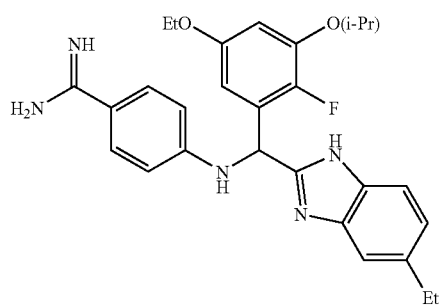

N-(4-ethyl-2-nitrophenyl)acetamide (180.1)

To 5 mL acetic anhydride, was added 4-ethylaniline (0.50 mL, 4.02 mmol). The mixture was cooled to 0° C., then fuming red nitric acid (0.35 mL) was added, dropwise. The mixture was stirred at rt for 15 h, then was diluted with EtOAc. The organic phase was washed with sat. NaHCO₃, water and brine, dried (Na₂SO₄) and concentrated to afford 555 mg of Intermediate 180.1, which was used in the following step without further purification.

4-ethyl-2-nitrobenzenamine (180.2)

Intermediate 180.1 (413 mg) in EtOH/water/conc. HCl (3:4:1) was refluxed for 12 h, then was diluted with EtOAc. The aqueous layer was made basic with sat. NaHCO₃, then the layers were separated. The organic phase was washed with water and brine, dried (Na₂SO₄) and concentrated to afford 317 mg of Intermediate 180.2 as a brown/orange solid.

Example 180

According to the procedure for the preparation of Example 179, Intermediate 180.2 was converted to Example 180. LCMS (2 min gradient) RT=1.51 min, 490.1 (M+H)⁺; ¹H NMR (400 MHz, CD₃OD) δ ppm 1.27-1.34 (m, 12 H) 2.83 (q, J=7.47 Hz, 2 H) 3.95 (q, J=7.03 Hz, 2 H) 4.63 (qd, J=6.08, 5.93 Hz, 1 H) 6.52 (dd, J=4.83, 3.08 Hz, 1 H) 6.57 (s, 1 H) 6.74 (dd, J=7.03, 3.08 Hz, 1 H) 6.95 (d, J=9.23 Hz, 2 H) 7.45 (d, J=8.35 Hz, 1 H) 7.54 (s, 1 H) 7.63 (d, J=8.35 Hz, 1 H) 7.69 (d, J=8.79 Hz, 2 H).

Example 181

4-((5,6-difluoro-1H-benzo[d]imidazol-2-yl)(5-ethoxy-2-fluoro-3-isopropoxyphenyl)methylamino)benzamidine bis-trifluoroacetic acid salt

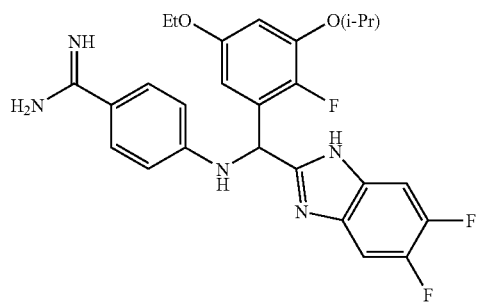

According to the procedure for the preparation of Example 177, 5,6-difluoro-1H-benzo[d]imidazole was converted to Example 181. LCMS (2 min gradient) RT=1.53 min, 498.2 (M+H)+; 1H NMR (400 MHz, CD3OD) δ ppm 1.27-1.33 (m, 9 H) 3.92 (q, J=7.03 Hz, 2 H) 4.55-4.64 (m, J=6.01, 6.01, 6.01, 6.01, 6.01, 6.01 Hz, 1 H) 6.29 (s, 1 H) 6.49 (dd, J=4.83, 3.08 Hz, 1 H) 6.65 (dd, J=6.81, 2.86 Hz, 1 H) 6.85 (d, J=9.23 Hz, 2 H) 7.48 (t, J=8.57 Hz, 2 H) 7.63 (d, J=8.79 Hz, 2 H).

Example 182

4-((5-chloro-6-fluoro-1H-benzo[d]imidazol-2-yl)(5-ethoxy-2-fluoro-3-isopropoxyphenyl)methylamino)benzamidine bis-trifluoroacetic acid salt

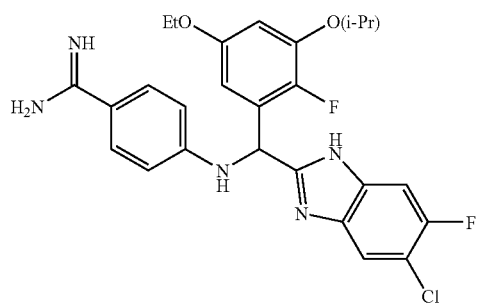

According to the procedure for the preparation of Example 177, 5-chloro-6-fluoro-1H-benzo[d]imidazole was converted to Example 182. LCMS (2 min gradient) RT=1.68 min, 514.1 (M+H)+; 1H NMR (400 MHz, CD3OD) δ ppm 1.27-1.34 (m, 9 H) 3.91 (q, J=7.03 Hz, 2 H) 4.59 (qd, J=6.08, 5.93 Hz, 1 H) 6.25 (s, 1 H) 6.49 (dd, J=4.83, 3.08 Hz, 1 H) 6.64 (dd, J=6.81, 2.86 Hz, 1 H) 6.83 (d, J=8.79 Hz, 2 H) 7.42 (d, J=9.23 Hz, 1 H) 7.62 (d, J=9.23 Hz, 2 H) 7.66 (d, J=6.59 Hz, 1 H).

Example 183

4-((5-ethoxy-2-fluoro-3-isopropoxyphenyl)(1-phenyl-1H-pyrazol-3-yl)methylamino)benzamidine trifluoroacetic acid salt

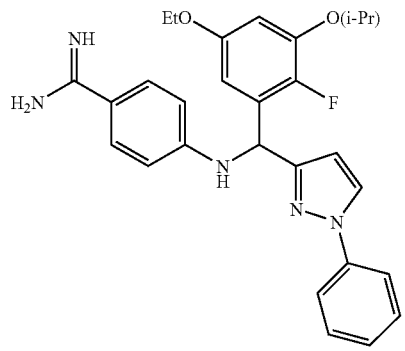

4-((5-ethoxy-2-fluoro-3-isopropoxyphenyl)(1H-pyrazol-3-yl)methylamino)benzonitrile (183.1)

To a solution of 1-(1,1-diethoxyethyl)-1H-pyrazole (Jones, C. D., et al., *J. Med. Chem.* 1990, 33, 416-429) (51.0 mg, 0.277 mmol) in 2 mL THF at −40° C., was added BuLi (1.4 M in hexanes, 0.217 mL, 0.304 mmol). The mixture was stirred at −40° C. for 20 min, then a solution of Intermediate 7.2 (90.4 mg, 0.277 mmol) in 0.6 mL THF was added dropwise. The mixture was stirred and allowed to warm from −40° C. to 0° C. over 45 min, then was quenched with ice. The mixture was acidified to pH 3 with 0.3 mL 1 N HCl. The mixture was diluted with EtOAc, washed with H2O and brine, dried (Na2SO4) and concentrated. The crude product was purified by flash chromatography (0 to 100% EtOAc/hexanes gradient) to afford 91.3 mg of Intermediate 183.1 as a colorless solid.

4-((5-ethoxy-2-fluoro-3-isopropoxyphenyl)(1-phenyl-1H-pyrazol-3-yl)methylamino)benzonitrile (183.2)

To a mixture of Intermediate 183.1 (39.5 mg, 0.100 mmol) and 3A molecular sieves (30 mg) in 1 mL CH2Cl2 at rt, was added TEA (0.028 mL, 0.20 mmol), pyridine (16 mg, 0.20 mmol) and phenylboronic acid (24.4 mg, 0.20 mmol). The mixture was stirred until the boronic acid dissolved, then Cu(OAc)2 (27.3 mg, 0.150 mmol) was added. The mixture was stirred for 5.5 h, then was diluted with EtOAc. The organic phase was washed with 0.5N HCl, H2O, sat. NaHCO3 and brine, dried (Na2SO4) and concentrated. The crude product was purified by flash chromatography (0 to 50% EtOAc/hexanes gradient) to afford 33.4 mg of Intermediate 183.2 as a pale yellow solid.

Example 183

A solution of Intermediate 183.2 (29 mg) in 2 mL 3 M NH2OH in DMSO was converted to the amide oxime, acylated and hydrogenated as in Example 1 to afford after HPLC purification 20.1 mg of Example 183. LCMS (2 min gradient) RT=1.67 min, 488.3 (M+H)+; 1H NMR (400 MHz, CD3OD) δ ppm 1.27-1.34 (m, 9 H) 3.86-3.93 (m, J=6.92, 6.92, 6.81, 2.20 Hz, 2 H) 4.56 (qd, J=6.08, 5.93 Hz, 1 H) 6.09 (s, 1 H) 6.39 (d, J=2.20 Hz, 1 H) 6.54-6.57 (m, 2 H) 6.80 (d, J=8.79

Hz, 2 H) 7.31 (t, J=7.47 Hz, 1 H) 7.47 (t, J=7.91 Hz, 2 H) 7.59 (d, J=8.79 Hz, 2 H) 7.74 (d, J=8.35 Hz, 2 H) 8.16 (d, J=2.20 Hz, 1 H).

Example 184

2-(3-((4-carbamimidoylphenylamino)(5-ethoxy-2-fluoro-3-isopropoxyphenyl)methyl)-1H-pyrazol-1-yl)benzamide trifluoroacetic acid salt

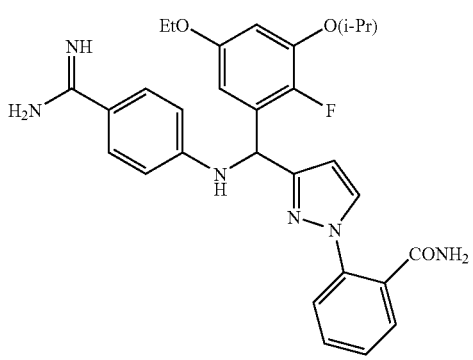

2-(3-((4-cyanophenylamino)(5-ethoxy-2-fluoro-3-isopropoxyphenyl)methyl)-1H-pyrazol-1-yl)benzamide (184.1)

To a mixture of Intermediate 183.1 (39.5 mg, 0.100 mmol) and 3A molecular sieves (30 mg) in 1 mL CH$_2$Cl$_2$ at rt, was added TEA (0.028 mL, 0.20 mmol), pyridine (16 mg, 0.20 mmol) and 2-carbamoylphenylboronic acid (24.7 mg, 0.15 mmol). The mixture was stirred until the boronic acid dissolved, then Cu(OAc)$_2$ (27.3 mg, 0.150 mmol) was added. The mixture was stirred for 40 h, then additional boronic acid (12 mg) and Cu(OAc)$_2$ (13 mg) were added. The reaction was stirred 4 h at 50° C. and 4 h at 80° C., then was diluted with EtOAc. The organic phase was washed with 0.5 N HCl, H$_2$O, sat. NaHCO$_3$ and brine, dried (Na$_2$SO$_4$) and concentrated. The crude product was purified by flash chromatography (0 to 100% EtOAc/hexanes gradient) to afford 12.3 mg of Intermediate 184.1. LCMS (2 min gradient) RT=1.81 min, 536.2 (M+Na)$^+$.

Example 184

A solution of Intermediate 184.1 (12.3 mg) in 2 mL 3 M NH$_2$OH in DMSO was converted to the amide oxime, acylated and hydrogenated as in Example 1 to afford after HPLC purification 9.9 mg of Example 184. LCMS (4 min gradient, A=95% H$_2$O/5% CH$_3$CN/0.1% TFA, B=5% H$_2$O/95% CH$_3$CN/0.1% TFA) RT=3.70 min, 531.21 (M+H)$^+$; $^1$H NMR (400 MHz, CD$_3$OD) δ ppm 1.26-1.34 (m, 9 H) 3.86-3.94 (m, 2 H) 4.55 (dq, J=6.15, 6.01 Hz, 1 H) 6.06 (s, 1 H) 6.36 (d, J=2.20 Hz, 1 H) 6.52-6.56 (m, J=3.73, 3.52, 3.41, 3.41 Hz, 2 H) 6.78 (d, J=8.79 Hz, 2 H) 7.46-7.51 (m, 1 H) 7.55-7.63 (m, 5 H) 7.88 (d, J=2.20 Hz, 1 H).

Example 185

4-((5-ethoxy-2-fluoro-3-isopropoxyphenyl)(4-phenyloxazol-2-yl)methylamino)benzamidine trifluoroacetic acid salt

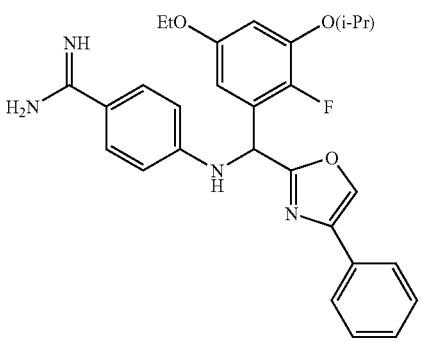

4-((5-ethoxy-2-fluoro-3-isopropoxyphenyl)(4-phenyloxazol-2-yl)methylamino)benzonitrile (185.1)

To a solution of 4-phenyloxazole (Whitney, S. E., et al., *J. Org. Chem.* 1990, 55, 929-935) (50 mg, 0.344 mmol) in 2 mL THF at rt, was added borane.THF (1 M in THF, 0.344 mL, 0.344 mmol). The mixture was cooled to −78° C., then BuLi (1.4 M in hexanes, 0.270 mL, 0.378 mmol) was added. The bright orange solution was stirred at −78° C. for 20 min, then a solution of Intermediate 7.2 (112 mg, 0.344 mmol) in 0.6 mL THF was added dropwise. The mixture was stirred at −78° C. for 10 min, then was allowed to warm to 0° C. over 10 min. The mixture was stirred at 0° C. for 15 min, then was quenched with 0.2 mL AcOH and 0.2 mL MeOH. The mixture was stirred at rt for 20 min, then was diluted with EtOAc. The organic phase was washed with H$_2$O and brine, dried (Na$_2$SO$_4$) and concentrated. The crude product was purified by flash chromatography (0 to 50% EtOAc/hexanes gradient) to afford 87.7 mg of Intermediate 185.1.

Example 185

A solution of Intermediate 185.1 (82 mg) in 2 mL 3 M NH$_2$OH in DMSO was converted to the amide oxime, acylated and hydrogenated as in Example 1 to afford after HPLC purification 67.3 mg of Example 185. LCMS (2 min gradient) RT=1.75 min, 489.3 (M+H)$^+$; $^1$H NMR (400 MHz, CD$_3$OD) δ ppm 1.28-1.34 (m, 9 H) 3.93 (q, J=6.88 Hz, 2 H) 4.58 (dq, J=6.15, 6.01 Hz, 1 H) 6.22 (s, 1 H) 6.56-6.59 (m, 1 H) 6.61 (dd, J=6.81, 2.86 Hz, 1 H) 6.87 (d, J=8.79 Hz, 2 H) 7.30 (t, J=7.47 Hz, 1 H) 7.39 (t, J=7.69 Hz, 2 H) 7.62 (d, J=8.79 Hz, 2 H) 7.75 (d, J=7.47 Hz, 2 H) 8.25 (s, 1 H).

Example 186

4-((5-ethoxy-2-fluoro-3-isopropoxyphenyl)(2-phenyloxazol-4-yl)methylamino)benzamidine trifluoroacetic acid salt

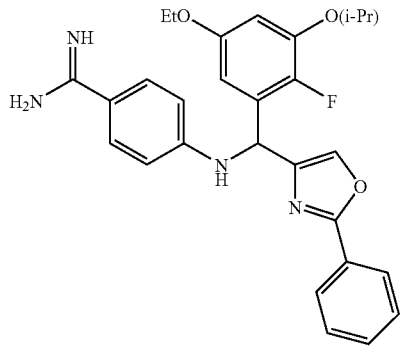

4-((5-ethoxy-2-fluoro-3-isopropoxyphenyl)(2-phenyloxazol-4-yl)methylamino)benzonitrile (186.1)

To a solution of 2-phenyloxazole (50 mg, 0.344 mmol) in 2 mL THF at −78° C., was added BuLi (1.4 M in THF, 0.270 mL, 0.378 mmol). The yellow slurry was stirred at −78° C. for 5 min, then a solution of Intermediate 7.2 (112 mg, 0.344 mmol) in 0.6 mL THF was added dropwise. The mixture was stirred at −78° C. for 10 min and at rt for 30 min, then was quenched with sat. NH$_4$Cl. The mixture was diluted with EtOAc, washed with H$_2$O and brine, dried (Na$_2$SO$_4$) and concentrated. The crude product was purified by flash chromatography (column#1: 0 to 50% EtOAc/hexanes gradient, column #2: 0 to 75% Et$_2$O/hexanes) to afford 107 mg of Intermediate 186.1 as a pale yellow solid. LCMS (2 min gradient) RT=2.16 min, 472.2 (M+H)$^+$.

Example 186

A solution of Intermediate 186.1 (100 mg) in 2 mL 3 M NH$_2$OH in DMSO was converted to the amide oxime, acylated and hydrogenated as in Example 1 to afford after HPLC purification 89.9 mg of Example 186. LCMS (2 min gradient) RT=1.73 min, 489.3 (M+H)$^+$; $^1$H NMR (400 MHz, CD$_3$OD) δ ppm 1.29-1.35 (m, 9 H) 3.93 (qd, J=7.03, 1.76 Hz, 2 H) 4.59 (dq, J=6.15, 6.01 Hz, 1 H) 6.22 (s, 1 H) 6.58 (dd, J=4.83, 3.08 Hz, 1 H) 6.63 (dd, J=6.81, 2.86 Hz, 1 H) 6.84 (d, J=8.79 Hz, 2 H) 6.98 (s, 1 H) 7.46-7.51 (m, 3 H) 7.60-7.64 (m, 2 H) 7.96-8.00 (m, 2 H).

Example 187

4-((3-ethoxy-4-isopropoxyphenyl)(3-phenyl-1,2,4-oxadiazol-5-yl)methylamino)benzamidine trifluoroacetic acid salt

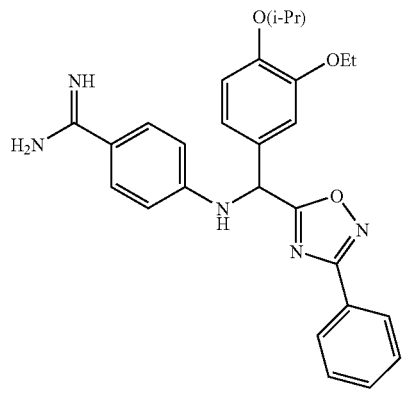

N'-({2-[(4-cyanophenyl)amino]-2-(3-ethoxy-4-isopropoxyphenyl)acetyl}oxy)benzenecarboximidamide (187.1)

To a mixture of 2-(4-cyanophenylamino)-2-(3-ethoxy-4-isopropoxyphenyl)acetic acid (US2004242585, which is incorporated herein by reference) (525 mg, 1.48 mg) and benzene amideoxime (242 mg, 1.78 mmol) in 10 mL CH$_2$Cl$_2$/DMF (9:1) at 0° C., were added HOAt (242 mg, 1.78 mmol), DIC (0.279 mL, 1.78 mmol) and TEA (0.248 mL, 1.78 mmol). The mixture was stirred at 0° C. for 15 min, then at rt for 6 h. The mixture was diluted with EtOAc, washed with H$_2$O, 1 N HCl, H$_2$O, sat. NaHCO$_3$ and brine, dried (Na$_2$SO$_4$) and concentrated. The crude product was purified by flash chromatography (0 to 100% EtOAc/hexanes gradient) to afford 700 mg of Intermediate 187.1 as a white solid.

4-((3-ethoxy-4-isopropoxyphenyl)(3-phenyl-1,2,4-oxadiazol-5-yl)methylamino)benzonitrile (187.2)

To a solution of Intermediate 187.1 (159 mg, 0.336 mmol) in 2 mL THF at rt, was added TBAF (1 M in THF, 0.37 mL, 0.37 mmol). The mixture was stirred at rt for 4 h, then diluted with EtOAc. The organic phase was washed with H$_2$O and brine, dried (Na$_2$SO$_4$) and concentrated. The crude product was purified by flash chromatography (0 to 40% EtOAc/hexanes gradient) to afford 22.4 mg of Intermediate 187.2 as a colorless glass. LCMS (2 min gradient) RT=2.10 min, 337.3 (M−C$_7$H$_5$N$_2$)$^+$.

Example 187

A solution of Intermediate 187.2 (22 mg) in 2 mL 3 M NH$_2$OH in DMSO was converted to the amide oxime, acylated and hydrogenated as in Example 1 to afford after HPLC purification 15.0 mg of Example 187. LCMS (2 min gradient) RT=1.70 min, 472.3 (M+H)$^+$; $^1$H NMR (400 MHz, CD$_3$OD) δ ppm 1.29 (d, J=6.15 Hz, 6 H) 1.38 (t, J=7.03 Hz, 3 H) 4.06 (q, J=7.03 Hz, 2 H) 4.53 (qd, J=6.08, 5.93 Hz, 1 H) 6.18 (s, 1 H) 6.90 (d, J=8.79 Hz, 2 H) 6.96-7.00 (m, 1 H) 7.05-7.09 (m, 1 H) 7.19 (d, J=2.20 Hz, 1 H) 7.47-7.56 (m, 3 H) 7.62 (d, J=8.79 Hz, 2 H) 8.04 (d, J=6.59 Hz, 2 H).

Example 188

2-(2-((4-carbamimidoylphenylamino)(5-ethyl-2-fluoro-3-methoxyphenyl)methyl)-1H-imidazol-4-yl)benzamide bis-trifluoroacetic acid salt

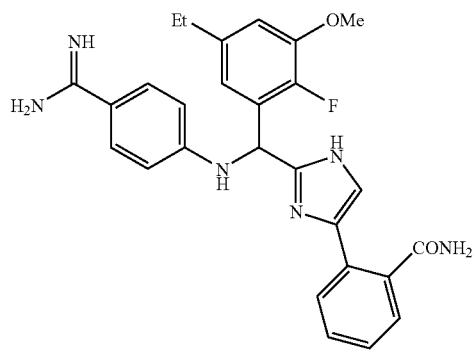

5-ethyl-2-fluorophenol (188.1)

To a solution of 1-ethyl-4-fluorobenzene (5.0 g, 40.3 mmol) and PMDTA (8.5 mL, 40.7 mmol) in 20 mL THF at −40° C., was added BuLi (1.4 M in hexanes, 31.6 mL, 44.3 mmol). The tan suspension was stirred at −60° C. for 40 min, was recooled to −78° C., then B(OMe)$_3$ (9.03 mL, 80.6 mmol). The mixture was stirred at −78° C. for 30 min, then was allowed to warm to rt. The reaction was quenched with 8 mL AcOH, then was cooled to 0° C. and treated with 9.8 mL 30% H$_2$O$_2$. The mixture was stirred for 30 min, then was quenched with aq. Na$_2$SO$_3$. The mixture was diluted with hexanes, washed with H$_2$O (3×) and brine, dried (Na$_2$SO$_4$), filtered through 2″ silica gel (eluting with 20% EtOAc/hexanes), then concentrated to afford 5.42 g of Intermediate 188.1 as a pale yellow oil.

tert-butyl(5-ethyl-2-fluorophenoxy)dimethylsilane (188.2)

To a solution of Intermediate 188.1 (5.42 g, 38.7 mmol) in 25 mL DMF at rt, were added imidazole (2.90 g, 42.5 mmol) and TBS-Cl (5.83 mmol). The mixture was stirred for 1.5 h, then was diluted with hexanes. The organic phase was washed with H$_2$O (3×) and brine, dried (Na$_2$SO$_4$), then concentrated. Purification by flash chromatography (100% hexanes) afforded 7.50 g of Intermediate 188.2 as a colorless oil.

3-(tert-butyldimethylsilyloxy)-5-ethyl-2-fluorobenzaldehyde (188.3)

To a solution of Intermediate 188.2 (7.50 g, 29.5 mmol) and PMDTA (6.5 mL, 31.1 mmol) in 30 mL THF at −78° C., was added BuLi (1.4 M in hexanes, 23.2 mL, 44.3 mmol). The thick slurry was stirred at −40° C. for 30 min, was recooled to −70° C. DMF (4.57 mL, 59 mmol) was added. The yellow solution was removed from the cooling bath and allowed to warm to rt and stirred 1 h. The reaction was quenched with sat. NH$_4$Cl, then was diluted with hexanes. The organic phase was washed with H$_2$O (3×) and brine, dried (Na$_2$SO$_4$), filtered through 2″ silica gel (eluting with 5% EtOAc/hexanes), then concentrated to afford 8.03 g of Intermediate 188.3 as a pale yellow oil.

(E)-4-(3-(tert-butyldimethylsilyloxy)-5-ethyl-2-fluorobenzylideneamino)benzonitrile (188.4)

According to the procedure for Intermediate 1.1, Intermediate 188.3 (3.72 g, 13.17 mmol) and 4-aminobenzonitrile (1.56 g, 13.17 mmol) afforded 5.10 g of Intermediate 188.4 as an orange oil.

4-((4-bromo-1-trityl-1H-imidazol-2-yl)(3-(tert-butyldimethylsilyloxy)-5-ethyl-2-fluorophenyl)methylamino)benzonitrile (188.5)

According to the procedure for the preparation of Intermediate 28.1, reaction of 4-bromo-1-triphenylmethyl-imidazole (100 mg) with Intermediate 188.4 (102 mg) afforded 130 mg of Intermediate 188.5.

2-(2-((4-cyanophenylamino)(5-ethyl-2-fluoro-3-hydroxyphenyl)methyl)-1-trityl-1H-imidazol-4-yl)benzamide (188.6)

According to the procedure for the preparation of Intermediate 138.2, Intermediate 188.5 (127 mg, 0.165 mmol) was coupled with 2-carbamoylphenylboronic acid (35 mg, 0.214 mmol) to afford 66.7 mg of Intermediate 188.6. LCMS (2 min gradient) RT=1.19 min, 456.2 (M−Tr+2H)$^+$.

2-(2-((4-cyanophenylamino)(5-ethyl-2-fluoro-3-methoxyphenyl)methyl)-O-trityl-1H-imidazol-4-yl)benzamide (188.7)

A mixture of Intermediate 188.6 (22 mg, 0.0315 mmol), K$_2$CO$_3$ (5.2 mg, 0.038 mmol) and iodomethane (0.0059 mL, 0.0945 mmol) in 1 mL DMF was stirred at 70° C. for 2 h. The mixture was diluted with EtOAc, washed with H$_2$O (2×) and brine, dried (Na$_2$SO$_4$) and concentrated to afford 22 mg of Intermediate 188.7.

Example 188

A solution of Intermediate 188.7 (22 mg) in 1 mL 3 M NH$_2$OH in DMSO was converted to the amide oxime, acylated, hydrogenated and deprotected as in Example 1 to afford after HPLC purification 2.4 mg of Example 188. LCMS (4 min gradient) RT=1.99 min, 487.34 (M+H)$^+$; $^1$H NMR (400 MHz, CD$_3$OD) δ ppm 1.21 (t, J=7.69 Hz, 3 H) 2.63 (q, J=7.47 Hz, 2 H) 3.89 (s, 3 H) 6.40 (s, 1 H) 6.80 (dd, J=5.71, 1.32 Hz, 1 H) 6.89 (d, J=8.79 Hz, 2 H) 7.03-7.09 (m, 1 H) 7.56 (s, 1 H) 7.57-7.62 (m, 3 H) 7.67-7.73 (m, 3 H).

Example 189

2-(2-((4-carbamimidoylphenylamino)(3-ethoxy-5-ethyl-2-fluorophenyl)methyl)-1H-imidazol-4-yl)benzamide bis-trifluoroacetic acid salt

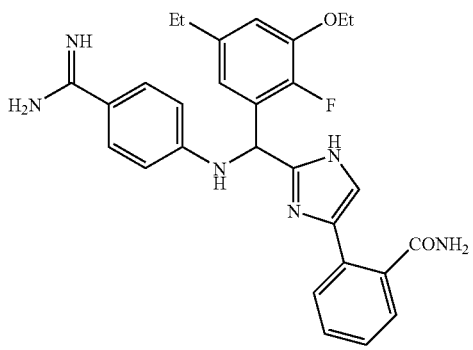

According to the procedure for the preparation of Example 188, Intermediate 188.6 was alkylated with iodoethane, then was converted to the amide oxime, acylated and hydrogenated as in Example 1 to afford after HPLC purification 9.9 mg of Example 189. LCMS (4 min gradient) RT=2.19 min, 501.34 (M+H)+; 1H NMR (400 MHz, CD3OD) δ ppm 1.19 (t, J=7.47 Hz, 3 H) 1.41 (t, J=7.03 Hz, 3 H) 2.62 (q, J=7.47 Hz, 2 H) 4.12 (q, J=7.03 Hz, 2 H) 6.39 (s, 1 H) 6.79 (dd, J=5.71, 1.32 Hz, 1 H) 6.89 (d, J=8.79 Hz, 2 H) 7.03 (dd, J=7.91, 1.76 Hz, 1 H) 7.55 (s, 1 H) 7.56-7.61 (m, 3 H) 7.68 (d, J=8.79 Hz, 3 H).

Example 190

2-(2-((4-carbamimidoylphenylamino)(5-ethyl-2-fluoro-3-isopropoxyphenyl)methyl)-1H-imidazol-4-yl)benzamide bis-trifluoroacetic acid salt

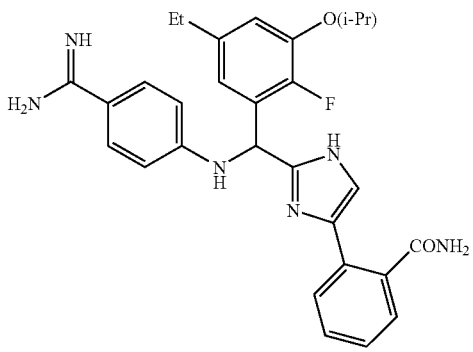

According to the procedure for the preparation of Example 188, Intermediate 188.6 was alkylated with 2-iodopropane, then was converted to the amide oxime, acylated, hydrogenated and deprotected as in Example 1 to afford after HPLC purification 7.9 mg of Example 190. LCMS (4 min gradient) RT=2.32 min, 515.35 (M+H)+; 1H NMR (400 MHz, CD3OD) δ ppm 1.19 (t, J=7.69 Hz, 3 H) 1.33 (d, J=5.71 Hz, 6 H) 2.61 (q, J=7.47 Hz, 2 H) 4.64 (dq, J=6.15, 6.01 Hz, 1 H) 6.34 (s, 1 H) 6.78 (d, J=3.95 Hz, 1 H) 6.88 (d, J=8.79 Hz, 2 H) 7.02 (d, J=6.15 Hz, 1 H) 7.52 (s, 1 H) 7.53-7.61 (m, 3 H) 7.67 (d, J=8.79 Hz, 3 H).

Example 191

4-((5-ethyl-2-fluoro-3-methoxyphenyl)(4-phenyl-1H-imidazol-2-yl)methylamino)benzamidine bis-trifluoroacetic acid salt

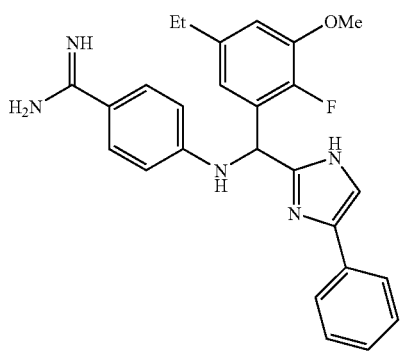

4-((3-(tert-butyldimethylsilyloxy)-5-ethyl-2-fluorophenyl)(4-phenyl-1-trityl-1H-imidazol-2-yl)methylamino)benzonitrile (191.1)

To a solution of Intermediate 8.1 (100 mg, 0.259 mmol) in 3 mL THF at 0° C., was added BuLi (1.4 M in THF, 178 μL, 0.285 mmol). The mixture was stirred at 0° C. for 20 min, then a solution of Intermediate 188.4 (103 mg, 0.259 mmol) in 0.6 mL THF was added dropwise. The mixture was stirred for 1.5 h with warming to rt, then was quenched with sat. NH4Cl. The mixture was diluted with EtOAc, washed with H2O and brine, dried (Na2SO4) and concentrated. The crude product was purified by flash chromatography (0 to 30% EtOAc/hexanes gradient) to afford 72 mg of Intermediate 191.1 as a white solid.

4-((5-ethyl-2-fluoro-3-hydroxyphenyl)(4-phenyl-1-trityl-1H-imidazol-2-yl)methylamino)benzonitrile (191.2)

To a solution of Intermediate 191.1 (72 mg, 0.0936 mmol) in 1 mL THF at rt, was added TBAF (1 M in THF, 0.094 mL, 0.094 mmol). The mixture was stirred at rt for 30 min, then concentrated. The mixture was diluted with EtOAc, washed with H2O (2×) and brine, dried (Na2SO4) and concentrated. The crude product was purified by flash chromatography (0 to 75% EtOAc/hexanes gradient) to afford 42 mg of Intermediate 191.2 as a colorless residue.

Example 191

According to the procedure for the preparation of Example 188, Intermediate 191.2 was alkylated with iodomethane, then was converted to the amide oxime, acylated, hydrogenated and deprotected as in Example 1 to afford after HPLC purification 3.3 mg of Example 191. LCMS (2 min gradient) RT=1.27 min, 444.24 (M+H)+; 1H NMR (400 MHz, CD3OD) δ ppm 1.20 (t, J=7.69 Hz, 3 H) 2.63 (q, J=7.47 Hz, 2 H) 3.89 (s, 3 H) 6.41 (s, 1 H) 6.79 (dd, J=5.49, 1.54 Hz, 1 H) 6.90 (d, J=8.79 Hz, 2 H) 7.07 (dd, J=7.91, 1.32 Hz, 1 H) 7.44-7.53 (m, 3 H) 7.70 (t, J=8.57 Hz, 4 H) 7.85 (s, 1 H).

Example 192

4-((3-ethoxy-5-ethyl-2-fluorophenyl)(4-phenyl-1H-imidazol-2-yl)methylamino)benzamidine bis-trifluoroacetic acid salt

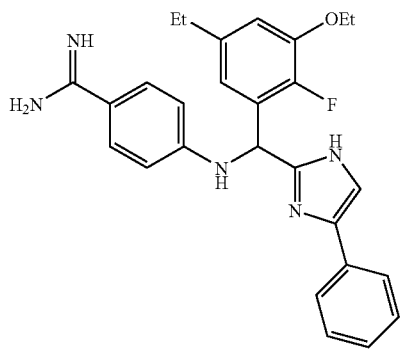

According to the procedure for the preparation of Example 188, Intermediate 191.2 was alkylated with iodoethane, then was converted to the amide oxime, acylated, hydrogenated and deprotected as in Example 1 to afford after HPLC purification 4.7 mg of Example 192. LCMS (2 min gradient) RT=1.36 min, 486.26 (M+H)$^+$; $^1$H NMR (400 MHz, CD$_3$OD) δ ppm 1.19 (t, J=7.69 Hz, 3 H) 1.40 (t, J=7.03 Hz, 3 H) 2.61 (q, J=7.76 Hz, 2 H) 4.12 (q, J=6.74 Hz, 2 H) 6.40 (s, 1 H) 6.78 (d, J=4.39 Hz, 1 H) 6.90 (d, J=8.79 Hz, 2 H) 7.04 (d, J=7.91 Hz, 1 H) 7.48 (dt, J=17.58, 7.25 Hz, 3 H) 7.70 (t, J=8.57 Hz, 4 H) 7.85 (s, 1 H).

Example 193

4-((5-ethyl-2-fluoro-3-isopropoxyphenyl)(4-phenyl-1H-imidazol-2-yl)methylamino)benzamidine bis-trifluoroacetic acid salt

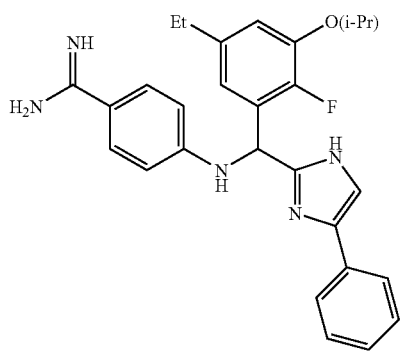

According to the procedure for the preparation of Example 188, Intermediate 191.2 was alkylated with 2-iodopropane, then was converted to the amide oxime, acylated, hydrogenated and deprotected as in Example 1 to afford after HPLC purification 4.9 mg of Example 193. LCMS (2 min gradient) RT=1.44 min, 472.29 (M+H)$^+$; $^1$H NMR (400 MHz, CD$_3$OD) δ ppm 1.19 (t, J=7.47 Hz, 3 H) 1.32 (d, J=6.15 Hz, 6 H) 2.61 (q, J=7.47 Hz, 2 H) 4.65 (qd, J=6.08, 5.93 Hz, 1 H) 6.39 (s, 1 H) 6.78 (dd, J=5.71, 1.76 Hz, 1 H) 6.89 (d, J=8.79 Hz, 2 H) 7.05 (dd, J=7.91, 1.76 Hz, 1 H) 7.44-7.53 (m, 3 H) 7.67-7.73 (m, 4 H) 7.85 (s, 1 H).

Example 194

4-((5-ethoxy-2-fluoro-3-isopropoxyphenyl)(5-phenyloxazol-2-yl)methylamino)benzamidine trifluoroacetic acid salt

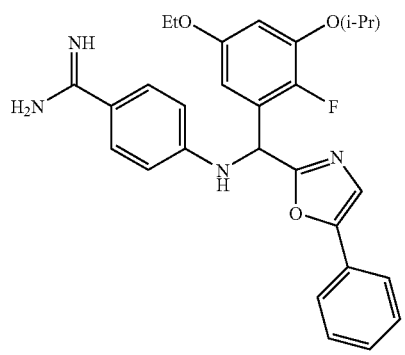

According to the procedure for the preparation of Example 185, 5-phenyloxazole (66 mg, 0.455 mmol) was converted to 24.9 mg of Example 194. LCMS (2 min gradient) RT=1.78 min, 489.28 (M+H)$^+$; $^1$H NMR (400 MHz, CD$_3$OD) δ ppm 1.28-1.34 (m, 9H) 3.93 (q, J=6.74 Hz, 2 H) 4.59 (dq, J=6.15, 6.01 Hz, 1 H) 6.24 (s, 1 H) 6.57 (dd, J=4.61, 2.86 Hz, 1 H) 6.63 (dd, J=6.81, 2.86 Hz, 1 H) 6.86 (d, J=8.79 Hz, 2 H) 7.34 (t, J=7.47 Hz, 1 H) 7.42 (t, J=7.47 Hz, 2 H) 7.48 (s, 1H) 7.63 (d, J=8.79 Hz, 2 H) 7.66 (d, J=7.47 Hz, 2 H).

Example 195

2-(2-((4-carbamimidoylphenylamino)(5-ethyl-2-fluoro-3-(methoxymethoxy)phenyl)methyl)-1H-imidazol-4-yl)benzamide bis-trifluoroacetic acid salt

According to the procedure for the preparation of Example 188, Intermediate 188.6 was alkylated with chloro(methoxy)methane, then was converted to the amide oxime, acylated, hydrogenated and deprotected as in Example 1 to afford after HPLC purification 8.8 mg of Example 195. LCMS (2 min gradient) RT=1.06 min, 517.2 (M+H)$^+$; $^1$H NMR (400 MHz, CD$_3$OD) δ ppm 1.19 (t, J=7.47 Hz, 3 H) 2.61 (q, J=7.47 Hz, 2 H) 3.49 (s, 3 H) 5.24 (s, 2 H) 6.35 (d, J=8.35 Hz, 1 H) 6.88 (d, J=7.91 Hz, 3 H) 7.17 (d, J=6.15 Hz, 1 H) 7.52-7.64 (m, 4 H) 7.68 (d, J=8.79 Hz, 3 H).

Example 196

2-(2-((4-carbamimidoylphenylamino)(5-ethyl-2-fluoro-3-propoxyphenyl)methyl)-1H-imidazol-4-yl)benzamide bis-trifluoroacetic acid salt

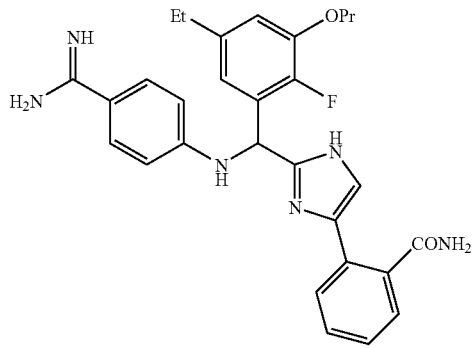

According to the procedure for the preparation of Example 188, Intermediate 188.6 was alkylated with allyl bromide, then was converted to the amide oxime, acylated, hydrogenated and deprotected as in Example 1 to afford after HPLC purification 17.0 mg of Example 196. LCMS (2 min gradient) RT=1.22 min, 515.3 (M+H)$^+$; $^1$H NMR (400 MHz, CD$_3$OD) δ ppm 1.05 (t, J=7.47 Hz, 3 H) 1.19 (t, J=7.47 Hz, 3 H) 1.77-1.86 (m, J=7.25, 6.98, 6.98, 6.98, 6.98 Hz, 2 H) 2.61 (q, J=7.47 Hz, 2 H) 4.02 (t, J=6.37 Hz, 2 H) 6.35 (s, 1 H) 6.78 (dd, J=5.71, 1.76 Hz, 1 H) 6.88 (d, J=8.79 Hz, 2 H) 7.02 (dd, J=7.91, 1.76 Hz, 1 H) 7.52 (s, 1 H) 7.52-7.63 (m, 3 H) 7.67 (d, J=9.23 Hz, 3 H).

Example 197

2-(2-((4-carbamimidoylphenylamino)(5-ethyl-2-fluoro-3-isobutoxyphenyl)methyl)-1H-imidazol-4-yl)benzamide bis-trifluoroacetic acid salt

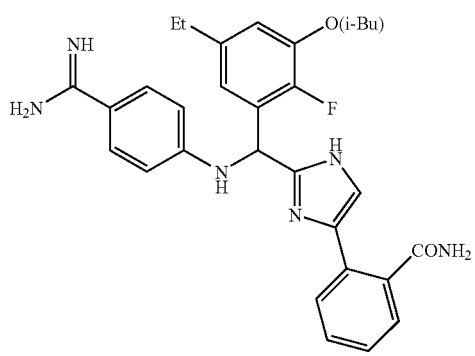

According to the procedure for the preparation of Example 188, Intermediate 188.6 was alkylated with 3-bromo-2-methylpropene, then was converted to the amide oxime, acylated, hydrogenated and deprotected as in Example 1 to afford after HPLC purification 7.4 mg of Example 197. LCMS (2 min gradient) RT=1.36 min, 529.3 (M+H)$^+$; $^1$H NMR (400 MHz, CD$_3$OD) δ ppm 1.04 (d, J=6.59 Hz, 6 H) 1.19 (t, J=7.47 Hz, 3 H) 2.08 (dt, J=13.18, 6.59 Hz, 1 H) 2.61 (q, J=7.76 Hz, 2 H) 3.82 (d, J=6.59 Hz, 2 H) 6.37 (s, 1 H) 6.78 (d, J=5.71 Hz, 1 H) 6.89 (d, J=8.79 Hz, 2 H) 7.02 (d, J=7.91 Hz, 1 H) 7.53 (s, 1 H) 7.55-7.61 (m, 3 H) 7.66-7.71 (m, 3 H).

Example 198

4-((5-ethyl-2-fluoro-3-methoxyphenyl)(4-(2-methoxyphenyl)-1H-imidazol-2-yl)methylamino)benzamidine bis-trifluoroacetic acid salt

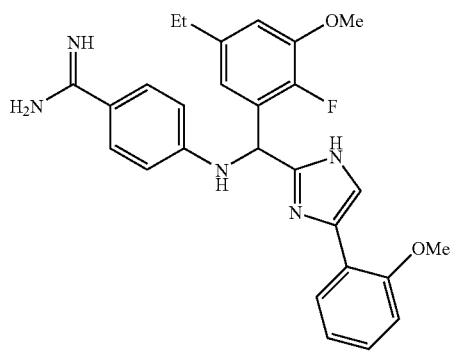

4-((5-ethyl-2-fluoro-3-hydroxyphenyl)(4-(2-methoxyphenyl)-1-trityl-1H-imidazol-2-yl)methylamino)benzonitrile (198.1)

According to the procedure for the preparation of Intermediate 138.2, Intermediate 188.5 (100 mg, 0.130 mmol) was coupled with 2-methoxyphenylboronic acid (29.5 mg, 0.194 mmol) to afford 73 mg of intermediate 198.1.

Example 198

According to the procedure for the preparation of Example 188, Intermediate 198.1 was alkylated with iodomethane, then was converted to the amide oxime, acylated, hydrogenated and deprotected as in Example 1 to afford after HPLC purification Example 198. LCMS (2 min gradient) RT=1.24 min, 474.3 (M+H)$^+$; $^1$H NMR (400 MHz, CD$_3$OD) δ ppm 1.20 (t, J=7.69 Hz, 3 H) 2.63 (q, J=7.47 Hz, 2 H) 3.89 (s, 3 H) 3.93 (s, 3 H) 6.41 (s, 1 H) 6.75 (dd, J=5.71, 1.76 Hz, 1 H) 6.87 (d, J=8.79 Hz, 2 H) 7.08 (t, J=7.69 Hz, 2 H) 7.18 (d, J=8.35 Hz, 1 H) 7.43-7.48 (m, 1 H) 7.65 (dd, J=7.69, 1.54 Hz, 1 H) 7.69 (d, J=8.79 Hz, 2 H) 7.78 (s, 1 H).

Example 199

4-((3-ethoxy-5-ethyl-2-fluorophenyl)(4-(2-methoxyphenyl)-1H-imidazol-2-yl)methylamino)benzamidine bis-trifluoroacetic acid salt

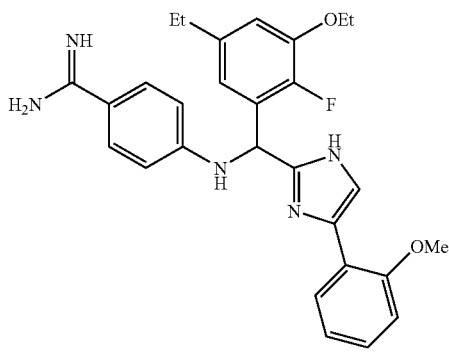

According to the procedure for the preparation of Example 188, Intermediate 198.1 was alkylated with iodoethane, then was converted to the amide oxime, acylated, hydrogenated and deprotected as in Example 1 to afford after HPLC purification Example 199. LCMS (2 min gradient) RT=1.35 min, 488.3 (M+H)+; 1H NMR (400 MHz, CD3OD) δ ppm 1.19 (t, J=7.69 Hz, 3 H) 1.41 (t, J=7.03 Hz, 3 H) 2.62 (q, J=7.47 Hz, 2 H) 3.94 (s, 3 H) 4.13 (q, J=6.74 Hz, 2 H) 6.42 (s, 1 H) 6.74 (d, J=4.39 Hz, 1 H) 6.88 (d, J=8.79 Hz, 2 H) 7.07 (q, 2 H) 7.19 (d, J=8.35 Hz, 1 H) 7.44-7.49 (m, 1 H) 7.65 (d, J=7.91 Hz, 1 H) 7.69 (d, J=8.79 Hz, 2 H) 7.79 (s, 1 H).

Example 200

4-((5-ethyl-2-fluoro-3-isopropoxyphenyl)(4-(2-methoxyphenyl)-1H-imidazol-2-yl)methylamino)benzamidine bis-trifluoroacetic acid salt

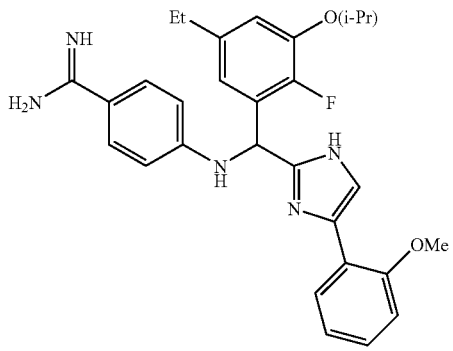

According to the procedure for the preparation of Example 188, Intermediate 198.1 was alkylated with 2-iodopropane, then was converted to the amide oxime, acylated, hydrogenated and deprotected as in Example 1 to afford after HPLC purification Example 200. LCMS (2 min gradient) RT=1.41 min, 502.3 (M+H)+; 1H NMR (400 MHz, CD3OD) δ ppm 1.19 (t, J=7.69 Hz, 3 H) 1.33 (d, J=6.15 Hz, 6 H) 2.61 (q, J=7.47 Hz, 2 H) 3.93 (s, 3 H) 4.59-4.70 (m, 1 H) 6.40 (s, 1 H) 6.74 (d, J=3.95 Hz, 1 H) 6.87 (d, J=8.79 Hz, 2 H) 7.04-7.10 (m, 2 H) 7.18 (d, J=8.35 Hz, 1 H) 7.45 (t, J=7.25 Hz, 1 H) 7.65 (dd, J=7.69, 1.54 Hz, 1 H) 7.69 (d, J=8.79 Hz, 2 H) 7.78 (s, 1 H).

Example 201

4-((5-ethyl-2-fluoro-3-methoxyphenyl)(4-(2-(methylsulfonyl)phenyl)-1H-imidazol-2-yl)methylamino)benzamidine bis-trifluoroacetic acid salt

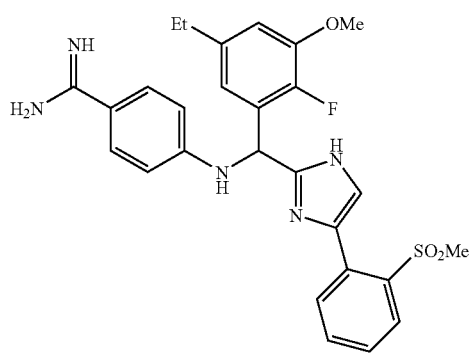

4-((5-ethyl-2-fluoro-3-hydroxyphenyl)(4-(2-(methylthio)phenyl)-1-trityl-1H-imidazol-2-yl)methylamino)benzonitrile (201.1)

According to the procedure for the preparation of Intermediate 138.2, Intermediate 188.5 (75 mg, 0.097 mmol) was coupled with 2-(methylthio)phenylboronic acid (24.5 mg, 0.146 mmol) to afford 69.6 mg of Intermediate 201.1.

4-((5-ethyl-2-fluoro-3-methoxyphenyl)(4-(2-(methylthio)phenyl)-1-trityl-1H-imidazol-2-yl)methylamino)benzonitrile (201.2)

A mixture of Intermediate 201.1 (23 mg), K2CO3 (17 mg) and iodomethane (0.01 mL) in 1 mL acetone was stirred at rt for 5 h. The mixture was filtered through a 1" pad of silica gel (eluting with EtOAc) and concentrated to afford 22.3 mg of intermediate 201.2. LCMS (2 min gradient) RT=2.30 min, 715.28 (M+H)+.

4-((5-ethyl-2-fluoro-3-methoxyphenyl)(4-(2-(methylsulfonyl)phenyl)-1-trityl-1H-imidazol-2-yl)methylamino)benzonitrile (201.3)

To Intermediate 201.2 (22.3 mg, 0.0312 mmol) in 1 mL CH2Cl2, was added 3-chloroperoxybenzoic acid (77%, 18.9 mg, 0.078 mmol). The mixture was stirred at rt for 20 min, then was diluted with EtOAc. The organic phase was washed with sat. Na2SO3, 1 N NaOH, water and brine, dried (Na2SO4) and concentrated to afford 25 mg of Intermediate 201.3. LCMS (2 min gradient) RT=2.19 min, 747.21 (M+H)+.

Example 201

A solution of Intermediate 201.3 (25 mg) in 1 mL 3 M NH2OH in DMSO was converted to the amide oxime, acylated, hydrogenated and deprotected as in Example 1 to afford after HPLC purification 11.5 mg of Example 201. LCMS (2 min gradient) RT=1.05 min, 522.2 (M+H)+; 1H NMR (400

MHz, CD$_3$OD) δ ppm 1.21 (t, J=7.47 Hz, 3 H) 2.63 (q, J=7.76 Hz, 2 H) 3.01 (s, 3 H) 3.89 (s, 3 H) 6.32 (s, 1 H) 6.81 (d, J=4.83 Hz, 1 H) 6.88 (d, J=8.79 Hz, 2 H) 7.03 (d, J=7.47 Hz, 1 H) 7.62-7.70 (m, 4 H) 7.74-7.82 (m, 2 H) 8.20 (d, J=7.47 Hz, 1 H).

Example 202

4-((3-ethoxy-5-ethyl-2-fluorophenyl)(4-(2-(methyl-sulfonyl)phenyl)-1H-imidazol-2-yl)methylamino)benzamidine bis-trifluoroacetic acid salt

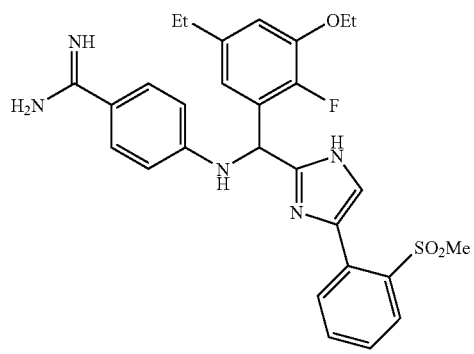

According to the procedure for the preparation of Example 201, Intermediate 201.1 was alkylated with iodoethane, oxidized, and then converted to the amide oxime, acylated, hydrogenated and deprotected as in Example 1 to afford after HPLC purification 11.8 mg of Example 202. LCMS (2 min gradient) RT=1.14 min, 536.2 (M+H)$^+$; $^1$H NMR (400 MHz, CD$_3$OD) δ ppm 1.20 (t, J=7.47 Hz, 3 H) 1.41 (t, J=7.03 Hz, 3 H) 2.61 (q, J=7.47 Hz, 2 H) 3.02 (s, 3 H) 4.12 (q, J=7.03 Hz, 2 H) 6.32 (s, 1 H) 6.80 (d, J=5.71 Hz, 1 H) 6.89 (d, J=8.79 Hz, 2 H) 7.02 (d, J=6.59 Hz, 1 H) 7.63-7.70 (m, 5 H) 7.75-7.83 (m, 2 H) 8.20 (d, J=7.47 Hz, 1 H).

Example 203

4-((5-ethyl-2-fluoro-3-isopropoxyphenyl)(4-(2-(methylsulfonyl)phenyl)-1H-imidazol-2-yl)methylamino)benzamidine bis-trifluoroacetic acid salt

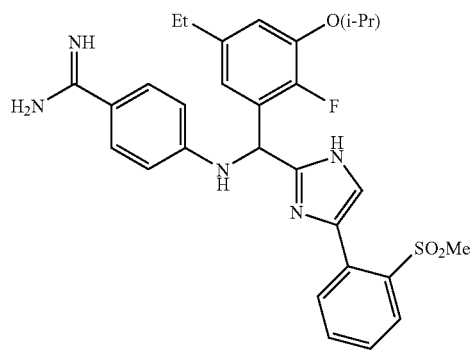

According to the procedure for the preparation of Example 201, Intermediate 201.1 was alkylated with 2-iodopropane, oxidized, and then converted to the amide oxime, acylated, hydrogenated and deprotected as in Example 1 to afford after HPLC purification 10.3 mg of Example 203. LCMS (2 min gradient) RT=1.22 min, 550.3 (M+H)$^+$; $^1$H NMR (400 MHz, CD$_3$OD) δ ppm 1.20 (t, J=7.69 Hz, 3 H) 1.33 (d, J=5.71 Hz, 6 H) 2.61 (q, J=7.62 Hz, 2 H) 3.02 (s, 3 H) 4.61-4.67 (m, 1 H) 6.31 (s, 1 H) 6.80 (d, J=3.95 Hz, 1 H) 6.88 (d, J=8.79 Hz, 2 H) 7.02 (d, J=6.15 Hz, 1 H) 7.63-7.70 (m, 4 H) 7.75-7.82 (m, 2 H) 8.19-8.21 (m, 1 H).

Example 204

2-(2-((4-carbamimidoylphenylamino)(5-ethyl-2-fluoro-3-((S)-tetrahydrofuran-3-yloxy)phenyl)methyl)-1H-imidazol-4-yl)benzamide bis-trifluoroacetic acid salt

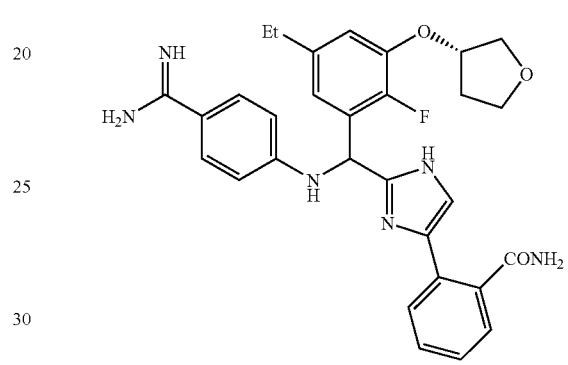

2-(2-((4-cyanophenylamino)(5-ethyl-2-fluoro-3-((S)-tetrahydrofuran-3-yloxy)phenyl)methyl)-1-trityl-1H-imidazol-4-yl)benzamide (204.1)

To a solution of triphenylphosphine (40.6 mg, 0.155 mmol) in 1 mL THF at 0° C., was added diethyl azidodicarboxylate (24.5 μL, 0.155 mmol), dropwise. The mixture was stirred at 0° C. for 20 min, then a solution of Intermediate 188.6 (36 mg, 0.052 mmol) and (R)-3-hydroxytetrahydrofuran (8.3 μL, 0.103 mmol) in 1 mL THF was added dropwise. The mixture was stirred at 0° C. for 15 min and at rt for 14 h, then was concentrated. The crude residue was purified by flash chromatography (0 to 100% EtOAc/hexanes gradient) to afford 40.5 mg of Intermediate 204.1, contaminated with triphenylphosphine. LCMS (2 min gradient) RT=2.00 min, 768.25 (M+H)$^+$.

Example 204

A solution of Intermediate 204.1 (40 mg) in 1 mL 3 M NH$_2$OH in DMSO was converted to the amide oxime, acylated, hydrogenated and deprotected as in Example 1 to afford after HPLC purification 16.5 mg of Example 204. LCMS (2 min gradient) RT=1.02 min, 543.3 (M+H)$^+$; $^1$H NMR (400 MHz, CD$_3$OD) δ ppm 1.20 (t, J=7.69 Hz, 3 H) 2.09-2.15 (m, 1 H) 2.22-2.31 (m, 1 H) 2.62 (q, J=7.62 Hz, 2 H) 3.88 (td, J=8.35, 3.95 Hz, 1 H) 3.93-3.99 (m, 3 H) 5.10 (d, J=3.08 Hz, 1 H) 6.37 (d, J=1.76 Hz, 1 H) 6.84 (d, J=5.71 Hz, 1 H) 6.89 (d, J=8.79 Hz, 2 H) 7.01 (d, J=6.15 Hz, 1 H) 7.54-7.61 (m, 4 H) 7.65-7.72 (m, 3 H).

Example 205

2-(2-((4-carbamimidoylphenylamino)(5-ethyl-2-fluoro-3-((R)-tetrahydrofuran-3-yloxy)phenyl)methyl)-1H-imidazol-4-yl)benzamide bis-trifluoroacetic acid salt

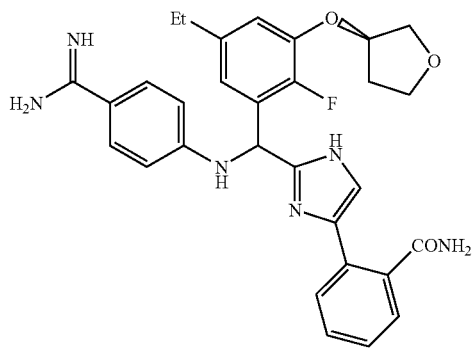

According to the procedure for the preparation of Example 204, Intermediate 188.6 (36 mg, 0.052 mmol) and (S)-3-hydroxytetrahydrofuran afforded 17.1 mg of Example 205 as a 1:1 mixture of diastereomers at the undefined stereocenter. LCMS (2 min gradient) RT=1.00 min, 543.3 (M+H)$^+$; $^1$H NMR (400 MHz, CD$_3$OD) δ ppm 1.20 (t, J=7.47 Hz, 3 H) 2.09-2.15 (m, 1 H) 2.22-2.31 (m, J=13.73, 8.35, 8.24, 5.71 Hz, 1 H) 2.62 (q, J=7.47 Hz, 2 H) 3.88 (td, J=8.35, 3.95 Hz, 1 H) 3.93-3.99 (m, 3 H) 5.07-5.13 (m, 1 H) 6.37 (d, J=1.76 Hz, 1 H) 6.84 (d, J=5.71 Hz, 1 H) 6.89 (d, J=8.79 Hz, 2 H) 7.00-7.03 (m, 1 H) 7.53-7.61 (m, 4 H) 7.65-7.72 (m, 3 H).

Example 206

N$^6$-((5-ethyl-2-fluoro-3-methoxyphenyl)(4-(2-methoxyphenyl)-1H-imidazol-2-yl)methyl)isoquinoline-1,6-diamine bis-trifluoroacetic acid salt

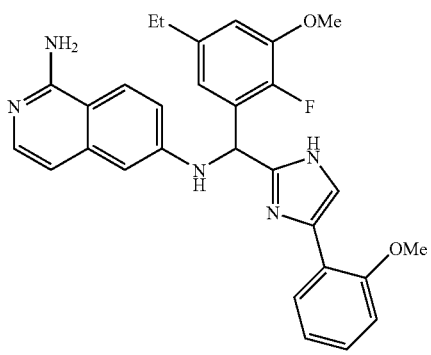

(4-bromo-1H-imidazol-2-yl)(3-(tert-butyldimethylsilyloxy)-5-ethyl-2-fluorophenyl)methanol (206.1)

To a solution of Intermediate 118.2 (870 mg, 3.42 mmol) and PMDTA (0.80 mL) in 10 ml THF at −78° C., was added BuLi (1.4 M in hexanes, 2.57 mL, 3.59 mmol). The mixture was stirred with warming to −40° C. over 30 min, recooled to −78° C., then a solution of Intermediate 175.1 (1.5 0 g, 3.59 mmol) in 10 mL THF was added. The mixture was slowly warmed to −30° C. over 1.5 h. The reaction was quenched with sat. NH$_4$Cl, then was diluted with EtOAc. The organic phase was washed with H$_2$O (2×) and brine, dried (Na$_2$SO$_4$) and concentrated. The crude product was purified by flash chromatography (0 to 30% EtOAc/hexanes gradient) to afford 2.14 g of Intermediate 206.1 as a colorless solid. LCMS (2 min gradient) RT=2.85 min, 671.32 (M+H)$^+$.

3-((4-bromo-1H-imidazol-2-yl)(hydroxy)methyl)-5-ethyl-2-fluorophenol (206.2)

To a solution of intermediate 206.1 (500 mg, 0.744 mmol) in 7 mL THF at 0° C., was added TBAF (1M in THF, 0.744 mL, 0.744 mmol). The mixture was stirred at 0° C. for 30 min, then concentrated. The mixture was diluted with EtOAc, washed with H$_2$O (2×) and brine, dried (Na$_2$SO$_4$) and concentrated. The crude product was triturated with 10% EtOAc/hexanes (10 mL) to afford after filtration 399 mg of Intermediate 191.2 as a white powder. LCMS (2 min gradient) RT=2.18 min, 579.13 (M+Na)$^+$.

(4-bromo-1H-imidazol-2-yl)(5-ethyl-2-fluoro-3-methoxyphenyl)methanol (206.3)

To a solution of Intermediate 206.2 (394 mg, 0.707 mmol) in 5 mL DMF at rt, were added K$_2$CO$_3$ (117 mg, 0.848 mmol) and iodomethane (132 μL, 2.12 mmol). The mixture was stirred at rt for 3 days, then diluted with EtOAc. The organic phase was washed with H$_2$O (2×), sat. Na$_2$SO$_3$, H$_2$O and brine, dried (Na$_2$SO$_4$) and concentrated. The crude product was purified by flash chromatography (0 to 60% EtOAc/hexanes gradient) to afford 359.4 mg of Intermediate 206.3 as a colorless solid.

di-tert-butyl (6-{[(4-bromo-1-trityl-1H-imidazol-2-yl)(5-ethyl-2-fluoro-3-methoxyphenyl)methyl]amino}isoquinolin-1-yl)imidodicarbonate (206.4)

To a solution of Intermediate 206.3 (356 mg, 0.624 mmol) and TEA (0.261 mL, 1.87 mmol) in 10 mL CH$_2$Cl$_2$ at 0° C., was added MsCl (0.121 mL, 1.56 mmol). The mixture was stirred at 0° C. for 1 h, then was diluted with EtOAc. The mixture was washed with ice water and brine, dried (Na$_2$SO$_4$) and concentrated to afford 350 mg of the chloro intermediate (4-bromo-2-(chloro(5-ethyl-2-fluoro-3-methoxyphenyl)methyl)-1-trityl-1H-imidazole), which was used without further purification.

To a solution of the chloro intermediate (350 mg, 0.594 mmol) in 5 mL CH$_3$CN and 2 mL CH$_2$Cl$_2$ at rt, was added DIEA (0.207 mL, 1.19 mmol), di-tert-butyl (6-aminoisoquinolin-1-yl)imidodicarbonate (235 mg, 0.653 mmol). The mixture was stirred at rt for 18 h and at 40° C. for 3 h, then was diluted with EtOAc. The organic phase was washed with H$_2$O and brine, dried (Na$_2$SO$_4$) and concentrated. The crude product was purified by flash chromatography (0 to 60% EtOAc/hexanes gradient) to afford 425 mg of Intermediate 206.4 as a colorless residue.

Example 206

To a degassed mixture of Intermediate 206.4 (70 mg, 0.0768 mmol), 2-methoxyphenylboronic acid (17.5 mg, 0.115 mmol) and Na$_2$CO$_3$ (32.6 mg, 0.307 mmol) was added Pd(PPh$_3$)$_4$ (8.9 mg, 0.0077 mmol). The mixture was stirred at 150° C. for 6 min in a microwave reactor, then was concentrated. The crude residue was dissolved in 1 mL TFA and stirred 30 min. The TFA was evaporated and the deprotected material was purified by preparative HPLC to afford 40.6 mg of Example 206 as a white powder. LCMS (2 min gradient) RT=1.34 min, 498.3 (M+H)+; 1H NMR (400 MHz, CD3OD) δ ppm 1.20 (t, J=7.47 Hz, 3 H) 2.63 (q, J=7.47 Hz, 2 H) 3.90 (s, 3 H) 3.92 (s, 3 H) 6.50 (s, 1 H) 6.76 (d, J=5.27 Hz, 1 H) 6.86 (s, 1 H) 6.93 (d, J=7.03 Hz, 1 H) 7.05-7.10 (m, 2 H) 7.17 (d, J=8.35 Hz, 1 H) 7.26 (dd, J=9.23, 2.20 Hz, 1 H) 7.37 (d, J=7.47 Hz, 1 H) 7.45 (t, J=7.91 Hz, 1 H) 7.65 (d, J=7.47 Hz, 1 H) 7.77 (s, 1 H) 8.20 (d, J=8.79 Hz, 1 H).

Example 207

N6-((5-ethyl-2-fluoro-3-methoxyphenyl)(4-(2-fluorophenyl)-1H-imidazol-2-yl)methyl)isoquinoline-1,6-diamine bis-trifluoroacetic acid salt

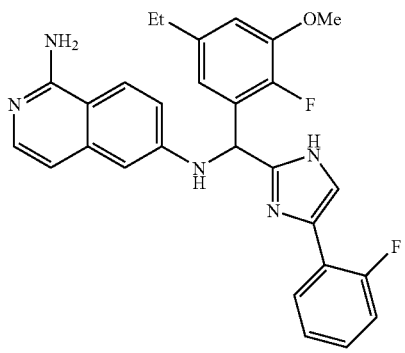

According to the procedure for the preparation of Example 206, coupling of Intermediate 206.4 (70 mg, 0.0768 mmol) and 2-fluorophenylboronic acid, followed by deprotection and HPLC purification afforded 40.9 mg of Example 207. LCMS (2 min gradient) RT=1.33 min, 486.3 (M+H)+; 1H NMR (400 MHz, CD3OD) δ ppm 1.20 (t, J=7.47 Hz, 3 H) 2.63 (q, J=7.76 Hz, 2 H) 3.89 (s, 3 H) 6.44 (s, 1 H) 6.80 (d, J=5.27 Hz, 1 H) 6.86 (d, J=1.76 Hz, 1 H) 6.92 (d, J=7.03 Hz, 1 H) 7.06 (d, J=7.03 Hz, 1 H) 7.24-7.33 (m, 3 H) 7.36 (d, J=7.03 Hz, 1 H) 7.42-7.48 (m, 1 H) 7.71 (d, J=2.20 Hz, 1 H) 7.80 (t, J=7.25 Hz, 1 H) 8.18 (d, J=9.23 Hz, 1 H).

Example 208

N6-((4-(2,3-difluorophenyl)-1H-imidazol-2-yl)(5-ethyl-2-fluoro-3-methoxyphenyl)methyl)isoquinoline-1,6-diamine bis-trifluoroacetic acid salt

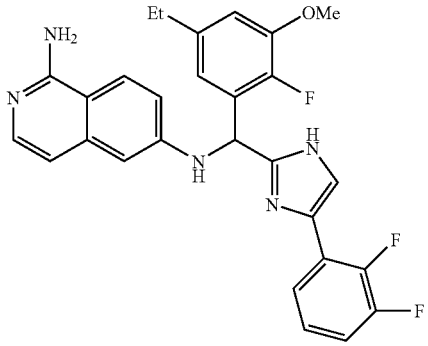

According to the procedure for the preparation of Example 206, coupling of Intermediate 206.4 (70 mg, 0.0768 mmol) and 2,3-difluorophenylboronic acid, followed by deprotection and HPLC purification afforded 36.7 mg of Example 208. LCMS (2 min gradient) RT=1.44 min, 504.3 (M+H)+; 1H NMR (400 MHz, CD3OD) δ ppm 1.19 (t, J=7.47 Hz, 3 H) 2.61 (q, J=7.62 Hz, 2 H) 3.89 (s, 3 H) 6.37 (s, 1 H) 6.80 (d, J=5.71 Hz, 1 H) 6.82 (s, 1 H) 6.90 (d, J=7.03 Hz, 1 H) 7.03 (d, J=7.91 Hz, 1 H) 7.22-7.29 (m, 3 H) 7.34 (d, J=7.03 Hz, 1 H) 7.63 (t, J=6.81 Hz, 1H) 7.69 (s, 1 H) 8.16 (d, J=9.23 Hz, 1 H).

Example 209

N6-((4-(3-fluorophenyl)-1H-imidazol-2-yl)(5-ethyl-2-fluoro-3-methoxyphenyl)methyl)isoquinoline-1,6-diamine bis-trifluoroacetic acid salt

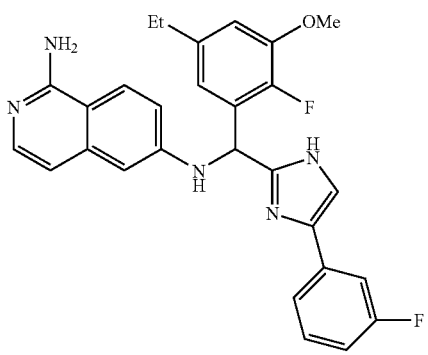

According to the procedure for the preparation of Example 206, coupling of Intermediate 206.4 (50 mg, 0.0548 mmol) and 3-fluorophenylboronic acid, followed by deprotection and HPLC purification afforded 31.0 mg of Example 209. LCMS (2 min gradient) RT=1.33 min, 486.3 (M+H)+; 1H NMR (400 MHz, CD3OD) δ ppm 1.19 (t, J=7.47 Hz, 3 H) 2.62 (q, J=7.76 Hz, 2 H) 3.89 (s, 3 H) 6.40 (s, 1 H) 6.80 (d, J=5.71 Hz, 1 H) 6.85 (s, 1 H) 6.91 (d, J=7.03 Hz, 1 H) 7.05 (d, J=7.91 Hz, 1 H) 7.13 (t, J=8.35 Hz, 1 H) 7.25 (dd, J=9.01, 2.42 Hz, 1 H) 7.35 (d, J=7.03 Hz, 1 H) 7.44-7.56 (m, 3 H) 7.78 (s, 1 H) 8.17 (d, J=9.23 Hz, 1 H).

Example 210

(2-(2-((1-aminoisoquinolin-6-ylamino)(5-ethyl-2-fluoro-3-methoxyphenyl)methyl)-1H-imidazol-4-yl)phenyl)methanol bis-trifluoroacetic acid salt

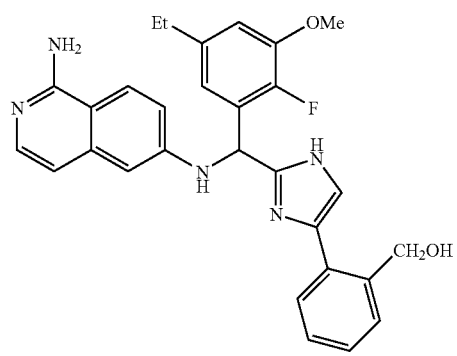

According to the procedure for the preparation of Example 206, coupling of Intermediate 206.4 (50 mg, 0.0548 mmol) and 2-(hydroxymethyl)phenylboronic acid, followed by deprotection and HPLC purification afforded 26.5 mg of Example 210. LCMS (2 min gradient) RT=1.16 min, 498.3 (M+H)+; 1H NMR (400 MHz, CD3OD) δ ppm 1.21 (t, J=7.69 Hz, 3 H) 2.64 (q, J=7.47 Hz, 2 H) 3.90 (s, 3 H) 4.49-4.57 (m, 2 H) 6.51 (s, 1 H) 6.85 (d, J=4.83 Hz, 1 H) 6.91 (d, J=1.76 Hz, 1 H) 6.93 (d, J=7.03 Hz, 1 H) 7.07 (d, J=7.91 Hz, 1 H) 7.27 (dd, J=9.23, 2.20 Hz, 1 H) 7.37 (d, J=7.03 Hz, 1 H) 7.41-7.51 (m, 3 H) 7.59 (d, J=6.15 Hz, 1 H) 7.75 (s, 1 H) 8.19 (d, J=9.23 Hz, 1 H).

Example 211

1-(2-(2-((1-aminoisoquinolin-6-ylamino)(5-ethyl-2-fluoro-3-methoxyphenyl)methyl)-1H-imidazol-4-yl)phenyl)ethanone bis-trifluoroacetic acid salt

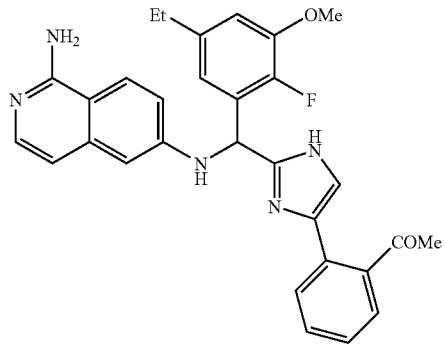

According to the procedure for the preparation of Example 206, coupling of Intermediate 206.4 (50 mg, 0.0548 mmol) and 2-acetylphenylboronic acid, followed by deprotection and HPLC purification afforded 31.5 mg of Example 211. LCMS (2 min gradient) RT=1.18 min, 510.3 (M+H)+; 1H NMR (400 MHz, CD3OD) δ ppm 1.23 (t, J=7.69 Hz, 3 H) 2.52 (s, 3 H) 2.66 (q, J=7.47 Hz, 2 H) 3.89 (s, 3 H) 6.42 (s, 1 H) 6.84 (d, J=5.71 Hz, 1 H) 6.87 (s, 1 H) 7.01 (d, J=7.03 Hz, 1 H) 7.07 (d, J=7.91 Hz, 1 H) 7.26 (dd, J=9.45, 1.98 Hz, 1 H) 7.38 (d, J=7.03 Hz, 1 H) 7.47 (s, 1 H) 7.52-7.56 (m, 1 H) 7.62-7.68 (m, 2 H) 7.99-8.03 (m, 1 H) 8.18 (d, J=9.23 Hz, 1 H).

Example 212

$N^6$-((5-ethyl-2-fluoro-3-methoxyphenyl)(4-(2-(methylthio)phenyl)-1H-imidazol-2-yl)methyl)isoquinoline-1,6-diamine bis-trifluoroacetic acid salt

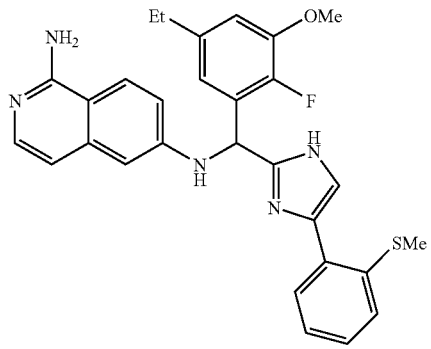

According to the procedure for the preparation of Example 206, coupling of Intermediate 206.4 (50 mg, 0.0548 mmol) and 2-(methylthio)phenylboronic acid, followed by deprotection and HPLC purification afforded 32.8 mg of Example 212. LCMS (2 min gradient) RT=1.24 min, 514.3 (M+H)+; 1H NMR (400 MHz, CD3OD) 5 ppm 1.21 (t, J=7.47 Hz, 3 H) 2.42 (s, 3 H) 2.64 (q, J=7.47 Hz, 2 H) 3.90 (s, 3 H) 6.46 (s, 1 H) 6.80 (d, J=5.27 Hz, 1 H) 6.86 (s, 1 H) 6.93 (d, J=7.47 Hz, 1 H) 7.07 (d, J=7.47 Hz, 1 H) 7.23-7.29 (m, 2 H) 7.37-7.48 (m, 4 H) 7.61 (s, 1 H) 8.18 (d, J=9.23 Hz, 1 H).

Example 213

$N^6$-((3-ethoxy-5-ethyl-2-fluorophenyl)(4-(3-ethylphenyl)-1H-imidazol-2-yl)methyl)isoquinoline-1,6-diamine bis-trifluoroacetic acid salt

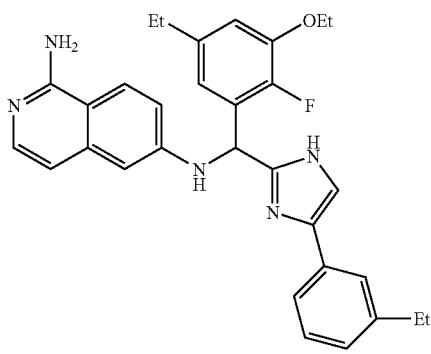

(4-bromo-1-trityl-1H-imidazol-2-yl)(3-ethoxy-5-ethyl-2-fluorophenyl)methanol (213.1)

According to the procedure for the preparation of intermediate 206.3, Intermediate 206.2 (1.01 g, 1.81 mmol) was alkylated with EtI to afford 1.02 g of Intermediate 213.1 a colorless solid.

di-tert-butyl (6-{[(4-bromo-1-trityl-1H-imidazol-2-yl)(3-ethoxy-5-ethyl-2-fluoro-phenyl)methyl]amino}isoquinolin-1-yl)imidodicarbonate (213.2)

According to the procedure for the preparation of Intermediate 206.4, Intermediate 213.1 (1.02 g, 1.74 mmol) was converted to the chloro intermediate, which was displaced with di-tert-butyl (6-aminoisoquinolin-1-yl)imidodicarbonate (688 mg, 1.91 mmol) to afford after flash chromatography (0 to 60% EtOAc/hexanes gradient) 1.47 g of Intermediate 213.2 as a pale yellow solid.

Example 213

According to the procedure for the preparation of Example 206, coupling of Intermediate 213.2 (30 mg, 0.0324 mmol) and 3-ethylphenylboronic acid, followed by deprotection and HPLC purification afforded 5.8 mg of Example 213. LCMS (2 min gradient) RT=1.54 min, 510.3 (M+H)+; 1H NMR (400 MHz, CD3OD) δ ppm 1.19 (t, J=7.47 Hz, 3 H) 1.26 (t, J=7.69 Hz, 3 H) 1.41 (t, J=7.03 Hz, 3 H) 2.61 (q, J=7.47 Hz, 2 H) 2.70 (q, J=7.76 Hz, 2 H) 4.13 (q, J=7.03 Hz, 2 H) 6.44 (s, 1 H) 6.79 (d, J=5.27 Hz, 1 H) 6.87 (s, 1 H) 6.93 (d, J=7.47 Hz, 1 H) 7.04 (d, J=7.47 Hz, 1 H) 7.23-7.29 (m, 3 H) 7.35-7.42 (m, 2 H) 7.52 (d, J=7.47 Hz, 1 H) 7.58 (s, 1 H) 7.75 (s, 1 H) 8.19 (d, J=9.23 Hz, 1 H).

Example 214

N6-((3-ethoxy-5-ethyl-2-fluorophenyl)(4-(3-propylphenyl)-1H-imidazol-2-yl)methyl)isoquinoline-1,6-diamine bis-trifluoroacetic acid salt

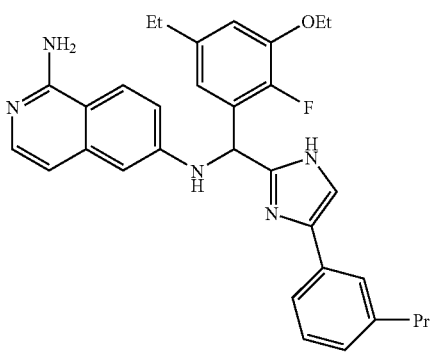

1-bromo-3-propylbenzene (214.1)

To a solution of 1-(3-bromophenyl)propan-1-one (2.00 g, 9.39 mmol) in 10 mL TFA, was added triethylsilane (4.50 mL, 28.2 mmol). The mixture was stirred at rt for 20 h, then concentrated. The crude material was purified by flash chromatography to afford 350 mg of Intermediate 214.1 as a colorless oil.

3-propylphenylboronic acid (214.2)

To a solution of Intermediate 214.1 (130 mg, 0.65 mmol) in 4 mL THF at −78° C., was added BuLi (1.4 M in hexanes, 0.557 mL, 0.78 mmol). The mixture was stirred 5 min at −78° C., then trimethylborate (0.109 mL, 0.975 mmol) was added. The reaction was stirred at −78° C. for 10 min, then was removed from the cooling bath and stirred 1 h. The reaction was quenched with 1 N HCl, then was diluted with EtOAc. The organic phase was washed with 1N HCl and brine, dried (Na$_2$SO$_4$) and concentrated to afford 83 mg of Intermediate 214.2 as a colorless oil, which was used without further purification in the following step.

Example 214

According to the procedure for the preparation of Example 206, coupling of Intermediate 213.2 (30 mg, 0.0324 mmol) and Intermediate 214.2, followed by deprotection and HPLC purification afforded 6.6 mg of Example 214. LCMS (2 min gradient) RT=1.64 min, 524.4 (M+H)$^+$; $^1$H NMR (400 MHz, CD$_3$OD) δ ppm 0.86 (t, J=7.25 Hz, 3 H) 1.09 (t, J=7.47 Hz, 3 H) 1.32 (t, J=7.03 Hz, 3H) 1.54-1.63 (m, J=7.58, 7.58, 7.58, 7.36, 7.25 Hz, 2 H) 2.49-2.57 (m, 4 H) 4.04 (q, J=7.03 Hz, 2 H) 6.33 (s, 1 H) 6.69 (d, J=5.71 Hz, 1 H) 6.77 (s, 1 H) 6.83 (d, J=7.03 Hz, 1 H) 6.94 (d, J=7.47 Hz, 1 H) 7.16 (d, J=6.59 Hz, 2 H) 7.25-7.30 (m, 2 H) 7.43 (d, J=7.91 Hz, 1 H) 7.47 (s, 1 H) 7.65 (s, 1 H) 8.09 (d, J=9.23 Hz, 1 H).

Example 215

N6-((3-ethoxy-5-ethyl-2-fluorophenyl) (4-(2-methoxypyridin-3-yl)-1H-imidazol-2-yl)methyl)isoquinoline-1,6-diamine bis-trifluoroacetic acid salt

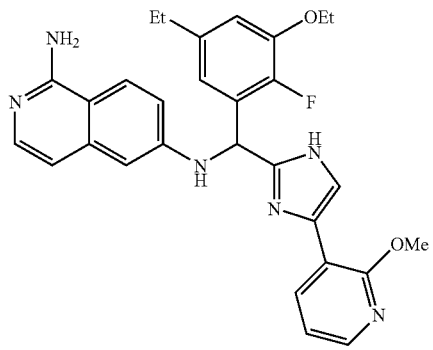

According to the procedure for the preparation of Example 206, coupling of Intermediate 213.2 (30 mg, 0.0324 mmol) and 2-methoxypyridin-3-ylboronic acid, followed by deprotection and HPLC purification afforded 9.1 mg of Example 215. LCMS (2 min gradient) RT=1.35 min, 513.4 (M+H)$^+$; $^1$H NMR (400 MHz, CD$_3$OD) δ ppm 1.19 (t, J=7.69 Hz, 3 H) 1.41 (t, J=7.03 Hz, 3 H) 2.61 (q, J=7.62 Hz, 2 H) 4.05 (s, 3 H) 4.14 (q, J=7.03 Hz, 2 H) 6.41 (s, 1 H) 6.77 (d, J=5.27 Hz, 1 H) 6.83 (s, 1 H) 6.91 (d, J=7.03 Hz, 1 H) 7.03 (d, J=7.47 Hz, 1 H) 7.08 (dd, J=7.69, 5.05 Hz, 1 H) 7.25 (dd, J=9.01, 11.98 Hz, 1 H) 7.36 (d, J=7.03 Hz, 1 H) 7.78 (s, 1 H) 8.12-8.19 (m, 3 H).

Example 216

N6-((3-ethoxy-5-ethyl-2-fluorophenyl)(4-(2-fluoropyridin-3-yl)-1H-imidazol-2-yl)methyl)isoquinoline-1,6-diamine bis-trifluoroacetic acid salt

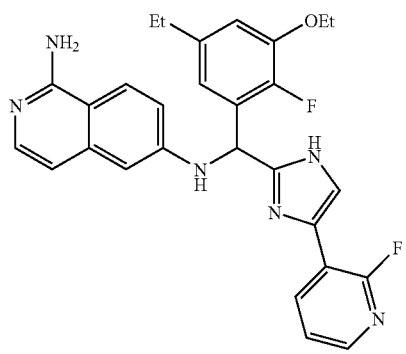

According to the procedure for the preparation of Example 206, coupling of Intermediate 213.2 (30 mg, 0.0324 mmol) and 2-fluoropyridin-3ylboronic acid, followed by deprotection and HPLC purification afforded 12.9 mg of Example 216. LCMS (2 min gradient) RT=1.36 min, 501.4 (M+H)$^+$; $^1$H NMR (400 MHz, CD$_3$OD) δ ppm 1.18 (t, J=7.69 Hz, 3 H) 1.42 (t, J=6.59 Hz, 3 H) 2.59 (q, J=7.47 Hz, 2 H) 4.10-4.16 (m, 2 H) 6.29 (s, 1 H) 6.78 (s, 2 H) 6.88 (d, J=7.47 Hz, 1 H) 6.98 (d, J=7.91 Hz, 1 H) 7.23 (d, J=9.23 Hz, 1 H) 7.33 (d, J=7.03 Hz, 1 H) 7.40 (t, 1 H) 7.62 (d, J=3.08 Hz, 1 H) 8.11 (d, J=4.83 Hz, 1 H) 8.14 (d, J=9.23 Hz, 1 H) 8.44 (t, J=8.57 Hz, 1 H).

Example 217

N6-[(4-Biphenyl-2-yl-1H-imidazol-2-yl)-(3-ethoxy-5-ethyl-2-fluoro-phenyl)-methyl]-isoquinoline-1,6-diamine bis-trifluoroacetic acid salt

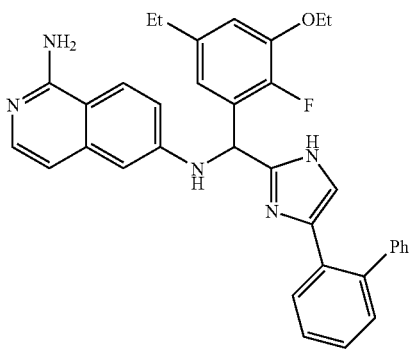

4-(2-bromophenyl)-1-trityl-1H-imidazole (217.1)

A mixture of 2-bromo-1-(3-bromophenyl)ethanone 1.15 g in 1.75 mL formamide was stirred at 170° C. for 4 h. The mixture was diluted with $CH_2Cl_2$ and made basic with sat. $NaHCO_3$. The layers were separated and the aqueous phase was extracted with $CH_2Cl_2$ (2×). The combined organic phase was washed with water and brine, dried ($Na_2SO_4$) and concentrated to afford 880 mg of 4-(2-bromophenyl)-1H-imidazole as an orange glass.

To a solution of 4-(2-bromophenyl)-1H-imidazole (880 mg, 3.94 mmol) in 10 mL DMF, were added TEA (0.605 mL, 4.34 mmol) and trityl chloride (1.21 g, 4.34 mmol). The mixture was stirred at rt for 14 h, then diluted with EtOAc. The organic phase was washed with $H_2O$ (2×) and brine, dried ($Na_2SO_4$), filtered through a 1" pad of silica gel and concentrated. The crude product was purified by flash chromatography (0 to 40% EtOAc/hexanes gradient) to afford 1.34 g of Intermediate 217.1 as an off-white solid. LCMS (50 to 100% B, 4 min gradient, A 95% $H_2O$/5% $CH_3CN$/0.1% TFA, B=5% $H_2O$/95% $CH_3CN$/0.1% TFA) RT=0.77 min, 465.2 $(M+H)^+$.

(4-(2-bromophenyl)-1-trityl-1H-imidazol-2-yl)(3-(tert-butyldimethylsilyloxy)-5-ethyl-2-fluorophenyl)methanol (217.2)

To a solution of Intermediate 217.1 (650 mg, 1.40 mmol) in 10 mL THF at 0° C., was added a solution of lithium diisopropylamide (2M in heptane/THF/ethylbenzene, 0838 mL, 1.68 mmol). The mixture was stirred at 0° C. for 30 min, then a solution of Intermediate 188.3 (356 mg, 1.26 mmol) in 2 mL THF. The mixture was stirred at 0° C. for 2 h, then was quenched with sat. $NH_4Cl$ and diluted with EtOAc. The organic phase was washed with $H_2O$ and brine, dried ($Na_2SO_4$) and concentrated. The crude product was purified by flash chromatography (0 to 40% EtOAc/hexanes gradient) to afford 510 mg of Intermediate 217.2 as a pale yellow solid. LCMS (50 to 100% B, 4 min gradient, A=95% $H_2O$/5% $CH_3CN$/0.1% TFA, B=5% $H_2O$/95% $CH_3CN$/0.1% TFA) RT=5.61 min, 747.67 $(M+H)^+$.

(4-(2-bromophenyl)-1-trityl-1H-imidazol-2-yl)(3-ethoxy-5-ethyl-2-fluorophenyl)methanol (217.3)

To a solution of intermediate 217.2 (500 mg, 0.669 mmol) in 5 mL THF at rt, was added TBAF (1M in THF, 0.669 mL, 0.669 mmol). The mixture was stirred at rt for 30 min. The mixture was diluted with EtOAc, washed with $H_2O$ (2×) and brine, dried ($Na_2SO_4$) and concentrated. The crude product was triturated with hexanes (10 mL) to afford 3-((4-(2-bromophenyl)-1-trityl-1H-imidazol-2-yl)(hydroxy)methyl)-5-ethyl-2-fluorophenol. To a solution of this product in 5 mL DMF at rt, were added $K_2CO_3$ (111 mg, 0.803 mmol) and iodoethane (161 μL, 2.01 mmol). The mixture was stirred at rt for 15 h, then diluted with EtOAc. The organic phase was washed with $H_2O$ (2×), sat. $Na_2SO_3$ and brine, dried ($Na_2SO_4$), filtered through a 1" pad of silica gel and concentrated to afford 433 mg of Intermediate 217.3 as an off-white solid.

di-tert-butyl (6-{[(4-(2-bromophenyl)-1-trityl-1H-imidazol-2-yl)(3-ethoxy-5-ethyl-2-fluorophenyl)methyl]amino}isoquinolin-1-yl)imidodicarbonate (217.4)

According to the procedure for the preparation of Intermediate 206.4, Intermediate 217.3 (424 mg, 0.641 mmol) was converted to the chloro intermediate, then displaced with di-tert-butyl (6-aminoisoquinolin-1-yl)imidodicarbonate to afford after flash chromatography (0 to 60% EtOAc/hexanes gradient) 615 mg of intermediate 217.4 as a pale yellow solid.

Example 217

According to the procedure for the preparation of Example 206, coupling of Intermediate 217.4 (50 mg, 0.0498 mmol) and phenylboronic acid, followed by deprotection and HPLC purification afforded 28.4 mg of Example 216. LCMS (2 min gradient) RT=1.46 min, 558.3 $(M+H)^+$; $^1H$ NMR (400 MHz, $CD_3OD$) δ ppm 1.21 (t, J=7.47 Hz, 3 H) 1.44 (t, J=7.03 Hz, 3 H) 2.62 (q, J=7.47 Hz, 2 H) 4.15 (q, J=7.03 Hz, 2 H) 6.30 (s, 1 H) 6.67 (dd, 1 H) 6.77 (d, J=2.20 Hz, 1 H) 6.93 (d, J=7.03 Hz, 1 H) 7.01-7.07 (m, 2 H) 7.17-7.22 (m, 4 H) 7.24-7.28 (m, 2 H) 7.41 (d, J=7.03 Hz, 1 H) 7.45-7.52 (m, 2 H) 7.57 (t, J=7.91 Hz, 2 H) 8.18 (d, J=9.23 Hz, 1 H).

Example 218

N6-((4-(2-bromophenyl)-1H-imidazol-2-yl)(3-ethoxy-5-ethyl-2-fluorophenyl)methyl)isoquinoline-1,6-diamine bis-trifluoroacetic acid salt

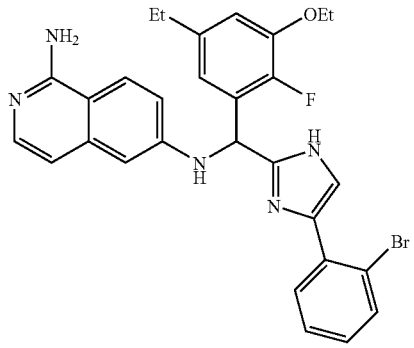

Intermediate 217.4 (43 mg) was dissolved in 1 mL TFA and stirred 25 min at rt. The TFA was evaporated and the crude product was purified by preparative HPLC to afford 26.0 mg of Example 218. LCMS (2 min gradient) RT=1.36 min, 560.2 (M+H)+; 1H NMR (400 MHz, CD3OD) δ ppm 1.20 (t, J=7.69 Hz, 3 H) 1.42 (t, J=7.03 Hz, 3 H) 2.63 (q, J=7.47 Hz, 2 H) 4.14 (q, J=7.03 Hz, 2 H) 6.45 (s, 1 H) 6.81 (dd, J=5.71, 1.76 Hz, 1 H) 6.88 (d, J=2.20 Hz, 1 H) 6.93 (d, J=7.03 Hz, 1 H) 7.05 (dd, J=7.91, 1.76 Hz, 1 H) 7.27 (dd, J=9.23, 2.20 Hz, 1 H) 7.36-7.40 (m, 2 H) 7.48 (td, J=7.58, 1.10 Hz, 1 H) 7.60 (dd, J=7.47, 1.76 Hz, 1 H) 7.69 (s, 1 H) 7.75 (dd, J=8.13, 1.10 Hz, 1 H) 8.19 (d, J=8.79 Hz, 1 H).

Example 219

3-(2-((1-aminoisoquinolin-6-ylamino)(3-ethoxy-5-ethyl-2-fluorophenyl)methyl)-1H-imidazol-4-yl)phenol bis-trifluoroacetic acid salt

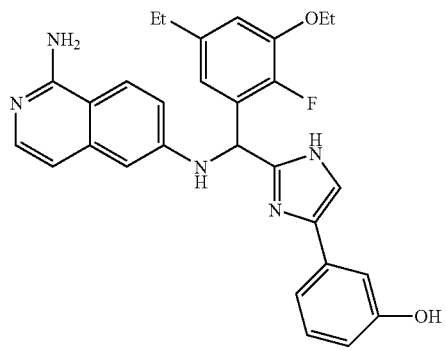

According to the procedure for the preparation of Example 206, coupling of Intermediate 213.2 (30 mg, 0.0324 mmol) and 3-hydroxyphenylboronic acid, followed by deprotection and HPLC purification afforded 23.4 mg of Example 219. LCMS (2 min gradient) RT=1.26 min, 498.4 (M+H)+; 1H NMR (400 MHz, CD3OD) δ ppm 1.20 (t, J=7.47 Hz, 3 H) 1.42 (t, J=7.03 Hz, 3 H) 2.62 (q, J=7.47 Hz, 2 H) 4.14 (q, J=7.03 Hz, 2 H) 6.44 (s, 1 H) 6.79 (d, J=3.95 Hz, 1 H) 6.82-6.88 (m, 2H) 6.93 (d, J=7.03 Hz, 1 H) 7.05 (dd, J=7.91, 1.76 Hz, 1 H) 7.12 (d, J=2.20 Hz, 1 H) 7.17 (d, J=7.91 Hz, 1 H) 7.24-7.31 (m, 2 H) 7.37 (d, J=7.03 Hz, 1 H) 7.71 (s, 1 H) 8.20 (d, J=9.23 Hz, 1 H).

Example 220

2-(2-((1-aminoisoquinolin-6-ylamino)(3-ethoxy-5-ethyl-2-fluorophenyl)methyl)-1H-imidazol-4-yl)benzenesulfonamide bis-trifluoroacetic acid salt

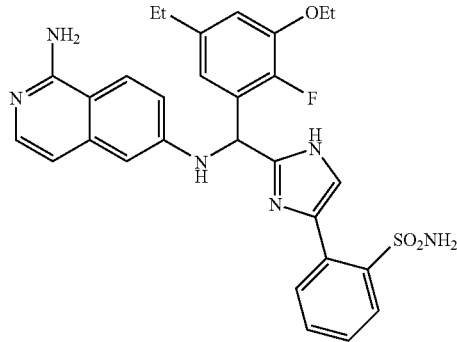

According to the procedure for the preparation of Example 206, coupling of Intermediate 213.2 (30 mg, 0.0324 mmol) and 2-(tert-butylamino)sulfonylphenylboronic acid, followed by deprotection (20 h in TFA at rt) and HPLC purification afforded 14.1 mg of Example 220. LCMS (2 min gradient) RT=1.22 min, 561.3 (M+H)+; 1H NMR (400 MHz, CD3OD) δ ppm 1.10 (t, J=7.47 Hz, 3 H) 1.31 (t, J=6.81 Hz, 3 H) 2.52 (q, J=7.62 Hz, 2 H) 4.03 (q, J=6.88 Hz, 2 H) 6.23 (s, 1 H) 6.72 (d, J=2.20 Hz, 1 H) 6.74 (dd, J=5.71, 1.76 Hz, 1 H) 6.89 (d, J=7.03 Hz, 2 H) 7.14 (dd, J=9.01, 2.42 Hz, 1 H) 7.25 (d, J=7.03 Hz, 1 H) 7.40 (s, 1 H) 7.46-7.56 (m, 3 H) 8.01 (d, J=7.91 Hz, 1 H) 8.05 (d, J=9.23 Hz, 1 H).

Example 221

2-(2-((1-aminoisoquinolin-6-ylamino)(3-chloro-5-ethyl-2-fluorophenyl)methyl)-1H-imidazol-4-yl)benzamide bis-trifluoroacetic acid salt

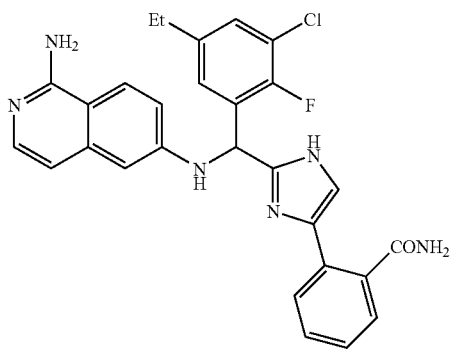

2-chloro-4-ethyl-1-fluorobenzene (221.1)

To a solution of 3'-chloro-4'-fluoroacetophenone (5.2 g, 30.1 mmol) in 30 mL TFA, was added triethylsilane (14.4 mL, 90.4 mmol). The mixture was stirred at rt for 15 h, then concentrated. The crude product was purified by flash chromatography (100% hexanes, 2×) to afford 1.35 g of Intermediate 221.1 as a colorless oil.

(4-bromo-1-trityl-1H-imidazol-2-yl)(3-chloro-5-ethyl-2-fluorophenyl)methanol (221.2)

To a solution of Intermediate 221.1 (100 mg, 0.631 mmol) and PMDTA (0.15 mL) in 5 mL THF at −70° C., was added BuLi (1.4 M in hexanes, 0.473 mL, 0.662 mmol). The mixture was stirred with warming to −40° C. over 30 min, recooled to −70° C., then a solution of Intermediate 175.1 (263 mg, 0.631 mmol) in 2 mL THF was added. The mixture was slowly warmed to −20° C. over 1 h. The reaction was quenched with sat. NH4Cl, then was diluted with EtOAc. The organic phase was washed with H2O (2×) and brine, dried (Na2SO4) and concentrated. The crude product was purified by flash chromatography (0 to 40% EtOAc/hexanes gradient) to afford 312 g of Intermediate 221.2 as a colorless solid. LCMS (50 to 100% B, 4 min gradient, A=95% H2O/5% CH3CN/0.1% TFA, B=5% H2O/95% CH3CN/0.1% TFA) RT=5.45 min, 575.28 (M+H)+.

di-tert-butyl (6-{[(4-bromo-1-trityl-1H-imidazol-2-yl)(3-chloro-5-ethyl-2-fluorophenyl)methyl]amino}isoquinolin-1-yl)imidodicarbonate (221.3)

According to the procedure for the preparation of Intermediate 206.4, Intermediate 221.2 (309 mg, 0.537 mmol) was converted to the chloro intermediate, then displaced with di-tert-butyl (6-aminoisoquinolin-1-yl)imidodicarbonate (rt for 15 h, 40° C. for 9 h, 50° C. for 6 h) to afford after flash chromatography (O to 50% EtOAc/hexanes gradient) 400 mg of Iintermediate 221.3 as a pale yellow solid. LCMS (50 to 100% B, 4 min gradient, A=95% H$_2$O/5% CH$_3$CN/0.1% TFA, B=5% H$_2$O/95% CH$_3$CN/0.1% TFA) RT=5.43 min, 918.76 (M+H)$^+$.

Example 221

According to the procedure for the preparation of Example 206, coupling of Intermediate 221.3 (50 mg, 0.0545 mmol) and 2-carbamoylphenylboronic acid, followed by deprotection and HPLC purification afforded 27.1 mg of Example 221. LCMS (2 min gradient) RT=1.27 min, 515.3 (M+H)$^+$; $^1$H NMR (400 MHz, CD$_3$OD) δ ppm 1.18-1.23 (m, 3 H) 2.65 (q, J=7.47 Hz, 2 H) 6.51 (s, 1 H) 6.89 (d, J=2.20 Hz, 1 H) 6.99 (d, J=7.03 Hz, 1 H) 7.22-7.28 (m, 2 H) 7.23 (d, J=1.76 Hz, 1 H) 7.24-7.28 (m, 3 H) 7.38 (d, J=7.03 Hz, 1 H) 7.46 (dd, J=6.81, 1.98 Hz, 1 H) 7.54-7.62 (m, 4 H) 7.70 (dd, J=6.37, 1.54 Hz, 1 H) 8.20 (d, J=8.79 Hz, 1 H).

Example 222

2-(2-((R)-(1-aminoisoquinolin-6-ylamino)(3-ethoxy-5-ethyl-2-fluorophenyl)methyl)-1H-imidazol-4-yl)benzamide bis-trifluoroacetic acid salt Example 223

2-(2-((S)-(1-aminoisoquinolin-6-ylamino)(3-ethoxy-5-ethyl-2-fluorophenyl)methyl)-1H-imidazol-4-yl)benzamide bis-trifluoroacetic acid salt Enantiomeric separation of Example 276

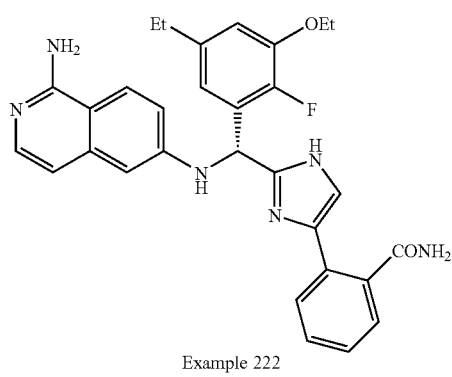

Example 222

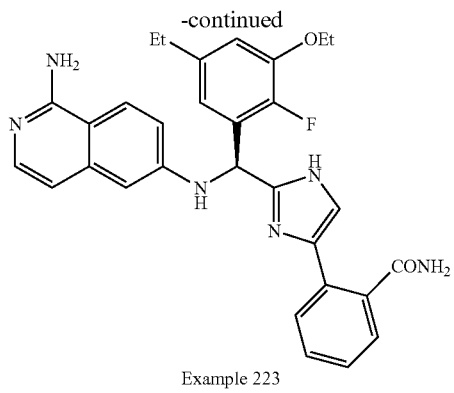

Example 223

Racemic Example 276 was separated by chiral chromatography: Chiralpak AD, 60% IPA/40% heptane+0.1% DEA to afford Example 222, followed by Example 223. Each enantiomer was converted to the TFA salt by treatment with TFA, followed by evaporation.

Example 224

2-(2-((1-aminoisoquinolin-6-ylamino)(3-ethoxy-5-ethyl-2-fluorophenyl)methyl)-1H-imidazol-4-yl)-5-chlorobenzoic acid bis-trifluoroacetic acid salt

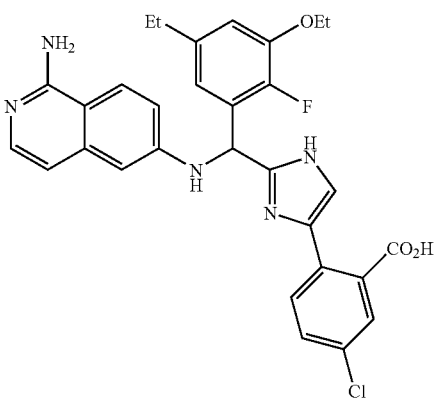

2-chloro-6-(4,4,5,5-tetramethyl-1,3,2-dioxaborolan-2-yl)benzoate (224.1)

According to procedure for the preparation of Intermediate 299.2, 5-chloro-2-iodobenzoic acid afforded after HPLC purification Intermediate 224.1. LC/MS (2 min gradient) RT=1.75 min, 297.2 (M+H)$^+$.

Example 224

According to procedure for the preparation of Example 241, coupling of Intermediate 276.1 with Intermediate 224.1, followed by deprotection with TFA afforded after HPLC purification Example 224. LCMS (4 min gradient, A=95% H$_2$O/5% CH$_3$CN/0.1% TFA, B=5% H$_2$O/95% CH$_3$CN/0.1% TFA) RT=3.47 min, 560.44 (M+H)$^+$; $^1$H NMR (400 MHz, CD$_3$OD) δ ppm 1.21 (t, J=7.69 Hz, 3 H) 1.41 (t, J=7.03 Hz, 3 H) 2.64 (q, J=7.76 Hz, 2 H) 4.13 (q, J=7.03 Hz, 2 H) 6.44 (s, 1 H) 6.77-6.84 (m, 1 H) 6.86 (d, J=2.20 Hz, 1 H) 7.01 (d, J=7.03 Hz, 1 H) 7.05 (d, J=7.91 Hz, 1 H) 7.26 (dd, J=9.23, 2.20 Hz, 1 H) 7.37 (d, J=7.03 Hz, 1 H) 7.56-7.72 (m, 3 H) 8.15 (d, J=8.35 Hz, 1 H) 8.18 (d, J=9.23 Hz, 1 H).

Example 225

2-(2-((1-aminoisoquinolin-6-ylamino)(3-ethoxy-5-ethyl-2-fluorophenyl)methyl)-1H-imidazol-4-yl)-6-fluorobenzoic acid bis-trifluoroacetic acid salt

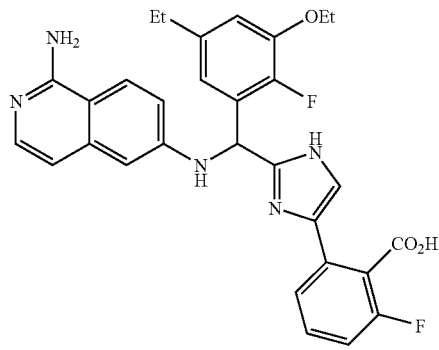

According to procedure for the preparation of Example 301, Example 226 was hydrolyzed to Example 225. LCMS (4 min gradient, A=95% H$_2$O/5% CH$_3$CN/0.1% TFA, B=5% H$_2$O/95% CH$_3$CN/0.1% TFA) RT=3.08 min, 544.44 (M+H)$^+$; $^1$H NMR (400 MHz, CD$_3$OD) δ ppm 1.19 (t, J=7.69 Hz, 3 H) 1.41 (t, J=6.81 Hz, 3 H) 2.62 (q, J=7.47 Hz, 2 H) 4.13 (q, J=7.03 Hz, 2 H) 6.44 (s, 1 H) 6.76-6.82 (m, 1 H) 6.85 (d, J=2.20 Hz, 1 H) 6.95 (d, J=7.03 Hz, 1 H) 7.01-7.09 (m, 1 H) 7.25 (dd, J=9.23, 2.64 Hz, 1 H) 7.30-7.34 (m, 1 H) 7.37 (d, J=7.03 Hz, 1 H) 7.41 (d, J=7.91 Hz, 1 H) 7.51-7.58 (m, 2 H) 8.18 (d, J=8.79 Hz, 1 H).

Example 226

Methyl-2-(2-((1-aminoisoquinolin-6-ylamino)(3-ethoxy-5-ethyl-2-fluorophenyl)methyl)-1H-imidazol-4-yl)-6-fluorobenzoate bis-trifluoroacetic acid salt

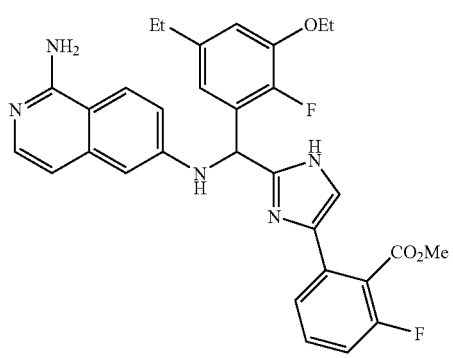

2-fluoro-6-(4,4,5,5-tetramethyl-1,3-dioxolan-2-yl)benzoic acid (226.1)

According to procedure for the preparation of Intermediate 299.2, 2-fluoro-6-iodobenzoic acid afforded after HPLC purification Intermediate 226.1. LC/MS (2 min gradient) RT=1.75 min, 297.2 (M+H)$^+$.

Example 226

According to procedure for the preparation of Example 241, coupling of Intermediate 276.1 with Intermediate 226.1, followed by deprotection with TFA afforded after HPLC purification Example 226. LCMS (4 min gradient, A=95% H$_2$O/5% CH$_3$CN/0.1% TFA, B=5% H$_2$O/95% CH$_3$CN/0.1% TFA) RT=3.66 min, 558.49 (M+H)$^+$; $^1$H NMR (400 MHz, CD$_3$OD) δ ppm 1.21 (t, J=7.69 Hz, 3 H) 1.41 (t, J=7.03 Hz, 3 H) 2.63 (q, J=7.62 Hz, 2 H) 3.73 (s, 3 H) 4.13 (q, J=7.03 Hz, 2 H) 6.41 (s, 1 H) 6.75-6.83 (m, 1 H) 6.85 (d, J=2.20 Hz, 1 H) 6.96 (d, J=7.03 Hz, 1 H) 7.00-7.10 (m, 1 H) 7.26 (dd, J=9.23, 2.64 Hz, 1 H) 7.30-7.46 (m, 3 H) 7.49-7.56 (m, 1 H) 7.58-7.69 (m, 1 H) 8.19 (d, J=9.23 Hz, 1 H).

Example 227

N$^6$-((3-ethoxy-5-ethyl-2-fluorophenyl)(4-(2-(furan-3-yl)phenyl)-1H-imidazol-2-yl)methyl)isoquinoline-1,6-diamine bis-trifluoroacetic acid salt

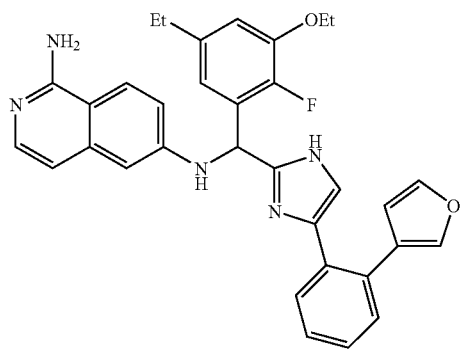

According to the procedure for the preparation of Example 206, coupling of Intermediate 217.4 (50 mg, 0.0498 mmol) and furan-3-ylboronic acid, followed by deprotection and HPLC purification afforded 26.8 mg of Example 227. LCMS (2 min gradient) RT=1.39 min, 548.4 (M+H)$^+$; $^1$H NMR (400 MHz, CD$_3$OD) δ ppm 1.21 (t, J=7.47 Hz, 3 H) 1.42 (t, J=7.03 Hz, 3 H) 2.63 (q, J=7.76 Hz, 2 H) 4.15 (q, J=7.03 Hz, 2 H) 6.23 (s, 1 H) 6.38 (s, 1 H) 6.73-6.76 (m, 1 H) 6.83 (d, J=2.20 Hz, 1 H) 6.96 (d, J=7.03 Hz, 1 H) 7.06 (d, J=7.91 Hz, 1 H) 7.23 (dd, J=9.23, 2.20 Hz, 1 H) 7.36-7.37 (m, 1 H) 7.41 (d, J=8.79 Hz, 3 H) 7.42-7.46 (m, 1 H) 7.49-7.54 (m, 3 H) 8.19 (d, J=8.79 Hz, 1 H).

Example 228

2-{2-[(1-Amino-isoquinolin-6-ylamino)-(5-ethyl-2-fluoro-biphenyl-3-yl)-methyl]-1H-imidazol-4-yl}-benzamide bis-trifluoroacetic acid salt

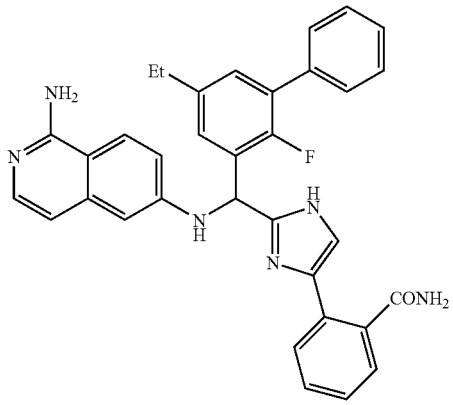

2-bromo-4-ethyl-1-fluorobenzene (228.1)

To a solution of 3'-bromo-4'-fluoroacetophenone (6.80 g, 31.3 mmol) in 31 mL TFA, was added triethylsilane (15 mL). The mixture was stirred at rt for 20 h, then concentrated. The crude product was purified by flash chromatography (100% hexanes, 2×) to afford 4.33 g of Intermediate 228.1 as a colorless oil.

5-Ethyl-2-fluoro-biphenyl (228.2)

To a degassed mixture of Intermediate 228.1 (104 mg, 0.512 mmol), phenylboronic acid (94 mg, 0.768 mmol) and $Na_2CO_3$ (217 mg, 2.05 mmol) in 4 mL DME/$H_2O$ (3:1) was added Pd(PPh$_3$)$_4$ (59 mg, 0.051 mmol). The mixture was stirred at 150° C. for 5 min in a microwave oven, then was diluted with EtOAc, washed with water and brine, dried ($Na_2SO_4$) and concentrated. The crude product was purified by flash chromatography (100% hexanes) to afford Intermediate 228.2.

(4-Bromo-1-trityl-1H-imidazol-2-yl)-(5-ethyl-2-fluoro-biphenyl-3-yl)-methanol (228.3)

To a solution of Intermediate 228.2 (85 mg, 0.424 mmol) and PMDTA (0.10 mL, 0.478 mmol) in 4 ml THF at −78° C., was added BuLi (1.4 M in hexanes, 0.334 mL, 0.467 mmol). The mixture was stirred with warming to −40° C. over 30 min, recooled to −78° C., then a solution of Intermediate 175.1 (177 mg, 0.424 mmol) in 1.5 mL THF was added. The mixture was warmed to rt over 0.5 h. The reaction was quenched with sat. NH$_4$Cl, then was diluted with EtOAc. The organic phase was washed with $H_2O$ (2×) and brine, dried ($Na_2SO_4$) and concentrated. The crude product was purified by flash chromatography (0 to 30% EtOAc/hexanes gradient) to afford 194 mg of Intermediate 228.3 as a colorless solid.

di-tert-butyl (6-{[(4-bromo-1-trityl-1H-imidazol-2-yl)(5-ethyl-2-fluoro-biphenyl)methyl]amino}isoquinolin-1-yl)imidodicarbonate (228.4)

According to the procedure for the preparation of Intermediate 206.4, Intermediate 228.3 (189 mg, 0.306 mmol) was converted to the chloro intermediate, then displaced with di-tert-butyl (6-aminoisoquinolin-1-yl)imidodicarbonate (rt for 16 h and 50° C. of 24 h) to afford after flash chromatography (0 to 60% EtOAc/hexanes gradient) 239 mg of Intermediate 228.4 as a white solid.

Example 228

According to the procedure for the preparation of Example 206, coupling of Intermediate 228.4 (50 mg, 0.052 mmol) and 2-carbamoylphenylboronic acid, followed by deprotection and HPLC purification afforded 10.3 mg of Example 228. LCMS (2 min gradient) RT=1.43 min, 557.4 (M+H)$^+$; $^1$H NMR (400 MHz, CD$_3$OD) δ ppm 1.25 (t, J=7.5 Hz, 1 H) 2.72 (q, J=7.5 Hz, 2 H) 6.56 (s, 1 H) 6.92 (d, J=2.20 Hz, 1 H) 7.00 (d, J=7.03 Hz, 1 H) 7.27-7.31 (m, 2 H) 7.37-7.48 (m, 5 H) 7.54-7.63 (m, 6 H) 7.70-7.73 (m, 1 H) 8.20 (d, J=9.23 Hz, 1 H).

Example 229

2-{2-[(1-Amino-isoquinolin-6-ylamino)-(5-ethyl-2-fluoro-3'-methyl-biphenyl-3-yl)-methyl]-1H-imidazol-4-yl}-benzamide bis-trifluoroacetic acid salt

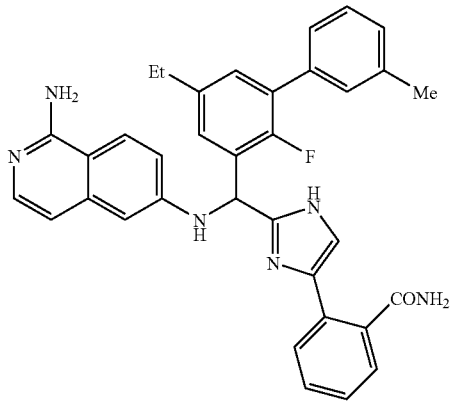

According to the procedure for the preparation of Example 228, Intermediate 228.1 was coupled with 2-tolylboronic acid. Following the same synthetic sequence afforded Example 229. LCMS (2 min gradient) RT=1.47 min, 571.4 (M+H)$^+$; $^1$H NMR (400 MHz, CD$_3$OD) δ ppm 1.25 (t, J=7.47 Hz, 3 H) 2.39 (s, 3 H) 2.71 (q, J=7.47 Hz, 2 H) 6.56 (s, 1 H) 6.93 (d, J=2.20 Hz, 1 H) 7.00 (d, J=7.03 Hz, 1 H) 7.20-7.24 (m, J=3.52 Hz, 1 H) 7.26-7.34 (m, 4 H) 7.36-7.43 (m, 3 H) 7.56-7.63 (m, 4 H) 7.72 (d, J=6.15 Hz, 1 H) 8.21 (d, J=9.23 Hz, 1 H).

Example 230

2-(2-((1-aminoisoquinolin-6-ylamino)(5-ethyl-2-fluoro-3-morpholinophenyl)methyl)-1H-imidazol-4-yl)benzamide tris-trifluoroacetic acid salt

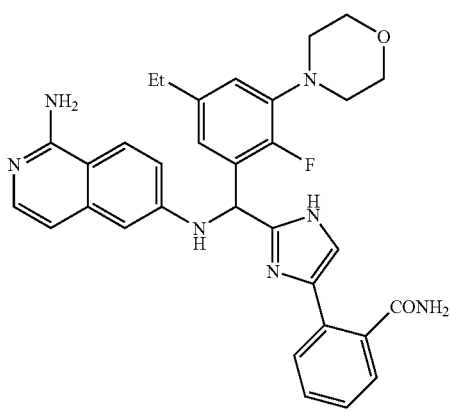

4-(5-ethyl-2-fluorophenyl)morpholine (230.1)

To Intermediate 228.1 (203 mg, 1.00 mmol), BINAP (39.8 mg, 0.06 mmol), sodium tert-butoxide (115.3 mg, 1.20 mmol), morpholine (105 μL, 1.2 mmol) and Pd$_2$(dba)$_3$ (27.5 mg, 0.03 mmol), was added 5 mL toluene. The reaction vial was sealed and stirred at 85° C. for 15 h. The mixture was filtered through a 1" pad of silica gel, eluting with 20% EtOAc/hexanes. The crude product was purified by flash chromatography (0 to 20% EtOAc/hexanes gradient) to afford 185 mg of intermediate 230.1. LCMS (2 min gradient) RT=1.66 min, 210.3 (M+H)$^+$.

Example 230

According to the procedure for the preparation of Example 228, Intermediate 230.1 was converted to Example 230. LCMS (2 min gradient) RT=1.26 min, 566.50 (M+H)$^+$; $^1$H NMR (400 MHz, CD$_3$OD) δ ppm 1.20 (t, J=7.47 Hz, 3 H) 2.63 (q, J=7.47 Hz, 2 H) 3.06-3.13 (m, J=4.39 Hz, 5 H) 3.80-3.84 (m, J=4.61, 4.61 Hz, 5 H) 6.47 (s, 1 H) 6.87-6.90 (m, 2 H) 6.99 (d, J=7.03 Hz, 2 H) 7.27 (dd, J=9.01, 2.42 Hz, 1 H) 7.38 (d, J=7.03 Hz, 1 H) 7.55-7.62 (m, 4 H) 7.71 (d, J=7.03 Hz, 1 H) 8.19 (d, J=9.23 Hz, 1 H).

Example 231

2-(2-((1-aminoisoquinolin-6-ylamino)(5-ethyl-2-fluoro-3-(pyrrolidin-1-yl)phenyl)methyl)-1H-imidazol-4-yl)benzamide tris-trifluoroacetic acid salt

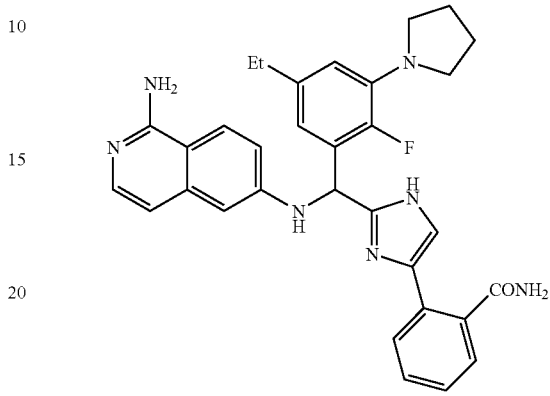

According to the procedure for the preparation of Example 230, replacement of morpholine with pyrrolidine afforded Example 231. LCMS (2 min gradient) RT=1.45 min, 550.50 (M+H)$^+$; $^1$H NMR (400 MHz, CD$_3$OD) δ ppm 1.18 (t, J=7.69 Hz, 3 H) 1.94-1.99 (m, 4 H) 2.57 (q, J=7.76 Hz, 2 H) 3.37-3.43 (m, J=2.20 Hz, 4 H) 6.43 (s, 1 H) 6.52 (d, J=5.27 Hz, 1 H) 6.68 (d, J=7.47 Hz, 1 H) 6.88 (d, J=1.76 Hz, 1 H) 6.99 (d, J=7.03 Hz, 1 H) 7.27 (dd, J=9.23, 2.20 Hz, 1 H) 7.38 (d, J=7.03 Hz, 1 H) 7.54-7.62 (m, 4 H) 7.72 (d, J=6.59 Hz, 1 H) 8.19 (d, J=9.23 Hz, 1 H).

Example 232

(R)-N$^6$-((5-ethyl-2-fluorophenyl)(4-phenyl-1H-imidazol-2-yl)methyl)isoquinoline-1,6-diamine bis-trifluoroacetic acid salt

Example 233

(S)-N$^6$-((5-ethyl-2-fluorophenyl)(4-phenyl-1H-imidazol-2-yl)methyl)isoquinoline-1,6-diamine bis-trifluoroacetic acid salt

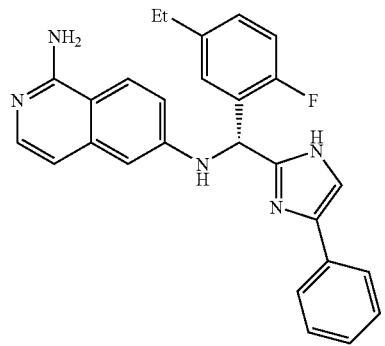

Example 232

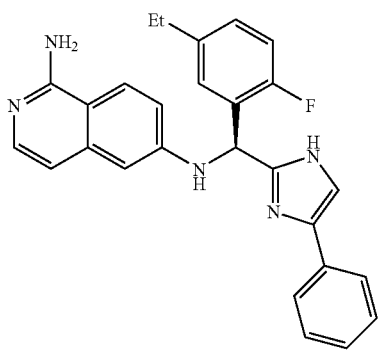

Example 233

Racemic Example 273 was separated via preparative chiral chromatography. Chiralpak AD 30. ×250 mm 5 micron CO₂/MeOH/EtOH/DEA (70/15/15/0.1), 60 ml/min. RT=8.6 min and 12.4 min. Each enantiomer was re-purified by preparative HPLC to provide the bis-TFA salts.

Example 234

4-((5-ethoxy-2-fluoro-3-isopropoxyphenyl)(4-(pyridin-4-yl)-1H-imidazol-2-yl)methylamino)benzamidine bis-trifluoroacetic acid salt

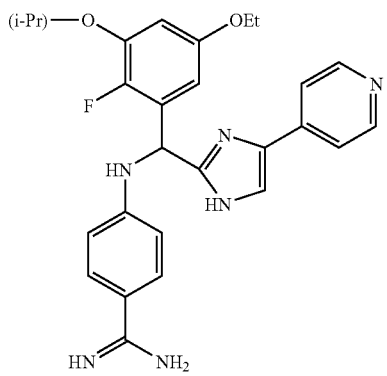

According to the procedure for the preparation of Example 77, coupling of Intermediate 66.3 with pyridin-4-ylboronic acid directly afforded after HPLC purification Example 234. LC/MS (2 min gradient) RT=1.16 min, 489.3 (M+H)⁺; ¹H NMR (400 MHz, CD₃OD) δ ppm 1.25-1.37 (m, 9 H) 3.92 (q, J=7.03 Hz, 2H) 4.52-4.64 (m, 1 H) 6.15 (s, 1 H) 6.50 (dd, J=4.83, 3.08 Hz, 1 H) 6.61 (dd, J=6.81, 2.86 Hz, 1 H) 6.82 (d, J=8.79 Hz, 2 H) 7.63 (d, J=9.23 Hz, 2 H) 8.21 (s, 1 H) 8.33 (d, J=6.59 Hz, 2 H) 8.66 (d, J=6.59 Hz, 2 H).

Example 235

4-((5-ethoxy-2-fluoro-3-isopropoxyphenyl)(4-(pyridin-3-yl)-1H-imidazol-2-yl)methylamino)benzamidine bis-trifluoroacetic acid salt

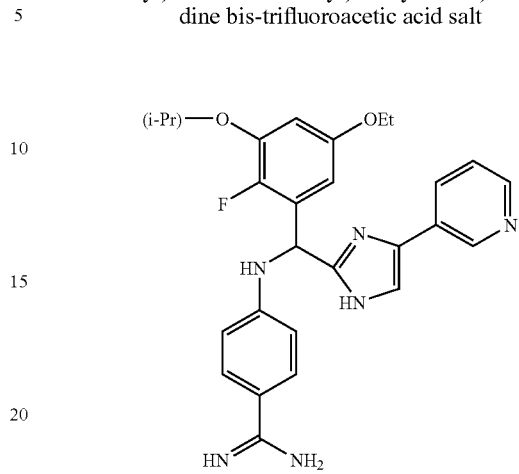

According to the procedure for the preparation of Example 77, coupling of Intermediate 66.3 with pyridin-3-lboronic acid directly afforded after HPLC purification Example 235. LC/MS (2 min gradient) RT=1.15 min, 489.3 (M+H)⁺; ¹H NMR (400 MHz, CD₃OD) δ ppm 1.25-1.37 (m, 9 H) 3.92 (q, J=7.03 Hz, 2 H) 4.53-4.65 (m, 1 H) 6.14 (s, 1 H) 6.48 (dd, J=4.83, 3.08 Hz, 1 H) 6.64 (dd, J=6.81, 2.86 Hz, 1 H) 6.81 (d, J=8.79 Hz, 2 H) 7.63 (d, J=9.23 Hz, 2 H) 7.88 (m, 3 H), 8.60 (d, J=6.59 Hz, 1 H) 8.69 (d, J=6.59 Hz, 1 H).

Example 236

4-((4-(1H-pyrazol-4-yl)-1H-imidazol-2-yl)(5-ethoxy-2-fluoro-3-isopropoxyphenyl)methylamino)benzamidine bis-trifluoroacetic acid salt

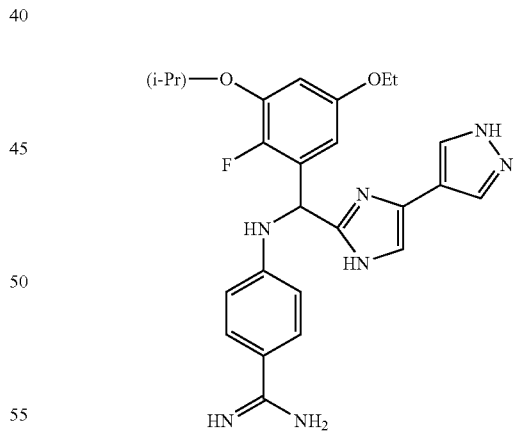

According to procedure for the preparation of Example 77, coupling of Intermediate 66.3 with 1H-pyrazol-4-ylboronic acid, followed by hydrogenation and deprotection as in example 66 afforded after HPLC purification Example 236. LC/MS (2 min gradient) RT=1.17 min, 478.3 (M+H)⁺; ¹H NMR (400 MHz, CD₃OD) δ ppm 3.91-4.02 (m, J=7.03, 7.03, 7.03 Hz, 9 H) 4.56-4.69 (m, 1 H) 6.38 (s, 1 H) 6.49 (dd, J=4.61, 2.86 Hz, 1 H) 6.72 (dd, J=6.81, 2.86 Hz, 1 H) 6.90 (d, J=8.79 Hz, 2 H) 7.64 (s, 1 H) 7.69 (d, J=8.79 Hz, 2 H) 8.02 (s, 2 H).

Example 237

4-((5-ethoxy-2-fluoro-3-isopropoxyphenyl)(4-(1-methyl-1H-pyrazol-4-yl)-1H-imidazol-2-yl)methylamino)benzamidine bis-trifluoroacetic acid salt

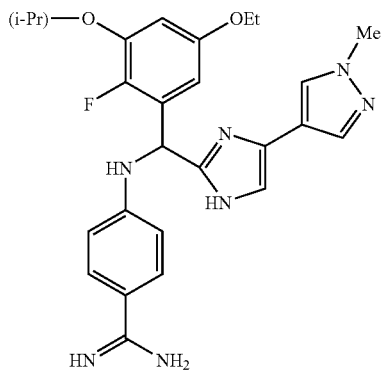

N-((4-(1H-pyrazol-4-yl)-1-trityl-1H-imidazol-2-yl)(5-ethoxy-2-fluoro-3-isopropoxyphenyl)methyl)-4-(5-methyl-1,2,4-oxadiazol-3-yl)benzenamine (237.1)

According to the procedure for the preparation of Intermediate 77.1, Intermediate 66.3 was coupled with 1H-pyrazol-4-ylboronic acid. The crude product was purified by flash chromatography (0 to 100% EtOAc/hexanes, gradient) to afford 30 mg (20%) of Intermediate 237.1.

N-((5-ethoxy-2-fluoro-3-isopropoxyphenyl)(4-(1-methyl-1H-pyrazol-4-yl)-1-trityl-1H-imidazol-2-yl)methyl)-4-(5-methyl-1,2,4-oxadiazol-3-yl)benzenamine (237.2)

To a solution of Intermediate 237.1 (30 mg, 0.04 mmol) in THF (1 mL) at 0° C. was added NaH (3.16 mg, 0.08 mmol), stirred at 0° C. for 30 min, then MeI was added and the reaction mixture was warmed up to rt over 1 h. The reaction mixture was then partitioned between EtOAc and sat. NH$_4$Cl, the organic layer was dried (Na$_2$SO$_4$), filtered and concentrated. The crude product was purified by flash chromatography (0 to 100% EtOAc/hexanes, gradient) to afford 20 mg (62%) of Intermediate 237.2.

Example 237

Intermediate 237.2 was hydrogenated and deprotected as in Example 66 to afford after HPLC purification Example 237. LC/MS (2 min gradient) RT=1.20 min, 492.2 (M+H)$^+$; $^1$H NMR (400 MHz, CD$_3$OD) δ ppm 1.26-1.47 (m, 9 H) 3.86-4.02 (m, 5 H) 4.51-4.70 (m, 1 H) 6.36 (s, 1 H) 6.47 (dd, J=4.61, 2.86 Hz, 1 H) 6.72 (dd, J=7.03, 2.64 Hz, 1 H) 6.89 (d, J=8.79 Hz, 2 H) 7.59 (s, 1 H) 7.68 (d, J=8.79 Hz, 2 H) 7.82 (s, 1 H) 8.00 (s, 1 H).

Example 238

4-((5-ethoxy-2-fluoro-3-isopropoxyphenyl)(4-(1-ethyl-1H-pyrazol-4-yl)-1H-imidazol-2-yl)methylamino)benzamidine bis-trifluoroacetic acid salt

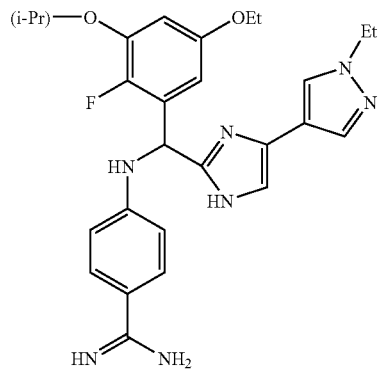

According to procedure for the preparation of Example 237, Intermediate 237.1 was alkylated with EtI, followed by hydrogenation and deprotection as in Example 66 to afford after HPLC purification Example 238. LC/MS (2 min gradient) RT=1.27 min, 506.3 (M+H)$^+$; $^1$H NMR (400 MHz, CD$_3$OD) δ ppm 1.27-1.39 (m, 9 H) 1.47 (t, J=7.25 Hz, 3 H) 3.95 (q, J=6.88 Hz, 2 H) 4.22 (q, J=7.47 Hz, 2 H) 4.55-4.70 (m, 1 H) 6.35 (s, 1 H) 6.47 (dd, J=4.83, 2.64 Hz, 1 H) 6.72 (dd, J=7.03, 3.08 Hz, 1 H) 6.89 (d, J=8.79 Hz, 2 H) 7.59 (s, 1 H) 7.68 (d, J=8.79 Hz, 2 H) 7.83 (s, 1 H) 8.05 (s, 1 H).

Example 239

4-((4-cyclopropyl-1H-imidazol-2-yl)(5-ethoxy-2-fluoro-3-isopropoxyphenyl)methylamino)benzamidine bis-trifluoroacetic acid salt

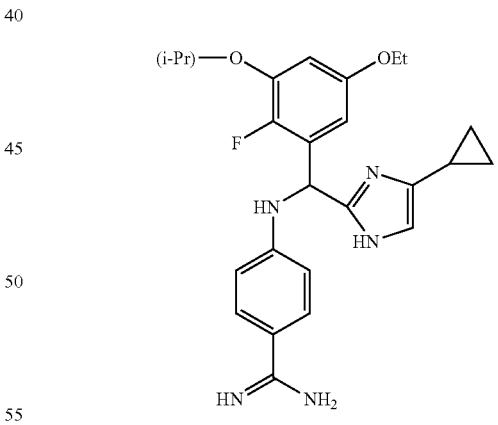

According to procedure for the preparation of Example 77, coupling of Intermediate 66.3 with cyclopropylboronic acid, followed by hydrogenation and deprotection as in Example 66 afforded after HPLC purification Example 239. LC/MS (2 min gradient) RT=1.22 min, 452.3 (M+H)$^+$; $^1$H NMR (400 MHz, CD$_3$OD) δ ppm 0.68-0.85 (m, J=5.27, 1.76 Hz, 2 H) 0.96-1.14 (m, J=8.35, 2.20 Hz, 2 H) 1.23-1.41 (m, J=5.71, 5.71 Hz, 9 H) 1.78-2.08 (m, 1 H) 3.95 (q, J=7.03 Hz, 2 H) 4.50-4.72 (m, 1 H) 6.30 (s, 1 H) 6.44 (dd, J=4.61, 2.86 Hz, 1 H) 6.86 (d, J=8.79 Hz, 2 H) 7.16 (s, 1 H) 7.67 (d, J=8.79 Hz, 2 H).

Example 240

4-((4-butyl-1H-imidazol-2-yl)(5-ethoxy-2-fluoro-3-isopropoxyphenyl)methylamino)benzamidine bis-trifluoroacetic acid salt

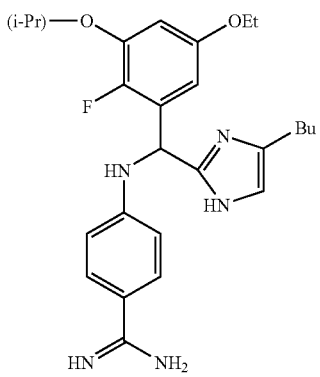

According to procedure for the preparation of Example 75, coupling of Intermediate 66.3 with but-2-enyltributylstannane, followed by hydrogenation and deprotection as in Example 66 afforded after HPLC purification Example 240. LC/MS (2 min gradient) RT=1.35 min, 468.3 (M+H)$^+$; $^1$H NMR (400 MHz, CD$_3$OD) δ ppm 0.94 (d, J=6.59 Hz, 6 H) 1.20-1.46 (m, J=6.59, 6.59 Hz, 10 H) 1.80-2.06 (m, 2 H) 2.56 (d, J=7.03 Hz, 2 H) 3.94 (q, J=6.74 Hz, 2 H) 4.51-4.76 (m, 1 H) 6.33 (s, 1 H) 6.42 (s, 1 H) 6.72 (d, J=3.96 Hz, 1 H) 6.87 (d, J=8.79 Hz, 2 H) 7.27 (s, 1 H) 7.68 (d, J=8.79 Hz, 2 H).

Example 241

2-(2-((1-aminoisoquinolin-6-ylamino)(5-ethoxy-2-fluoro-3-isopropoxyphenyl)methyl)-1H-imidazol-4-yl)benzamide bis-trifluoroacetic acid salt

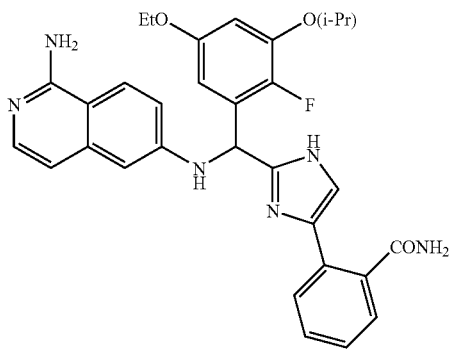

(4-bromo-1-trityl-1H-imidazol-2-yl)(3-(tert-butyldimethylsilyloxy)-5-ethoxy-2-fluorophenyl)methyl methanesulfonate (241.1)

To a solution of 4-bromo-1-trityl-1H-imidazole (1 g, 2.57 mmol) in 10 mL THF at 0° C., was added BuLi, dropwise (1.38 M, 1.84 mL, 2.57 mmol). The mixture was stirred for 30 min at 0° C., then a solution of 3-(tert-butyldimethyl silyloxy)-5-ethoxy-2-fluorobenzaldehyde (806 mg, 2.57 mmol), prepared according to WO2003066588 A1, which is incorporated herein by reference, in 3 mL of THF was added dropwise. The mixture was warmed up to rt over 1 h, quenched with sat. NH$_4$Cl and diluted with EtOAc. The organic phase was washed with H$_2$O and brine, dried (Na$_2$SO$_4$), filtered and concentrated. The crude product was purified by flash chromatography (0 to 30% EtOAc/hexanes, gradient) to afford 1.3 g (70%) of Intermediate 241.1.

di-tert-butyl (6-{[(4-bromo-1-trityl-1H-imidazole-2-yl)(3-(tert-butyldimethylsilyloxy)-5-ethoxy-2-fluorophenyl)methyl]amino}isoquinolin-1-yl)imidadicarbonate (241.2)

To a solution of Intermediate 241.1 (400 mg, 0.6 mmol), Et$_3$N (0.85 mL, 6 mmol) in 5 mL CH$_2$Cl$_2$ at 0° C., was added MsCl (0.38 mL, 4.8 mmol) dropwise. The mixture was allowed to warm up to rt over 1 h, then quenched with ice water and diluted with EtOAc. The organic phase was washed with H$_2$O and brine, dried (Na$_2$SO$_4$), filtered and concentrated to afford the chloro intermediate. To a suspension of this intermediate in 8 mL CH$_3$CN at rt, were added DIEA (153 uL, 0.9 mmol) and 1-(di-(tert-butyloxycarbonyl)amino)-6-aminoisoquinoline (231 mg, 0.642 mmol). The mixture was stirred at rt for 16 h and at 50° C. for 4 h, then was diluted with EtOAc. The organic phase was washed with H$_2$O and brine, dried (Na$_2$SO$_4$), filtered and concentrated. The crude product was purified by flash chromatography (0 to 50% EtOAc/hexanes, gradient) to afford 500 mg (85%) of Intermediate 241.2.

di-tert-butyl (6-{[(4-bromo-1-trityl-1H-imidazole-2-yl)(5-ethoxy-3-hydroxy-2-fluoro-phenyl)methyl]amino}isoquinolin-1-yl)imidadicarbonate (241.3)

A solution of Intermediate 241.2 (170 mg, 0.165 mmol) and TBAF (1 N, 0.17 mL) in 3 mL THF was stirred at rt for 2 h, the reaction mixture was then partitioned between EtOAc and H$_2$O, the organic layer was dried over (Na$_2$SO$_4$), filtered and concentrated. The residue was purified by flash chromatography (0 to 50% EtOAc/hexanes, gradient) to afford 80 mg (60%) of Intermediate 241.3.

di-tert-butyl (6-{[(4-bromo-1-trityl-1H-imidazole-2-yl)(5-ethoxy-3-isopropoxy-2-fluoro-phenyl)methyl]amino}isoquinolin-1-yl)imidadicarbonate (241.4)

A mixture of Intermediate 241.3 (70 mg, 0.07 mmol), 2-iodopropane (51.2 mg, 0.3 mmol), K$_2$CO$_3$ (20.4 mg, 0.14 mmol) in 1 mL DMF was heated at 80° C. for 4 h. The reaction mixture was then partionated between EtOAc and H$_2$O, the organic layer was dried over (Na$_2$SO$_4$), filtered and concentrated. The residue was purified by flash chromatography (0 to 50% EtOAc/hexanes, gradient) to afford 60 mg (80%) of Intermediate 241.4.

Example 241

To a degassed mixture of Intermediate 241.4 (30 mg, 0.031 mmol), 2-carbamoylphenylboronic acid (10 mg, 0.062 mmol), Na$_2$CO$_3$ (13 mg, 0.12 mmol) in 2 mL DME/H$_2$O (3:1) was added Pd(PPh$_3$)$_4$ (5 mg, 0.004 mmol). The mixture was stirred at 150° C. for 5 min in a microwave oven, then was concentrated to dryness. The crude material was stirred with 1 mL of TFA at rt for 30 min. This mixture was then concentrated and purified by HPLC to afford Example 241. LC/MS (2 min gradient) RT=1.25 min, 555.2 (M+H)$^+$; $^1$H NMR (400

MHz, CD$_3$OD) δ ppm 1.34 (t, J=5.93 Hz, 9 H) 3.98 (dd, J=7.03, 2.20 Hz, 2 H) 4.54-4.75 (m, 1 H) 6.43-6.57 (m, 2 H) 6.74 (dd, J=6.81, 2.86 Hz, 1 H) 6.88 (d, J=2.20 Hz, 1 H) 6.99 (d, J=7.03 Hz, 1 H) 7.26 (dd, J=9.23, 2.20 Hz, 1 H) 7.38 (d, J=7.03 Hz, 1 H) 7.51-7.65 (m, 4 H) 7.72 (d, J=6.59 Hz, 1 H) 8.20 (d, J=9.23 Hz, 1 H).

Example 242

2-(2-((1-aminoisoquinolin-6-ylamino)(5-ethoxy-2-fluoro-3-((S)-tetrahydrofuran-3-yloxy)phenyl)methyl)-1H-imidazol-4-yl)benzamide bis-trifluoroacetic acid salt

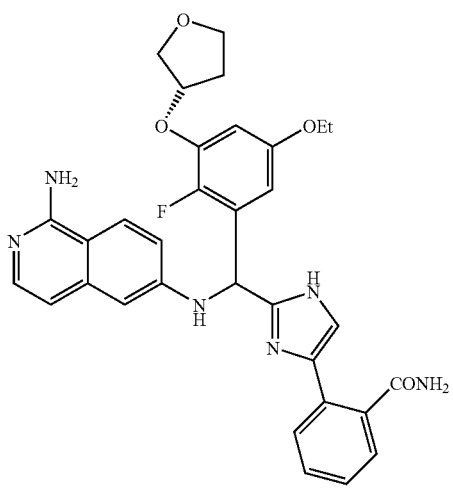

di-tert-butyl (6-{[(4-bromo-1-trityl-1H-imidazole-2-yl)(5-ethoxy-2-fluoro-3-((S)-tetrahydrofuran-3-yloxy)phenyl)methyl]amino}isoquinolin-1-yl)imidadicarbonate (242.1)

To triphenylphosphine (50 mg, 0.19 mmoml) in THF (2 mL) at 0° C., was added diethylazodicarboxylate (33 mg, 0.19 mmol). The mixture was stirred at 0° C. for 30 min, then a solution of Intermediate 241.3 (45 mg, 0.048) and (R)-tetrahydrofuran-3-ol in 1 mL THF, dropwise. The mixture was allowed to warm to rt and stir for 15 h, then was concentrated. The crude product was purified by flash chromatography (0 to 40% EtOAc/hexanes, gradient) to afford 30 mg (62%) of Intermediate 242.1.

Example 242

To a degassed mixture of Intermediate 242.1 (30 mg, 0.03 mmol), 2-carbamoylphenylboronic acid (10 mg, 0.06 mmol), Na$_2$CO$_3$ (13 mg, 0.12 mmol) in 2 mL DME/H$_2$O (3:1) was added Pd(PPh$_3$)$_4$ (5 mg, 0.004 mmol). The mixture was stirred at 150° C. for 5 min in a microwave oven, then concentrated to dryness. The crude material was stirred with 1 mL of TFA at rt for 30 min. This mixture was then concentrated and purified by HPLC to afford Example 242. LC/MS (4 min gradient) RT=1.97 min, 583.2 (M+H)$^+$; $^1$H NMR (400 MHz, CD$_3$OD) δ ppm 1.23 (t, J=7.25 Hz, 3 H) 2.06-2.19 (m, 1 H) 2.19-2.37 (m, 1 H) 3.82-4.03 (m, 5 H) 6.51 (d, J=3.08 Hz, 1 H) 6.53-6.64 (m, 1 H) 6.73 (dd, J=6.59, 2.20 Hz, 1 H) 6.90 (d, J=2.20 Hz, 1 H) 6.99 (d, J=7.03 Hz, 1 H) 7.27 (dd, J=9.23, 2.20 Hz, 1 H) 7.38 (d, J=7.03 Hz, 1 H) 7.54-7.68 (m, J=5.49, 5.49 Hz, 4 H) 7.66-7.86 (m, 1 H) 7.67-7.82 (m, 1 H) 8.20 (d, J=9.23 Hz, 1 H) 8.20 (d, J=9.23 Hz, 2 H).

Example 243

2-(2-((1-aminoisoquinolin-6-ylamino)(2-fluoro-5-methylphenyl)methyl)-1H-imidazol-4-yl)benzamide bis-trifluoroacetic acid salt

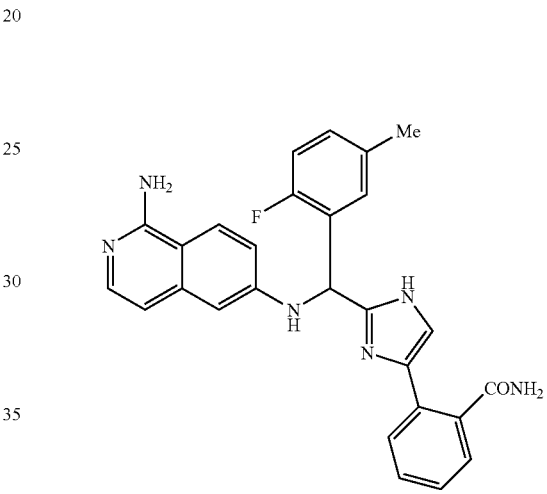

di-tert-butyl (6-{[(4-bromo-1-trityl-1H-imidazole-2-yl)(2-fluoro-5-methylphenyl)methyl]amino}isoquinolin-1-yl)imidadicarbonate (243.1)

According to the procedure for the preparation of Intermediate 241.2, reaction of 2-fluoro-5-methylbenzaldehyde with the 4-bromo-1-trityl-1H-imidazole followed by chloronation and displacement with 1-(di-(tert-butyloxycarbonyl)amino)-6-aminoisoquinoline afforded Intermediate 243.1.

Example 243

According to procedure for the preparation of Example 241, coupling of Intermediate 243.1 with 2-carbamoylphenylboronic acid, followed by deprotection afforded after HPLC purification Example 243. LC/MS (2 min gradient) RT=1.02 min, 467.2 (M+H)$^+$; $^1$H NMR (400 MHz, CD$_3$OD) δ ppm 2.35 (s, 3 H) 6.46 (s, 1 H) 6.88 (d, J=2.64 Hz, 1 H) 6.98 (d, J=7.03 Hz, 1 H) 7.09-7.21 (m, 1 H) 7.26 (dd, J=8.79, 2.20 Hz, 2 H) 7.38 (d, J=7.03 Hz, 1 H) 7.50-7.64 (m, 4 H) 7.71 (d, J=7.03 Hz, 1 H) 8.19 (d, J=9.23 Hz, 1 H).

Example 244

2-(2-((1-aminoisoquinolin-6-ylamino)(3-vinylphenyl)methyl)-1H-imidazol-4-yl)benzamide bis-trifluoroacetic acid salt

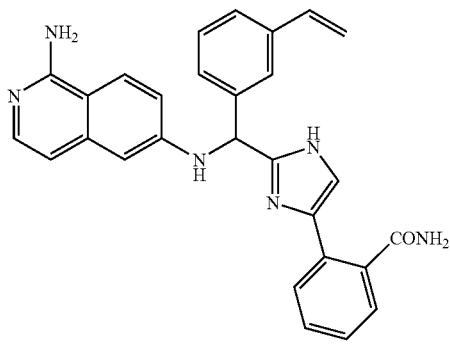

According to the procedure for the preparation of Example 243, reaction of 3-vinylbenzaldehyde with the 4-bromo-1-trityl-1H-imidazole, followed by chloronation, displacement, Suzuki coupling and deprotection afforded after HPLC purification Example 244. LC/MS (2 min gradient) RT=1.08 min, 461.2 (M+H)$^+$; $^1$H NMR (400 MHz, CD$_3$OD) δ ppm 5.31 (d, J=10.99 Hz, 1 H) 5.87 (d, J=17.58 Hz, 1 H) 6.31 (s, 1 H) 6.69-6.88 (m, 2 H) 6.99 (d, J=7.47 Hz, 1 H) 7.26 (dd, J=9.23, 2.64 Hz, 1 H) 7.35-7.42 (m, 2 H) 7.47 (t, J=7.47 Hz, 1 H) 7.53-7.65 (m, 6 H) 7.69-7.78 (m, 1 H) 8.18 (d, J=8.79 Hz, 1 H).

Example 245

2-(2-((1-aminoisoquinolin-6-ylamino)(5-ethoxy-2-fluorophenyl)methyl)-1H-imidazol-4-yl)benzamide bis-trifluoroacetic acid salt

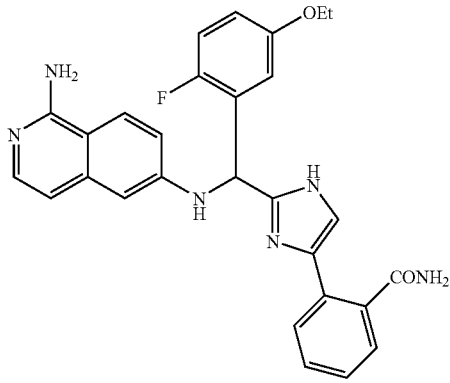

According to the procedure for the preparation of Example 243, reaction of 5-ethoxy-2-fluorobenzaldehyde with the 4-bromo-1-trityl-1H-imidazole, followed by chloronation, displacement, Suzuki coupling and deprotection afforded after HPLC purification Example 245. LC/MS (2 min gradient) RT=1.07 min, 497.2 (M+H)$^+$; $^1$H NMR (400 MHz, CD$_3$OD) δ ppm 6.50 (s, 1 H) 6.89 (d, J=2.64 Hz, 1 H) 6.95-7.07 (m, 3 H) 7.20 (t, J=9.45 Hz, 1 H) 7.27 (dd, J=9.23, 2.20 Hz, 1 H) 7.38 (d, J=7.03 Hz, 1 H) 7.56-7.63 (m, 4 H) 7.72 (d, J=6.15 Hz, 1 H) 8.20 (d, J=9.23 Hz, 1 H).

Example 246

2-(2-((1-aminoisoquinolin-6-ylamino)(4-fluoro-3-methoxyphenyl)methyl)-1H-imidazol-4-yl)benzamide bis-trifluoroacetic acid salt

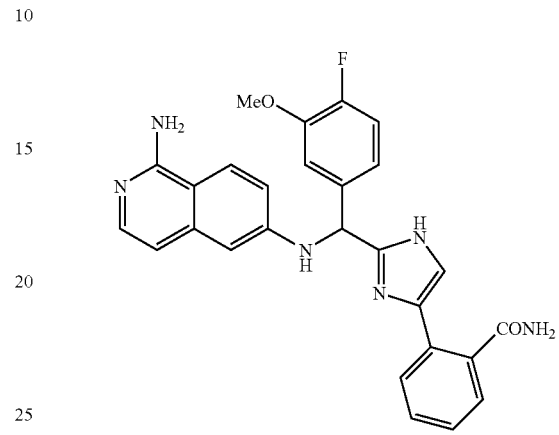

According to the procedure for the preparation of Example 243, reaction of 4-fluoro-3-methoxybenzaldehyde with the 4-bromo-1-trityl-1H-imidazole, followed by chloronation, displacement, Suzuki coupling and deprotection afforded after HPLC purification Example 246. LC/MS (2 min gradient) RT=0.98 min, 483.2 (M+H)$^+$; $^1$H NMR (400 MHz, CD$_3$OD) δ ppm 3.79 (s, 3 H) 6.52 (s, 1 H) 6.90 (d, J=2.20 Hz, 1 H) 6.95-7.11 (m, 3 H) 7.21 (t, J=9.45 Hz, 1 H) 7.27 (dd, J=9.23, 2.64 Hz, 1 H) 7.38 (d, J=7.03 Hz, 1 H) 7.53-7.64 (m, 4 H) 7.68-7.81 (m, 1 H) 8.20 (d, J=8.79 Hz, 1 H).

Example 247

2-(2-((4-carbamimidoylphenylamino)(3-ethylphenyl)methyl)-1H-imidazol-4-yl)benzamide bis-trifluoroacetic acid salt

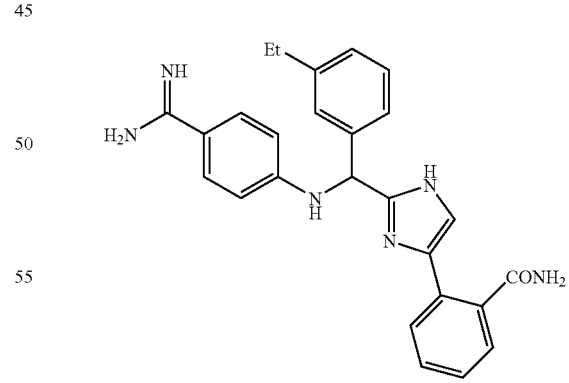

According to the procedure for the preparation of Example 243, reaction of 3-vinylbenzaldehyde with the 4-bromo-1-trityl-1H-imidazole, followed by chloronation, displacement, Suzuki coupling and deprotection afforded after HPLC purification Example 247. LC/MS (2 min gradient) RT=1.06 min, 439.2 (M+H)$^+$; $^1$H NMR (400 MHz, CD$_3$OD) δ ppm 1.21 (t, J=6.74 Hz, 3 H), 2.68 (q, J=6.75 Hz, 2 H), 5.87 (d, J=17.58

Hz, 1 H) 6.31 (s, 1 H) 6.99 (d, J=7.47 Hz, 1 H) 7.26 (dd, J=9.23, 2.64 Hz, 1 H) 7.35-7.42 (m, 2 H) 7.47 (t, J=7.47 Hz, 1 H) 7.53-7.65 (m, 6 H) 7.69-7.78 (m, 1 H) 8.18 (d, J=8.79 Hz, 1 H).

Example 248

2-(2-((4-carbamimidoylphenylamino)(2-fluoro-5-methylphenyl)methyl)-1H-imidazol-4-yl)benzamide bis-trifluoroacetic acid salt

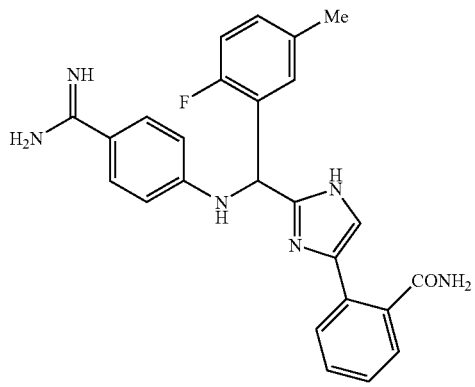

According to the procedure for the preparation of Example 243, reaction of 2-fluoro-5-methylbenzaldehyde with the 4-bromo-1-trityl-1H-imidazole, followed by chloronation, displacement with 4-(5-methyl-1,2,4-oxadiazol-3-yl)benzenamine, Suzuki coupling and deprotection afforded after HPLC purification Example 248. LC/MS (2 min gradient) RT=0.93 min, 443.2 (M+H)$^+$; $^1$H NMR (400 MHz, CD$_3$OD) δ ppm 2.33 (s, 3 H) 6.41 (s, 1 H) 6.90 (d, J=8.79 Hz, 2 H) 7.45 (t, J=7.69 Hz, 2 H) 7.53 (d, J=7.03 Hz, 1 H) 7.59 (d, J=8.79 Hz, 3 H) 7.69 (d, J=8.79 Hz, 2 H) 7.86 (d, J=7.03 Hz, 2 H).

Example 249

2-(2-((4-carbamimidoylphenylamino)(5-ethoxy-2-fluorophenyl)methyl)-1H-imidazol-4-yl)benzamide bis-trifluoroacetic acid salt

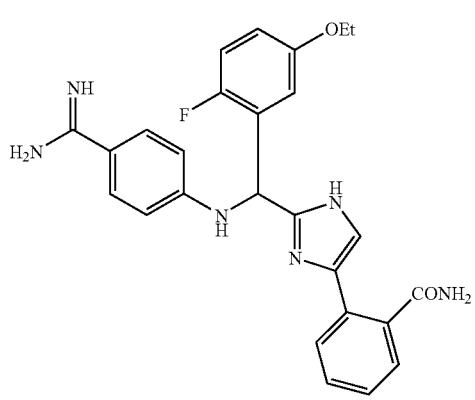

According to the procedure for the preparation of Example 243, reaction of 5-ethoxy-2-fluorobenzaldehyde with the 4-bromo-1-trityl-1H-imidazole, followed by chloronation, displacement with 4-(5-methyl-1,2,4-oxadiazol-3-yl)benzenamine, Suzuki coupling and deprotection afforded after HPLC purification Example 249. LC/MS (2 min gradient) RT=1.01 min, 473.2 (M+H)$^+$; $^1$H NMR (400 MHz, CD$_3$OD) δ ppm 1.31 (t, J=6.74 Hz, 3 H) 4.01 (q, J=6.75 Hz, 2 H) 6.41 (s, 1 H) 6.83 (d, J=8.79 Hz, 2 H) 7.40 (t, J=7.69 Hz, 2 H) 7.51 (d, J=7.03 Hz, 1 H) 7.59 (d, J=8.79 Hz, 3 H) 7.69 (d, J=8.79 Hz, 2 H) 7.86 (d, J=7.03 Hz, 2 H).

Example 250

2-(2-((4-carbamimidoylphenylamino)(5-fluoro-2-methoxyphenyl)methyl)-1H-imidazol-4-yl)benzamide bis-trifluoroacetic acid salt

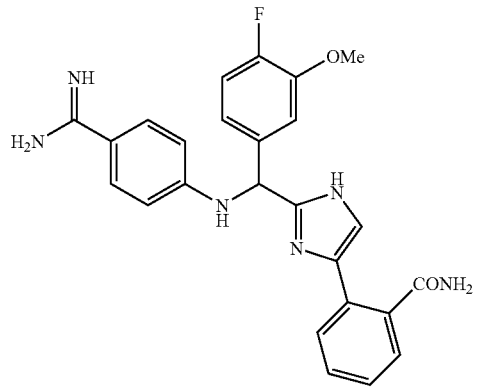

According to the procedure for the preparation of Example 243, reaction of 3-methoxy-4-fluorobenzaldehyde with the 4-bromo-1-trityl-1H-imidazole, followed by chloronation, displacement with 4-(5-methyl-1,2,4-oxadiazol-3-yl)benzenamine, Suzuki coupling and deprotection afforded after HPLC purification Example 250. LC/MS (2 min gradient) RT=1.01 min, 459.2 (M+H)$^+$; $^1$H NMR (400 MHz, CD$_3$OD) δ ppm 3.77 (s, 3 H) 6.43 (s, 1 H) 6.90 (d, J=8.79 Hz, 2 H) 6.95-7.09 (m, 2 H) 7.19 (t, J=9.45 Hz, 1 H) 7.51-7.64 (m, 4 H) 7.65-7.84 (m, 3 H).

Example 251

2-(2-((1-aminoisoquinolin-6-ylamino)(2-fluoro-5-methoxyphenyl)methyl)-1H-imidazol-4-yl)benzamide bis-trifluoroacetic acid salt

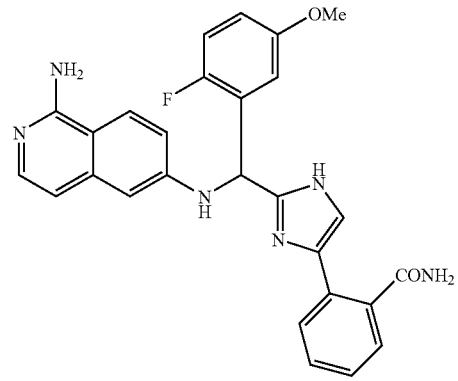

According to the procedure for the preparation of Example 243, reaction of 5-methoxy-2-fluorobenzaldehyde with the 4-bromo-1-trityl-1H-imidazole, followed by chloronation, displacement with 1-(di-(tert-butyloxycarbonyl)amino)-6- aminoisoquinoline, Suzuki coupling and deprotection afforded after HPLC purification Example 251. LC/MS (2 min gradient) RT=1.00 min, 483.2 (M+H)+; 1H NMR (400 MHz, CD3OD) δ ppm 3.91 (s, 3 H) 6.31 (s, 1 H) 6.85 (d, J=2.64 Hz, 1 H) 6.99 (d, J=7.03 Hz, 1 H) 7.03-7.12 (m, 1 H) 7.15-7.34 (m, 3 H) 7.38 (d, J=7.03 Hz, 1 H) 7.56-7.63 (m, 4 H) 7.71-7.78 (m, 1 H) 8.19 (d, J=9.23 Hz, 1 H).

Example 252

2-(2-((1-aminoisoquinolin-6-ylamino)(3-ethylphenyl)methyl)-1H-imidazol-4-yl)benzamide bis-trifluoroacetic acid salt

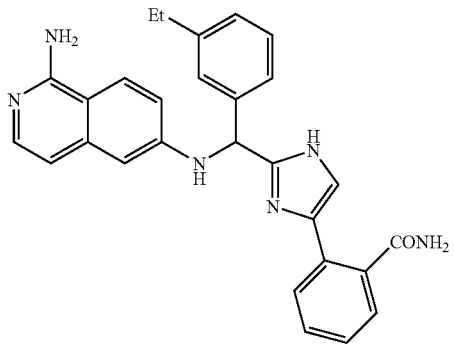

According to the procedure for the preparation of Example 243, reaction of 3-ethylbenzaldehyde, which was prepared from hydrogenation of 3-vinylbenzylaldehyde, with the 4-bromo-1-trityl-1H-imidazole, followed by chloronation, displacement with 1-(di-(tert-butyloxycarbonyl)amino)-6-aminoisoquinoline, Suzuki coupling and deprotection afforded after HPLC purification Example 252. LC/MS (2 min gradient) RT=1.18 min, 463.2 (M+H)+; 1H NMR (400 MHz, CD3OD) δ ppm 1.24 (t, J=7.47 Hz, 3 H) 2.70 (q, J=7.47 Hz, 2 H) 6.84 (d, J=2.64 Hz, 1 H) 6.99 (d, J=7.03 Hz, 1 H) 7.18-7.44 (m, 9 H) 7.57-7.63 (m, 2 H) 8.18 (d, J=9.23 Hz, 1 H).

Example 253

2-(2-((1-aminoisoquinolin-6-ylamino)(3-methylphenyl)methyl)-1H-imidazol-4-yl)benzamide bis-trifluoroacetic acid salt

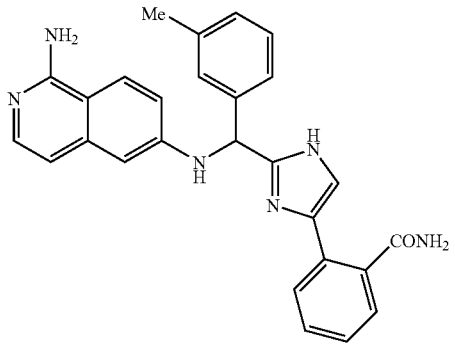

According to the procedure for the preparation of Example 243, reaction of 3-methylbenzaldehyde with the 4-bromo-1-trityl-1H-imidazole, followed by chloronation, displacement with 1-(di-(tert-butyloxycarbonyl)amino)-6-aminoisoquinoline, Suzuki coupling and deprotection afforded after HPLC purification Example 253. LCMS (4 min gradient, A=95% H2O/5% CH3CN/0.1% TFA, B=5% H2O/95% CH3CN/0.1% TFA) RT=2.85 min, 449.1 (M+H)+; 1H NMR (400 MHz, CD3OD) δ ppm 2.39 (s, 3 H) 6.24 (s, 1 H) 6.83 (s, 1 H) 6.99 (d, J=7.47 Hz, 1 H) 7.17-7.33 (m, 3 H) 7.32-7.45 (m, 3 H) 7.47-7.66 (m, 4 H) 7.67-7.82 (m, 1 H) 8.18 (d, J=8.79 Hz, 1 H).

Example 254

2-(2-((1-aminoisoquinolin-6-ylamino)(5-ethyl-2-fluorophenyl)methyl)-1H-imidazol-4-yl)benzamide bis-trifluoroacetic acid salt

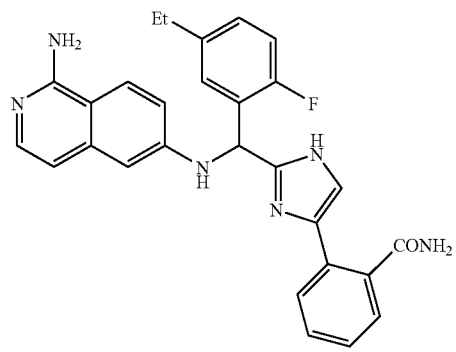

According to the procedure for the preparation of Example 243, reaction of 5-ethyl-2-fluorobenzaldehyde with the 4-bromo-1-trityl-1H-imidazole, followed by chloronation, displacement with 1-(di-(tert-butyloxycarbonyl)amino)-6-aminoisoquinoline, Suzuki coupling and deprotection afforded after HPLC purification Example 254. LCMS (4 min gradient, A=95% H2O/5% CH3CN/0.1% TFA, B=5% H2O/95% CH3CN/0.1% TFA) RT=2.70 min, 481.2 (M+H)+; 1H NMR (400 MHz, CD3OD) δ ppm 1.21 (t, J=7.69 Hz, 3 H) 2.67 (q, J=7.76 Hz, 2 H) 6.50 (s, 1 H) 6.90 (d, J=2.20 Hz, 1 H) 6.99 (d, J=7.03 Hz, 1 H) 7.13-7.32 (m, 4 H) 7.32-7.51 (m, 2 H) 7.51-7.66 (m, 4 H) 7.67-7.87 (m, 1 H) 8.20 (d, J=8.79 Hz, 1 H).

Example 255

2-(2-((1-aminoisoquinolin-6-ylamino)(3-ethoxy-4-fluorophenyl)methyl)-1H-imidazol-4-yl)benzamide bis-trifluoroacetic acid salt

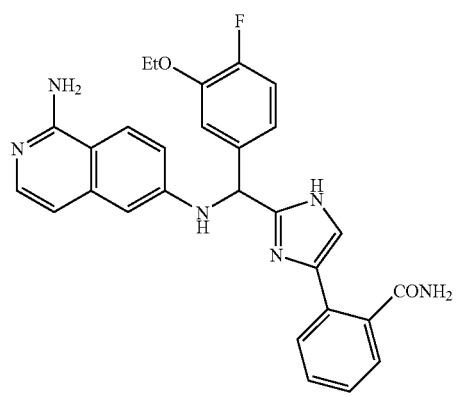

4-fluoro-3-hydroxybenzaldehyde (255.1)

To a solution of 4-fluoro-3-methoxybenzaldehyde (1.5 g, 10 mmol), 10 mL $CH_2Cl_2$ at 0° C., was added $BBr_3$ (30 mL, 1N, 30 mmol) dropwise. The mixture was allowed to warn up to rt over 1 h, then quenched with ice water and diluted with EtOAc. The organic phase was washed with sat. $NaHCO_3$ and brine, dried ($Na_2SO_4$), filtered and concentrated. The crude product was purified by flash chromatography (0 to 5% EtOAc/hexanes, gradient) to afford 1.2 mg (85%) of Intermediate 255.1.

3-ethoxy-4-fluorobenzaldehyde

A mixture of Intermediate 255.1 (330 mg, 2.3 mmol), EtI (0.5 mL, 9.2 mmol), $K_2CO_3$ (500 mg, 4.6 mmol) in 5 mL DMF was heated at 80° C. for 4 h. The reaction mixture was then partionated between EtOAc and $H_2O$, the organic layer was dried over ($Na_2SO_4$), filtered and concentrated. The residue was purified by flash chromatography (0 to 5% EtOAc/hexanes, gradient) to afford 300 mg (92%) of Intermediate 255.2.

Example 255

According to the procedure for the preparation of Example 243, reaction of 3-ethoxy-4-fluorobenzaldehyde with the 4-bromo-1-trityl-1H-imidazole, followed by chloronation, displacement with 1-(di-(tert-butyloxycarbonyl)amino)-6-aminoisoquinoline, Suzuki coupling and deprotection afforded after HPLC purification Example 255. LCMS (4 min gradient, A=95% $H_2O$/5% $CH_3CN$/0.1% TFA, B=5% $H_2O$/95% $CH_3CN$/0.1% TFA) RT=2.68 min, 497.2 (M+H)$^+$; $^1H$ NMR (400 MHz, $CD_3OD$) δ ppm 1.41 (t, J=7.03 Hz, 3 H) 4.03-4.26 (m, 2 H) 6.30 (s, 1 H) 6.84 (d, J=2.20 Hz, 1 H) 6.99 (d, J=7.03 Hz, 1 H) 7.02-7.11 (m, 1 H) 7.02-7.13 (m, 1 H) 7.17-7.31 (m, 3 H) 7.37 (d, J=7.03 Hz, 1 H) 7.52-7.65 (m, 4 H) 7.68-7.81 (m, 1 H) 8.19 (d, J=9.23 Hz, 1 H).

Example 256

2-(2-((4-carbamimidoylphenylamino)(3-ethoxy-4-fluorophenyl)methyl)-1H-imidazol-4-yl)benzamide bis-trifluoroacetic acid salt

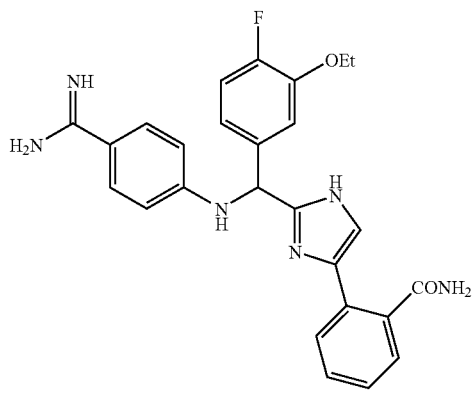

According to the procedure for the preparation of Example 243, reaction of 3-ethoxy-4-fluorobenzaldehyde with the 4-bromo-1-trityl-1H-imidazole, followed by chloronation, displacement with 4-(5-methyl-1,2,4-oxadiazol-3-yl)benze-namine, Suzuki coupling and deprotection afforded after HPLC purification Example 256. LCMS (4 min gradient, A=95% $H_2O$/5% $CH_3CN$/0.1% TFA, B=5% $H_2O$/95% $CH_3CN$/0.1% TFA) RT=2.80 min, 473.2 (M+H)$^+$; $^1H$ NMR (400 MHz, $CD_3OD$) δ ppm 1.41 (t, J=7.03 Hz, 3 H) 4.04-4.21 (m, 2 H) 6.19 (s, 1 H) 6.87 (d, J=8.79 Hz, 2 H) 6.98-7.09 (m, 1 H) 7.13-7.29 (m, 2 H) 7.55-7.63 (m, 4 H) 7.68 (d, J=9.23 Hz, 2 H) 7.71-7.75 (m, 1 H).

Example 257

(R)-2-(2-((4-carbamimidoylphenylamino)(3-ethylphenyl)methyl)-1N-imidazol-4-yl)benzamide bis-trifluoroacetic acid salt

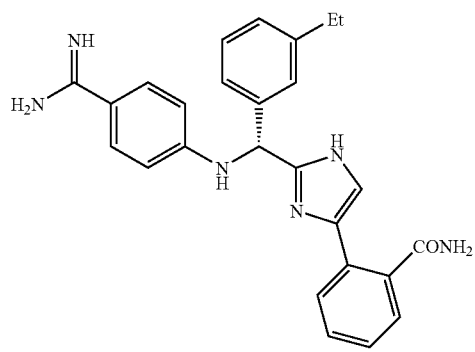

4-((4-bromo-1-trityl-1H-imidazol-2-yl)(3-ethylphenyl)methylamino)benzonitrile (257.1)

Chloronation of Intermediate 252.1, followed by displacement with 4-aminobenzonitrile according to the procedure for the preparation of Intermediate 241.2, afforded Intermediate 257.1.

2-(2-((4-cyanophenylamino)(3-ethylphenyl)methyl)-1-trityl-1H-imidazol-4-yl)benzamide (257.2)

According to procedure for the preparation of Example 241, coupling of Intermediate 257.1 with 2-carbamoylphenylboronic acid, the crude material was purified by flash chromatography (0 to 50% EtOAc/hexanes, gradient) to afford Intermediate 257.2.

2-(2-((4-(N'-hydroxycarbamimidoyl)phenylamino)(3-ethylphenyl)methyl)-1-trityl-1H-imidazol-4-yl)benzamide (257.3)

Intermediate 257.2 was converted to amide oxime, Intermediate 257.3, as described in Intermediate 66.1. Chiral separation of Intermediate 257.3 by Chiralpak IA column (heptane/ethanol (70:30)) afforded first the (R)-stereoisomer, Intermediate 257.3a, and second the (S)-stereoisomer, Intermediate 257.3b.

Example 257

Intermediate 257.3a was subject to hydrogenation and deprotection to afford after HPLC purification Example 257. LC/MS (2 min gradient) RT=1.06 min, 439.2 (M+H)$^+$; $^1H$ NMR (400 MHz, $CD_3OD$) δ ppm 1.23 (t, J=7.47 Hz, 3 H)

2.69 (q, J=7.47 Hz, 2 H) 6.18 (s, 1 H) 6.87 (d, J=8.79 Hz, 2 H) 7.15-7.33 (m, 5 H) 7.34-7.45 (m, 2 H) 7.59 (d, J=3.08 Hz, 2 H) 7.68 (d, J=9.23 Hz, 2 H).

Example 258

(S)-2-(2-((4-carbamimidoylphenylamino)(3-ethylphenyl)methyl)-1H-imidazol-4-yl)benzamide bis-trifluoroacetic acid salt

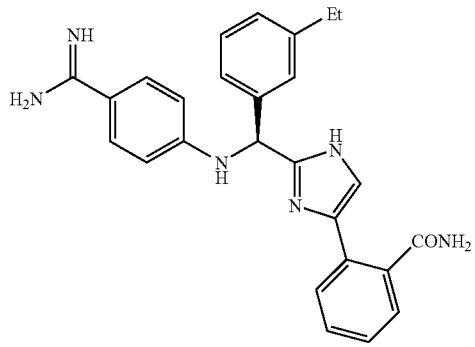

Intermediate 257.3b was subject to hydrogenation and deprotection to afford after HPLC purification Example 258. LC/MS (2 min gradient) RT=1.06 min, 439.2 (M+H)+; 1H NMR (400 MHz, CD3OD) 5 ppm 1.23 (t, J=7.47 Hz, 3 H) 2.69 (q, J=7.47 Hz, 2 H) 6.18 (s, 1 H) 6.87 (d, J=8.79 Hz, 2 H) 7.15-7.33 (m, 5 H) 7.34-7.45 (m, 2 H) 7.59 (d, J=3.08 Hz, 2 H) 7.68 (d, J=9.23 Hz, 2 H).

Example 259

2-(2-((4-carbamimidoylphenylamino)(5-ethoxy-2-fluoro-3-isopropoxyphenyl)methyl)-1-methyl-1H-imidazol-4-yl)benzamide bis-trifluoroacetic acid salt

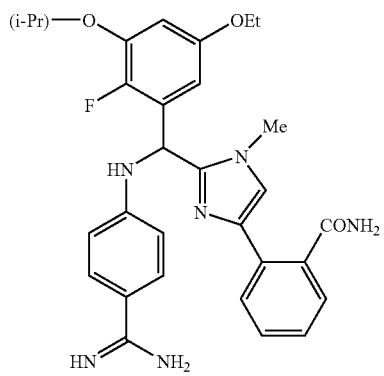

4-((4-bromo-1-methyl-1H-imidazol-2-yl)(5-ethoxy-2-fluoro-3-isopropoxyphenyl)methylamino)benzamidine (259.1)

To a solution of 4-bromo-1-methyl-1H-imidazole (161 mg, 1 mmol) in 2 mL THF at −78° C. was added 1.36 M solution of BuLi in THF (0.9 mL, 1.2 mmol). The mixture was stirred at −78° C. for 30 min, then a solution of Intermediate 7.3 (326, 1 mmol) in 1 mL THF was added dropwise. The mixture was stirred and allowed to warm to rt overnight, then was quenched with sat. NH4Cl, the organic layer was diluted with EtOAc, washed with H2O and brine, dried over (Na2SO4), filtered and concentrated. The crude product was purified by flash chromatography (0 to 50% EtOAc/hexanes, gradient) to afford 110 mg (60%) of Intermediate 259.1.

Example 259

According to procedure for the preparation of Example 28, coupling of Intermediate 259.1 with 2-carbamoylphenylboronic acid, followed by amide oxime formation, acylation, hydrogenation and deprotection as in Example 1 to afford after HPLC purification Example 259. LC/MS (2 min gradient) RT=1.14 min, 545.2 (M+H)+; 1H NMR (400 MHz, CD3OD) 5 ppm 3.81-3.87 (m, 9 H) 3.98 (q, 2 H) 4.54-4.71 (m, 1 H) 6.43-6.52 (m, 2 H) 6.74 (dd, J=7.03, 3.08 Hz, 1 H) 6.90 (d, J=8.79 Hz, 2 H) 7.52-7.61 (m, 3 H) 7.67-7.76 (m, 4 H).

Example 260

2-(2-((1-aminoisoquinolin-6-ylamino)(3-methoxyphenyl)methyl)-1H-imidazol-4-yl)benzamide bis-trifluoroacetic acid salt

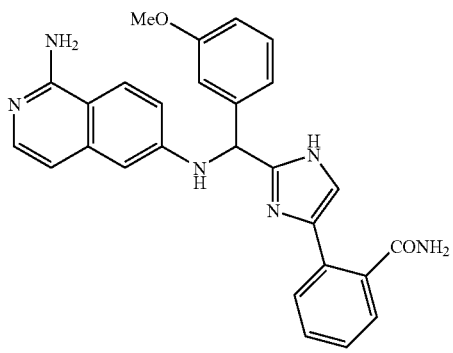

According to the procedure for the preparation of Example 243, reaction of 3-methoxybenzaldehyde with the 4-bromo-1-trityl-1H-imidazole, followed by chloronation, displacement with 1-(di-(tert-butyloxycarbonyl)amino)-6-aminoisoquinoline, Suzuki coupling and deprotection afforded after HPLC purification Example 260. LC/MS (2 min gradient) RT=0.97 min, 465.2 (M+H)+; 1H NMR (400 MHz, CD3OD) δ ppm 3.82 (s, 3 H) 6.25 (s, 1 H) 6.83 (d, J=2.20 Hz, 1 H) 6.98 (d, J=7.03 Hz, 1 H) 7.02 (dd, J=8.35, 1.76 Hz, 1 H) 7.05-7.15 (m, 2 H) 7.25 (dd, J=9.23, 2.20 Hz, 1 H) 7.37 (d, J=7.03 Hz, 1 H) 7.41 (t, J=7.91 Hz, 1 H) 7.50-7.64 (m, 3 H) 7.71 (d, J=7.03 Hz, 1 H) 8.18 (d, J=9.23 Hz, 1 H).

Example 261

2-(2-((4-carbamimidoylphenylamino)(3-methoxyphenyl)methyl)-1H-imidazol-4-yl)benzamide bis-trifluoroacetic acid salt

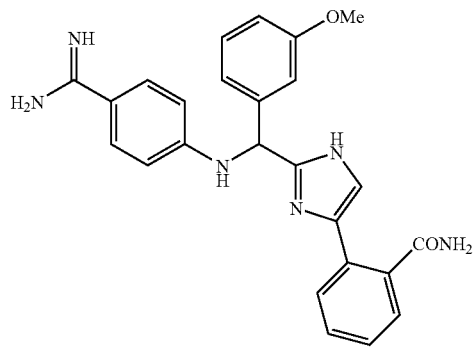

4-((4-bromo-1-trityl-1H-imidazol-2-yl)(5-ethyl-2-fluorophenyl)methylamino)benzonitrile (261.1)

According to the procedure for the preparation of Intermediate 241.2, reaction of 3-methoxybenzaldehyde with the 4-bromo-1-trityl-1H-imidazole, followed by chloronation, displacement with 4-aminobenzonitrile, afforded Intermediate 261.1.

Example 261

According to procedure for the preparation of Example 241, coupling of Intermediate 261.1 with 2-carbamoylphenylboronic acid, followed by amide oxime formation, acylation, hydrogenation and deprotection as in Example 1 to afford after HPLC purification Example 261. LC/MS (2 min gradient) RT=1.14 min, 441.2 (M+H)$^+$; $^1$H NMR (400 MHz, CD$_3$OD) δ ppm 3.78 (s, 3 H) 5.75 (s, 1 H) 6.76 (d, J=8.79 Hz, 2 H) 6.85-6.94 (m, 1 H) 6.93-7.03 (m, 3 H) 7.11 (s, 1 H) 7.15 (m, 2 H) 7.19-7.44 (m, J=7.91, 7.91 Hz, 2 H) 7.60 (d, J=9.23 Hz, 2 H).

Example 262

2-(2-((4-carbamimidoylphenylamino)(5-ethyl-2-fluorophenyl)methyl)-1-methyl-1H-imidazol-4-yl)benzamide bis-trifluoroacetic acid salt

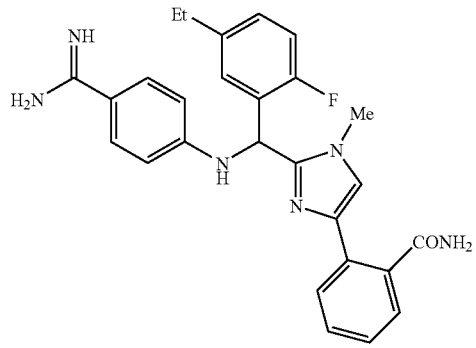

4-(5-ethyl-2-fluorostyryl)benzonitrile (262.1)

According to procedure for the preparation of Intermediate 1.1, 5-ethyl-2-fluorobenzaldehyde (900 mg, 5.88 mmol) and 4-aminobenzonitrile (694 mg, 5.88 mmol) afforded 950 mg of Intermediate 262.1

4-((4-bromo-1-methyl-1H-imidazol-2-yl)(5-ethyl-2-fluorophenyl)methylamino)benzonitrile (262.2)

According to procedure for the preparation of Intermediate 259.1, Intermediate 262.1 and 4-bromo-1-methyl-1H-imidazole afforded Intermediate 262.2.

Example 262

According to procedure for the preparation of Example 241, coupling of Intermediate 262.2 with 2-carbamoylphenylboronic acid, followed by amide oxime formation, acylation, hydrogenation and deprotection as in Example 1 to afford after HPLC purification Example 262. LCMS (4 min gradient, A=95% H$_2$O/5% CH$_3$CN/0.1% TFA, B=5% H$_2$O/95% CH$_3$CN/0.1% TFA) RT=2.80 min, 471.2 (M+H)$^+$; $^1$H NMR (400 MHz, CD$_3$OD) δ ppm 1.20 (t, J=7.47 Hz, 3 H) 2.66 (q, J=7.47 Hz, 2 H) 3.81 (s, 3 H) 6.47 (s, 1 H) 6.90 (d, J=8.79 Hz, 2 H) 7.13-7.24 (m, 1 H) 7.27 (dd, J=7.03, 2.20 Hz, 1 H) 7.31-7.41 (m, 1 H) 7.50-7.64 (m, 3 H) 7.65-7.75 (m, 4 H).

Example 263

2-(2-((4-carbamimidoylphenylamino)(5-ethyl-2-fluorophenyl)methyl)-1H-imidazol-4-yl)benzamide bis-trifluoroacetic acid salt

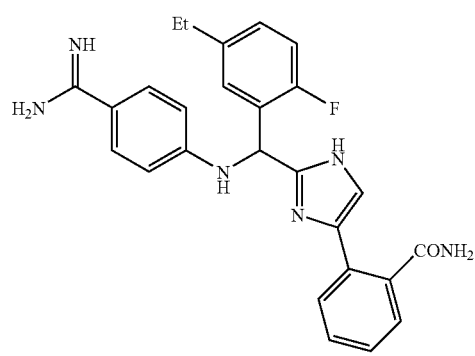

According to the procedure for the preparation of Example 262, reaction of 2-fluoro-5-ethylbenzaldehyde with the 4-bromo-1-trityl-1H-imidazole, followed by chloronation, displacement with 4-aminobenzonitrile, Suzuki coupling, amidine formation and deprotection afforded after HPLC purification Example 263. LCMS (4 min gradient, A=95% H$_2$O/5% CH$_3$CN/0.1% TFA, B=5% H$_2$O/95% CH$_3$CN/0.1% TFA) RT=2.75 min, 457.2 (M+H)$^+$; $^1$H NMR (400 MHz, CD$_3$OD) δ ppm 1.20 (t, J=7.69 Hz, 3 H) 2.64 (q, J=7.69 Hz, 2 H) 6.42 (s, 1 H) 6.90 (d, J=9.23 Hz, 2 H) 7.13-7.20 (m, 1 H) 7.28 (dd, J=7.03, 2.20 Hz, 1 H) 7.30-7.39 (m, 1 H) 7.53-7.63 (m, 4 H) 7.66-7.77 (m, 3 H).

Example 264

4-((5-ethyl-2-fluorophenyl)(1-phenyl-1H-pyrazol-3-yl)methylamino)benzamidine trifluoroacetic acid salt

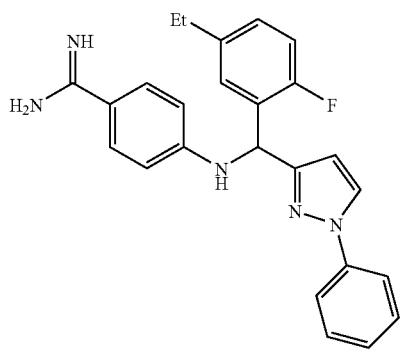

4-((5-ethyl-2-fluorophenyl)(1H-pyrazol-3-yl)methylamino)benzonitrile (264.1)

According to procedure for the preparation of Intermediate 183.1, reaction of Intermediate 262.1 with 1-(1,1-diethoxyethyl)-1H-pyrazole afforded Intermediate 264.1.

4-((5-ethyl-2-fluorophenyl)(1-phenyl-1H-pyrazol-3-yl)methylamino)benzonitrile (264.2)

To a mixture of Intermediate 264.1 (40 mg, 0.125 mmol), 4 A molecular sieves, TEA (70 uL, 0.25 mmol), pyridine (20 mg, 0.25 mmol), phenyl boronic acid (31 mg, 0.25 mmol) in CH$_2$Cl$_2$ was added Cu(OAc)$_2$ (34 mg, 0.19 mmol). The reaction mixture was stirred at rt for 2 h, which was then diluted with EtOAc and washed with 0.5 N HCl, H$_2$O, sat NaHCO$_3$ and brine, dried over (Na$_2$SO$_4$), filtered and concentrated. The crude product was purified by flash chromatography (0 to 50% EtOAc/hexanes, gradient) to afford 20 mg (45%) of Intermediate 264.2.

Example 264

Intermediate 264.2 was subject to amide oxime formation, acylation and hydrogenation as in example 1 to afford after HPLC purification Example 264. LC/MS (2 min gradient) RT=1.66 min, 414.3 (M+H)$^+$; $^1$H NMR (400 MHz, CD$_3$OD) δ ppm 1.03-1.26 (m, 3 H) 2.57 (q, J=7.47 Hz, 2 H) 6.12 (s, 1 H) 6.38 (d, J=2.64 Hz, 1 H) 6.81 (d, J=8.79 Hz, 2 H) 6.98-7.09 (m, 1 H) 7.12-7.21 (m, 1 H) 7.31 (t, J=7.47 Hz, 2 H) 7.47 (t, J=7.91 Hz, 2 H) 7.58 (d, J=8.79 Hz, 2 H) 7.74 (d, J=7.91 Hz, 2 H) 8.16 (d, J=2.64 Hz, 1 H).

Example 265

2-(3-((4-carbamimidoylphenylamino)(5-ethyl-2-fluorophenyl)methyl)-1H-pyrazol-1-yl)benzamide trifluoroacetic acid salt

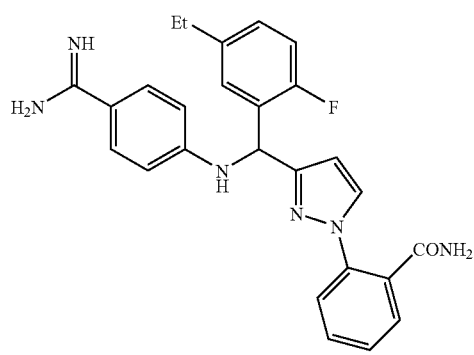

According to procedure for the preparation of Intermediate 264.2, coupling of Intermediate 264.1 with 2-carbamoylphenylboronic acid, followed by amide oxime formation, acylation and hydrogenation as in example 1 to afford after HPLC purification Example 265. LC/MS (2 min gradient) RT=1.38 min, 457.2 (M+H)$^+$; $^1$H NMR (400 MHz, CD$_3$OD) δ ppm 1.03-1.26 (m, 3 H) 2.55 (q, J=7.47 Hz, 2 H) 6.10 (s, 1 H) 6.38 (d, J=2.64 Hz, 1 H) 6.81 (d, J=8.79 Hz, 1 H) 6.98-7.09 (m, 1 H) 7.12-7.21 (m, 1 H) 7.31 (t, J=7.47 Hz, 2 H) 7.47 (t, J=7.91 Hz, 2 H) 7.58 (d, J=8.79 Hz, 2 H) 7.74 (d, J=7.91 Hz, 2 H) 8.16 (d, J=2.64 Hz, 1 H).

Example 266

4-((3-ethyl-4-fluorophenyl)(1-phenyl-1H-pyrazol-3-yl)methylamino)benzamidine trifluoroacetic acid salt

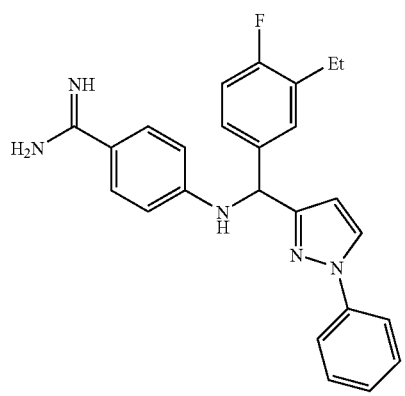

4-((3-ethyl-4-fluorophenyl)(1H-pyrazol-3-yl)methylamino)benzonitrile (266.1)

According to procedure for the preparation of Intermediate 183.1, reaction of (E)-4-(3-ethyl-4-fluorobenzylideneamino)benzonitrile (prepared from 3-ethyl-4-fluorobenzaldehyde (250 mg, 1.63 mmol) and 4-aminobenzonitrile (192 mg, 1.63 mmol) as in preparation of Intermediate 1.1) with 1-(1,1-diethoxyethyl)-1H-pyrazole afforded Intermediate 266.1.

Example 266

According to procedure for the preparation of Intermediate 264.2, coupling of Intermediate 266.1 with phenylboronic acid, followed by amide oxime formation, acylation and hydrogenation as in Example 1 to afford after HPLC purification Example 266. LCMS (4 min gradient, A=95% $H_2O$/5% $CH_3CN$/0.1% TFA, B=5% $H_2O$/95% $CH_3CN$/0.1% TFA) RT=4.39 min, 414.2 $(M+H)^+$; $^1H$ NMR (400 MHz, $CD_3OD$) δ ppm 1.19 (t, J=7.69 Hz, 3 H) 2.65 (q, J=7.62 Hz, 2 H) 5.84 (s, 1 H) 6.36 (d, J=2.64 Hz, 1 H) 6.81 (d, J=9.23 Hz, 2 H) 6.94-7.08 (m, 1 H) 7.31 (t, J=7.47 Hz, 2 H) 7.38 (dd, J=7.47, 2.20 Hz, 1 H) 7.47 (t, J=7.91 Hz, 2 H) 7.57 (d, J=9.23 Hz, 2 H) 7.74 (d, J=7.47 Hz, 2 H) 8.15 (d, J=2.20 Hz, 1 H).

Example 267

2-(3-((4-carbamimidoylphenylamino)(3-ethyl-4-fluorophenyl)methyl)-1H-pyrazol-1-yl)benzamide trifluoroacetic acid salt

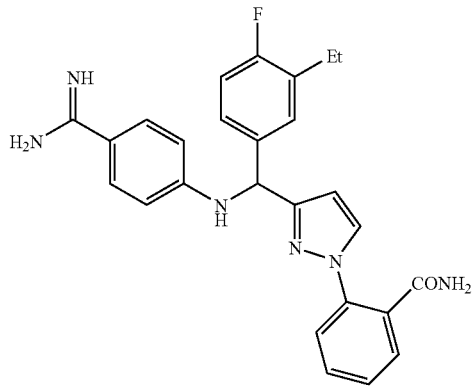

According to procedure for the preparation of Intermediate 264.2, coupling of Intermediate 266.1 with 2-carbamoylphenylboronic acid, followed by amide oxime formation, acylation and hydrogenation as in Example 1 to afford after HPLC purification Example 267. LC/MS (2 min gradient) RT=1.13 min, 457.2 $(M+H)^+$; $^1H$ NMR (400 MHz, $CD_3OD$) δ ppm 1.19 (t, J=7.69 Hz, 3 H) 2.65 (q, J=7.62 Hz, 2 H) 5.84 (s, 1 H) 6.36 (d, J=2.64 Hz, 1 H) 6.81 (d, J=9.23 Hz, 2 H) 6.90-7.06 (m, 1 H) 7.31 (t, J=7.47 Hz, 2 H) 7.38 (dd, J=7.47, 2.20 Hz, 1 H) 7.47 (t, J=7.91 Hz, 2 H) 7.57 (d, J=9.23 Hz, 2 H) 7.72 (d, J=7.47 Hz, 2 H) 8.25 (d, J=2.20 Hz, 1 H).

Example 268

2-(2-((4-carbamimidoylphenylamino)(3-ethyl-4-fluorophenyl)methyl)-1H-imidazol-4-yl)benzamide bis-trifluoroacetic acid salt

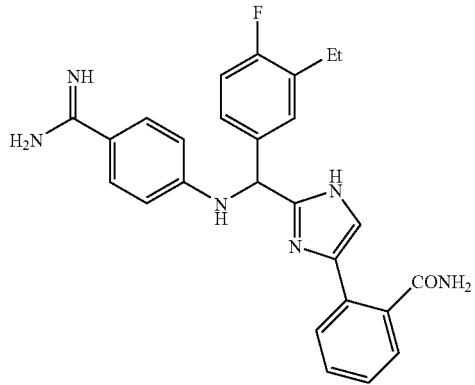

4-((4-bromo-1-trityl-1H-imidazol-2-yl)(3-ethyl-4-fluorophenyl)methylamino)benzonitrile (268.1)

According to procedure for the preparation of Intermediate 259.1, Intermediate 266.1 (127 mg, 0.5 mmol) and 4-bromo-1-trityl-1H-imidazole (195 mg, 0.5 mmol) afforded Intermediate 268.1 (120 mg).

Example 268

According to procedure for the preparation of Example 241, coupling of Intermediate 268.1 with 2-carbamoylphenylboronic acid, followed by amide oxime formation, acylation, hydrogenation and deprotection as in Example 1 to afford after HPLC purification Example 268. LCMS (4 min gradient, A=95% $H_2O$/5% $CH_3CN$/0.1% TFA, B=5% $H_2O$/95% $CH_3CN$/0.1% TFA) RT=2.75 min, 457.2 $(M+H)^+$.

Example 269

2-(2-((1-aminoisoquinolin-6-ylamino)(5-ethyl-2-fluoro-3-isopropoxyphenyl)methyl)-1H-imidazol-4-yl)benzamide bis-trifluoroacetic acid salt

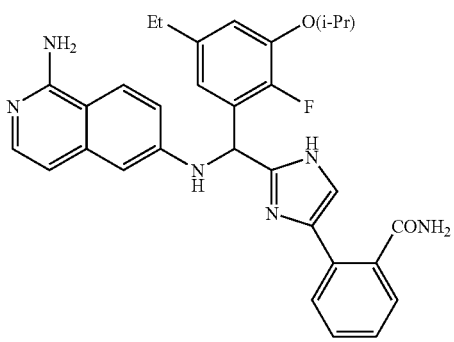

di-tert-butyl (6-{[(4-bromo-1-trityl-1H-imidazole-2-yl)(5-ethyl-2-fluoro-3-hydroxyphenyl)methyl]amino}isoquinolin-1-yl)imidadicarbonate (269.1)

According to the procedure for the preparation of Intermediate 241.3, reaction of 3-(tert-butyldimethylsilyloxy)-5-ethyl-2-fluorobenzaldehyde with the 4-bromo-1-trityl-1H-imidazole, followed by chloronation, displacement with 1-(di-(tert-butyloxycarbonyl)amino)-6-aminoisoquinoline and desilylation, afforded Intermediate 269.1.

di-tert-butyl (6-{[(4-bromo-1-trityl-1H-imidazole-2-yl)(5-ethyl-2-fluoro-3-isopropoxyphenyl)methyl]amino}isoquinolin-1-yl)imidadicarbonate (269.2)

According to the procedure for the preparation of Intermediate 188.7, alkylation of Intermediate 269.1 with 2-iodopropane, afforded Intermediate 269.2.

Example 269

According to procedure for the preparation of Example 241, coupling of Intermediate 269.2 with 2-carbamoylphenylboronic acid, followed by deprotection afforded after HPLC purification Example 269. LC/MS (2 min gradient) RT=1.26 min, 539.2 $(M+H)^+$; $^1H$ NMR (400 MHz, $CD_3OD$), δ ppm 1.20 (t, J=7.47 Hz, 3 H) 1.33 (d, J=6.15 Hz, 6 H) 2.62 (q, J=7.69 Hz, 2 H) 4.59-4.71 (m, 1 H) 6.49 (s, 1 H) 6.81 (d, J=3.96 Hz, 1 H) 6.89 (d, J=2.20 Hz, 1 H) 6.99 (d, J=7.03 Hz, 1 H) 7.06 (d, J=7.47 Hz, 1 H) 7.27 (dd, J=9.23, 2.20 Hz, 1 H) 7.38 (d, 1 H) 7.55-7.64 (m, 4 H) 7.72 (d, 1 H) 8.19 (d, J=8.79 Hz, 1 H).

Example 270

N⁶-((5-ethoxy-2-fluorophenyl)(4-phenyl-1H-imidazol-2-yl)methyl)isoquinoline-1,6-diamine bis-trifluoroacetic acid salt

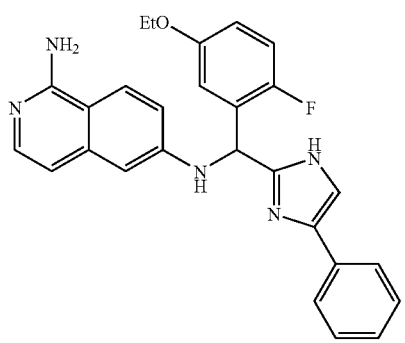

According to procedure for the preparation of Example 241, coupling of Intermediate 245.2 with phenylboronic acid, followed by deprotection afforded after HPLC purification Example 270. LC/MS (2 min gradient) RT=1.26 min, 439.2 (M+H)⁺; ¹H NMR (400 MHz, CD₃OD) δ ppm 1.34 (t, J=6.81 Hz, 3 H) 4.00 (q, J=7.32 Hz, 2 H) 6.53 (s, 1 H) 6.88-6.97 (m, 2 H) 6.97-7.09 (m, 2 H) 7.20 (t, J=9.45 Hz, 1 H) 7.28 (dd, J=9.23, 2.64 Hz, 1 H) 7.37 (d, J=7.03 Hz, 1 H) 7.41-7.55 (m, 3 H) 7.73 (d, J=7.03 Hz, 2 H) 7.85 (s, 1 H) 8.21 (d, J=9.23 Hz, 1 H).

Example 271

2-(2-((4-carbamimidoylphenylamino)(3-ethyl-5-fluorophenyl)methyl)-1H-imidazol-4-yl)benzamide bis-trifluoroacetic acid salt

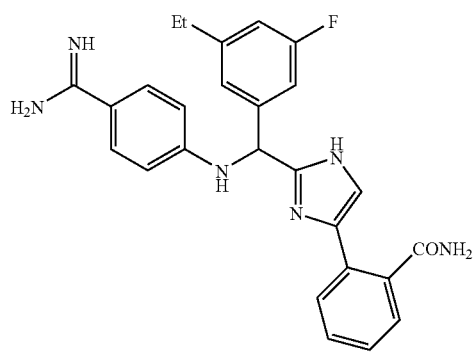

According to the procedure for the preparation of Example 262, reaction of 3-fluoro-5-vinylbenzaldehyde with the 4-bromo-1-trityl-1H-imidazole, followed by chloronation, displacement with 4-aminobenzonitrile, Suzuki coupling, amidine formation and deprotection afforded after HPLC purification Example 271. LC/MS (2 min gradient) RT=1.09 min, 457.2 (M+H)⁺; ¹H NMR (400 MHz, CD₃OD) δ ppm 1.24 (t, J=7.69 Hz, 3 H) 2.70 (q, J=7.47 Hz, 2 H) 6.23 (s, 1 H) 6.87 (d, J=8.79 Hz, 2 H) 7.08 (t, J=9.67 Hz, 2 H) 7.20 (s, 1 H) 7.56 (s, 1 H) 7.57-7.62 (m, 3 H) 7.68 (d, J=8.79 Hz, 2 H) 7.70-7.76 (m, 1 H).

Example 272

(Z)-4-((5-ethoxy-2-fluorophenyl)(4-phenyl-1H-imidazol-2-yl)methylamino)-N'-hydroxybenzamidine bis-trifluoroacetic acid salt

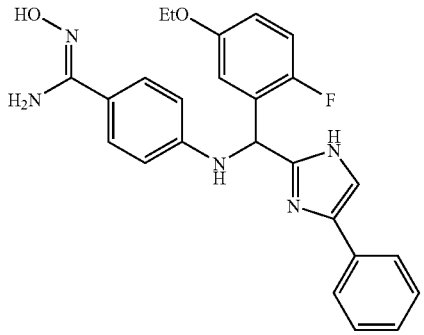

4-((4-bromo-1-trityl-1H-imidazol-2-yl)(5-ethoxy-2-fluorophenyl)methylamino)benzonitrile (272.1)

Chlorination of Intermediate 245.1, followed by displacement with 4-aminobenzonitrile according to the procedure for the preparation of Intermediate 241.2, afforded Intermediate 272.1.

Example 272

According to procedure for the preparation of Example 241, coupling of Intermediate 272.1 with 2-carbamoylphenylboronic acid, followed by amide oxime formation, acylation, hydrogenation and deprotection as in Example 1 to afford after HPLC purification Example 272. LC/MS (2 min gradient) RT=1.17 min, 446.2 (M+H)⁺; ¹H NMR (400 MHz, CD₃OD) δ ppm 1.33 (t, J=6.81 Hz, 3 H) 3.98 (q, J=7.03 Hz, 2 H) 6.43 (s, 1 H) 6.91 (d, J=8.79 Hz, 2 H) 6.96-7.05 (m, 2 H) 7.16 (t, J=9.67 Hz, 1 H) 7.43-7.52 (m, 3 H) 7.56 (d, J=8.79 Hz, 2 H) 7.72 (d, J=6.59 Hz, 2 H) 7.84 (s, 1 H).

Example 273

N⁶-((5-ethyl-2-fluorophenyl)(4-phenyl-1H-imidazol-2-yl)methyl)isoquinoline-1,6-diamine bis-trifluoroacetic acid salt

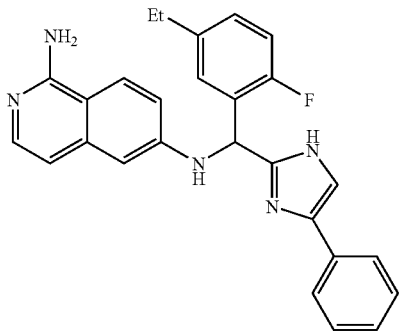

According to the procedure for the preparation of Example 243, reaction of 5-ethyl-2-fluorobenzaldehyde with the 4-bromo-1-trityl-1H-imidazole, followed by chloronation, displacement with 1-(di-(tert-butyloxycarbonyl)amino)-6-aminoisoquinoline, Suzuki coupling with phenylboronic acid and deprotection afforded after HPLC purification Example 253. LC/MS (2 min gradient) RT=1.29 min, 438.2 (M+H)+; ¹H NMR (400 MHz, CD₃OD) δ ppm 1.19 (t, J=7.47 Hz, 3 H) 2.65 (q, J=7.47 Hz, 2 H) 6.50 (s, 1 H) 6.89 (d, J=2.20 Hz, 1 H) 6.93 (d, J=7.47 Hz, 1H) 7.13-7.23 (m, 2 H) 7.24-7.32 (m, 2 H) 7.32-7.40 (m, 2 H) 7.41-7.56 (m, 3 H) 7.72 (d, J=7.03 Hz, 2 H) 7.82 (s, 1 H) 8.20 (d, J=9.23 Hz, 1 H).

Example 274

4-((5-ethyl-2-fluorophenyl)(4-phenyl-1H-imidazol-2-yl)methylamino)-N'-hydroxybenzamidine bis-trifluoroacetic acid salt

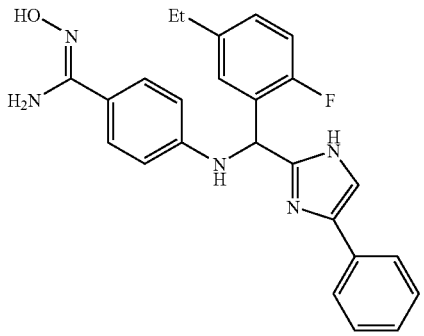

According to procedure for the preparation of Example 241, coupling of Intermediate 263.1 with phenylboronic acid, followed by amide oxime formation, and deprotection as in Example 1 to afford after HPLC purification Example 274. LC/MS (2 min gradient) RT=1.22 min, 430.3 (M+H)+; ¹H NMR (400 MHz, CD₃OD) δ ppm 1.19 (t, J=7.47 Hz, 3 H) 2.64 (q, J=7.76 Hz, 2 H) 6.42 (s, 1 H) 6.90 (d, J=8.35 Hz, 2 H) 7.06-7.21 (m, 1 H) 7.28 (d, J=7.03 Hz, 1 H) 7.30-7.37 (m, 1 H) 7.44-7.53 (m, 3 H) 7.56 (d, J=8.35 Hz, 2 H) 7.72 (d, J=7.03 Hz, 2 H) 7.84 (s, 1 H).

Example 275

4-((5-ethyl-2-fluorophenyl)(4-phenyl-1H-imidazol-2-yl)methylamino)benzamidine bis-trifluoroacetic acid salt

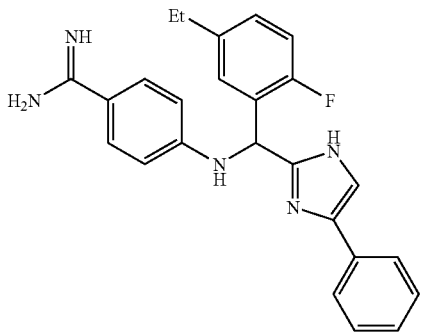

According to procedure for the preparation of Example 241, coupling of Intermediate 263.1 with phenylboronic acid, followed by amide oxime formation, acylation, hydrogenation and deprotection as in example 1 to afford after HPLC purification Example 275. LC/MS (2 min gradient) RT=1.23 min, 414.3 (M+H)+; ¹H NMR (400 MHz, CD₃OD) δ ppm 1.19 (t, J=7.69 Hz, 3 H) 2.64 (q, J=7.47 Hz, 2 H) 6.46 (s, 1 H) 6.91 (d, J=9.23 Hz, 2 H) 7.16 (t, 1 H) 7.26-7.38 (m, 2 H) 7.41-7.55 (m, 3 H) 7.65-7.77 (m, 4 H) 7.85 (s, 1 H).

Example 276

2-(2-((1-aminoisoquinolin-6-ylamino)(3-ethoxy-5-ethyl-2-fluorophenyl)methyl)-1H-imidazol-4-yl)benzamide bis-trifluoroacetic acid salt

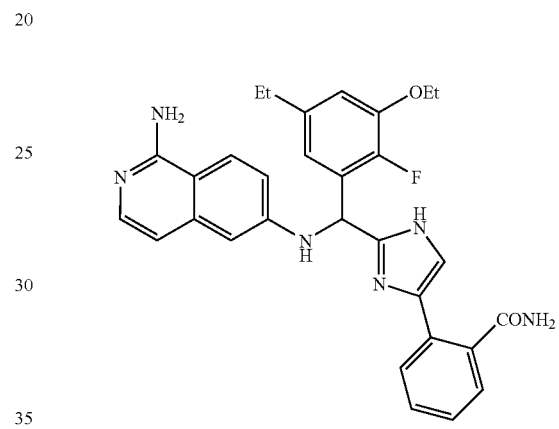

di-tert-butyl (6-{[(4-bromo-1-trityl-1H-imidazole-2-yl)(5-ethyl-2-fluoro-3-ethoxyphenyl)methyl]amino}isoquinolin-1-yl)imidadicarbonate (276.1)

According to the procedure for the preparation of Intermediate 269.1, reaction of 3-(tert-butyldimethylsilyloxy)-5-ethyl-2-fluorobenzaldehyde with the 4-bromo-1-trityl-1H-imidazole, followed by chloronation, displacement with 1-(di-(tert-butyloxycarbonyl)amino)-6-aminoisoquinoline, desilylation and alkylation with iodoethane, afforded Intermediate 276.1.

Example 276

According to procedure for the preparation of Example 241, coupling of Intermediate 276.1 with 2-carbamoylphenylboronic acid, followed by deprotection afforded after HPLC purification Example 276. LC/MS (2 min gradient) RT=1.22 min, 525.3 (M+H)+; ¹H NMR (400 MHz, CD₃OD) δ ppm 1.20 (t, J=7.47 Hz, 3 H) 1.41 (t, J=7.03 Hz, 3 H) 2.63 (q, J=7.62 Hz, 2 H) 4.13 (q, J=6.74 Hz, 2 H) 6.49 (s, 1 H) 6.81 (d, J=4.39 Hz, 1 H) 6.89 (d, J=2.20 Hz, 1 H) 6.99 (d, J=7.03 Hz, 1 H) 7.05 (d, J=6.15 Hz, 1 H) 7.27 (dd, J=9.23, 2.20 Hz, 1 H) 7.38 (d, J=7.03 Hz, 1 H) 7.54-7.65 (m, 4 H) 7.68-7.75 (m, 1 H) 8.19 (d, J=9.23 Hz, 1 H).

Example 277

2-(2-((1-aminoisoquinolin-6-ylamino)(5-ethyl-2-fluoro-3-methoxyphenyl)methyl)-1H-imidazol-4-yl)benzamide bis-trifluoroacetic acid salt

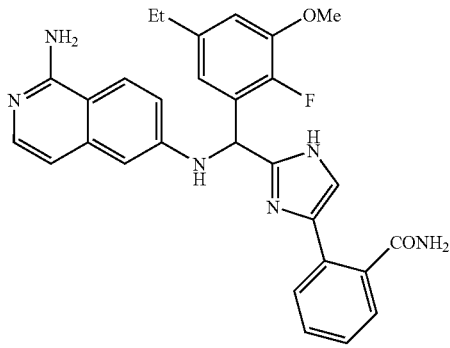

di-tert-butyl (6-{[(4-bromo-1-trityl-1H-imidazole-2-yl)(5-ethyl-2-fluoro-3-methoxyphenyl)methyl]amino}isoquinolin-1-yl)imidadicarbonate (277.1)

According to the procedure for the preparation of Intermediate 269.1, reaction of 3-(tert-butyldimethylsilyloxy)-5-ethyl-2-fluorobenzaldehyde with the 4-bromo-1-trityl-1H-imidazole, followed by chloronation, displacement with 1-(di-(tert-butyloxycarbonyl)amino)-6-aminoisoquinoline, desilylation and alkylation with MeI, afforded Intermediate 277.1.

Example 277

According to procedure for the preparation of Example 241, coupling of Intermediate 277.1 with 2-carbamoylphenylboronic acid, followed by deprotection afforded after HPLC purification Example 277. LC/MS (2 min gradient) RT=1.10 min, 511.2 (M+H)+; 1H NMR (400 MHz, CD3OD) δ ppm 1.21 (t, J=7.69 Hz, 3 H) 1.21 (t, J=7.69 Hz, 2 H) 2.65 (q, J=7.62 Hz, 2 H) 3.89 (s, 3 H) 6.48 (s, 1 H) 6.82 (d, J=4.39 Hz, 1 H) 6.89 (d, J=2.20 Hz, 1 H) 6.99 (d, J=7.03 Hz, 1 H) 7.08 (d, J=6.15 Hz, 1 H) 7.26 (dd, J=9.01, 2.42 Hz, 1 H) 7.38 (d, J=7.03 Hz, 1 H) 7.53-7.65 (m, 4 H) 7.68-7.80 (m, 1 H) 8.19 (d, J=9.23 Hz, 1 H).

Example 278

N6-((5-ethyl-2-fluorophenyl)(4-(2-methoxyphenyl)-1H-imidazol-2-yl)methyl)isoquinoline-1,6-diamine bis-trifluoroacetic acid salt

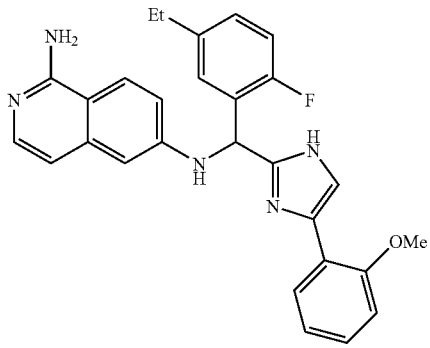

According to procedure for the preparation of Example 241, coupling of Intermediate 254.2 with 2-methoxyphenylboronic acid, followed by deprotection afforded after HPLC purification Example 278. LC/MS (2 min gradient) RT=1.34 min, 468.4 (M+H)+; 1H NMR (400 MHz, CD3OD) δ ppm 1.20 (t, J=7.47 Hz, 3 H) 2.65 (q, J=7.62 Hz, 2 H) 3.92 (s, 3 H) 6.54 (s, 1 H) 6.87 (d, J=2.20 Hz, 1 H) 6.93 (d, J=7.03 Hz, 1 H) 7.08 (t, J=7.69 Hz, 1 H) 7.15-7.22 (m, 2 H) 7.23-7.30 (m, 2 H) 7.36 (t, J=6.81 Hz, 2 H) 7.45 (t, J=7.47 Hz, 1 H) 7.65 (d, J=7.47 Hz, 1 H) 7.80 (s, 1 H) 8.21 (d, J=8.79 Hz, 1 H).

Example 279

2-(2-((1-aminoisoquinolin-6-ylamino)(5-ethyl-2-fluoro-3-((R)-tetrahydrofuran-3-yloxy)phenyl)methyl)-1H-imidazol-4-yl)benzamide bis-trifluoroacetic acid salt

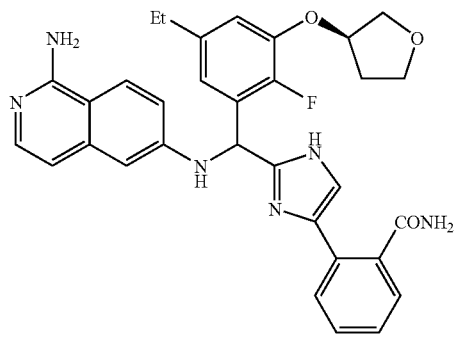

di-tert-butyl (6-{[(4-bromo-1-trityl-1H-imidazole-2-yl)(5-ethyl-2-fluoro-3-((R)-tetrahydrofuran-3-yloxy)phenyl)methyl]amino}isoquinolin-1-yl)imidadicarbonate (279.1)

According to procedure for the preparation of Intermediate 242.1, Intermediate 269.1 (88 mg, 0.1 mmol) and (S)-tetrahydrofuran-3-ol (16.9 mg, 0.19 mmol) afforded 80 mg of Intermediate 279.1.

Example 279

According to procedure for the preparation of Example 241, coupling of Intermediate 279.1 with 2-carbamoylphenylboronic acid, followed by deprotection afforded after HPLC purification Example 277. LCMS (4 min gradient, A=95% H2O/5% CH3CN/0.1% TFA, B=5% H2O/95% CH3CN/0.1% TFA) RT=3.00 min, 567.46 (M+H)+; 1H NMR (400 MHz, CD3OD) δ ppm 1.21 (t, J=7.47 Hz, 3 H) 2.04-2.18 (m, 1 H) 2.20-2.34 (m, 1 H) 2.64 (q, J=7.47 Hz, 2 H) 3.84-3.92 (m, 1 H) 3.92-4.05 (m, 4 H) 6.50 (d, J=1.76 Hz, 1 H) 6.83-6.92 (m, 2 H) 6.99 (d, J=7.47 Hz, 1 H) 7.04 (d, J=7.47 Hz, 1 H) 7.27 (dd, J=9.23, 2.20 Hz, 1 H) 7.38 (d, J=7.03 Hz, 1 H) 7.53-7.64 (m, 4 H) 7.72 (d, J=7.03 Hz, 1 H) 8.20 (d, J=9.23 Hz, 1 H).

Example 280

N[6]-((4-bromo-1H-imidazol-2-yl)(5-ethyl-2-fluoro-3-((R)-tetrahydrofuran-3-yloxy)phenyl)methyl)isoquinoline-1,6-diamine bis-trifluoroacetic acid salt

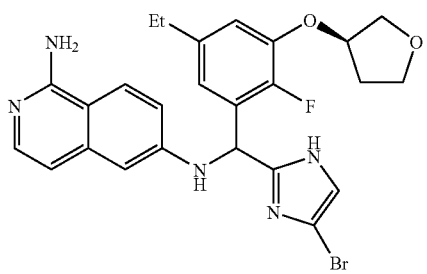

Intermediate 279.1 was deprotected with TFA to afford after HPLC purification Example 280. LCMS (4 min gradient, A=95% H$_2$O/5% CH$_3$CN/0.1% TFA, B=5% H$_2$O/95% CH$_3$CN/0.1% TFA) RT=3.80 min, 513.46 (M+H)$^+$; $^1$H NMR (400 MHz, CD$_3$OD) δ ppm 1.17 (t, J=7.47 Hz, 3 H) 2.13 (d, J=6.15 Hz, 1 H) 2.18-2.31 (m, 1 H) 2.58 (q, J=7.62 Hz, 2 H) 3.84-3.91 (m, 1 H) 3.92-4.00 (m, 4 H) 6.17 (s, 1 H) 6.73 (s, 1 H) 6.78 (d, J=5.27 Hz, 1 H) 6.86 (d, J=7.03 Hz, 1 H) 6.94 (d, J=7.91 Hz, 1 H) 7.12-7.24 (m, 2 H) 7.33 (d, J=7.03 Hz, 1 H) 8.12 (d, J=8.79 Hz, 1H).

Example 281

2-(2-((1-aminoisoquinolin-6-ylamino)(5-ethyl-2-fluoro-3-((S)-tetrahydrofuran-3-yloxy)phenyl)methyl)-1H-imidazol-4-yl)benzamide bis-trifluoroacetic acid salt

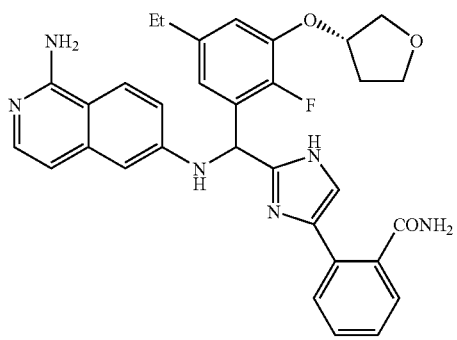

di-tert-butyl (6-{[(4-bromo-1-trityl-1H-imidazole-2-yl)(5-ethyl-2-fluoro-3-((S)-tetrahydrofuran-3-yloxy)phenyl)methyl]amino}isoquinolin-1-yl)imidadicarbonate (281.1)

According to procedure for the preparation of Intermediate 242.1, Intermediate 269.1 (88 mg, 0.1 mmol) and (R)-tetrahydrofuran-3-ol (16.9 mg, 0.19 mmol) afforded 100 mg of Intermediate 281.1.

Example 281

According to procedure for the preparation of Example 241, coupling of Intermediate 281.1 with 2-carbamoylphenylboronic acid, followed by deprotection afforded after HPLC purification Example 281. LCMS (4 min gradient, A=95% H$_2$O/5% CH$_3$CN/0.1% TFA, B=5% H$_2$O/95% CH$_3$CN/0.1% TFA) RT=3.16 min, 567.2 (M+H)$^+$; $^1$H NMR (400 MHz, CD$_3$OD) δ ppm 1.20 (t, J=7.47 Hz, 3 H) 2.06-2.18 (m, 1 H) 2.20-2.34 (m, 1 H) 2.64 (q, J=7.47 Hz, 2 H) 3.84-3.91 (m, 1 H) 3.92-4.01 (m, 4 H) 6.50 (d, J=2.20 Hz, 1 H) 6.76-6.92 (m, 2 H) 6.98 (d, J=7.03 Hz, 1 H) 7.04 (d, J=7.91 Hz, 1 H) 7.26 (dd, J=9.01, 2.42 Hz, 1 H) 7.38 (d, J=7.03 Hz, 1 H) 7.52-7.63 (m, 4 H) 7.71 (d, J=7.03 Hz, 1 H) 8.19 (d, J=9.23 Hz, 1 H).

Example 282

2-(2-((1-aminoisoquinolin-6-ylamino)(5-ethyl-2-fluoro-3-isobutoxyphenyl)methyl)-1H-imidazol-4-yl)benzamide bis-trifluoroacetic acid salt

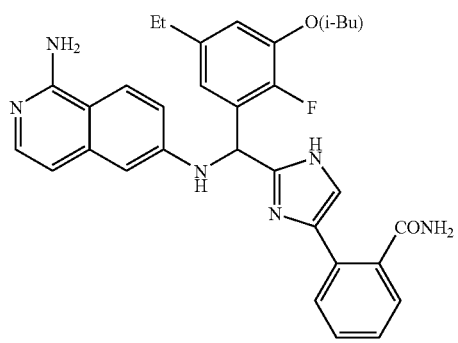

di-tert-butyl (6-{[(4-bromo-1-trityl-1H-imidazole-2-yl)(5-ethyl-2-fluoro-3-isobutoxyphenyl)methyl]amino}isoquinolin-1-yl)imidadicarbonate (282.1)

According to procedure for the preparation of Intermediate 242.1, Intermediate 269.1 (88 mg, 0.1 mmol) and 2-methylpropan-1-ol (14 mg, 0.19 mmol) afforded 70 mg of Intermediate 282.1.

Example 282

According to procedure for the preparation of Example 241, coupling of Intermediate 282.1 with 2-carbamoylphenylboronic acid, followed by deprotection afforded after HPLC purification Example 282. LCMS (4 min gradient, A=95% H$_2$O/5% CH$_3$CN/0.1% TFA, B=5% H$_2$O/95% CH$_3$CN/0.1% TFA) RT=3.86 min, 553.5 (M+H)$^+$; $^1$H NMR (400 MHz, CD$_3$OD) δ ppm 1.04 (d, J=6.59 Hz, 6 H) 1.20 (t, J=7.47 Hz, 3 H) 1.95-2.22 (m, 1 H) 2.63 (q, J=7.76 Hz, 2 H) 3.84 (d, J=6.59 Hz, 2 H) 6.50 (s, 1 H) 6.81 (d, J=3.95 Hz, 1 H) 6.89 (d, J=2.64 Hz, 1 H) 6.99 (d, J=7.03 Hz, 1 H) 7.05 (d, J=7.47 Hz, 1 H) 7.27 (dd, J=9.01, 2.42 Hz, 1 H) 7.38 (d, J=7.03 Hz, 1 H) 7.56-7.64 (m, 4 H) 7.68-7.79 (m, 1 H) 8.20 (d, J=9.23 Hz, 1 H).

Example 283

2-(2-((1-aminoisoquinolin-6-ylamino)(3-(cyclopropylmethoxy)-5-ethyl-2-fluorophenyl)methyl)-1H-imidazol-4-yl)benzamide bis-trifluoroacetic acid salt

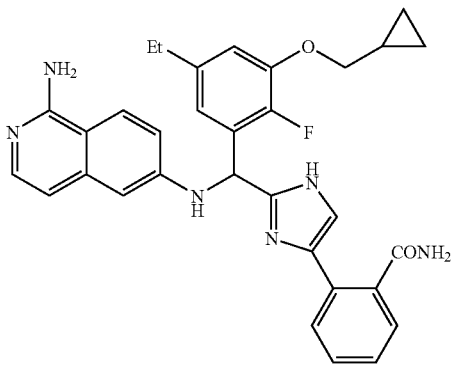

di-tert-butyl (6-{[(4-bromo-1-trityl-1H-imidazole-2-yl)(3-(cyclopropylmethoxy)-5-ethyl-2-fluorophenyl)methyl]amino}isoquinolin-1-yl)imidadicarbonate (283.1)

According to procedure for the preparation of Intermediate 242.1, Intermediate 269.1 (88 mg, 0.1 mmol) and cyclopropylmethanol (14 mg, 0.19 mmol) afforded 110 mg of Intermediate 283.1.

Example 283

According to procedure for the preparation of Example 241, coupling of Intermediate 283.1 with 2-carbamoylphenylboronic acid, followed by deprotection afforded after HPLC purification Example 283. LCMS (4 min gradient, A=95% H$_2$O/5% CH$_3$CN/0.1% TFA, B=5% H$_2$O/95% CH$_3$CN/0.1% TFA) RT=3.14 min, 551.5 (M+H)$^+$; $^1$H NMR (400 MHz, CD$_3$OD) δ ppm 0.27-0.42 (m, 2 H) 0.53-0.68 (m, 2 H) 1.20 (t, J=7.69 Hz, 3 H) 2.62 (q, J=7.76 Hz, 2 H) 3.92 (d, J=7.03 Hz, 2 H) 6.49 (s, 1 H) 6.81 (d, J=4.83 Hz, 1 H) 6.89 (d, J=2.20 Hz, 1 H) 7.00 (d, J=7.03 Hz, 1 H) 7.04 (d, J=7.91 Hz, 1 H) 7.27 (dd, J=9.23, 2.20 Hz, 1 H) 7.38 (d, J=7.03 Hz, 1H) 7.54-7.66 (m, 4 H) 7.69-7.77 (m, 1 H) 8.20 (d, J=9.23 Hz, 1 H).

Example 284

2-(2-((1-aminoisoquinolin-6-ylamino)(5-ethyl-2-fluoro-3-(1-methylpiperidin-4-yloxy)phenyl)methyl)-1H-imidazol-4-yl)benzamide bis-trifluoroacetic acid salt

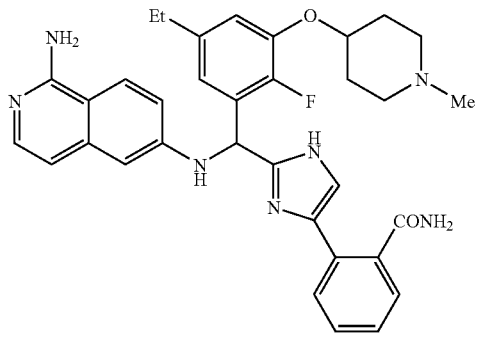

di-tert-butyl (6-{[(4-bromo-1-trityl-1H-imidazole-2-yl)(5-ethyl-2-fluoro-3-(1-methylpiperidin-4-yloxy)phenyl)methyl]amino}isoquinolin-1-yl)imidadicarbonate (284.1)

According to procedure for the preparation of Intermediate 242.1, Intermediate 269.1 (88 mg, 0.1 mmol) and 1-methylpiperidin-4-ol (20 mg, 0.19 mmol) afforded 70 mg of Intermediate 284.1.

Example 284

According to procedure for the preparation of Example 241, coupling of Intermediate 284.1 with 2-carbamoylphenylboronic acid, followed by deprotection afforded after HPLC purification Example 284. LCMS (4 min gradient, A=95% H$_2$O/5% CH$_3$CN/0.1% TFA, B=5% H$_2$O/95% CH$_3$CN/0.1% TFA) RT=2.67 min, 594.5 (M+H)$^+$; $^1$H NMR (400 MHz, CD$_3$OD) δ ppm 1.21 (t, J=7.47 Hz, 3 H) 1.92 (d, J=12.30 Hz, 1 H) 2.02-2.19 (m, 1 H) 2.18-2.31 (m, 1 H) 2.31-2.47 (m, 1 H) 2.64 (q, J=7.76 Hz, 2 H) 2.82-3.00 (m, 3 H) 3.15 (t, J=12.52 Hz, 1 H) 3.26-3.36 (m, 1 H) 3.39-3.51 (m, 1 H) 3.51-3.70 (m, 1 H) 4.48-4.70 (m, 1 H) 6.35-6.61 (m, 1 H) 6.82-6.96 (m, 2 H) 6.99 (d, J=7.03 Hz, 1 H) 7.18 (t, J=7.47 Hz, 1 H) 7.27 (d, J=9.23 Hz, 1 H) 7.39 (d, J=7.03 Hz, 1 H) 7.51-7.66 (m, 4 H) 7.72 (d, J=7.03 Hz, 1 H) 8.20 (d, J=9.23 Hz, 1 H).

Example 285

2-(2-((1-aminoisoquinolin-6-ylamino)(3-(3-(dimethylamino)-2,2-dimethylpropoxy)-5-ethyl-2-fluorophenyl)methyl)-1H-imidazol-4-yl)benzamide bis-trifluoroacetic acid salt

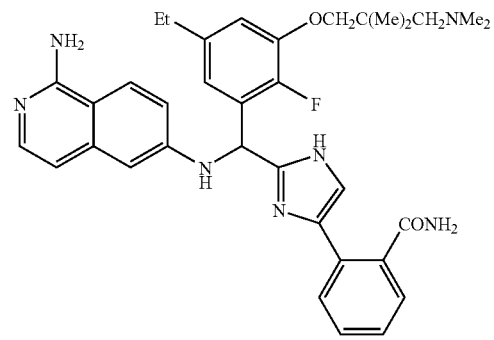

di-tert-butyl (6-{[(4-bromo-1-trityl-1H-imidazole-2-yl)(3-(3-(dimethylamino)-2,2-dimethylpropoxy)-5-ethyl-2-fluorophenyl)methyl]amino}isoquinolin-1-yl)imidadicarbonate (285.1)

According to procedure for the preparation of Intermediate 242.1, Intermediate 269.1 (88 mg, 0.1 mmol) and 3-(dimethylamino)-2,2-dimethylpropan-1-ol (30 mg, 0.19 mmol) afforded 70 mg of Intermediate 285.1.

Example 285

According to procedure for the preparation of Example 241, coupling of Intermediate 285.1 with 2-carbamoylphenylboronic acid, followed by deprotection afforded after HPLC purification Example 285. LCMS (4 min gradient, A=95% H₂O/5% CH₃CN/0.1% TFA, B=5% H₂O/95% CH₃CN/0.1% TFA) RT=3.06 min, 610.6 (M+H)⁺; ¹H NMR (400 MHz, CD₃OD) δ ppm 0.78-1.71 (m, 3 H) 2.64 (q, J=7.47 Hz, 2 H) 2.92-3.08 (m, 6 H) 3.19-3.48 (s, 2 H) 4.01 (s, 2 H) 6.56 (s, 1 H) 6.86-6.94 (m, 2 H) 6.98 (d, J=7.03 Hz, 1 H) 7.12 (d, J=7.47 Hz, 1 H) 7.27 (dd, J=9.23, 2.20 Hz, 1 H) 7.38 (d, J=7.03 Hz, 1 H) 7.52-7.67 (m, 4 H) 7.71 (d, J=5.71 Hz, 1 H) 8.20 (d, J=9.23 Hz, 1 H).

Example 286

N⁶-((3-ethoxy-5-ethyl-2-fluorophenyl)(4-(4-methoxypyridin-3-yl)-1H-imidazol-2-yl)methyl)isoquinoline-1,6-diamine bis-trifluoroacetic acid salt

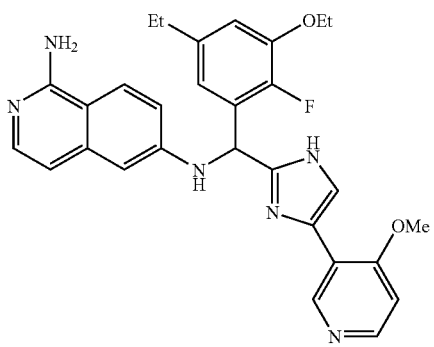

According to procedure for the preparation of Example 241, coupling of Intermediate 276.1 with 4-methoxypyridin-3-ylboronic acid, followed by deprotection afforded after HPLC purification Example 286. LC/MS (2 min gradient) RT=1.36 min, 513.4 (M+H)⁺; ¹H NMR (400 MHz, CD₃OD) δ ppm 1.17 (t, J=7.69 Hz, 3 H) 1.40 (t, J=7.03 Hz, 3 H) 2.58 (q, J=7.62 Hz, 2 H) 4.01 (s, 3 H) 4.12 (q, J=7.03 Hz, 2 H) 6.30 (s, 1 H) 6.73-6.83 (m, 2 H) 6.87 (d, J=7.03 Hz, 1 H) 6.98 (d, J=7.91 Hz, 1 H) 7.23 (dd, J=9.23, 2.20 Hz, 1 H) 7.33 (d, J=7.47 Hz, 1 H) 7.93 (s, 1 H) 8.15 (d, J=9.23 Hz, 1 H) 8.19 (d, J=1.76 Hz, 1 H) 8.33 (d, J=2.64 Hz, 1 H) 8.67 (d, J=1.76 Hz, 1 H).

Example 287

N⁶-((3-ethoxy-5-ethyl-2-fluorophenyl)(4-(5-methoxypyridin-3-yl)-1H-imidazol-2-yl)methyl)isoquinoline-1,6-diamine bis-trifluoroacetic acid salt

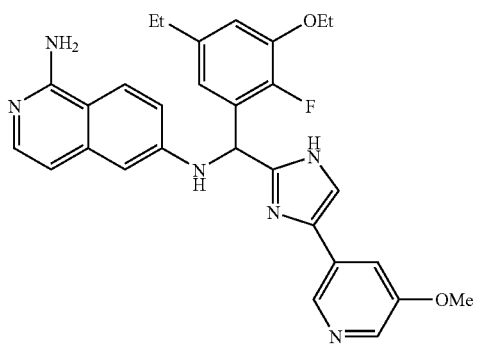

According to procedure for the preparation of Example 241, coupling of Intermediate 276.1 with 5-methoxypyridin-3-ylboronic acid, followed by deprotection afforded after HPLC purification Example 287. LC/MS (2 min gradient) RT=1.27 min, 513.4 (M+H)⁺; ¹H NMR (400 MHz, CD₃OD) δ ppm 1.12 (t, J=7.47 Hz, 3 H) 1.37 (t, J=7.03 Hz, 3 H) 2.54 (q, J=7.76 Hz, 2 H) 4.08 (q, J=7.03 Hz, 2 H) 4.26 (s, 3 H) 6.23 (s, 1 H) 6.66-6.78 (m, 2 H) 6.81 (d, J=7.03 Hz, 1 H) 6.91 (d, J=7.91 Hz, 1 H) 7.20 (dd, J=9.01, 2.42 Hz, 1 H) 7.29 (d, J=7.03 Hz, 1 H) 7.65 (d, J=7.03 Hz, 1 H) 7.83 (s, 1 H) 8.10 (d, J=8.79 Hz, 1 H) 8.56 (d, J=6.59 Hz, 1 H) 9.12 (s, 1 H).

Example 288

N⁶-((3-ethoxy-5-ethyl-2-fluorophenyl)(4-(4-methylpyridin-3-yl)-1H-imidazol-2-yl)methyl)isoquinoline-1,6-diamine bis-trifluoroacetic acid salt

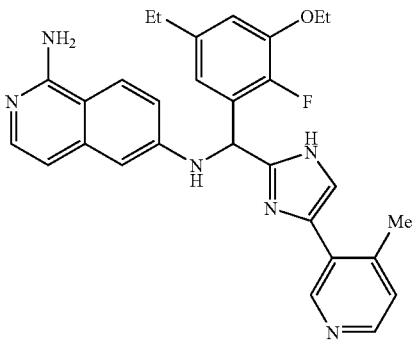

According to procedure for the preparation of Example 241, coupling of Intermediate 276.1 with 4-methylpyridin-3-ylboronic acid, followed by deprotection afforded after HPLC purification Example 288. LC/MS (2 min gradient) RT=1.27 min, 497.4 (M+H)⁺; ¹H NMR (400 MHz, CD₃OD) δ ppm 1.17 (t, J=7.69 Hz, 3 H) 1.40 (t, J=7.03 Hz, 3 H) 2.58 (q, J=7.62 Hz, 2 H) 2.71 (s, 3 H) 4.11 (q, J=6.74 Hz, 2 H) 6.32 (s, 1 H) 6.80 (d, J=2.20 Hz, 1 H) 6.83 (dd, J=5.71, 1.76 Hz, 1 H) 6.87 (d, J=7.03 Hz, 1 H) 6.96 (dd, J=7.69, 1.98 Hz, 1 H) 7.24 (dd, J=9.23, 2.64 Hz, 1 H) 7.33 (d, J=7.03 Hz, 1 H) 7.71 (s, 1 H) 7.88 (d, J=6.15 Hz, 1 H) 8.14 (d, J=9.23 Hz, 1 H) 8.56 (d, J=6.15 Hz, 1 H) 9.02 (s, 1 H).

Example 289

2-(2-((1-aminoisoquinolin-6-ylamino)(5-ethyl-2-fluoro-3-propoxyphenyl)methyl)-1H-imidazol-4-yl)benzamide bis-trifluoroacetic acid salt

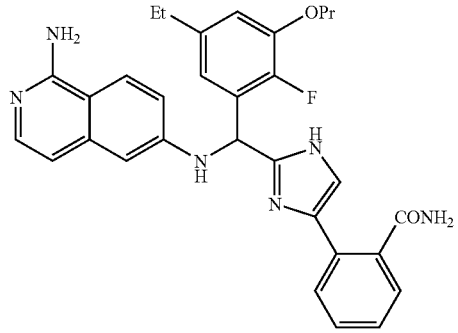

223 di-tert-butyl (6-{[(4-bromo-1-trityl-1H-imidazole-2-yl)(5-ethyl-2-fluoro-3-propoxyphenyl)methyl]amino}isoquinolin-1-yl)imidadicarbonate (289.1)

According to procedure for the preparation of Intermediate 242.1, Intermediate 269.1 (88 mg, 0.1 mmol) and propan-1-ol (11 mg, 0.19 mmol) afforded 70 mg of Intermediate 289.1.

Example 289

According to procedure for the preparation of Example 241, coupling of Intermediate 289.1 with 2-carbamoylphenylboronic acid, followed by deprotection afforded after HPLC purification Example 289. LCMS (4 min gradient, A=95% H$_2$O/5% CH$_3$CN/0.1% TFA, B=5% H$_2$O/95% CH$_3$CN/0.1% TFA) RT=3.16 min, 539.6 (M+H)$^+$; $^1$H NMR (400 MHz, CD$_3$OD) δ ppm 1.04 (t, 3 H) 1.20 (t, J=7.69 Hz, 3 H) 1.81 (q, J=6.59 Hz, 2 H) 2.63 (q, J=7.47 Hz, 2 H) 4.03 (t, J=6.37 Hz, 2 H) 6.46 (s, 1 H) 6.77-6.83 (m, 1 H) 6.88 (d, J=2.20 Hz, 1 H) 6.99 (d, J=7.03 Hz, 1 H) 7.04 (d, J=7.91 Hz, 1 H) 7.26 (dd, J=9.23, 2.20 Hz, 1 H) 7.37 (d, J=7.03 Hz, 1 H) 7.55 (s, 1 H) 7.60 (t, J=4.39 Hz, 3 H) 7.70 (d, J=6.59 Hz, 1 H) 8.19 (d, J=9.23 Hz, 1 H).

Example 290

N$^6$-((3-ethoxy-5-ethyl-2-fluorophenyl)(4-(3-methoxyphenyl)-1H-imidazol-2-yl)methyl)isoquinoline-1,6-diamine bis-trifluoroacetic acid salt

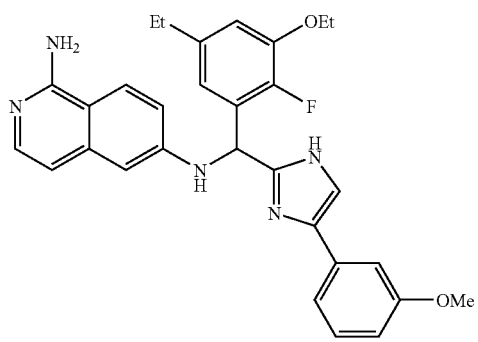

According to procedure for the preparation of Example 241, coupling of Intermediate 276.1 with 3-methoxyphenylboronic acid, followed by deprotection afforded after HPLC purification Example 290. LC/MS (2 min gradient) RT=1.38 min, 512.5 (M+H)$^+$; $^1$H NMR (400 MHz, CD$_3$OD) δ ppm 1.18 (t, J=7.69 Hz, 3 H) 1.40 (t, J=7.03 Hz, 3 H) 2.61 (q, J=7.76 Hz, 2 H) 3.84 (s, 3 H) 4.13 (q, J=7.03 Hz, 1H) 6.42 (s, 1 H) 6.78 (d, J=5.27 Hz, 1 H) 6.85 (s, 1 H) 6.92 (d, J=7.03 Hz, 1 H) 6.97 (d, J=8.35 Hz, 1 H) 7.03 (d, J=7.91 Hz, 1 H) 7.20-7.32 (m, 3 H) 7.33-7.38 (m, 2 H) 7.77 (s, 1 H) 8.18 (d, J=9.23 Hz, 1 H).

224

Example 291

N$^6$-((3-ethoxy-5-ethyl-2-fluorophenyl)(4-(2-(methylthio)phenyl)-1H-imidazol-2-yl)methyl)isoquinoline-1,6-diamine bis-trifluoroacetic acid salt

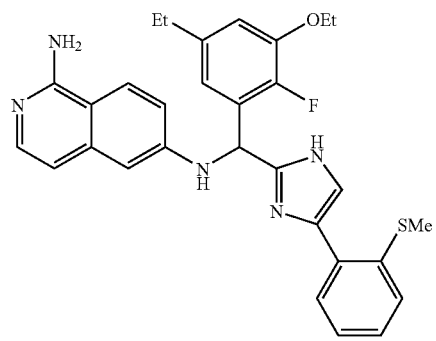

According to procedure for the preparation of Example 241, coupling of Intermediate 276.1 with 2-(methylthio)phenylboronic acid, followed by deprotection afforded after HPLC purification Example 291. LC/MS (2 min gradient) RT=1.35 min, 528.4 (M+H)$^+$; $^1$H NMR (400 MHz, CD$_3$OD) δ ppm 1.20 (t, J=7.47 Hz, 3 H) 1.41 (t, J=7.03 Hz, 3 H) 2.42 (s, 3 H) 2.62 (q, J=7.47 Hz, 1 H) 4.14 (q, J=7.03 Hz, 1 H) 6.39-6.54 (m, 1 H) 6.79 (d, J=5.71 Hz, 1 H) 6.87 (d, J=2.20 Hz, 1 H) 6.93 (d, J=7.03 Hz, 1 H) 7.05 (d, J=7.91 Hz, 1 H) 7.21-7.32 (m, 2 H) 7.36-7.52 (m, 4 H) 7.58-7.67 (m, 1 H) 8.19 (d, J=8.79 Hz, 1 H).

Example 292

2-(2-((1-aminoisoquinolin-6-ylamino)(3-ethoxy-5-ethyl-2-fluorophenyl)methyl)-1H-imidazol-4-yl)phenol bis-trifluoroacetic acid salt

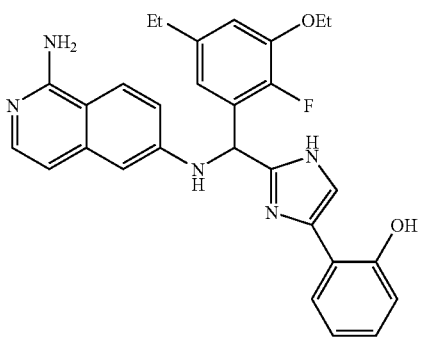

According to procedure for the preparation of Example 241, coupling of Intermediate 276.1 with 2-hydroxylphenylboronic acid, followed by deprotection afforded after HPLC purification Example 292. LC/MS (2 min gradient) RT=1.33 min, 498.4 (M+H)$^+$; $^1$H NMR (400 MHz, CD$_3$OD) δ ppm 1.19 (t, J=7.47 Hz, 3 H) 1.41 (t, J=6.81 Hz, 3 H) 2.61 (q, J=7.47 Hz, 2 H) 4.13 (q, J=7.03 Hz, 2 H) 6.49 (s, 1 H) 6.67-6.81 (m, 1 H) 6.84 (d, J=2.64 Hz, 1 H) 6.88-6.99 (m, 3 H) 7.04 (d, J=7.91 Hz, 1 H) 7.18-7.30 (m, 2 H) 7.36 (d, J=7.03 Hz, 1 H) 7.61 (d, J=7.91 Hz, 1 H) 7.78 (s, 1 H) 8.19 (d, J=9.23 Hz, 1 H).

Example 293

2-(2-((1-aminoisoquinolin-6-ylamino)(3-ethoxy-5-ethyl-2-fluorophenyl)methyl)-1H-imidazol-4-yl)benzoic acid bis-trifluoroacetic acid salt

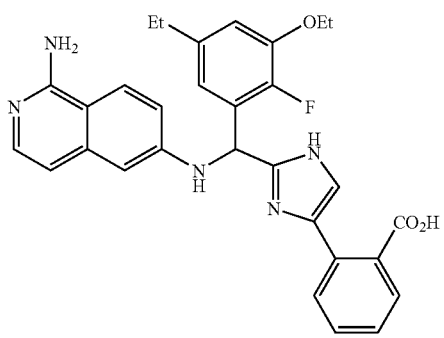

According to procedure for the preparation of Example 241, coupling of Intermediate 276.1 with 2-boronobenzoic acid, followed by deprotection afforded after HPLC purification Example 293. LC/MS (2 min gradient) RT=1.24 min, 526.4 (M+H)$^+$; $^1$H NMR (400 MHz, CD$_3$OD) δ ppm 1.20 (t, J=7.03 Hz, 3 H) 1.40 (t, J=7.03 Hz, 3 H) 2.62 (q, J=7.47 Hz, 2 H) 4.12 (q, J=7.03 Hz, 2 H) 6.41 (d, J=3.52 Hz, 1 H) 6.82 (d, J=3.95 Hz, 1 H) 6.85 (d, J=2.20 Hz, 1 H) 7.00 (d, J=7.03 Hz, 1 H) 7.04 (d, J=7.91 Hz, 1 H) 7.26 (dd, J=9.23, 2.20 Hz, 1 H) 7.37 (d, J=7.03 Hz, 1 H) 7.52 (d, J=2.20 Hz, 1 H) 7.57-7.69 (m, 4 H) 8.01 (d, J=7.03 Hz, 1 H).

Example 294

3-(2-((1-aminoisoquinolin-6-ylamino)(3-ethoxy-5-ethyl-2-fluorophenyl)methyl)-1H-imidazol-4-yl)benzoic acid bis-trifluoroacetic acid salt

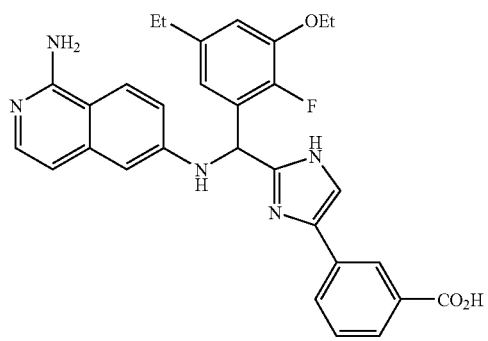

According to procedure for the preparation of Example 241, coupling of Intermediate 276.1 with 3-boronobenzoic acid, followed by deprotection afforded after HPLC purification Example 291. LC/MS (2 min gradient) RT=1.31 min, 526.4 (M+H)$^+$; $^1$H NMR (400 MHz, CD$_3$OD) δ ppm 1.18 (t, J=7.47 Hz, 2 H) 1.40 (t, J=7.03 Hz, 2 H) 2.61 (q, J=7.76 Hz, 2 H) 4.13 (q, J=7.03 Hz, 2 H) 6.34-6.50 (m, 1 H) 6.80 (d, J=5.71 Hz, 1 H) 6.86 (s, 1 H) 6.92 (d, J=7.03 Hz, 1 H) 7.03 (d, J=7.91 Hz, 1 H) 7.25 (d, J=9.23 Hz, 1 H) 7.35 (d, J=7.47 Hz, 1 H) 7.58 (t, J=7.69 Hz, 1 H) 7.74-7.86 (m, 1 H) 7.95 (d, J=7.91 Hz, 1 H) 8.04 (d, J=7.47 Hz, 1 H) 8.18 (d, J=9.23 Hz, 1 H) 8.39 (s, 1 H).

Example 295

3-(2-((1-aminoisoquinolin-6-ylamino)(3-ethoxy-5-ethyl-2-fluorophenyl)methyl)-1H-imidazol-4-yl)benzonitrile bis-trifluoroacetic acid salt

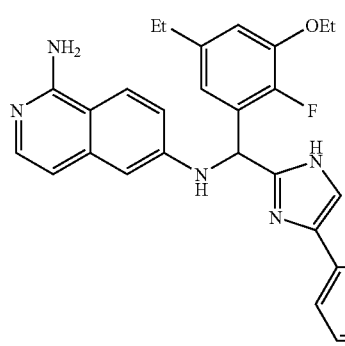

According to procedure for the preparation of Example 241, coupling of Intermediate 276.1 with 3-cyanophenylboronic acid, followed by deprotection afforded after HPLC purification Example 295. LC/MS (2 min gradient) RT=1.37 min, 507.4 (M+H)$^+$; $^1$H NMR (400 MHz, CD$_3$OD) δ ppm 1.17 (t, J=7.69 Hz, 3 H) 1.40 (t, J=7.03 Hz, 3 H) 2.60 (q, J=7.76 Hz, 2 H) 4.12 (q, J=7.03 Hz, 2 H) 6.34 (d, J=2.20 Hz, 1 H) 6.72-6.84 (m, 2 H) 6.89 (d, J=7.03 Hz, 1 H) 7.00 (d, J=7.91 Hz, 1 H) 7.24 (dd, J=9.01, 2.42 Hz, 1 H) 7.34 (d, J=7.03 Hz, 1 H) 7.61 (t, J=7.91 Hz, 1 H) 7.67-7.73 (m, 1 H) 7.67-7.73 (m, 1 H) 7.78 (d, J=3.08 Hz, 1 H) 8.03 (d, J=8.35 Hz, 1 H) 8.12 (s, 1 H) 8.16 (d, J=9.23 Hz, 1 H).

Example 296

Methyl 2-(2-((1-aminoisoquinolin-6-ylamino)(3-ethoxy-5-ethyl-2-fluorophenyl)methyl)-1H-imidazol-4-yl)-6-methylbenzoate bis-trifluoroacetic acid salt

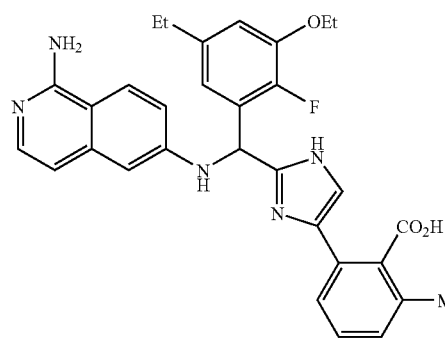

Methyl 2-methyl-6-(4,4,5,5-tetramethyl-1,3,2-dioxaborolan-2-yl)benzoate (296.1)

To a degassed mixture of methyl 2-iodo-6-methylbenzoate (220 mg, 0.9 mmol), 4,4,5,5-tetramethyl-1,3,2-dioxaborolane (0.16 mL, 1.1 mmol), TEA (0.4 mL, 2.7 mmol) in 2 mL dioxane was added Pd(PPh$_3$)$_2$Cl$_2$ (20 mg, 0.03 mmol). The mixture was stirred at 165° C. for 10 min in a microwave oven. The mixture was diluted with EtOAc, washed with sat. NH$_4$C$_1$, H$_2$O and brine, dried over (Na$_2$SO$_4$), filtered and concentrated. The crude product was purified by HPLC to afford 65 mg (35%) of Intermediate 296.1.

Example 296

According to procedure for the preparation of Example 241, coupling of Intermediate 276.1 with Intermediate 296.1, followed by deprotection afforded after HPLC purification Example 296. LC/MS (2 min gradient) RT=1.37 min, 554.4 (M+H)$^+$; $^1$H NMR (400 MHz, CD$_3$OD) δ ppm 1.21 (t, J=7.47 Hz, 3 H) 1.41 (t, J=7.03 Hz, 3 H) 2.37 (s, 3 H) 2.63 (q, J=7.76 Hz, 2 H) 3.70 (s, 3 H) 4.13 (q, J=7.03 Hz, 2 H) 6.49 (s, 1 H) 6.81 (d, J=3.95 Hz, 1 H) 6.88 (d, J=2.20 Hz, 1 H) 6.96 (d, J=7.03 Hz, 1 H) 7.05 (d, J=7.91 Hz, 1 H) 7.27 (dd, J=9.23, 2.20 Hz, 1 H) 7.34-7.41 (m, 2 H) 7.41-7.53 (m, 3 H) 8.20 (d, J=9.23 Hz, 1 H).

Example 297

2-(2-((1-aminoisoquinolin-6-ylamino)(3-ethoxy-5-ethyl-2-fluorophenyl)methyl)-1H-imidazol-4-yl)-6-methylbenzamide bis-trifluoroacetic acid salt

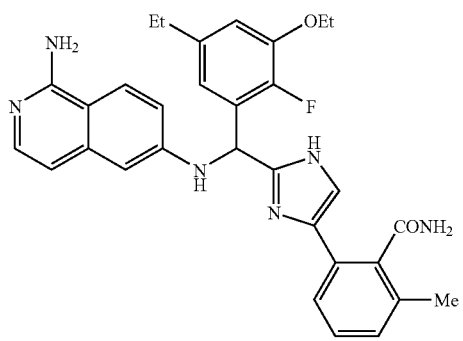

A mixture of Example 296 in 1 mL of 7 N NH$_3$/MeOH was heated at 90° C. for 4 h. The reaction mixture was concentrated and purified with HPLC to afford Example 297. LC/MS (2 min gradient) RT=1.29 min, 539.4 (M+H)$^+$; $^1$H NMR (400 MHz, CD$_3$OD) δ ppm 1.19 (t, J=7.47 Hz, 3 H) 1.41 (t, J=6.81 Hz, 3 H) 2.44 (s, 3 H) 2.62 (q, J=7.76 Hz, 2 H) 4.13 (q, J=7.03 Hz, 2 H) 6.46 (s, 1 H) 6.72-6.81 (m, 1 H) 6.86 (d, J=2.20 Hz, 1 H) 6.94 (d, J=7.03 Hz, 1 H) 7.04 (d, J=7.91 Hz, 1 H) 7.25 (dd, J=9.23, 2.20 Hz, 1 H) 7.34-7.45 (m, 4 H) 7.53 (s, 1 H) 8.19 (d, J=9.23 Hz, 1 H).

Example 298

(3-(2-((1-aminoisoquinolin-6-ylamino)(3-ethoxy-5-ethyl-2-fluorophenyl)methyl)-1H-imidazol-4-yl)phenyl)methanol bis-trifluoroacetic acid salt

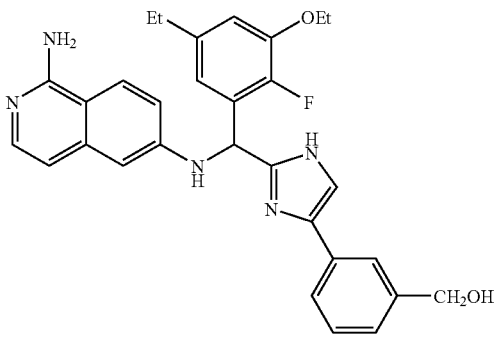

According to procedure for the preparation of Example 241, coupling of Intermediate 276.1 with 3-(hydroxymethyl) phenylboronic acid, followed by deprotection afforded after HPLC purification Example 298. LC/MS (2 min gradient) RT=1.25 min, 512.4 (M+H)$^+$; $^1$H NMR (400 MHz, CD$_3$OD) δ ppm 1.19 (t, J=7.47 Hz, 3 H) 1.41 (t, J=7.03 Hz, 3 H) 2.62 (q, J=7.47 Hz, 2 H) 4.14 (q, 2 H) 4.66 (s, 2 H) 6.46 (s, 1 H) 6.79 (d, J=3.96 Hz, 1 H) 6.88 (d, J=2.64 Hz, 1 H) 6.93 (d, J=7.03 Hz, 1 H) 7.05 (d, J=7.91 Hz, 1 H) 7.27 (dd, J=9.23, 2.20 Hz, 1 H) 7.37 (d, J=7.03 Hz, 1 H) 7.40-7.50 (m, 2 H) 7.62 (d, J=7.47 Hz, 1 H) 7.72 (s, 1 H) 7.81 (s, 1 H) 8.20 (d, J=9.23 Hz, 1 H).

Example 299

Methyl 2-(2-((1-aminoisoquinolin-6-ylamino)(3-ethoxy-5-ethyl-2-fluorophenyl)methyl)-H-imidazol-4-yl)-3-methylbenzoate bis-trifluoroacetic acid salt

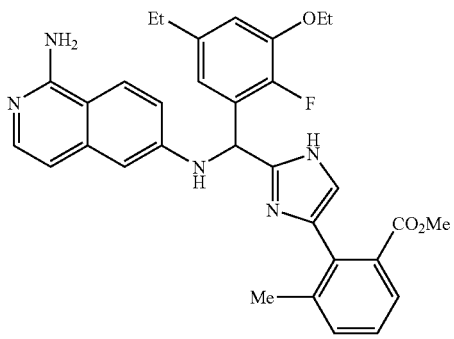

Methyl 2-iodo-3-methylbenzoate (299.1)

To a solution of 2-iodo-3-methylbenzoic acid (500 mg, 0.48 mmol) in benzene/MeOH (2 mL, 10:1) was added TMSCHN$_2$ (1 mL, 2N), the reaction mixture was stirred at rt for 30 min and then concentrated. The crude product was purified by flash chromatography (0 to 10% EtOAc/Hexanes, gradient) to afford 500 mg (91%) of Intermediate 299.1.

3-Methyl-2-(4,4,5,5-tetramethyl-1,3,2-dioxaborolan-2-yl)benzoate (299.2)

According to procedure for the preparation of Intermediate 296.1, Suzuki coupling of Intermediate 299.1 with 4,4,5,5-tetramethyl-1,3,2-dioxaborolane afforded after HPLC purification Intermediate 299.2. LC/MS (2 min gradient) RT=1.77 min, 277.23 (M+H)$^+$.

Example 299

According to procedure for the preparation of Example 241, coupling of Intermediate 276.1 with Intermediate 299.2, followed by deprotection with TFA afforded after HPLC purification Example 299. LC/MS (2 min gradient) RT=1.29 min, 554.3 (M+H)$^+$; $^1$H NMR (400 MHz, CD$_3$OD) δ ppm 1.23 (t, J=7.69 Hz, 3 H) 1.41 (t, J=7.03 Hz, 3 H) 2.65 (q, J=7.47 Hz, 2 H) 3.73 (s, 3 H) 4.13 (q, J=7.03 Hz, 2 H) 6.50 (s, 1 H) 6.83 (d, J=4.39 Hz, 1 H) 6.87 (d, J=2.20 Hz, 1 H) 6.99 (d, J=7.03 Hz, 1 H) 7.07 (d, J=7.91 Hz, 1 H) 7.27 (dd, J=9.23, 2.20 Hz, 1 H) 7.40 (d, J=7.03 Hz, 1 H) 7.45 (s, 1 H) 7.50-7.64 (m, 2 H) 7.91 (d, J=7.91 Hz, 1 H) 8.20 (d, J=8.79 Hz, 1 H).

Example 300

2-(2-((1-aminoisoquinolin-6-ylamino)(3-ethoxy-5-ethyl-2-fluorophenyl)methyl)-1H-imidazol-4-yl)-3-methylbenzamide bis-trifluoroacetic acid salt

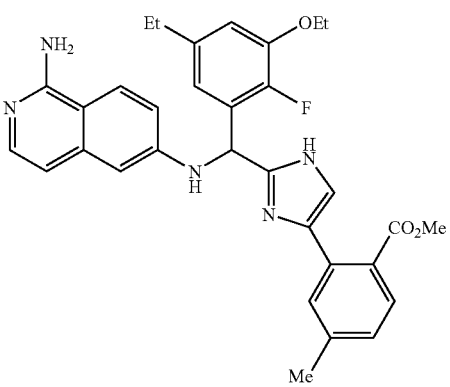

According to procedure for the preparation of Example 297, Example 299 was converted to Example 300. LC/MS (2 min gradient) RT=1.19 min, 539.4 (M+H)$^+$; $^1$H NMR (400 MHz, CD$_3$OD) δ ppm 1.23 (t, J=7.69 Hz, 3 H) 1.43 (t, J=6.81 Hz, 3 H) 2.19 (s, 3 H) 4.16 (q, J=7.03 Hz, 2 H) 6.49 (s, 1 H) 6.81 (d, J=3.96 Hz, 1 H) 6.90 (d, J=2.20 Hz, 1 H) 7.02 (d, J=7.47 Hz, 1 H) 7.08 (d, J=6.15 Hz, 1 H) 7.28 (dd, J=9.23, 2.20 Hz, 1 H) 7.38-7.43 (m, 2 H) 7.49 (d, J=7.03 Hz, 2 H) 7.51-7.57 (m, 1 H) 8.21 (d, J=8.79 Hz, 1 H).

Example 301

2-(2-((1-aminoisoquinolin-6-ylamino)(3-ethoxy-5-ethyl-2-fluorophenyl)methyl)-1H-imidazol-4-yl)-3-methylbenzoic acid bis-trifluoroacetic acid salt

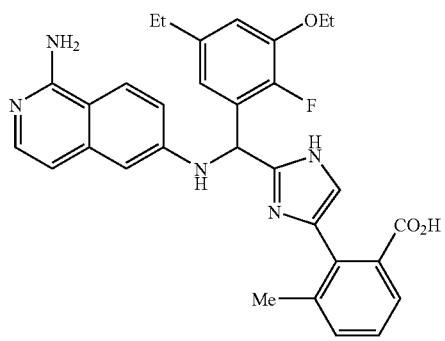

A mixture of Example 299 (20 mg, 0.04 mmol), 2 N LiOH (0.25 mL, 0.5 mmol) in 1 mL MeOH was stirred at rt for 15 h. The reaction mixture was the neutralized to pH ~6 and concentrated. HPLC purification afforded 15 mg Example 301. LCMS (4 min gradient, A=95% H$_2$O/5% CH$_3$CN/0.1% TFA, B=5% H$_2$O/95% CH$_3$CN/0.1% TFA) RT=3.42 min, 540.4 (M+H)$^+$; $^1$H NMR (400 MHz, CD$_3$OD) δ ppm 1.21 (t, J=7.69 Hz, 3 H) 1.41 (t, J=7.03 Hz, 3 H) 2.17 (s, 3 H) 2.64 (q, J=7.47 Hz, 2 H) 4.14 (q, J=7.03 Hz, 2 H) 6.48 (s, 1 H) 6.80 (d, J=4.39 Hz, 1 H) 6.86 (d, J=2.20 Hz, 1 H) 6.99 (d, J=7.47 Hz, 1 H) 7.06 (d, J=7.47 Hz, 1 H) 7.27 (dd, J=9.23, 2.20 Hz, 1 H) 7.35-7.43 (m, 2 H) 7.47-7.62 (m, 2 H) 7.94 (d, J=7.91 Hz, 1 H) 8.19 (d, J=9.23 Hz, 1 H).

Example 302

Methyl 2-(2-((1-aminoisoquinolin-6-ylamino)(3-ethoxy-5-ethyl-2-fluorophenyl)methyl)-1H-imidazol-4-yl)-4-methylbenzoate bis-trifluoroacetic acid salt According to procedure for the preparation of Example 241, coupling of Intermediate 276.1 with methyl 4-methyl-2-(4,4,5,5-tetramethyl-1,3,2-dioxaborolan-2-yl)benzoate, which was prepared from methyl 2-bromo-4-methylbenzoate according to the procedure for the preparation of Intermediate 296.1, followed by deprotection afforded after HPLC purification Example 302. LC/MS (2 min gradient) RT=1.26 min, 554.3 (M+H)+; 1H NMR (400 MHz, CD3OD) δ ppm 1.23 (t, J=7.47 Hz, 3 H) 1.41 (t, J=7.03 Hz, 3 H) 2.43 (s, 3 H) 2.65 (q, J=7.62 Hz, 2 H) 3.74 (s, 3 H) 4.14 (q, J=7.03 Hz, 2 H) 6.45 (s, 1 H) 6.85 (d, J=3.95 Hz, 1 H) 6.88 (d, J=2.20 Hz, 1 H) 7.00 (d, J=7.03 Hz, 1 H) 7.06 (d, J=7.91 Hz, 1 H) 7.21-7.31 (m, 1 H) 7.38 (s, 1 H) 7.45 (d, J=8.35 Hz, 1 H) 7.54 (s, 1 H) 7.89 (d, J=7.91 Hz, 1 H) 8.03 (d, J=7.91 Hz, 1 H) 8.19 (d, J=9.23 Hz, 1 H).

Example 303

2-(2-((1-aminoisoquinolin-6-ylamino)(3-ethoxy-5-ethyl-2-fluorophenyl)methyl)-1H-imidazol-4-yl)-4-methylbenzoic acid bis-trifluoroacetic acid salt

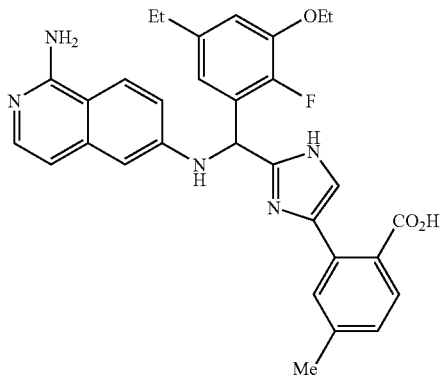

According to procedure for the preparation of Example 297, Example 302 was hydrolyzed to Example 303. HPLC purification afforded Example 301. LCMS (4 min gradient, A=95% H2O/5% CH3CN/0.1% TFA, B=5% H2O/95% CH3CN/0.1% TFA) RT=3.63 min, 540.4 (M+H)+; 1H NMR (400 MHz, CD3OD) δ ppm 1.21 (t, J=7.69 Hz, 3 H) 1.41 (t, J=6.81 Hz, 3 H) 2.43 (s, 3 H) 4.13 (q, J=7.03 Hz, 1 H) 6.44 (s, 1 H) 6.75-6.84 (m, 1 H) 6.86 (d, J=2.20 Hz, 1 H) 6.97-7.11 (m, 2 H) 7.27 (dd, J=9.23, 2.64 Hz, 1 H) 7.35-7.40 (m, 2 H) 7.44 (d, J=7.91 Hz, 1 H) 7.53 (s, 1 H) 8.07 (d, J=7.91 Hz, 1 H) 8.19 (d, J=9.23 Hz, 1 H).

Example 304

2-(2-((1-aminoisoquinolin-6-ylamino)(3-ethoxy-5-ethyl-2-fluorophenyl)methyl)-1H-imidazol-4-yl)-4-methylbenzamide bis-trifluoroacetic acid salt

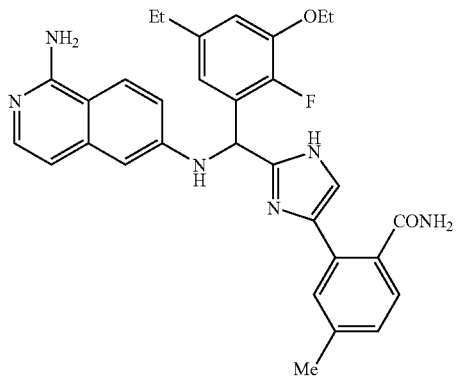

According to procedure for the preparation of Example 297, Example 302 was converted to Example 304. LC/MS (2 min gradient) RT=1.19 min, 539.4 (M+H)+; 1H NMR (400 MHz, CD3OD) δ ppm 1.20 (t, J=7.47 Hz, 3 H) 1.41 (t, J=7.03 Hz, 3 H) 2.42 (s, 3 H) 4.13 (q, J=7.03 Hz, 2 H) 6.43 (s, 1 H) 6.77-6.83 (m, 1 H) 6.86 (d, J=2.20 Hz, 1 H) 6.98 (d, J=7.03 Hz, 1 H) 7.01-7.09 (m, 1 H) 7.25 (dd, J=9.23, 2.64 Hz, 1 H) 7.37 (d, J=7.03 Hz, 2 H) 7.44 (s, 1 H) 7.51 (s, 1 H) 7.59 (d, J=7.91 Hz, 1 H).

Example 305

2-(2-((1-aminoisoquinolin-6-ylamino)(3-ethoxy-5-ethyl-2-fluorophenyl)methyl)-1H-imidazol-4-yl)-6-fluorobenzamide bis-trifluoroacetic acid salt

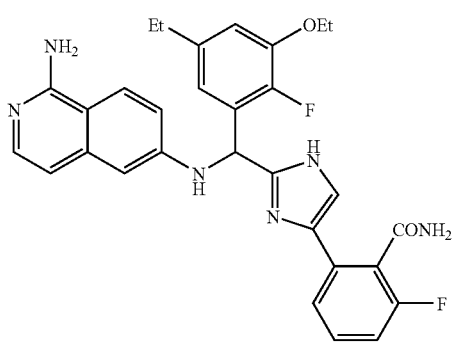

A mixture of Example 225 (4 mg, 0.01 mmol), NH4Cl (3 mg, 0.06 mmol), EDCI (11 mg, 0.06 mmol), HOAt (8.2 mg, 0.06 mmol) NaHCO3 (10 mg, 0.12 mmol) in 2 mL DMF/CH2Cl2 (1:1) was stirred at rt for 3 h. The reaction mixture was then concentrated and purified by HPLC to afford Example 305. LCMS (4 min gradient, A=95% H2O/5% CH3CN/0.1% TFA, B=5% H2O/95% CH3CN/0.1% TFA) RT=3.29 min, 543.3 (M+H)+; 1H NMR (400 MHz, CD3OD) δ ppm 1.19 (t, J=7.69 Hz, 3 H) 1.41 (t, J=6.81 Hz, 3 H) 2.61 (q, J=7.76 Hz, 2 H) 4.11 (q, J=6.81 Hz, 2 H) 6.41 (s, 1 H) 6.74-6.81 (m, 1 H) 6.84 (d, J=2.20 Hz, 1 H) 6.93 (d, J=7.03 Hz, 1 H) 7.03 (s, 1 H) 7.23 (d, J=2.20 Hz, 1 H) 7.26 (d, J=2.20 Hz, 1 H) 7.29 (s, 1 H) 7.36 (d, J=7.03 Hz, 1 H) 7.45-7.50 (m, 2 H) 7.55 (s, 1 H).

Example 306

2-(2-((1-aminoisoquinolin-6-ylamino)(3-ethoxy-5-ethyl-2-fluorophenyl)methyl)-1H-imidazol-4-yl)-5-chlorobenzamide bis-trifluoroacetic acid salt

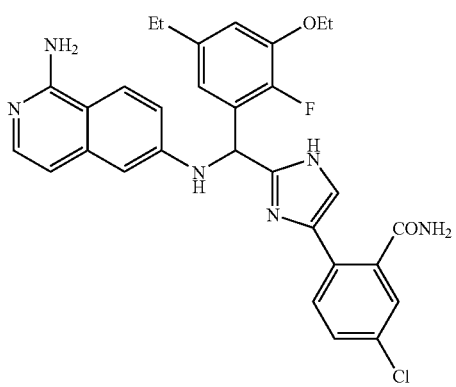

According to procedure for the preparation of Example 305, Example 224 was converted to Example 306. LCMS (4 min gradient, A=95% H2O/5% CH3CN/0.1% TFA, B=5%

H₂O/95% CH₃CN/0.1% TFA) RT=3.17 min, 559.4 (M+H)⁺; ¹H NMR (400 MHz, CD₃OD) δ ppm 1.20 (t, J=7.69 Hz, 3 H) 1.40 (t, J=7.03 Hz, 3 H) 2.62 (q, J=7.62 Hz, 2 H) 4.13 (q, J=6.88 Hz, 2 H) 6.45 (s, 1 H) 6.76-6.84 (m, 1 H) 6.87 (d, J=2.20 Hz, 1 H) 6.97 (d, J=7.03 Hz, 1 H) 7.01-7.07 (m, 1 H) 7.26 (dd, J=9.01, 2.42 Hz, 1 H) 7.37 (d, J=7.03 Hz, 1 H) 7.53-7.58 (m, 1 H) 7.59 (s, 1 H) 7.66 (d, J=8.35 Hz, 1 H) 7.69 (d, J=2.20 Hz, 1 H) 8.18 (d, J=9.23 Hz, 1 H).

Example 307

3-(2-((1-aminoisoquinolin-6-ylamino)(3-ethoxy-5-ethyl-2-fluorophenyl)methyl)-1H-imidazol-4-yl)-N-(2-hydroxyethyl)benzamide bis-trifluoroacetic acid salt

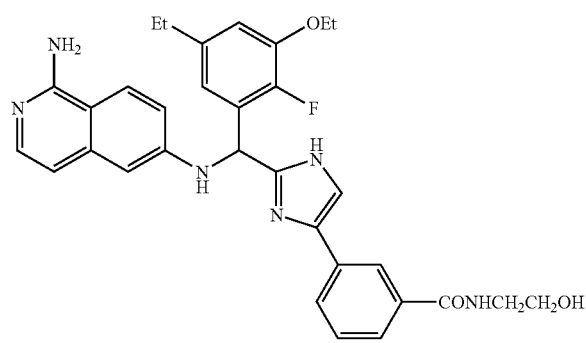

A mixture of Example 293 (10 mg, 0.02 mmol), 2-aminoethanol (10 uL, 0.1 mmol), BOP (11 mg, 0.025 mmol), TEA (0.05 mL) in 1 mL DMF was stirred at rt for 1 h. The reaction mixture was diluted with MeOH and purified by HPLC to afford Example 307. LC/MS (4 min gradient) RT=2.17 min, 569.4 (M+H)⁺; ¹H NMR (400 MHz, CD₃OD) δ ppm 1.16 (t, J=7.47 Hz, 3 H) 1.34 (t, J=7.03 Hz, 3 H) 2.47 (q, J=7.76 Hz, 2 H) 3.37 (t, J=5.71 Hz, 2 H) 3.57 (t, J=5.71 Hz, 2 H) 3.99 (q, J=7.03 Hz, 2 H) 6.28 (s, 1 H) 6.66 (d, J=5.71 Hz, 1 H) 6.72 (s, 1 H) 6.78 (d, J=7.03 Hz, 1 H) 6.89 (d, J=7.91 Hz, 1 H) 7.12 (dd, J=9.23, 2.20 Hz, 1 H) 7.22 (d, J=7.03 Hz, 1 H) 7.43 (t, J=7.91 Hz, 1 H) 7.62-7.70 (m, 1 H) 7.69-7.79 (m, 1 H) 8.00-8.13 (m, 2 H).

Example 308

N⁶-((3-ethoxy-5-ethyl-2-fluorophenyl)(4-phenyl-1H-imidazol-2-yl)methyl)isoquinoline-1,6-diamine bis-trifluoroacetic acid salt

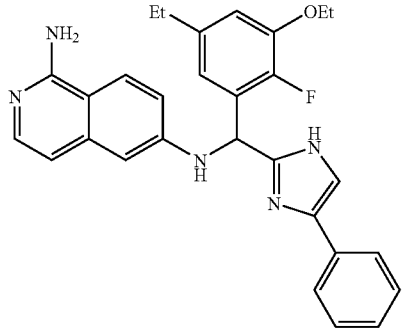

According to the procedure for the preparation of Example 206, coupling of Intermediate 213.2 and phenylboronic acid, followed by deprotection and HPLC purification afforded Example 308. LCMS (4 min gradient) RT=2.12 min, 482.2 (M+H)⁺.

Example 309

(2-(2-((1-aminoisoquinolin-6-ylamino)(3-ethoxy-5-ethyl-2-fluorophenyl)methyl)-1H-imidazol-4-yl)phenyl)methanol bis-trifluoroacetic acid salt

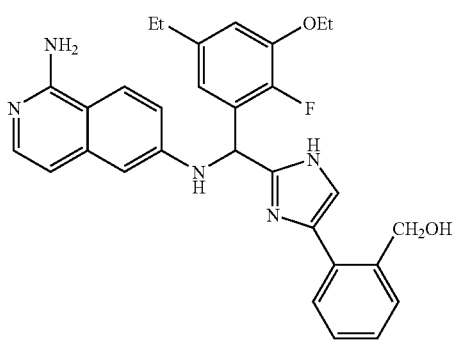

According to the procedure for the preparation of Example 206, coupling of Intermediate 213.2 and 2-(hydroxymethyl)phenylboronic acid, followed by deprotection and HPLC purification afforded Example 309. LCMS (4 min gradient) RT=1.96 min, 512.3 (M+H)⁺, 534.2 (M+H)⁺.

Example 310

1-(2-(2-((1-aminoisoquinolin-6-ylamino)(3-ethoxy-5-ethyl-2-fluorophenyl)methyl)-1H-imidazol-4-yl)phenyl)ethanone bis-trifluoroacetic acid salt

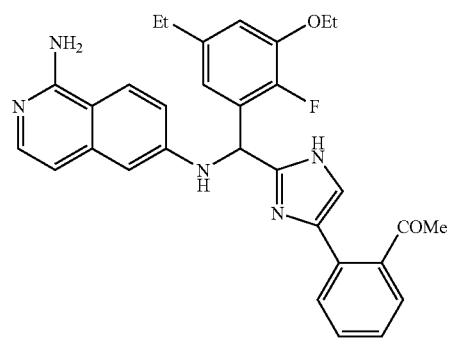

According to the procedure for the preparation of Example 206, coupling of Intermediate 213.2 and 2-acetylphenylboronic acid, followed by deprotection and HPLC purification afforded Example 310. LCMS (4 min gradient) RT=2.04 min, 524.1 (M+H)⁺, 546.1 (M+H)⁺.

Example 327

4-(2-((1-aminoisoquinolin-6-ylamino)(3-ethoxy-5-ethyl-2-fluorophenyl)methyl)-1H-imidazol-4-yl)phenol bis-trifluoroacetic acid salt

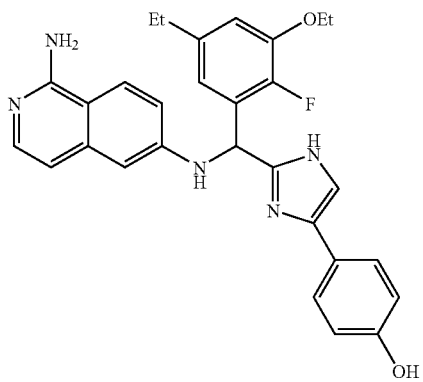

According to the procedure for the preparation of Example 206, coupling of Intermediate 213.2 and 4-hydroxyphenylboronic acid, followed by deprotection and HPLC purification afforded Example 327. LCMS (4 min gradient) RT=2.50 min, 498.51 (M+H)$^+$.

Example 328

$N^6$-((3-ethoxy-5-ethyl-2-fluorophenyl)(4-(furan-3-yl)-1H-imidazol-2-yl)methyl)isoquinoline-1,6-diamine bis-trifluoroacetic acid salt

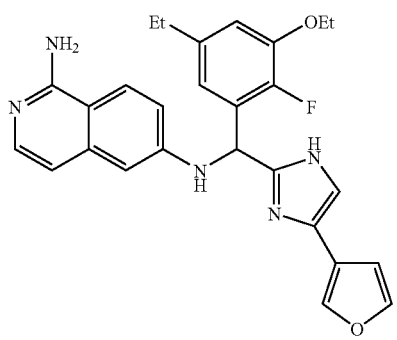

According to the procedure for the preparation of Example 206, coupling of Intermediate 213.2 and 3-furanboronic acid, followed by deprotection and HPLC purification afforded Example 328. LCMS (4 min gradient) RT=2.51 min, 472.54 (M+H)$^+$.

Example 329

$N^6$-((3-ethoxy-5-ethyl-2-fluorophenyl)(4-m-tolyl-1H-imidazol-2-yl)methyl)isoquinoline-1,6-diamine bis-trifluoroacetic acid salt

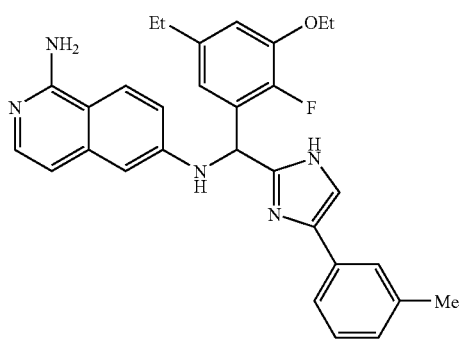

According to the procedure for the preparation of Example 206, coupling of Intermediate 213.2 and m-tolylboronic acid, followed by deprotection and HPLC purification afforded Example 329. LCMS (4 min gradient) RT=2.86 min, 496.60 (M+H)$^+$.

Example 330

$N^6$-((3-ethoxy-5-ethyl-2-fluorophenyl)(4-o-tolyl-1H-imidazol-2-yl)methyl)isoquinoline-1,6-diamine bis-trifluoroacetic acid salt

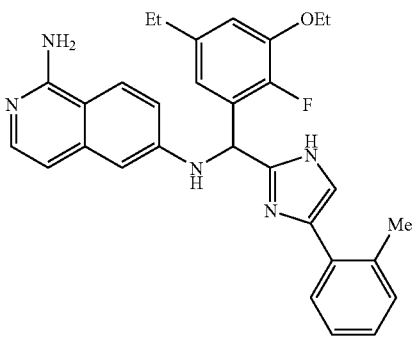

According to the procedure for the preparation of Example 206, coupling of Intermediate 213.2 and o-tolylboronic acid, followed by deprotection and HPLC purification afforded Example 330. LCMS (4 min gradient) RT=2.67 min, 496.57 (M+H)$^+$.

Example 331

N6-((3-ethoxy-5-ethyl-2-fluorophenyl)(4-(2-methoxyphenyl)-1H-imidazol-2-yl)methyl)isoquinoline-1,6-diamine bis-trifluoroacetic acid salt

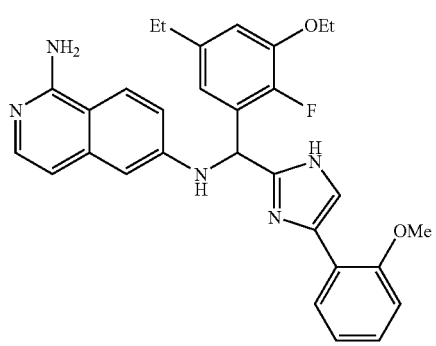

According to the procedure for the preparation of Example 206, coupling of Intermediate 213.2 and 2-methoxyphenylboronic acid, followed by deprotection and HPLC purification afforded Example 331. LCMS (4 min gradient) RT=2.74 min, 512.59 (M+H)+.

Example 333

N6-((3-ethoxy-5-ethyl-2-fluorophenyl)(4-(5-methylfuran-2-yl)-1H-imidazol-2-yl)methyl)isoquinoline-1,6-diamine bis-trifluoroacetic acid salt

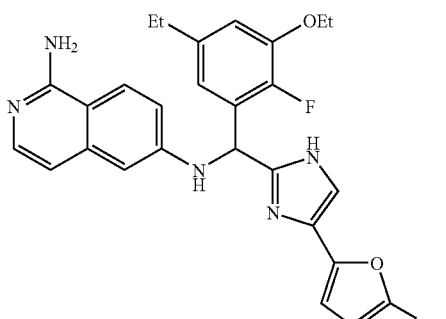

According to the procedure for the preparation of Example 206, coupling of Intermediate 213.2 and 5-methylfuran-2-ylboronic acid, followed by deprotection and HPLC purification afforded Example 333. LCMS (4 min gradient) RT=486.45 min, (M+H)+.

Example 334

N6-((3-ethoxy-5-ethyl-2-fluorophenyl)(4-(pyridin-3-yl)-1H-imidazol-2-yl)methyl)isoquinoline-1,6-diamine bis-trifluoroacetic acid salt

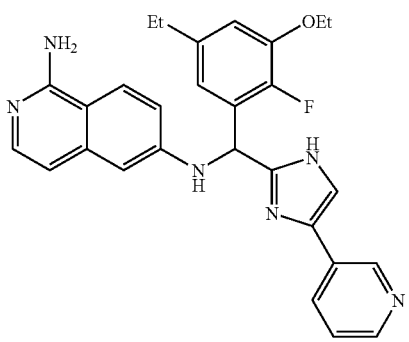

According to the procedure for the preparation of Example 206, coupling of Intermediate 213.2 and pyridin-3-ylboronic acid, followed by deprotection and HPLC purification afforded Example 334. LCMS (4 min gradient) RT=2.34 min, 483.60(M+H)+.

Examples 311-326 and 335-357

General Structure

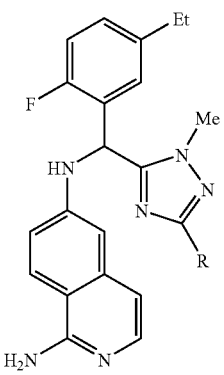

3,5-dibromo-1-methyl-H-1,2,4-triazole (311.1)

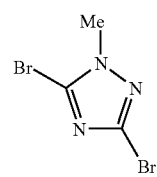

To a solution of 3,5-dibromo-1H-1,2,4-triazole (3.68 g, 16.2 mmol) in 50 mL DMF cooded to 0° C. was added NaH (778 mg, 19.5 mmol in a 60% oil dispersion) and stirred 30 min. Iodomethane (2 mL, 32.4 mmol) was added dropwise and the reaction was stirred 18 h at rt. The mixture was diluted

5-ethyl-2-fluorobenzaldehyde (311.2)

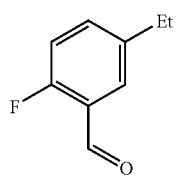

To a solution of 1-ethyl-4-fluorobenzene (10 g, 80.6 mmol) and PMDTA (17 mL) in THF (60 mL) cooled to −78° C. was added 1.6 M n-butyl lithium (56 mL, 89 mmol) dropwise and the mixture stirred for 40 min at −60° C. Mixture cooled to −78° C. and added DMF (16 mL, 202 mmol) before allowing the mixture to warm to 23° C. Quenched with aqueous NH$_4$Cl and extracted with EtOAc (3×50 mL). Organic layer was washed with H$_2$O and brine before concentrating to afford 11.6 g of Intermediate 311.2. $^1$H-NMR (CDCl$_3$)=1.18 (t, 3 H), δ 2.58 (q, 2 H), δ 7.04 (t, 1 H), δ 7.35 (m, 1 H), δ 7.62 (m, 1 H), δ 10.31 (s, 1 H).

(5-bromo-2-methyl-2H-1,2,4-triazol-3-yl)(5-ethyl-2-fluorophenyl)methanol (311.3)

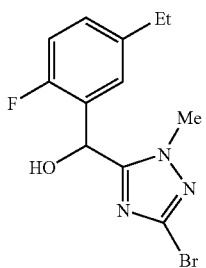

To a solution of Intermediate 311.1 (11.6 g, 48.2 mmol) in THF (200 mL) cooled to −78° C. was added n-BuLi (1.6 M in Hexane, 30 mL, 48.2 mmol) dropwise and stirred 30 min before adding Intermediate 311.2 (6.1 g, 40.1 mmol) in THF (20 mL) dropwise. Solution was stirred 1 h before warming to 23° C. and quenching with aqueous NH$_4$Cl. Extracted with EtOAc (3×50 mL), washed with H$_2$O, brine, dried (Na$_2$SO$_4$) and concentrated. The crude product was purified by flash chromatography (0 to 100% EtOAc/hexanes gradient) to afford 10 g of Intermediate 311.3. LCMS (2 min gradient) RT=1.58 min, 315.18 (M+H)$^+$.

di-tert-butyl 6-((5-bromo-2-methyl-2H-1,2,4-triazol-3-yl)(5-ethyl-2-fluorophenyl) methylamino)isoquinolin-1-ylcarbamate (311.4)

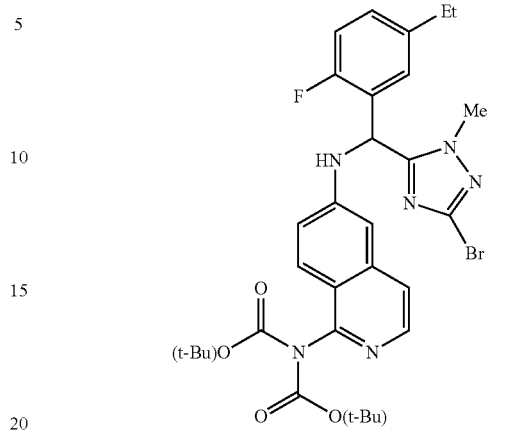

To a solution of Intermediate 311.3 (4.5 g, 14.3 mmol) and N-ethyl-N-isopropylpropan-2-amine (5.0 mL, 28.7 mmol) in CH$_3$CN (30 mL) at −15° C. was added methanesulfonic anhydride (4 g, 23 mmol). Mixture was stirred for 1 h as the temperature was raised to 23° C. 1-(di-(tert-butyloxycarbonyl)amino)-6-aminoisoquinoline (10.3 g, 28.7 mmol) was added as a solid and the mixture stirred 18 h at 23° C. Mixture was concentrated and purified by flash chromatography (0 to 60% EtOAc/hexanes gradient) to afford 5 g of Intermediate 311.4. $^1$H NMR (400 MHz, CDCl$_3$) δ ppm 1.09 (t, 3 H) 1.3(s, 18 H) 2.53 (q, 2 H) 3.86 (s, 3 H) 6.13 (d, 1 H) 6.70 (s, 1 H) 7.05 (m, 1 H) 7.08 (m, 1 H) 7.25 (d, 1 H) 7.35 (d, 1 H) 7.72 (d, 1 H) 8.21 (d, 1 H).

General procedure: A mixture of Intermediate 311.4 (600 uL of 957 mg, 1.45 mmol in 14.6 mL DME solution, 0.06 mmol), K$_2$CO$_3$ (250 uL of a 478 mg, 3.46 mmol in 7.21 mL H$_2$O solution, 0.12 mmol), polystyrene supported tetrakistriphenylphosphine palladium (27 mg, 0.003 mmol), and a boronic acid (0.12 mmol) was heated at 180° C. for 20 min. in a PC microwave and purified by preparative HPLC purification to afford Examples 311-326 and 335-357.

Example 311

N$^6$-((5-(4-chlorophenyl)-2-methyl-2H-1,2,4-triazol-3-yl)(5-ethyl-2-fluorophenyl)methyl)isoquinoline-1,6-diamine trifluoroacetic acid salt

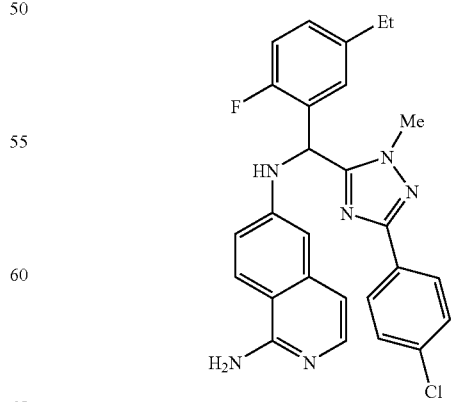

LCMS (4 min gradient) RT=3.53 min, 487.50 (M+H)$^+$.

Example 312

N[6]-((5-ethyl-2-fluorophenyl)(2-methyl-5-p-tolyl-2H-1,2,4-triazol-3-yl)methyl) isoquinoline-1,6-diamine trifluoroacetic acid salt

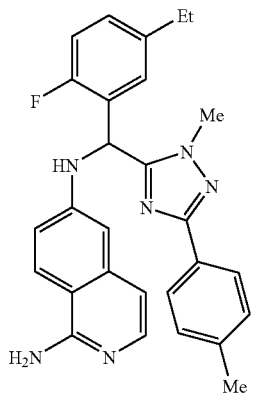

LCMS (4 min gradient) RT=3.39 min, 467.57 (M+H)[+].

Example 313

N[6]-((5-ethyl-2-fluorophenyl)(5-(4-methoxyphenyl)-2-methyl-2H-1,2,4-triazol-3-yl)methyl)isoquinoline-1,6-diamine trifluoroacetic acid salt

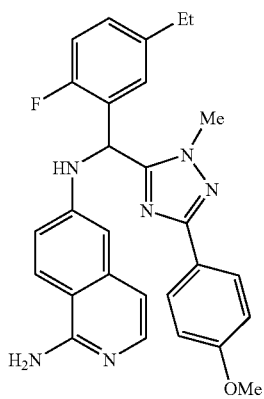

LCMS (4 min gradient) RT=3.25 min, 483.54 (M+H)[+].

Example 314

N[6]-((5-ethyl-2-fluorophenyl)(2-methyl-5-m-tolyl-2H-1,2,4-triazol-3-yl)methyl) isoquinoline-1,6-diamine trifluoroacetic acid salt

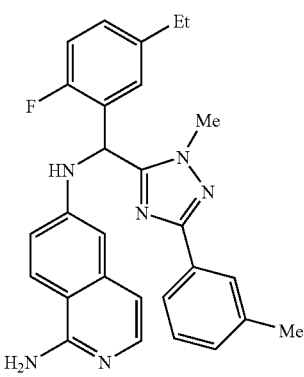

LCMS (4 min gradient) RT=3.41 min, 467.54 (M+H)[+].

Example 315

N[6]-((5-ethyl-2-fluorophenyl)(2-methyl-5-o-tolyl-2H-1,2,4-triazol-3-yl)methyl) isoquinoline-1,6-diamine trifluoroacetic acid salt

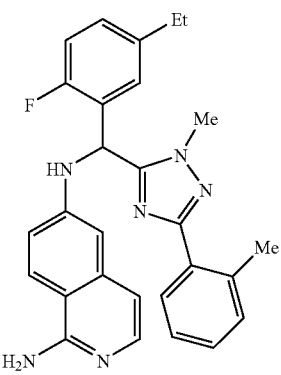

LCMS (4 min gradient) RT=3.33 min, 467.57 (M+H)[+].

Example 316

N[6]-((5-ethyl-2-fluorophenyl)(2-methyl-5-o-biphenyl-2H-1,2,4-triazol-3-yl) methyl) isoquinoline-1,6-diamine trifluoroacetic acid salt

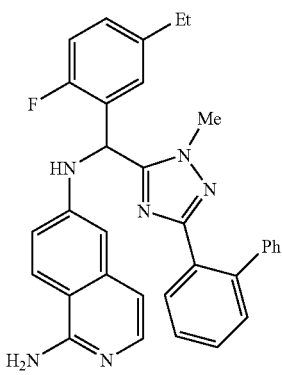

LCMS (4 min gradient) RT=3.41 min, 529.55 (M+H)[+].

Example 317

N[6]-((5-ethyl-2-fluorophenyl)(2-methyl-5-(3-(trifluoromethyl)phenyl)-2H-1,2,4-triazol-3-yl)methyl)isoquinoline-1,6-diamine trifluoroacetic acid salt

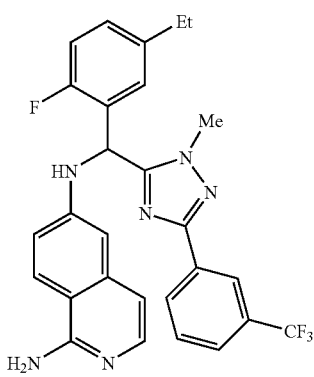

LCMS (4 min gradient) RT=3.57 min, 521.51 (M+H)[+].

Example 318

N[6]-((5-ethyl-2-fluorophenyl)(5-(3-methoxyphenyl)-2-methyl-2H-1,2,4-triazol-3-yl)methyl)isoquinoline-1,6-diamine trifluoroacetic acid salt

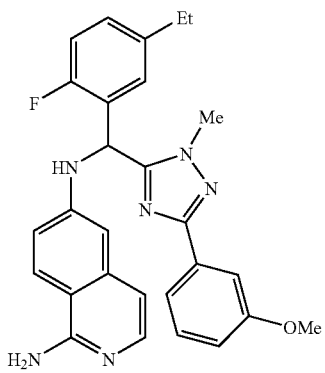

LCMS (4 min gradient) RT=3.28 min, 483.54 (M+H)[+].

Example 319

N-(3-(5-((1-aminoisoquinolin-6-ylamino)(5-ethyl-2-fluorophenyl)methyl)-1-methyl-1H-1,2,4-triazol-3-yl)phenyl)acetamide trifluoroacetic acid salt

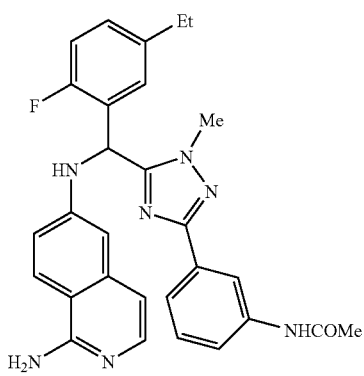

LCMS (4 min gradient) RT=2.99 min, 510.54 (M+H)[+].

Example 320

N[6]-((5-ethyl-2-fluorophenyl)(5-(2-methoxyphenyl)-2-methyl-2H-1,2,4-triazol-3-yl)methyl)isoquinoline-1,6-diamine trifluoroacetic acid salt

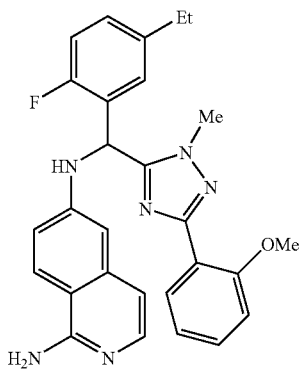

LCMS (4 min gradient) RT=3.09 min, 483.54 (M+H)[+].

Example 321

N[6]-((5-ethyl-2-fluorophenyl)(2-methyl-5-(2-(trifluoromethyl)phenyl)-2H-1,2,4-triazol-3-yl)methyl)isoquinoline-1,6-diamine trifluoroacetic acid salt

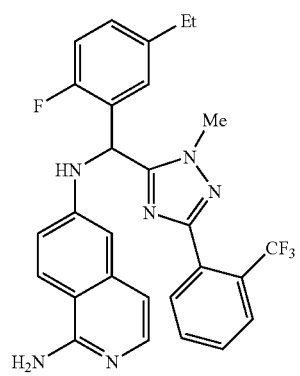

LCMS (4 min gradient) RT=3.22 min, 521.53 (M+H)[+].

Example 322

N[6]-((5-ethyl-2-fluorophenyl)(2-methyl-5-(pyridin-3-yl)-2H-1,2,4-triazol-3-yl)methyl)isoquinoline-1,6-diamine trifluoroacetic acid salt

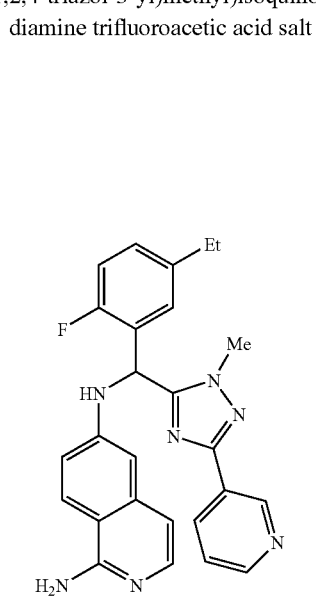

LCMS (4 min gradient) RT=2.43 min, 454.60 (M+H)[+].

Example 323

3-(5-((1-aminoisoquinolin-6-ylamino)(5-ethyl-2-fluorophenyl)methyl)-1-methyl-1H-1,2,4-triazol-3-yl)phenol trifluoroacetic acid salt

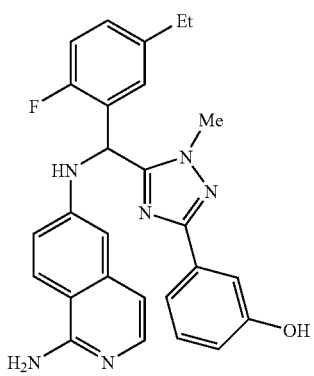

LCMS (4 min gradient) RT=2.96 min, 496.54 (M+H)[+].

Example 324

N[6]-((5-(4-(dimethylamino)phenyl)-2-methyl-2H-1,2,4-triazol-3-yl)(5-ethyl-2-fluorophenyl)methyl)isoquinoline-1,6-diamine bis-trifluoroacetic acid salt

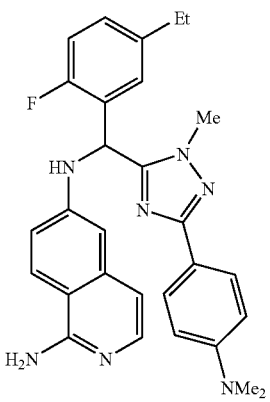

LCMS (4 min gradient) RT=2.75 min, 496.57 (M+H)+.

Example 325

1-(3-(5-((1-aminoisoquinolin-6-ylamino)(5-ethyl-2-fluorophenyl)methyl)-1-methyl-1H-1,2,4-triazol-3-yl)phenyl)ethanone trifluoroacetic acid salt

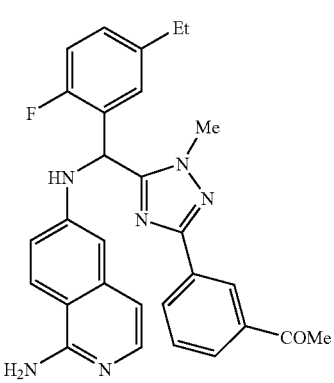

LCMS (4 min gradient) RT=3.17 min, 495.48 (M+H)+.

Example 326

1-(2-(5-((1-aminoisoquinolin-6-ylamino)(5-ethyl-2-fluorophenyl)methyl)-1-methyl-1H-1,2,4-triazol-3-yl)phenyl)ethanone trifluoroacetic acid salt

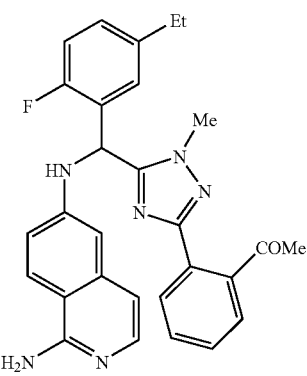

LCMS (4 min gradient) RT=3.03 min, 495.54 (M+H)+.

Example 335

N[6]-((5-ethyl-2-fluorophenyl)(2-methyl-5-phenyl-2H-1,2,4-triazol-3-yl)methyl) isoquinoline-1,6-diamine trifluoroacetic acid salt

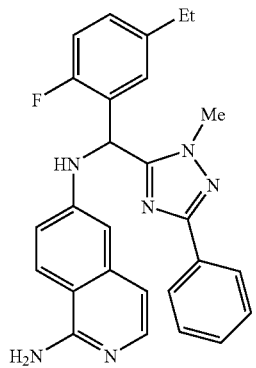

LCMS (4 min gradient) RT=1.79 min, 453.35 (M+H)+.

Example 336

N[6]-((5-ethyl-2-fluorophenyl)(2-methyl-5-(thiophen-3-yl)-2H-1,2,4-triazol-3-yl)methyl)isoquinoline-1,6-diamine trifluoroacetic acid salt

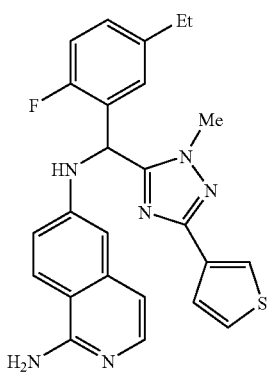

LCMS (4 min gradient) RT=3.17 min, 459.23 (M+H)$^+$.

Example 337

N[6]-((5-(3-chlorophenyl)-2-methyl-2H-1,2,4-triazol-3-yl)(5-ethyl-2-fluorophenyl) methyl)isoquinoline-1,6-diamine trifluoroacetic acid salt

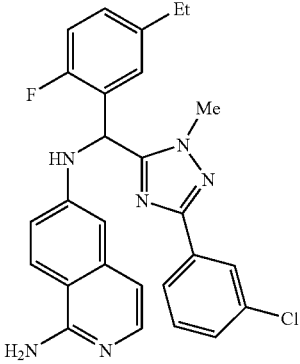

LCMS (4 min gradient) RT=3.32 min, 487.29 (M+H)$^+$.

Example 338

N[6]-((5-(2-chlorophenyl)-2-methyl-2H-1,2,4-triazol-3-yl)(5-ethyl-2-fluorophenyl) methyl)isoquinoline-1,6-diamine trifluoroacetic acid salt

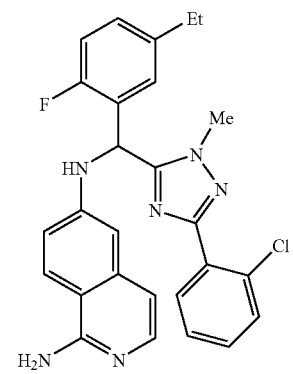

LCMS (4 min gradient) RT=3.23 min, 487.25 (M+H)$^+$.

Example 339

N[6]-((5-(2,4-dichlorophenyl)-2-methyl-2H-1,2,4-triazol-3-yl)(5-ethyl-2-fluorophenyl)methyl)isoquinoline-1,6-diamine trifluoroacetic acid salt

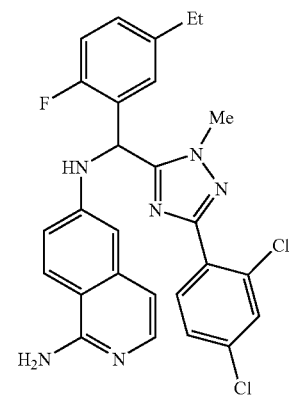

LCMS (4 min gradient) RT=3.56 min, 521.21 (M+H)$^+$.

Example 340

N[6]-((5-(2,4-dichlorophenyl)-2-methyl-2H-1,2,4-triazol-3-yl)(5-ethyl-2-fluorophenyl)methyl)isoquinoline-1,6-diamine trifluoroacetic acid salt

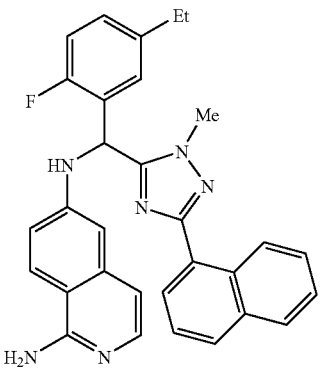

LCMS (4 min gradient) RT=3.47 min, 503.30 (M+H)+.

Example 341

N[6]-((5-ethyl-2-fluorophenyl)(5-(4-fluorophenyl)-2-methyl-2H-1,2,4-triazol-3-yl)methyl)isoquinoline-1,6-diamine trifluoroacetic acid salt

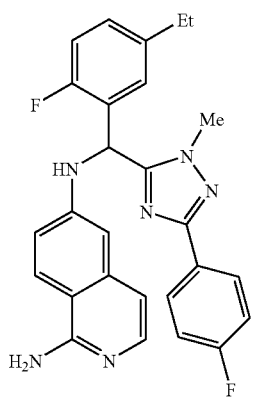

LCMS (4 min gradient) RT=3.37 min, 471.27 (M+H)+.

Example 343

N[6]-((5-ethyl-2-fluorophenyl)(5-(3-fluorophenyl)-2-methyl-2H-1,2,4-triazol-3-yl)methyl)isoquinoline-1,6-diamine trifluoroacetic acid salt

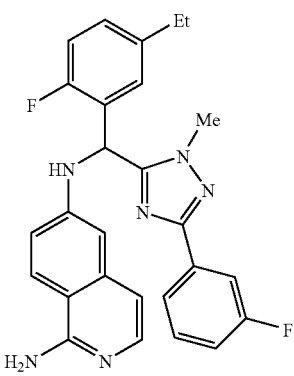

LCMS (4 min gradient) RT=3.39 min, 471.29 (M+H)+.

Example 344

N[6]-((5-(2-chlorophenyl)-2-methyl-2H-1,2,4-triazol-3-yl)(5-ethyl-2-fluorophenyl) methyl)isoquinoline-1,6-diamine trifluoroacetic acid salt

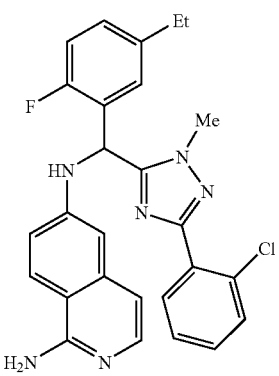

LCMS (4 min gradient) RT=3.23 min, 487.25 (M+H)+.

Example 345

N$^6$-((5-ethyl-2-fluorophenyl)(5-(2-fluorophenyl)-2-methyl-2H-1,2,4-triazol-3-yl)methyl)isoquinoline-1,6-diamine trifluoroacetic acid slt

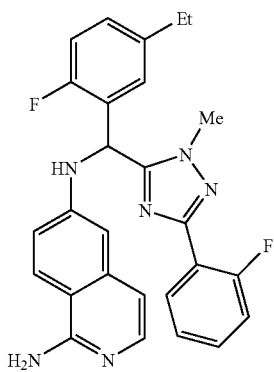

LCMS (4 min gradient) RT=3.19 min, 471.26 (M+H)$^+$

Example 346

N$^6$-((5-(benzo[d][1,3]dioxol-5-yl)-2-methyl-2H-1,2,4-triazol-3-yl)(5-ethyl-2-fluorophenyl)methyl)isoquinoline-1,6-diamine trifluoroacetic acid salt

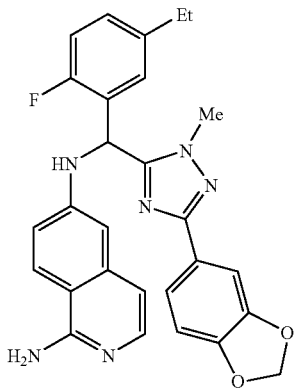

LCMS (4 min gradient) RT=3.28 min, 497.27 (M+H)$^+$.

Example 347

N$^6$-((5-ethyl-2-fluorophenyl)(2-methyl-5-(pyridin-4-yl)-2H-1,2,4-triazol-3-yl)methyl) isoquinoline-1,6-diamine trifluoroacetic acid salt

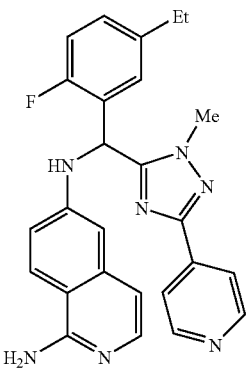

LCMS (4 min gradient) RT=2.34 min, 454.29 (M+H)$^+$.

Example 348

2-(5-((1-aminoisoquinolin-6-ylamino)(5-ethyl-2-fluorophenyl)methyl)-1-methyl-1H-1,2,4-triazol-3-yl)phenol trifluoroacetic acid salt

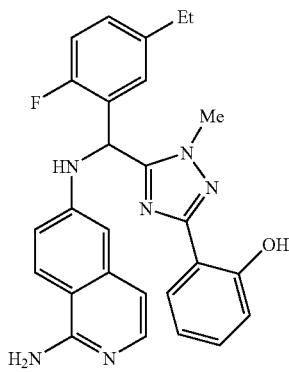

LCMS (4 min gradient) RT=3.35 min, 469.29 (M+H)$^+$.

Example 349

N6-((5-(2,3-dichlorophenyl)-2-methyl-2H-1,2,4-triazol-3-yl)(5-ethyl-2-fluorophenyl) methyl)isoquinoline-1,6-diamine trifluoroacetic acid salt

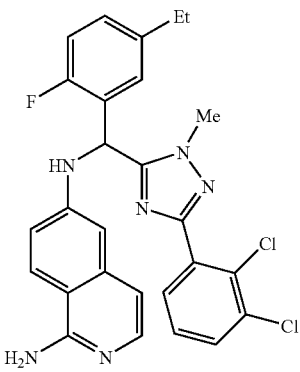

LCMS (4 min gradient) RT=3.45 min, 521.21 (M+H)$^+$.

Example 350

N6-((5-ethyl-2-fluorophenyl)(2-methyl-5-(2-(methylthio)phenyl)-2H-1,2,4-triazol-3-yl)methyl)isoquinoline-1,6-diamine trifluoroacetic acid salt

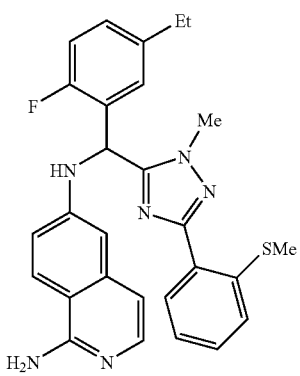

LCMS (4 min gradient) RT=3.21 min, 499.25 (M+H)$^+$.

Example 351

3-(5-((1-aminoisoquinolin-6-ylamino)(5-ethyl-2-fluorophenyl)methyl)-1-methyl-1H-1,2,4-triazol-3-yl)benzonitrile trifluoroacetic acid salt

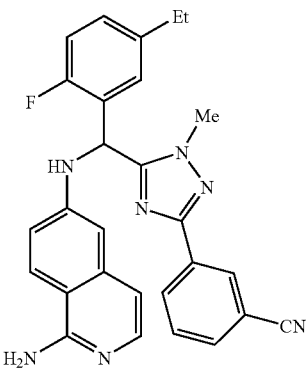

LCMS (4 min gradient) RT=3.23 min, 478.29 (M+H)$^+$.

Example 352

N6-((5-ethyl-2-fluorophenyl)(5-(furan-3-yl)-2-methyl-2H-1,2,4-triazol-3-yl)methyl) isoquinoline-1,6-diamine trifluoroacetic acid salt

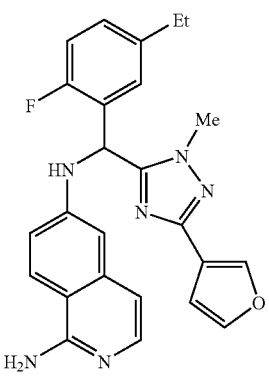

LCMS (4 min gradient) RT=3.00 min, 443.29 (M+H)$^+$.

Example 353

N-(2-(5-((1-aminoisoquinolin-6-ylamino)(5-ethyl-2-fluorophenyl)methyl)-1-methyl-1H-1,2,4-triazol-3-yl)phenyl)methanesulfonamide trifluoroacetic acid salt

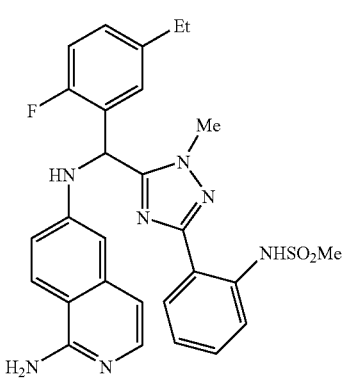

LCMS (4 min gradient) RT=3.18 min, 546.28 (M+H)$^+$.

Example 354

N-(2-(5-((1-aminoisoquinolin-6-ylamino)(5-ethyl-2-fluorophenyl)methyl)-1-methyl-1H-1,2,4-triazol-3-yl)phenyl)acetamide trifluoroacetic acid salt

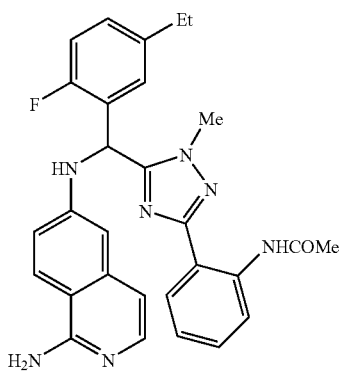

LCMS (4 min gradient) RT=3.21 min, 510.32 (M+H)$^+$.

Example 355

N$^6$-((5-ethyl-2-fluorophenyl)(2-methyl-5-(pyrimidin-5-yl)-2H-1,2,4-triazol-3-yl)methyl) isoquinoline-1,6-diamine bis-trifluoroacetic acid salt

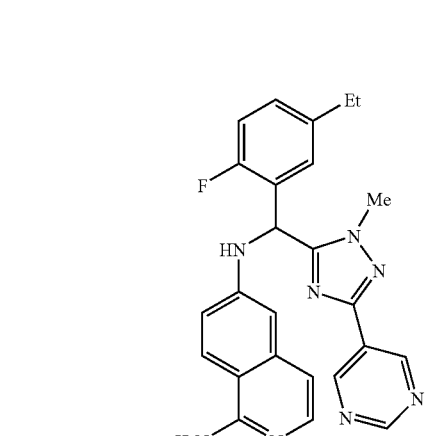

LCMS (4 min gradient) RT=2.83 min, 455.17 (M+H)$^+$.

Example 356

N$^6$-((5-(3-((dimethylamino)methyl)phenyl)-2-methyl-2H-1,2,4-triazol-3-yl)(5-ethyl-2-fluorophenyl)methyl)isoquinoline-1,6-diamine bis-trifluoroacetic acid salt

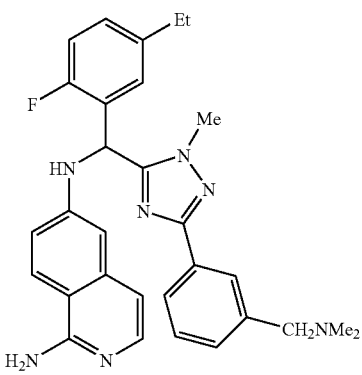

LCMS (4 min gradient) RT=2.52 min, 510.32 (M+H)$^+$.

Example 357

N⁶-((5-(5-chloro-2-methoxyphenyl)-2-methyl-2H-1,2,4-triazol-3-yl)(5-ethyl-2-fluorophenyl)methyl)isoquinoline-1,6-diamine trifluoroacetic acid salt

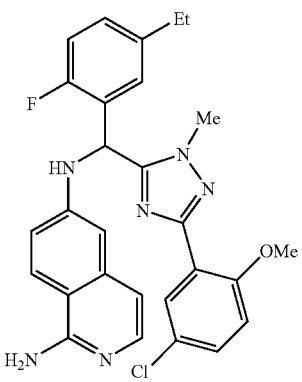

LCMS (4 min gradient) RT=3.41 min, 517.26 (M+H)⁺.

Example 358

4-((5-ethoxy-2-fluoro-3-isopropoxyphenyl)(2-methyl-2H-1,2,4-triazol-3-yl)methylamino)benzamidine trifluoroacetic acid salt

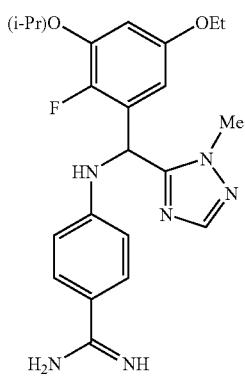

To a solution of 5-bromo-1-methyl-1H-1,2,4-triazole (100 mg, 0.40 mmol) in THF (4 mL) was added BuLi (1.6 M in Hexane, 0.26 mL, 0.4 mmol). The mixture was stirred at −78° C. for 15 min, then a solution of Intermediate 7.3 (100 mg, 0.31 mmol) in THF (2 mL) was added dropwise. The mixture was stirred at −78° C. for 30 min, before warming to 23° C., and quenching with aqueous NH₄Cl. The mixture was diluted with EtOAc, washed with H₂O and brine, dried (Na₂SO₄) and concentrated. The crude product was purified by flash chromatography (0 to 100% EtOAc/hexanes gradient). The material was then dissolved in 2 mL 3 M NH₂OH in DMSO and was converted to the amide oxime, acylated and hydrogenated as in Example 1 to afford 45 mg of Example 358. LCMS (2 min gradient) RT=1.42 min, 427.22 (M+H)⁺; ¹H NMR (400 MHz, CDCl₃) δ ppm 1.21 (t, J=6.81 Hz, 3H) 1.26 (d, J=4.83 Hz, 6H) 3.75 (q, J=7.03 Hz, 2H) 3.88 (s, 3H) 4.36-4.45 (m, 1H) 6.11 (s, 1H) 6.29-6.35 (m, 1H) 6.39 (dd, J=7.03, 2.64 Hz, 1H) 6.64 (d, J=8.35 Hz, 2H) 7.22 (s, 2H) 7.48 (d, J=8.35 Hz, 2H) 7.87 (s, 1H) 9.74 (s, 2H).

Example 359

2-(5-((4-carbamimidoylphenylamino)(5-ethoxy-2-fluoro-3-isopropoxyphenyl)methyl)-1H-1,2,4-triazol-3-yl)benzamide trifluoroacetic acid salt

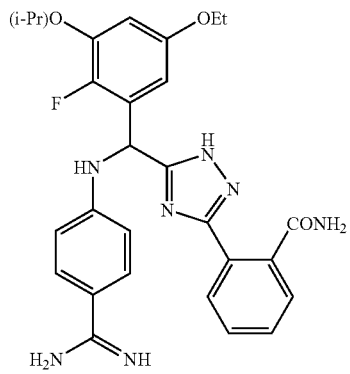

3,5-dibromo-1-trityl-1H-1,2,4-triazole (359.1)

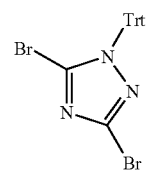

Trityl chloride (6.8 g, 24 mmol) was added to a solution of 3,5-dibromo-1H-1,2,4-triazole (5 g, 22 mmol) and triethylamine (3.4 mL, 24.2 mmol) in DMF (100 mL) and stirred 16 h. The mixture was poured into rapidly stirred water (300 mL). The white precipitate was collected, washed with hexanes and dried on high vacuum to yield 10.2 g of Intermediate 359.1 as a white solid. ¹H NMR (400 MHz, CDCl₃) δ ppm 7.09-7.17 (m, 6H) 7.28-7.35 (m, 9H).

4-((5-bromo-2-trityl-2H-1,2,4-triazol-3-yl)(5-ethoxy-2-fluoro-3-isopropoxyphenyl)methylamino)benzonitrile (359.2)

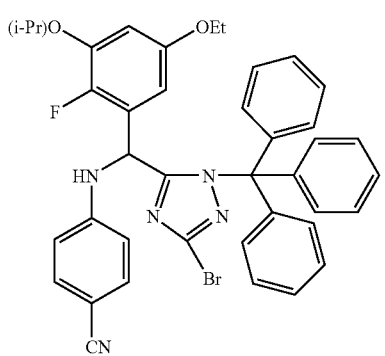

To a solution of Intermediate 359.1 (748 mg, 1.6 mmol) in THF (10 mL) was added BuLi (1.6 M in THF, 1.02 mL, 1.6 mmol). The mixture was stirred at −78° C. for 15 min, then a solution of Intermediate 7.3 (500 mg, 1.53 mmol) in THF (5 mL) was added dropwise. The mixture was stirred at −78° C. for 30 min, before warming to 23° C., and quenching with aqueous NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) followed by preparative HPLC purification to afford 320 mg of Intermediate 359.2. LCMS (2 min gradient) RT=2.45 min, 717.2 (M+H)$^+$; $^1$H NMR (400 MHz, MeOD) δ ppm 1.25-1.33 (m, 9H) 3.93 (q, 2H) 4.41 (m, 1H) 6.15 (d, 2H) 6.52 (m, 1H) 6.82 (m, 1H) 7.03-7.21 (m, 18H).

2-(5-((4-cyanophenylamino)(5-ethoxy-2-fluoro-3-isopropoxyphenyl)methyl)-1-trityl-1H-1,2,4-triazol-3-yl)benzamide. (359.3)

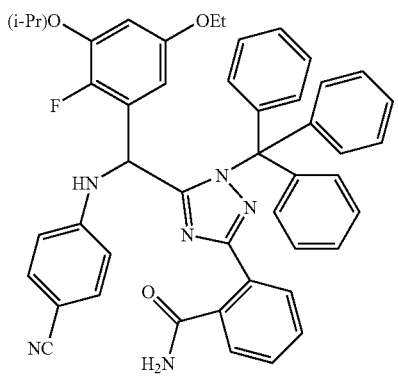

A degassed mixture of Intermediate 359.2 (50 mg, 0.07 mmol), 2-carbamoyl phenyl boronic acid (23 mg, 0.14 mmol), tri-tert-butylphosphine palladium (14.2 mg, 0.028 mmol) and K$_3$PO$_4$ (45 mg, 0.21 mmol) in 2 mL 1,4-dioxane was heated at 110° C. for 20 min with a PC microwave. Diluted with DCM (10 mL) filtered, washed with brine, dried (Na$_2$SO$_4$), concentrated and purified by flash chromatography (0 to 100% Hexane/EtOAc gradient) to afford 92 mg of Intermediate 359.3. LCMS (2 min gradient) RT=2.23 min, 756.3 (M+H)$^+$.

Example 359

Intermediate 359.3 was then dissolved in 2 mL 3 M NH$_2$OH in DMSO and was converted to the amide oxime, acylated and hydrogenated as in Example 1. The resulting material was dissolved in MeOH (2 mL) and stirred with 3 drops of TFA for 30 min prior to purification on preparative HPLC to afford 1.9 mg of Example 359. LCMS (2 min gradient) RT=1.47 min, 532.15 (M+H)$^+$; $^1$H NMR (400 MHz, MeOD) δ ppm 1.28-1.35 (m, 9H) 3.89-3.98 (m, 2H) 4.51-4.64 (m, 1H) 6.16 (s, 1H) 6.55-6.63 (m, 2H) 6.81 (d, J=9.23 Hz, 2H) 7.55-7.63 (m, 4H) 7.65-7.69 (m, 1H) 7.73-7.79 (m, 1H).

Example 360

4-((5-ethoxy-2-fluoro-3-isopropoxyphenyl)(5-(2-(methylthio)phenyl)-2H-1,2,4-triazol-3-yl)methylamino)benzamidine trifluoroacetic acid salt

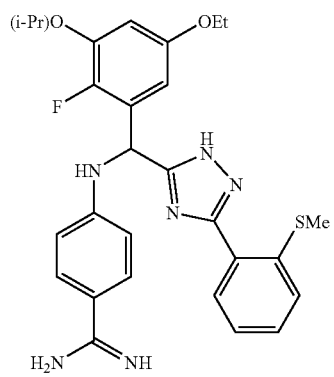

4-((5-ethoxy-2-fluoro-3-isopropoxyphenyl)(5-(2-(methylthio)phenyl)-2-trityl-2H-1,2,4-triazol-3-yl)methylamino)benzonitrile (360.1)

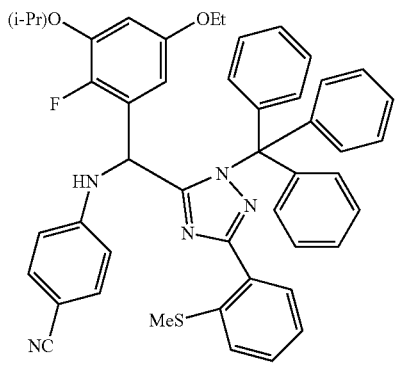

A degassed mixture of Intermediate 359.1 (50 mg, 0.07 mmol), 2-(methylthio) phenylboronic acid (61 mg, 0.363 mmol), tri-tert-butylphosphine palladium (14.2 mg, 0.028 mmol) and K$_3$PO$_4$ (45 mg, 0.21 mmol) in 2 mL 1,4-dioxane was heated at 110° C. for 20 min with a PC microwave. The mixture was diluted with DCM (10 mL) filtered, washed with brine, dried (Na$_2$SO$_4$), concentrated and purified by flash chromatography (0 to 100% Hexane/EtOAc gradient) to afford 70 mg of Intermediate 360.1 LCMS (2 min gradient) RT=2.69 min, 759.3 (M+H)$^+$.

Example 360

Intermediate 360.1 dissolved in 2 mL 3 M NH$_2$OH in DMSO was converted to the amide oxime, acylated and hydrogenated as in Example 1. The resulting material was dissolved in MeOH (2 mL) and stirred with 3 drops of TFA for 30 min prior to purification on preparative HPLC to afford Example 360. LCMS (2 min gradient) RT=1.69 min, 535.28 (M+H)$^+$; $^1$H NMR (400 MHz, MeOD) δ ppm 1.30-1.35 (m, 9H) 2.43 (s, 3H) 3.91-3.99 (m, 2H) 4.52-4.63 (m, 1H) 6.20 (s, 1H) 6.56-6.65 (m, 2H) 6.83 (d, J=8.79 Hz, 2H) 7.27 (t, J=7.25

Hz, 1H) 7.42-7.50 (m, 2H) 7.54 (d, J=7.91 Hz, 1H) 7.62 (d, J=8.79 Hz, 2H) 8.26 (s, 1H) 8.78 (s, 1H).

Example 361

4-((5-ethoxy-2-fluoro-3-isopropoxyphenyl)(5-(2-methoxyphenyl)-2H-1,2,4-triazol-3-yl)methylamino)benzamidine trifluoroacetic acid salt

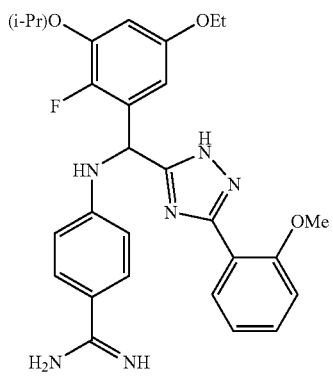

4-((5-ethoxy-2-fluoro-3-isopropoxyphenyl)(5-(2-methoxyphenyl)-2-trityl-2H-1,2,4-triazol-3-yl)methylamino)benzonitrile (361.1)

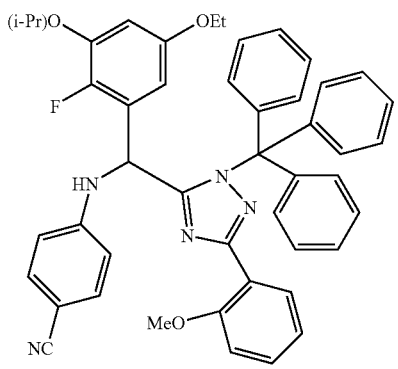

A degassed mixture of intermediate 359.1 (50 mg, 0.07 mmol), 2-methoxyphenyl boronic acid (55 mg, 0.363 mmol), tri-tert-butylphosphine palladium (14.2 mg, 0.028 mmol) and $K_3PO_4$ (45 mg, 0.21 mmol) in 2 mL 1,4-dioxane was heated at 110° C. for 20 min with a PC microwave. The mixture was diluted with DCM (10 mL) filtered, washed with brine, dried ($Na_2SO_4$), concentrated and purified by flash chromatography (0 to 100% Hexane/EtOAc gradient) to afford 123 mg of Intermediate 361.1. LCMS (2 min gradient) RT=2.60 min, 743.4 (M+H)+.

Example 361

Intermediate 361.1 dissolved in 2 mL 3 M $NH_2OH$ in DMSO was converted to the amide oxime, acylated and hydrogenated as in Example 1. The resulting material was dissolved in MeOH (2 mL) and stirred with 3 drops of TFA for 30 min prior to purification on preparative HPLC to afford 31 mg of Example 361. LCMS (2 min gradient) RT=1.74 min, 519.31 (M+H)+; $^1$H NMR (400 MHz, $CDCl_3$) δ ppm 1.21-1.30 (m, 9H) 3.78-3.87 (m, 2H) 3.94 (s, 3H) 4.37-4.45 (m, 1H) 6.17 (s, 1H) 6.41 (dd, J=6.72, 2.81 Hz, 1H) 6.48 (dd, J=4.65, 2.93 Hz, 1H) 6.64 (d, J=8.56 Hz, 2H) 6.88 (s, 2H) 7.00 (d, J=8.56 Hz, 1H) 7.06 (t, J=7.70 Hz, 1H) 7.34 (d, J=8.56 Hz, 2H) 7.41-7.50 (m, 1H) 8.08 (dd, J=7.83, 1.47 Hz, 1H) 9.15 (s, 2H).

Example 362

4-((5-ethoxy-2-fluoro-3-isopropoxyphenyl)(5-(2-fluorophenyl)-2H-1,2,4-triazol-3-yl)methylamino)benzamidine trifluoroacetic acid salt

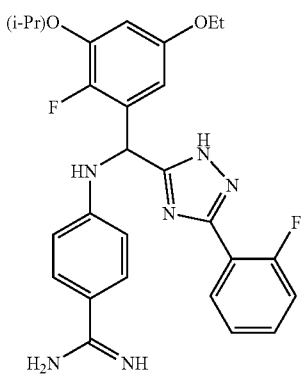

4-((5-ethoxy-2-fluoro-3-isopropoxyphenyl)(5-(2-fluorophenyl)-2-trityl-2H-1,2,4-triazol-3-yl)methylamino)benzonitrile 362.1

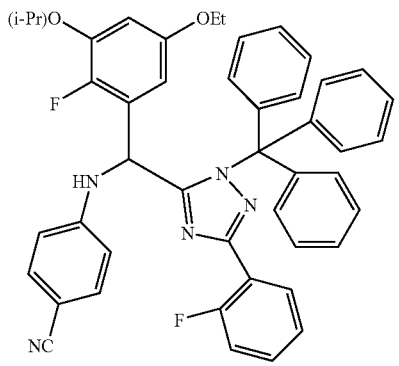

A degassed mixture of intermediate 359.1 (50 mg, 0.07 mmol), 2-fluorophenylboronic acid (51 mg, 0.363 mmol), tri-tert-butylphosphine palladium (14.2 mg, 0.028 mmol) and $K_3PO_4$ (45 mg, 0.21 mmol) in 2 mL 1,4-dioxane was heated at 110° C. for 20 min with a PC microwave. The mixture was diluted with DCM (10 mL) filtered, washed with brine, dried ($Na_2SO_4$), concentrated and purified by flash chromatography (0 to 100% Hexane/EtOAc gradient) to afford 113 mg of Intermediate 362.1. LCMS (2 min gradient) RT=2.64 min, 731.4 (M+H)+.

Example 362

Intermediate 362.1 dissolved in 2 mL 3 M $NH_2OH$ in DMSO was converted to the amide oxime, acylated and hydrogenated as in Example 1. The resulting material was dissolved in MeOH (2 mL) and stirred with 3 drops of TFA for 30 min prior to purification on preparative HPLC to afford 61 mg of Example 362. LCMS (2 min gradient) RT=1.67 min, 507.29 (M+H)+; $^1$H NMR (400 MHz, MeOD) δ ppm 1.30-1.37 (m, 9H) 3.92 (q, J=6.85 Hz, 2H) 4.50-4.63 (m, 1H) 6.20 (s, 1H) 6.57 (dd, J=6.72, 2.81 Hz, 1H) 6.64 (dd, J=4.89, 2.93 Hz, 1H) 6.84 (d, J=8.80 Hz, 2H) 7.25-7.35 (m, 2H) 7.48-7.56 (m, 1H) 7.62 (d, J=8.56 Hz, 2H) 7.99-8.06 (m, 1H).

Example 363

4-((5-ethoxy-2-fluoro-3-isopropoxyphenyl)(5-(2-fluorophenyl)-2-methyl-2H-1,2,4-triazol-3-yl)methylamino)benzamidine trifluoroacetic acid salt

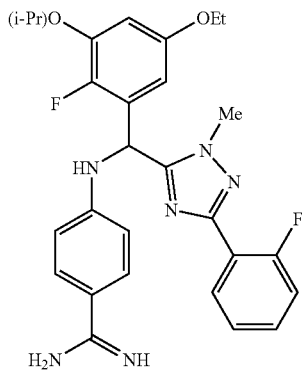

4-((5-bromo-2-methyl-2H-1,2,4-triazol-3-yl)(5-ethoxy-2-fluoro-3-isopropoxyphenyl) methylamino) benzonitrile (363.1)

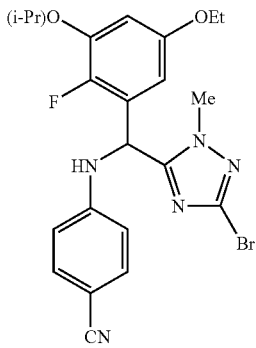

To a solution of Intermediate 311.2 (482 mg, 2 mmol) in THF (10 mL) was added BuLi (1.6 M in THF, 1.3 mL, 2 mmol). The mixture was stirred at −78° C. for 15 min, then a solution of Intermediate 7.3 (500 mg, 1.53 mmol) in THF (5 mL) was added dropwise. The mixture was stirred at −78° C. for 30 min, before warming to 23° C., and quenching with aqueous NH$_4$Cl. The mixture was diluted with EtOAc, washed with H$_2$O and brine, dried (Na$_2$SO$_4$) and concentrated. The crude product was purified by flash chromatography (0 to 40% EtOAc/hexanes gradient) followed by preparative HPLC purification to afford 320 mg of Intermediate 363.1. LCMS (2 min gradient) RT=2.01 min, 488 (M+H)+; $^1$H NMR (400 MHz, CDCl$_3$) δ ppm 1.25-1.31 (m, 9H) 3.77 (s, 3H) 3.79 (q, 2H) 4.44 (m, 1H) 5.95 (m, 1H) 6.29 (m, 1H) 6.41 (m, 1H) 6.58 (d, 2H) 7.36 (d, 2H)

Example 363

A degassed mixture of Intermediate 363.1 (100 mg, 0.21 mmol), 2-fluorophenylboronic acid (57 mg, 0.41 mmol), tri-tert-butylphosphine palladium (42 mg, 0.082 mmol) and K$_3$PO$_4$ (130 mg, 0.62 mmol) in 2 mL 1,4-dioxane was heated at 80° C. for 3 h. The mixture was diluted with DCM (10 mL) filtered, washed with brine, dried (Na$_2$SO$_4$), concentrated and purified by flash chromatography (0 to 100% Hexane/EtOAc gradient). The product was then dissolved in 2 mL 3 M NH$_2$OH in DMSO and was converted to the amide oxime, acylated and hydrogenated as in Example 1 to afford 2.6 mg of Example 363. LCMS (2 min gradient) RT=1.78 min, 521.26 (M+H)+; $^1$H NMR (400 MHz, MeOD) δ ppm 1.31-1.35 (m, J=5.93, 2.42 Hz, 9H) 3.91 (q, J=7.03 Hz, 2H) 3.95 (s, 3H) 4.54-4.64 (m, 1H) 6.37 (s, 1H) 6.51 (dd, J=5.05, 2.86 Hz, 1H) 6.62 (dd, J=7.03, 3.08 Hz, 1H) 6.85-6.91 (m, 2H) 7.18-7.28 (m, 2H) 7.40-7.49 (m, 1H) 7.64 (d, J=8.79 Hz, 2H) 7.90-7.97 (m, 1H).

Example 364

4-((5-ethoxy-2-fluoro-3-isopropoxyphenyl)(5-(2-methoxyphenyl)-2-methyl-2H-1,2,4-triazol-3-yl)methylamino)benzamidine trifluoroacetic acid salt

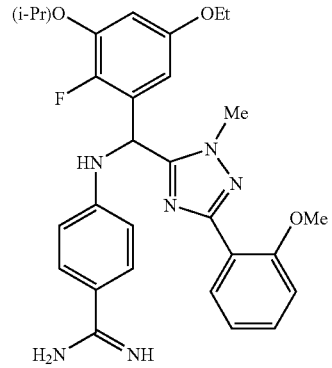

A degassed mixture of Intermediate 363.1 (100 mg, 0.21 mmol), 2-methoxyphenyl boronic acid (62 mg, 0.41 mmol), tri-tert-butylphosphine palladium (42 mg, 0.082 mmol) and K$_3$PO$_4$ (130 mg, 0.62 mmol) in 2 mL 1,4-dioxane was heated at 80° C. for 3 h. The mixture was diluted with DCM (10 mL) filtered, washed with brine, dried (Na$_2$SO$_4$), concentrated and purified by flash chromatography (0 to 100% Hexane/EtOAc gradient). The product was then dissolved in 2 mL 3 M NH$_2$OH in DMSO and was converted to the amide oxime, acylated and hydrogenated as in Example 1 to afford 5 mg of Example 364. LCMS (2 min gradient) RT=1.68 min, 533.33 (M+H)+; $^1$H NMR (400 MHz, MeOD) δ ppm 1.33 (dd, J=6.15, 2.20 Hz, 9H) 3.85 (s, 3H) 3.87-3.95 (m, 5H) 4.53-4.64 (m, 1H) 6.50 (dd, J=4.83, 3.08 Hz, 1H) 6.62 (dd, J=6.81, 2.86 Hz, 1H) 6.88 (d, J=8.79 Hz, 2H) 7.01 (t, J=7.47 Hz, 1H) 7.12 (d, J=8.35 Hz, 1H) 7.38-7.45 (m, 1H) 7.64 (d, J=8.79 Hz, 2H) 7.71 (dd, J=7.91, 1.76 Hz, 1H).

Example 365

4-((5-ethoxy-2-fluoro-3-isopropoxyphenyl)(2-methyl-5-(2-(methylthio)phenyl)-2H-1,2,4-triazol-3-yl)methylamino)benzamidine trifluoroacetic acid salt

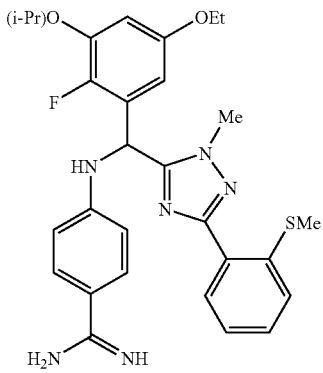

A degassed mixture of Intermediate 363.1 (100 mg, 0.21 mmol), 2-(methylthio)phenyl boronic acid (69 mg, 0.41 mmol), tri-tert-butylphosphine palladium (42 mg, 0.082 mmol) and K₃PO₄ (130 mg, 0.62 mmol) in 2 mL 1,4-dioxane was heated at 80° C. for 3 h. The mixture was diluted with DCM (10 mL) filtered, washed with brine, dried (Na₂SO₄), concentrated and purified by flash chromatography (0 to 100% Hexane/EtOAc gradient). The product was then dissolved in 2 mL 3 M NH₂OH in DMSO and was converted to the amide oxime, acylated and hydrogenated as in Example 1 to afford Example 365. LCMS (2 min gradient) RT=1.79 min, 549.31 (M+H)$^+$; $^1$H NMR (400 MHz, MeOD) δ ppm 1.30-1.36 (m, 9H) 3.87-3.99 (m, 8H) 4.53-4.64 (m, 1H) 6.36 (s, 1H) 6.51 (dd, J=4.83, 2.64 Hz, 1H) 6.61 (dd, J=6.81, 2.86 Hz, 1H) 6.88 (d, J=8.79 Hz, 2H) 7.06-7.17 (m, 2H) 7.17-7.25 (m, 2H) 7.35-7.46 (m, 2H) 7.60-7.68 (m, 2H).

Example 366

2-(5-((4-carbamimidoylphenylamino)(5-ethoxy-2-fluoro-3-isopropoxyphenyl)methyl)-1-methyl-1H-1,2,4-triazol-3-yl)benzamide trifluoroacetic acid salt

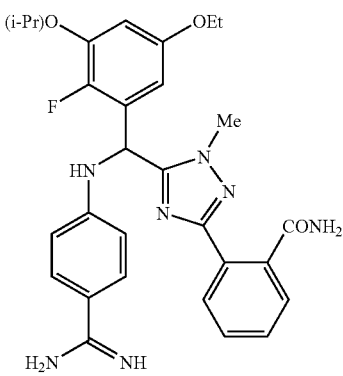

A degassed mixture of Intermediate 363.1 (100 mg, 0.21 mmol), 2-carbamoylphenyl boronic acid (68 mg, 0.41 mmol), tri-tert-butylphosphine palladium (42 mg, 0.082 mmol) and K₃PO₄ (130 mg, 0.62 mmol) in 2 mL 1,4-dioxane was heated at 80° C. for 3 h. The mixture was diluted with DCM (10 mL) filtered, washed with brine, dried (Na₂SO₄), concentrated and purified by flash chromatography (0 to 100% Hexane/EtOAc gradient). The product was then dissolved in 2 mL 3 M NH₂OH in DMSO and was converted to the amide oxime, acylated and hydrogenated as in Example 1 to afford 22 mg of Example 366. LCMS (2 min gradient) RT=1.52 min, 546.32 (M+H)$^+$; $^1$H NMR (400 MHz, MeOD) δ ppm 1.30-1.36 (m, J=5.93, 3.74 Hz, 9H) 3.86-3.97 (m, 5H) 4.53-4.62 (m, 1H) 6.32 (s, 1H) 6.52 (dd, J=4.83, 3.08 Hz, 1H) 6.57-6.63 (m, 1H) 6.80-6.90 (m, 2H) 7.45-7.56 (m, 3H) 7.61-7.66 (m, 2H) 7.83 (d, J=6.15 Hz, 1H).

Example 367

N$^6$-((5-ethyl-2-fluorophenyl)(2-methyl-5-phenyl-2H-1,2,4-triazol-3-yl)methyl) isoquinoline-1,6-diamine trifluoroacetic acid salt

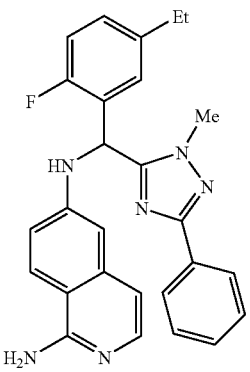

A mixture of Intermediate 311.4 (250 mg, 0.38 mmol), phenylboronic acid (93 mg, 0.76 mmol), Na₂CO₃ (121 mg, 1.14 mmol), tetrakistriphenylphosphine palladium (220 mg, 0.19 mmol) and 3:1 DME/H₂O (2 mL) in a sealed PC microwave vial was degassed (3× with Ar) and heated at 130° C. for 5 min. The mixture was diluted with EtOAc, filtered, purified by flash chromatography (0 to 60% Hexane/EtOAc gradient) and stirred in TFA (5 mL) for 10 min. before purifying with preparative HPLC to afford 47 mg of Example 367. LCMS (2 min gradient) RT=1.79 min, 453.35 (M+H)$^+$; $^1$H NMR (400 MHz, MeOD) δ ppm 1.15 (t, J=7.47 Hz, 3H) 2.60 (q, J=7.47 Hz, 2H) 3.93 (s, 3H) 6.83-6.93 (m, 2H) 7.13 (dd, J=10.55, 8.35 Hz, 1H) 7.23-7.46 (m, 7H) 8.00 (dd, J=7.69, 1.98 Hz, 2H) 8.14 (d, J=9.23 Hz, 1H).

Example 368

N⁶-((3-ethoxy-5-ethyl-2-fluorophenyl)(2-methyl-5-phenyl-2H-1,2,4-triazol-3-yl)methyl)isoquinoline-1,6-diamine trifluoroacetic acid salt

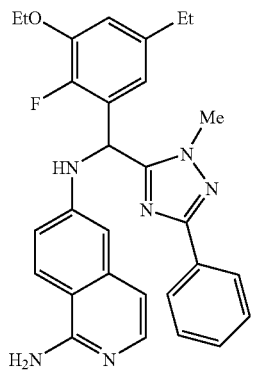

tert-butyl(5-ethyl-2-fluorophenoxy)dimethylsilane (368.1)

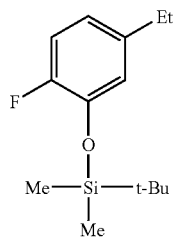

To a mixture of 5-ethyl-2-fluorophenol (10 g, 71.4 mmol) and imidazole (5.4 g, 78.5 mmol) in DMF (100 mL) was added t-butyldimethylsilylchloride (10.8 g, 71.4 mmol) and stirred 18 h. Diluted with EtOAc and washed with H₂O (3×50 mL) and brine, dried (Na₂SO₄) and concentrated. The crude product was purified by flash chromatography (0 to 60% EtOAc/hexanes gradient) to afford 12.2 g of intermediate 368.1. ¹H NMR (400 MHz, CDCl₃) δ ppm 0.15 (s, 6H) 0.97 (s, 9H) 1.16 (t, J=7.47 Hz, 3H) 2.52 (q, J=7.76 Hz, 2H) 6.63-6.72 (m, 2H) 6.90 (dd, J=10.77, 8.13 Hz, 1H).

3-(tert-butyldimethylsilyloxy)-5-ethyl-2-fluorobenzaldehyde (368.2)

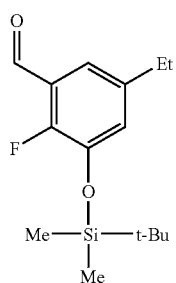

A mixture of Intermediate 368.1 (7.5 g, 29.5 mmol) and PMDTA (7 mL) in THF (50 mL) was cooled to −78° C. 1.6 M n-butyl lithium (21 mL, 32.4 mmol) was added dropwise and the mixture was stirred for 40 min at −60° C. The mixture was cooled to −78° C. and added DMF (4.6 mL, 59 mmol) before allowing the mixture to warm to 23° C. The mixture was quenched with aqueous NH₄Cl and extracted with EtOAc (3×50 mL). The organic layer was washed with H₂O and brine, passed through a 2″ SiO₂ plug eluting with EtOAc/Hex (95/5), dried (Na₂SO₄) and concentrated to afford 7 g of Intermediate 368.2. ¹H NMR (400 MHz, CDCl₃) δ ppm 0.21 (s, 6H) 0.97-1.03 (m, 9H) 1.21 (t, J=7.69 Hz, 3H) 2.59 (q, J=7.76 Hz, 2H) 6.99 (dd, J=8.13, 2.42 Hz, 1H) 7.20-7.29 (m, 1H) 10.30 (s, 1H).

(3-(tert-butyldimethylsilyloxy)-5-ethyl-2-fluorophenyl)(2-methyl-5-phenyl-2H-1,2,4-triazol-3-yl)methanol (368.3)

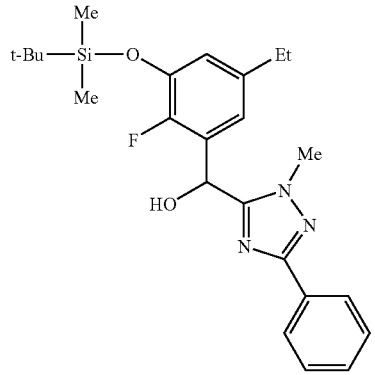

To a solution of 1-methyl-3-phenyl-1H-1,2,4-triazole (310 mg, 1.95 mmol, see *J. Chem. Soc.*, 1954, 3319-3322) in THF (25 mL) cooled to −78° C. was added 1.6 M n-butyl lithium (1.33 mL, 2.12 mmol) dropwise and stirred for 15 min. Next a solution of Intermediate 368.2 (500 mg, 1.77 mmol) in THF (5 mL) was added dropwise and stirred for 5 min before allowing the mixture to warm to 23° C. The mixture was quenched with aqueous NH₄Cl and extracted with EtOAc (3×50 mL). The organic layer was washed with H₂O, brine, dried (Na₂SO₄) and concentrated. The crude product was purified by flash chromatography (0 to 60% EtOAc/hexanes gradient) to afford 440 mg of Example 368.3. HPLC (2 min gradient) RT=2.42 min.

N⁶-((3-(tert-butyldimethylsilyloxy)-5-ethyl-2-fluorophenyl)(2-methyl-5-phenyl-2H-1,2,4-triazol-3-yl)methyl)isoquinoline-1-di-tert-butylcarbamate-6-diamine (368.4)

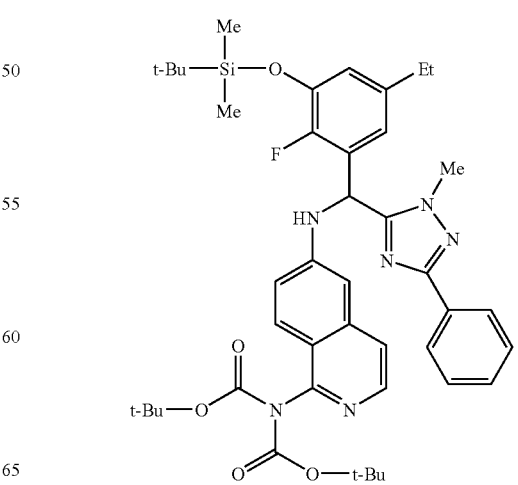

A solution of Intermediate 368.2 (394 mg, 0.50 mmol) and 1 M TBAF (in THF) in THF (10 mL) was stirred for 2 h. The mixture was dilute with EtOAc and washed with $H_2O$ (3×50 mL) and brine, dried ($Na_2SO_4$) and concentrated. The crude product was purified by flash chromatography (0 to 60% EtOAc/hexanes gradient) to afford 324 mg of Intermediate 368.1. LCMS (2 min gradient) RT=2.06 min, 669.5 $(M+H)^+$.

$N^6$-((3-hydroxy-5-ethyl-2-fluorophenyl)(2-methyl-5-phenyl-2H-1,2,4-triazol-3-yl)methyl)isoquinoline-1-di-tert-butylcarbamate-6-diamine (368.5)

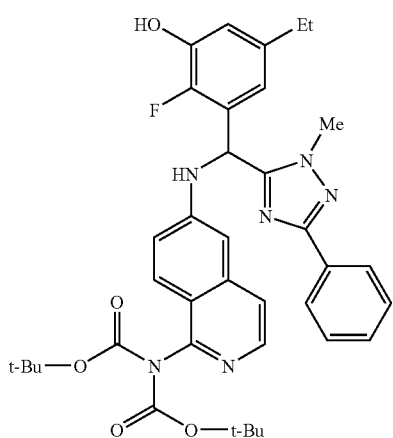

To a solution of Intermediate 368.3 (440 mg, 1 mmol) and N-ethyl-N-isopropylpropan-2-amine (0.35 mL, 2 mmol) in ACN (30 mL) at −15° C. was added methanesulfonic anhydride (279 mg, 1.6 mmol). The mixture was stirred for 1 h as the temperature was raised to 23° C. 1-(di-(tert-butyloxycarbonyl)amino)-6-aminoisoquinoline (359 mg, 1 mmol) was added as a solid and the mixture stirred 18 h at 50° C. The mixture was concentrated and purified by flash chromatography (0 to 60% EtOAc/hexanes gradient) to afford 394 mg of Intermediate 368.2. $^1$H NMR (400 MHz, $CDCl_3$) δ ppm 0.04-0.20 (s, 6H) 0.77-1.02 (m, 12H) 1.08-1.37 (s, 18H) 1.09-1.32 (s, 9H) 2.35 (q, J=7.47 Hz, 2H) 3.82 (s, 3H) 5.96-8.33 (m, 13H).

Example 368

To a mixture of Intermediate 368.5 (80 mg, 0.12 mmol) and $K_2CO_3$ (83 mg, 0.6 mmol) in DMF (1 mL) stirred for 5 min was added iodoethane (24 mg, 0.15 mmol). The mixture was stirred for 2 h and diluted with EtOAc and washed with $H_2O$ (3×50 mL) and brine, dried ($Na_2SO_4$) and concentrated. The crude product was purified by flash chromatography (0 to 60% EtOAc/hexanes gradient) to afford 67 mg of material. This material was dissolved in EtOAc (2 mL) at 0° C. before adding 4 M HCl in 1,4-dioxane (2 mL) and stirring for 18 h at 23° C. The crude product was purified by preparative HPLC purification to afford 33 mg of Example 368. LCMS (2 min gradient) RT=1.82 min, 497.43 $(M+H)^+$; $^1$H NMR (400 MHz, $CDCl_3$) δ ppm 1.11 (t, 3H) 1.49 (t, 2H) 2.52 (q, 2H) 3.96 (s, 3H) 4.11 (q, 2H) 6.26 (s, 1H) 6.72-6.76 (m, 4H) 7.10 (d, 1H) 7.26 (m, 1H) 7.45 (m, 3H) 8.06 (m, 2H).

Example 369

$N^6$-((5-ethyl-2-fluoro-3-isopropoxyphenyl)(2-methyl-5-phenyl-2H-1,2,4-triazol-3-yl)methyl)isoquinoline-1,6-diamine trifluoroacetic acid salt

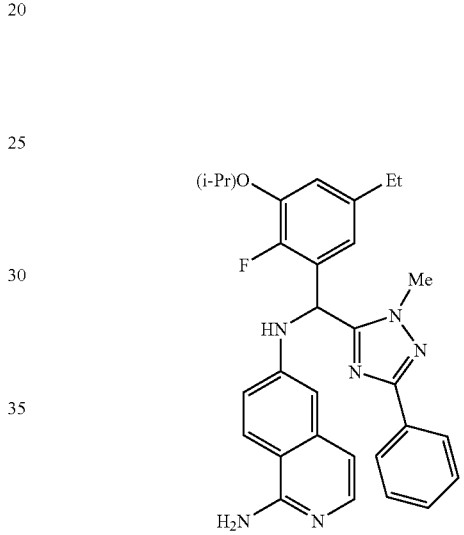

Example 369

To a mixture of Intermediate 368.5 (80 mg, 0.12 mmol) and $K_2CO_3$ (83 mg, 0.6 mmol) in DMF (1 mL) stirred for 5 min was added 2-iodopropane (26 mg, 0.15 mmol). The mixture was stirred for 2 h and diluted with EtOAc and washed with $H_2O$ (3×50 mL) and brine, dried ($Na_2SO_4$) and concentrated. The crude product was purified by flash chromatography (0 to 60% EtOAc/hexanes gradient) to afford 68 mg of material. This material was dissolved in EtOAc (2 mL) at 0° C. before adding 4 M HCl in 1,4-dioxane (2 mL) and stirring for 18 h at 23° C. The crude product was purified by preparative HPLC purification to afford 33 mg of Example 369. LCMS (2 min gradient) RT=1.87 min, 511.45 $(M+H)^+$; $^1$H NMR (400 MHz, $CDCl_3$) δ ppm 1.11 (t, 3H) 1.39 (d, 6H) 2.52 (q, 2H) 4.00 (s, 3H) 4.55 (q, 1H) 6.32 (s, 1H) 6.69-6.81 (m, 4H) 7.10 (d, 1H) 7.25 (m, 1H) 7.45 (m, 2H) 7.90 (d, 2H) 8.06 (m, 2H).

Example 370

4-((3-ethylphenyl)(2-methyl-5-phenyl-2H-1,2,4-triazol-3-yl)methylamino)-N'-hydroxybenzamidine trifluoroacetic acid salt

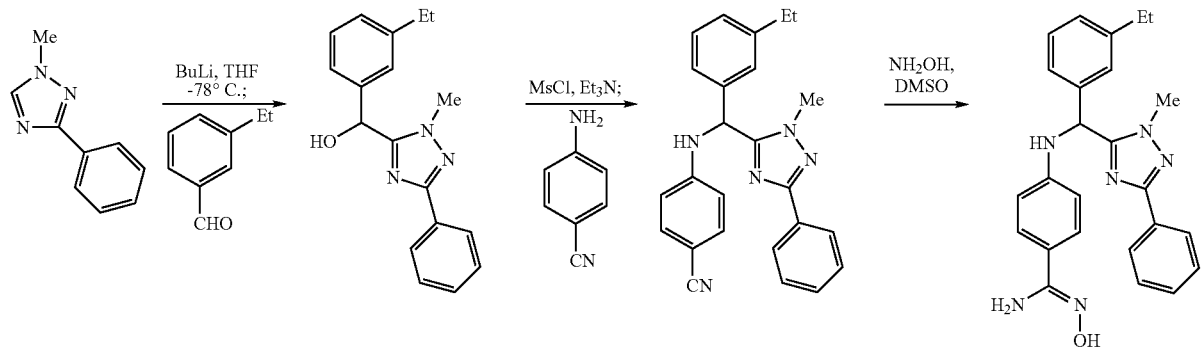

Example 370

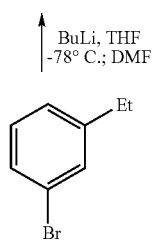

3-ethylbenzaldehyde (370.1)

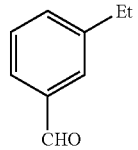

(3-ethylphenyl)(2-methyl-5-phenyl-2H-1,2,4-triazol-3-yl)methanol (370.2)

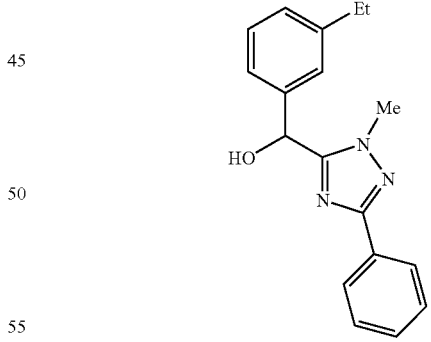

To a solution of 1-bromo-3-ethylbenzene (5 g, 27.2 mmol) in THF (135 mL) at −78° C. was added butyl lithium (1.6 M in hexanes, 18 mL, 28.8 mmol) dropwise. The mixture was stirred at −78° C. for 5 min. DMF (2.1 mL, 27.2 mmol) was added and the mixture was warmed to ambient temperature over 2 h. The mixture was diluted with diethyl ether (500 mL), washed with sat. NaHCO$_3$ and brine, dried (Na$_2$SO$_4$) and concentrated to yield 4 g of Intermediate 370.1 as a clear oil. $^1$H NMR (400 MHz, CDCl$_3$) δ ppm 1.27 (t, J=7.58 Hz, 3H) 2.73 (q, J=7.58 Hz, 2H) 7.39-7.51 (m, 2H) 7.64-7.76 (m, 2H) 9.99 (s, 1H).

To a solution of 1-methyl-3-phenyl-1H-1,2,4-triazole (284 mg, 1.8 mmol, see *J. Chem. Soc.*, 1954, 3319-3322) in THF (112 mL) at −78° C. was added BuLi (1.15 mL, 1.6 M in hexanes, 1.8 mmol). The reaction was stirred for 5 minutes at −78° C. and a solution of intermediate 370.1 (200 mg, 1.5 mmol) in THF (2 mL) was added dropwise. The mixture was warmed to ambient temperature over 2 h. Ammonium chloride (80 mg) was added to the mixture and it was concentrated. Purification of the crude material afforded 350 mg of intermediate 370.2 as a white solid. LCMS 294.2 (M+H)$^+$.

5-(chloro(3-ethylphenyl)methyl)-1-methyl-3-phenyl-1H-1,2,4-triazole (370.3)

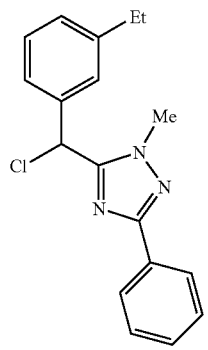

Intermediate 370.2 (350 mg, 1.2 mmol) was dissolved in $CH_2Cl_2$ (10 mL) and $Et_3N$ (0.50 mL, 3.6 mmol) and cooled to 0° C., MsCl (0.092 mL, 1.2 mmol) was added dropwise and the mixture was stirred at 0° C. for 2 h. The reaction mixture was diluted with $CH_2Cl_2$ (20 mL), washed with $H_2O$, brine, dried ($Na_2SO_4$) and concentrated to yield 370 mg of Intermediate 370.3 as a clear oil. $^1$H NMR (400 MHz, $CDCl_3$) δ ppm 1.15 (t, J=7.58 Hz, 3H) 2.56 (q, 2H) 3.71 (s, 3H) 6.30 (s, 1H) 7.09-7.16 (m, 1H) 7.21-7.29 (m, 2H) 7.28-7.43 (m, 3H) 7.99-8.05 (m, 2H).

4-((3-ethylphenyl)(2-methyl-5-phenyl-2H-1,2,4-triazol-3-yl)methylamino)benzonitrile (370.4)

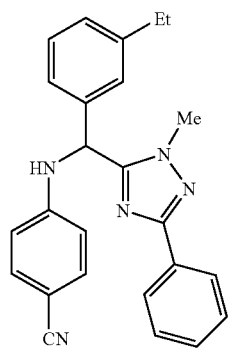

4-Aminobenzonitrile (35 mg, 0.30 mmol) was added to a solution of Intermediate 370.3 (93 mg, 0.30 mmol) and $Et_3N$ (0.125 mL, 0.9 mmol) in acetonitrile (1.5 mL) and heated 16 h at 75° C. The mixture was concentrated and purified by flash chromatography to yield 60 mg of Intermediate 370.3 as an off-white solid. LCMS 394.31 $(M+H)^+$.

Example 370

Intermediate 370.3 (60 mg, 0.15 mmol) was stirred at 60° C. for 2 h in a 3.0 M solution of $NH_2OH$ in DMSO. The mixture was diluted with EtOAc (40 mL), washed with sat. $NaHCO_3$ and brine, dried ($Na_2SO_4$) and concentrated. Purification by preparative HPLC afforded 25 mg of Example 370 as a white solid. LCMS 427.34 $(M+H)^+$; $^1$H NMR (400 MHz, $CD_3OD$) δ ppm 1.20 (t, J=7.58 Hz, 3H) 2.64 (q, J=7.58 Hz, 2H) 3.86 (s, 3H) 6.11 (s, 1H) 6.87 (d, J=9.05 Hz, 2H) 7.17-7.27 (m, 2H) 7.28-7.35 (m, 2H) 7.37-7.44 (m, 3H) 7.48 (d, J=9.05 Hz, 2H) 7.99 (dd, J=7.70, 1.83 Hz, 2H).

Example 371

4-((3-ethylphenyl)(2-methyl-5-phenyl-2H-1,2,4-triazol-3-yl)methylamino)benzamidine trifluoroacetic acid salt

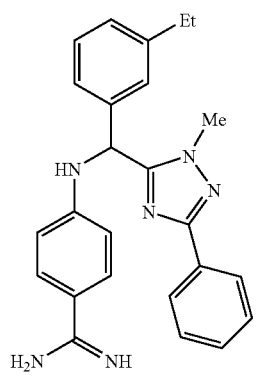

Acetic anhydride (0.1 mL) was added to Example 370 (25 mg) in $CH_2Cl_2$ (2 mL) and stirred 1 h at ambient temperature. Volatiles were removed in vacuo. The intermediate was dissolved in methanol (2 mL) and stirred with 10% Pd—C under hydrogen atmosphere for 2 h. The mixture was filtered through celite, concentrated and purified by preparative HPLC to yield 11 mg of Example 371. LCMS 411.33 $(M+H)^+$; $^1$H NMR (400 MHz, $CD_3OD$) δ ppm 1.20 (t, J=7.58 Hz, 3 H) 2.65 (q, J=7.66 Hz, 2H) 3.86 (s, 3H) 6.13 (s, 1H) 6.87 (d, J=8.80 Hz, 2H) 7.16-7.29 (m, 2H) 7.28-7.36 (m, 2H) 7.37-7.46 (m, 3H) 7.61 (d, J=9.05 Hz, 2H) 7.95-8.05 (m, 2H).

Example 372

4-(aminomethyl)-N-((3-ethylphenyl)(2-methyl-5-phenyl-2H-1,2,4-triazol-3-yl)methyl)benzenamine trifluoroacetic acid salt

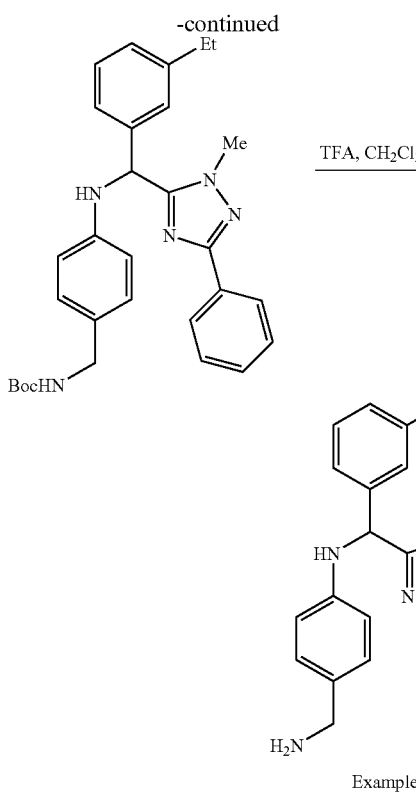

TFA, CH₂Cl₂ →

Example 372 tert-butyl 4-((3-ethylphenyl)(2-methyl-5-phenyl-2H-1,2,4-triazol-3-yl)methylamino)benzylcarbamate (372.1)

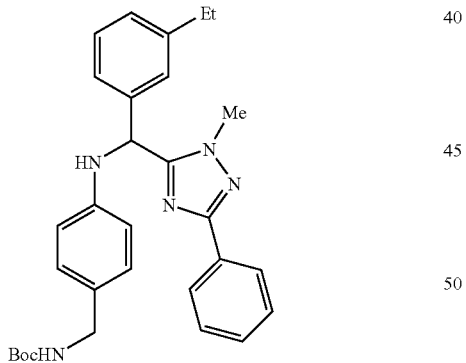

tert-Butyl 4-aminobenzylcarbamate (31 mg, 0.14 mmol) was added to a solution of intermediate 370.3 (43 mg,) and Et₃N (0.1 mL) in acetonitrile (1 mL) and stirred at 80° C. for 16 h. The mixture was concentrated and purified by flash chromatography (EtOAc/hexanes) to yield 43 mg of intermediate 372.1 as a white solid. LCMS 498.38 (M+H)⁺.

Example 372

TFA (0.5 mL) was added to a solution of Intermediate 372.1 (43 mg, 0.087 mmol) in CH₂Cl₂ (2 mL) at 0° C. The mixture was stirred for 2 h, concentrated, and purified by preparative HPLC to afford 31 mg of Example 372. LCMS 420.32 (M+Na)⁺; ¹H NMR (400 MHz, CD₃OD) δ ppm 1.19 (t, J=7.70 Hz, 3H) 2.63 (q, J=7.58 Hz, 2H) 3.87 (s, 3H) 3.93 (s, 2H) 6.03 (s, 1H) 6.80 (d, J=8.31 Hz, 2H) 7.14-7.26 (m, 4H) 7.26-7.34 (m, 2H) 7.36-7.47 (m, 3H).

Example 373

4-((3-ethylphenyl)(2-methyl-5-phenyl-2H-1,2,4-triazol-3-yl)methylamino)-2-fluoro-N'-hydroxybenzamidine trifluoroacetic acid salt

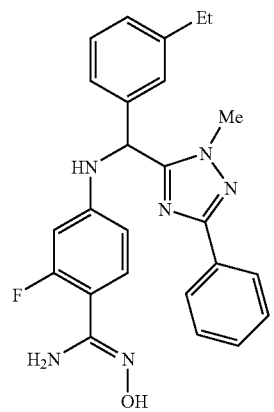

4-((3-ethylphenyl)(2-methyl-5-phenyl-2H-1,2,4-triazol-3-yl)methylamino)-2-fluorobenzonitrile (373.1)

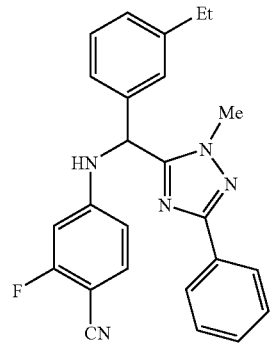

According to the procedure for the preparation of Intermediate 370.4, 4-amino-2-fluorobenzonitrile (46 mg, 0.34 mmol) gave 75 mg of Intermediate 373.1 as a white solid. LCMS 412.30 (M+H)⁺.

Example 373

Following the procedure for Example 370, Intermediate 373.1 (75 mg, 0.18 mmol) yielded 63 mg of Example 373 as a clear oil. LCMS 445.27 (M+H)⁺; ¹H NMR (400 MHz, CD₃OD) δ ppm 1.20 (t, J=7.58 Hz, 3H) 2.64 (q, J=7.58 Hz, 2H) 3.34 (s, 1H) 3.84 (s, 3H) 6.10 (s, 1H) 6.64 (dd, J=13.69,

Example 374

4-((3-ethylphenyl)(2-methyl-5-phenyl-2H-1,2,4-triazol-3-yl)methylamino)-2-fluorobenzamidine trifluoroacetic acid salt

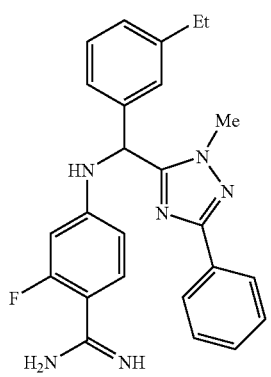

Example 373 (40 mg, 0.09 mmol) was acylated and hydrogenated as in Example 371 to afford 23 mg of Example 374 as a white solid. LCMS 429.32 (M+H); $^1$H NMR (400 MHz, CD$_3$OD) δ ppm 1.20 (t, J=7.58 Hz, 3H) 2.64 (q, J=7.74 Hz, 2H) 3.85 (s, 3H) 6.12 (s, 1H) 6.63 (dd, J=14.43, 2.20 Hz, 1H) 6.70 (dd, J=8.80, 2.20 Hz, 1H) 7.17-7.27 (m, 2H) 7.28-7.35 (m, 2H) 7.36-7.52 (m, 4H) 7.96-8.04 (m, 2H).

Example 375

N$^6$-((3-ethylphenyl)(2-methyl-5-phenyl-2H-1,2,4-triazol-3-yl)methyl)isoquinoline-1,6-diamine trifluoroacetic acid salt

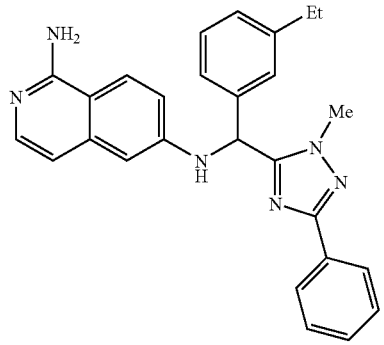

N$^6$-((3-ethylphenyl)(2-methyl-5-phenyl-2I-1,2,4-triazol-3-yl)methyl)-N$^1$,N$^1$-di-(tert-butoxycarbonyl)isoquinoline-1,6-diamine (375.1)

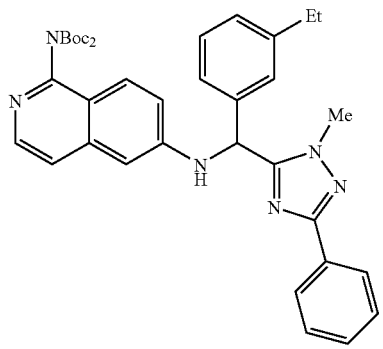

1-(Di-(tert-butyloxycarbonyl)amino)-6-aminoisoquinoline (128 mg, 0.36 mmol) was added to a solution of Intermediate 370.3 (11 mg, 0.36 mmol) and Et$_3$N (0.15 mL, 1.1 mmol) and stirred 16 h at 75° C. The mixture was concentrated and purified by flash chromatography (EtOAc/hexanes) to yield 106 mg of Example 375.1. LCMS 635.44 (M+H).

Example 375

Intermediate 375.1 (105 mg, 0.17 mmol) was dissolved and cooled to 0° C. HCl (2.4 mL, 4.0 M in dioxane) was added dropwise. The mixture was warmed to ambient temperature over 2 h and stirred 16 h. Concentration and purification by preparatory HPLC afforded 40 mg of Example 375 as a white solid. LCMS 435.31 (M+H); $^1$H NMR (400 MHz, CD$_3$OD) δ ppm 1.18 (t, J=7.58 Hz, 3H) 2.63 (q, J=7.58 Hz, 2H) 3.87 (s, 3H) 6.22 (s, 1H) 6.75-6.89 (m, 2H) 7.12-7.52 (m, 9H) 7.99 (dd, J=7.83, 1.71 Hz, 2H) 8.08 (d, J=9.29 Hz, 2H).

Example 376

(Z)-4-((3-ethylphenyl)(2-methyl-5-phenyl-2H-1,2,4-triazol-3-yl)methylamino)-2,5-difluoro-N'-hydroxybenzamidine trifluoroacetic acid salt

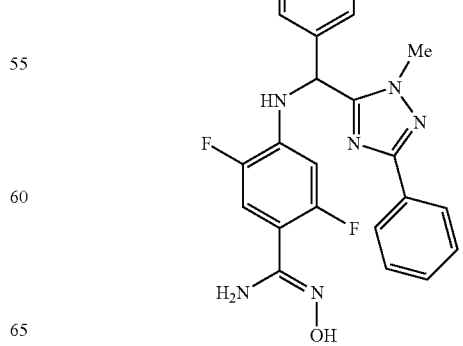

4-((3-ethylphenyl)(2-methyl-5-phenyl-2H-1,2,4-triazol-3-yl)methylamino)-2,5-difluorobenzonitrile (376.1)

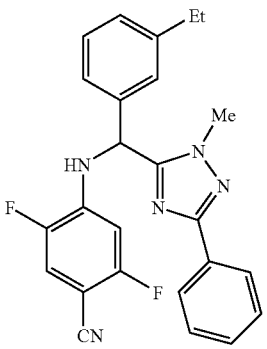

According to the procedure for the preparation of Intermediate 370.4, 4-amino-2,5-difluorobenzonitrile (50 mg, 0.32 mmol) gave 90 mg of intermediate 376.1 as a white solid. $^1$H NMR (400 MHz, CDCl$_3$) δ ppm 1.23 (t, J=7.58 Hz, 3H) 2.67 (q, J=7.42 Hz, 2H) 4.46 (s, 1H) 5.62 (d, J=5.87 Hz, 1H) 6.53 (dd, J=9.78, 7.09 Hz, 2H) 7.14-7.24 (m, 2H) 7.26-7.37 (m, 3H) 7.39-7.52 (m, 3H) 8.09-8.15 (m, 2H).

Example 376

Following the procedure for Example 370, Intermediate 376.1 (90 mg, 0.21 mmol) yielded 68 mg of Example 373 as a white solid. LCMS 463.31 (M+H); $^1$H NMR (400 MHz, CD$_3$OD) δ ppm 1.19 (t, J=7.47 Hz, 3H) 2.64 (q, 2H) 3.84 (s, 3H) 6.16 (s, 1H) 6.75 (dd, J=12.74, 7.03 Hz, 1H) 7.20 (d, J=7.03 Hz, 1H) 7.25-7.38 (m, 4H) 7.38-7.47 (m, 3H) 8.01 (dd, J=7.91, 1.76 Hz, 2H).

Example 377

4-((3-ethylphenyl)(2-methyl-5-phenyl-2H-1,2,4-triazol-3-yl)methylamino)-2,5-difluorobenzamidine trifluoroacetic acid salt

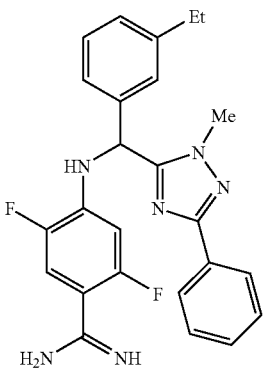

Example 376 (60 mg, 0.13 mmol) was acylated and hydrogenated as in Example 371 to afford 24 mg of Example 377 as a white solid. LCMS 447.34 (M+H); $^1$H NMR (500 MHz, CD$_3$OD) δ ppm 1.20 (t, J=7.70 Hz, 3H) 2.65 (q, J=7.33 Hz, 2H) 3.85 (s, 3H) 6.17 (s, 1H) 6.74 (dd, J=13.20, 6.60 Hz, 1H) 7.18-7.24 (m, J=7.15 Hz, 1H) 7.26-7.37 (m, 3H) 7.37-7.45 (m, 4H) 8.01 (d, J=7.70 Hz, 2H).

Example 380

4-((3-ethylphenyl)(5-phenyl-2H-1,2,4-triazol-3-yl)methylamino)-N'-hydroxybenzamidine trifluoroacetic acid salt

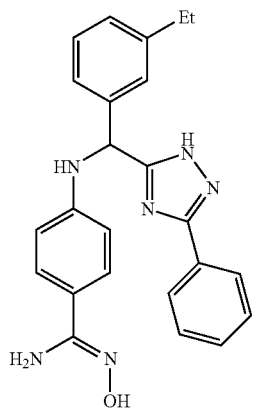

(E)-4-(3-ethylbenzylideneamino)benzonitrile (380.1)

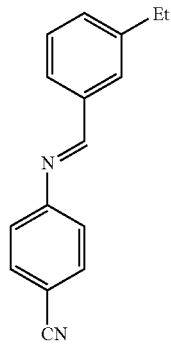

Similar to the procedure for the preparation of Intermediate 1.1, 2-ethyl benzaldehyde and 4-aminobenzonitrile afforded Intermediate 380.1 as a yellow solid. $^1$H NMR (400 MHz, CDCl$_3$) δ ppm 1.16 (t, 3H) 2.57 (q, J=7.76 Hz, 2H) 4.59 (s, 1H) 6.55 (d, J=8.35 Hz, 2H) 7.03-7.15 (m, 3H) 7.20 (t, J=7.47 Hz, 1H) 7.31 (d, J=8.79 Hz, 2H).

283

4-((3-ethylphenyl)(5-phenyl-2-trityl-2H-1,2,4-triazol-3-yl)methylamino)benzonitrile (380.2)

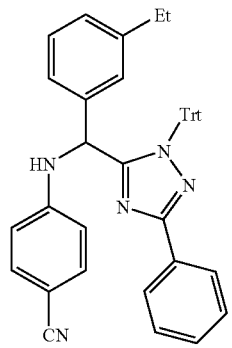

BuLi (0.295 mL, 1.6 M in hexanes, 0.47 mmol) was added dropwise to a solution of 3-phenyl-1-trityl-1H-1,2,4-triazole (182 mg, 0.47 mmol) in THF (4 mL) at −78° C. The mixture was stirred for 10 min. A solution of Intermediate 380.1 (100 mg, 0.43 mmol) in THF (0.7 mL) was added dropwise. The mixture was warmed to ambient temperature over 1 h. Ammonium chloride (50 mg) was added and the mixture was concentrated. Purification by flash chromatography afforded 215 mg of Intermediate 380.2. $^1$H NMR (400 MHz, CDCl$_3$) δ ppm 1.18 (t, J=7.58 Hz, 3H) 2.52 (q, J=7.74 Hz, 2H) 5.09 (d, J=9.05 Hz, 1H) 6.93 (d, J=7.34 Hz, 1H) 6.98-7.10 (m, 1H) 7.11-7.20 (m, 3H) 7.20-7.27 (m, 8H) 7.33-7.48 (m, 12H) 8.06-8.18 (m, 3H).

Example 380

Intermediate 380.2 was dissolved in 3.0 M NH$_2$OH in DMSO (4 mL) and stirred at 60° C. for 2 h. The mixture was diluted with EtOAc (50 mL), washed with sat. NaHCO$_3$ and brine, dried (MgSO$_4$) and concentrated to give 200 mg crude material. The crude material (40 mg) was dissolved in AcOH (90%, 1 mL) and heated at 60° C. for 30 min. The mixture was concentrated and purified by flash chromatography to yield 10 mg of Example 380 as a white solid. LCMS 413.31 (M+H); $^1$H NMR (400 MHz, CD$_3$OD) δ ppm 1.20 (t, J=7.70 Hz, 3H) 2.64 (q, J=7.58 Hz, 2H) 5.88 (s, 1H) 6.82 (d, J=8.80 Hz, 2H) 7.10-7.21 (m, 1H) 7.24-7.33 (m, 2H) 7.36 (s, 1H) 7.41-7.54 (m, 5H) 7.88-8.02 (m, 2H).

Example 381

4-((3-ethylphenyl)(5-phenyl-2H-1,2,4-triazol-3-yl)methylamino)benzamidine trifluoroacetic acid salt

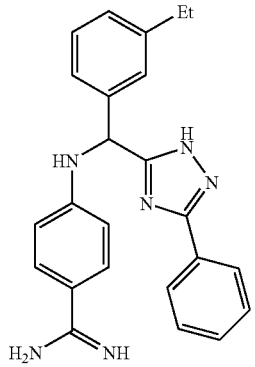

284

Intermediate 380.2 was dissolved in 3.0 M NH$_2$OH in DMSO (4 mL) and stirred at 60° C. for 2 h. The mixture was diluted with EtOAc (50 mL), washed with sat. NaHCO$_3$ and brine, dried (MgSO$_4$) and concentrated to give 200 mg crude material. The crude material (160 mg) was dissolved in CH$_2$Cl$_2$ (4 mL). Acidic anhydride (0.2 mL) was added and the mixture was stirred at ambient temperature for 1 h. The residue was dissolved and MeOH, Pd—C (20 mg) was added and the mixture was stirred under hydrogen atmosphere for 2 h. The mixture was filtered through Celite and concentrated. The crude material was dissolved in AcOH (90%, 2 mL) and stirred at 60° C. for 30 min. The mixture was concentrated and purified by preparative HPLC to yield 10 mg of Example 381 as a white solid. LCMS 397.33 (M+H); $^1$H NMR (400 MHz, CD$_3$OD) δ ppm 1.20 (t, J=7.58 Hz, 3H) 2.64 (q, J=7.66 Hz, 2H) 5.90 (s, 1H) 6.82 (d, J=8.80 Hz, 2H) 7.16 (d, J=6.60 Hz, 1H) 7.24-7.33 (m, 2H) 7.36 (s, 1H) 7.42-7.52 (m, 3H) 7.59 (d, J=8.80 Hz, 2H) 7.95 (dd, J=5.87, 2.45 Hz, 2H).

Example 382

4-((3-ethylphenyl)(2-methyl-5-phenyl-2H-1,2,4-triazol-3-yl)methylamino)-3-fluorobenzamidine trifluoroacetic acid salt

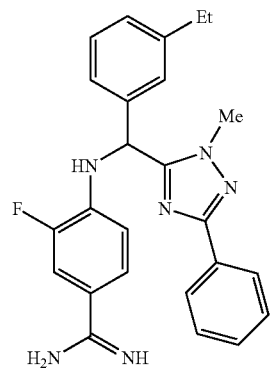

4-((3-ethylphenyl)(2-methyl-5-phenyl-2H-1,2,4-triazol-3-yl)methylamino)-3-fluorobenzonitrile (382.1)

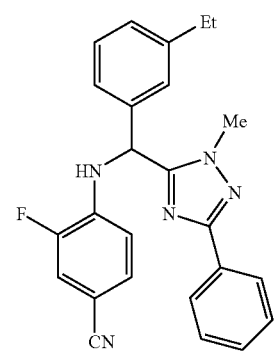

Methansulfonic anhydride (77 mg, 0.44 mmol) was added to a solution of Intermediate 370.2 (81 mg, 0.28 mmol) and diisopropylethylamine (0.2 mL, 1.16 mmol) in CH$_2$Cl$_2$ (2.5 mL) at 0° C. The mixture was stirred for 1 h at 0° C. and then 4-amino-3-fluorobenzonitrile (136 mg, 1 mmol) was added. The mixture was stirred for 1 h at ambient temperature, diluted with CH$_2$Cl$_2$ (40 mL), washed with sat. NaHCO$_3$ and brine, dried (Na$_2$SO$_4$) and concentrated. Purification by flash chromatography (EtOAc, hexanes) afforded 65 mg of Intermediate 382.1. $^1$H NMR (400 MHz, CDCl$_3$) δ ppm 1.11 (t, J=7.58 Hz, 3H) 2.54 (q, J=7.58 Hz, 2H) 3.69 (s, 3 H) 5.60 (d, J=5.87 Hz, 1H) 6.10-6.16 (m, J=1.96 Hz, 1H) 7.06-7.24 (m, 6H) 7.27-7.39 (m, 3H) 7.99-8.04 (m, 2H).

Example 382

Intermediate 382.1 (65 mg, 0.15 mmol) was dissolved in 3.0 M NH$_2$OH in DMSO (4 mL) and stirred at 60° C. for 2 h. The mixture was diluted with EtOAc (50 mL), washed with sat. NaHCO$_3$ and brine, dried (MgSO$_4$) and concentrated. The crude material was dissolved in CH$_2$Cl$_2$ (1 mL). Acidic anhydride (0.1 mL) was added and the mixture was stirred at ambient temperature for 1 h. The residue was dissolved in MeOH (2 mL), Pd—C (10 mg) was added and the mixture was stirred under hydrogen atmosphere for 2 h. The mixture was filter through Celite and concentrated. Purification by preparatory HPLC afforded 16 mg of Example 382 as a white solid. LCMS 429.37 (M+H); $^1$H NMR (400 MHz, CD$_3$OD) δ ppm 1.20 (t, J=7.58 Hz, 3H) 2.65 (q, J=7.58 Hz, 2H) 3.86 (s, 3H) 6.19 (s, 1H) 6.93 (t, J=8.56 Hz, 1H) 7.18-7.23 (m, J=7.09 Hz, 1H) 7.27-7.33 (m, 2H) 7.34-7.36 (m, 1H) 7.38-7.45 (m, 3H) 7.48 (dd, J=8.68, 2.32 Hz, 1H) 7.56 (dd, J=12.47, 2.20 Hz, 1H) 8.00 (dd, J=7.83, 1.71 Hz, 1H).

Example 383

4-((3-ethylphenyl)(2-methyl-5-phenyl-2H-1,2,4-triazol-3-yl)methylamino)-3,5-difluorobenzamidine trifluoroacetic acid salt

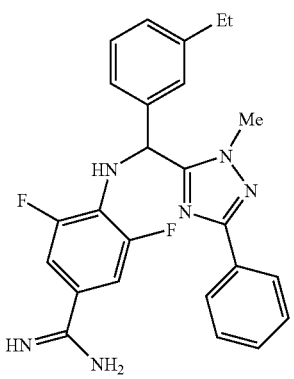

4-amino-3,5-difluorobenzonitrile (383.1)

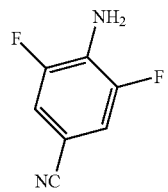

A solution of CuCN (135 mg, 1.51 mmol) and 4-bromo-2,6-difluorobenzenamine (200 mg, 0.96 mmol) in DMF (4 mL) was sealed in a microwave vial and degassed with Ar. The mixture was heated in microwave at 220° C. for 17.5 min. Ammonium hydroxide (10 mL) and water (10 mL) were added to the mixture and it was extracted with EtOAc (2×20 mL). The organics were combined, washed with sat. NaHCO$_3$ and brine, dried (Na$_2$SO$_4$) and concentrated. Purification by flash chromatography yielded 116 mg of Intermediate 383.1 as a white solid. LCMS 155.3 (M+H); $^1$H NMR (400 MHz, CDCl$_3$) δ ppm 4.27 (bs, 2H) 7.12 (dd, J=5.87, 2.20 Hz, 2H).

4-((3-ethylphenyl)(2-methyl-5-phenyl-2H-1,2,4-triazol-3-yl)methylamino)-3,5-difluorobenzonitrile (383.2)

Following the same procedure as Intermediate 382.1, 4-amino-3,5-difluorobenzonitrile (154 mg, 1 mmol) yielded 95 mg of Intermediate 383.2. $^1$H NMR (400 MHz, CDCl$_3$) δ ppm 1.08 (t, J=7.58 Hz, 3H) 2.51 (q, J=7.58 Hz, 2H) 3.66 (s, 3H) 5.82 (d, J=7.34 Hz, 1H) 5.99 (d, J=8.56 Hz, 1H) 6.95-7.01 (m, 2H) 7.02-7.18 (m, 4H) 7.27-7.38 (m, 3H) 7.97-8.03 (m, 2H).

Example 383

According to the procedure for Example 382, 95 mg of Intermediate 383.2 afforded 39 mg of Example 383. LCMS 447.36 (M+H); $^1$H NMR (400 MHz, CD$_3$OD) δ ppm 1.18 (t, J=7.58 Hz, 3H) 2.62 (q, J=7.58 Hz, 2H) 3.82 (s, 3H) 6.35 (s, 1H) 7.17 (d, J=7.09 Hz, 1H) 7.22-7.34 (m, 3H) 7.38-7.46 (m, 5H) 8.00 (dd, J=7.83, 1.71 Hz, 2H).

Example 384

4-((5-ethyl-2-fluorophenyl)(5-phenyl-2H-1,2,4-triazol-3-yl)methylamino)benzamidine trifluoroacetic acid salt

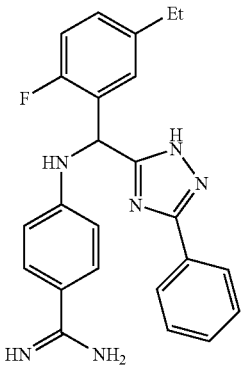

(5-ethyl-2-fluorophenyl)(5-phenyl-2-trityl-2H-1,2,4-triazol-3-yl)methanol (384.1)

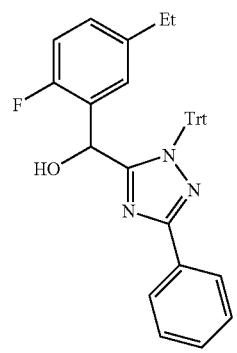

According to the procedure for Intermediate 370.1, 3-phenyl-1-trityl-1H-1,2,4-triazole (250 mg, 0.66 mmol) and 5-ethyl-2-fluorobenzaldehyde (100 mg, 0.66 mmol) afforded 294 mg of Intermediate 384.1 as a white solid. $^1$H NMR (400 MHz, CD$_3$OD) δ ppm 1.06 (t, J=7.70 Hz, 3H) 2.41 (q, J=7.58 Hz, 2H) 2.89 (d, J=9.05 Hz, 1H) 5.41 (d, J=9.29 Hz, 1H) 6.60 (dd, J=9.90, 8.44 Hz, 1H) 6.82-6.93 (m, 1H) 6.96 (dd, J=7.34, 2.20 Hz, 1H) 7.02-7.09 (m, 6H) 7.09-7.16 (m, 9H) 7.24-7.39 (m, 4H) 7.98-8.10 (m, 2H).

4-((5-ethyl-2-fluorophenyl)(5-phenyl-2-trityl-2H-1,2,4-triazol-3-yl)methylamino)benzonitrile (384.2)

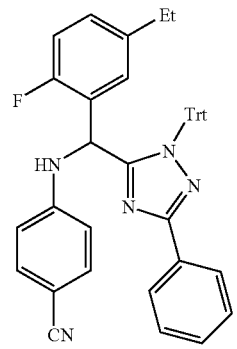

Following the procedure for Intermediate 382.1, Intermediate 384.1 (280 mg, 0.52 mmol) gave 245 mg of Intermediate 384.2 as a white solid. LCMS 622.5 (M+H).

Example 384

According to the procedure for Example 381, Intermediate 384.2 (90 mg, 0.14 mmol) yielded 19 mg of Example 384 as a white solid. LCMS 415.21 (M+H); $^1$H NMR (400 MHz, CD$_3$OD) δ ppm 1.15 (t, J=7.70 Hz, 3H) 2.58 (q, J=7.58 Hz, 2H) 6.19 (s, 1H) 6.71-6.91 (m, 2H) 7.05 (dd, J=10.03, 8.56 Hz, 1H) 7.11-7.28 (m, 1H) 7.34 (dd, J=7.09, 2.20 Hz, 1H) 7.40-7.54 (m, 3H) 7.61 (d, J=8.80 Hz, 2H) 7.86-8.07 (m, 2H).

Example 385

4-((5-ethyl-2-fluorophenyl)(2-methyl-5-phenyl-2H-1,2,4-triazol-3-yl)methylamino)benzamidine trifluoroacetic acid salt

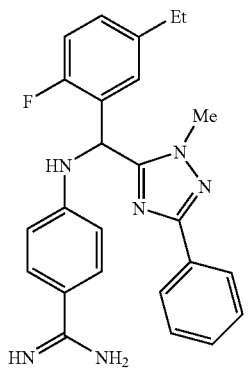

(5-ethyl-2-fluorophenyl)(2-methyl-5-phenyl-2H-1,2,4-triazol-3-yl)methanol (385.1)

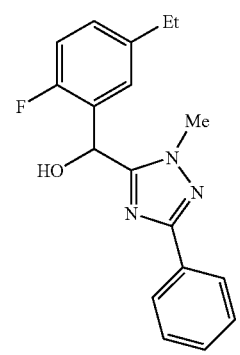

According to the procedure for Intermediate 370.2, 1-methyl-3-phenyl-1H-1,2,4-triazole (105 mg, 0.66 mmol) and 5-ethyl-2-fluorobenzaldehyde (100 mg, 0.66 mmol) afforded 159 mg of Intermediate 385.1 as a white solid. $^1$H NMR (400 MHz, CDCl$_3$) δ ppm 1.12 (t, J=7.70 Hz, 3H) 2.47 (q, J=7.42 Hz, 2H) 2.95 (d, J=9.05 Hz, 1H) 5.48 (d, J=9.29 Hz, 1H) 6.67 (dd, J=9.90, 8.44 Hz, 1H) 6.87-6.99 (m, 1H) 7.03 (dd, J=7.34, 2.20 Hz, 1H) 7.08-7.15 (m, 6H) 7.15-7.22 (m, 10H) 7.30-7.48 (m, 5H) 8.04-8.16 (m, 2H).

4-((5-ethyl-2-fluorophenyl)(2-methyl-5-phenyl-2H-1,2,4-triazol-3-yl)methylamino)benzonitrile (385.2)

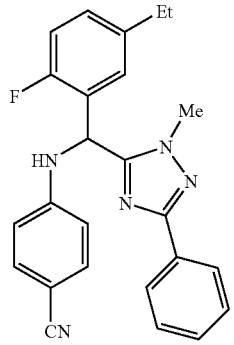

Following the procedure for Intermediate 382.1, Intermediate 385.1 (150 mg, 0.48 mmol) gave 155 mg of Intermediate 385.2 as a white solid. $^1$H NMR (400 MHz, CDCl$_3$) δ ppm 0.95 (t, J=7.58 Hz, 3H) 2.35 (q, J=7.58 Hz, 2H) 3.59 (s, 3H) 5.87 (d, J=6.11 Hz, 1H) 6.35 (d, J=5.87 Hz, 1H) 6.48-6.57 (m, 2H) 6.86-6.94 (m, 1H) 6.95-7.02 (m, 1H) 7.11-7.19 (m, 1H) 7.22-7.32 (m, 5H).

Example 385

According to the procedure for Example 382, Intermediate 385.2 (155 mg, 0.38 mmol) yielded 35 mg of Example 385 as a white solid. LCMS 429.24 (M+H); $^1$H NMR (400 MHz, CD$_3$OD) δ ppm 1.12 (t, J=7.58 Hz, 3H) 2.55 (q, J=7.58 Hz, 2H) 3.88 (s, 3H) 6.32 (s, 1H) 6.86 (d, J=8.56 Hz, 2H) 7.03-7.13 (m, 1H) 7.15-7.24 (m, 1H) 7.30 (dd, J=7.09, 1.96 Hz, 1H) 7.34-7.43 (m, 3H) 7.63 (d, J=8.80 Hz, 2H) 7.94-8.02 (m, 2H).

Example 386

N$^6$-((4-ethoxy-5-ethyl-2-fluorophenyl)(2-methyl-5-phenyl-2H-1,2,4-triazol-3-yl)methyl)isoquinoline-1,6-diamine trifluoroacetic acid salt

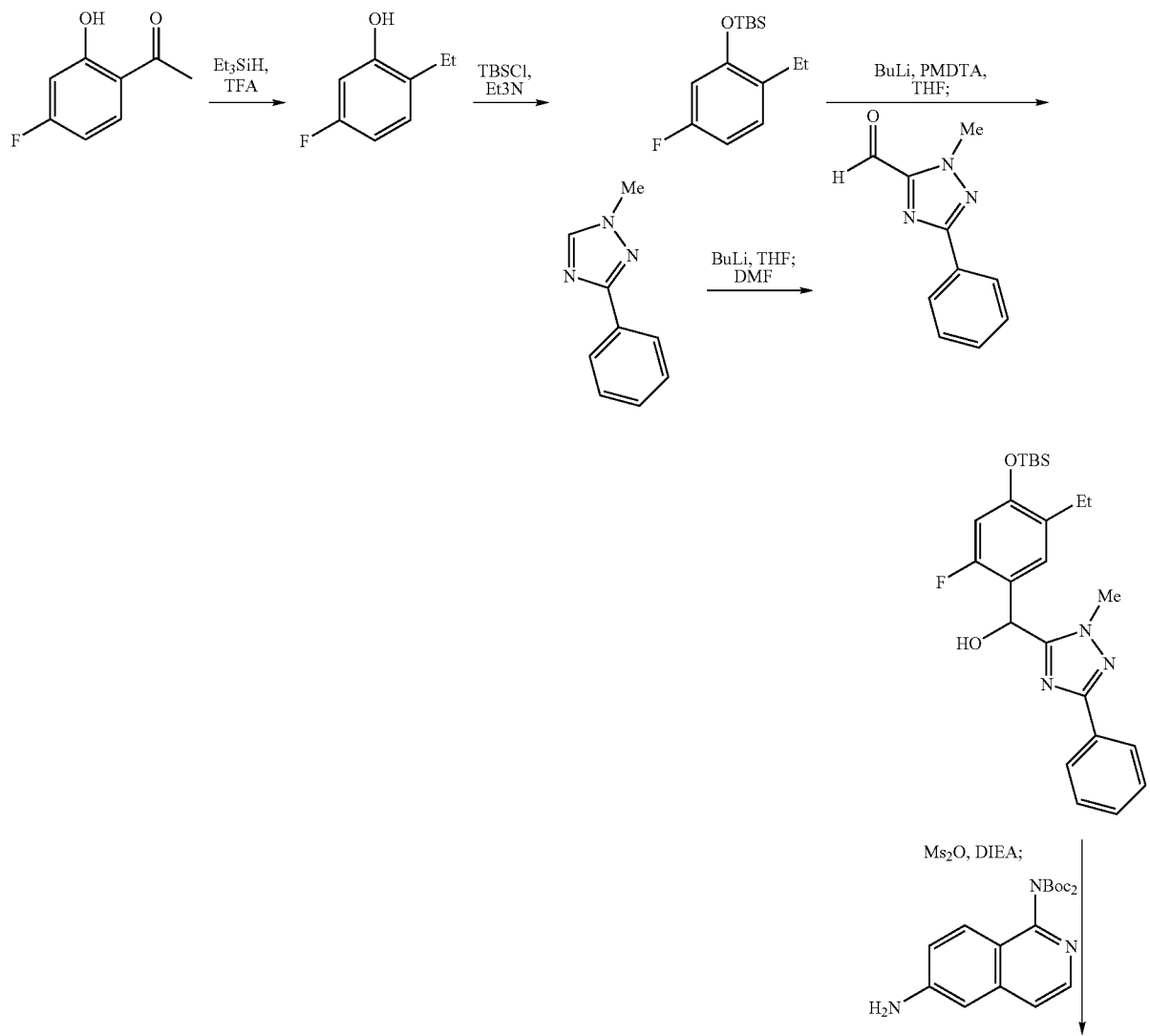

-continued

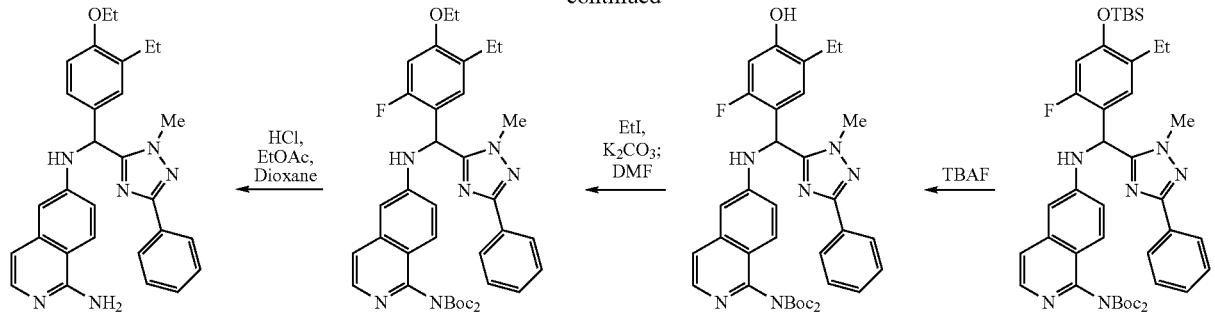

Example 386

2-methyl-5-phenyl-2H-1,2,4-triazole-3-carbaldehyde (386.1)

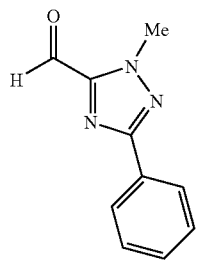

BuLi (10.6 mL, 1.6 M in hexane, 17.0 mmol) was added dropwise to at solution of 1-methyl-3-phenyl-1H-1,2,4-triazole (2.7 g, 17.0 mmol) in THF (85 mL) at −78° C. The mixture was warmed to −40° C. over 15 min and recooled to −78° C. DMF (1.32 mL, 17 mmol) was added dropwise and the mixture was warmed to ambient temperature over 2 h. Water was added to the mixture and it was extracted with EtOAc (3×). The organics were combined, washed with brine, dried (Na$_2$SO$_4$) and concentrated. Purification by flash chromatography (EtOAc, hexanes) yielded 2.75 g of Intermediate 386.1 as a white solid. $^1$H NMR (400 MHz, CDCl$_3$) δ ppm 4.22 (s, 3H) 7.34-7.56 (m, 3H) 8.10 (dd, J=7.58, 1.71 Hz, 2H) 10.03 (s, 1H).

tert-butyl(2-ethyl-5-fluorophenoxy)dimethylsilane (386.3)

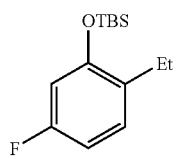

Triethylsilane (3.1 mL, 19.5 mmol) was added dropwise to a solution of 1-(4-fluoro-2-hydroxyphenyl)ethanone (1 g, 6.5 mmol) in TFA (13 mL). The mixture was stirred at ambient temperature and concentrated. Purification by flash chromatography (19:1, hexanes/EtOAc) afforded 600 mg of 2-ethyl-5-fluorophenol as a clear oil. Et$_3$N (1.2 mL, 8.6 mmol) and TBSCl (715 mg, 4.7 mmol) were added to a solution of intermediate 386.2 (600 mg, 4.3 mmol) in CH$_2$Cl$_2$ and the solution was stirred overnight. Water was added to the mixture and it was extracted with CH$_2$Cl$_2$. The organics were combined, washed with brine, dried (Na$_2$SO$_4$) and concentrated. Purification by flash chromatography (hexanes) yielded 768 mg of Intermediate 386.3 as a clear oil. $^1$H NMR (400 MHz, CDCl$_3$) δ ppm 0.23 (s, 6H) 1.01 (s, 9H) 1.15 (t, J=7.46 Hz, 3H) 2.55 (q, J=7.58 Hz, 2H) 6.49 (dd, J=10.52, 2.45 Hz, 1H) 6.59 (dt, J=8.38, 2.57 Hz, 1H) 7.01-7.08 (m, 1H).

(4-(tert-butyldimethylsilyloxy)-5-ethyl-2-fluorophenyl)(2-methyl-5-phenyl-2H-1,2,4-triazol-3-yl)methanol (386.4)

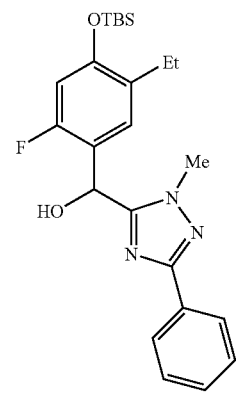

BuLi (0.67 mL, 1.6 M in hexanes, 1.1 mmol) was added dropwise to a solution of Intermediate 386.3 (250 mg, 0.98 mmol) and PMDTA (0.20 mL, 0.98 mmol) in THF (4 mL) at −78° C. The mixture was warmed to −40° C. and stirred for 30 min. After recooling the reaction to −78° C., Intermediate 386.1 (203 mg, 1.08 mmol) in THF (2 mL) was added and the mixture was warmed to ambient temperature over 2 h. Water was added to the mixture and it was extracted with EtOAc. The organics were combined, washed with brine, dried (Na$_2$SO$_4$) and concentrated. Purification by flash chromatography (hexanes, EtOAc) yielded 292 mg of Intermediate 386.4 as a clear oil. LCMS 442.34 (M+H).

293

N6-((4-(tert-butyldimethylsilyloxy)-5-ethyl-2-fluorophenyl)(2-methyl-5-phenyl-2H-1,2,4-triazol-3-yl)methyl)-N1,N1-di-(tert-butoxycarbonyl)isoquinoline-1,6-diamine (386.5)

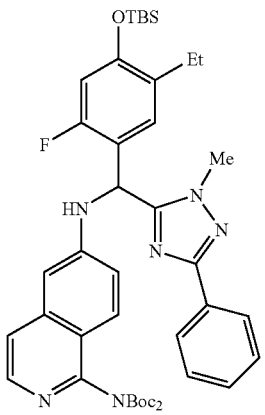

Methanesulfonic anhydride (184 mg, 1.3 mmol) was added to a solution of Intermediate 386.4 (292 mg, 0.66 mmol) and Et3N (0.30 mL, 2.2 mmol) in CH2Cl2 (5 mL) at 0° C. The mixture was stirred 1 h at 0° C., 1-(di-(tert-butyloxycarbonyl)amino)-6-aminoisoquinoline (475 mg, 1.3 mmol) was added and it was stirred 16 h at ambient temperature. Water (10 mL) was added and the mixture was extracted with EtOAc (3×25 mL). The organics were combined, washed with brine, dried (Na2SO4) and concentrated. Purification by flash chromatography (hexanes, EtOAc) yielded 280 mg of Intermediate 386.5 as a yellow solid. LCMS 783.53 (M+H).

4-[(N1,N1-di-(tert-butoxycarbonyl)1-aminoisoquinolin-6-ylamino](2-methyl-5-phenyl-2H-1,2,4-triazol-3-yl)methyl)-2-ethyl-5-fluorophenol (386.6)

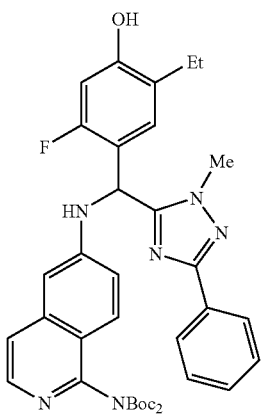

Intermediate 386.5 (280 mg, 0.35 mmol) was dissolved in THF (2 mL) and cooled to 0° C. TBAF (2 mL, 1 M in THF, 2 mmol) was added and the mixture was stirred at 0° C. for 2 h. The mixture was diluted with EtOAc (100 mL) and washed with brine, dried (Na2SO4) and concentrated. Purification by flash chromatography (hexanes, EtOAc) yielded 185 mg of Intermediate 386.6 as a yellow solid. LCMS 669.54 (M+H).

294

N6-((4-ethoxy-5-ethyl-2-fluorophenyl)(2-methyl-5-phenyl-2H-1,2,4-triazol-3-yl)methyl)-N1,N1-di-(tert-butoxycarbonyl)isoquinoline-1,6-diamine (386.7)

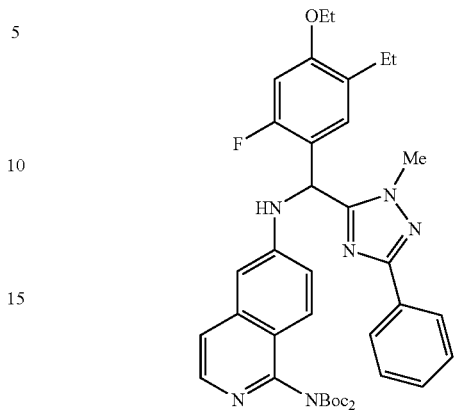

Potassium carbonate (50 mg) and EtI (0.033 mL, 0.40 mmol) were added to a solution of Intermediate 386.6 (90 mg, 0.14 mmol) in DMF (1 mL) and stirred at ambient temperature for 4 h. The mixture was diluted with EtOAc (50 mL), washed with brine, dried (Na2SO4) and concentrated. Purification by flash chromatography (hexanes, EtOAc) yielded 80 mg of Intermediate 386.7 as a yellow solid. LCMS 697.57 (M+H).

Example 386

HCl (2 mL, 4.0 M in dioxane) was added to a solution of Intermediate 386.7 (0.11 mmol) in EtOAc (2 mL) at 0° C. The mixture was stirred 16 h at ambient temperature. Concentration and purification by preparatory HPLC afforded 30 mg of Example 386 as a white solid. LCMS 497.38 (M+H); $^1$H NMR (400 MHz, CD3OD) δ ppm 1.06 (t, J=7.46 Hz, 3H) 1.38 (t, J=6.97 Hz, 3H) 2.52 (q, J=7.34 Hz, 2H) 3.88 (s, 3H) 4.02 (q, J=7.01 Hz, 2H) 6.36 (s, 1H) 6.78 (d, J=12.47 Hz, 1H) 6.80-6.91 (m, 2H) 7.16 (d, J=8.80 Hz, 1H) 7.30 (d, J=7.09 Hz, 1H) 7.33-7.44 (m, 3H) 7.94-8.02 (m, 2H) 8.10 (d, J=9.29 Hz, 1H).

Example 387

N6-((5-ethyl-2-fluoro-4-methoxyphenyl)(2-methyl-5-phenyl-2H-1,2,4-triazol-3-yl)methyl)isoquinoline-1,6-diamine trifluoroacetic acid salt

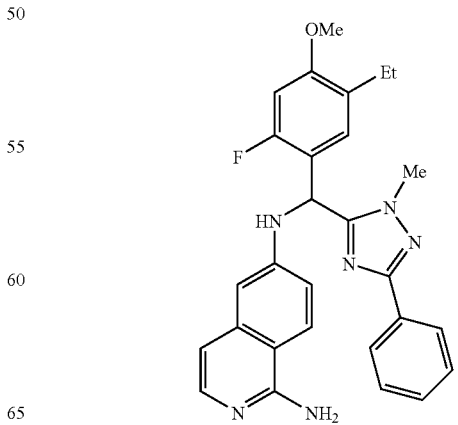

N[6]-((5-ethyl-2-fluoro-4-methoxyphenyl)(2-methyl-5-phenyl-2H-1,2,4-triazol-3-yl)methyl)-N[1],N[1]-di-(tert-butoxycarbonyl)isoquinoline-1,6-diamine (387.1)

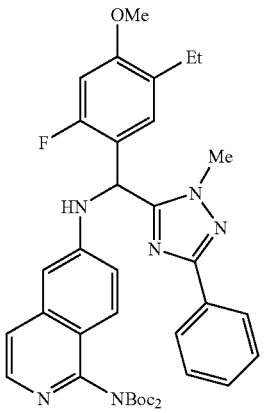

According to the procedure for Intermediate 386.6, Intermediate 385.5 (90 mg, 0.135 mmol) and MeI (0.025 mL, 0.4 mmol) gave 85 mg of Intermediate 387.1 as a yellow solid. LCMS 683.53 (M+H).

Example 387

Following the procedure for Example 386, Intermediate 387.1 (85 mg) afforded 30 mg of Example 387 as a white solid. LCMS 483.36 (M+H); $^1$H NMR (400 MHz, CD$_3$OD) δ ppm 1.04 (t, J=7.58 Hz, 3H) 2.51 (q, J=7.58 Hz, 2H) 3.81 (s, 3H) 3.88 (s, 3H) 6.37 (s, 1H) 6.72-6.92 (m, 3H) 7.17 (d, J=8.56 Hz, 1H) 7.23 (dd, J=9.17, 2.32 Hz, 1H) 7.30 (d, J=7.09 Hz, 1H) 7.33-7.43 (m, 3H) 7.93-8.03 (m, 2H) 8.10 (d, J=9.05 Hz, 1H).

Example 388

N[6]-((3,3-dimethyl-1,3-dihydroisobenzofuran-5-yl)(2-methyl-5-phenyl-2H-1,2,4-triazol-3-yl)methyl)isoquinoline-1,6-diamine trifluoroacetic acid salt

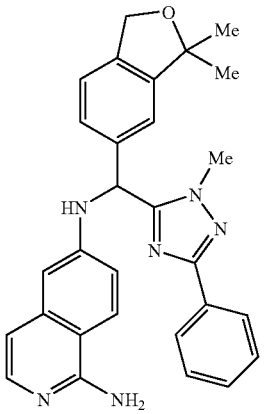

2-(5-bromo-2-(hydroxymethyl)phenyl)propan-2-ol (388.1)

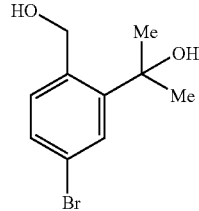

MeMgBr (3.1 mL, 3.0 M in Et$_2$O, 9.3 mmol) was added to a solution of 6-bromoisobenzofuran-1(3H)-one (1 g, 4.7 mmol) in THF (25 mL) at −78° C. The mixture was allowed to warm to ambient temperature over 2 h, quenched with sat. aq. NH$_4$Cl (10 mL) and extracted with EtOAc (3×50 mL). The organics were washed with brine, dried (Na$_2$SO$_4$) and concentrated to yield 1.11 g of Intermediate 388.1 as a white solid. $^1$H NMR (400 MHz, CDCl$_3$) δ ppm 1.64 (s, 1H) 4.77 (s, 2H) 7.15 (d, J=8.56 Hz, 1H) 7.36 (dd, J=8.56, 2.20 Hz, 1H) 7.46 (d, J=2.20 Hz, 1H).

6-bromo-1,1-dimethyl-1,3-dihydroisobenzofuran (388.2)

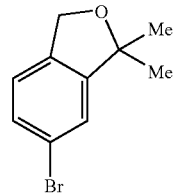

H$_2$SO$_4$ (0.4 mL conc, 1.6 mL H$_2$O) was added to a solution of Intermediate 388.1 (0.25 g, 1.02 mmol) in dioxane (2 mL). The mixture was stirred at 60° C., diluted with H$_2$O (10 mL), extracted with hexanes (2×25 mL). The organics were combined, washed with brine, dried (Na$_2$SO$_4$) and concentrated to yield 200 mg of Intermediate 388.2 as a clear oil. $^1$H NMR (400 MHz, CDCl$_3$) δ ppm 1.47 (s, 6H) 5.01 (s, 2H) 6.98 (m, 1H) 7.32 (m, 1H) 7.37 (m, 1H).

(3,3-dimethyl-1,3-dihydroisobenzofuran-5-yl)(2-methyl-5-phenyl-2H-1,2,4-triazol-3-yl)methanol (388.3)

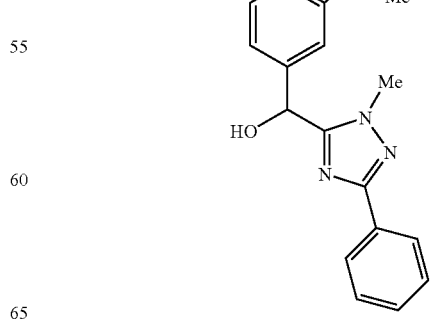

BuLi (0.36 mL, 1.6 M in hexanes, 0.57 mmol) was added dropwise to a solution of Intermediate 388.2 (110 mg, 0.49 mmol) in THF (5 mL) at −78° C. After stirring 5 min, a solution of Intermediate 386.1 (100 mg, 0.54 mmol) in THF (3 mL) was added. The mixture was warmed to 0° C. over 2 h and quenched with sat. NH$_4$Cl (1 mL). The mixture was diluted with H$_2$O (20 mL) and extracted with EtOAc (3×20 mL). The organics were combined, washed with brine, dried (Na$_2$SO$_4$) and concentrated. Purification by flash chromatography (hexanes, EtOAc) yielded 63 mg of Intermediate 388.3 as a white solid. $^1$H NMR (400 MHz, CDCl$_3$) δ ppm 1.37 (s, 6 H) 3.48 (s, 3H) 4.90 (s, 2H) 5.68 (s, 1H) 6.01 (s, 1H) 6.93-7.00 (m, 1H) 7.10-7.14 (m, 1H) 7.14-7.19 (m, 1H) 7.28-7.38 (m, 3H) 7.89-7.95 (m, 2H)

N$^6$-((3,3-dimethyl-1,3-dihydroisobenzofuran-5-yl)(2-methyl-5-phenyl-2H-1,2,4-triazol-3-yl)methyl)-N$^1$,N$^1$-di-(tert-butoxycarbonyl)isoquinoline-1,6-diamine (388.4)

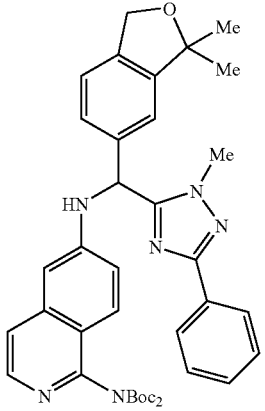

According to the procedure for Intermediate 386.4, Intermediate 388.3 (63 mg, 0.19 mmol) afforded 54 mg of Intermediate 386.5 as a clear oil. LCMS 677.56 (M+H).

Example 388

Following the procedure for Example 386, Intermediate 388.1 (54 mg, 0.080 mmol) afforded 26 mg of Example 388 as a white solid. LCMS 477.39 (M+H); $^1$H NMR (400 MHz, CD$_3$OD) δ ppm 1.46 (s, 6H) 3.91 (s, 3H) 5.02 (s, 2H) 6.28 (s, 1H) 6.79-6.95 (m, 2H) 7.19-7.28 (m, 2H) 7.31 (d, J=7.09 Hz, 1H) 7.35-7.46 (m, 5H) 7.99 (dd, J=7.46, 2.08 Hz, 2H) 8.11 (d, J=9.29 Hz, 1H).

Example 389

N$^6$-((2,3-dihydrobenzofuran-5-yl)(2-methyl-5-phenyl-2H-1,2,4-triazol-3-yl)methyl)isoquinoline-1,6-diamine trifluoroacetic acid salt

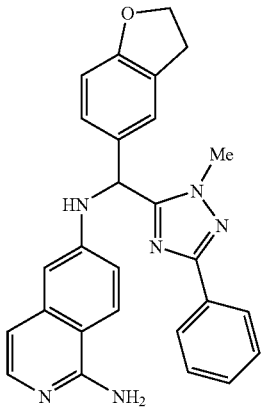

(2,3-dihydrobenzofuran-5-yl)(2-methyl-5-phenyl-2H-1,2,4-triazol-3-yl)methanol (389.1)

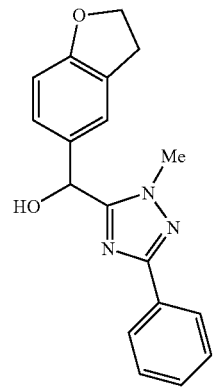

According to the procedure for Intermediate 388.3, 5-bromo-2,3-dihydrobenzofuran (100 mg, 0.5 mmol) was converted to 67 mg of Intermediate 389.1. $^1$H NMR (400 MHz, CDCl$_3$) δ ppm 3.09 (t, J=8.68 Hz, 2H) 3.54 (s, 3H) 4.51 (t, J=8.68 Hz, 2H) 5.97 (s, 1H) 6.70 (d, J=8.31 Hz, 1H) 7.07 (d, J=8.07 Hz, 1H) 7.11-7.17 (m, 1H) 7.33-7.45 (m, 3H) 7.97-8.07 (m, 2H).

N$^6$-((2,3-dihydrobenzofuran-5-yl)(2-methyl-5-phenyl-2H-1,2,4-triazol-3-yl)methyl)-N$^1$,N$^1$-di-(tert-butoxycarbonyl)isoquinoline-1,6-diamine (389.2)

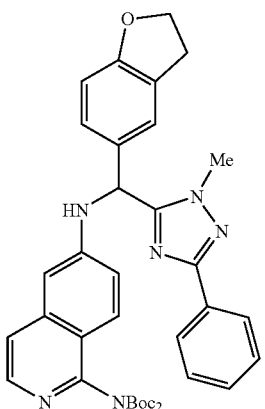

According to the procedure for Intermediate 386.4, Intermediate 389.1 (67 mg, 0.22 mmol) afforded 58 mg of Intermediate 388.2 as a clear oil. LCMS 649.52 (M+H).

Example 389

Following the procedure for Example 386, Intermediate 388.1 (58 mg, 0.090 mmol) afforded 25 mg of Example 389 as a white solid. LCMS 449.33 (M+H); $^1$H NMR (400 MHz, CD$_3$OD) δ ppm 3.17 (t, J=8.68 Hz, 2H) 3.88 (s, 3H) 4.52 (t, J=8.68 Hz, 2H) 6.14 (s, 1H) 6.85 (d, J=7.09 Hz, 1H) 7.18-7.26 (m, 2H) 7.26-7.35 (m, 2H) 7.34-7.48 (m, 3H) 7.91-8.04 (m, 2H) 8.09 (d, J=9.05 Hz, 1H).

Example 390

N$^6$-((4-chloro-5-ethyl-2-fluorophenyl)(2-methyl-5-phenyl-2H-1,2,4-triazol-3-yl)methyl)isoquinoline-1,6-diamine trifluoroacetic acid salt

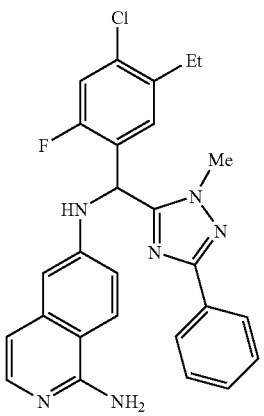

2-chloro-1-ethyl-4-fluorobenzene (390.1)

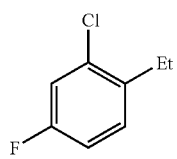

Et$_3$SiH (2.3 mL, 14.5 mmol) was added to a solution of 1-(2-chloro-4-fluorophenyl)ethanone (1 g, 5.8 mmol) in TFA (12 mL) and the mixture was stirred for 4 h at ambient temperature. Concentration and purification by flash chromatography (hexanes) afforded 650 mg of Intermediate 790.1 as a clear oil. $^1$H NMR (400 MHz, CDCl$_3$) δ ppm 1.20 (t, J=7.58 Hz, 3H) 2.71 (q, J=7.58 Hz, 2H) 6.86-6.94 (m, 1H) 7.08 (dd, J=8.68, 2.57 Hz, 1H) 7.17 (dd, J=8.44, 6.24 Hz, 1H).

4-chloro-5-ethyl-2-fluorobenzaldehyde (390.2)

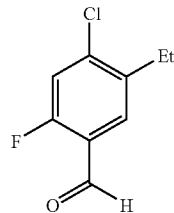

TiCl$_4$ (0.90 mL) was added to 2-chloro-1-ethyl-4-fluorobenzene (645 mg, 4.1 mmol) at 0° C. and stirred to 10 min. Dichloro(methoxy)methane (0.725 mL) was added and the mixture was stirred overnight at ambient temperature. The mixture was diluted with CH$_2$Cl$_2$ (50 mL) and poured onto crushed ice (40 g). After stirring 30 min the layers were separated. The organic layer was washed with H$_2$O (2×), brine (2×), dried (Na$_2$SO$_4$) and concentrated. Purification by flash chromatography (hexanes, EtOAc) yielded 440 mg of intermediate 390.2 as a light brown oil. $^1$H NMR (400 MHz, CDCl$_3$) δ ppm 1.18 (t, J=7.58 Hz, 3H) 2.69 (q, J=7.58 Hz, 2H) 7.05-7.29 (m, 1H) 7.67 (m, 1H) 10.23 (s, 1H).

(4-chloro-5-ethyl-2-fluorophenyl)(2-methyl-5-phenyl-2H-1,2,4-triazol-3-yl)methanol (390.3)

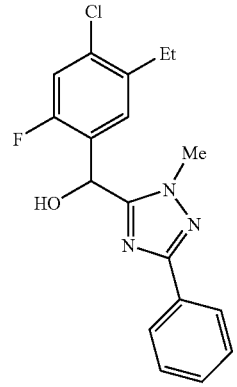

According to the procedure for Intermediate 370.2, 1-methyl-3-phenyl-1H-1,2,4-triazole (80 mg, 0.50 mmol) and Intermediate 390.2 (105 mg, 0.55 mmol) afforded 156 mg of Intermediate 390.3 as a white solid. LCMS 346.26 (M+H).

Example 390

According to the procedure for Intermediate 386.5, Intermediate 390.3 (88 mg, 0.25 mmol) afforded the crude di-Boc protected intermediate. Following the procedure for Example 386 afforded 49 mg of Example 393 as a white solid. LCMS 487.32 (M+H); $^1$H NMR (400 MHz, CD$_3$OD) δ ppm 1.09 (t, J=7.58 Hz, 3H) 2.66 (q, J=7.58 Hz, 2H) 3.93 (s, 3H) 6.44 (s, 1H) 6.80-6.90 (m, 2H) 7.21-7.29 (m, 2H) 7.31 (d, J=7.09 Hz, 1H) 7.34-7.43 (m, 4H) 7.91-8.00 (m, 2H) 8.13 (d, J=9.29 Hz, 1H).

Example 391

N[6]-((2,4-difluoro-5-methoxyphenyl)(2-methyl-5-phenyl-2H-1,2,4-triazol-3-yl)methyl)isoquinoline-1,6-diamine trifluoroacetic acid salt

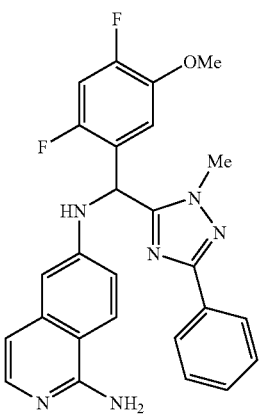

2,4-difluoro-5-methoxybenzaldehyde (391.1)

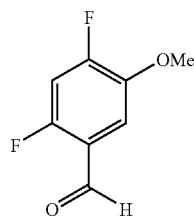

Following the procedure for Intermediate 390.2, 2-chloro-4-fluoro-1-methoxybenzene (1.0 g, 6.3 mmol) afforded 830 mg of Intermediate 391.1 as a white solid. $^1$H NMR (400 MHz, CDCl$_3$) δ ppm 3.91 (s, 3H) 7.18-7.29 (m, 1H) 7.32 (d, J=5.81 Hz, 1H) 10.27 (s, 1H).

(2,4-difluoro-5-methoxyphenyl)(2-methyl-5-phenyl-2H-1,2,4-triazol-3-yl)methanol (391.2)

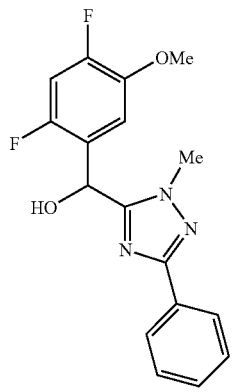

According to the procedure for Intermediate 370.2, 1-methyl-3-phenyl-1H-1,2,4-triazole (70 mg, 0.44 mmol) and Intermediate 391.1 (80 mg, 0.48 mmol) afforded 108 mg of Intermediate 391.2 as a white solid. LCMS 332.28 (M+H).

Example 391

According to the procedure for Intermediate 386.5, Intermediate 391.2 (95 mg, 0.29 mmol) afforded the crude di-Boc protected intermediate. Following the procedure for Example 386 afforded 49 mg of Example 391 as a white solid. LCMS 473.36 (M+H); $^1$H NMR (400 MHz, CD$_3$OD) δ ppm 3.76 (s, 3H) 3.95 (s, 3H) 6.43 (s, 1H) 6.75-6.92 (m, 2H) 7.08 (t, J=10.39 Hz, 1H) 7.17-7.28 (m, 2H) 7.29-7.44 (m, 4H) 7.97 (dd, J=7.70, 1.83 Hz, 2H) 8.13 (d, J=9.29 Hz, 1H).

Example 392

N[6]-((4-chloro-2-fluoro-5-methoxyphenyl)(2-methyl-5-phenyl-2H-1,2,4-triazol-3-yl)methyl)isoquinoline-1,6-diamine trifluoroacetic acid salt

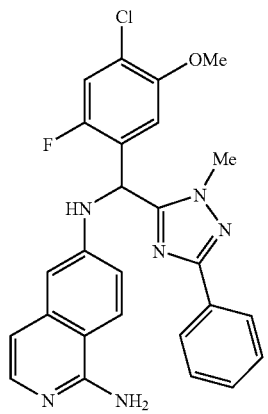

4-chloro-2-fluoro-5-methoxybenzaldehyde (392.1)

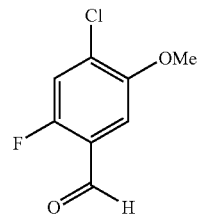

Following the procedure for Intermediate 390.2, 2-chloro-4-fluoro-1-methoxybenzene (1.0 g, 6.3 mmol) afforded 840 mg of Intermediate 392.1 as a white solid. $^1$H NMR (400 MHz, CDCl$_3$) δ ppm 3.91 (s, 3H) 6.90-7.00 (m, 1H) 7.41 (dd, J=9.35, 6.32 Hz, 1H) 10.27 (s, 1H)

(4-chloro-2-fluoro-5-methoxyphenyl)(2-methyl-5-phenyl-2H-1,2,4-triazol-3-yl)methanol (392.2)

According to the procedure for Intermediate 370.2, 1-methyl-3-phenyl-1H-1,2,4-triazole (65 mg, 0.40 mmol) and Intermediate 392.1 (80 mg, 0.45 mmol) afforded 94 mg of Intermediate 392.2 as a white solid. LCMS 348.25 (M+H).

Example 392

According to the procedure for Intermediate 386.5, Intermediate 392.2 (95 mg, 0.29 mmol) afforded the crude di-Boc protected intermediate. Following the procedure for Example 386 afforded 43 mg of Example 392 as a white solid. LCMS 489.31 (M+H); $^1$H NMR (400 MHz, CD$_3$OD) δ ppm 3.76 (s, 3H) 3.96 (s, 3H) 6.45 (s, 1H) 6.81-6.94 (m, 2H) 7.20 (d, J=6.36 Hz, 2H) 7.22-7.34 (m, 3H) 7.33-7.43 (m, 3H) 7.91-8.03 (m, 2H) 8.14 (d, J=9.29 Hz, 1H).

Example 393

N$^6$-((7-ethyl-3-methylbenzofuran-5-yl)(2-methyl-5-phenyl-2H-1,2,4-triazol-3-yl)methyl)isoquinoline-1,6-diamine trifluoroacetic acid salt

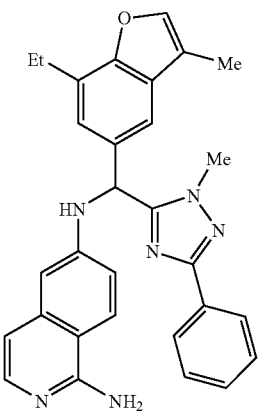

(7-ethyl-3-methyl benzofuran-5-yl)(2-methyl-5-phenyl-2H-1,2,4-triazol-3-yl)methanol (393.1)

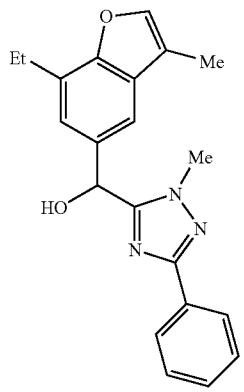

According to the procedure for Intermediate 388.3, 5-bromo-7-ethyl-3-methylbenzofuran (103 mg, 0.43 mmol) was converted to 100 mg of Intermediate 393.1 as a yellow oil. LCMS 348.33 (M+H).

Example 393

According to the procedure for Intermediate 386.5, Intermediate 393.1 (100 mg, 0.29 mmol) afforded the crude di-Boc protected intermediate. Following the procedure for Example 386 afforded 39 mg of Example 393 as a white solid. LCMS 489.46 (M+H); $^1$H NMR (400 MHz, CD$_3$OD) δ ppm 1.26 (t, J=7.58 Hz, 3H) 2.17 (d, J=1.22 Hz, 3H) 2.86 (q, J=7.42 Hz, 2H) 3.87 (s, 3H) 6.33 (s, 1H) 6.71-6.92 (m, 2H) 7.16-7.29 (m, 3H) 7.31-7.39 (m, 3H) 7.51 (dd, J=3.67, 1.47 Hz, 2H) 7.93-8.00 (m, 2H) 8.06 (d, J=9.05 Hz, 1H).

Example 394

N$^6$-((2-methyl-5-phenyl-2H-1,2,4-triazol-3-yl)(3-methylbenzofuran-5-yl)methyl)isoquinoline-1,6-diamine trifluoroacetic acid salt

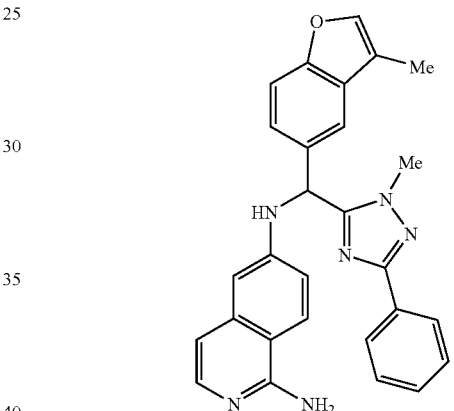

(2-methyl-5-phenyl-2H-1,2,4-triazol-3-yl)(3-methyl-benzofuran-5-yl)methanol (394.1)

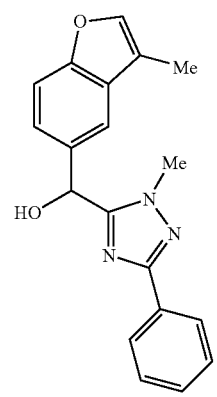

According to the procedure for Intermediate 388.3, 5-bromo-7-ethyl-3-methylbenzofuran (90 mg, 0.43 mmol) was converted to 85 mg of Intermediate 394.1 as a colorless oil. LCMS 302.29(M+H).

Example 394

According to the procedure for Intermediate 386.5, Intermediate 394.1 (85 mg, 0.27 mmol) afforded the crude di-Boc protected intermediate. Following the procedure for Example 386 afforded 20 mg of Example 394 as a white solid. LCMS 461.43 (M+H); $^1$H NMR (400 MHz, CD$_3$OD) δ ppm 2.21 (d, J=1.47 Hz, 3H) 3.89 (s, 3H) 6.36 (s, 1H) 6.82-6.88 (m, 2H) 7.21-7.31 (m, 2H) 7.37-7.44 (m, 4H) 7.46-7.51 (m, 1H) 7.54 (d, J=1.22 Hz, 1H) 7.72 (d, J=1.71 Hz, 1H) 7.96-8.03 (m, 2H) 8.10 (d, J=9.29 Hz, 1H).

Example 395

N$^6$-((5-ethyl-2-fluoro-4-isopropoxyphenyl)(2-methyl-5-phenyl-2H-1,2,4-triazol-3-yl)methyl)isoquinoline-1,6-diamine trifluoroacetic acid salt

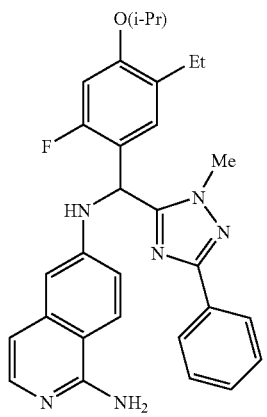

According to the procedure for Intermediate 386.6, Intermediate 385.5 (50 mg, 0.075 mmol) and iPrI (0.022 mL, 0.4 mmol) gave 31 mg of Intermediate 395.1 as a clear oil. LCMS 711.71 (M+H).

Example 395

Following the procedure for Example 386, Intermediate 395.1 (31 mg) afforded 20 mg of Example 395 as a white solid. LCMS 511.47 (M+H); $^1$H NMR (400 MHz, CD$_3$OD) δ ppm 1.05 (t, J=7.46 Hz, 3H) 1.31 (d, J=5.87 Hz, 6H) 2.50 (q, J=7.50 Hz, 2H) 3.89 (s, 3H) 4.53-4.64 (m, 1H) 6.35 (s, 1H) 6.76-6.91 (m, 3H) 7.15 (d, J=8.80 Hz, 1H) 7.23 (dd, J=9.29, 2.45 Hz, 1H) 7.30 (d, J=7.09 Hz, 1H) 7.35-7.43 (m, 3H) 7.95-8.02 (m, 2H) 8.10 (d, J=9.29 Hz, 1H).

Example 396

N$^6$-((4-(benzyloxy)-5-ethyl-2-fluorophenyl)(2-methyl-5-phenyl-2H-1,2,4-triazol-3-yl)methyl)isoquinoline-1,6-diamine trifluoroacetic acid salt

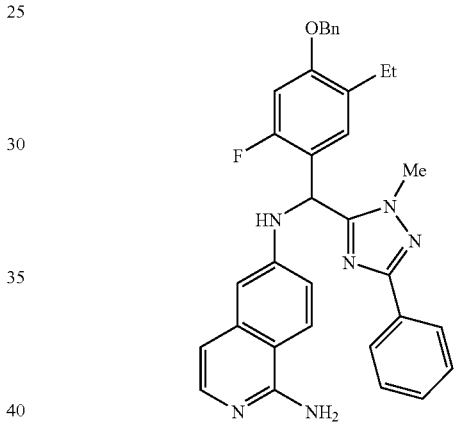

N$^6$-((5-ethyl-2-fluoro-4-isopropoxyphenyl)(2-methyl-5-phenyl-2H-1,2,4-triazol-3-yl)methyl)-N$^1$,N$^1$-di-(tert-butoxycarbonyl)isoquinoline-1,6-diamine (395.1)

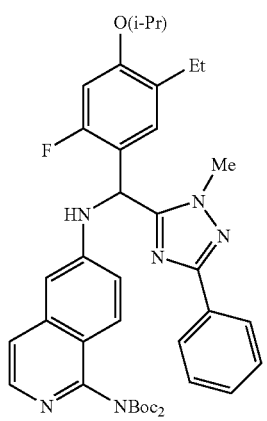

N$^6$-((4-(benzyloxy)-5-ethyl-2-fluorophenyl)(2-methyl-5-phenyl-2H-1,2,4-triazol-3-yl)methyl)-N$^1$,N$^1$-di-(tert-butoxycarbonyl)isoquinoline-1,6-diamine (396.1)

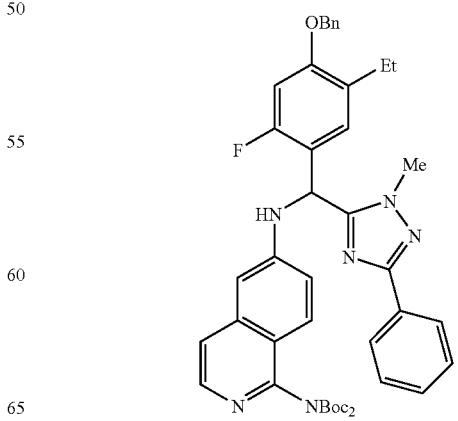

307

According to the procedure for Intermediate 386.6, Intermediate 385.5 (50 mg, 0.075 mmol) and BnBr (0.009 mL, 0.075 mmol) gave 46 mg of Intermediate 396.1 as a clear oil. LCMS 759.75 (M+H).

Example 396

Following the procedure for Example 386, Intermediate 396.1 (46 mg) afforded 20 mg of Example 396 as a white solid. LCMS 559.49 (M+H); $^1$H NMR (400 MHz, CD$_3$OD) δ ppm 1.08 (t, J=7.46 Hz, 3H) 2.57 (q, J=7.42 Hz, 2H) 3.88 (s, 3H) 5.08 (s, 2H) 6.37 (s, 1H) 6.81-6.91 (m, 3H) 7.18-7.26 (m, 2H) 7.28-7.43 (m, 9H) 7.96-8.01 (m, 2H) 8.10 (d, J=9.29 Hz, 1H).

Example 397

N$^6$-((5-ethyl-2-fluoro-3-morpholinophenyl)(4-(pyridin-3-yl)-1H-imidazol-2-yl)methyl)isoquinoline-1,6-diamine.2.5 TFA salt

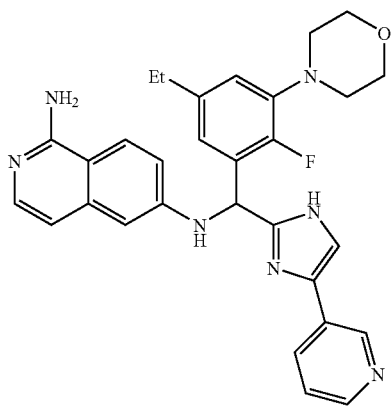

According to the procedure for the preparation of Example 228, Intermediate 230.1 (47 mg) was coupled with pyridine-3-ylboronic acid, then treated with TFA and purified by preparative HPLC to afford Example 397. LCMS (2 min gradient) RT=1.10 min, 524.23 (M+H)$^+$; $^1$H NMR (400 MHz, CD$_3$OD) δ ppm 1.16 (t, J=7.69 Hz, 3H) 2.58 (q, J=7.76 Hz, 2H) 3.08 (q, J=3.95 Hz, 4H) 3.83 (t, J=4.61 Hz, 4H) 6.28 (s, 1H) 6.78 (d, J=2.20 Hz, 1H) 6.87 (d, J=6.59 Hz, 2H) 6.93 (d, J=7.91 Hz, 1H) 7.23 (dd, J=9.23, 2.20 Hz, 1H) 7.33 (d, J=7.03 Hz, 1H) 7.86 (dd, J=8.35, 5.27 Hz, 1H) 7.89 (s, 1H) 8.14 (d, J=9.23 Hz, 1H) 8.61 (d, J=4.39 Hz, 1H) 8.65 (d, J=8.35 Hz, 1H) 9.09 (s, 1H).

308

Example 398

2-(2-((1-aminoisoquinolin-6-ylamino)(5-ethyl-2-fluoro-3-(2-oxopyrrolidin-1-yl)phenyl)methyl)-1H-imidazol-4-yl)benzamide bis-trifluoroacetic acid salt

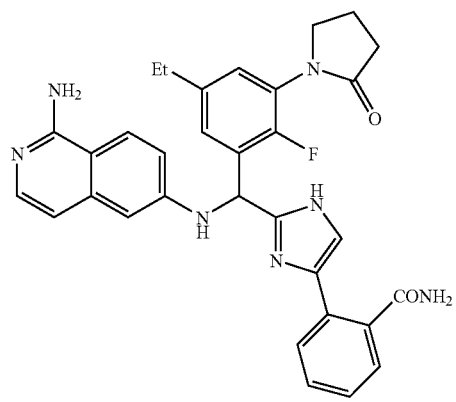

3-bromo-5-ethyl-2-fluorobenzaldehyde (398.1)

To a solution of diisopropylamine (0.449 mL, 3.20 mmol) in 10 mL THF at −15° C., was added BuLi (1.6M, 1.85 mL, 2.95 mmol). The mixture was stirred 10 min at −10° C., then was cooled to −78° C. A solution of 2-bromo-4-ethyl-1-fluorobenzene (228.1) in 2 mL THF was added, then the mixture was stirred at −70° C. for 25 min. DMF (0.381 mL, 4.92 mmol) was added, then the reaction was removed from the cooling bath and stirred 30 min. The reaction was quenched with sat. NH$_4$Cl, then was diluted with EtOAc. The organic phase was washed with H$_2$O and brine, dried (Na$_2$SO$_4$) and concentrated. The crude product was purified by flash chromatography (0-20% EtOAc/hexanes gradient) to afford 429 mg of Intermediate 398.1 at a colorless solid. LCMS (2 min gradient) RT=1.70 min, 231.0 (M+H)$^+$; $^1$H NMR (400 MHz, CDCl$_3$) δ ppm 1.25 (t, J=7.69 Hz, 3H) 2.67 (q, J=7.47 Hz, 2H) 7.61-7.66 (m, 2H) 10.33 (s, 1H).

3-bromo-5-ethyl-2-fluorobenzaldehyde (398.2)

To Intermediate 398.1 (115 mg, 0.50 mmol), Xantphos (22 mg, 0.0375 mmol), Cs$_2$CO$_3$ (228 mg, 0.700 mmol), 2-pyrrolidinone (46 µL, 0.60 mmol) and Pd$_2$dba$_3$ (11.5 mg), was added 2 mL dioxane. The mixture was stirred at 105° C. for 64 h in a sealed tube, then was diluted with EtOAc. The suspension was filtered and the filtrate concentrated. The crude product was purified by flash chromatography (0 to 80% EtOAc/hexanes gradient) to afford 77 mg of Intermediate 398.2 as a yellow oil. LCMS (2 min gradient) RT=1.25 min, 236.19 (M+H)$^+$.

1-(3-((4-bromo-1-trityl-1H-imidazol-2-yl)(hydroxy)methyl)-5-ethyl-2-fluorophenyl)pyrrolidin-2-one (398.3)

To a solution of 4-bromo-1-trityl-1H-imidazole (83 mg, 0.213 mmol) in 3 mL THF at 0° C., was added BuLi (1.6M, 146 µL, 0.234 mmol). The white suspension was stirred at 0° C. for 45 min, then a solution of 398.2 (50 mg, 0.213 mmol) in 0.6 mL THF was added. The mixture was removed from the ice bath and stirred 25 min, then was quenched with sat.

NH$_4$Cl. The mixture was diluted with EtOAc and was washed with H$_2$O and brine, dried (Na$_2$SO$_4$) and concentrated. The crude product was purified by flash chromatography (0-100% EtOAc/hexanes gradient) to afford 67.5 mg of Intermediate 398.3 at a colorless solid. LCMS (2 min gradient) RT=2.12 min, 646.41 (M+Na)$^+$.

di-tert-butyl (6-{[(4-bromo-1-trityl-1H-imidazol-2-yl) (5-ethyl-2-fluoro-3-(2-oxopyrrolidin-1-yl)phenyl) methyl]amino}isoquinolin-1-yl)imidodicarbonate (398.4)

According to the procedure for the preparation of Intermediate 206.4, Intermediate 398.3 (65 mg, 0.104 mmol) was converted to the chloro intermediate, then displaced with di-tert-butyl (6-aminoisoquinolin-1-yl)imidodicarbonate (rt for 14 h) to afford after flash chromatography (0 to 100% EtOAc/hexanes gradient) 53.3 mg of Intermediate 398.4 as a colorless solid. LCMS (2 min gradient) RT=2.14 min, 723.1 (M+(H−Tr)+H)$^+$.

Example 398

According to the procedure for the preparation of Example 206, coupling of Intermediate 398.4 (40 mg, 0.042 mmol) and 2-carbamoylphenylboronic acid, followed by deprotection and HPLC purification afforded 18.1 mg of Example 398. LCMS (2 min gradient) RT=1.02 min, 564.22 (M+H)$^+$; $^1$H NMR (400 MHz, CD$_3$OD) δ ppm 1.22 (t, J=7.69 Hz, 3H) 2.22-2.30 (m, 2H) 2.58 (t, J=7.91 Hz, 2H) 2.68 (q, J=7.62 Hz, 2H) 3.83-3.91 (m, 2H) 6.49 (s, 1H) 6.90 (d, J=2.64 Hz, 1H) 6.99 (d, J=7.03 Hz, 1H) 7.26 (dd, J=9.23, 2.64 Hz, 1H) 7.29 (dd, J=6.37, 1.98 Hz, 1H) 7.37-7.40 (m, 2H) 7.54-7.63 (m, 4H) 7.69-7.71 (m, 1H) 8.20 (d, J=9.23 Hz, 1H).

Example 399

2-(2-((1-aminoisoquinolin-6-ylamino)(5-ethyl-2-fluoro-3-(3-methyl-2-oxoimidazolidin-1-yl)phenyl) methyl)-1H-imidazol-4-yl)benzamide bis-trifluoroacetic acid salt

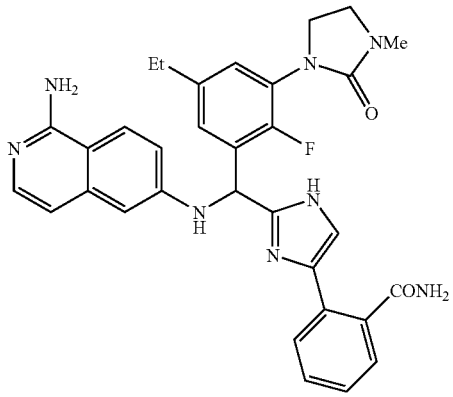

According to the procedure for the preparation of Example 398, replacement of 2-pyrrolidinone with 1-methyl-2-imidazolidinone afforded Example 399. LCMS (2 min gradient) RT=1.02 min, 579.21 (M+H)$^+$; $^1$H NMR (400 MHz, CD$_3$OD) δ ppm 1.21 (t, J=7.47 Hz, 3H) 2.66 (q, J=7.47 Hz, 2H) 2.87 (s, 3H) 3.57 (t, J=8.13 Hz, 2H) 3.85 (q, J=8.06 Hz, 2H) 6.49 (s, 1H) 6.90 (d, J=2.20 Hz, 1H) 6.99 (d, J=7.03 Hz, 1H) 7.21 (dd, J=6.37, 1.98 Hz, 1H) 7.26 (dd, J=9.23, 2.64 Hz, 1H) 7.37-7.41 (m, 2H) 7.55-7.62 (m, 4H) 7.69-7.72 (m, 1H) 8.20 (d, J=9.23 Hz, 1H).

Example 400

2-(2-((1-aminoisoquinolin-6-ylamino)(3-ethoxy-5-ethyl-2-fluorophenyl)methyl)-4-phenyl-1H-imidazol-1-yl)acetic acid

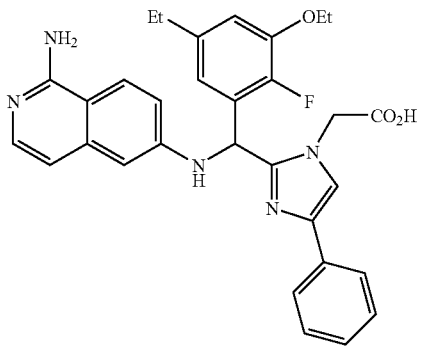

di-tert-butyl (6-{[(4-bromo-1H-imidazol-2-yl) (3-ethoxy-5-ethyl-2-fluorophenyl)methyl] amino}isoquinolin-1-yl)imidodicarbonate (400.1)

A solution of Intermediate 198.1 (100 mg) in 2 mL 90% aq. AcOH was stirred at 50° C. for 1 h, then concentrated. The residue was diluted with EtOAc and washed with sat. NaHCO$_3$, H$_2$O and brine, dried (Na$_2$SO$_4$) and concentrated. The crude product was purified by flash chromatography (0-100% EtOAc/hexanes gradient) to afford 53 mg of intermediate 400.1 at a yellow solid. LCMS (2 min gradient) RT=1.78 min, 684.2 (M+H)$^+$.

tert-butyl 2-(2-((1-(di-tert-butyl imidodicarbonate) isoquinolin-6-ylamino)(3-ethoxy-5-ethyl-2-fluorophenyl)methyl)-4-bromo-1H-imidazol-1-yl)acetate (400.2)

To a solution of Intermediate 400.1 (50 mg, 0.073 mmol) in 1 mL THF at rt, was added NaH (60%, 7.3 mg, 0.183 mmol). The mixture was stirred at rt for 5 min, then added tert-butyl bromoacetate (11.9 μL, 0.0803 mmol). The mixture was stirred for 20 min, then additional tert-butyl bromoacetate (2 μL) was added. The mixture was stirred for 1 h, then was quenched with sat. NH$_4$Cl. The mixture was diluted with EtOAc and was washed with H$_2$O and brine, dried (Na$_2$SO$_4$) and concentrated. The crude product was purified by flash chromatography (0-60% EtOAc/hexanes gradient) to afford 42 mg of Intermediate 400.2 at a tan solid. LCMS (2 min gradient) RT=1.95 min, 798.2 (M+H)$^+$.

Example 400

According to the procedure for the preparation of Example 206, coupling of Intermediate 400.2 (21 mg, 0.026 mmol) and phenylboronic acid, followed by deprotection and HPLC purification afforded 4.5 mg of Example 400. LCMS (2 min gradient) RT=1.31 min, 540.10 (M+H)$^+$; $^1$H NMR (400 MHz, METHANOL-D3) δ ppm 1.19 (t, J=7.47 Hz, 3H) 1.40 (t, J=6.59 Hz, 3H) 2.60 (q, J=7.76 Hz, 2H) 4.12 (q, J=7.03 Hz, 2H) 4.81 (d, J=18.02 Hz, 1H) 5.08 (d, J=18.02 Hz, 1H) 6.36 (s, 1H) 6.79-6.82 (m, 1H) 6.92-6.95 (m, 2H) 7.04 (dd, J=7.91, 1.76 Hz, 1H) 7.28 (dd, J=9.23, 2.20 Hz, 1H) 7.35 (d, J=7.47 Hz, 1H) 7.39-7.46 (m, 3H) 7.66 (dd, J=8.13, 1.10 Hz, 2H) 7.81 (s, 1H) 8.17 (d, J=9.23 Hz, 1H).

Example 401

2-(2-((1-aminoisoquinolin-6-ylamino)(3-ethoxy-5-ethyl-2-fluorophenyl)methyl)-4-(2-carbamoylphenyl)-1H-imidazol-1-yl)acetic acid According to the procedure for the preparation of Example 206, coupling of Intermediate 400.2 (21 mg, 0.026 mmol) and 2-carbamoylphenylboronic acid, followed by deprotection and HPLC purification afforded 4.0 mg of Example 401. LCMS (2 min gradient) RT=1.15 min, 583.14 (M+H)$^+$; $^1$H NMR (400 MHz, METHANOL-D3) δ ppm 1.20 (t, J=7.47 Hz, 3H) 1.41 (t, J=7.03 Hz, 3H) 2.62 (q, J=7.62 Hz, 2H) 4.13 (q, J=7.03 Hz, 2H) 4.78 (d, J=18.02 Hz, 1H) 5.10 (d, J=18.02 Hz, 1H) 6.38 (s, 1H) 6.79 (d, J=3.96 Hz, 1H) 6.96 (dd, J=4.83, 2.20 Hz, 2H) 7.05 (d, J=7.91 Hz, 1H) 7.26 (dd, J=9.01, 2.42 Hz, 1H) 7.37 (d, J=7.03 Hz, 1H) 7.50-7.60 (m, 3H) 7.64-7.67 (m, 1H) 7.68 (s, 1H) 8.17 (d, J=9.23 Hz, 1H).

Example 402

2-(2-((1-aminoisoquinolin-6-ylamino)(3-ethoxy-5-ethyl-2-fluorophenyl)methyl)-4-phenyl-1H-imidazol-1-yl)acetamide bis-trifluoroacetic acid

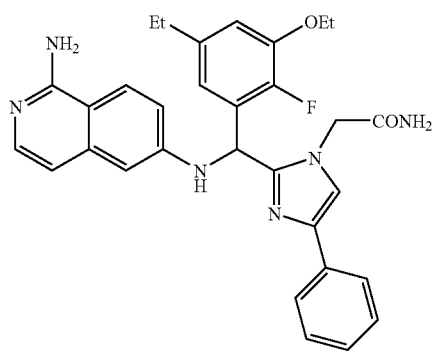

To a mixture of Example 400 (15 mg, 0.020 mmol) and ammonium chloride (4.2 mg, 0.078 mmol) in 0.5 mL DMF, were added TEA (27.2 µL, 0.195 mmol) and BOP (12.9 mg, 0.0293 mmol). The mixture was stirred at rt for 1 h, then was purified by preparative HPLC to afford 10.5 mg of Example 402 as a white powder. LCMS (2 min gradient) RT=1.36 min, 539.11 (M+H)$^+$; $^1$H NMR (400 MHz, CD$_3$OD) δ ppm 1.18 (t, J=7.69 Hz, 3H) 1.41 (t, J=7.03 Hz, 3H) 2.60 (q, J=7.47 Hz, 2H) 4.13 (q, J=7.03 Hz, 2H) 4.65 (d, J=17.14 Hz, 1H) 4.96 (d, J=17.58 Hz, 1H) 6.28 (s, 1H) 6.75 (dd, J=5.71, 1.32 Hz, 1H) 6.96 (d, J=7.03 Hz, 1H) 7.01 (d, J=2.20 Hz, 1H) 7.04 (d, J=7.91 Hz, 1H) 7.28 (dd, J=9.23, 2.64 Hz, 1H) 7.33-7.44 (m, 4H) 7.66 (d, J=7.03 Hz, 2H) 7.74 (s, 1H) 8.16 (d, J=9.23 Hz, 1H).

Example 403

2-(2-((1-aminoisoquinolin-6-ylamino)(3-ethoxy-5-ethyl-2-fluorophenyl)methyl)-4-phenyl-1H-imidazol-1-yl)-N-methylacetamide bis-trifluoroacetic acid

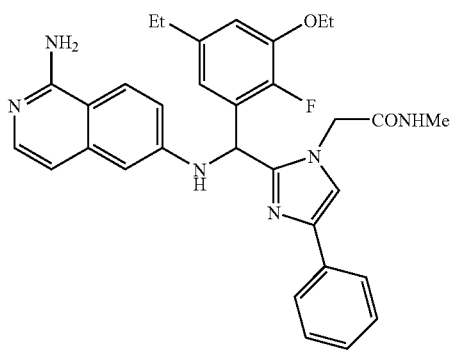

According to the procedure for the preparation of Example 402, coupling of Example 400 (15 mg, 0.020 mmol) with methylamine (2M in THF, 39 µL, 0.078 mmol) afforded after HPLC purification 10.1 mg of Example 403. LCMS (2 min gradient) RT=1.36 min, 553.48 (M+H)$^+$; $^1$H NMR (400 MHz, CD$_3$OD) δ ppm 1.18 (t, J=7.69 Hz, 3H) 1.41 (t, J=7.03 Hz, 3H) 2.59 (q, J=7.47 Hz, 2H) 2.73 (s, 3H) 4.13 (q, J=7.03 Hz, 2H) 4.67 (d, J=16.70 Hz, 1H) 4.91 (d, J=16.70 Hz, 1H) 6.31 (s, 1H) 6.73-6.76 (m, 1H) 6.97 (d, J=7.47 Hz, 1H) 6.99 (d, J=2.20 Hz, 1H) 7.03 (d, J=7.91 Hz, 1H) 7.28 (dd, J=9.23, 2.20 Hz, 1H) 7.34-7.38 (m, 2H) 7.42 (t, J=7.47 Hz, 2H) 7.67 (d, J=7.03 Hz, 2H) 7.72 (s, 1H) 8.17 (d, J=9.23 Hz, 1H).

Example 404

2-(2-((1-aminoisoquinolin-6-ylamino)(3-ethoxy-5-ethyl-2-fluorophenyl)methyl)-4-phenyl-1H-imidazol-1-yl)-N,N-dimethylacetamide bis-trifluoroacetic acid

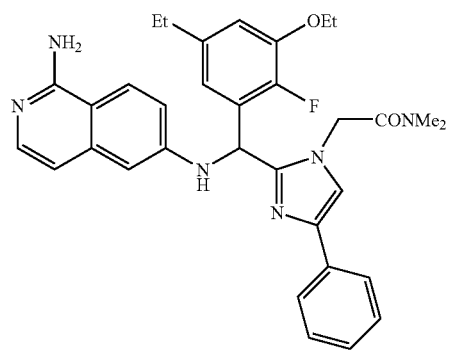

According to the procedure for the preparation of Example 402, coupling of Example 400 (15 mg, 0.020 mmol) with dimethylamine hydrochloride (6.4 mg, 0.078 mmol) afforded after HPLC purification 10.4 mg of Example 404. LCMS (2 min gradient) RT=1.33 min, 567.52 (M+H)$^+$; $^1$H NMR (400 MHz, CD$_3$OD) δ ppm 1.19 (t, J=7.69 Hz, 3H) 1.42 (t, J=7.03 Hz, 3H) 2.61 (q, J=7.62 Hz, 2H) 2.92 (s, 3H) 3.02 (s, 3H) 4.13 (q, J=7.03 Hz, 2H) 4.87 (d, J=17.14 Hz, 1H) 5.29 (d, J=17.14

Hz, 1H) 6.30 (s, 1H) 6.78-6.80 (m, 1H) 6.97 (d, J=7.03 Hz, 1H) 7.00 (d, J=2.20 Hz, 1H) 7.04 (d, J=7.91 Hz, 1H) 7.28 (dd, J=9.23, 2.64 Hz, 1H) 7.34-7.46 (m, 4H) 7.36 (d, J=7.03 Hz, 2H) 7.42 (q, J=7.03 Hz, 3H) 7.66 (d, J=7.03 Hz, 2H) 7.69 (s, 1H) 8.17 (d, J=9.23 Hz, 1H).

Example 405

2-(2-((1-aminoisoquinolin-6-ylamino)(3-ethoxy-5-ethyl-2-fluorophenyl)methyl)-4-phenyl-1H-imidazol-1-yl)-1-(pyrrolidin-1-yl)ethanone bis-trifluoroacetic acid

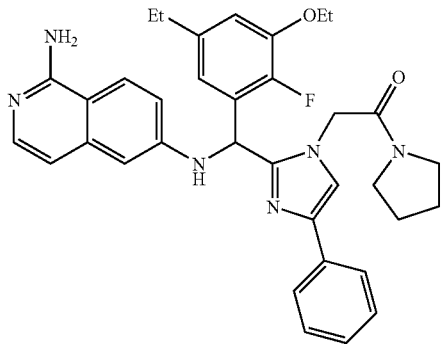

According to the procedure for the preparation of Example 402, coupling of Example 400 (15 mg, 0.020 mmol) with pyrrolidine (6.5 uL, 0.078 mmol) afforded after HPLC purification 11.3 mg of Example 405. LCMS (2 min gradient) RT=1.38 min, 593.52 (M+H)$^+$; $^1$H NMR (400 MHz, CD$_3$OD) δ ppm 1.19 (t, J=7.69 Hz, 3H) 1.42 (t, J=6.81 Hz, 3H) 1.83-1.90 (m, 2H) 1.99 (ddd, J=17.03, 6.26, 6.15 Hz, 2H) 2.61 (q, J=7.47 Hz, 2H) 3.32-3.39 (m, 2H) 3.41-3.47 (m, 2H) 4.13 (q, J=7.03 Hz, 2H) 4.82 (d, J=117.14 Hz, 1H) 5.19 (d, J=17.14 Hz, 1H) 6.36 (s, 1H) 6.77-6.79 (m, 1H) 6.96-7.01 (m, 2H) 6.98-7.00 (m, 2H) 7.04 (d, J=7.91 Hz, 1H) 7.28 (dd, J=9.01, 2.42 Hz, 1H) 7.35-7.46 (m, 4H) 7.66 (d, J=7.03 Hz, 2H) 7.73 (s, 1H) 8.18 (d, J=9.23 Hz, 1H).

Example 406

N$^6$-((5-ethyl-2-fluoro-3-morpholinophenyl)(4-phenyl-1H-imidazol-2-yl)methyl)isoquinoline-1,6-diamine bis-trifluoroacetic acid

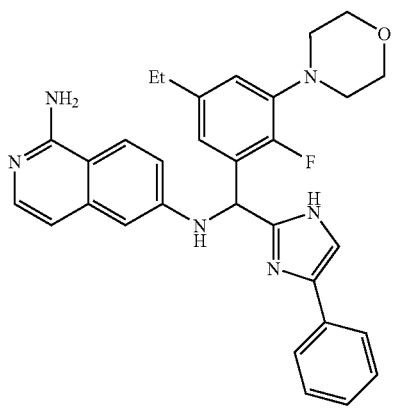

5-ethyl-2-fluoro-3-morpholinobenzaldehyde (406.1)

To a solution of Intermediate 230.1 (102 mg, 0.487 mmol) and PMDTA (0.132 mL, 0.634 mmol) in 3 mL THF at −78° C., was added BuLi (1.6 M in THF, 0.365 mL, 0.584 mmol). The mixture was allowed to warm to −45° C. over 20 min, then was recooled to −78° C. DMF (75 μL) was added, then the reaction mixture was removed from the cooling bath and stirred 20 min before being quenched with sat. NH$_4$Cl. The mixture was diluted with EtOAc, washed with water and brine, dried (Na$_2$SO$_4$) and concentrated. The crude residue was purified by flash chromatography (0 to 35% EtOAc/hexanes gradient) to afford 77 mg of Intermediate 406.1. LCMS (2 min gradient) RT=1.47 min, 238.18 (M+H)$^+$.

(5-ethyl-2-fluoro-3-morpholinophenyl)(4-phenyl-1-trityl-1H-imidazol-2-yl)methanol (406.2)

To a solution of Intermediate 8.1 (122 mg, 0.316 mmol) in 2 mL THF at 0° C., was added BuLi (1.6 M in THF, 0.236 mL, 0.379 mmol). The mixture was stirred at 0° C. for 45 min, then a solution of Intermediate 406.1 (75 mg, 0.316 mmol) in 0.9 mL THF was added dropwise. The mixture was stirred at rt for 30 min, then was quenched with sat. NH$_4$Cl. The mixture was diluted with EtOAc, washed with H$_2$O and brine, dried (Na$_2$SO$_4$) and concentrated. The crude product was purified by flash chromatography (0 to 60% EtOAc/hexanes gradient) to afford 162 mg of Intermediate 406.2 as a colorless glass. LCMS (2 min gradient) RT=1.93 min, 624.26 (M+H)$^+$.

di-tert-butyl (6-{[(4-phenyl-1-trityl-1H-imidazol-2-yl) (5-ethyl-2-fluoro-3-morpholinophenyl)phenyl) methyl]amino}isoquinolin-1-yl)imidodicarbonate (406.3)

According to the procedure for the preparation of Intermediate 206.4, Intermediate 406.2 (162 mg, 0.260 mmol) was converted to the chloro intermediate, then displaced with di-tert-butyl (6-aminoisoquinolin-1-yl)imidodicarbonate (rt for 18 h) to afford after flash chromatography (column #1: 0 to 75% EtOAc/hexanes gradient, column #2: 0 to 75% acetone/hexanes gradient) 234 mg of Intermediate 406.3 as a colorless solid. LCMS (2 min gradient) RT=2.28 min, 723.66 (M+(H−Tr)+H)$^+$.

Example 406

A solution of Intermediate 406.3 (30 mg) in 1 mL TFA was stirred at rt for 25 min, then concentrated. The product was purified by preparative HPLC to afford 20.1 mg of Example 406. LCMS (2 min gradient) RT=1.38 min, 593.52 (M+H)$^+$; $^1$H NMR (400 MHz, CD$_3$OD) δ ppm 1.19 (t, J=7.47 Hz, 3H) 2.62 (q, J=7.47 Hz, 2H) 3.05-3.14 (m, 4H) 3.82 (t, J=4.61 Hz, 4H) 6.46 (s, 1H) 6.86 (dd, J=6.15, 1.76 Hz, 1H) 6.89 (d, J=2.64 Hz, 1H) 6.93 (d, J=7.03 Hz, 1H) 7.00 (dd, J=8.13, 1.98 Hz, 1H) 7.27 (dd, J=9.01, 2.42 Hz, 1H) 7.37 (d, J=7.03 Hz, 1H) 7.42-7.51 (m, 3H) 7.72 (d, J=7.03 Hz, 2H) 7.79 (s, 1H) 8.20 (d, J=9.23 Hz, 1H).

Example 407

2-(2-((1-aminoisoquinolin-6-ylamino)(5-ethyl-2-fluoro-3-morpholinophenyl)methyl)-4-phenyl-1H-imidazol-1-yl)acetic acid bis-trifluoroacetic acid

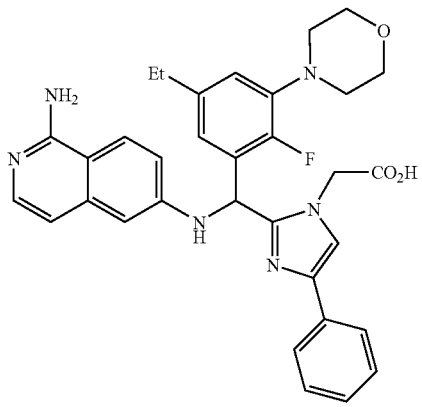

di-tert-butyl (6-{[(4-phenyl-1H-imidazol-2-yl)(5-ethyl-2-fluoro-3-morpholinophenyl)phenyl]methyl]amino}isoquinolin-1-yl)imidodicarbonate (407.1)

A solution of Intermediate 406.3 (115 mg) in 90% aq. acetic acid (2 mL) was stirred at rt for 4 h, then was concentrated. The residue was dissolved in EtOAc, washed with sat NaHCO$_3$ and brine, dried (Na$_2$SO$_4$) and concentrated. The product was purified by flash chromatography (0 to 100% EtOAC/hexanes gradient) to afford 71 mg of Intermediate 407.1 as a colorless solid. LCMS (2 min gradient) RT=1.69 min, 723.62 (M+H)$^+$.

tert-butyl 2-(2-((1-(di-tert-butyl imidodicarbonate)isoquinolin-6-ylamino)(5-ethyl-2-fluoro-3-morpholinophenyl)methyl)-4-phenyl-1H-imidazol-1-yl)acetate (407.2)

To a solution of intermediate 407.1 (71 mg, 0.098 mmol) in 1 mL THF at 0° C., was added NaH (60%, 9.8 mg, 0.246 mmol). The mixture was stirred for 5 min, then tert-butyl bromoacetate (21.7 µL, 0.147 mmol) was added. The mixture was stirred at 0° C. for 30 min, then was quenched with sat. NH$_4$Cl. The mixture was diluted with EtOAc, washed with H$_2$O and brine, dried (Na$_2$SO$_4$) and concentrated. The product was purified by flash chromatography (0 to 100% EtOAC/hexanes gradient) to afford 76 mg of Intermediate 407.2 as a colorless solid. LCMS (2 min gradient) RT=1.88 min, 837.33 (M+H)$^+$.

Example 407

A solution of Intermediate 407.2 (76 mg) in 1 mL TFA was stirred at rt for 2 h, then concentrated. The residue was purified by preparative HPLC to afford 53.6 mg of Example 407. LCMS (2 min gradient) RT=1.33 min, 581.36 (M+H)$^+$; $^1$H NMR (400 MHz, CD$_3$OD) δ ppm 1.18 (t, J=7.69 Hz, 3H) 2.59 (q, J=7.62 Hz, 2H) 3.04-3.13 (m, 4H) 3.82 (t, J=4.61 Hz, 4H) 4.77 (d, J=18.02 Hz, 1H) 5.03 (d, J=18.02 Hz, 1H) 6.35 (s, 1H) 6.86 (dd, J=5.93, 1.98 Hz, 1H) 6.91-6.95 (m, 2H) 6.97 (d, J=7.91 Hz, 1H) 7.27 (dd, J=9.23, 2.64 Hz, 1H) 7.33-7.45 (m, 4H) 7.67 (d, J=7.03 Hz, 2H) 7.76 (s, 1H) 8.16 (d, J=9.23 Hz, 1H).

Example 408

2-(2-((1-aminoisoquinolin-6-ylamino)(3-ethoxy-5-ethyl-2-fluorophenyl)methyl)-1H-imidazol-4-yl)-N-methylbenzamide bis-trifluoroacetic acid salt

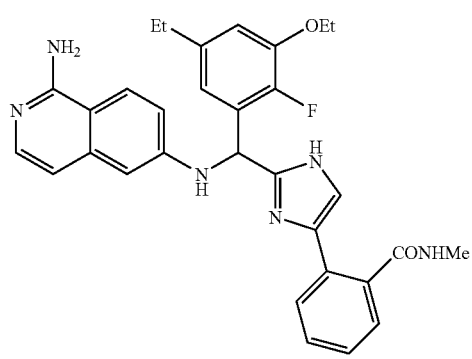

According to the procedure for the preparation of Example 307, coupling of Example 293 (15 mg, 0.028 mmol) with methylamine (2 M in THF, 24 uL) afforded after preparative HPLC 12 mg of Example 408. LC/MS (2 min gradient) RT=1.40 min, 539.14 (M+H)$^+$; $^1$H NMR (400 MHz, CD$_3$OD) δ ppm 1.21 (t, J=7.47 Hz, 3H) 1.41 (t, J=7.03 Hz, 3H) 2.64 (q, J=7.47 Hz, 2H) 2.78 (s, 3H) 4.14 (q, J=7.03 Hz, 2H) 6.48 (s, 1H) 6.80-6.86 (m, 1H) 6.89 (d, J=2.20 Hz, 1H) 6.99 (d, J=7.03 Hz, 1H) 7.06 (d, J=7.91 Hz, 1H) 7.27 (dd, J=9.01, 2.42 Hz, 1H) 7.39 (d, J=7.03 Hz, 1H) 7.49-7.75 (m, 5H) 8.20 (d, J=8.79 Hz, 1H).

Example 409

(2-(2-((1-aminoisoquinolin-6-ylamino)(3-ethoxy-5-ethyl-2-fluorophenyl)methyl)-1H-imidazol-4-yl)phenyl)(pyrrolidin-1-yl)methanone bis-trifluoroacetic acid salt

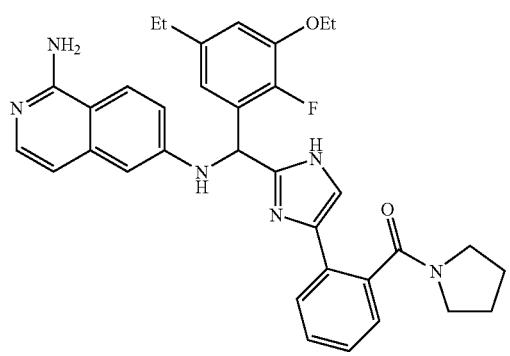

According to the procedure for the preparation of Example 307, coupling of Example 293 (15 mg, 0.028 mmol) with pyrrolidine (5 mg, 0.07 mmol) afforded after preparative HPLC 12 mg of Example 409. LC/MS (2 min gradient) RT=1.49 min, 579.10 (M+H)$^+$; $^1$H NMR (400 MHz, CD$_3$OD)

δ ppm 1.21 (t, J=7.69 Hz, 3H) 1.41 (t, J=7.03 Hz, 3H) 1.67-1.79 (m, 2H) 1.79-1.89 (m, 2H) 2.63 (q, J=7.62 Hz, 2H) 3.04 (d, J=7.47 Hz, 2H) 3.43 (t, J=6.81 Hz, 2H) 4.13 (q, J=6.88 Hz, 2H) 6.46 (s, 1H) 6.85 (d, J=5.71 Hz, 1H) 6.90 (d, J=2.20 Hz, 1H) 6.96 (d, J=7.03 Hz, 1H) 7.02-7.11 (m, 1H) 7.28 (dd, J=9.23, 2.20 Hz, 1H) 7.39 (d, J=7.03 Hz, 1H) 7.43-7.52 (m, 2H) 7.58 (dd, J=6.37, 2.86 Hz, 2H) 7.63-7.71 (m, 1H) 8.21 (d, J=9.23 Hz, 1H).

Example 410

(2-(2-((1-aminoisoquinolin-6-ylamino)(3-ethoxy-5-ethyl-2-fluorophenyl)methyl)-1H-imidazol-4-yl)phenyl)((S)-3-hydroxypyrrolidin-1-yl)methanone bis-trifluoroacetic acid salt

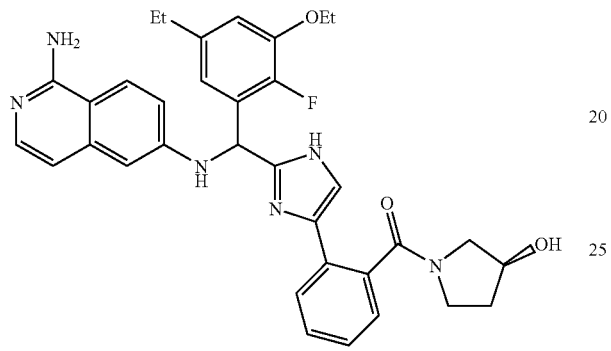

According to the procedure for the preparation of Example 307, coupling of Example 293 (15 mg, 0.028 mmol) with (R)-pyrrolidin-3-ol (6 mg, 0.07 mmol) afforded after preparative HPLC 13 mg of Example 409. LC/MS (2 min gradient) RT=1.41 min, 595.13 (M+H)+; 1H NMR (400 MHz, CD3OD) δ ppm 1.20 (t, J=7.47 Hz, 3H) 1.41 (t, J=6.81 Hz, 3H) 1.74-2.11 (m, 2H) 2.63 (q, J=7.47 Hz, 2H) 3.07 (dd, J=11.64, 7.69 Hz, 2H) 3.41-3.68 (m, 2H) 4.07-4.20 (m, 2H) 4.34 (d, J=39.55 Hz, 1H) 6.45 (s, 1H) 6.78-6.85 (m, 1H) 6.88 (dd, J=5.49, 2.42 Hz, 1H) 6.93-6.99 (m, 1H) 7.05 (d, J=6.15 Hz, 1H) 7.26 (dd, J=9.01, 2.42 Hz, 1H) 7.38 (d, J=7.03 Hz, 1H) 7.46-7.52 (m, 2H) 7.54-7.62 (m, 2H) 7.65-7.72 (m, 1H) 8.19 (d, J=9.23 Hz, 1H).

Example 411

2-(2-((1-aminoisoquinolin-6-ylamino)(3-ethoxy-5-ethyl-2-fluorophenyl)methyl)-1H-imidazol-4-yl)-N-ethylbenzamide bis-trifluoroacetic acid salt

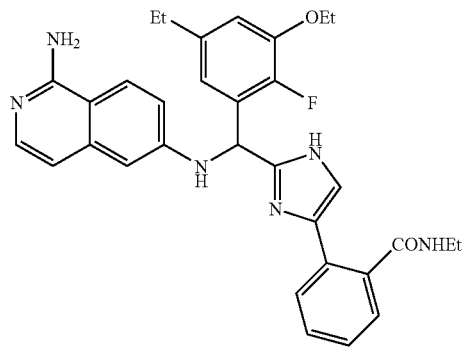

According to the procedure for the preparation of Example 307, coupling of Example 293 (15 mg, 0.028 mmol) with ethylamine (2 M in THF, 24 uL) afforded after preparative HPLC 13 mg of Example 411. LC/MS (2 min gradient) RT=1.41 min, 553.16 (M+H)+; 1H NMR (400 MHz, CD3OD) δ ppm 1.02-1.14 (m, 3H) 1.21 (t, J=7.69 Hz, 3H) 1.41 (t, J=7.03 Hz, 3H) 2.64 (q, J=7.47 Hz, 2H) 3.18-3.28 (m, 2H) 4.14 (q, J=6.74 Hz, 2H) 6.50 (s, 1H) 6.83 (d, J=4.39 Hz, 1H) 6.90 (d, J=2.64 Hz, 1H) 6.98 (d, J=7.47 Hz, 1H) 7.06 (d, J=7.91 Hz, 1H) 7.28 (dd, J=9.23, 2.20 Hz, 1H) 7.39 (d, J=7.03 Hz, 1H) 7.51-7.66 (m, 5H) 8.21 (d, J=9.23 Hz, 1H).

Example 412

2-(2-((1-aminoisoquinolin-6-ylamino)(3-ethoxy-5-ethyl-2-fluorophenyl)methyl)-1H-imidazol-4-yl)-N-(3-hydroxypropyl)benzamide bis-trifluoroacetic acid salt

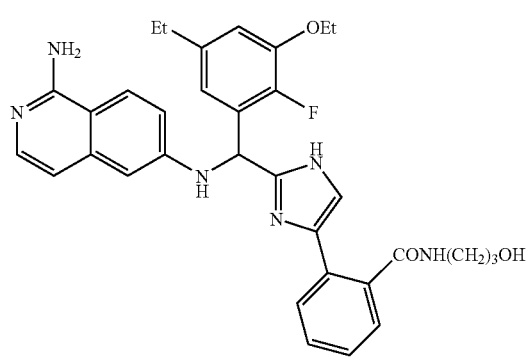

According to the procedure for the preparation of Example 307, coupling of Example 293 (15 mg, 0.028 mmol) with 3-aminopropan-1-ol (5 mg, 0.07 mmol) afforded after preparative HPLC 12 mg of Example 412. LC/MS (2 min gradient) RT=1.35 min, 538.14 (M+H)+; 1H NMR (400 MHz, CD3OD) δ ppm 1.21 (t, J=7.69 Hz, 3H) 1.41 (t, J=7.03 Hz, 3H) 1.59-1.79 (m, 2H) 2.64 (q, J=7.47 Hz, 2H) 3.56 (t, J=6.15 Hz, 2H) 4.14 (q, J=7.03 Hz, 2H) 6.48 (s, 1H) 6.75-6.86 (m, 1H) 6.89 (d, J=2.20 Hz, 1H) 6.99 (d, J=7.03 Hz, 1H) 7.06 (d, J=7.91 Hz, 1H) 7.27 (dd, J=9.23, 2.20 Hz, 1H) 7.39 (d, J=7.03 Hz, 1H) 7.49-7.72 (m, 5H) 8.20 (d, J=9.23 Hz, 1H).

Example 413 tert-butyl 2-(2-(2-((1-aminoisoquinolin-6-ylamino)(3-ethoxy-5-ethyl-2-fluorophenyl)methyl)-1H-imidazol-4-yl)benzamido)acetate bis-trifluoroacetic acid salt

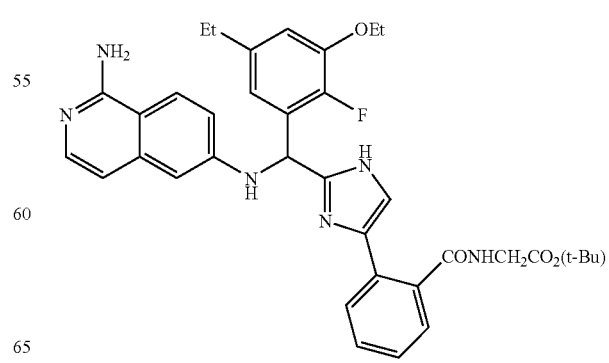

According to the procedure for the preparation of Example 307, coupling of Example 293 (15 mg, 0.028 mmol) with tert-butyl 2-aminoacetate (7 mg, 7 mmol) afforded after preparative HPLC 13 mg of Example 413. LC/MS (2 min gradient) RT=1.53 min, 639.15 (M+H)+.

Example 414

2-(2-(2-((1-aminoisoquinolin-6-ylamino)(3-ethoxy-5-ethyl-2-fluorophenyl)methyl)-1H-imidazol-4-yl)benzamido)acetic acid bis-trifluoroacetic acid salt

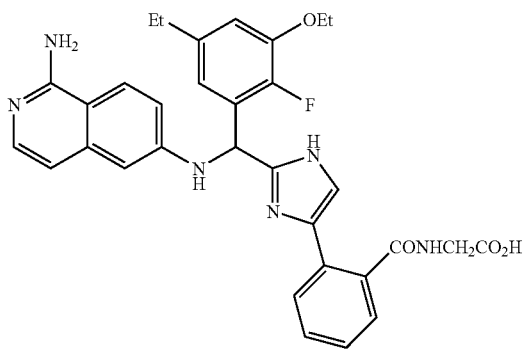

A mixture of Example 413 (10 mg, 0.016 mmol) and TFA (1 mL) was stirred at rt for 2 h. The reaction mixture was then concentrated and afforded after preparative HPLC 8 mg of Example 411. LC/MS (2 min gradient) RT=1.31 min, 583.40 (M+H)+; $^1$H NMR (400 MHz, CD$_3$OD) δ ppm 1.11 (t, J=7.69 Hz, 3H) 1.32 (t, J=6.81 Hz, 3H) 2.53 (q, J=7.47 Hz, 2H) 3.79-3.99 (m, 2H) 4.04 (q, J=7.03 Hz, 2H) 6.34 (s, 1H) 6.59-6.78 (m, 2H) 6.82-7.00 (m, 2H) 7.16 (dd, J=9.23, 2.20 Hz, 1H) 7.27 (d, J=7.03 Hz, 1H) 7.38-7.66 (m, 5H) 8.08 (d, J=9.23 Hz, 1H).

Example 415

2-(2-((1-aminoisoquinolin-6-ylamino)(3-ethoxy-5-ethyl-2-fluorophenyl)methyl)-5,6-dimethyl-1H-benzo[d]imidazol-1-yl)acetic acid bis-trifluoroacetic acid salt

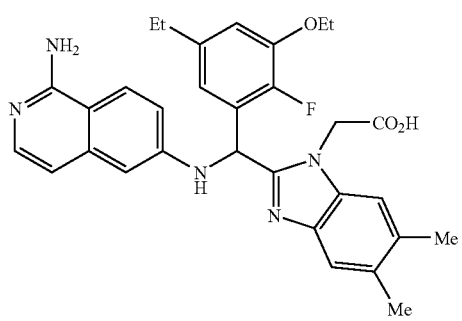

5,6-dimethyl-1-trityl-1H-benzo[d]imidazole (415.1)

A mixture of 5,6-dimethyl-1H-benzo[d]imidazole (500 mg, 3.42 mmol), trityl chloride (1.05 g, 3.76 mmol) and TEA (524 μL, 3.76 mmol) in 5 mL DMF was stirreds at rt for 3 h. The mixture was diluted with EtOAc, washed with H$_2$O and brine, dried (Na$_2$SO$_4$) and concentrated. The crude residue was purified by flash chromatography (0 to 100% EtOAc/hexanes gradient) to afford 1.31 g of Intermediate 415.1.

(3-(tert-butyldimethylsilyloxy)-5-ethyl-2-fluorophenyl)(5,6-dimethyl-1-trityl-1H-benzo[d]imidazol-2-yl)methanol (415.2)

To a solution of intermediate 415.1 (100 mg, 0.257 mmol) in 2 mL THF at 0° C., was added BuLi (1.6 M in hexanes, 193 μL, 0.309 mmol). The mixture was stirred at 0° C. for 20 min, then a solution of 3-(tert-butyldimethylsilyloxy)-5-ethyl-2-fluorobenzaldehyde (188.3) (72.6 mg, 0.257 mmol) in 0.6 mL THF was added. The mixture was removed from the ice bath and stirred 70 min, then was quenched with sat. NH$_4$Cl. The mixture was diluted with EtOAc, washed with H$_2$O and brine, dried (Na$_2$SO$_4$) and concentrated. The crude residue was purified by flash chromatography (0 to 40% EtOAc/hexanes gradient) to afford 115 mg of intermediate 415.2. LCMS (2 min gradient) RT=2.24 min, 671.13 (M+H)+.

(5,6-dimethyl-1-trityl-1H-benzo[d]imidazol-2-yl)(3-ethoxy-5-ethyl-2-fluorophenyl)methanol (415.3)

To a solution of Intermediate 415.2 (115 mg, 0.171 mmol) in 2 mL THF at rt, was added TBAF (1 M in THF, 171 μL, 0.171 mmol). The mixture was stirred at rt for 20 min, then was diluted with EtOAc, washed with H$_2$O (2×) and brine, dried (Na$_2$SO$_4$) and concentrated. The crude residue was purified by flash chromatography (0 to 80% EtOAc/hexanes gradient) to afford 34 mg of 3-((5,6-dimethyl-1-trityl-1H-benzo[d]imidazol-2-yl)(hydroxy)methyl)-5-ethyl-2-fluorophenol as a white solid.

To a solution of this phenol (34 mg, 0.061 mmol) in 2 mL DMF, were added K$_2$CO$_3$ (10 mg, 0.073 mmol) and iodoethane (15 μL, 0.18 mmol). The mixture was stirred at rt for 16 h, then was diluted with EtOAc. The organic phase was washed with H$_2$O and brine, dried (Na$_2$SO$_4$), filtered through a 1" pad of silica gel and concentrated to afford 35.7 mg of Intermediate 415.3. LCMS (2 min gradient) RT=1.97 min, 585.47 (M+H)+.

di-tert-butyl (6-{[(5,6-dimethyl-1-trityl-1H-benzo[d]imidazol-2-yl)(3-ethoxy-5-ethyl-2-fluorophenyl)phenyl)methyl]amino}isoquinolin-1-yl)imidodicarbonate (415.4)

According to the procedure for the preparation of Intermediate 206.4, Intermediate 415.3 (35.7 mg, 0.061 mmol) was converted to the chloro intermediate, then displaced with di-tert-butyl (6-aminoisoquinolin-1-yl)imidodicarbonate (rt for 18 h, 50° C. for 10 h) to afford after flash chromatography (0 to 60% EtOAc/hexanes gradient) 42 mg of Intermediate 415.4 as a colorless solid. LCMS (2 min gradient) RT=2.21 min, 684.54 (M+(H-Tr)+H)+.

di-tert-butyl (6-{[(5,6-dimethyl-1H-benzo[d]imidazol-2-yl)(3-ethoxy-5-ethyl-2-fluorophenyl)phenyl)methyl]amino}isoquinolin-1-yl)imidodicarbonate (415.5)

A solution of Intermediate 415.4 (42 mg) in 90% aq. acetic acid (2 mL) was stirred at rt for 50 min, then was concentrated. The residue was dissolved in EtOAc, washed with sat NaHCO$_3$ and brine, dried (Na$_2$SO$_4$) and concentrated. The product was purified by flash chromatography (0 to 100%

EtOAC/hexanes gradient) to afford 31 mg of Intermediate 415.5 as a pinkish white solid. LCMS (2 min gradient) RT=1.80 min, 684.2 (M+H)+.

tert-butyl 2-(2-((1-(di-tert-butyl imidodicarbonate) isoquinolin-6-ylamino)(3-ethoxy-5-ethyl-2-fluorophenyl)methyl)-5,6-dimethyl-1H-benzo[d]imidazol-2-yl)acetate (415.6)

To a solution of Intermediate 415.5 (31 mg, 0.045 mmol) in 1 mL THF at 0° C., was added NaH (60%, 4.5 mg, 0.113 mmol). The mixture was stirred for 5 min, then tert-butyl bromoacetate (10 µL, 0.068 mmol) was added. The mixture was stirred at 0° C. for 30 min, then was quenched with sat. NH4Cl. The mixture was diluted with EtOAc, washed with H2O and brine, dried (Na2SO4) and concentrated. The product was purified by flash chromatography (0 to 80% EtOAC/hexanes gradient) to afford 26 mg of Intermediate 415.6 as a colorless solid. LCMS (2 min gradient) RT=1.93 min, 798.74 (M+H)+.

Example 415

A solution of Intermediate 415.6 (26 mg) in 1 mL TFA was stirred at rt for 2 h, then concentrated. The residue was purified by preparative HPLC to afford 20.0 mg of Example 415. LCMS (2 min gradient) RT=1.38 min, 542.42 (M+H)+; $^1$H NMR (400 MHz, CD3OD) δ ppm 1.07 (t, J=7.47 Hz, 3H) 1.30 (t, J=7.03 Hz, 3H) 2.30 (s, 3H) 2.33 (s, 3H) 2.48 (q, J=7.47 Hz, 2H) 4.03 (q, J=7.03 Hz, 2H) 4.73 (d, J=18.02 Hz, 1H) 5.09 (d, J=18.02 Hz, 1H) 6.34 (s, 1H) 6.67 (dd, J=5.71, 1.76 Hz, 1H) 6.79 (d, J=7.03 Hz, 1H) 6.85 (d, J=2.20 Hz, 1H) 6.94 (dd, J=7.91, 1.76 Hz, 1H) 7.18-7.23 (m, 2H) 7.37 (d, J=8.35 Hz, 2H) 8.06 (d, J=9.23 Hz, 1H).

Example 416

N6-((2-fluoro-5-(prop-1-en-2-yl)phenyl)(2-methyl-5-phenyl-2H-1,2,4-triazol-3-yl)methyl)isoquinoline-1,6-diamine

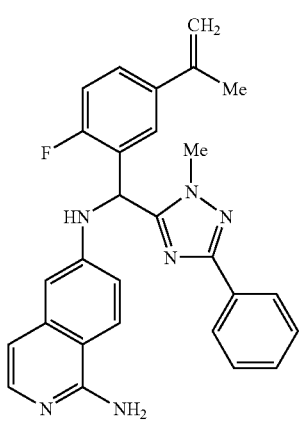

2-(3-bromo-4-fluorophenyl)-2-methyl-1,3-dioxolane (416.1)

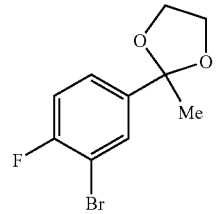

1-(3-bromo-4-fluorophenyl)ethanone (7.5 g, 34.5 mmol), ethylene glycol (10 mL) and a catalytic amount of tosyl acid was refluxed in toluene (100 mL) for 18 h with a Dean-Stark trap. The crude reaction mixture was quenched with H2O (100 mL) extracted with EtOAc (3×50 mL), washed organic layer with H2O, brine, dried (Na2SO4) and concentrated. The crude product was purified by flash chromatography (0 to 100% EtOAc/hexanes gradient) to afford 8.8 g of Intermediate 416.1. $^1$H NMR (400 MHz, CDCl3) δ ppm 1.61 (s, 3H) 3.69-3.81 (m, 2H) 3.97-4.09 (m, 2H) 7.07 (t, J=8.35 Hz, 1H) 7.32-7.43 (m, 1H) 7.67 (dd, J=6.59, 2.20 Hz, 1H).

2-fluoro-5-(2-methyl-1,3-dioxolan-2-yl)benzaldehyde (416.2)

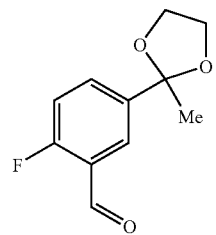

Intermediate 416.1 (1 g, 3.83 mmol) in THF (20 mL) was cooled to −78° C. before adding 1.6 M n-BuLi (2.63 mL, 4.2 mmol) drop-wise. The reaction was stirred for 10 min before quenching with DMF (0.6 mL, 7.7 mmol) and allowing to warm to rt. The crude reaction mixture was quenched with NH4Cl (10 mL), extracted with EtOAc (3×10 mL), washed organic layer with H2O, brine, dried (Na2SO4) and concentrated. The crude product was purified by flash chromatography (0 to 100% EtOAc/hexanes gradient) to afford 550 mg of Intermediate 416.2. $^1$H NMR (400 MHz, CDCl3) δ ppm 1.63 (s, 3H) 3.51-3.92 (m, 2H) 3.90-4.35 (m, 2H) 7.09-7.19 (m, 1H) 7.65-7.79 (m, 1H) 7.99 (dd, J=6.81, 2.42 Hz, 1H) 10.35 (s, 1H).

323

(2-fluoro-5-(2-methyl-1,3-dioxolan-2-yl)phenyl)(2-methyl-5-phenyl-2H-1,2,4-triazol-3-yl)methanol (416.3)

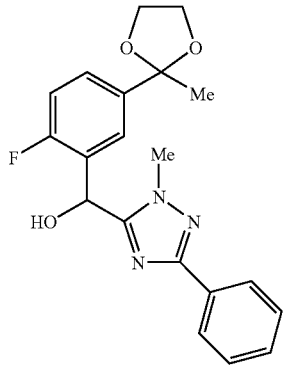

To a solution of 1-methyl-3-phenyl-1H-1,2,4-triazole (1.56 g, 9.83 mmol) in THF (50 mL) cooled to −78° C. was added 1.6 M n-butyl lithium (6.76 ml, 10.8 mmol) drop-wise and stirred for 30 min. Next a solution of Intermediate 416.2 (2.46 g, 11.8 mmol) in THF (15 mL) was added drop-wise and stirred for 5 min before allowing the mixture to warm to 23° C. The reaction mixture was quenched with aqueous NH$_4$Cl and extracted with EtOAc (3×50 mL). The organic layer was washed with H$_2$O, brine, dried (Na$_2$SO$_4$) and concentrated. The crude product was purified by flash chromatography (0 to 100% EtOAc/hexanes gradient) to afford 3.6 g of Intermediate 416.3. $^1$H NMR (400 MHz, CDCl$_3$) δ ppm 1.59 (s, 3H) 3.62 (s, 3H) 3.66-3.78 (m, 2H) 3.91-4.04 (m, 2H) 6.22 (s, 1H) 6.94-7.07 (m, 1H) 7.32-7.49 (m, 5H) 7.70 (dd, J=7.25, 2.42 Hz, 1H) 7.97-8.05 (m, 2H).

1-(4-fluoro-3-(hydroxy(2-methyl-5-phenyl-2H-1,2,4-triazol-3-yl)methyl)phenyl)ethanone (416.4)

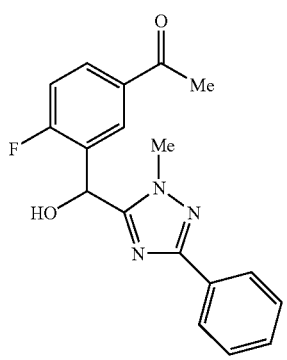

Intermediate 416.3 (500 mg, 1.36 mmol) was heated in a solution of Acetone:Acetic Acid:H$_2$O (2:1:1, 8 mL) at 125° C. for 30 min using a PC microwave. The reaction product was then concentrated and purified by flash chromatography (0 to 100% EtOAc/hexanes gradient) to afford 580 mg of Intermediate 416.4. LCMS (2 min gradient) RT=1.59 min, 326.31 (M+H)$^+$.

324 di-tert-butyl-6-((5-acetyl-2-fluorophenyl)(2-methyl-5-phenyl-2H-1,2,4-triazol-3-yl)methylamino)isoquinolin-1-ylcarbamate (416.5)

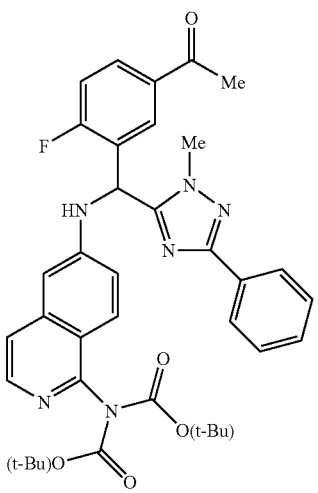

Intermediate 416.4 (400 mg, 1.23 mmol), DIEA (0.5 mL, 2.5 mmol) and CH$_3$CN (15 mL) were cooled to −15° C. before adding methanesulfonic acid anhydride (342 mg, 1.97 mmol) and stirring for 1 h. To the stirred solution was added 1-(di-(tert-butyloxycarbonyl)amino)-6-aminoisoquinoline (442 mg, 1.23 mmol) and the reaction mixture was heated at 50° C. for 4 h. The reaction product was then concentrated and purified by flash chromatography (0 to 100% EtOAc/hexanes gradient) to afford 580 mg of Intermediate 416.5. LCMS (2 min gradient) RT=1.91 min, 667.59 (M+H)$^+$.

Example 416

Triphenylphosphonium methylbromide (129 mg, 0.36 mg) and 1.6 M n-BuLi (0.23 mL, 0.36 mmol) in THF (2 mL) were stirred for 10 min at rt before adding Intermediate 416.5 (40 mg, 0.06 mmol) and heating at 150° C. for 10 min using a PC microwave. The reaction product was concentrated, re-dissolved in MeOH and flushed thru a SCX column with excess MeOH. 8.2 mg of Example 416 was isolated by washing the SCX column with 2M NH$_3$-MeOH and purifying via preparative HPLC. LCMS (2 min gradient) RT=1.83 min, 465.08 (M+H)$^+$; $^1$H NMR (400 MHz, CDCl$_3$) δ ppm 3.48 (s, 3H) 3.88 (s, 3H) 5.02 (s, 1H) 5.21 (s, 1H) 6.18 (s, 1H) 6.66-6.83 (m, 2H) 7.04-7.19 (m, 2H) 7.34-7.58 (m, 6H) 7.92 (d, J=9.23 Hz, 1H) 8.01 (s, 1H) 8.08 (d, J=6.59 Hz, 2H).

Example 417

N6-((2-fluoro-5-isopropylphenyl)(2-methyl-5-phenyl-2H-1,2,4-triazol-3-yl)methyl)isoquinoline-1,6-diamine

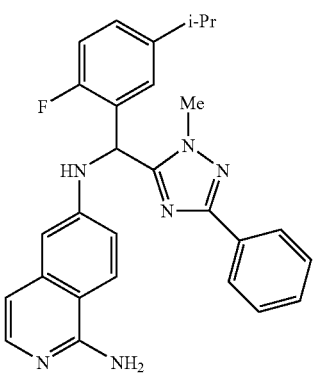

To a solution of Example 416 (6.0 mg, 0.013 mmol) and MeOH (1 mL) was added a catalytic amount of 10% Pd/C and stirred for 1 h under 1 atm of hydrogen. Reaction was filtered and concentrated to yield 1.9 mg of Example 417 pure. 467.32 (M+H)+; 1H-NMR (400 MHz, CDCl3) δ ppm 1.10 (dd, J=7.03, 3.95 Hz, 6H) 2.68-2.88 (m, 1H) 3.86 (s, 3H) 6.11-6.19 (m, 1H) 6.67-6.76 (m, 2H) 7.03-7.19 (m, 4H) 7.37-7.50 (m, 4H) 7.98 (d, J=8.79 Hz, 1H) 8.10 (d, J=6.59 Hz, 2H).

Example 418

1-(3-((1-aminoisoquinolin-6-ylamino)(2-methyl-5-phenyl-2H-1,2,4-triazol-3-yl)methyl)-4-fluorophenyl)ethanol

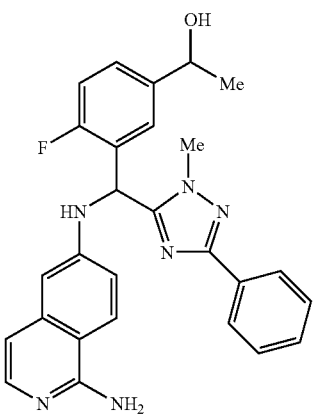

Intermediate 416.5 (130 mg, 0.195 mmol) in THF (15 mL) was stirred at rt before adding tri-t-butoxide lithiumhydride (1 mL, 0.98 mmol) and heating for 3 h at 55° C. The reaction mixture was quenched with H2O (15 mL) extracted with EtOAc (3×10 mL), dried (MgSO4), and concentrated. The crude material was re-dissolved in a 50/50 solution of 4 M HCl/dioxane and EtOAc and stirred for 18 h before concentrating and purifying on preparative HPLC to afford 11.6 mg of Example 418. 469.44 (M+H)+; 1H NMR (400 MHz, CDCl3) δ ppm 1.37 (d, J=6.59 Hz, 3H) 3.90 (d, J=6.15 Hz, 3H) 4.81 (q, J=6.15 Hz, 1H) 6.22 (s, 1H) 6.44-6.61 (m, 2H) 6.88-7.02 (m, 2H) 7.11-7.22 (m, 1H) 7.29-7.47 (m, 4H) 7.50-7.67 (m, 1H) 7.69-7.87 (m, 1H) 7.94-8.11 (m, 2H).

Example 421

2-(2-((1-aminoisoquinolin-6-ylamino)(5-ethyl-2-fluoro-3-((S)-tetrahydrofuran-3-yloxy)phenyl)methyl)-4-phenyl-1H-imidazol-1-yl)acetic acid bis-trifluoroacetic acid salt

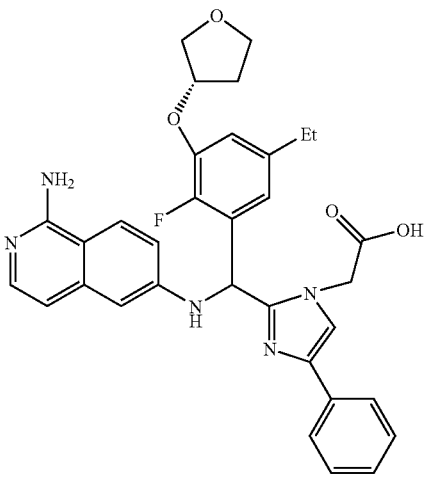

di-tert-butyl (6-{[(4-phenyl-1-trityl-1H-imidazole-2-yl)(3-hydroxy)-5-ethyl-2-fluorophenyl)methyl]amino}isoquinolin-1-yl)imidodicarbonate (421.1)

According to the procedure for the preparation of Example 243, reaction of 3-(tert-butyldimethylsilyloxy)-5-ethyl-2-fluorobenzaldehyde (Intermediate 368.2) with the 4-Phenyl-1-trityl-1H-imidazole, followed by chlorination, displacement with 1-(di-(tert-butyloxycarbonyl)amino)-6-aminoisoquinoline and TBS deprotection with TBAF afforded Intermediate 421.1. LC/MS (2 min gradient) RT=2.29 min, 896.26 (M+H)+.

di-tert-butyl (6-{[(4-phenyl-1-trityl-H-imidazole-2-yl)(3-(S)-tetrahydrofuran-3-ol)-5-ethyl-2-fluorophenyl)methyl]amino}isoquinolin-1-yl)imidodicarbonate (421.2)

According to procedure for the preparation of Intermediate 242.1, Intermediate 421.1 (88 mg, 0.1 mmol) and (R)-tetrahydrofuran-3-ol (16.9 mg, 0.19 mmol) afforded 70 mg of Intermediate 421.2. LC/MS (2 min gradient) RT=2.33 min, 966.26 (M+H)+.

di-tert-butyl (6-{[(4-phenyl-1H-imidazole-2-yl)(3-(S)-tetrahydrofuran-3-ol)-5-ethyl-2-fluorophenyl)methyl]amino}isoquinolin-1-yl)imidodicarbonate (421.3)

A solution of Intermediate 421.2 (70 mg, 0.1 mmol) and 1 mL 90% aq. AcOH was stirred at rt for 2 h, then concentrated. The residue was diluted with EtOAc and washed with sat. NaHCO3, H2O and brine, dried (Na2SO4) and concentrated. The crude product was purified by flash chromatography (0-100% EtOAc/hexanes gradient) to afford 40 mg of Intermediate 421.3. LC/MS (2 min gradient) RT=1.69 min, 724.17 (M+H)⁺.

di-tert-butyl (6-{[(4-phenyl-1H-tert-butylacetate-1H-imidazole-2-yl)(3-(S)-tetrahydrofuran-3-ol)-5-ethyl-2-fluorophenyl)methyl]amino}isoquinolin-1-yl)imidodicarbonate (421.4)

According to procedure for the preparation of Intermediate 400.2, Intermediate 421.3 (40 mg, 0.1 mmol) and tert-butyl bromoacetate (12 μL) afforded 20 mg of Intermediate 421.4. LC/MS (2 min. gradient) RT=1.79 min, 838.3 (M+H)⁺.

Example 421

A solution of Intermediate 421.4 (20 mg, 0.05 mmol) in 1 mL TFA was stirred at rt for 30 min. then concentrated. The residue was purified by HPLC to afford 7 mg of Example 421. LC/MS (2 min gradient) RT=1.45 min, 582.05 (M+H)⁺; ¹H NMR (400 MHz, CD₃OD) δ ppm 1.09 (t, J=7.47 Hz, 3H) 1.98-2.25 (m, 2H) 2.5.1 (q, J=7.47 Hz, 2H) 3.78 (d, J=4.39 Hz, 1H) 3.83-3.89 (m, 4H) 4.72 (d, J=18.02 Hz, 1H) 4.97 (d, J=18.02 Hz, 1H) 6.27 (s, 1H) 6.76 (d, J=5.71 Hz, 1H) 6.80-6.88 (m, 2H) 6.92 (d, J=7.91 Hz, 1H) 7.11-7.40 (m, 5H) 7.57 (d, J=7.47 Hz, 2H) 7.68 (s, 1H) 8.07 (d, J=9.23 Hz, 1H).

Example 422

2-(2-((1-aminoisoquinolin-6-ylamino)(5-ethyl-2-2-fluoro-3-((R)-tetrahydrofuran-3-yloxy)phenyl)methyl)-4-phenyl-1H-imidazol-1-yl)acetic acid bis-trifluoroacetic acid salt

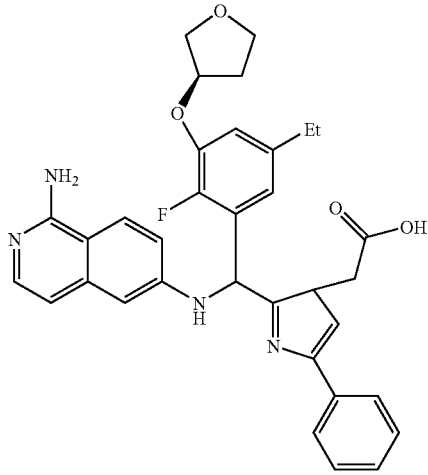

According to procedure for the preparation of Example 421, Intermediate 421.1 (88 mg, 0.1 mmol) and (S)-tetrahydrofuran-3-ol (116.9 mg, 0.19 mmol) afforded 20 mg of Example 422. LC/MS (2 min. gradient) RT=1.43 min, 582.07 (M+H)⁺; ¹H NMR (400 MHz, CD₃OD) δ ppm 1.09 (t, J=7.47 Hz, 3H) 1.98-2.25 (m, 2H) 2.51 (q, J=7.47 Hz, 2H) 3.78 (d, J=4.39 Hz, 1H) 3.83-3.89 (m, 4H) 4.72 (d, J=18.02 Hz, 1H) 4.97 (d, J=18.02 Hz, 1H) 6.27 (s, 1H) 6.76 (d, J=5.71 Hz, 1H) 6.80-6.88 (m, 2H) 6.92 (d, J=7.91 Hz, 1H) 7.11-7.40 (m, 5H) 7.57 (d, J=7.47 Hz, 2H) 7.68 (s, 1H) 8.07 (d, J=9.23 Hz, 1H).

Example 423

2-(2-((1-aminoisoquinolin-6-ylamino)(5-ethyl-2-fluoro-3-(tetrahydro-2H-pyran-4-yloxy)phenyl)methyl)-4-phenyl-1H-imidazol-1-yl)acetic acid bis-trifluoroacetic acid salt

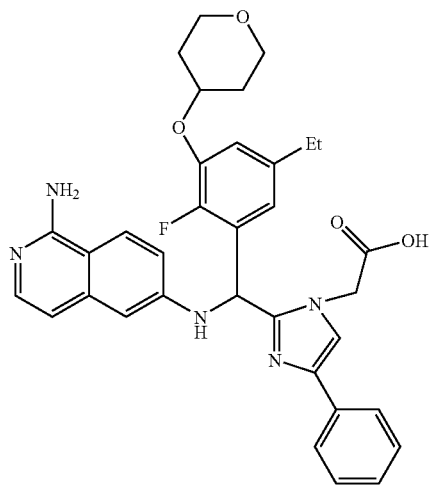

According to procedure for the preparation of Example 421, Intermediate 421.1 (88 mg, 0.1 mmol) and tetrahydro-2H-pyran-4-ol (16.9 mg, 0.19 mmol) afforded 19 mg of Example 423. LC/MS (2 min gradient) RT=1.32 min, 596.07 (M+H)⁺. ¹H NMR (400 MHz, CD₃OD) δ ppm 1.18 (t, J=7.69 Hz, 3H) 1.57-1.84 (m, 2H) 1.95-2.13 (m, 2H) 2.60 (q, J=7.47 Hz, 2H) 3.50-3.67 (m, 2H) 3.84-4.04 (m, 2H) 4.53-4.68 (m, 1H) 4.78-4.84 (m, 1H) 5.09 (d, J=18.02 Hz, 1H) 6.38 (s, 1H) 6.80-6.89 (m, 1H) 6.89-6.99 (m, 2H) 7.10 (dd, J=7.69, 1.98 Hz, 1H) 7.28 (dd, J=9.23, 2.64 Hz, 1H) 7.35 (d, J=7.03 Hz, 1H) 7.37-7.50 (m, 3H) 7.66 (d, J=7.03 Hz, 2H) 7.81 (s, 1H) 8.17 (d, J=9.23 Hz, 1H).

Example 424

2-(2-((1-aminoisoquinolin-6-ylamino)(3-ethoxy-5-ethyl-2-fluorophenyl)methyl)-4-phenyl-1H-imidazol-1-yl)-N-cyclobutylacetamide bis-trifluoroacetic acid salt

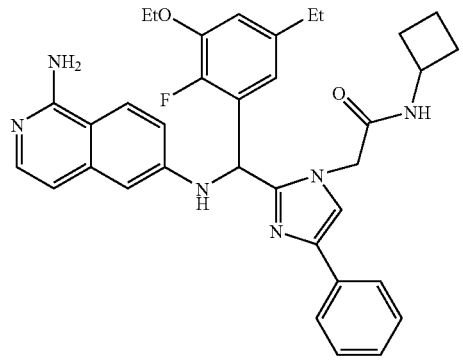

According to procedure for the preparation of Example 402, Example 400 (20 mg, 0.03 mmol) and cyclobutyl amine (2 μL, 0.05 mmol) afforded 20 mg of Example 424. LC/MS (2 min gradient) RT=1.57 min, 593.12 (M+H)⁺. ¹H NMR (400 MHz, CD₃OD) δ ppm 1.16 (t, 3H) 1.41 (t, J=7.03 Hz, 3H) 1.64-1.81 (m, 2H) 1.85-2.04 (m, 2H) 2.09-2.35 (m, 2H) 2.59 (q, J=7.47 Hz, 2H) 4.13 (q, J=7.03 Hz, 2H) 4.28 (q, J=8.06 Hz, 1H) 4.63 (d, J=17.14 Hz, 1H) 4.92 (d, J=17.14 Hz, 1H) 6.29 (s, 1H) 6.72 (d, J=3.95 Hz, 1H) 6.92-7.00 (m, 2H) 7.04 (d, J=7.91 Hz, 1H) 7.27 (dd, J=9.23, 2.20 Hz, 1H) 7.33-7.52 (m, 4H) 7.65 (d, J=6.59 Hz, 2H) 7.75 (s, 1H) 8.17 (d, J=9.23 Hz, 1H) 8.56 (d, J=7.03 Hz, 1H).

According to procedure for the preparation of Example 402, Example 400 (20 mg, 0.03 mmol) and 2-aminoethanol (2 μL, 0.05 mmol) afforded 17 mg of Example 426. LC/MS (2 min gradient) RT=1.32 min, 583.15 (M+H)⁺. ¹H NMR (400 MHz, CD₃OD) δ ppm 1.19 (t, J=7.69 Hz, 3H) 1.40 (t, J=7.03 Hz, 3H) 2.61 (q, J=7.76 Hz, 2H) 2.93 (m, 2H) 3.61 (t, J=5.71 Hz, 2H) 4.13 (q, J=7.03 Hz, 2H) 4.73 (d, J=116.70 Hz, 1H) 5.00 (d, J=17.14 Hz, 1H) 6.35 (s, 1H) 6.78 (d, J=5.71 Hz, 1H) 6.97 (d, J=7.47 Hz, 1H) 7.00-7.11 (m, 2H) 7.29 (dd, J=9.23, 2.20 Hz, 1H) 7.36 (d, J=7.03 Hz, 1H) 7.38-7.50 (m, 3H) 7.65 (d, J=7.91 Hz, 2H) 7.82 (s, 1H) 8.18 (d, J=9.23 Hz, 1H).

Example 425

2-(2-((1-aminoisoquinolin-6-ylamino)(3-ethoxy-5-ethyl-2-fluorophenyl)methyl)-4-phenyl-1H-imidazol-1-yl)-N-cyclopropylacetamide bis-trifluoroacetic acid salt

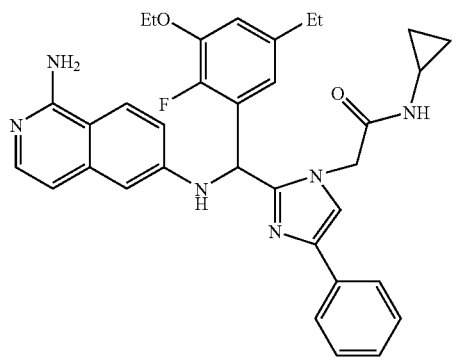

Example 427

2-(2-((1-aminoisoquinolin-6-ylamino)(3-ethoxy-5-ethyl-2-fluorophenyl)methyl)-4-phenyl-1H-imidazol-1-yl)-N-phenylacetamide bis-trifluoroacetic acid salt

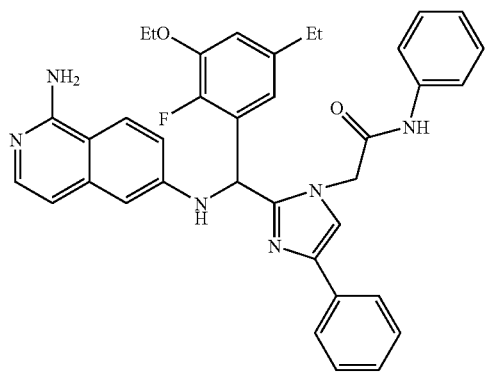

According to procedure for the preparation of Example 402, Example 400 (20 mg, 0.03 mmol) and cyclopropyl amine (2 μL, 0.05 mmol) afforded 18 mg of Example 425. LC/MS (20 min gradient) RT=1.57 min, 593.12 (M+H)⁺. ¹H NMR (400 MHz, CD₃OD) δ ppm 0.48 (d, J=2.20 Hz, 2H) 0.64-0.81 (m, 2H) 1.19 (t, J=7.47 Hz, 3H) 1.41 (t, J=7.03 Hz, 3H) 2.50-2.75 (m, 3H) 4.13 (q, J=6.74 Hz, 2H) 4.65 (d, J=16.70 Hz, 1H) 4.94 (d, J=16.70 Hz, 1H) 6.32 (s, 1H) 6.75 (d, J=3.95 Hz, 1H) 6.94-7.02 (m, 2H) 7.05 (d, J=7.91 Hz, 1H) 7.29 (dd, J=9.01, 2.42 Hz, 1H) 7.34-7.50 (m, 4H) 7.65 (d, J=7.03 Hz, 2H) 7.79 (s, 1H) 8.19 (d, J=9.23 Hz, 1H).

According to procedure for the preparation of Example 402, Example 400 (20 mg, 0.03 mmol) and aniline (4 μL, 0.05 mmol) afforded 19 mg of Example 427. LC/MS (2 min gradient) RT=1.56 min, 615.15 (M+H)⁺. ¹H NMR (400 MHz, CD₃OD) δ ppm 2.06 (t, J=7.69 Hz, 3H) 2.44 (t, J=7.03 Hz, 3H) 0.95 (q, J=7.76 Hz, 2H) 3.86-4.11 (m, 2H) 4.96 (d, J=17.14 Hz, 1H) 5.16 (d, J=16.70 Hz, 1H) 6.58 (s, 1H) 6.79 (d, J=4.39 Hz, 1H) 6.87-6.95 (m, 2H) 6.98 (d, J=2.20 Hz, 1H) 7.10 (t, J=7.25 Hz, 1H) 7.23-7.42 (m, 3H) 7.35 (d, J=7.03 Hz, 1H) 7.37-7.50 (m, 5H) 7.70 (d, J=7.03 Hz, 2H) 7.82 (s, 1H) 8.13 (d, J=9.23 Hz, 1H).

Example 426

2-(2-((1-aminoisoquinolin-6-ylamino)(3-ethoxy-5-ethyl-2-fluorophenyl)methyl)-4-phenyl-1H-imidazol-1-yl)-1-(2-hydroxyethyl)acetamide bis-trifluoroacetic acid salt

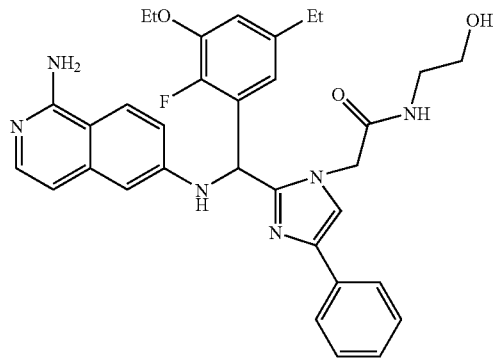

Example 428

2-(2-((1-aminoisoquinolin-6-ylamino)(3-ethoxy-5-ethyl-2-fluorophenyl)methyl)-4-phenyl-1H-imidazol-1-yl)-N-(2-aminoacetamide)acetamide bis-trifluoroacetic acid salt

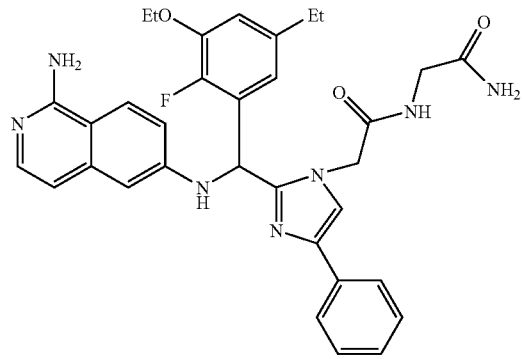

According to procedure for the preparation of Example 402, Example 400 (20 mg, 0.03 mmol) and 2-aminoacetamide (5 mg, 0.05 mmol) afforded 17 mg of Example 428. LC/MS (2 min gradient) RT=1.29 min, 596.11 (M+H)+. $^1$H NMR (400 MHz, CD$_3$OD) δ ppm 1.19 (t, J=7.69 Hz, 3H) 1.40 (t, J=7.03 Hz, 3H) 2.61 (q, J=7.47 Hz, 2H) 3.90 (d, J=6.59 Hz, 2H) 4.13 (q, J=6.88 Hz, 2H) 4.80 (d, J=17.14 Hz, 1H) 5.05 (d, J=16.70 Hz, 1H) 6.35 (s, 1H) 6.84 (d, J=4.39 Hz, 1H) 6.96 (d, J=7.47 Hz, 1H) 6.99-7.10 (m, 2H) 7.28 (dd, J=9.23, 2.20 Hz, 1H) 7.34 (d, J=7.03 Hz, 1H) 7.37-7.49 (m, 3H) 7.65 (d, J=7.03 Hz, 2H) 7.78 (s, 1H) 8.16 (d, J=9.23 Hz, 1H).

Example 429

2-(2-((1-aminoisoquinolin-6-ylamino)(3-ethoxy-5-ethyl-2-fluorophenyl)methyl)-4-phenyl-1H-imidazol-1-yl)-N-(2,2,2-trifluoroethyl)acetamide bis-trifluoroacetic acid salt

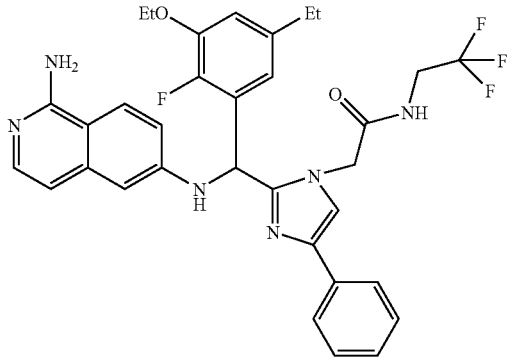

According to procedure for the preparation of Example 402, Example 400 (20 mg, 0.03 mmol) and 2,2,2-trifluoroethanamine (5 mg, 0.05 mmol) afforded 17 mg of Example 429. LC/MS (2 min gradient) RT=2.68 min, 621.44 (M+H)+. $^1$H NMR (400 MHz, CD$_3$OD) δ ppm 1.18 (t, J=7.69 Hz, 2H) 1.41 (t, J=7.03 Hz, 2H) 2.60 (q, J=7.76 Hz, 2H) 4.13 (q, J=6.88 Hz, 2H) 4.73 (d, J=17.14 Hz, 1H) 5.06 (d, J=17.58 Hz, 2H) 6.24 (s, 1H) 6.74 (d, J=3.95 Hz, 1H) 6.91-7.00 (m, 2H) 7.04 (d, J=7.91 Hz, 1H) 7.28 (dd, J=9.01, 2.42 Hz, 1H) 7.32-7.47 (m, 4H) 7.67 (d, J=7.03 Hz, 2H) 7.75 (s, 1H) 8.17 (d, J=9.23 Hz, 1H).

Example 430

4-(2-(2-((1-aminoisoquinolin-6-ylamino)(3-ethoxy-5-ethyl-2-fluorophenyl)methyl)-4-phenyl-1H-imidazol-1-yl)acetyl)piperazin-2-one bis-trifluoroacetic acid salt

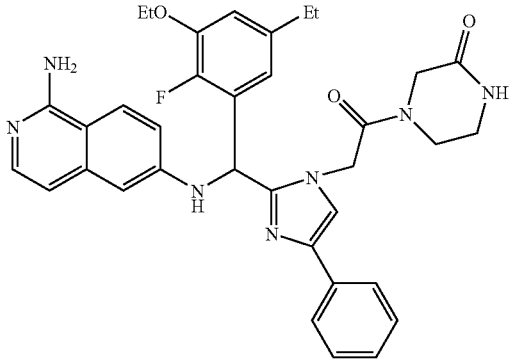

According to procedure for the preparation of Example 402, Example 400 (20 mg, 0.03 mmol) and piperazin-2-one (8 mg, 0.05 mmol) afforded 17 mg of Example 430. LC/MS (2 min gradient) RT=2.25 min, 622.48 (M+H)+. $^1$H NMR (400 MHz, CD$_3$OD) δ ppm 1.19 (t, J=7.69 Hz, 3H) 1.41 (t, J=7.03 Hz, 3H) 2.60 (q, J=7.47 Hz, 2H) 3.33-3.45 (m, 2H) 3.58-3.81 (m, 2H) 3.87-4.04 (m, 2H) 4.08-4.20 (m, 2H) 5.06 (d, J=17.14 Hz, 1H) 5.46 (d, J=17.14 Hz, 1H) 6.31-6.45 (m, 1H) 6.79 (d, J=3.95 Hz, 1H) 6.95 (d, J=7.03 Hz, 1H) 6.98-7.08 (m, 2H) 7.28 (dd, J=9.23, 2.20 Hz, 1H) 7.37 (d, J=7.03 Hz, 1H) 7.39-7.51 (m, 3H) 7.66 (d, J=7.03 Hz, 2H) 7.72-7.80 (m, 1H) 8.18 (d, J=8.79 Hz, 1H).

Example 431

N-((1H-imidazol-5-yl)methyl)-2-(2-((1-aminoisoquinolin-6-ylamino)(3-ethoxy-5-ethyl-2-fluorophenyl)methyl)-4-phenyl-1H-imidazol-1-yl)acetamide bis-trifluoroacetic acid salt

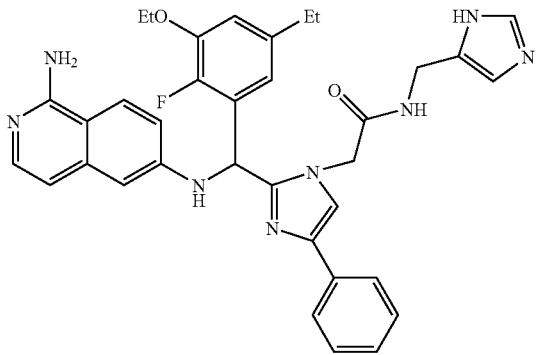

According to procedure for the preparation of Example 402, Example 400 (20 mg, 0.03 mmol) and (1H-imidazol-5-yl)methanamine (8 mg, 0.05 mmol) afforded 18 mg of Example 431. LC/MS (2 min gradient) RT=1.42 min, 619.06 (M+H)+. $^1$H NMR (400 MHz, CD$_3$OD) δ ppm 1.16 (t, J=7.47 Hz, 2H) 1.41 (t, J=7.03 Hz, 2H) 2.58 (q, J=7.62 Hz, 2H) 4.13 (q, J=7.03 Hz, 2H) 4.47-4.74 (m, 2H) 4.84 (d, J==17.14 Hz, 1H) 5.09 (d, J=17.14 Hz, 1H) 6.31 (s, 1H) 6.75 (d, J=4.39 Hz, 1H) 6.89 (d, J=7.03 Hz, 1H) 6.93 (d, J=2.20 Hz, 1H) 6.97-7.08 (m, 1H) 7.25 (dd, J=9.01, 2.42 Hz, 1H) 7.32-7.38 (m, 2H) 7.41 (t, J=7.25 Hz, 2H) 7.45 (s, 2H) 7.66 (d, J=7.03 Hz, 1H) 7.71 (s, 1H) 8.15 (d, J=9.23 Hz, 1H).

Example 432

2-(2-((1-aminoisoquinolin-6-ylamino)(3-(3-(dimethylamino)-2,2-dimethylpropoxy)-5-ethyl-2-fluorophenyl)methyl)-4-phenyl-1H-imidazol-1-yl)acetic acid bis-trifluoroacetic acid salt

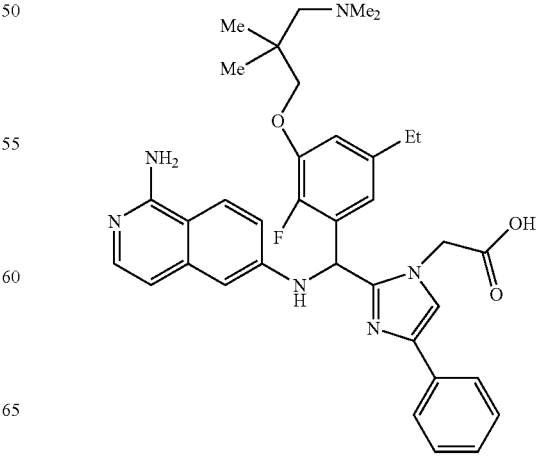

According to procedure for the preparation of Example 421, Intermediate 421.1 (88 mg, 0.1 mmol) and 3-(dimethylamino)-2,2-dimethylpropan-1-ol (17.9 mg, 0.19 mmol) afforded 19 mg of Example 432. LC/MS (2 min gradient) RT=1.37 min, 625.36 (M+H)+. $^1$H NMR (400 MHz, CD$_3$OD) δ ppm 1.07-1.35 (m, 9H) 2.60 (t, J=7.47 Hz, 2H) 2.97 (s, 6H) 4.00 (s, 1H) 4.75-4.84 (m, 1H) 4.97-5.10 (m, 1H) 6.39 (s, 1H) 6.83-6.98 (m, 3H) 7.10 (d, J=7.91 Hz, 1H) 7.22-7.31 (m, 1H) 7.31-7.48 (m, 4H) 7.68 (d, J=7.47 Hz, 2H) 7.73-7.82 (m, 1H) 8.17 (d, J=9.23 Hz, 1H)

Example 433

2-(2-((1-aminoisoquinolin-6-ylamino)(5-ethyl-2-fluoro-3-(1-methylpiperidin-4-yloxy)phenyl)methyl)-4-phenyl-1H-imidazol-1-yl)acetic acid bis-trifluoroacetic acid salt

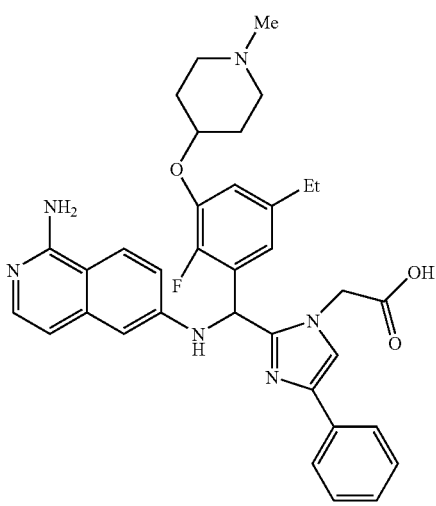

According to procedure for the preparation of Example 421, Intermediate 421.1 (88 mg, 0.1 mmol) and 1-methylpiperidin-4-ol (16.9 mg, 0.19 mmol) afforded 19 mg of Example 433. LC/MS (2 min gradient) RT=1.32 min, 609.36 (M+H)+. $^1$H NMR (400 MHz, CD$_3$OD) δ ppm 1.19 (t, J=7.47 Hz, 3H) 2.12-2.26 (m, 2H) 2.28-2.43 (m, 2H) 2.63 (q, J=7.76 Hz, 2H) 3.38 (d, J=8.35 Hz, 4H) 3.64-3.94 (m, 1H) 4.32 (s, 2H) 6.53 (s, 1H) 6.86-6.99 (m, 3H) 7.18 (d, J=7.47 Hz, 1H) 7.27 (dd, J=9.23, 2.20 Hz, 1H) 7.37 (d, J=7.03 Hz, 1H) 7.41-7.54 (m, 3H) 7.73 (d, J=7.03 Hz, 2H) 7.82 (s, 1H) 8.20 (d, J=9.23 Hz, 1H).

Example 434

2-(2-((1-aminoisoquinolin-6-ylamino)(3-(3-(dimethylamino)-2,2-dimethylpropoxy)-5-ethyl-2-fluorophenyl)methyl)-4-phenyl-1H-imidazol-1-yl)-N,N-dimethylacetamide bis-trifluoroacetic acid salt

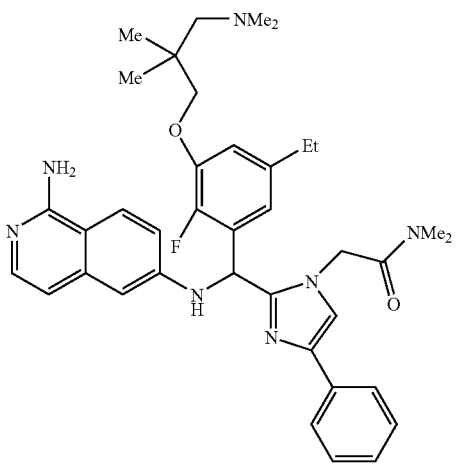

According to procedure for the preparation of Example 402, Example 432 (8 mg, 0.01 mmol) and dimethylamine hydrochloride (2 mg, 0.02 mmol) afforded 6 mg of Example 434. LC/MS (2 min gradient) RT=1.10 min, 652.27 (M+H)+. $^1$H NMR (400 MHz, CD$_3$OD) δ ppm 1.15-1.39 (m, 9H) 2.57-2.68 (m, 2H) 2.92-3.01 (m, 12H) 3.21 (q, J=7.03 Hz, 2H) 4.00 (s, 2H) 4.28-4.41 (m, 2H) 5.02 (d, J=17.58 Hz, 1H) 5.35 (d, J=17.14 Hz, 1H) 6.40 (s, 1H) 6.95 (dd, J=12.52, 6.37 Hz, 2H) 7.02 (s, 1H) 7.13 (d, J=7.91 Hz, 1H) 7.29 (d, J=9.23 Hz, 1H) 7.38 (d, J=7.03 Hz, 1H) 7.40-7.51 (m, 3H) 7.66 (d, J=7.91 Hz, 2H) 7.79 (s, 1H) 8.20 (d, J=8.79 Hz, 1H).

Example 435

2-(2-((1-aminoisoquinolin-6-ylamino)(3-ethoxy-5-ethyl-2-fluorophenyl)methyl)-1H-imidazol-4-yl)-6-fluoro-N-methylbenzamide bis-trifluoroacetic acid salt

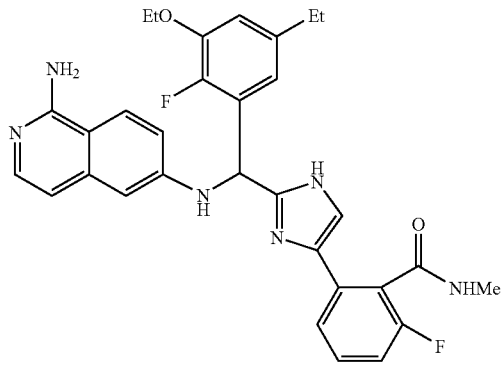

According to procedure for the preparation of Example 307, Example 225 (38 mg, 0.07 mmol) and methylamine (70 µL, 2N solution, 0.14 mmol) afforded 30 mg of Example 435.

LC/MS (2 min gradient) RT=1.50 min, 557.32 (M+H)+. 1H NMR (400 MHz, CD3OD) δ ppm 1.20 (t, J=7.69 Hz, 3H) 1.40 (t, J=7.03 Hz, 3H) 2.62 (q, J=7.47 Hz, 2H) 3.25-3.34 (m, 3H) 4.13 (q, J=7.03 Hz, 2H) 6.51 (s, 1H) 6.79-6.84 (m, 1H) 6.89 (d, J=2.20 Hz, 1H) 6.95 (d, J=7.03 Hz, 1H) 7.04 (d, J=7.91 Hz, 1H) 7.27 (dd, J=9.23, 2.64 Hz, 1H) 7.33 (t, J=8.79 Hz, 1H) 7.35-7.41 (m, 1H) 7.45 (d, J=7.91 Hz, 1H) 7.52-7.55 (m, 1H) 7.55-7.65 (m, 1H) 8.20 (d, J=8.79 Hz, 1H).

Example 436

2-(2-((1-aminoisoquinolin-6-ylamino)(3-ethoxy-5-ethyl-2-fluorophenyl)methyl)-1-(2-(methylamino)-2-oxoethyl)-1H-imidazol-4-yl)-6-fluoro-N-methylbenzamide bis-trifluoroacetic acid salt

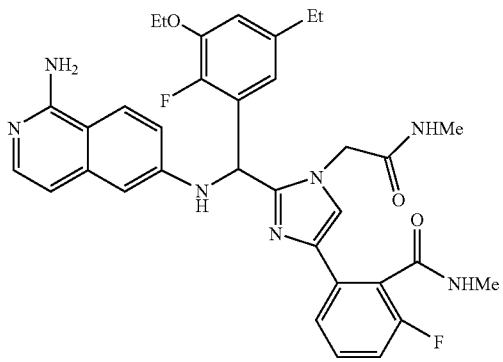

tert-butyl 2-fluoro-6-iodobenzoate (436.1)

To a refluxing suspension of 2-fluoro-6-iodobenzoic acid (533 mg, 2 mmol) in anhydrous benzene (3 mL), was added N,N-dimethylformamide di-tert-butyl acetal (1.64 g, 8 mmol) over 10 min. The solution was refluxed for a further 30 min, cooled and washed with H2O, NaHCO3 and brine, dried (Na2SO4) and concentrated. The crude product was purified by flash chromatography (0-10% EtOAc/hexanes gradient) to afford 400 mg of Intermediate 436.1.

tert-butyl 2-fluoro-6-(4,4,5,5-tetramethyl-1,3,2-dioxaborolan-2-yl)benzoate (436.2)

To a degassed mixture of tert-butyl 2-fluoro-6-iodobenzoate (161 mg, 0.5 mmol), 4,4,5,5-tetramethyl-1,3,2-dioxaborolane (0.1 mL, 0.6 mmol) and TEA (0.25 mL, 1.5 mmol) in 2 mL dioxane, was added Pd(PPh3)2Cl2 (7 mg, 0.01 mmol). The mixture was stirred at 165° C. for 10 min in a microwave oven. The mixture was diluted with EtOAc, washed with sat. NH4Cl, H2O and brine, dried over (Na2SO4), filtered and concentrated. The crude product was purified by flash chromatography (0-10% EtOAc/hexanes gradient) to afford 50 mg (45%) of Intermediate 436.2.

2-(2-((1-aminoisoquinolin-6-ylamino)(3-ethoxy-5-ethyl-2-fluorophenyl)methyl)-1-(carboxymethyl)-1H-imidazol-4-yl)-6-fluorobenzoic acid (436.3)

According to procedure for the preparation of Example 241, coupling of Intermediate 400.2 (45 mg, 0.06 mmol) with Intermediate 436.2 (26 mg, 0.085 mmol), followed by 2 h TFA deprotection afforded after HPLC purification 25 mg of Intermediate 436.3. LC/MS (2 min gradient) RT=1.59 min, 602.2 (M+H)+.

Example 436

According to procedure for the preparation of Example 402, Intermediate 436.3 (25 mg, 0.03 mmol), methyl amine (45 μL, 2N solution, 0.09 mmol) and BOP (0.09 mmol) afforded 22 mg of Example 436. LC/MS (2 min gradient) RT=1.57 min, 628.32 (M+H)+. 1H NMR (400 MHz, CD3OD) δ ppm 1.20 (t, J=7.69 Hz, 3H) 1.41 (t, J=6.81 Hz, 3H) 2.62 (q, J=7.62 Hz, 2H) 2.73 (s, 6H) 4.13 (q, J=6.74 Hz, 2H) 4.69 (d, J=17.14 Hz, 1H) 5.00 (d, J=16.70 Hz, 1H) 6.35 (s, 1H) 6.74 (d, J=3.95 Hz, 1H) 6.92-7.13 (m, 3H) 7.20-7.34 (m, 2H) 7.34-7.45 (m, 2H) 7.46-7.59 (m, 1H) 7.64 (s, 1H) 8.18 (d, J=9.23 Hz, 1H).

Examples 437 and 438

2-(2-((1-aminoisoquinolin-6-ylamino)(3-ethoxy-5-ethyl-2-fluorophenyl)methyl)-4-phenyl-1H-imidazol-1-yl)propanoic acid bis-trifluoroacetic acid salt, diastereomers 1 and 2

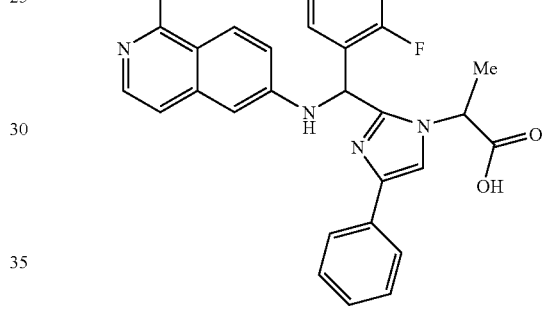

tert-butyl 2-(2-((1-(di-tert-butyl imidodicarbonate)isoquinolin-6-ylamino)(3-ethoxy-5-ethyl-2-fluorophenyl)methyl)-4-bromo-1H-imidazol-1-yl)propionate (437.1)

To a solution of intermediate 400.1 (50 mg, 0.073 mmol) in THF at 0° C., was added sodium hydride (60%, 7.3 mg, 0.183 mmol). The mixture was stirred at 0° C. for 5 min, then a solution of (R)-tert-butyl 2-(trifluoromethylsulfonyloxy)propanoate (prepared according to U.S. Pat. No. 4,584,285, which is incorporated herein by reference) (30.5 mg, 0.110 mmol) in 0.5 mL THF. The mixture was stirred at 0° C. for 45 min, then was quenched with ammonium chloride. The mixture was diluted with EtOAc, washed with H2O and brine, dried (Na2SO4) and concentrated. The crude residue was purified by flash chromatography (0 to 75% EtOAc/hexanes gradient) to afford 48 mg of intermediate 437.1. LC/MS (2 min gradient) RT=2.06 min, 812.4 (M+H)+.

Examples 437 and 438

According to the procedure for the preparation of Example 206, coupling of Intermediate 437.1 (47 mg, 0.058 mmol) and phenylboronic acid, followed by deprotection for 2 h in TFA and HPLC purification afforded 7.9 mg of Example 437 followed by 5.8 mg of Example 438.

Example 437: LCMS (2 min gradient) RT=1.42 min, 554.42 (M+H)+; 1H NMR (400 MHz, CD3OD) 5 ppm 1.17 (t, J=7.69 Hz, 3H) 1.39 (t, J=7.03 Hz, 3H) 1.87 (d, J=7.03 Hz, 3H) 2.57 (q, J=7.76 Hz, 2H) 4.11 (q, J=7.03 Hz, 2H) 5.31-5.37 (m, 1H) 6.50 (s, 1H) 6.73 (dd, J=5.71, 1.76 Hz, 1H) 6.89 (d, J=2.20 Hz, 1H) 6.93 (d, J=7.03 Hz, 1H) 6.98 (dd, J=7.91, 1.76 Hz, 1H) 7.26 (dd, J=9.23, 2.64 Hz, 1H) 7.33-7.39 (m, 2H) 7.43 (t, J=7.47 Hz, 2H) 7.70 (dd, J=8.35, 1.32 Hz, 2H) 7.99 (s, 1H) 8.16 (d, J=9.23 Hz, 1H).

Example 438: LCMS (2 min gradient) RT=1.51 min, 554.44 (M+H)+; 1H NMR (400 MHz, CD3OD) δ ppm 1.17 (t, J=7.47 Hz, 3H) 1.41 (t, J=7.03 Hz, 3H) 1.67 (d, J=7.47 Hz, 3H) 2.60 (q, J=7.62 Hz, 2H) 4.13 (q, J=7.03 Hz, 2H) 5.13-5.18 (m, 1H) 6.39 (s, 1H) 6.76-6.78 (m, 1H) 6.88 (d, J=2.64 Hz, 1H) 6.90 (d, J=7.03 Hz, 1H) 7.05 (dd, J=7.91, 1.76 Hz, 1H) 7.26 (dd, J=9.23, 2.20 Hz, 1H) 7.32-7.38 (m, 2H) 7.42 (t, J=7.25 Hz, 2H) 7.69 (dd, J=8.57, 1.10 Hz, 2H) 7.98 (s, 1H) 8.16 (d, J=9.23 Hz, 1H).

Example 439

2-(2-((1-aminoisoquinolin-6-ylamino)(5-ethyl-2-fluoro-3-morpholinophenyl)methyl)-4-phenyl-1H-imidazol-1-yl)-N,N-dimethylacetamide bis-trifluoroacetic acid salt

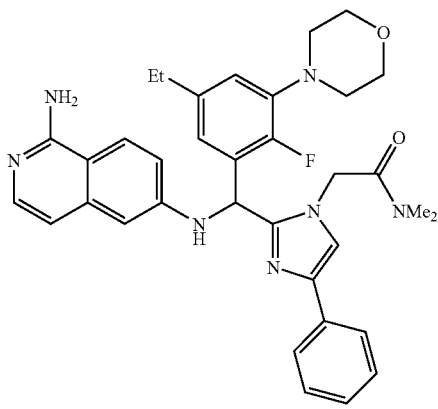

To a solution of Example 407 (15 mg, 0.026 mmol) in 1 mL DMF were added TEA (27 μL), dimethylamine hydrochloride (6.4 mg) and BOP (12.9 mg). The mixture was stirred at it for 3 h, then was purified by preparative HPLC to afford 13.3 mg of Example 439. (2 min gradient) RT=1.25 min, 608.45 (M+H)+; 1H NMR (400 MHz, CD3OD) δ ppm 1.19 (t, J=7.47 Hz, 3H) 2.61 (q, J=7.47 Hz, 2H) 2.90 (s, 3H) 3.00 (s, 3H) 3.04-3.13 (m, 4H) 3.81 (t, J=4.61 Hz, 4H) 4.84-4.88 (m, 1H) 5.30 (d, J=17.14 Hz, 1H) 6.31 (s, 1H) 6.86 (d, J=4.39 Hz, 1H) 6.95-7.01 (m, 3H) 7.28 (dd, J=9.23, 2.20 Hz, 1H) 7.36 (d, J=7.03 Hz, 1H) 7.39-7.46 (m, 3H) 7.65 (d, J=7.47 Hz, 2H) 7.73 (s, 1H) 8.18 (d, J=9.23 Hz, 1H).

Example 440

2-(2-((1-aminoisoquinolin-6-ylamino)(3-ethoxy-5-ethyl-2-fluorophenyl)methyl)-4-(pyridin-3-yl)-1H-imidazol-1-yl)acetic acid bis-trifluoroacetic acid salt

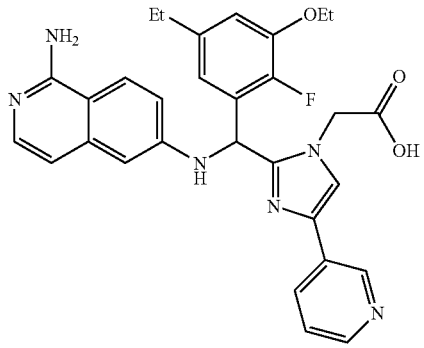

According to the procedure for the preparation of Example 206, coupling of Intermediate 400.2 (46 mg, 0.057 mmol) and 3-pyridylboronic acid, followed by deprotection (2 h treatment with TFA) and HPLC purification afforded 27.1 mg of Example 440. LCMS (2 min gradient) RT=1.25 min., 541.39 (M+H)+; 1H NMR (400 MHz, CD3OD) δ ppm 1.14 (t, J=7.47 Hz, 3H) 1.41 (t, J=7.03 Hz, 3H) 2.54 (q, J=7.47 Hz, 2H) 4.11 (q, J=7.03 Hz, 2H) 4.75 (d, J=18.46 Hz, 1H) 4.97 (d, J=18.02 Hz, 1H) 6.24 (s, 1H) 6.73 (dd, J=5.93, 1.98 Hz, 1H) 6.86 (s, 1H) 6.88 (d, J=3.52 Hz, 1H) 6.93 (dd, J=7.91, 1.76 Hz, 1H) 7.24 (dd, J=9.23, 2.20 Hz, 1H) 7.31 (d, J=7.03 Hz, 1H) 7.83 (dd, J=8.13, 5.49 Hz, 1H) 7.87 (s, 1H) 8.10 (d, J=9.23 Hz, 1H) 8.55 (dd, J=5.71, 1.32 Hz, 1H) 8.62-8.65 (m, J=8.24, 1.65, 1.54 Hz, 1H) 9.07 (d, J=1.76 Hz, 1H).

Example 441

2-(2-((1-aminoisoquinolin-6-ylamino)(3-ethoxy-5-ethyl-2-fluorophenyl)methyl) 4-(furan-3-yl)-1H-imidazol-1-yl)acetic acid bis-trifluoroacetic acid salt

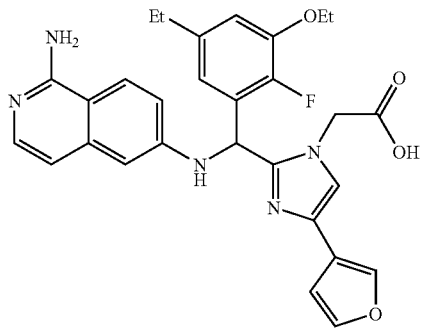

According to the procedure for the preparation of Example 206, coupling of Intermediate 400.2 (46 mg, 0.057 mmol) and 3-furanylboronic acid, followed by deprotection (2 h treatment with TFA) and HPLC purification afforded 26.0 mg of Example 441. LCMS (2 min. gradient) RT=1.31 min, 530.37 (M+H)+; 1H NMR (400 MHz, CD3OD) δ ppm 1.18 (t, J=7.47 Hz, 3H) 1.40 (t, J=7.03 Hz, 3H) 2.60 (q, J=7.76 Hz, 2H) 4.12 (q, J=7.03 Hz, 2H) 4.74 (d, J=18.02 Hz, 1H) 5.02 (d, J=17.58

Hz, 1H) 6.31 (s, 1H) 6.73-6.75 (m, 1H) 6.77 (dd, J=5.71, 1.76 Hz, 1H) 6.93 (d, J=3.95 Hz, 1H) 6.94 (s, 1H) 7.04 (dd, J=7.91, 1.76 Hz, 1H) 7.27 (dd, J=9.23, 2.20 Hz, 1H) 7.35 (d, J=7.03 Hz, 1H) 7.59 (t, J=1.54 Hz, 1H) 7.66 (s, 1H) 7.95 (s, 1H) 8.17 (d, J=9.23 Hz, 1H).

Example 442

2-(2-((1-aminoisoquinolin-6-ylamino)(3-ethoxy-5-ethyl-2-fluorophenyl)methyl)-4-phenyl-1H-imidazol-1-yl)-N-ethylacetamide

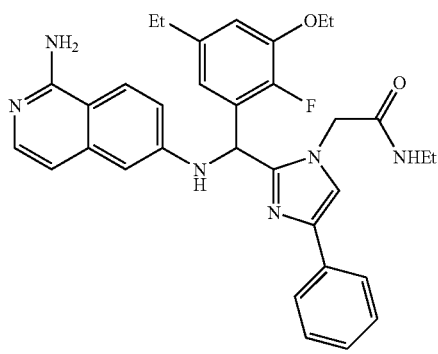

According to the procedure for the preparation of Example 402, coupling of Example 400 (18 mg, 0.023 mmol) with ethylamine (2M in THF, 46 µL, 0.092 mmol) afforded after HPLC purification 5.9 mg of Example 442. LCMS (2 min gradient) RT=1.42 min, 567.45 (M+H)$^+$; $^1$H NMR (400 MHz, CD$_3$OD) δ ppm 1.13 (t, J=7.25 Hz, 3H) 1.20 (t, J=7.69 Hz, 3H) 1.41 (t, J=6.81 Hz, 3H) 2.62 (q, J=7.76 Hz, 2H) 3.18-3.28 (m, 2H) 4.13 (q, J=7.03 Hz, 2H) 4.71 (d, J=17.14 Hz, 1H) 5.03 (d, J=17.14 Hz, 1H) 6.37 (s, 1H) 6.75-6.77 (m, 1H) 6.99 (d, J=7.03 Hz, 1H) 7.05 (d, J=2.20 Hz, 1H) 7.06-7.10 (m, 1H) 7.31 (dd, J=9.01, 2.42 Hz, 1H) 7.38 (d, J=7.03 Hz, 1H) 7.43-7.49 (m, 3H) 7.65 (dd, J=7.69, 1.54 Hz, 2H) 7.89 (s, 1H) 8.20 (d, J=9.23 Hz, 1H).

Example 443

2-(2-((1-aminoisoquinolin-6-ylamino)(3-ethoxy-5-ethyl-2-fluorophenyl)methyl)-4-phenyl-1H-imidazol-1-yl)-N-ethyl-N-methylacetamide bis-trifluoroacetic acid salt

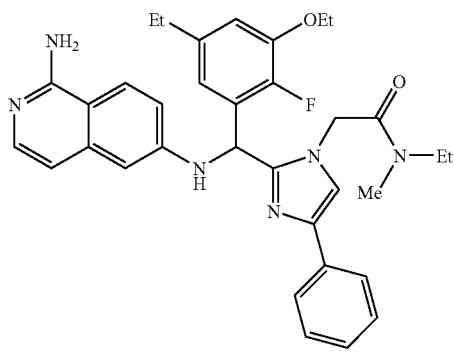

According to the procedure for the preparation of Example 402, coupling of Example 400 (18 mg, 0.023 mmol) with methylethylamine (7.9 µL, 0.092 mmol) afforded after HPLC purification 16.3 mg of Example 443. LCMS (2 min gradient) RT=1.40 min, 581.45 (M+H)$^+$; $^1$H NMR 3:2 mixture of amide bond isomers (400 MHz, CD$_3$OD) δ ppm 1.09 (t, J=7.25 Hz, 2H) 1.16-1.23 (m, 4H) 1.41 (t, J=7.03 Hz, 3H) 2.62 (q, J=7.47 Hz, 2H) 2.92 (s, 1H) 3.00 (s, 2H) 3.35-3.41 (m, 2H) 4.13 (q, J=6.74 Hz, 2H) 4.94 (s, 1H) 5.36-5.45 (m, J=17.14, 17.14 Hz, 1H) 6.35 (s, 1H) 6.81 (t, J=5.71 Hz, 1H) 6.98 (dd, J=7.03, 2.20 Hz, 1H) 7.04 (dd, J=6.59, 2.20 Hz, 1H) 7.08 (d, J=8.35 Hz, 1H) 7.30 (dd, J=9.23, 1.76 Hz, 1H) 7.38 (d, J=7.03 Hz, 1H) 7.43-7.49 (m, 3H) 7.63-7.67 (m, 2H) 7.84 (d, J=7.47 Hz, 1H) 8.20 (d, J=9.23 Hz, 1H)

Example 444

2-(2-((1-aminoisoquinolin-6-ylamino)(3-ethoxy-5-ethyl-2-fluorophenyl)methyl)-4-phenyl-1H-imidazol-1-yl)-N-isopropylacetamide bis-trifluoroacetic acid salt

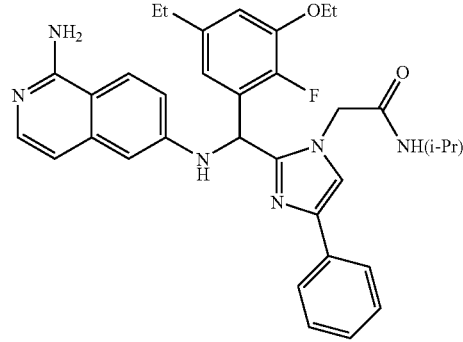

According to the procedure for the preparation of Example 402, coupling of Example 400 (18 mg, 0.023 mmol) with isopropylamine (7.8 µL, 0.092 mmol) afforded after HPLC purification 14.5 mg of Example 444. LCMS (2 min gradient) RT=1.47 min, 581.45 (M+H)$^+$; $^1$H NMR (400 MHz, CD$_3$OD) δ ppm 1.14 (d, J=6.59 Hz, 3H) 1.16 (d, J=6.59 Hz, 3H) 1.17-1.21 (m, 3H) 1.41 (t, J=6.81 Hz, 3H) 2.62 (q, J=7.62 Hz, 2H) 3.98 (qd, J=6.52, 6.37 Hz, 1H) 4.13 (q, J=6.74 Hz, 2H) 4.66 (d, J=17.14 Hz, 1H) 5.01 (d, J=16.70 Hz, 1H) 6.34 (s, 1H) 6.74 (dd, J=5.71, 1.76 Hz, 1H) 6.98 (d, J=7.03 Hz, 1H) 7.04 (d, J=2.20 Hz, 1H) 7.08 (dd, J=7.91, 1.76 Hz, 1H) 7.30 (dd, J=9.23, 2.20 Hz, 1H) 7.38 (d, J=7.03 Hz, 1H) 7.43-7.48 (m, 3H) 7.64 (d, J=1.32 Hz, 1H) 7.66 (d, J=1.76 Hz, 1H) 7.89 (s, 1H) 8.20 (d, J=9.23 Hz, 1H).

Example 445

2-(2-((1-aminoisoquinolin-6-ylamino)(3-ethoxy-5-ethyl-2-fluorophenyl)methyl)-4-phenyl-1H-imidazol-1-yl)-1-morpholinoethanone bis-trifluoroacetic acid salt

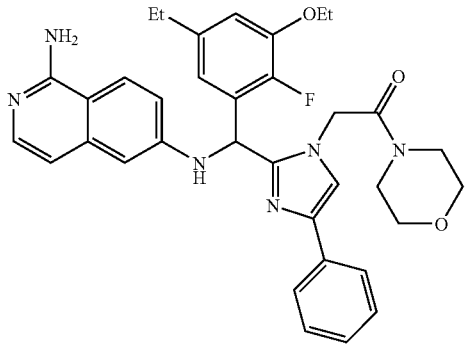

According to the procedure for the preparation of Example 402, coupling of Example 400 (18 mg, 0.023 mmol) with morpholine (8.0 µL, 0.092 mmol) afforded after HPLC purification 14.5 mg of Example 445. LCMS (2 min gradient) RT=1.36 min, 609.47 (M+H)$^+$; $^1$H NMR (400 MHz, CD$_3$OD) δ ppm 1.20 (t, J=7.69 Hz, 3H) 1.41 (t, J=7.03 Hz, 3H) 2.63 (q, J=7.76 Hz, 2H) 4.14 (q, J=7.03 Hz, 2H) 4.97 (d, J=17.14 Hz, 1H) 5.46 (d, J=17.14 Hz, 1H) 6.41 (s, 1H) 6.80 (dd, J=5.71, 1.76 Hz, 1H) 6.97 (d, J=7.47 Hz, 1H) 7.04 (d, J=2.20 Hz, 1H) 7.08 (dd, J=7.91, 1.76 Hz, 1H) 7.31 (dd, J=9.23, 2.20 Hz, 1H) 7.38 (d, J=7.03 Hz, 1H) 7.44-7.50 (m, 3H) 7.63-7.66 (m, J=7.69, 1.98 Hz, 2H) 7.85 (s, 1H) 8.21 (d, J=9.23 Hz, 1H).

Example 446

2-(2-((1-aminoisoquinolin-6-ylamino)(3-ethoxy-5-ethyl-2-fluorophenyl)methyl)-4-(pyridin-3-yl)-1H-imidazol-1-yl)-N,N-dimethylacetamide bis-trifluoroacetic acid salt

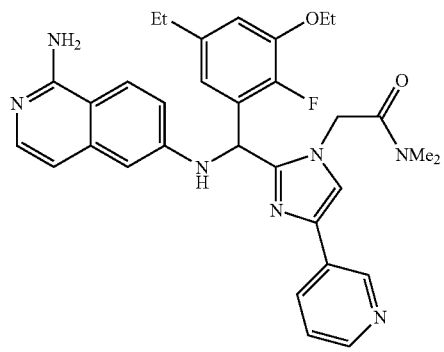

According to the procedure for the preparation of Example 402, coupling of Example 440 (15 mg) with dimethylamine hydrochloride (6.4 mg, 0.078 mmol) afforded after HPLC purification 14.8 mg of Example 446. LCMS (2 min gradient) RT=1.26 min, 568.13 (M+H)$^+$; $^1$H NMR (400 MHz, CD$_3$OD) δ ppm 1.14 (t, J=7.47 Hz, 3H) 1.42 (t, J=7.03 Hz, 3H) 2.54 (q, J=7.47 Hz, 2H) 2.88 (s, 3H) 2.99 (s, 3H) 4.11 (q, J=7.03 Hz, 2H) 4.77-4.86 (m, 1H) 5.16 (d, J=17.14 Hz, 1H) 6.22 (s, 1H) 6.74 (dd, J=5.71, 1.76 Hz, 1H) 6.90 (dd, J=4.61, 2.42 Hz, 2H) 6.94 (dd, J=7.91, 1.76 Hz, 1H) 7.24 (dd, J=9.23, 2.20 Hz, 1H) 7.32 (d, J=7.47 Hz, 1H) 7.83 (s, 1H) 7.91 (dd, J=8.35, 5.71 Hz, 1H) 8.11 (d, J=9.23 Hz, 1H) 8.59 (d, J=4.83 Hz, 1H) 8.73 (d, J=8.35 Hz, 1H) 9.10 (s, 1H).

Example 447

2-(2-((1-aminoisoquinolin-6-ylamino)(3-ethoxy-5-ethyl-2-fluorophenyl)methyl)-4-(furan-3-yl)-1H-imidazol-1-yl)-N,N-dimethylacetamide bis-trifluoroacetic acid salt

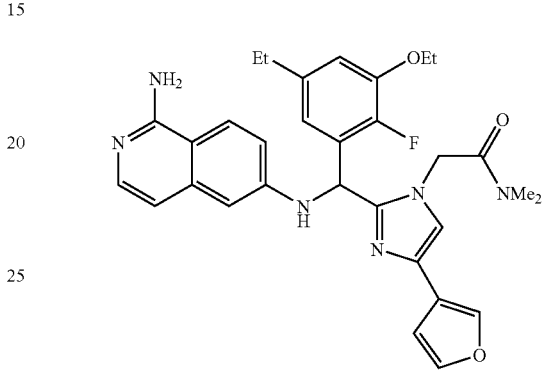

According to the procedure for the preparation of Example 402, coupling of Example 441 (15 mg) with dimethylamine hydrochloride (6.4 mg, 0.078 mmol) afforded after HPLC purification 12.6 mg of Example 447. LCMS (2 min gradient) RT=1.22 min, 557.17 (M+H)$^+$; $^1$H NMR (400 MHz, CD$_3$OD) δ ppm 1.19 (t, J=7.69 Hz, 3H) 1.41 (t, J=7.03 Hz, 3H) 2.61 (q, J=7.47 Hz, 2H) 2.92 (s, 3H) 3.00 (s, 3H) 4.13 (q, J=7.03 Hz, 2H) 4.84 (d, J=17.14 Hz, 1H) 5.30 (d, J=17.14 Hz, 1H) 6.27 (s, 1H) 6.74 (dd, J=1.76, 0.88 Hz, 1H) 6.77 (dd, J=5.71, 1.76 Hz, 1H) 6.97 (d, J=7.03 Hz, 1H) 7.01 (d, J=2.20 Hz, 1H) 7.06 (dd, J=7.91, 1.76 Hz, 1H) 7.28 (dd, J=9.23, 2.64 Hz, 1H) 7.37 (d, J=7.03 Hz, 1H) 7.59-7.61 (m, 2H) 7.96 (s, 1H) 8.18 (d, J=9.23 Hz, 1H).

Example 448

2-(2-((1-aminoisoquinolin-6-ylamino)(3-ethoxy-5-ethyl-2-fluorophenyl)methyl)-4-phenyl-1H-imidazol-1-yl)ethanol bis-trifluoroacetic acid salt

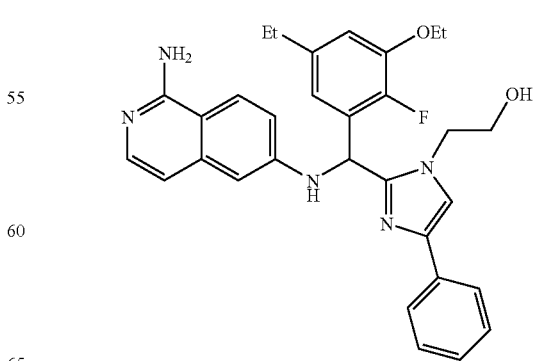

(3-(tert-butyldimethylsilyloxy)-5-ethyl-2-fluorophenyl) (4-phenyl-1-trityl-1H-imidazol-2-yl)methanol (448.1)

To a solution of 4-phenyl-1-trityl-1H-imidazole (8.1) (1.37 g, 3.54 mmol) in 20 mL THF at 0° C., was added BuLi (1.6 M in hexanes, 2.66 mL, 4.25 mmol). The mixture was stirred at 0° C. for 30 min, then a solution of 3-(tert-butyldimethylsilyloxy)-5-ethyl-2-fluorobenzaldehyde (188.3) (1.00 g, 3.54 mmol) in 3 mL THF was added dropwise. The mixture was stirred at 0° C. for 5 min, was removed from the cooling bath and stirred 45 min, then was quenched with sat. $NH_4Cl$. The mixture was diluted with EtOAc, washed with $H_2O$ and brine, dried ($Na_2SO_4$) and concentrated. The crude product was purified by flash chromatography (0 to 40% EtOAc/hexanes gradient) to afford 1.75 g of Intermediate 448.1 as a white foam. LCMS (2 min gradient) RT=2.22 min, 669.28 $(M+H)^+$.

5-ethyl-2-fluoro-3-(hydroxy(4-phenyl-1-trityl-1H-imidazol-2-yl)methyl)phenol (448.2)

To a solution of intermediate 448.1 (1.74 g, 2.60 mmol) in 10 mL THF at rt, was added TBAF (1M in THF, 2.60 mL, 2.60 mmol). The mixture was stirred at rt for 30 min, then was diluted with EtOAc, washed with $H_2O$ (2×) and brine, dried ($Na_2SO_4$) and concentrated. The crude product was triturated with hexanes (10 mL) to afford after filtration 1.32 g of intermediate 448.2 as a white solid. LCMS (2 min gradient) RT=1.81 min, 555.3 $(M+H)^+$.

(3-ethoxy-5-ethyl-2-fluorophenyl)(4-phenyl-1-trityl-1H-imidazol-2-yl)methanol (448.3)

To a solution of Intermediate 448.2 (1.00 g, 1.80 mmol) in 10 mL DMF at rt, were added $K_2CO_3$ (229 mg, 2.16 mmol) and iodoethane (432 μL, 5.4 mmol). The mixture was stirred at rt for 19 h, then diluted with EtOAc. The organic phase was washed with $H_2O$ (2×), sat. $Na_2SO_3$ and brine, dried ($Na_2SO_4$), filtered through 1" $SiO_2$ and concentrated to afford 1.05 g of Intermediate 448.3 as a colorless solid. LCMS (2 min gradient) RT=1.92 min, 583.3 $(M+H)^+$.

di-tert-butyl (6-{[(4-phenyl-1-trityl-1H-imidazol-2-yl)(3-ethoxy-5-ethyl-2-fluorophenyl)methyl]amino}isoquinolin-1-yl)imidodicarbonate (448.4)

To a solution of Intermediate 448.3 (1.05 g, 1.80 mmol) and TEA (0.753 mL, 5.40 mmol) in 10 mL $CH_2Cl_2$ at 0° C., was added MsCl (0.35 mL, 4.5 mmol). The mixture was stirred at 0° C. for 30 min, then was diluted with EtOAc. The mixture was washed with water (2×) and brine, dried ($Na_2SO_4$) and concentrated to afford the chloro intermediate (2-(chloro(3-ethoxy-5-ethyl-2-fluorophenyl)methyl)-4-phenyl-1-trityl-1H-imidazole), which was used without further purification.

To a solution of the chloro intermediate (1.80 mmol) in 5 mL $CH_3CN$ and 2 mL $CH_2Cl_2$ at rt, was added DIEA (0.627 mL, 3.6 mmol), di-tert-butyl (6-aminoisoquinolin-1-yl)imidodicarbonate (712 mg, 1.98 mmol). The mixture was stirred at rt for 19 h, then was diluted with EtOAc. The organic phase was washed with $H_2O$ (2×) and brine, dried ($Na_2SO_4$) and concentrated. The crude product was purified by flash chromatography (0 to 80% EtOAc/hexanes gradient) to afford 1.41 g of Intermediate 448.4 as an off-white solid. LCMS (2 min gradient) RT=2.32 min, 682.29 $(M+(H-Tr)+H)^+$.

di-tert-butyl (6-{[(4-phenyl-1H-imidazol-2-yl)(3-ethoxy-5-ethyl-2-fluorophenyl)methyl]amino}isoquinolin-1-yl)imidodicarbonate (448.5)

A solution of intermediate 448.4 (780 mg, 0.844 mmol) in 90% aq. AcOH was stirred at rt for 3.5 h, then concentrated. The residue was dissolved in EtOAc. The solution was washed with sat. $NaHCO_3$, $H_2O$ and brine. The organic phase was dried ($Na_2SO_4$), then concentrated. The crude product was purified by flash chromatography (0 to 80% EtOAc/hexanes gradient) to afford 544 mg of intermediate 448.5 as a white solid. LCMS (2 min. gradient) RT=1.82 min, 682.56 $(M+H)^+$.

Ethyl 2-(2-((1-(di-tert-butylimidodicarbonate)isoquinolin-6-ylamino)(3-ethoxy-5-ethyl-2-fluorophenyl)methyl)-4-bromo-1H-imidazol-1-yl)acetate (448.6)

To a solution of Intermediate 448.5 (44 mg, 0.065 mmol) in 1 mL THF at 0° C., was added NaH (60%, 6.5 mg, 0.161 mmol). The mixture was stirred at 0° C. for 5 min, then ethyl bromoacetate (10.7 μL, 0.097 mmol) was added. The mixture was stirred for 1 h at 0° C., then was quenched with sat. $NH_4Cl$. The mixture was diluted with EtOAc and was washed with $H_2O$ and brine, dried ($Na_2SO_4$) and concentrated. The crude product was purified by flash chromatography (0-100% EtOAc/hexanes gradient) to afford 28 mg of Intermediate 448.6 at a colorless residue. LCMS (2 min gradient) RT=1.95 min, 768.19 $(M+H)^+$.

Example 448

To a solution of intermediate 448.6 (28 mg, 0.036 mmol) in 1 mL THF at 0° C., was added $LiBH_4$ (2M in THF, 46 μL, 0.091 mmol). The mixture was stirred 1.5 h at 0° C., then 2 h at rt. Additional $LiBH_4$ (2M in THF, 50 μL, 0.10 mmol) was added and the mixture was stirred for 20 h. The reaction was quenched with $H_2O$, then evaporated under a stream of nitrogen. The crude material was dissolved in 2 mL TFA and stirred for 20 min. The mixture was concentrated and purified by preparative HPLC to afford 10.2 mg of Example 448 as a white powder. LCMS (2 min gradient) RT=1.38 min, 526.08 $(M+H)^+$; $^1H$ NMR (400 MHz, $CD_3OD$) δ ppm 1.18 (t, J=7.69 Hz, 3H) 1.41 (t, J=7.03 Hz, 3H) 2.61 (q, J=7.47 Hz, 2H) 3.87 (ddd, J=11.64, 7.25, 4.83 Hz, 1H) 3.96 (dt, J=11.86, 3.52 Hz, 1H) 4.13 (q, J=7.03 Hz, 2H) 4.19-4.24 (m, 2H) 6.60 (s, 1H) 6.76 (dd, J=5.71, 1.76 Hz, 1H) 6.90 (d, J=7.03 Hz, 1H) 7.00 (d, J=2.64 Hz, 1H) 7.06 (dd, J=7.91, 1.76 Hz, 1H) 7.29 (dd, J=9.23, 2.20 Hz, 1H) 7.35 (d, J=7.03 Hz, 1H) 7.38-7.47 (m, 3H) 7.66 (dd, J=8.13, 1.54 Hz, 2H) 7.90 (s, 1H) 8.18 (d, J=9.23 Hz, 1H).

Example 449

N6-((1-allyl-4-phenyl-1H-imidazol-2-yl)(3-ethoxy-5-ethyl-2-fluorophenyl)methyl)isoquinoline-1,6-diamine bis-trifluoroacetic acid salt

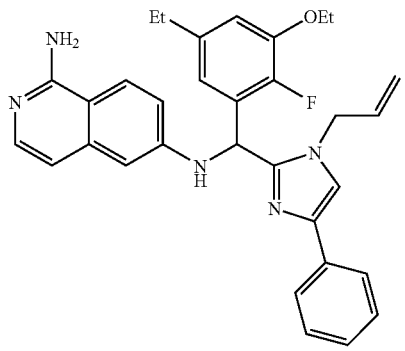

To a solution of Intermediate 448.5 (40 mg, 0.059 mmol) in 1 mL THF at 0° C., was added NaH (60%, 5.9 mg, 0.15 mmol). The mixture was stirred at 0° C. for 5 min, then allyl bromide (7.6 μL, 0.088 mmol) was added. The mixture was stirred at rt for 2 h, then was concentrated. The product was dissolved in 1 mL TFA and stirred 20 min, then was concentrated. The crude product was purified by preparative HPLC to afford 17.4 mg of Example 449 as an off-white powder. LCMS (2 min gradient) RT=1.53 min, 522.07 (M+H)+; 1H NMR (400 MHz, CD3OD) δ ppm 1.18 (t, J=7.47 Hz, 3H) 1.40 (t, J=7.03 Hz, 3H) 2.61 (q, J=7.47 Hz, 2H) 4.13 (q, J=7.03 Hz, 2H) 5.15 (d, J=17.14 Hz, 1H) 5.25 (d, J=10.55 Hz, 1H) 5.77-5.87 (m, 1H) 6.52 (s, 1H) 6.83 (d, J=5.71 Hz, 1H) 6.87 (d, J=2.20 Hz, 1H) 6.93 (d, J=7.03 Hz, 1H) 7.04-7.07 (m, 1H) 7.27 (dd, J=9.23, 2.20 Hz, 1H) 7.37 (d, J=7.03 Hz, 1H) 7.43-7.50 (m, 3H) 7.67 (dd, J=7.69, 1.54 Hz, 2H) 7.93 (s, 1H) 8.21 (d, J=9.23 Hz, 1H).

Example 450

N6-((3-ethoxy-5-ethyl-2-fluorophenyl)(1-(2-methylallyl)-4-phenyl-1f-imidazol-2-yl)methyl)isoquinoline-1,6-diamine bis-trifluoroacetic acid salt

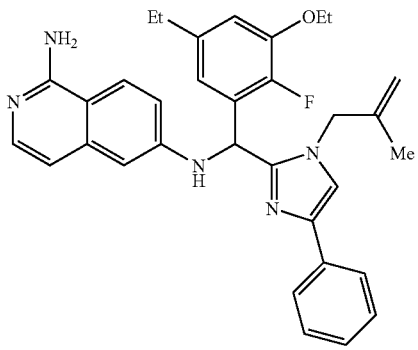

To a solution of Intermediate 448.5 (40 mg, 0.059 mmol) in 1 mL THF at 0° C., was added NaH (60%, 5.9 mg, 0.15 mmol). The mixture was stirred at 0° C. for 5 min, then 2-methyl-3-bromopropene (8 μL) was added. The mixture was stirred at rt for 3.25 h, then was concentrated. The product was dissolved in 1 mL TFA and stirred 30 min, then was concentrated. The crude product was purified by preparative HPLC to afford 30 mg of Example 450 as a white powder. LCMS (2 min gradient) RT=1.59 min, 536.12 (M+H)+; 1H NMR (400 MHz, CD3OD) δ ppm 1.16 (t, J=7.47 Hz, 3H) 1.40 (t, J=6.81 Hz, 3H) 1.65 (s, 3H) 2.58 (q, J=7.47 Hz, 2H) 4.12 (q, J=6.88 Hz, 2H) 4.62 (s, 1H) 4.69 (d, 1H) 4.78 (d, 1H) 4.90 (s, 1H) 6.36 (s, 1H) 6.79 (d, J=2.20 Hz, 1H) 6.81 (dd, J=5.71, 1.76 Hz, 1H) 6.89 (d, J=7.03 Hz, 1H) 6.99 (dd, J=7.91, 1.76 Hz, 1H) 7.23 (dd, J=9.01, 2.42 Hz, 1H) 7.33-7.36 (m, 2H) 7.42 (t, J=7.25 Hz, 2H) 7.69 (d, J=7.03 Hz, 2H) 7.72 (s, 1H) 8.16 (d, J=9.23 Hz, 1H).

Example 451

3-(2-((1-aminoisoquinolin-6-ylamino)(3-ethoxy-5-ethyl-2-fluorophenyl)methyl)-4-phenyl-1H-imidazol-1-yl)propanoic acid bis-trifluoroacetic acid salt

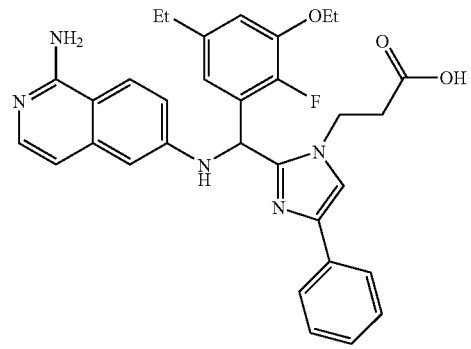

To a solution of Intermediate 448.5 (50 mg, 0.073 mmol) in 1 mL THF at 0° C., was added NaH (60%, 7.3 mg, 0.18 mmol). The mixture was stirred at 0° C. for 5 min, then tert-butyl 3-bromopropanoate (18 μL, 0.11 mmol) was added. The mixture was stirred at rt for 20 h, then was concentrated. The crude product was stirred in 1 mL TFA for 2.5 h, concentrated, then was purified by preparative HPLC to afford 23 mg of Example 451 as a white powder. LCMS (2 min gradient) RT=1.60 min, 554.27 (M+H)+; 1H NMR (400 MHz, CD3OD) δ ppm 1.18 (t, J=7.69 Hz, 3H) 1.41 (t, J=7.03 Hz, 3H) 2.60 (q, J=7.47 Hz, 2H) 2.75 (ddd, J=17.80, 5.49, 5.27 Hz, 1H) 2.86-2.94 (m, 1H) 4.13 (q, J=7.03 Hz, 2H) 4.21 (ddd, J=14.28, 5.71, 5.49 Hz, 1H) 4.42 (ddd, J=14.39, 8.90, 5.71 Hz, 1H) 6.63 (s, 1H) 6.78 (dd, J=5.71, 1.76 Hz, 1H) 6.95-7.00 (m, 2H) 7.04 (dd, J=7.91, 1.76 Hz, 1H) 7.29 (dd, J=9.01, 2.42 Hz, 1H) 7.34-7.45 (m, 4H) 7.64-7.68 (m, 2H) 7.88 (s, 1H) 8.17 (d, J=9.23 Hz, 1H).

Example 452

3-(2-((1-aminoisoquinolin-6-ylamino)(3-ethoxy-5-ethyl-2-fluorophenyl)methyl)-4-phenyl-1H-imidazol-1-yl)-N,N-dimethylpropanamide bis-trifluoroacetic acid salt

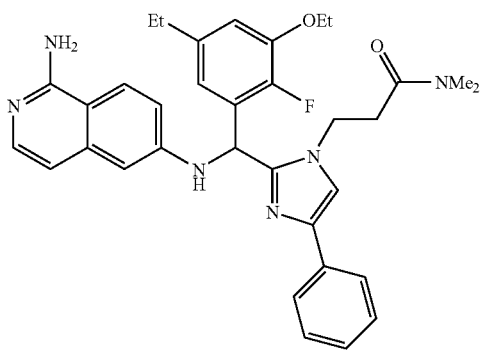

According to the procedure for the preparation of Example 402, coupling of Example 451 (14.6 mg, 0.019 mmol) with dimethylamine hydrochloride (6.4 mg, 0.078 mmol) afforded after HPLC purification 13.6 mg of Example 452. LCMS (2 min gradient) RT=1.38 min, 581.14 (M+H)$^+$; $^1$H NMR (400 MHz, CD$_3$OD) δ ppm 1.17 (t, J=7.47 Hz, 3H) 1.40 (t, J=7.03 Hz, 3H) 2.60 (q, J=7.76 Hz, 2H) 2.78 (ddd, J=17.25, 5.05, 4.94 Hz, 1H) 2.96 (s, 3H) 2.98 (s, 3H) 2.99-3.05 (m, 1H) 4.13 (q, J=7.03 Hz, 1H) 4.16-4.24 (m, 1H) 4.42 (ddd, J=14.06, 9.01, 5.05 Hz, 1H) 6.76 (s, 1H) 6.78 (dd, J=5.71, 1.76 Hz, 1H) 6.94 (d, J=7.03 Hz, 1H) 7.05 (dd, J=7.91, 1.76 Hz, 1H) 7.09 (d, J=2.20 Hz, 1H) 7.32 (dd, J=9.23, 2.20 Hz, 1H) 7.35-7.45 (m, 4H) 7.63-7.66 (m, J=7.03 Hz, 2H) 7.89 (s, 1H) 8.18 (d, J=9.23 Hz, 1H).

Example 453

2-(2-((1-aminoisoquinolin-6-ylamino)(5-ethyl-2-fluoro-3-(1-methylpiperidin-4-yloxy)phenyl)methyl)-4-phenyl-1H-imidazol-1-yl)-N,N-dimethylacetamide bis-trifluoroacetic acid salt

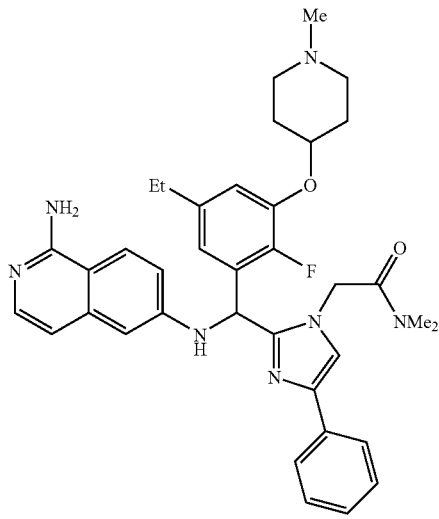

According to the procedure for the preparation of Example 402, coupling of Example 433 (6 mg) with dimethylamine hydrochloride (4 mg) afforded after HPLC purification 5.6 mg of Example 453. LCMS (2 min gradient) RT=1.10 min, 636.08 (M+H)$^+$; $^1$H NMR (400 MHz, CD$_3$OD) δ ppm 1.19 (t, J=7.47 Hz, 3H) 2.14-2.24 (m, 2H) 2.31-2.41 (m, 2H) 2.59-2.66 (m, 3H) 2.88 (d, 1H) 2.97 (d, J=7.47 Hz, 3H) 3.03 (d, J=15.38 Hz, 3H) 3.39 (s, 3H) 3.73-3.81 (m, 1H) 3.92-3.99 (m, 1H) 4.48 (d, J=11.86 Hz, 2H) 6.49 (s, 1H) 6.89 (s, 1H) 6.92 (d, J=7.03 Hz, 2H) 7.17 (d, J=7.91 Hz, 1H) 7.26 (d, J=9.23 Hz, 1H) 7.36 (d, J=7.03 Hz, 1H) 7.39-7.49 (m, 3H) 7.72 (d, J=7.03 Hz, 2H) 7.77 (d, J=1.76 Hz, 1H) 8.19 (d, J=9.23 Hz, 1H).

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders" as used herein includes arterial or venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of coagulation factor VIIa.

The effectiveness of compounds of the present invention as inhibitors of the coagulation factors VIIa, IXa, Xa, XIa, plasma kallikrein or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, preferred compounds of the present invention, such as the particular compounds disclosed in the above examples, have been identified to be active and exhibit $K_i$'s of equal to or less than 15 µM in the Factor VIIa assay, thereby demonstrating the utility of the compounds of the present invention as especially effective inhibitors of coagulation Factor VIIa. More preferred compounds have $K_i$'s of equal to or less than 5 µM, preferably equal to or less than 1 µM, more preferably equal to or less than 0.5 µM, even more preferably equal to or less than 0.1 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 µM (Haematologic Technologies) and the synthetic substrate S-2366 (pyroGlu-Pro-Arg-pNA; Chromogenix) at a concentration of 0.0002-0.00025 M. In general, compounds tested in the Factor XIa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and/or contact activation system, and as anticoagulants for the prevention or treatment of thromboembolic disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and $K_i=IC_{50}/(1+S/K_m)$ for a competitive inhibitor where:

$v_o$ is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention can be administered alone or in combination with one or more additional therapeutic agents. These other agents include, but are not limited to, other anti-coagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and O-blockers (for example propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glicosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of plasma kallikrein, thrombin, factor VIIa, IXa, Xa and/or XIa. Such compounds may be provided in a commercial kit, for example, for use in pharmaceutical research involving plasma kallikrein, thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma kallikrein, thrombin, factor VIIa, IXa, Xa, and/or XIa. For example, the presence of plasma kallikrein, thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound of Formula (I):

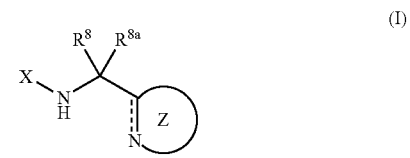

or a stereoisomer, a tautomer, or a pharmaceutically acceptable salt thereof, wherein:

X is selected from:

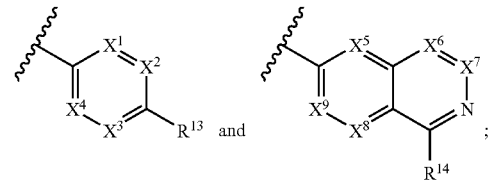

wherein $X^1$, $X^2$, $X^3$, $X^4$, $X^5$, $X^6$, $X^7$, $X^8$, and $X^9$ are independently $CR^6$ or N, provided that X does not contain more than three ring nitrogen atoms;

$R^6$ is, independently at each occurrence, H, —$(CH_2)_r$—$OR^a$, F, Cl, Br, $OCF_3$, CN, $NO_2$, —$NR^bR^c$, —$(CF_2)_r$$CF_3$, or $C_{1-6}$ alkyl substituted with 0-2 $R^e$;

$R^8$ is phenyl substituted with 0-5 $R^{8b}$, or a 5- to 6-membered heteroaryl comprising: carbon atoms and 1-4 heteroatoms selected from N, O, and S, wherein said heteroaryl is substituted with 0-5 $R^{8b}$;

$R^{8a}$ is H or $C_{1-4}$ alkyl;

$R^{8b}$ is, independently at each ocurrence, H, —$(CH_2)_r$—$OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^c$$R^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-7}$ cycloalkyl substituted with 0-2 $R^e$, —$(CH_2)_r$—$C_{3-7}$ cycloalkenyl substituted with 0-2 $R^e$, —$(CH_2)_r$-phenyl substituted with 0-4 $R^f$, —$(CH_2)_r$-5- to 6-membered heteroaryl comprising: carbon atoms and 1-4 heteroatoms selected from N, O, and $S(O)_p$, or —$(CH_2)_r$-4- to 7-membered heterocycle comprising: carbon atoms and 1-4 heteroatoms selected from N, O, and S(O)$_p$, wherein said heteroaryl and heterocycle are substituted with 0-4 R$^f$;

alternatively, two R$^{8b}$ groups on two adjacent carbon atoms may be taken together with the carbon atoms to which they are attached, to form a 5- to 7-membered carbocycle or heterocycle comprising: carbon atoms and 0-4 heteroatoms selected from N, O, and S(O)$_p$, wherein said carbocycle and heterocycle are substituted with 0-3 R$^f$;

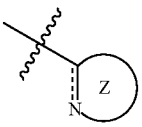

is a 5- to 6-membered heteroaryl including the nitrogen atom shown in the ring, comprising: carbon atoms and additional 0-3 heteroatoms selected from N, NR$^{11}$, NR$^{11a}$, O, and S, and ring Z is substituted with 0-1 R$^{12}$ and 0-3 R$^{12a}$; provided that: all three valences of the nitrogen atom shown in ring Z are satisfied by ring bonds;

optionally, ring Z is fused to a 5- to 10-membered carbocycle or heterocycle comprising: carbon atoms and additional 0-4 heteroatoms selected from N, NR$^{11}$, NR$^{11a}$, O, and S(O)$_p$, wherein said carbocycle and heterocycle are fully unsaturated or partially saturated and are substituted with 0-1 R$^{12}$ and 0-3 R$^{12a}$;

R$^{11}$ and R$^{11a}$ are, independently at each occurrence, H, C$_{1-6}$ alkyl substituted with 0-4 R$^e$, —(C$_{0-4}$ alkyl)-(C$_{6-10}$ aryl), —(C$_{0-4}$ alkyl)-(5- to 10-membered heteroaryl comprising: carbon atoms and 1-4 heteroatoms selected from N, O, and S(O)$_p$); wherein said aryl and heteroaryl are substituted with 0-4 R$^f$;

R$^{12}$ and R$^{12a}$ are, independently at each occurrence, H, —(CH$_2$)$_r$—OR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-7}$ cycloalkyl substituted with 0-2 R$^e$, —(CH$_2$)$_r$—C$_{3-7}$ cycloalkenyl substituted with 0-2 R$^e$, —(CH$_2$)$_r$-phenyl substituted with 0-4 R$^f$, —(CH$_2$)$_r$-naphthyl substituted with 0-4 R$^f$, —(CH$_2$)$_r$-5- to 10-membered heteroaryl comprising: carbon atoms and 1-4 heteroatoms selected from N, O, and S(O)$_p$, or —(CH$_2$)$_r$-4- to 8-membered heterocycle comprising: carbon atoms and 1-4 heteroatoms selected from N, O, and S(O)$_p$; wherein said heteroaryl and heterocycle are substituted with 0-4 R$^f$;

R$^{13}$ is —C(=NR$^h$)NR$^b$R$^c$ or —CR$^a$R$^a$NR$^b$R$^c$;

R$^{14}$ is —NR$^b$R$^c$, H, or C$_{1-4}$ alkyl;

R$^{a1}$ is, independently at each occurrence, C$_{1-6}$ alkyl substituted with 0-4 R$^j$, —(CH$_2$)$_r$—C$_{3-7}$ cycloalkyl substituted with 0-4 R$^f$, —(CH$_2$)$_r$—C$_{6-10}$ aryl, or —(CH$_2$)$_r$-5- to 10-membered heteroaryl comprising: carbon atoms and 1-4 heteroatoms selected from NR$^b$, O, and S(O)$_p$; wherein said aryl and heterocycle are optionally substituted with 0-4 R$^f$;

R$^a$ is, independently at each occurrence, H or R$^{a1}$;

R$^b$ is, independently at each occurrence, H, C$_{1-6}$ alkyl, —(CH$_2$)$_n$-phenyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$ alkyl)-C(O)—, (5- to 10-membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl)-NHC(O)—, (5- to 10-membered heteroaryl)-C$_{0-4}$ alkyl-NHC(O)—, (C$_{1-6}$ alkyl)-S(O)$_2$—, (C$_{6-10}$ aryl)-C$_{0-4}$ alkyl-S(O)$_2$—, or (5- to 10-membered heteroaryl)-C$_{0-4}$ alkyl-S(O)$_2$—, wherein said phenyl, aryl and heteroaryl are substituted with 0-2 R$^f$; said heteroaryl comprises: carbon atoms and 1-4 heteroatoms selected from N, O, and S(O)$_p$;

R$^c$ is, independently at each occurrence, H, C$_{1-6}$ alkyl substituted with 0-3 R$^j$, or —(CH$_2$)$_n$-phenyl substituted with 0-3 R$^j$;

alternatively, R$^b$ and R$^c$, when attached to the same nitrogen atom, may be taken together with the nitrogen atom to form a 4- to 10-membered heterocycle comprising: carbon atoms and 1-4 heteroatoms selected from N, O, and S(O)$_p$, wherein said heterocycle is substituted with 0-3 R$^f$;

R$^d$ is, independently at each occurrence, H, C$_{1-6}$ alkyl, —(CH$_2$)$_r$—C$_{3-10}$ carbocycle substituted with 0-3 R$^f$, or a —(CH$_2$)$_r$-5- to 12-membered heterocycle comprising: carbon atoms and 1-4 heteroatoms selected from N, O, and S(O)$_p$, wherein said heterocycle is substituted with 0-3 R$^f$;

alternatively, R$^c$ and R$^d$, when attached to the same nitrogen atom, may be taken together with the nitrogen atom to form a 4- to 10-membered heterocycle comprising: carbon atoms and 1-4 heteroatoms selected from N, O, and S(O)$_p$, wherein said heterocycle is substituted with 0-3 R$^f$;

R$^e$ is, independently at each occurrence, =O, OR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, —(CH$_2$)$_r$C$_{3-10}$ carbocycle substituted with 0-3 R$^f$, or a —(CH$_2$)$_r$-5- to 12-membered heterocycle comprising: carbon atoms and 1-4 heteroatoms selected from N, O, and S(O)$_p$, wherein said heterocycle is substituted with 0-3 R$^f$;

R$^f$ is, independently at each occurrence, H, =O, —(CH$_2$,OR$^g$, F, Cl, Br, I, CN, NO$_2$, —OCF$_3$, —NR$^b$R$^c$, —C(O)R$^g$, —C(O)OR$^g$, —NR$^c$C(O)R$^g$, —C(O)NR$^c$R$^c$, —SO$_2$NR$^c$R$^c$, —NR$^c$SO$_2$NR$^c$R$^c$, —NR$^c$SO$_2$—C$_{1-4}$ alkyl, —NR$^c$SO$_2$CF$_3$, —NR$^c$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, —(CH$_2$)$_r$—C$_{3-10}$ carbocycle substituted with 0-3 R$^j$, or a —(CH$_2$)$_r$-5- to 12-membered heterocycle comprising: carbon atoms and 1-4 heteroatoms selected from N, O, and S(O)$_p$, wherein said heterocycle is substituted with 0-3 R$^j$;

R$^g$ is, independently at each occurrence, H, C$_{1-6}$ alkyl, or —(CH$_2$)$_n$-phenyl;

R$^h$ is, independently at each occurrence, H, OH, C$_{1-6}$ alkyl, C$_{1-4}$ alkoxy, (C$_{6-10}$ aryl)-C$_{1-4}$ alkoxy, —(CH$_2$)$_n$-phenyl, (C$_{1-6}$ alkyl)C(O)—, (C$_{6-10}$ aryl)-C$_{0-4}$ alkyl-C(O)—, (C$_{3-6}$ cycloalkyl)-C$_{0-4}$ alkyl-C(O)—, (5-10 membered heteroaryl)-C$_{0-4}$ alkyl-C(O)—, (C$_{1-4}$ alkyl)OC(O)—, (C$_{6-10}$ aryl)-C$_{1-4}$ alkyl-OC(O)—, (C$_{1-4}$ alkyl)-C(O)O— (C$_{1-4}$ alkyl)-OC(O)—, (C$_{6-10}$ aryl)-C(O)O—(C$_{1-4}$ alkyl)-OC(O)—, (5-10 membered heteroaryl)-C$_{0-4}$ alkyl-OC(O)—, C$_{1-4}$ alkoxy, (C$_{1-4}$ alkyl)C(O)O—, or (C$_{6-10}$ aryl)-(C$_{0-4}$alkyl)-C(O)O—; wherein said phenyl, aryl and heteroaryl are substituted with 0-2 R$^f$; said heteroaryl comprises: carbon atoms and 1-4 heteroatoms selected from N, O, and S(O)$_p$;

R$^i$ is, independently at each occurrence, OR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$—C$_{1-4}$ alkyl, —NR$^c$SO$_2$CF$_3$, —NR$^c$SO$_2$—phenyl, —S(O)$_2$CF$_3$, —S(O)$_p$—C$_{1-4}$ alkyl, —S(O)$_p$-phenyl, —(CF$_2$)$_r$CF$_3$, —(CH$_2$)$_r$—C$_{3-10}$ carbocycle substituted with 0-3 R$^f$, or a —(CH$_2$)$_r$-5- to 12-membered heterocycle comprising: carbon atoms and 1-4 heteroatoms selected from N, O, and S(O)$_p$, wherein said heterocycle is substituted with 0-3 R$^f$;

R$^j$ is, independently at each occurrence, H, =O, —(CH$_2$)$_r$OR$^g$, F, Cl, Br, I, CN, NO$_2$, —OCF$_3$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, C$_{2-6}$ alkynyl, (C$_{1-6}$ alkyl)C(O)—, (C$_{3-6}$ cycloalkyl)-C$_{0-4}$ alkyl-C(O)—, (C$_{6-10}$ aryl)-(C$_{0-4}$alkyl)-C(O)—, (5-10 membered heteroaryl)-C$_{0-4}$ alkyl-C(O)—, (C$_{1-6}$ alkyl)-NHC(O)—, (C$_{1-6}$ alkyl)$_2$-NHC(O)—, (C$_{6-10}$ aryl)-C$_{0-4}$ alkyl-NHC(O)—, (5-10 membered heteroaryl)-C$_{0-4}$ alkyl-NHC(O)—, (C$_{1-6}$ alkyl)-S(O)$_2$—, (C$_{6-10}$ aryl)-C$_{0-4}$ alkyl-S(O)$_2$—, (5-10 membered heteroaryl)-C$_{0-4}$ alkyl-S(O)$_2$—, —(CH$_2$)$_r$—C$_{3-10}$ carbocycle, or a —(CH$_2$)$_r$-5- to 12-membered heterocycle comprising: carbon atoms and 1-4 heteroatoms selected from N, O, and S(O)$_p$; wherein said heteroaryl comprises: carbon atoms and 1-4 heteroatoms selected from N, O, and S(O)$_p$;

n, at each occurrence, is selected from 0, 1, 2, 3, and 4;

p, at each occurrence, is selected from 0, 1, and 2; and r, at each occurrence, is selected from 0, 1, 2, 3, and 4.

2. A compound of Formula (Ia):

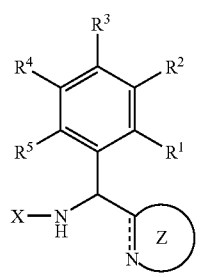

(Ia)

or a stereoisomer, a tautomer, or a pharmaceutically acceptable salt thereof, wherein:

R$^1$, R$^2$, R$^3$, R$^4$, and R$^5$ are, independently at each occurrence, H, —(CH$_2$)$_r$—OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl substituted with 0-2 R$^e$, C$_{2-6}$ alkenyl substituted with 0-2R$^e$, C$_{2-6}$ alkynyl substituted with 0-2 R$^e$, —(CH$_2$)$_r$—C$_{3-7}$ cycloalkyl substituted with 0-2 R$^e$, —(CH$_2$)$_r$C$_{3-7}$ cycloalkenyl substituted with 0-2 R$^e$, —(CH$_2$)$_r$-phenyl substituted with 0-4 R$^f$, —(CH$_2$)$_r$-5-to 6-membered heteroaryl comprising: carbon atoms and 1-4 heteroatoms selected from N, O, and S(O)$_p$, or —(CH$_2$)$_r$-4- to 7-membered heterocycle comprising: carbon atoms and 1-4 heteroatoms selected from N, O, and S(O)$_p$, wherein said heteroaryl and heterocycle are substituted with 0-4R$^f$;

alternatively, R$^2$ and R$^3$, R$^3$ and R$^4$, or R$^4$ and R$^5$ may be taken together with the carbon atoms to which they are attached, to form a 5- to 7-membered carbocycle or heterocycle comprising: carbon atoms and 0-4 heteroatoms selected from N, O, and S(O)$_p$, wherein said carbocycle and heterocycle are substituted with 0-3 R$^f$;

X is selected from

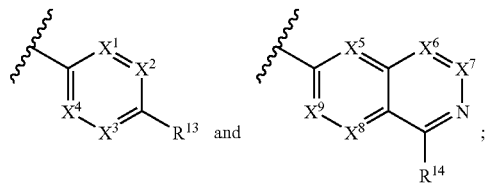

wherein X$^1$, X$^2$, X$^3$, X$^4$, X$^5$, X$^6$, X$^7$, X$^8$, and X$^9$ are independently CR$^6$ or N, provided that X does not contain more than three ring nitrogen atoms;

R$^6$ is, independently at each occurrence, H, —(CH$_2$)$_r$—OR$^a$, F, Cl, Br, OCF$_3$, CN, NO$_2$, —NR$^b$R$^c$, —(CF$_2$)$_r$CF$_3$, or C$_{1-6}$ alkyl substituted with 0-2 R$^e$;

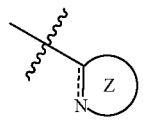

is a 5- to 6-membered heteroaryl including the nitrogen atom shown in the ring, comprising: carbon atoms and additional 0-3 heteroatoms selected from N, NR$^{11}$, NR$^{11a}$, O, and S, and ring Z is substituted with 0-1 R$^{12}$ and 0-3 R$^{12a}$; provided that: all three valences of the nitrogen atom shown in ring Z are satisfied by ring bonds;

optionally, ring Z is fused to a 5- to 7-membered carbocycle or heterocycle comprising: carbon atoms and additional 0-4 heteroatoms selected from N, NR$^{11}$, NR$^{11a}$, O, and S(O)$_p$, wherein said carbocycle and heterocycle are fully unsaturated or partially saturated and substituted with 0-1 R$^{12}$ and 0-3 R$^{12a}$;

R$^{11}$ and R$^{11a}$ are, independently at each occurrence, H, C$_{1-6}$ alkyl substituted with 0-4 R$^e$, —(C$_{0-4}$ alkyl)-(C$_{6-10}$ aryl), —(C$_{0-4}$ alkyl)-(5- to 10-membered heteroaryl comprising: carbon atoms and 1-4 heteroatoms selected from N, O, and S(O)$_p$); wherein said aryl and heteroaryl are substituted with 0-4 R$^f$;

R$^{12}$ and R$^{12a}$ are, independently at each ocurrence, H, —(CH$_2$)$_r$—OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-7}$ cycloalkyl substituted with 0-2 R$^e$, —(CH$_2$)$_r$—C$_{3-7}$ cycloalkenyl substituted with 0-2 R$^e$, —(CH$_2$)$_r$-phenyl substituted with 0-4 R$^f$, —(CH$_2$)$_r$-naphthyl substituted with 0-4 R$^f$, —(CH$_2$)$_r$-5- to 10-membered heteroaryl comprising: carbon atoms and 1-4 heteroatoms selected from N, O, and S(O)$_p$, or —(CH$_2$)$_r$-4- to 8-membered heterocycle comprising: carbon atoms and 1-4 heteroatoms selected from N, O, and $S(O)_p$; wherein said heteroaryl and heterocycle are substituted with 0-4 $R^f$, $R^{13}$ is —C(=$NR^h$)$NR^bR^c$ or —$CR^aR^aNR^bR^c$;

$R^{14}$ is —$NR^bR^c$, H, or $C_{1-4}$ alkyl;

$R^{a1}$ is, independently at each occurrence, $C_{1-6}$ alkyl substituted with 0-4 $R^j$, —$(CH_2)_r$—$C_{3-7}$ cycloalkyl substituted with 0-4 $R^f$, —$(CH_2)_r$—$C_{6-10}$aryl, or —$(CH_2)_r$-5- to 10-membered heterocycle comprising: carbon atoms and 1-4 heteroatoms selected from $NR^b$, O, and $S(O)_p$; wherein said aryl and heterocycle are optionally substituted with 0-4 $R^f$;

$R^a$ is, independently at each occurrence, H or $R^{a1}$;

$R^b$ is, independently at each occurrence, H, $C_{1-6}$ alkyl, —$(CH_2)_n$-phenyl, ($C_{1-6}$ alkyl)C(O)—, ($C_{3-6}$ cycloalkyl)-$C_{0-4}$alkyl-C(O)—, ($C_{6-10}$ aryl)-($C_{0-4}$alkyl)-C(O)—, (5- to 10-membered heteroaryl)-$C_{0-4}$ alkyl-C(O)—, ($C_{1-6}$ alkyl)-NHC(O)—, ($C_{1-6}$ alkyl)$_2$-NHC(O)—, ($C_{6-10}$ aryl)-$C_{0-4}$ alkyl-NHC(O)—, (5- to 10-membered heteroaryl)-$C_{0-4}$ alkyl-NHC(O)—, ($C_{1-6}$ alkyl)-$S(O)_2$—, ($C_{6-10}$ aryl)-$C_{0-4}$ alkyl-$S(O)_2$—, or (5- to 10-membered heteroaryl)-$C_{0-4}$ alkyl-$S(O)_2$—, wherein said phenyl, aryl and heteroaryl are substituted with 0-2 $R^f$; said heteroaryl comprises: carbon atoms and 1-4 heteroatoms selected from N, O, and $S(O)_p$;

$R^c$ is, independently at each occurrence, H, $C_{1-6}$ alkyl substituted with 0-3 $R^j$, or —$(CH_2)_n$-phenyl substituted with 0-3 $R^j$;

alternatively, $R^b$ and $R^c$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-3 $R^f$;

$R^e$ is, independently at each occurrence, =O, $OR^a$, $SR^a$, F, Cl, Br, I, CN, $NO_2$, —$OCF_3$, —$NR^bR^c$, —C(O)$R^a$, —C(O)$OR^a$, —$NR^dC(O)R^a$, —C(O)$NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, —$(CF_2)_rCF_3$, $(CH_2)_r$—$C_{3-10}$ carbocycle substituted with 0-3 $R^f$, or a —$(CH_2)_r$-5- to 12-membered heterocycle comprising: carbon atoms and 1-4 heteroatoms selected from N, O, and $S(O)_p$, wherein said heterocycle is substituted with 0-3 $R^f$;

$R^f$ is, independently at each occurrence, H, =O, —$(CH_2)_r$ $OR^g$, $SR^g$, F, Cl, Br, I, CN, $NO_2$, —$OCF_3$, —$NR^cR^c$, —C(O)$R^g$, —C(O)$OR^g$, —$NR^cC(O)R^g$, —C(O)$NR^c R^c$, —$SO_2NR^cR^c$, —$NR^cSO_2NR^cR^c$, —$NR^cSO_2$—$C_{1-4}$ alkyl, —$NR^cSO_2CF_3$, —$NR^cSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, —$(CH_2)_r$—$C_{3-10}$ carbocycle substituted with 0-3 $R^j$, or a —$(CH_2)_r$-5-to 12-membered heterocycle comprising: carbon atoms and 1-4 heteroatoms selected from N, O, and $S(O)_p$, wherein said heterocycle is substituted with 0-3 $R^j$;

$R^g$ is, independently at each occurrence, H, $C_{1-6}$ alkyl, or —$(CH_2)_n$-phenyl;

$R^h$ is, independently at each occurrence, H, OH, $C_{1-6}$ alkyl, $C_{1-4}$ alkoxy, ($C_{6-10}$ aryl)-$C_{1-4}$ alkoxy, —$(CH_2)_n$-phenyl, ($C_{1-6}$ alkyl)C(O)—, ($C_{6-10}$ aryl)-$C_{0-4}$ alkyl-C(O)—, ($C_{3-6}$ cycloalkyl)-$C_{0-4}$ alkyl-C(O)—, (5-10 membered heteroaryl)-$C_{0-4}$ alkyl-C(O)—, ($C_{1-4}$ alkyl)OC(O)—, ($C_{6-10}$ aryl)-$C_{1-4}$ alkyl-OC(O)—, ($C_{1-4}$ alkyl)-C(O)O—($C_{1-4}$ alkyl)-OC(O)—, ($C_{6-10}$ aryl)-C(O)O—($C_{1-4}$ alkyl)-OC(O)—, (5-10 membered heteroaryl)-$C_{0-4}$ alkyl-OC(O)—, $C_{1-4}$ alkoxy, ($C_{1-4}$ alkyl)C(O)O—, or ($C_{6-10}$ aryl)-($C_{0-4}$ alkyl)-C(O)O—; wherein said phenyl, aryl and heteroaryl are substituted with 0-2 $R^f$; wherein said heteroaryl comprises: carbon atoms and 1-4 heteroatoms selected from N, O, and $S(O)_p$;

$R^j$ is, independently at each occurrence, H, =O, —$(CH_2)_r$ $OR^g$, $SR^g$, F, Cl, Br, I, CN, $NO_2$, —$OCF_3$, —$NR^gR^g$, —C(O)$R^g$, —C(O)$OR^g$, —$NR^gC(O)R^g$, —C(O)$NR^g R^g$, —$SO_2NR^gR^g$, —$NR^gSO_2NR^gR^g$, —$NR^gSO_2$— $C_{1-4}$ alkyl, —$NR^gSO_2CF_3$, —$NR^gSO_2$-phenyl, —$S(O)_2 CF_3$, —$S(O)_p$—$C_{1-4}$ alkyl, —$S(O)_p$-phenyl, —$(CF_2)_r CF_3$, $C_{1-6}$ alkyl, $C_{2-6}$ alkenyl, $C_{2-6}$ alkynyl, ($C_{1-6}$ alkyl) C(O)—, ($C_{3-6}$ cycloalkyl)-$C_{0-4}$ alkyl-C(O)—, ($C_{6-10}$ aryl)-($C_{0-4}$alkyl)-C(O)—, (5-10 membered heteroaryl)-$C_{0-4}$ alkyl-C(O)—, ($C_{1-6}$ alkyl)-NHC(O)—, ($C_{1-6}$ alkyl)$_2$ —NHC(O)—, ($C_{6-10}$ aryl)-$C_{0-4}$ alkyl-NHC (O)—, (5-10 membered heteroaryl)-$C_{0-4}$ alkyl-NHC (O)—, ($C_{1-6}$ alkyl)-$S(O)_2$—, ($C_{6-10}$ aryl)-$C_{0-4}$ alkyl-$S(O)_2$—, (5-10 membered heteroaryl)-$C_{0-4}$ alkyl-S $(O)_2$—, —$(CH_2)_r$—$C_{3-10}$ carbocycle, or a —$(CH_2)_r$-5- to 12-membered heterocycle comprising: carbon atoms and 1-4 heteroatoms selected from N, O, and $S(O)_p$; wherein said heteroaryl comprises: carbon atoms and 1-4 heteroatoms selected from N, O, and $S(O)_p$;

n, at each occurrence, is selected from 0, 1, 2, 3, and 4;

p, at each occurrence, is selected from 0, 1, and 2; and r, at each occurrence, is selected from 0, 1, 2, 3, and 4.

3. A compound according to claim 2, wherein:

$R^1$ is H;

$R^2$ is H, F, Br, Cl, $C_{2-4}$ alkenyl, $C_{2-4}$ alkynyl, $C_{3-6}$ cycloalkyl, —O—$C_{1-4}$ alkyl, —O—$C_{3-6}$ cycloalkyl, or $C_{1-4}$ alkyl substituted with 0-1 OH;

$R^3$, $R^4$, and $R^5$ are, independently at each ocurrence, H, —$(CH_2)_r$—$OR^a$, $SR^a$, F, Cl, Br, I, CN, $NO_2$, —$OCF_3$, —$NR^bR^c$, —C(O)$R^a$, —C(O)$OR^a$, —$NR^dC(O)R^a$, —C(O)$NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2 R^{a1}$, —$S(O)R^{a1}$, —$(CF_2)_rCF_3$; $C_{1-6}$ alkyl, $C_{2-6}$ alkenyl, $C_{2-6}$ alkynyl, tetrahydrofuran-3-yloxy, 1-pyrrolidinyl, N-morpholinyl, 1-Me-piperidin-4-yloxy, 3-(dimethylamino)-2,2-dimethylpropoxy, phenyl substituted with 0-2 $R^f$, or benzyl substituted with 0-2 $R^f$;

alternatively, $R^2$ and $R^3$, $R^3$ and $R^4$, or $R^4$ and $R^5$ may be taken together with the carbon atoms to which they are attached, to form a 5- to 6-membered carbocycle or heterocycle comprising: carbon atoms and 0-4 heteroatoms selected from N, O, and $S(O)_p$, wherein said carbocycle and heterocycle are substituted with 0-3 $R^f$; and $R^6$ is, independently at each occurrence, —$(CH_2)_r$—$OR^a$, F, Cl, Br, $OCF_3$, CN, $NO_2$, —$NR^bR^c$, or —$(CF_2)_rCF_3$.

4. A compound according to claim 2, wherein:

$R^3$, $R^4$, and $R^5$ are, independently at each ocurrence, H, —$(CH_2)_r$—$OR^a$, $SR^a$, F, Cl, Br, I, CN, $NO_2$, —$OCF_3$, —$NR^bR^c$, —C(O)$R^a$, —C(O)$OR^a$, —$NR^dC(O)R^a$, —C(O)$NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2 R^{a1}$, —$S(O)R^{a1}$, —$(CF_2)_rCF_3$, $C_{1-6}$ alkyl, $C_{2-6}$ alkenyl, C$_{2-6}$ alkynyl, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-methyl-2-oxoimidazolidin-1-yl 3-(dimethylamino)-2,2-dimethylpropoxy, phenyl substituted with 0-2R$^f$, or benzyl substituted with 0-2 R$^f$;

alternatively, R$^2$ and R$^3$, R$^3$ and R$^4$, or R$^4$ and R$^5$ may be taken together with the carbon atoms to which they are attached, to form a 5- to 6-membered carbocycle or heterocycle comprising: carbon atoms and 0-3 heteroatoms selected from N, O, and S(O)$_p$, wherein said carbocycle and heterocycle are substituted with 0-3 R$^f$;

X is 4-C(=NH)NH$_2$-phenyl, 4-C(=NOH)NH$_2$-phenyl, 4-CH$_2$NH$_2$-phenyl, isoquinolin-6-yl, 1-NH$_2$-isoquinolin-6-yl, quinazolin-7-yl, 4-NH$_2$-quinazolin-7-yl, phthalazin-6-yl, or 1-NH$_2$-phthalazin-6-yl; and X is substituted with 0-2 R$^6$;

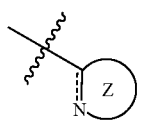

is substituted with 0-1R$^{12}$ and 0-3R$^{12a}$ and is selected from:

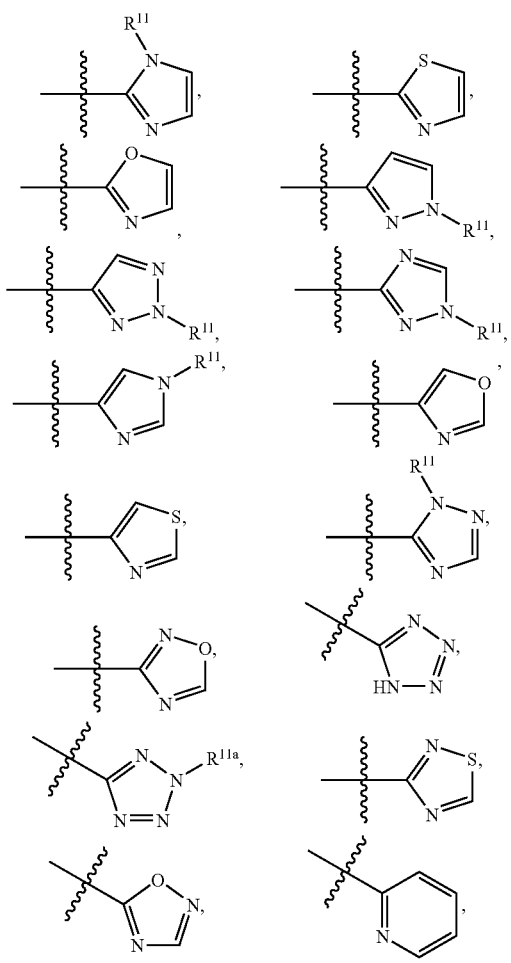

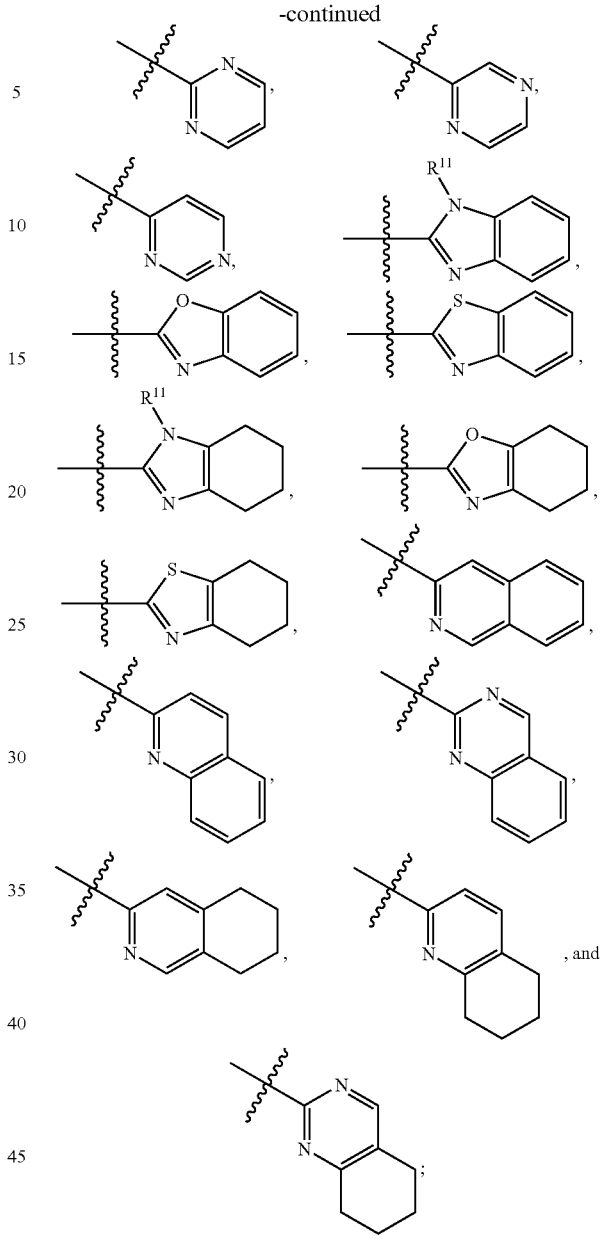

R$^{12}$ and R$^{12a}$ are, independently at each ocurrence, H, —(CH$_2$)$_r$—OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-7}$ cycloalkyl substituted with 0-3 R$^f$, —(CH$_2$)$_r$-phenyl substituted with 0-4R$^f$, —(CH$_2$)$_r$-naphthyl substituted with 0-4R$^f$, or —(CH$_2$)$_r$-5- to 10-membered heterocycle comprising: carbon atoms and 1-4 heteroatoms selected from N, O, and S(O)$_p$, wherein said heteroaryl is substituted with 0-4 R$^f$;

R$^{a1}$ is, independently at each occurrence, H, C$_{1-4}$ alkyl substituted with 0-2 R$^j$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said cycloalkyl, aryl and heteroaryl groups are optionally substituted with 0-2 $R^f$;

$R^c$ is, independently at each occurrence, H, $C_{1-6}$ alkyl substituted with 0-2 $R^j$, or —$(CH_2)_n$-phenyl substituted with 0-2 $R^j$;

$R^d$ is, independently at each occurrence, H, $C_{1-6}$ alkyl, —$(CH_2)_r$—$C_{3-10}$ carbocycle substituted with 0-3 $R^f$, or a —$(CH_2)_r$—5— to 12-membered heterocycle comprising: carbon atoms and 1-4 heteroatoms selected from N, O, and $S(O)_p$, wherein said heterocycle is substituted with 0-3 $R^f$;

alternatively, $R^c$ and $R^d$, when attached to the same nitrogen atom, may be taken together with the nitrogen atom to form a 4- to 10-membered heterocycle comprising: carbon atoms and 1-4 heteroatoms selected from N, O, and $S(O)_p$, wherein said heterocycle is substituted with 0-2 $R^f$;

$R^e$ is, independently at each occurrence, =O, $OR^a$, $SR^a$, F, Cl, Br, I, CN, $NO_2$, —$OCF_3$, —$NR^bR^c$, —$C(O)R^a$, —$C(O)OR^a$, —$NR^dC(O)R^a$, —$C(O)NR^cR^d$, —$SO_2NR^cR^d$, —$NR^cSO_2NR^cR^d$, —$NR^cSO_2R^{a1}$, —$NR^cSO_2CF_3$, —$S(O)_2CF_3$, —$S(O)_2R^{a1}$, —$S(O)R^{a1}$, or —$(CF_2)_rCF_3$; and $R^j$ is, independently at each occurrence, H, =O, —$(CH_2)_r$—$OR^g$, $SR^g$, F, Cl, Br, I, CN, $NO_2$, —$OCF_3$, —$NR^gR^g$, —$C(O)R^g$, —$C(O)OR^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CF_2)_rCF_3$, or $C_{1-6}$ alkyl.

5. A compound according to claim 2, wherein:

$R^1$ is H;

$R^2$ is H, Me, Et, i-Pr, vinyl, ethynyl, prop-1-en-2-yl, —CH(OH)Me, OMe, or OEt;

$R^3$ is H, F, Cl, OMe, OEt, O(i-Pr), or OBn;

$R^4$ is H, OMe, OEt, OPr, O(i-Pr), O(i-Bu), —$O(CH_2OMe)$, —$OCH_2C(Me)_2CH_2NMe_2$, cyclopentoxy, cyclohexoxy, cyclopropylmethoxy, Ph, 3-Me-Ph, tetrahydrofuran-3-yloxy, tetrahydro-2H-pyran-4-yloxy, 1-pyrrolidinyl, N-morpholinyl, 1-Me-piperidin-4-yloxy, 2-oxooxazolidin-3-yl, 3-Me-2-oxoimidazolidin-1-yl or 3-(dimethylamino)-2,2-dimethylpropoxy;

$R^5$ is H or F;

alternatively,

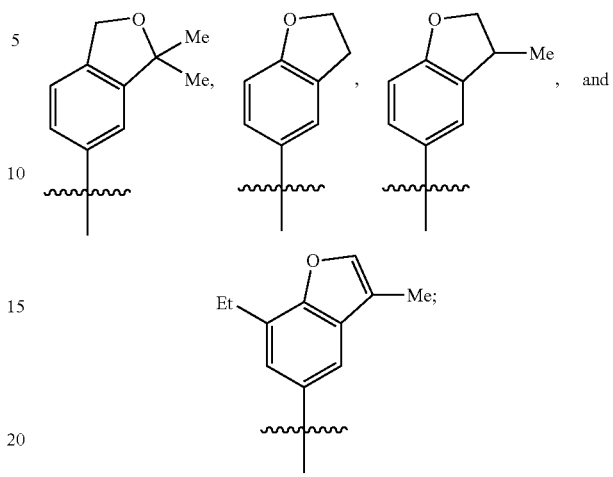

is selected from:

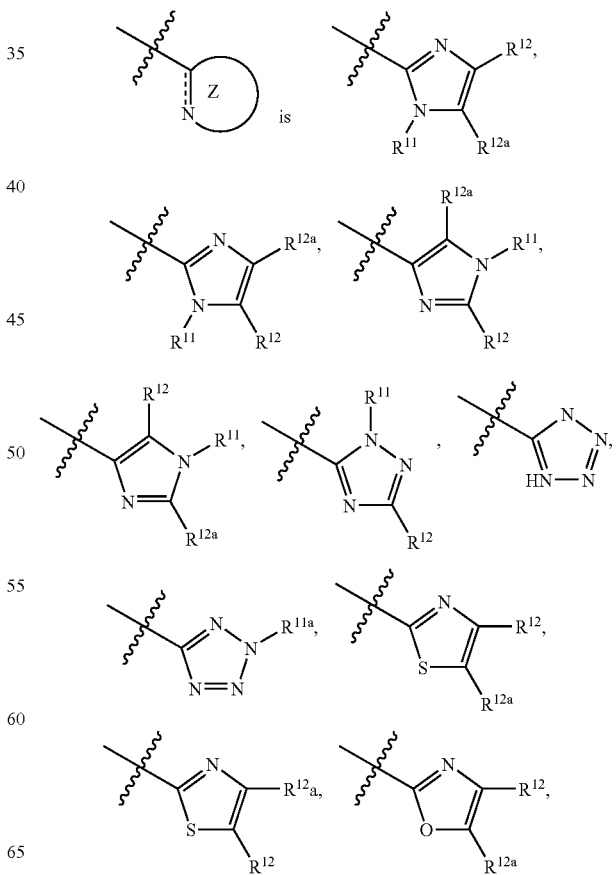

X is 4-C(=NH)NH$_2$-Ph, 2-F-4-C(=NH)NH$_2$-Ph, 3-F-4-C(=NH)NH$_2$-Ph, 2,5-diF-4-C(=NH)NH$_2$-Ph, 2,6-diF-4-C(=NH)NH$_2$-Ph, 4-C(=NOH)NH$_2$-Ph, 2,5-diF-4-C(=NOH)NH$_2$-Ph, 4-CH$_2$NH$_2$-Ph, isoquinolin-6-yl, 1-NH$_2$-isoquinolin-6-yl, quinazolin-7-yl, 4-NH$_2$-quinazolin-7-yl, phthalazin-6-yl, or 1-NH$_2$-phthalazin-6-yl;

-continued

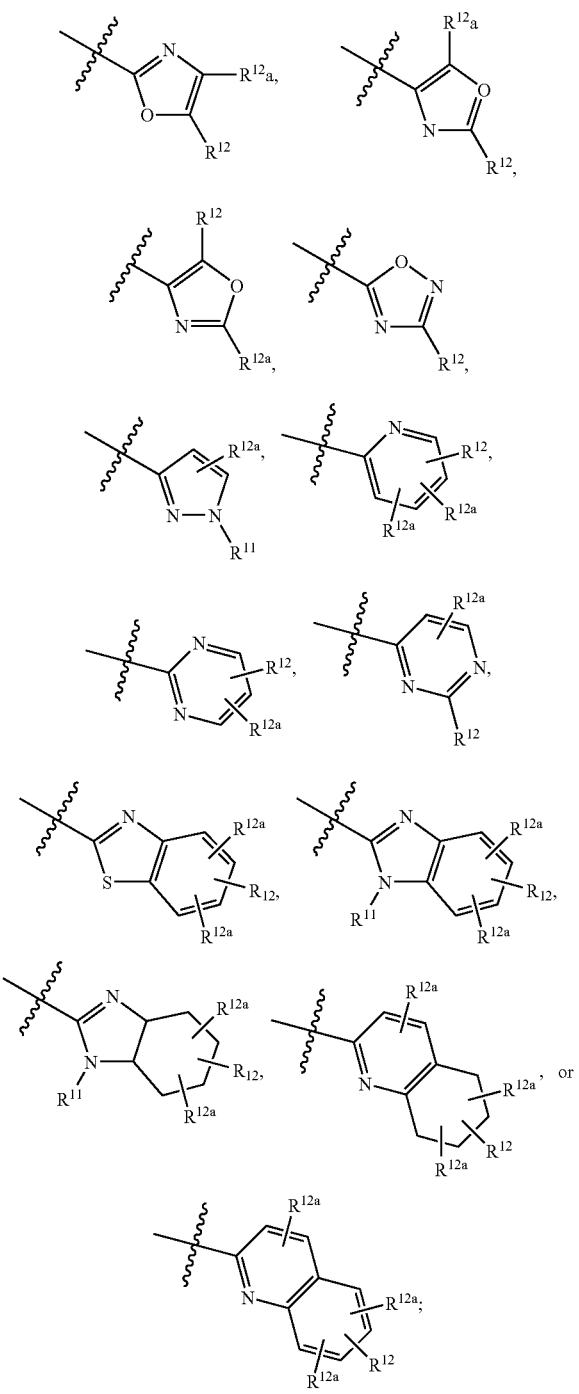

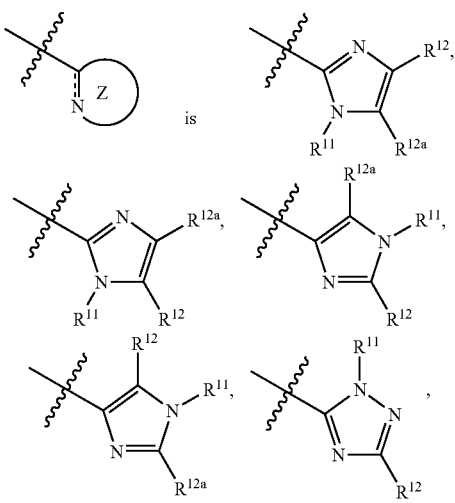

$R^{11}$ is, independently at each occurrence, H, $C_{1-4}$ alkyl, $C_{2-4}$ alkenyl, —$CH_2CH_2OH$, Ph, 2-$CONH_2$-Ph, —$CH_2CO_2H$, —$CH_2CH_2CO_2H$, —$CH(Me)CO_2H$, —$C(Me)_2CO_2H$, —$CH_2CONH_2$, —$CH_2CONHMe$, —$CH_2CONHEt$, —$CH_2CONH(i-Pr)$, —$CH_2CONH(CH_2CH_2OH)$, —$CH_2CONH(CH_2CONH_2)$, —$CH_2CONH(CH_2CF_3)$, —$CH_2CONH(cyclopropyl)$, —$CH_2CONH(cyclobutyl)$, —$CH_2CONHPh$, —$CH_2CONMe_2$, —$CH_2CH_2CONMe_2$, —$CH_2CON(Me)Et$, —$CH_2OBn$, —$CH_2CO(1\text{-pyrrolidinyl})$, $R^{11a}$ is, independently at each occurrence, H, Ph or Bn;

$R^{12}$ is, independently at each occurrence, H, F, Cl, Br, $CF_3$, $C_{1-4}$ alkyl, $OR^a$, $SR^a$, —$OCF_3$, —$NR^bR^c$, $C_{3-7}$ cycloalkyl, 2-(2-Me-1,3-dioxolan-2-yl)-phenyl, 3-(2-Me-1,3-dioxolan-2-yl)-phenyl, 4-(2-Me-1,3-dioxolan-2-yl)-phenyl, phenyl substituted with 0-3 $R^f$, naphthyl substituted with 0-3 $R^f$, or a heterocycle substituted with 0-3 $R^f$, wherein said heterocycle is selected from: furanyl, thienyl, pyrazolyl, pyrrolidinyl, pyridyl, pyrimidinyl, tetrahydropyrimidinyl, morpholinyl, piperidinyl, indolinyl, benzofuryl, dihydrobenzofuranyl, and methylenedioxyphenyl;

$R^{12a}$ is, independently at each occurrence, H, F, Cl, Br, $C_{1-4}$ alkyl, $C_{1-4}$ alkoxy, $NH_2$, or Ph;

$R^a$ is, independently at each occurrence, H, $C_{1-6}$ alkyl, or $C_{3-7}$ cycloalkyl;

$R^b$ is, independently at each occurrence, H, $C_{1-6}$ alkyl, —$(CH_2)_n$-phenyl, or $(C_{1-6}$ alkyl)C(O)—;

$R^c$ is, independently at each occurrence, H, $C_{1-6}$ alkyl substituted with 0-2 $R^j$, or —$(CH_2)_n$-phenyl substituted with 0-2 $R^j$;

$R^f$ is, independently at each occurrence, $C_{1-4}$ alkyl, $C_{1-4}$ alkoxy, OH, SMe, —$CH_2OH$, —$CH(Me)OH$, —$CH_2OMe$, F, Cl, Br, $CF_3$, $OCF_3$, CN, COMe, COEt, $CO_2H$, $CO_2Me$, $CO_2Et$, $NH_2$, $NMe_2$, —$CH_2NMe_2$, $CONH_2$, CONHMe, $CONMe_2$, CONHEt, —$CONHCH_2CH_2OH$, —NHCOMe-Ph, —NHCOEt-Ph, $SO_2Me$, $SO_2Et$, —$NHSO_2Me$, $SO_2NH_2$, Ph, OPh, OBn, furanyl, or thienyl.

6. A compound according to claim 5, wherein:

-continued

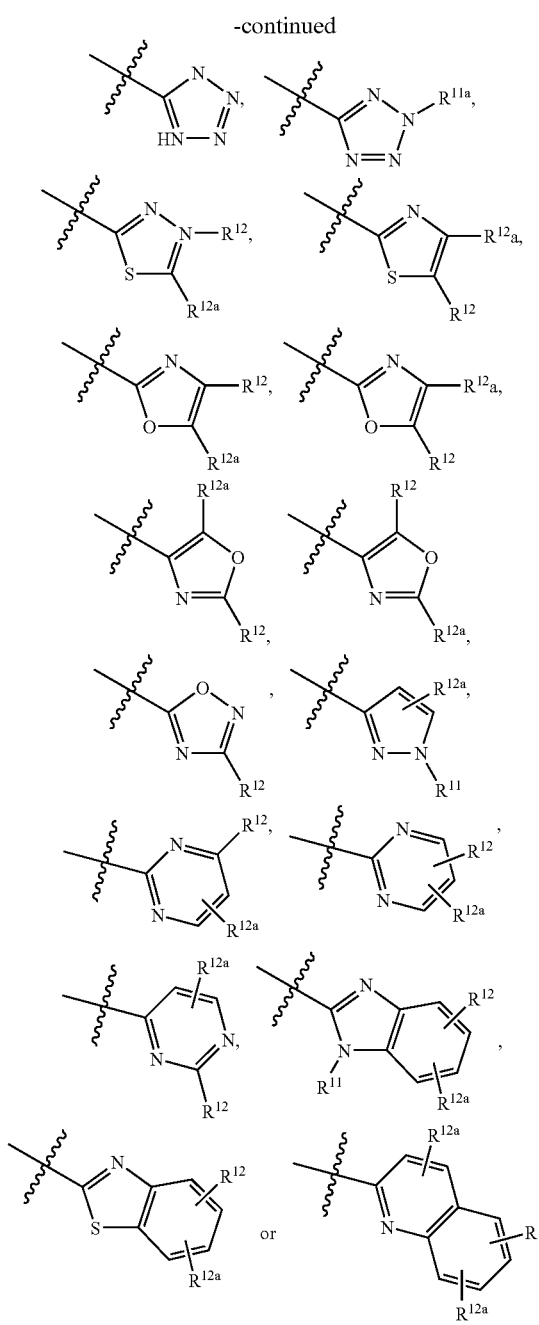

R[12] is, independently at each occurrence, H, Me, Et, Bu, F, Cl, Br, CF₃, OMe, OEt, OPr, O(i-Pr), O(i-Bu), SMe, NHMe, NMe₂, —N(Me)COMe, cyclopropyl, cyclopentyl, cyclohexyl, cyclobutoxy, cyclopentoxy, Ph, 2-Me-Ph, 3-Me-Ph, 4-Me-Ph, 2-Et-Ph, 3-Et-Ph, 3-Pr-Ph, 2-i-Pr-Ph, 2-OH-Ph, 3-OH-Ph, 4-OH-Ph, 2-CH₂OH-Ph, 3-CH₂OH-Ph, 4-CH₂OH-Ph, 2-CH(Me)OH-Ph, 2-CH₂OMe-Ph, 2-OMe-Ph, 3-OMe-Ph, 4-OMe-Ph, 2-OEt-Ph, 3-OEt-Ph, 2-OPr-Ph, 2-O(i-Pr)-Ph, 3-O(i-Pr)-Ph, 2-SMe-Ph, 2-OCF₃-Ph, 3-OCF₃-Ph, 2-F-Ph, 3-F-Ph, 4-F-Ph, 2-Cl-Ph, 3-Cl-Ph, 4-Cl-Ph, 2-Br-Ph, 2-CF₃-Ph, 3-CF₃-Ph, 4-CF₃-Ph, 2-CN-Ph, 3-CN-Ph, 2-COMe-Ph, 3-COMe-Ph, 2-COEt-Ph, 2-CO₂H-Ph, 3-CO₂H-Ph, 2-CO₂Me-Ph, 3-CO₂Me-Ph, 4-CO₂Me-Ph, 2-CO₂Et-Ph, 2-NMe₂-Ph, 4-NMe₂-Ph, 2-CH₂NMe₂-Ph, 3-CH₂NMe₂-Ph, 2-CONH₂-Ph, 3-CONH₂-Ph, 4-CONH₂-Ph, 2-CONHMe-Ph, 3-CONHMe-Ph, 4-CONHMe-Ph, 2-CONHEt-Ph, 2-CONMe₂-Ph, 3-CONH(CH₂)₂OH-Ph, 2-CONH(CH₂)₃OH-Ph, 2-CONHCH₂CO₂H-Ph, 2-CONHCH₂CO₂(t-Bu)-Ph, 2-NHCOMe-Ph, 3-NHCOMe-Ph, 4-NHCOMe-Ph, 2-NHCOEt-Ph, 2-SO₂Me-Ph, 3-SO₂Me-Ph, 2-SO₂Et-Ph, 2-NHSO₂Me-Ph, 3-NHSO₂Me-Ph, 2-SO₂NH₂-Ph, 2-Ph-Ph, 3-Ph-Ph, 4-Ph-Ph, 2-OPh-Ph, 2-OBn-Ph, 3-OBn-Ph, 2-(2-Me-1,3-dioxolan-2-yl)-Ph, 2-(1-pyrrolidinyl)-Ph, 2-(3-OH-pyrrolidin-1-yl)-Ph, 2,5-diMe-Ph, 2,6-diMe-Ph, 2,3-diF-Ph, 2,3-diCl-Ph, 2,4-diCl-Ph, 3,5-diCl-Ph, 2-OMe-5-Cl-Ph, 2-CO₂H-5-Me-Ph, 2-CO₂H-6-Me-Ph, 2-CO₂H-3-F-Ph, 2-CO₂H-4-Cl-Ph, 2-CO₂Me-3-Me-Ph, 2-CO₂Me-5-Me-Ph, 2-CO₂Me-6-Me-Ph, 2-CO₂Me-3-F-Ph, 2-CONH₂-3-Me-Ph, 2-CONH₂-5-Me-Ph, 2-CONH₂-6-Me-Ph, 2-CONH₂-3-F-Ph, 2-CONH₂-4-Cl-Ph, 2-CONHMe-3-F-Ph, 2-(3-furanyl)-Ph, 1-naphthyl, 2-naphthyl, 2-furanyl, 3-furanyl, 5-Me-furan-2-yl, 3-thienyl, 4-pyrazolyl, 1-Me-pyrazol-4-yl, 1-Et-pyrazol-4-yl, 1,4,5,6-tetrahydropyrimidin-5-yl, 1-pyrrolidinyl, 2-CH₂OH-pyrrolidin-1-yl, 2-CH₂OMe-pyrrolidin-1-yl, 2-CONH₂-pyrrolidin-1-yl, N-morpholinyl, 1-piperidinyl, 3-pyridyl, 4-pyridyl, 4-Me-pyrid-3-yl, 2-F-pyrid-3-yl, 2-OMe-pyrid-3-yl, 4-OMe-pyrid-3-yl, 5-OMe-pyrid-3-yl, 5-pyrimidinyl, 3,4-methylenedioxyphenyl, 2-benzofuranyl, 5-indolyl, or dihydrobenzofuran-5-yl; and R[12a] is, independently at each occurrence, H, F, Cl, Me, OMe, NH₂, or Ph.

7. A compound according to claim 5, wherein:

R[2] is H, Me, Et, i-Pr, vinyl, prop-1-en-2-yl, —CH(OH)Me, OMe, or OEt;

R[3] is H or F;

R[4] is H, OMe, OEt, OPr, O(i-Pr), O(i-Bu), —O(CH₂OMe), cyclohexoxy, cyclopropylmethoxy, Ph, 3-Me-Ph, tetrahydrofuran-3-yloxy, tetrahydro-2-H-pyran-4-yloxy, 1-pyrrolidinyl, N-morpholinyl, 1-Me-piperidin-4-yloxy, or 3-(dimethylamino)-2,2-dimethylpropoxy;

X is 4-C(=NH)NH₂-Ph, or 1-NH₂-isoquinolin-6-yl; alternatively,

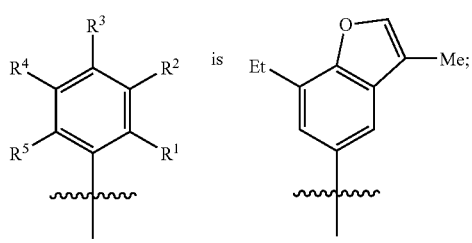

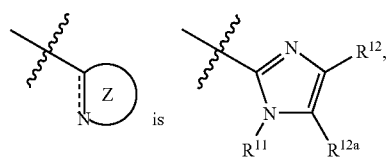

-continued

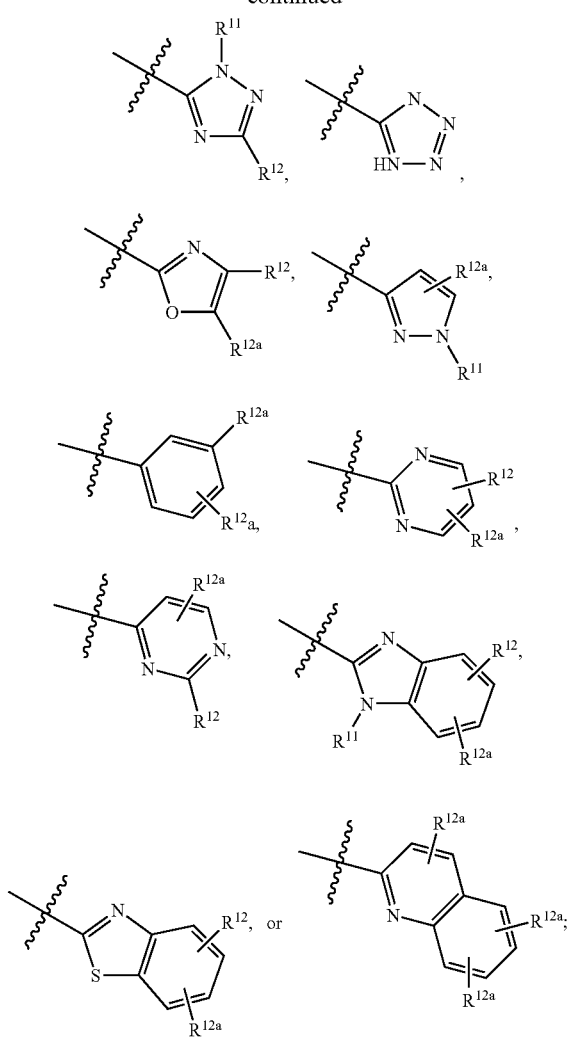

R$^{12}$ is, independently at each occurrence, H, Me, Et, Bu, Br, CF$_3$, OMe, OEt, OPr, O(i-Pr), O(i-Bu), SMe, cyclopropyl, cyclopentyl, Ph, 2-Me-Ph, 3-Me-Ph, 2-Et-Ph, 2-i-Pr-Ph, 2-OH-Ph, 3-OH-Ph, 4-OH-Ph, 2-CH$_2$OH-Ph, 3-CH$_2$OH-Ph, 2-CH(Me)OH-Ph, 2-CH$_2$OMe-Ph, 2-OMe-Ph, 2-OEt-Ph, 2-OPr-Ph, 2-SMe-Ph, 3-OCF$_3$-Ph, 2-F-Ph, 3-F-Ph, 4-F-Ph, 3-Cl-Ph, 2-Br-Ph, 2-CF$_3$-Ph, 2-CN-Ph, 3-CN-Ph, 2-COMe-Ph, 2-COEt-Ph, 2-CO$_2$H-Ph, 2-CO$_2$Me-Ph, 2-CO$_2$Et-Ph, 2-CONH$_2$-Ph, 3-CONH$_2$-Ph, 2-CONHMe-Ph, 3-CONHMe-Ph, 2-CONHEt-Ph, 2-CONMe$_2$-Ph, 2-CONH(CH$_2$)$_3$OH-Ph, 2-CONHCH$_2$CO$_2$H-Ph, 2-CONHCH$_2$CO$_2$(t-Bu)-Ph, 2-NHCOMe-Ph, 2-SO$_2$Me-Ph, 2-NHSO$_2$Me-Ph, 2-SO$_2$NH$_2$-Ph, 2-(2-Me-1,3-dioxolan-2-yl)-Ph, 2-(1-pyrrolidinyl)-Ph, 2-(3-OH-pyrrolidin-1-yl)-Ph, 2,5-diMe-Ph, 2,6-diMe-Ph, 2-CO$_2$H-3-F-Ph, 2-CO$_2$Me-3-Me-Ph, 2-CO$_2$Me-6-Me-Ph, 2-CO$_2$Me-3-F-Ph, 2-CONH$_2$-3-Me-Ph, 2-CONH$_2$-6-Me-Ph, 2-CONH$_2$-3-F-Ph, 1-naphthyl, 2-furanyl, 3-furanyl, 3-thienyl, 4-pyrazolyl, or 3-pyridyl; and R$^{12a}$ is, independently at each occurrence, H, Me, NH$_2$, or Ph.

8. A compound according to claim 6, wherein:
X is 1-NH$_2$-isoquinolin-6-yl;

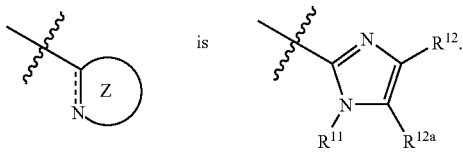

9. A compound according to claim 6, wherein:
X is 1-NH$_2$-isoquinolin-6-yl;

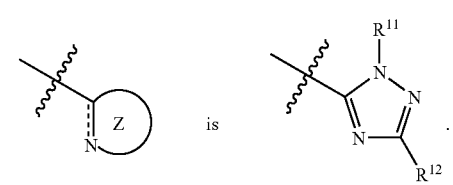

10. A compound according to claim 2, wherein:
R$^1$ is H;
R$^2$ is H, F, Br, Cl, C$_{2-4}$ alkenyl, C$_{2-4}$ alkynyl, C$_{3-6}$ cycloalkyl, —O—C$_{1-4}$ alkyl, —O—C$_{3-6}$ cycloalkyl, or C$_{1-4}$ alkyl substituted with 0-1 OH;
R$^3$, R$^4$, and R$^5$ are, independently at each ocurrence, H, —(CH$_2$)$_r$—OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, —(CF$_2$)$_r$CF$_3$, C$_{1-6}$ alkyl, C$_{2-6}$ alkenyl, C$_{2-6}$ alkynyl, tetrahydrofuran-3-yloxy, tetrahydro-2-H-pyran-4-yloxy, 1-pyrrolidinyl, N-morpholinyl, 1-Me-piperidin-4-yloxy, 3-(dimethylamino)-2,2-dimethylpropoxy, phenyl substituted with 0-2 R$^f$, or benzyl substituted with 0-2 R$^f$;
alternatively,

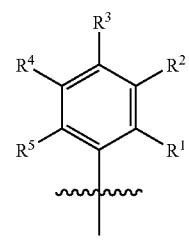

is:

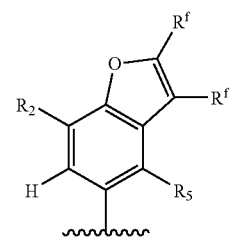

X is 4-C(=NH)NH$_2$-Ph, 4-C(=NOH)NH$_2$-Ph, 4-CH$_2$NH$_2$-Ph, isoquinolin-6-yl, 1-NH$_2$-isoquinolin-6-yl, quinazolin-7-yl, 4-NH$_2$-quinazolin-7-yl, phthalazin-6-yl, or 1-NH$_2$— phthalazin-6-yl; and X is substituted with 0-1 R$^6$;

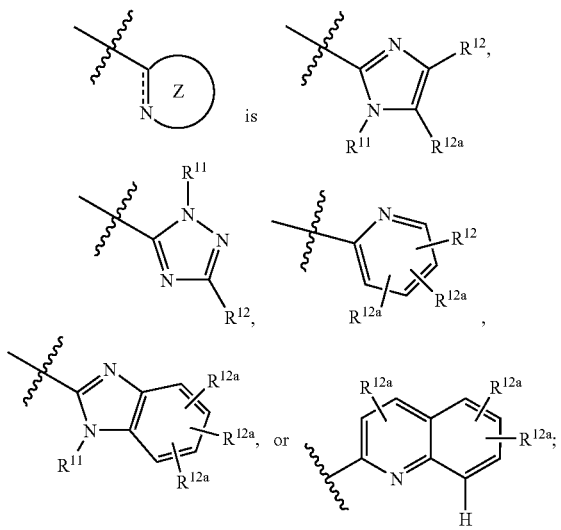

is $R^6$ is, independently at each occurrence, —(CH$_2$)$_r$—OR$^a$, F, Cl, Br, OCF$_3$, CN, NO$_2$, —NR$^b$R$^c$, or —(CF$_2$)$_r$CF$_3$;

$R^{11}$ is, independently at each occurrence, H, C$_{1-6}$ alkyl substituted with 0-4 R$^e$, C$_{2-6}$ alkyl substituted with 0-4 R$^e$, —(C$_{0-4}$ alkyl)-(C$_{6-10}$ aryl), —(C$_{0-4}$ alkyl)-(5- to 10-membered heteroaryl comprising: carbon atoms and 1-4 heteroatoms selected from N, O, and S; wherein said aryl and heteroaryl are substituted with 0-4 R$^f$;

$R^{12}$ is, independently at each occurrence, phenyl substituted with 0-3 R$^f$, furanyl substituted with 0-3 R$^f$, or pyridyl substituted with 0-3 R$^f$;

$R^{12a}$ is, independently at each occurrence, H, F, Cl, Br, C$_{1-4}$ alkyl, C$_{1-4}$ alkoxy, NH$_2$, or Ph;

$R^a$ is, independently at each occurrence, H, C$_{1-6}$ alkyl, or C$_{3-7}$ cycloalkyl;

$R^{a1}$ is, independently at each occurrence, H, C$_{1-4}$ alkyl substituted with 0-2 R$^j$, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said cycloalkyl, aryl and heteroaryl groups are optionally substituted with 0-2 R$^f$;

$R^b$ is, independently at each occurrence, H, C$_{1-6}$ alkyl, —(CH$_2$)$_n$-phenyl, (C$_{1-6}$ alkyl)C(O)—, phenyl-(C$_{0-2}$ alkyl)-C(O)—, (5- to 6-membered heteroaryl)-C$_{0-2}$ alkyl-C(O)—, (C$_{1-6}$ alkyl)-NHC(O)—, (C$_{1-6}$ alkyl)$_2$—NHC(O)—, phenyl-C$_{0-2}$ alkyl-NHC(O)—, (5- to 6-membered heteroaryl)-C$_{0-2}$ alkyl-NHC(O)—, (C$_{1-6}$ alkyl)-S(O)$_2$—, phenyl-C$_{0-2}$ alkyl-S(O)$_2$—, or (5- to 6-membered heteroaryl)-C$_{0-2}$ alkyl-S(O)$_2$—, wherein said phenyl and heteroaryl are substituted with 0-2 R$^f$; said heteroaryl comprises: carbon atoms and 1-4 heteroatoms selected from N, O, and S(O)$_p$;

$R^c$ is, independently at each occurrence, H, C$_{1-6}$ alkyl substituted with 0-2 R$^j$, or —(CH$_2$)$_n$-phenyl substituted with 0-2 R$^j$;

alternatively, R$^b$ and R$^c$, when attached to the same nitrogen atom, may be taken together with the nitrogen atom to form a 5- to 6-membered heterocycle comprising: carbon atoms and 1-2 heteroatoms selected from N, O, and S(O)$_p$, wherein said heterocycle is substituted with 0-2 R$^f$;

$R^d$ is, independently at each occurrence, H, C$_{1-6}$ alkyl, —(CH$_2$)$_r$—C$_{3-7}$ cycloalkyl substituted with 0-2 R$^f$, —(CH$_2$)$_r$-phenyl substituted with 0-2 R$^f$, or a —(CH$_2$)$_r$-5- to 6-membered heterocycle comprising: carbon atoms and 1-4 heteroatoms selected from N, O, and S(O)$_p$, wherein said heterocycle is substituted with 0-2 R$^f$;

alternatively, R$^c$ and R$^d$, when attached to the same nitrogen atom, may be taken together with the nitrogen atom to form a 4- to 7-membered heterocycle comprising: carbon atoms and 1-4 heteroatoms selected from N, O, and S(O)$_p$, wherein said heterocycle is substituted with 0-2 R$^f$;

$R^e$ is, independently at each occurrence, =O, OR$^a$, SR$^a$, F, Cl, Br, I, CN, NO$_2$, —OCF$_3$, —NR$^b$R$^c$, —C(O)R$^a$, —C(O)OR$^a$, —NR$^d$C(O)R$^a$, —C(O)NR$^c$R$^d$, —SO$_2$NR$^c$R$^d$, —NR$^c$SO$_2$NR$^c$R$^d$, —NR$^c$SO$_2$R$^{a1}$, —NR$^c$SO$_2$CF$_3$, —S(O)$_2$CF$_3$, —S(O)$_2$R$^{a1}$, —S(O)R$^{a1}$, or —(CF$_2$)$_r$CF$_3$;

$R^f$ is, independently at each occurrence, H, C$_{1-4}$ alkyl, C$_{1-4}$ alkoxy, OH, SMe, —CH$_2$OH, —CH(Me)OH, —CH$_2$OMe, F, Cl, Br, CF$_3$, OCF$_3$, CN, COMe, COEt, CO$_2$H, CO$_2$Me, CO$_2$Et, NH$_2$, NMe$_2$, —CH$_2$NMe$_2$, CONH$_2$, CONHMe, CONMe$_2$, CONHEt, —CONHCH$_2$CH$_2$OH, —NHCOMe-Ph, —NHCOEt-Ph, SO$_2$Me, SO$_2$Et, —NHSO$_2$Me, SO$_2$NH$_2$, Ph, OPh, OBn, furanyl, or thienyl;

$R^g$ is, independently at each occurrence, H, C$_{1-6}$ alkyl, or —(CH$_2$)$_n$-phenyl;

$R^j$ is, independently at each occurrence, H, =O, —(CH$_2$)$_r$ OR$^g$, SR$^g$, F, Cl, Br, I, CN, NO$_2$, —OCF$_3$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CF$_2$)$_r$CF$_3$, or C$_{1-6}$ alkyl;

n, at each occurrence, is selected from 0, 1, 2, and 3;
p, at each occurrence, is selected from 0, 1, and 2; and
r, at each occurrence, is selected from 0, 1, 2, and 3.

11. A compound according to claim 1, wherein the compound is selected from the group consisting of:
4-((3-ethoxy-4-isopropoxyphenyl)(1H-imidazol-2-yl)methylamino)benzamidine,
4-((3-ethoxy-4-isopropoxyphenyl)(thiazol-2-yl)methylamino)benzamidine,
4-(benzo[d]thiazol-2-yl(3-ethoxy-4-isopropoxyphenyl)methylamino)benzamidine,
4-((3-ethoxy-4-isopropoxyphenyl)(pyridin-2-yl)methylamino)benzamidine,
4-(benzo[d]thiazol-2-yl(5-ethoxy-2-fluoro-3-isopropoxyphenyl)methylamino)benzamidine,
4-((5-ethoxy-2-fluoro-3-isopropoxyphenyl)(4-phenyl-1H-imidazol-2-yl)methylamino)benzamidine,
4-((5-ethoxy-2-fluoro-3-isopropoxyphenyl)(1-methyl-1H-benzo[d]imidazol-2-yl)methylamino)benzamidine,
4-((1-(benzyloxymethyl)-1H-benzo[d]imidazol-2-yl)(5-ethoxy-2-fluoro-3-isopropoxyphenyl)methylamino)benzamidine,
4-((1H-benzo[d]imidazol-2-yl)(5-ethoxy-2-fluoro-3-isopropoxyphenyl)methylamino)benzamidine,
4-((5-ethoxy-2-fluoro-3-isopropoxyphenyl)(1H-tetrazol-5-yl)methylamino)benzamidine,
4-((5-ethoxy-2-fluoro-3-isopropoxyphenyl)(1-methyl-4-phenyl-1H-imidazol-2-yl)methylamino)benzamidine,
4-((5-ethoxy-2-fluoro-3-isopropoxyphenyl)(1-methyl-5-phenyl-1H-imidazol-2-yl)methylamino)benzamidine,
4-((5-ethoxy-2-fluoro-3-isopropoxyphenyl)(2-phenyl-1H-imidazol-4-yl)methylamino)benzamidine,
4-((5-ethoxy-2-fluoro-3-isopropoxyphenyl)(4-phenylthiazol-2-yl)methylamino)benzamidine, 4-((5-ethoxy-2-fluoro-3-isopropoxyphenyl)(5-phenyl-2H-1,2,4-triazol-3-yl)methylamino)benzamidine,
4-((5-ethoxy-2-fluoro-3-isopropoxyphenyl)(quinolin-2-yl)methylamino)benzamidine,
4-((4,5-diphenyl-1H-imidazol-2-yl)(5-ethoxy-2-fluoro-3-isopropoxyphenyl)methylamino)benzamidine,
4-((5-ethoxy-2-fluoro-3-isopropoxyphenyl)(5-methyl-4-phenyl-1H-imidazol-2-yl)methylamino)benzamidine,
4-((5-ethoxy-2-fluoro-3-isopropoxyphenyl)(2-phenyl-2H-tetrazol-5-yl)methylamino)benzamidine,
N-((5-ethoxy-2-fluoro-3-isopropoxyphenyl)(4-phenyl-1H-imidazol-2-yl)methyl)isoquinolin-6-amine,
N$^6$-((5-ethoxy-2-fluoro-3-isopropoxyphenyl)(4-phenyl-1H-imidazol-2-yl)methyl)isoquinoline-1,6-diamine,
4-((5-ethoxy-2-fluoro-3-isopropoxyphenyl)(4-m-tolyl-1H-imidazol-2-yl)methylamino)benzamidine,
4-((4-bromo-1H-imidazol-2-yl)(5-ethoxy-2-fluoro-3-isopropoxyphenyl)methylamino)benzamidine,
4-((5-ethoxy-2-fluorophenyl)(4-phenyl-1H-imidazol-2-yl)methylamino)benzamidine,
4-((5-ethoxy-2-fluoro-3-isopropoxyphenyl)(6-phenylpyridin-2-yl)methylamino)benzamidine,
4-((4,6-dichlorobenzo[d]thiazol-2-yl)(5-ethoxy-2-fluoro-3-isopropoxyphenyl)methylamino)benzamidine,
4-((5-ethoxy-2-fluoro-3-isopropoxyphenyl)(4-(3-(methylsulfonyl)phenyl)-1H-imidazol-2-yl)methylamino)benzamidine,
4-((5-ethoxy-2-fluoro-3-isopropoxyphenyl)(5,6,7,8-tetrahydroquinolin-2-yl)methylamino)benzamidine,
4-((5-ethoxy-2-fluoro-3-isopropoxyphenyl)(4,5,6,7-tetrahydro-1H-benzo[d]imidazol-2-yl)methylamino)benzamidine,
4-((5-ethoxy-2-fluoro-3-isopropoxyphenyl)(4-(furan-2-yl)-1H-imidazol-2-yl)methylamino)benzamidine,
4-((4-(benzofuran-2-yl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-(trifluoromethyl)phenyl)-1H-imidazol-2-yl)methylamino)benzamidine,
4-((5-ethoxy-2-fluoro-3-isopropoxyphenyl)(4-p-tolyl-1H-imidazol-2-yl)methylamino)benzamidine,
4-((5-ethoxy-2-fluoro-3-isopropoxyphenyl)(4-o-tolyl-1H-imidazol-2-yl)methylamino)benzamidine,
4-((4-(2,5-dimethylphenyl)-1H-imidazol-2-yl)(5-ethoxy-2-fluoro-3-isopropoxyphenyl)methylamino)benzamidine,
4-((4-(2-chlorophenyl)-1H-imidazol-2-yl)(5-ethoxy-2-fluoro-3-isopropoxyphenyl)methylamino)benzamidine,
4-((4-(3-chlorophenyl)-1H-imidazol-2-yl)(5-ethoxy-2-fluoro-3-isopropoxyphenyl)methylamino)benzamidine,
4-((4-(4-chlorophenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-methoxyphenyl)-1H-imidazol-2-yl)methylamino)benzamidine,
4-((5-ethoxy-2-fluoro-3-isopropoxyphenyl)(4-(3-methoxyphenyl)-1H-imidazol-2-yl)methylamino)benzamidine,
4-((5-ethoxy-2-fluoro-3-isopropoxyphenyl)(4-(4-methoxyphenyl)-1H-imidazol-2-yl)methylamino)benzamidine,
4-((5-ethoxy-2-fluoro-3-isopropoxyphenyl)(4-(3-(trifluoromethyl)phenyl)-1H-imidazol-2-yl)methylamino)benzamidine,
4-((5-ethoxy-2-fluoro-3-isopropoxyphenyl)(4-(3-hydroxyphenyl)-1H-imidazol-2-yl)methylamino)benzamidine,
4-((4-(1H-indol-5-yl)-1H-imidazol-2-yl)(5-ethoxy-2-fluoro-3-isopropoxyphenyl)methylamino)benzamidine,
methyl 3-(2-((4-carbamimidoylphenylamino)(5-ethoxy-2-fluoro-3-isopropoxyphenyl)methyl)-1H-imidazol-4-yl)benzoate,
methyl 4-(2-((4-carbamimidoylphenylamino)(5-ethoxy-2-fluoro-3-isopropoxyphenyl)methyl)-1H-imidazol-4-yl)benzoate,
4-((5-ethoxy-2-fluoro-3-isopropoxyphenyl)(4-(3-fluorophenyl)-1H-imidazol-2-yl)methylamino)benzamidine,
4-((5-ethoxy-2-fluoro-3-isopropoxyphenyl)(4-(4-fluorophenyl)-1H-imidazol-2-yl)methylamino)benzamidine,
4-((4-(23-dihydrobenzofuran-5-yl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-hydroxyphenyl)-1H-imidazol-2-yl)methylamino)benzamidine,
4-((5-ethoxy-2-fluoro-3-isopropoxyphenyl)(4-(4-hydroxyphenyl)-1H-imidazol-2-yl)methylamino)benzamidine,
4-(2-((4-carbamimidoylphenylamino)(5-ethoxy-2-fluoro-3-isopropoxyphenyl)methyl)-1H-imidazol-4-yl)benzamide,
4-(2-((4-carbamimidoylphenylamino)(5-ethoxy-2-fluoro-3-isopropoxyphenyl)methyl)-1H-imidazol-4-yl)-N-methylbenzamide,
3-(2-((4-carbamimidoylphenylamino)(5-ethoxy-2-fluoro-3-isopropoxyphenyl)methyl)-1H-imidazol-4-yl)benzamide,
3-(2-((4-carbamimidoylphenylamino)(5-ethoxy-2-fluoro-3-isopropoxyphenyl)methyl)-1H-imidazol-4-yl)-N-methylbenzamide,
N-(3-(2-((4-carbamimidoylphenylamino)(5-ethoxy-2-fluoro-3-isopropoxyphenyl)methyl)-1H-imidazol-4-yl)phenyl)acetamide,
4-((4-(2-(benzyloxy)phenyl)-1H-imidazol-2-yl)(5-ethoxy-2-fluoro-3-isopropoxyphenyl)methylamino)benzamidine,
4-((4-(3-(benzyloxy)phenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(furan-3-yl)-1H-imidazol-2-yl)methylamino)benzamidine,
4-((5-ethoxy-2-fluoro-3-isopropoxyphenyl)(4-(2-(methoxymethyl)phenyl)-1H-imidazol-2-yl)methylamino)benzamidine,
4-((5-ethoxy-2-fluoro-3-isopropoxyphenyl)(4-(naphthalen-1-yl)-1H-imidazol-2-yl)methylamino)benzamidine,
4-((5-ethoxy-2-fluoro-3-isopropoxyphenyl)(4-(naphthalen-2-yl)-1H-imidazol-2-yl)methylamino)benzamidine,
N-(2-(2-((4-carbamimidoylphenylamino)(5-ethoxy-2-fluoro-3-isopropoxyphenyl)methyl)-1H-imidazol-4-yl)phenyl)acetamide, 4-((5-ethoxy-2-fluoro-3-isopropoxyphenyl)(4-(2-phenoxyphenyl)-1H-imidazol-2-yl)methylamino)benzamidine,
4-((5-ethoxy-2-fluoro-3-isopropoxyphenyl)(4-(thiophen-3-yl)-1H-imidazol-2-yl)methylamino)benzamidine,
4-((5-ethoxy-2-fluoro-3-isopropoxyphenyl)(4-(biphen-1-yl)-1H-imidazol-2-yl)methylamino)benzamidine,
4-((5-ethoxy-2-fluoro-3-isopropoxyphenyl)(4-(biphen-2-yl)-1H-imidazol-2-yl)methylamino)benzamidine,
4-((5-ethoxy-2-fluoro-3-isopropoxyphenyl)(4-(2-ethoxyphenyl)-1H-imidazol-2-yl)methylamino)benzamidine,
4-((5-ethoxy-2-fluoro-3-isopropoxyphenyl)(4-(3-ethoxyphenyl)-1H-imidazol-2-yl)methylamino)benzamidine,
N-(4-(2-((4-carbamimidoylphenylamino)(5-ethoxy-2-fluoro-3-isopropoxyphenyl)methyl)-1H-imidazol-4-yl)phenyl)acetamide,
4-((5-ethoxy-2-fluoro-3-isopropoxyphenyl)(4-(3-ethylphenyl)-1H-imidazol-2-yl)methylamino)benzamidine,
4-((5-ethoxy-2-fluoro-3-isopropoxyphenyl)(4-(3-(methylsulfonamido)phenyl)-1H-imidazol-2-yl)methylamino)benzamidine,
4-((4-(2-(dimethylamino)phenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-(hydroxymethyl)phenyl)-1H-imidazol-2-yl)methylamino)benzamidine,
4-((5-ethoxy-2-fluoro-3-isopropoxyphenyl)(4-(4-(hydroxymethyl)phenyl)-1H-imidazol-2-yl)methylamino)benzamidine,
4-((4-(2,6-dimethylphenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(3-isopropoxyphenyl)-1H-imidazol-2-yl)methylamino)benzamidine,
4-((5-ethoxy-2-fluoro-3-isopropoxyphenyl)(4-(2-isopropoxyphenyl)-1H-imidazol-2-yl)methylamino)benzamidine,
4-((5-ethoxy-2-fluoro-3-isopropoxyphenyl)(4-(3-(trifluoromethoxy)phenyl)-1H-imidazol-2-yl)methylamino)benzamidine,
4-((4-(2-cyanophenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-isopropylphenyl)-1H-imidazol-2-yl)methylamino)benzamidine,
4-((6-chloroquinolin-2-yl)(5-ethoxy-2-fluoro-3-isopropoxyphenyl)methylamino)benzamidine,
4-((8-chloroquinolin-2-yl)(5-ethoxy-2-fluoro-3-isopropoxyphenyl)methylamino)benzamidine,
4-((4,8-dimethylquinolin-2-yl)(5-ethoxy-2-fluoro-3-isopropoxyphenyl)methylamino)benzamidine,
4-((5-ethoxy-2-fluoro-3-isopropoxyphenyl)(4-(2-(methylsulfonyl)phenyl)-1H-imidazol-2-yl)methylamino)benzamidine,
4-((5-ethoxy-2-fluoro-3-isopropoxyphenyl)(4-(2-(trifluoromethoxy)phenyl)-1H-imidazol-2-yl)methylamino)benzamidine,
4-((5-ethoxy-2-fluoro-3-isopropoxyphenyl)(4-(pyrimidin-2-yl)-1H-imidazol-2-yl)methylamino)benzamidine,
4-((5-ethoxy-2-fluoro-3-isopropoxyphenyl)(4-(4-methoxypyridin-3-yl)-1H-imidazol-2-yl)methylamino)benzamidine,
4-((4-(2-acetylphenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-(2-methyl-1,3-dioxolan-2-yl)phenyl)-1H-imidazol-2-yl)methylamino)benzamidine,
4-((5-ethoxy-2-fluoro-3-isopropoxyphenyl)(4-(2-propoxyphenyl)-1H-imidazol-2-yl)methylamino)benzamidine,
4-((4-(2-((dimethylamino)methyl)phenyl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(2-(methylsulfonamido)phenyl)-1H-imidazol-2-yl)methylamino)benzamidine,
4-((5-ethoxy-2-fluoro-3-isopropoxyphenyl)(4-(2-fluorophenyl)-1H-imidazol-2-yl)methylamino)benzamidine,
2-(2-((4-carbamimidoylphenylamino)(5-ethoxy-2-fluoro-3-isopropoxyphenyl)methyl)-1H-imidazol-4-yl)benzoic acid,
methyl 2-(2-((4-carbamimidoylphenylamino)(5-ethoxy-2-fluoro-3-isopropoxyphenyl)methyl)-1H-imidazol-4-yl)benzoate,
4-((5-ethoxy-2-fluoro-3-isopropoxyphenyl)(4-(2-(ethylsulfonyl)phenyl)-1H-imidazol-2-yl)methylamino)benzamidine,
ethyl 2-(2-((4-carbamimidoylphenylamino)(5-ethoxy-2-fluoro-3-isopropoxyphenyl)methyl)-1H-imidazol-4-yl)benzoate,
4-((5-ethoxy-2-fluoro-3-isopropoxyphenyl)(4-(1 sL5,6-tetrahydropyrimidin-5-yl)-1H-imidazol-2-yl)methylamino)benzamidine,
4-((4-cyclohexyl-1H-imidazol-2-yl)(5-ethoxy-2-fluoro-3-isopropoxyphenyl)methylamino)benzamidine,
4-({(5-Ethoxy-2-fluoro-3-isopropoxy-phenyl)-[4-(2-sulfamoyl-phenyl)-1H-imidazol-2-yl]-methyl}-amino)-benzamidine,
4-((5-ethoxy-2-fluoro-3-isopropoxyphenyl)(4-(2-(ethylsulfonyl)phenyl)-1H-imidazol-2-yl)methylamino)benzamidine,
4-((5-ethoxy-2-fluoro-3-isopropoxyphenyl)(4-(2-(1-hydroxyethyl)phenyl)-1H-imidazol-2-yl)methylamino)benzamidine,
4-((5-ethoxy-2-fluoro-3-(1-methylpiperidin-4-yloxy)phenyl)(4-phenyl-1H-imidazol-2-yl)methylamino)benzamidine,
4-((5-ethoxy-2-fluoro-3-((R)-tetrahydrofuran-3-yloxy)phenyl)(4-phenyl-1H-imidazol-2-yl)methylamino)benzamidine,
4-((5-ethoxy-2-fluoro-3-((S)-tetrahydrofuran-3-yloxy)phenyl)(4-phenyl-1H-imidazol-2-yl)methylamino)benzamidine,
4-((3-(cyclohexyloxy)-5-ethoxy-2-fluorophenyl)(4-phenyl-1H-imidazol-2-yl)methylamino)benzamidine,
4-((3-(3-(dimethylamino)-2,2-dimethylpropoxy)-5-ethoxy-2-fluorophenyl)(4-phenyl-1H-imidazol-2-yl)methylamino)benzamidine,
4-((5-ethoxy-2-fluoro-3-isopropoxyphenyl)(4-(2-propionylphenyl)-1H-imidazol-2-yl)methylamino)benzamidine,
$N^6$-((5-ethoxy-2-fluoro-3-(1-methylpiperidin-4-yloxy)phenyl)(4-phenyl-1H-imidazol-2-yl)methyl)isoquinoline-1,6-diamine, N$^6$-((5-ethoxy-2-fluoro-3-((R)-tetrahydrofuran-3-yloxy)
phenyl)(4-phenyl-1H-imidazol-2-yl)methyl)isoquino-
line-1,6-diamine,
N$^6$-((5-ethoxy-2-fluoro-3-((S)-tetrahydrofuran-3-yloxy)
phenyl)(4-phenyl-1H-imidazol-2-yl)methyl)isoquino-
line-1,6-diamine,
N$^6$-((3-(cyclohexyloxy)-5-ethoxy-2-fluorophenyl)(4-phe-
nyl-1H-imidazol-2-yl)methyl)isoquinoline-1,6-di-
amine,
N$^6$-((3-(3-(dimethylamino)-2,2-dimethylpropoxy)-5-
ethoxy-2-fluorophenyl)(4-phenyl-1H-imidazol-2-yl)
methyl)isoquinoline-1,6-diamine,
2-(2-((4-carbamimidoylphenylamino)(5-ethoxy-2-fluoro-
3-isopropoxyphenyl)methyl)-1H-imidazol-4-yl)-N-
ethylbenzamide,
2-(2-((4-carbamimidoylphenylamino)(5-ethoxy-2-fluoro-
3-isopropoxyphenyl)methyl)-1H-imidazol-4-yl)-N,N-
dimethylbenzamide,
2-(2-((4-carbamimidoylphenylamino)(5-ethoxy-2-fluoro-
3-isopropoxyphenyl)methyl)-1H-imidazol-4-yl)-N-
methylbenzamide,
2-(2-((4-carbamimidoylphenylamino)(5-ethoxy-2-fluoro-
3-((S)-tetrahydrofuran-3-yloxy)phenyl)methyl)-1H-
imidazol-4-yl)benzamide,
4-((5-ethoxy-2-fluoro-3-isopropoxyphenyl)(6-methoxy-
pyridin-2-yl)methylamino)benzamidine,
4-((5-ethoxy-2-fluoro-3-isopropoxyphenyl)(6-(furan-3-
yl)pyridin-2-yl)methylamino)benzamidine,
4-((5-ethoxy-2-fluoro-3-isopropoxyphenyl)(6-(pyrroli-
din-1-yl)pyridin-2-yl)methylamino)benzamidine,
4-((5-ethoxy-2-fluoro-3-isopropoxyphenyl)(6-morpholi-
nopyridin-2-yl)methylamino)benzamidine,
(2R)-1-(6-((4-carbamimidoylphenylamino)(5-ethoxy-2-
fluoro-3-isopropoxyphenyl)methyl)pyridin-2-yl)pyrro-
lidine-2-carboxamide,
(2S)-1-(6-((4-carbamimidoylphenylamino)(5-ethoxy-2-
fluoro-3-isopropoxyphenyl)methyl)pyridin-2-yl)pyrro-
lidine-2-carboxamide,
4-((5-ethoxy-2-fluoro-3-isopropoxyphenyl)(6-(piperidin-
1-yl)pyridin-2-yl)methylamino)benzamidine,
4-((5-ethoxy-2-fluoro-3-isopropoxyphenyl)(6-((S)-2-(hy-
droxymethyl)pyrrolidin-1-yl)pyridin-2-yl)methy-
lamino)benzamidine,
4-((5-ethoxy-2-fluoro-3-isopropoxyphenyl)(6-((R)-2-
(hydroxymethyl)pyrrolidin-1-yl)pyridin-2-yl)methy-
lamino)benzamidine,
4-((6-cyclopentylpyridin-2-yl)(5-ethoxy-2-fluoro-3-iso-
propoxyphenyl)methylamino)benzamidine,
4-((5-ethoxy-2-fluoro-3-isopropoxyphenyl)(6-((R)-2-
(methoxymethyl)pyrrolidin-1-yl)pyridin-2-yl)methy-
lamino)benzamidine,
4-((5-ethoxy-2-fluoro-3-isopropoxyphenyl)(6-((S)-2-
(methoxymethyl)pyrrolidin-1-yl)pyridin-2-yl)methy-
lamino)benzamidine,
4-((5-ethoxy-2-fluoro-3-isopropoxyphenyl)(6-methylpy-
ridin-2-yl)methylamino)benzamidine,
4-((5-ethoxy-2-fluoro-3-isopropoxyphenyl)(6-(trifluo-
romethyl)pyridin-2-yl)methylamino)benzamidine,
4-((5-ethoxy-2-fluoro-3-isopropoxyphenyl)(6-ethoxypy-
ridin-2-yl)methylamino)benzamidine,
4-((5-ethoxy-2-fluoro-3-isopropoxyphenyl)(6-isopro-
poxypyridin-2-yl)methylamino)benzamidine,
4-((6-cyclobutoxypyridin-2-yl)(5-ethoxy-2-fluoro-3-iso-
propoxyphenyl)methylamino)benzamidine,
4-((6-(cyclopentyloxy)pyridin-2-yl)(5-ethoxy-2-fluoro-3-
isopropoxyphenyl)methylamino)benzamidine,
4-((5-ethoxy-2-fluoro-3-isopropoxyphenyl)(pyridin-2-yl)
methylamino)benzamidine,
4-((5-ethoxy-2-fluoro-3-isopropoxyphenyl)(6-propoxy-
pyridin-2-yl)methylamino)benzamidine,
4-((5-ethoxy-2-fluoro-3-isopropoxyphenyl)(6-isobutoxy-
pyridin-2-yl)methylamino)benzamidine,
4-((5-ethoxy-2-fluoro-3-isopropoxyphenyl)(6-ethylpyri-
din-2-yl)methylamino)benzamidine,
4-((6-(dimethylamino)pyridin-2-yl)(5-ethoxy-2-fluoro-3-
isopropoxyphenyl)methylamino)benzamidine,
4-((5-ethoxy-2-fluoro-3-isopropoxyphenyl)(6-(meth-
ylthio)pyridin-2-yl)methylamino)benzamidine,
4-((5-ethoxy-2-fluoro-3-isopropoxyphenyl)(6-(methy-
lamino)pyridin-2-yl)methylamino)benzamidine,
N-(6-((4-carbamimidoylphenylamino)(5-ethoxy-2-
fluoro-3-isopropoxyphenyl)methyl)pyridin-2-yl)-N-
methylacetamide,
4-((6-amino-2-(methylthio)pyrimidin-4-yl)(5-ethoxy-2-
fluoro-3-isopropoxyphenyl)methylamino)benzami-
dine,
4-((5-ethoxy-2-fluoro-3-isopropoxyphenyl)(2-methoxy-
pyrimidin-4-yl)methylamino)benzamidine,
4-((5-ethoxy-2-fluoro-3-isopropoxyphenyl)(2-(meth-
ylthio)pyrimidin-4-yl)methylamino)benzamidine,
4-((5-ethoxy-2-fluoro-3-isopropoxyphenyl)(4-methyl-
1H-benzo[d]imidazol-2-yl)methylamino)benzamidine,
4-((5,6-dimethyl-1H-benzo[d]imidazol-2-yl)(5-ethoxy-2-
fluoro-3-isopropoxyphenyl)methylamino)benzami-
dine,
4-((5-ethoxy-2-fluoro-3-isopropoxyphenyl)(5-methyl-
1H-benzo[d]imidazol-2-yl)methylamino)benzamidine,
4-((5-ethoxy-2-fluoro-3-isopropoxyphenyl)(5-methoxy-
1H-benzo[d]imidazol-2-yl)methylamino)benzamidine,
(Z)-2-(2-((4-(N'-hydroxycarbamimidoyl)phenylamino)
(3-ethylphenyl)methyl)-1H-imidazol-4-yl)benzamide,
4-((5-ethoxy-2-fluoro-3-isopropoxyphenyl)(4-methoxy-
1H-benzo[d]imidazol-2-yl)methylamino)benzamidine,
4-((5-chloro-1H-benzo[d]imidazol-2-yl)(5-ethoxy-2-
fluoro-3-isopropoxyphenyl)methylamino)benzami-
dine,
4-((4,5-dimethyl-1H-benzo[d]imidazol-2-yl)(5-ethoxy-2-
fluoro-3-isopropoxyphenyl)methylamino)benzami-
dine,
4-((5-ethoxy-2-fluoro-3-isopropoxyphenyl)(5-ethyl-1H-
benzo[d]imidazol-2-yl)methylamino)benzamidine,
4-((5,6-difluoro-1H-benzo[d]imidazol-2-yl)(5-ethoxy-2-
fluoro-3-isopropoxyphenyl)methylamino)benzami-
dine,
4-((5-chloro-6-fluoro-1H-benzo[d]imidazol-2-yl)(5-
ethoxy-2-fluoro-3-isopropoxyphenyl)methylamino)
benzamidine,
4-((5-ethoxy-2-fluoro-3-isopropoxyphenyl)(1-phenyl-
1H-pyrazol-3-yl)methylamino)benzamidine,
2-(3-((4-carbamimidoylphenylamino)(5-ethoxy-2-fluoro-
3-isopropoxyphenyl)methyl)-1H-pyrazol-1-yl)benza-
mide,
4-((5-ethoxy-2-fluoro-3-isopropoxyphenyl)(4-phenylox-
azol-2-yl)methylamino)benzamidine,
4-((5-ethoxy-2-fluoro-3-isopropoxyphenyl)(2-phenylox-
azol-4-yl)methylamino)benzamidine,
4-((3-ethoxy-4-isopropoxyphenyl)(3-phenyl-1,2,4-oxa-
diazol-5-yl)methylamino)benzamidine,
2-(2-((4-carbamimidoylphenylamino)(5-ethyl-2-fluoro-
3-methoxyphenyl)methyl)-1H-imidazol-4-yl)benza-
mide,
2-(2-((4-carbamimidoylphenylamino)(3-ethoxy-5-ethyl-
2-fluorophenyl)methyl)-1H-imidazol-4-yl)benzamide, 2-(2-((4-carbamimidoylphenylamino)(5-ethyl-2-fluoro-3-isopropoxyphenyl)methyl)-1H-imidazol-4-yl)benzamide,
4-((5-ethyl-2-fluoro-3-methoxyphenyl)(4-phenyl-1H-imidazol-2-yl)methylamino)benzamidine,
4-((3-ethoxy-5-ethyl-2-fluorophenyl)(4-phenyl-1H-imidazol-2-yl)methylamino)benzamidine,
4-((5-ethyl-2-fluoro-3-isopropoxyphenyl)(4-phenyl-1H-imidazol-2-yl)methylamino)benzamidine,
4-((5-ethoxy-2-fluoro-3-isopropoxyphenyl)(5-phenyloxazol-2-yl)methylamino)benzamidine,
2-(2-((4-carbamimidoylphenylamino)(5-ethyl-2-fluoro-3-(methoxymethoxy)phenyl)methyl)-1H-imidazol-4-yl)benzamide,
2-(2-((4-carbamimidoylphenylamino)(5-ethyl-2-fluoro-3-propoxyphenyl)methyl)-1H-imidazol-4-yl)benzamide,
2-(2-((4-carbamimidoylphenylamino)(5-ethyl-2-fluoro-3-isobutoxyphenyl)methyl)-1H-imidazol-4-yl)benzamide,
4-((5-ethyl-2-fluoro-3-methoxyphenyl)(4-(2-methoxyphenyl)-1H-imidazol-2-yl)methylamino)benzamidine,
4-((3-ethoxy-5-ethyl-2-fluorophenyl)(4-(2-methoxyphenyl)-1H-imidazol-2-yl)methylamino)benzamidine,
4-((5-ethyl-2-fluoro-3-isopropoxyphenyl)(4-(2-methoxyphenyl)-1H-imidazol-2-yl)methylamino)benzamidine,
4-((5-ethyl-2-fluoro-3-methoxyphenyl)(4-(2-(methylsulfonyl)phenyl)-1H-imidazol-2-yl)methylamino)benzamidine,
4-((3-ethoxy-5-ethyl-2-fluorophenyl)(4-(2-(methylsulfonyl)phenyl)-1H-imidazol-2-yl)methylamino)benzamidine,
4-((5-ethyl-2-fluoro-3-isopropoxyphenyl)(4-(2-(methylsulfonyl)phenyl)-1H-imidazol-2-yl)methylamino)benzamidine,
2-(2-((4-carbamimidoylphenylamino)(5-ethyl-2-fluoro-3-((S)-tetrahydrofuran-3-yloxy)phenyl)methyl)-1H-imidazol-4-yl)benzamide,
2-(2-((4-carbamimidoylphenylamino)(5-ethyl-2-fluoro-3-((R)-tetrahydrofuran-3-yloxy)phenyl)methyl)-1H-imidazol-4-yl)benzamide,
$N^6$-((5-ethyl)-2-fluoro-3-methoxyphenyl)(4-(2-methoxyphenyl)-1H-imidazol-2-yl)methyl)isoquinoline-1,6-diamine,
$N^6$-((5-ethyl)-2-fluoro-3-methoxyphenyl)(4-(2-fluorophenyl)-1H-imidazol-2-yl)methyl)isoquinoline-1,6-diamine,
$N^6$-((4-(2,3-difluorophenyl)-1H-imidazol-2-yl)(5-ethyl-2-fluoro-3-methoxyphenyl)methyl)isoquinoline-1,6-diamine,
$N^6$-((4-(3-fluorophenyl)-1H-imidazol-2-yl)5-ethyl)-2-fluoro-3-methoxyphenyl)methyl)isoquinoline-1,6-diamine,
(2-(2-((1-aminoisoquinolin-6-ylamino)(5-ethyl-2-fluoro-3-methoxyphenyl)methyl)-1H-imidazol-4-yl)phenyl)methanol,
1-(2-(2-((1-aminoisoquinolin-6-ylamino)(5-ethyl-2-fluoro-3-methoxyphenyl)methyl)-1H-imidazol-4-yl)phenyl)ethanone,
$N^6$-((5-ethyl)-2-fluoro-3-methoxyphenyl)(4-(2-(methylthio)phenyl)-1H-imidazol-2-yl)methyl)isoquinoline-1,6-diamine,
$N^6$-((3-ethoxy-5-ethyl)-2-fluorophenyl)(4-(3-ethylphenyl)-1H-imidazol-2-yl)methyl)isoquinoline-1,6-diamine,
$N^6$-((3-ethoxy-5-ethyl)-2-fluorophenyl)(4-(3-propylphenyl)-1H-imidazol-2-yl)methyl)isoquinoline-1,6-diamine,
$N^6$-((3-ethoxy-5-ethyl)-2-fluorophenyl)(4-(2-methoxypyridin-3-yl)-1H-imidazol-2-yl)methyl)isoquinoline-1,6-diamine,
$N^6$-((3-ethoxy-5-ethyl)-2-fluorophenyl)(4-(2-fluoropyridin-3-yl)-1H-imidazol-2-yl)methyl)isoquinoline-1,6-diamine,
N6-[(4-Biphenyl-2-yl-1H-imidazol-2-yl)-(3-ethoxy-5-ethyl-2-fluoro-phenyl)- methyl]-isoquinoline-1,6-diamine,
$N^6$-((4-(2-bromophenyl)-1H-imidazol-2-yl)(3-ethoxy-5-ethyl)-2-fluorophenyl)methyl)isoquinoline-1,6-diamine,
3-(2-((1-aminoisoquinolin-6-ylamino)(3-ethoxy-5-ethyl-2-fluorophenyl)methyl)-1H-imidazol-4-yl)phenol,
2-(2-((1-aminoisoquinolin-6-ylamino)(3-ethoxy-5-ethyl-2-fluorophenyl)methyl)-1H-imidazol-4-yl)benzenesulfonamide,
2-(2-((1-aminoisoquinolin-6-ylamino)(3-chloro-5-ethyl-2-fluorophenyl)methyl)-1H-imidazol-4-yl)benzamide,
2-(2-((R)-(1-aminoisoquinolin-6-ylamino)(3-ethoxy-5-ethyl-2-fluorophenyl)methyl)-1H-imidazol-4-yl)benzamide,
2-(2-((S)-(1-aminoisoquinolin-6-ylamino)(3-ethoxy-5-ethyl-2-fluorophenyl)methyl)-1H-imidazol-4-yl)benzamide,
2-(2-((1-aminoisoquinolin-6-ylamino)(3-ethoxy-5-ethyl-2-fluorophenyl)methyl)-1H-imidazol-4-yl)-5-chlorobenzoic acid,
2-(2-((1-aminoisoquinolin-6-ylamino)(3-ethoxy-5-ethyl-2-fluorophenyl)methyl)-1H-imidazol-4-yl)-6-fluorobenzoic acid,
methyl-2-(2-((1-aminoisoquinolin-6-ylamino)(3-ethoxy-5-ethyl-2-fluorophenyl)methyl)-1H-imidazol-4-yl)-6-fluorobenzoate,
$N^6$-((3-ethoxy-5-ethyl)-2-fluorophenyl)(4-(2-(furan-3-yl)phenyl)-1H-imidazol-2-yl)methyl)isoquinoline-1,6-diamine,
2-{2-[(1-Amino-isoquinolin-6-ylamino)-(5-ethyl-2-fluoro-biphenyl-3-yl)-methyl]-1H-imidazol-4-yl}-benzamide,
2-{2-[(1-Amino-isoquinolin-6-ylamino)-(5-ethyl-2-fluoro-3'-methyl-biphenyl-3-yl)-methyl]-1H-imidazol-4-yl}-benzamide,
2-(2-((1-aminoisoquinolin-6-ylamino)(5-ethyl-2-fluoro-3-morpholinophenyl)methyl)-1H-imidazol-4-yl)benzamide,
2-(2-((1-aminoisoquinolin-6-ylamino)(5-ethyl-2-fluoro-3-(pyrrolidin-1-yl)phenyl)methyl)-1H-imidazol-4-yl)benzamide,
(R)-1$N^6$-((5-ethyl)-2-fluorophenyl)(4-phenyl-1H-imidazol-2-yl)methyl)isoquinoline-1,6-diamine,
(S)-1$N^6$-((5-ethyl)-2-fluorophenyl)(4-phenyl-1H-imidazol-2-yl)methyl)isoquinoline- 1,6-diamine,
4-((5-ethoxy-2-fluoro-3-isopropoxyphenyl)(4-(pyridin-4-yl)-1H-imidazol-2-yl)methylamino)benzamidine,
4-((5-ethoxy-2-fluoro-3-isopropoxyphenyl)(4-(pyridin-3-yl)-1H-imidazol-2-yl)methylamino)benzamidine,
4-((4-(1H-pyrazol-4-yl)-1H-imidazol-2-yl)(5-ethoxy-2-fluoro-3-isopropoxyphenyl)methylamino)benzamidine,
4-((5-ethoxy-2-fluoro-3-isopropoxyphenyl)(4-(1-methyl-1H-pyrazol-4-yl)-1H- imidazol-2-yl)methylamino)benzamidine, 4-((5-ethoxy-2-fluoro-3-isopropoxyphenyl)(4-(1-ethyl-1H-pyrazol-4-yl)-1H-imidazol-2-yl)methylamino)benzamidine, 4-((4-cyclopropyl-1H-imidazol-2-yl)(5-ethoxy-2-fluoro-3-isopropoxyphenyl)methylamino)benzamidine, 4-((4-butyl-1H-imidazol-2-yl)(5-ethoxy-2-fluoro-3-isopropoxyphenyl)methylamino)benzamidine, 2-(2-((1-aminoisoquinolin-6-ylamino)(5-ethoxy-2-fluoro-3-isopropoxyphenyl)methyl)-1H-imidazol-4-yl)benzamide, 2-(2-((1-aminoisoquinolin-6-yloxyamino)(5-ethoxy-2-fluoro-3-((S)-tetrahydrofuran-3-yloxy)phenyl)methyl)-1H-imidazol-4-yl)benzamide, 2-(2-((1-aminoisoquinolin-6-ylamino)(2-fluoro-5-methylphenyl)methyl)-1H-imidazol-4-yl)benzamide, 2-(2-((1-aminoisoquinolin-6-ylamino)(3-vinylphenyl)methyl)-1H-imidazol-4-yl)benzamide, 2-(2-((1-aminoisoquinolin-6-ylamino)(5-ethoxy-2-fluorophenyl)methyl)-1H-imidazol-4-yl)benzamide, 2-(2-((4-carbamimidoylphenylamino)(3-ethylphenyl)methyl)-1H-imidazol-4-yl)benzamide, 2-(2-((4-carbamimidoylphenylamino)(2-fluoro-5-methylphenyl)methyl)-1H-imidazol-4-yl)benzamide, 2-(2-((4-carbamimidoylphenylamino)(5-ethoxy-2-fluorophenyl)methyl)-1H-imidazol-4-yl)benzamide, 2-(2-((4-carbamimidoylphenylamino)(5-fluoro-2-methoxyphenyl)methyl)-1H-imidazol-4-yl)benzamide, 2-(2-((1-aminoisoquinolin-6-ylamino)(2-fluoro-5-methoxyphenyl)methyl)-1H-imidazol-4-yl)benzamide, 2-(2-((1-aminoisoquinolin-6-ylamino)(3-ethylphenyl)methyl)-1H-imidazol-4-yl)benzamide, 2-(2-((1-aminoisoquinolin-6-ylamino)(3-methylphenyl)methyl)-1H-imidazol-4-yl)benzamide, 2-(2-((1-aminoisoquinolin-6-ylamino)(5-ethyl-2-fluorophenyl)methyl)-1H-imidazol-4-yl)benzamide, 2-(2-((1-aminoisoquinolin-6-ylamino)(3-ethoxy-4-fluorophenyl)methyl)-1H-imidazol-4-yl)benzamide, 2-(2-((4-carbamimidoylphenylamino)(3-ethoxy-4-fluorophenyl)methyl)-1H-imidazol-4-yl)benzamide, (R)-2-(2-((4-carbamimidoylphenylamino)(3-ethylphenyl)methyl)-1H-imidazol-4-yl)benzamide, (S)-2-(2-((4-carbamimidoylphenylamino)(3-ethylphenyl)methyl)-1H-imidazol-4-yl)benzamide, 2-(2-((4-carbamimidoylphenylamino)(5-ethoxy-2-fluoro-3-isopropoxyphenyl)methyl)-1-methyl-1H-imidazol-4-yl)benzamide, 2-(2-((1-aminoisoquinolin-6-ylamino)(3-methoxyphenyl)methyl)-1H-imidazol-4-yl)benzamide, 2-(2-((4-carbamimidoylphenylamino)(3-methoxyphenyl)methyl)-1H-imidazol-4-yl)benzamide, 2-(2-((4-carbamimidoylphenylamino)(5-ethyl-2-fluorophenyl)methyl)-1-methyl-1H-imidazol-4-yl)benzamide, 2-(2-((4-carbamimidoylphenylamino)(5-ethyl-2-fluorophenyl)methyl)-1H-imidazol-4-yl)benzamide, 4-((5-ethyl-2-fluorophenyl)(1-phenyl-1H-pyrazol-3-yl)methylamino)benzamidine, 2-(3-((4-carbamimidoylphenylamino)(5-ethyl-2-fluorophenyl)methyl)-1H-pyrazol-1-yl)benzamide, 4-((3-ethyl-4-fluorophenyl)(1-phenyl-1H-pyrazol-3-yl)methylamino)benzamidine, 2-(3-((4-carbamimidoylphenylamino)(3-ethyl-4-fluorophenyl)methyl)-1H-pyrazol-1-yl)benzamide, 2-(2-((4-carbamimidoylphenylamino)(3-ethyl-4-fluorophenyl)methyl)-1H-imidazol-4-yl)benzamide, 2-(2-((1-aminoisoquinolin-6-ylamino)(5-ethyl-2-fluoro-3-isopropoxyphenyl)methyl)-1H-imidazol-4-yl)benzamide, $N^6$-((5-ethoxy-2-fluorophenyl)(4-phenyl-1H-imidazol-2-yl)methyl)isoquinoline-1,6-diamine, 2-(2-((4-carbamimidoylphenylamino)(3-ethyl-5-fluorophenyl)methyl)-1H-imidazol-4-yl)benzamide, (Z)-4-((5-ethoxy-2-fluorophenyl)(4-phenyl-1H-imidazol-2-yl)methylamino)-N'-hydroxybeuzamidine, $N^6$-((5-ethyl)-2-fluorophenyl)(4-phenyl-1H-imidazol-2-yl)methyl)isoquinoline-1,6-diamine, 4-((5-ethyl-2-fluorophenyl)(4-phenyl-1H-imidazol-2-yl)methylamino)-N'-hydroxybeuzamidine, 4-((5-ethyl-2-fluorophenyl)(4-phenyl-1H-imidazol-2-yl)methylamino)benzamidine, 2-(2-((1-aminoisoquinolin-6-ylamino)(3-ethoxy-5-ethyl-2-fluorophenyl)methyl)-1H-imidazol-4-yl)benzamide, 2-(2-((1-aminoisoquinolin-6-ylamino)(5-ethyl-2-fluoro-3-methoxyphenyl)methyl)-1H-imidazol-4-yl)benzamide, $N^6$-((5-ethyl)-2-fluorophenyl)(4-(2-methoxyphenyl)-1H-imidazol-2-yl)methyl)isoquinoline-1,6-diamine, 2-(2-((1-aminoisoquinolin-6-ylamino)(5-ethyl-2-fluoro-3-((R)-tetrahydrofuran-3-yloxy)phenyl)methyl)-1H-imidazol-4-yl)benzamide, $N^6$-((4-bromo-1H-imidazol-2-yl)(5-ethyl-2-fluoro-3-((R)-tetrahydrofuran-3-yloxy)phenyl)methyl)isoquinoline-1,6-diamine, 2-(2-((1-aminoisoquinolin-6-yloxyamino)(5-ethyl)-2-fluoro-3-((S)-tetrahydrofuran-3-yloxy)phenyl)methyl)-1H-imidazol-4-yl)benzamide, 2-(2-((1-aminoisoquinolin-6-ylamino)(5-ethyl-2-fluoro-3-isobutoxyphenyl)methyl)-1H-imidazol-4-yl)benzamide, 2-(2-((1-aminoisoquinolin-6-ylamino)(3-(cyclopropylmethoxy)-5-ethyl-2-fluorophenyl)methyl)-1H-imidazol-4-yl)benzamide, 2-(2-((1-aminoisoquinolin-6-ylamino)(5-ethyl-2-fluoro-3-(1-methylpiperidin-4-yloxy)phenyl)methyl)-1H-imidazol-4-yl)benzamide, 2-(2-((1-aminoisoquinolin-6-ylamino)(3-(3-(dimethylamino)-2,2-dimethylpropoxy)-5-ethyl-2-fluorophenyl)methyl)-1H-imidazol-4-yl)benzamide, $N^6$-((3-ethoxy-5-ethyl)-2-fluorophenyl)(4-(4-methoxypyridin-3-yl)-1H-imidazol-2-yl)methyl)isoquinoline-1,6-diamine, $N^6$-((3-ethoxy-5-ethyl)-2-fluorophenyl)(4-(5-methoxypyridin-3-yl)-1H-imidazol-2-yl)methyl)isoquinoline-1,6-diamine, $N^6$-((3-ethoxy-5-ethyl)-2-fluorophenyl)(4-(4-methylpyridin-3-yl)-1H-imidazol-2-yl)methyl)isoquinoline-1,6-diamine, 2-(2-((1-aminoisoquinolin-6-ylamino)(5-ethyl-2-fluoro-3-propoxyphenyl)methyl)-1H-imidazol-4-yl)benzamide, $N^6$-((3-ethoxy-5-ethyl)-2-fluorophenyl)(4-(3-methoxyphenyl)-1H-imidazol-2-yl)methyl)isoquinoline-1,6-diamine, $N^6$-((3-ethoxy-5-ethyl)-2-fluorophenyl)(4-(2-(methylthio)phenyl)-1H-imidazol-2yl)methyl)isoquinoline-1,6-diamine, 2-(2-((1-aminoisoquinolin-6-ylamino)(3-ethoxy-5-ethyl-2-fluorophenyl)methyl)-1H-imidazol-4-yl)phenol, 2-(2-((1-aminoisoquinolin-6-ylamino)(3-ethoxy-5-ethyl-2-fluorophenyl)methyl)-1H-imidazol-4-yl)benzoic acid, 3-(2-((1-aminoisoquinolin-6-ylamino)(3-ethoxy-5-ethyl-2-fluorophenyl)methyl)-1H-imidazol-4-yl)benzoic acid,
3-(2-((1-aminoisoquinolin-6-ylamino)(3-ethoxy-5-ethyl-2-fluorophenyl)methyl)-1H-imidazol-4-yl)benzonitrile,
methyl 2-(2-((1-aminoisoquinolin-6-ylamino)(3-ethoxy-5-ethyl-2-fluorophenyl)methyl)-1H-imidazol-4-yl)-6-methylbenzoate,
2-(2-((1-aminoisoquinolin-6-ylamino)(3-ethoxy-5-ethyl-2-fluorophenyl)methyl)-1H-imidazol-4-yl)-6-methylbenzamide,
(3-(2-((1-aminoisoquinolin-6-ylamino)(3-ethoxy-5-ethyl-2-fluorophenyl)methyl)-1H-imidazol-4-yl)phenyl)methanol,
methyl 2-(2-((1-aminoisoquinolin-6-ylamino)(3-ethoxy-5-ethyl-2-fluorophenyl)methyl)-1H-imidazol-4-yl)-3-methylbenzoate,
2-(2-((1-aminoisoquinolin-6-ylamino)(3-ethoxy-5-ethyl-2-fluorophenyl)methyl)-1H-imidazol-4-yl)-3-methylbenzamide,
2-(2-((1-aminoisoquinolin-6-ylamino)(3-ethoxy-5-ethyl-2-fluorophenyl)methyl)-1H-imidazol-4-yl)-3-methylbenzoic acid,
methyl 2-(2-((1-aminoisoquinolin-6-ylamino)(3-ethoxy-5-ethyl-2-fluorophenyl)methyl)-1H-imidazol-4-yl)-4-methylbenzoate,
2-(2-((1-aminoisoquinolin-6-ylamino)(3-ethoxy-5-ethyl-2-fluorophenyl)methyl)-1H-imidazol-4-yl)-4-methylbenzoic acid,
2-(2-((1-aminoisoquinolin-6-ylamino)(3-ethoxy-5-ethyl-2-fluorophenyl)methyl)-1H-imidazol-4-yl)-4-methylbenzamide,
2-(2-((1-aminoisoquinolin-6-ylamino)(3-ethoxy-5-ethyl-2-fluorophenyl)methyl)-1H-imidazol-4-yl)-6-fluorobenzamide,
2-(2-((1-aminoisoquinolin-6-ylamino)(3-ethoxy-5-ethyl-2-fluorophenyl)methyl)-1H-imidazol-4-yl)-5-chlorobenzamide,
3-(2-((1-aminoisoquinolin-6-ylamino)(3-ethoxy-5-ethyl-2-fluorophenyl)methyl)-1H-imidazol-4-yl)-N-(2-hydroxyethyl)benzamide,
$N^6$-((3-ethoxy-5-ethyl-2-fluorophenyl)(4-phenyl-1H-imidazol-2-yl)methyl)isoquinoline-1,6-diamine,
(2-(2-((1-aminoisoquinolin-6-ylamino)(3-ethoxy-5-ethyl-2-fluorophenyl)methyl)-1H-imidazol-4-yl)phenyl)methanol,
1-(2-(2-((1-aminoisoquinolin-6-ylamino)(3-ethoxy-5-ethyl-2-fluorophenyl)methyl)-1H-imidazol-4-yl)phenyl)ethanone,
4-(2-((1-aminoisoquinolin-6-ylamino)(3-ethoxy-5-ethyl-2-fluorophenyl)methyl)-1H-imidazol-4-yl)phenol,
$N^6$-((3-ethoxy-5-ethyl)-2-fluorophenyl)(4-(furan-3-yl)-1H-imidazol-2-yl)methyl)isoquinoline-1,6-diamine,
$N^6$-((3-ethoxy-5-ethyl)-2-fluorophenyl)(4-m-tolyl-1H-imidazol-2-yl)methyl)isoquinoline-1,6-diamine,
$N^6$-((3-ethoxy-5-ethyl)-2-fluorophenyl)(4-o-tolyl-1H-imidazol-2-yl)methyl)isoquinoline-1,6-diamine,
$N^6$-((3-ethoxy-5-ethyl)-2-fluorophenyl)(4-(2-methoxyphenyl)-1H-imidazol-2-yl)methyl)isoquinoline-1,6-diamine,
$N^6$-((3-ethoxy-5-ethyl)-2-fluorophenyl)(4-(5-methylfuran-2-yl)-1H-imidazol-2-yl)methyl)isoquinoline-1,6-diamine,
$N^6$-((3-ethoxy-5-ethyl)-2-fluorophenyl)(4-(pyridin-3-yl)-1H-imidazol-2-yl)methyl)isoquinoline-1,6-diamine,
$N^6$-((5-(4-chlorophenyl)-2-methyl-2H-1,2,4-triazol-3-yl)(5-ethyl-2-fluorophenyl)methyl)isoquinoline-1,6-diamine,
$N^6$-((5-ethyl)-2-fluorophenyl)(2-methyl)-5-p-tolyl-2H-1,2,4-triazol-3-yl)methyl)isoquinoline-1,6-diamine,
$N^6$-((5-ethyl)-2-fluorophenyl)(5-(4-methoxyphenyl)-2-methyl)-2H-1,2,4-triazol-3-yl)methyl)isoquinoline-1,6-diamine,
$N^6$-((5-ethyl)-2-fluorophenyl)(2-methyl)-5-m-tolyl-2H-1,2,4-triazol-3-yl)methyl)isoquinoline-1,6-diamine,
$N^6$-((5-ethyl)-2-fluorophenyl)(2-methyl)-5-o-tolyl-2H-1,2,4-triazol-3-yl)methyl)isoquinoline-1,6-diamine,
$N^6$-((5-ethyl)-2-fluorophenyl)(2-methyl)-5-o-biphenyl-2H-1,2,4-triazol-3-yl)methyl)isoquinoline-1,6-diamine,
$N^6$-((5-ethyl)-2-fluorophenyl)(2-methyl)-5-(3-(trifluoromethyl)phenyl)-2H-1,2,4-triazol-3-yl)methyl)isoquinoline-1,6-diamine,
$N^6$-((5-ethyl)-2-fluorophenyl)(5-(3-methoxyphenyl)-2-methyl)-2H-1,2,4-triazol-3-yl)methyl)isoquinoline-1,6-diamine,
N-(3-(5-((1-aminoisoquinolin-6-ylamino)(5-ethyl-2-fluorophenyl)methyl)-1-methyl-1H-1,2,4-triazol-3-yl)phenyl)acetamide,
$N^6$-((5-ethyl)-2-fluorophenyl)(5-(2-methoxyphenyl)-2-methyl)-2H-1,2,4-triazol-3-yl)methyl)isoquinoline-1,6-diamine,
$N^6$-((5-ethyl)-2-fluorophenyl)(2-methyl)-5-(2-(trifluoromethyl)phenyl)-2H-1,2,4-triazol-3-yl)methyl)isoquinoline-1,6-diamine,
$N^6$-((5-ethyl)-2-fluorophenyl)(2-methyl)-5-(pyridin-3-yl)-2H-1,2,4-triazol-3-yl)methyl)isoquinoline-1,6-diamine,
3-(5-((1-aminoisoquinolin-6-ylamino)(5-ethyl-2-fluorophenyl)methyl)-1-methyl-1H-1,2,4-triazol-3-yl)phenol,
$N^6$-((5-(4-(dimethylamino)phenyl)-2-methyl-2H-1,2,4-triazol-3-yl)(5-ethyl-2-fluorophenyl)methyl)isoquinoline-1,6-diamine,
1-(3-(5-((1-aminoisoquinolin-6-ylamino)(5-ethyl-2-fluorophenyl)methyl)-1-methyl-1H-1,2,4-triazol-3-yl)phenyl)ethanone,
1-(2-(5-((1-aminoisoquinolin-6-ylamino)(5-ethyl-2-fluorophenyl)methyl)-1-methyl-1H-1,2,4-triazol-3-yl)phenyl)ethanone,
$N^6$-((5-ethyl-2-fluorophenyl)(2-methyl-5-phenyl-2H-1,2,4-triazol-3-yl)methyl)isoquinoline-1,6-diamine,
$N^6$-((5-ethyl-2-fluorophenyl)(2-methyl-5-(thiophen-3-yl)-2H-1,2,4-triazol-3-yl)methyl)isoquinoline-1,6-diamine,
$N^6$-((5-(3-chlorophenyl)-2-methyl-2H-1,2,4-triazol-3-yl)(5-ethyl-2-fluorophenyl)methyl)isoquinoline-1,6-diamine,
$N^6$-((5-(2-chlorophenyl)-2-methyl-2H-1,2,4-triazol-3-yl)(5-ethyl-2-fluorophenyl)methyl)isoquinoline-1,6-diamine,
$N^6$-((5-(2,4-dichlorophenyl)-2-methyl-2H-1,2,4-triazol-3-yl)(5-ethyl-2-fluorophenyl)methyl)isoquinoline-1,6-diamine,
$N^6$-((5-(2,4-dichlorophenyl)-2-methyl-2H-1,2,4-triazol-3-yl)(5-ethyl-2-fluorophenyl)methyl)isoquinoline-1,6-diamine,
$N^6$-((5-ethyl)-2-fluorophenyl)(5-(4-fluorophenyl)-2-methyl)-2H-1,2,4-triazol-3-yl)methyl)isoquinoline-1,6-diamine, N⁶-((5-ethyl)-2-fluorophenyl)(5-(3-fluorophenyl)-2-methyl)-2H-1,2,4-triazol-3-yl)methyl)isoquinoline-1,6-diamine,
N⁶-((5-(2-chlorophenyl)-2-methyl)-2H-1,2,4-triazol-3-yl)(5-ethyl-2-fluorophenyl)methyl)isoquinoline-1,6-diamine,
N⁶-((5-ethyl)-2-fluorophenyl)(5-(2-fluorophenyl)-2-methyl)-2H-1,2,4-triazol-3-yl)methyl)isoquinoline-1,6-diamine,
N⁶-((5-(benzo[d][1,3]dioxol-5-yl)-2-methyl-2H-1,2,4-triazol-3-yl)(5-ethyl-2-fluorophenyl)methyl)isoquinoline-1,6-diamine,
N⁶-((5-ethyl)-2-fluorophenyl)(2-methyl)-5-(pyridin-4-yl)-2H-1,2,4-triazol-3-yl)methyl)isoquinoline-1,6-diamine,
2-(5-((1-aminoisoquinolin-6-ylamino)(5-ethyl-2-fluorophenyl)methyl)-1-methyl-1H-1,2,4-triazol-3-yl)phenol,
N⁶-((5-(2,3-dichlorophenyl)-2-methyl-2H-1,2,4-triazol-3-yl)(5-ethyl-2-fluorophenyl)methyl)isoquinoline-1,6-diamine,
N⁶-((5-ethyl)-2-fluorophenyl)(2-methyl)-5-(2-(methylthio)phenyl)-2H-1,2,4-triazol-3-yl)methyl)isoquinoline-1,6-diamine,
3-(5-((1-aminoisoquinolin-6-ylamino)(5-ethyl-2-fluorophenyl)methyl)-1-methyl-1H-1,2,4-triazol-3-yl)benzonitrile,
N⁶-((5-ethyl)-2-fluorophenyl)(5-(furan-3-yl)-2-methyl)-2H-1,2,4-triazol-3-yl)methyl)isoquinoline-1,6-diamine,
N-(2-(5-((1-aminoisoquinolin-6-ylamino)(5-ethyl-2-fluorophenyl)methyl)-1-methyl-1H-1,2,4-triazol-3-yl)phenyl)methanesulfonamide,
N-(2-(5-((1-aminoisoquinolin-6-ylamino)(5-ethyl-2-fluorophenyl)methyl)-1-methyl-1H-1,2,4-triazol-3-yl)phenyl)acetamide,
N⁶-((5-ethyl)-2-fluorophenyl)(2-methyl)-5-(pyrimidin-5-yl)-2H-1,2,4-triazol-3-yl)methyl)isoquinoline-1,6-diamine,
N⁶((5-(3-((dimethylamino)phenyl)-2-methyl-2H-1,2,4-triazol-3-yl)(5-ethyl-2-fluorophenyl)methyl)isoquinoline-1,6-diamine,
N⁶-((5-(5-chloro-2-methoxyphenyl)-2-methyl)-2H-1,2,4-triazol-3-yl)(5-ethyl-2-fluorophenyl)methyl)isoquinoline-1,6-diamine,
4-((5-ethoxy-2-fluoro-3-isopropoxyphenyl)(2-methyl-2H-1,2,4-triazol-3-yl)methylamino)benzamidine,
2-(5-((4-carbamimidoylphenylamino)(5-ethoxy-2-fluoro-3-isopropoxyphenyl)methyl)-1H-1,2,4-triazol-3-yl)benzamide,
4-((5-ethoxy-2-fluoro-3-isopropoxyphenyl)(5-(2-(methylthio)phenyl)-2H-1,2,4-triazol-3-yl)methylamino)benzamidine,
4-((5-ethoxy-2-fluoro-3-isopropoxyphenyl)(5-(2-methoxyphenyl)-2H-1,2,4-triazol-3-yl)methylamino)benzamidine,
4-((5-ethoxy-2-fluoro-3-isopropoxyphenyl)(5-(2-fluorophenyl)-2H-1,2,4-triazol-3-yl)methylamino)benzamidine,
4-((5-ethoxy-2-fluoro-3-isopropoxyphenyl)(5-(2-fluorophenyl)-2-methyl-2H-1,2,4-triazol-3-yl)methylamino)benzamidine,
4-((5-ethoxy-2-fluoro-3-isopropoxyphenyl)(5-(2-methoxyphenyl)-2-methyl-2H-1,2,4-triazol-3-yl)methylamino)benzamidine,
4-((5-ethoxy-2-fluoro-3-isopropoxyphenyl)(2-methyl-5-(2-(methylthio)phenyl)-2H-1,2,4-triazol-3-yl)methylamino)benzamidine,
2-(5-((4-carbamimidoylphenylamino)(5-ethoxy-2-fluoro-3-isopropoxyphenyl)methyl)-1-methyl-1H-1,2,4-triazol-3-yl)benzamide,
N⁶-((5-ethyl)-2-fluorophenyl)(2-methyl)-5-phenyl-2H-1,2,4-triazol-3-yl)methyl)isoquinoline-1,6-diamine,
N⁶-((3-ethoxy-5-ethyl)-2-fluorophenyl)(2-methyl)-5-phenyl-2H-1,2,4-triazol-3-yl)methyl)isoquinoline-1,6-diamine,
N⁶-((5-ethyl)-2-fluoro-3-isopropoxyphenyl)(2-methyl)-5-phenyl-2H-1,2,4-triazol-3-yl)methyl)isoquinoline-1,6-diamine,
4-((3-ethylphenyl)(2-methyl-5-phenyl-2H-1,2,4-triazol-3-yl)methylamino)-N'-hydroxybeuzamidine,
4-((3-ethylphenyl)(2-methyl-5-phenyl-2H-1,2,4-triazol-3-yl)methylamino)benzamidine,
4-(aminomethyl)-N-((3-ethylphenyl)(2-methyl-5-phenyl-2H-1,2,4-triazol-3-yl)methyl)benzenamine,
4-((3-ethylphenyl)(2-methyl-5-phenyl-2H-1,2,4-triazol-3-yl)methylamino)-2-fluoro-N'-hydroxybenzamidine,
4-((3-ethylphenyl)(2-methyl-5-phenyl-2H-1,2,4-triazol-3-yl)methylamino)-2-fluorobeuzamidine,
N⁶-((3-ethylphenyl)(2-methyl)-5-phenyl-2H-1,2,4-triazol-3-yl)methyl)isoquinoline 1,6-diamine,
(Z)-4-((3-ethylphenyl)(2-methyl-5-phenyl-2H-1,2,4-triazol-3-yl)methylamino)-2,5-difluoro-N'-hydroxybenzamidine,
4-((3-ethylphenyl)(2-methyl-5-phenyl-2H-1,2,4-triazol-3-yl)methylamino)-2,5-difluorobeuzamidine,
4-((3-ethylphenyl)(5-phenyl-2H-1,2,4-triazol-3-yl)methylamino)-N'-hydroxybeuzamidine,
4-((3-ethylphenyl)(5-phenyl-2H-1,2,4-triazol-3-yl)methylamino)benzamidine,
4-((3-ethylphenyl)(2-methyl-5-phenyl-2H-1,2,4-triazol-3-yl)methylamino)-3-fluorobeuzamidine,
4-((3-ethylphenyl)(2-methyl-5-phenyl-2H-1,2,4-triazol-3-yl)methylamino)-3,5-difluorobeuzamidine,
4-((5-ethyl-2-fluorophenyl)(5-phenyl-2H-1,2,4-triazol-3-yl)methylamino)benzamidine,
4-((5-ethyl-2-fluorophenyl)(2-methyl-5-phenyl-2H-1,2,4-triazol-3-yl)methylamino)benzamidine,
N⁶-((4-ethoxy-5-ethyl)-2-fluorophenyl)(2-methyl)-5-phenyl-2H-1,2,4-triazol-3-yl)methyl)isoquinoline-1,6-diamine,
N⁶-((5-ethyl)-2-fluoro-4-methoxyphenyl)(2-methyl)-5-phenyl-2H-1,2,4-triazol-3-yl)methyl)isoquinoline-1,6-diamine,
N⁶-((3,3-dimethyl)-1,3-dihydroisobenzofuran-5-yl)(2-methyl-5-phenyl-2H-1,2,4-triazol-3-yl)methyl)isoquinoline-1,6-diamine,
N⁶-((2,3-dihydrobenzofuran-5-yl)2-methyl-5-phenyl-2H-1,2,4-triazol-3-yl)methyl)isoquinoline-1,6-diamine,
N⁶-((4-chloro-5-ethyl)-2-fluorophenyl)(2-methyl-5-phenyl-2H-1,2,4-triazol-3-yl)methyl)isoquinoline-1,6-diamine,
N⁶-((2,4-difluoro-5-methoxyphenyl)(2-methyl-5-phenyl-2H-1,2,4-triazol-3-yl)methyl)isoquinoline-1,6-diamine,
N⁶-((4-chloro-2-fluoro-5-methoxyphenyl)(2-methyl-5-phenyl-2H-1,2,4-triazol-3-yl)methyl)isoquinoline-1,6-diamine,
N⁶-((7-ethyl)-3-methylbenzofuran-5-yl)(2-methyl-5-phenyl-2H-1,2,4-triazol-3-yl)methyl)isoquinoline-1,6-diamine, N⁶-((2-methyl-5-phenyl-2H-1,2,4-triazol-3-yl)(3-methylbenzofuran-5-yl)methyl)isoquinoline-1,6-diamine,
N⁶-((5-ethyl)-2-fluoro-4-isopropoxyphenyl)(2-methyl-5-phenyl-2H-1,2,4-triazol-3-yl)methyl)isoquinoline-1,6-diamine,
N⁶-((4-(benzyloxy)-5-ethyl)-2-fluorophenyl)(2-methyl-5-phenyl-2H-1,2,4-triazol-3-yl)methyl)isoquinoline-1,6-diamine,
N⁶-((5-ethyl)-2-fluoro-3-morpholinophenyl)(4-(pyridin-3-yl)-1H-imidazol-2-yl)methyl)isoquinoline-1,6-diamine,
2-(2-((1-aminoisoquinolin-6-ylamino)(5-ethyl-2-fluoro-3-(2-oxopyrrolidin-1-yl)phenyl)methyl)-1H-imidazol-4-yl)benzamide,
2-(2-((1-aminoisoquinolin-6-ylamino)(5-ethyl-2-fluoro-3-(3-methyl-2-oxoimidazolidin-1-yl)phenyl)methyl)-1H-imidazol-4-yl)benzamide,
2-(2-((1-aminoisoquinolin-6-ylamino)(3-ethoxy-5-ethyl-2-fluorophenyl)methyl)-4-phenyl-1H-imidazol-1-yl)acetic acid,
2-(2-((1-aminoisoquinolin-6-ylamino)(3-ethoxy-5-ethyl-2-fluorophenyl)methyl)-4-(2-carbamoylphenyl)-1H-imidazol-1-yl)acetic acid,
2-(2-((1-aminoisoquinolin-6-ylamino)(3-ethoxy-5-ethyl-2-fluorophenyl)methyl)-4-phenyl-1H-imidazol-1-yl)acetamide,
2-(2-((1-aminoisoquinolin-6-ylamino)(3-ethoxy-5-ethyl-2-fluorophenyl)methyl)-4-phenyl-1H-imidazol-1-yl)-N-methylacetamide,
2-(2-((1-aminoisoquinolin-6-ylamino)(3-ethoxy-5-ethyl-2-fluorophenyl)methyl)-4-phenyl-1H-imidazol-1-yl)-N,N-dimethylacetamide,
2-(2-((1-aminoisoquinolin-6-ylamino)(3-ethoxy-5-ethyl-2-fluorophenyl)methyl)-4-phenyl-1H-imidazol-1-yl)-1-(pyrrolidin-1-yl)ethanone,
N⁶-((5-ethyl)-2-fluoro-3-morpholinophenyl)(4-phenyl-1H-imidazol-2-yl)methyl)isoquinoline-1,6-diamine,
2-(2-((1-aminoisoquinolin-6-ylamino)(5-ethyl-2-fluoro-3-morpholinophenyl)methyl)-4-phenyl-1H-imidazol-1-yl)acetic acid,
2-(2-((1-aminoisoquinolin-6-ylamino)(3-ethoxy-5-ethyl-2-fluorophenyl)methyl)-1H-imidazol-4-yl)-N-methylbenzamide,
(2-(2-((1-aminoisoquinolin-6-ylamino)(3-ethoxy-5-ethyl-2-fluorophenyl)methyl)-1H-imidazol-4-yl)phenyl)(pyrrolidin-1-yl)methanone,
(2-(2-((1-aminoisoquinolin-6-ylamino)(3-ethoxy-5-ethyl-2-fluorophenyl)methyl)-1H-imidazol-4-yl)phenyl)((S)-3-hydroxypyrrolidin-1-yl)methanone,
2-(2-((1-aminoisoquinolin-6-ylamino)(3-ethoxy-5-ethyl-2-fluorophenyl)methyl)-1H-imidazol-4-yl)-N-ethylbenzamide,
2-(2-((1-aminoisoquinolin-6-ylamino)(3-ethoxy-5-ethyl-2-fluorophenyl)methyl)-1H-imidazol-4-yl)-N-(3-hydroxypropyl)benzamide,
tert-butyl 2-(2-(2-((1-aminoisoquinolin-6-ylamino)(3-ethoxy-5-ethyl-2-fluorophenyl)methyl)-1H-imidazol-4-yl)benzamido)acetate,
2-(2-(2-((1-aminoisoquinolin-6-ylamino)(3-ethoxy-5-ethyl-2-fluorophenyl)methyl)-1H-imidazol-4-yl)benzamido)acetic acid,
2-(2-((1-aminoisoquinolin-6-ylamino)(3-ethoxy-5-ethyl-2-fluorophenyl)methyl)-5,6-dimethyl-1H-benzo[d]imidazol-1-yl)acetic acid,
N⁶-((2-fluoro-5-(prop-1-en-2-yl)phenyl)(2-methyl-5-phenyl-2H-1,2,4-triazol-3-yl)methyl)isoquinoline-1,6-diamine,
N⁶-((2-fluoro-5-isopropylphenyl)(2-methyl-5-phenyl-2H-1,2,4-triazol-3-yl)methyl)isoquinoline-1,6-diamine,
1-(3-((1-aminoisoquinolin-6-ylamino)(2-methyl-5-phenyl-2H-1,2,4-triazol-3-yl)methyl)-4-fluorophenyl)ethanol,
2-(2-((1-aminoisoquinolin-6-ylamino)(5-ethyl-2-fluoro-3-((S)-tetrahydrofuran-3-yloxy)phenyl)methyl)-4-phenyl-1H-imidazol-1-yl)acetic acid,
2-(2-((1-aminoisoquinolin-6-ylamino)(5-ethyl-2-fluoro-3-((R)-tetrahydrofuran-3-yloxy)phenyl)methyl)-4-phenyl-1H-imidazol-1-yl)acetic acid,
2-(2-((1-aminoisoquinolin-6-ylamino)(5-ethyl-2-fluoro-3-(tetrahydro-2H-pyran-4-yloxy)phenyl)methyl)-4-phenyl-1H-imidazol-1-yl)acetic acid,
2-(2-((1-aminoisoquinolin-6-ylamino)(3-ethoxy-5-ethyl-2-fluorophenyl)methyl)-4-phenyl-1H-imidazol-1-yl)-N-cyclobutylacetamide,
2-(2-((1-aminoisoquinolin-6-ylamino)(3-ethoxy-5-ethyl-2-fluorophenyl)methyl)-4-phenyl-1H-imidazol-1-yl)-N-cyclopropylacetamide,
2-(2-((1-aminoisoquinolin-6-ylamino)(3-ethoxy-5-ethyl-2-fluorophenyl)methyl)-4-phenyl-1H-imidazol-1-yl)-N-(2-hydroxyethyl)acetamide,
2-(2-((1-aminoisoquinolin-6-ylamino)(3-ethoxy-5-ethyl-2-fluorophenyl)methyl)-4-phenyl-1H-imidazol-1-yl)-N-phenylacetamide,
2-(2-((1-aminoisoquinolin-6-ylamino)(3-ethoxy-5-ethyl-2-fluorophenyl)methyl)-4-phenyl-1H-imidazol-1-yl)-N-(2-aminoacetamide)acetamide,
2-(2-((1-aminoisoquinolin-6-ylamino)(3-ethoxy-5-ethyl-2-fluorophenyl)methyl)-4-phenyl-1H-imidazol-1-yl)-N-(2,2,2-trifluoroethyl)acetamide,
4-(2-(2-((1-aminoisoquinolin-6-ylamino)(3-ethoxy-5-ethyl-2-fluorophenyl)methyl)-4-phenyl-1H-imidazol-1-yl)acetyl)piperazin-2-one,
N-((1H-imidazol-5-yl)methyl)-2-(2-((1-aminoisoquinolin-6-ylamino)(3-ethoxy-5-ethyl-2-fluorophenyl)methyl)-4-phenyl-1H-imidazol-1-yl)acetamide,
2-(2-((1-aminoisoquinolin-6-ylamino)(3-(3-(dimethylamino)-2,2-dimethylpropoxy)-5-ethyl-2-fluorophenyl)methyl)-4-phenyl-1H-imidazol-1-yl)acetic acid,
2-(2-((1-aminoisoquinolin-6-ylamino)(5-ethyl-2-fluoro-3-(1-methylpiperidin-4-yloxy)phenyl)methyl)-4-phenyl-1H-imidazol-1-yl)acetic acid,
2-(2-((1-aminoisoquinolin-6-ylamino)(3-(3-(dimethylamino)-2,2-dimethylpropoxy)-5-ethyl-2-fluorophenyl)methyl)-4-phenyl-1H-imidazol-1-yl)-N,N-dimethylacetamide,
2-(2-((1-aminoisoquinolin-6-ylamino)(3-ethoxy-5-ethyl-2-fluorophenyl)methyl)-1H-imidazol-4-yl)-6-fluoro-N-methylbenzamide,
2-(2-((1-aminoisoquinolin-6-ylamino)(3-ethoxy-5-ethyl-2-fluorophenyl)methyl)-1-(2-(methylamino)-2-oxoethyl)-1H-imidazol-4-yl)-6-fluoro-N-methylbenzamide,
2-(2-((1-aminoisoquinolin-6-ylamino)(3-ethoxy-5-ethyl-2-fluorophenyl)methyl)-4-phenyl-1H-imidazol-1-yl)propanoic acid,
2-(2-((1-aminoisoquinolin-6-ylamino)(5-ethyl-2-fluoro-3-morpholinophenyl)methyl)-4-phenyl-1H-imidazol-1-yl)-N,N-dimethylacetamide,
2-(2-((1-aminoisoquinolin-6-ylamino)(3-ethoxy-5-ethyl-2-fluorophenyl)methyl)-4-(pyridin-3-yl)-1H-imidazol-1-yl)acetic acid,
2-(2-((1-aminoisoquinolin-6-ylamino)(3-ethoxy-5-ethyl-2-fluorophenyl)methyl)-4-(furan-3-yl)-1H-imidazol-1-yl)acetic acid, 2-(2-((1-aminoisoquinolin-6-ylamino)(3-ethoxy-5-ethyl-
2-fluorophenyl)methyl)-4-phenyl-1H-imidazol-1-yl)-
N-ethylacetamide,
2-(2-((1-aminoisoquinolin-6-ylamino)(3-ethoxy-5-ethyl-
2-fluorophenyl)methyl)-4-phenyl-1H-imidazol-1-yl)-
N-ethyl-N-methylacetamide,
2-(2-((1-aminoisoquinolin-6-ylamino)(3-ethoxy-5-ethyl-
2-fluorophenyl)methyl)-4-phenyl-1H-imidazol-1-yl)-
N-isopropylacetamide,
2-(2-((1-aminoisoquinolin-6-ylamino)(3-ethoxy-5-ethyl-
2-fluorophenyl)methyl)-4-phenyl-1H-imidazol-1-yl)-
1-morpholinoethanone,
2-(2-((1-aminoisoquinolin-6-ylamino)(3-ethoxy-5-ethyl-
2-fluorophenyl)methyl)-4-(pyridin-3-yl)-1H-imidazol-
1-yl)-N,N-dimethylacetamide,
2-(2-((1-aminoisoquinolin-6-ylamino)(3-ethoxy-5-ethyl-
2-fluorophenyl)methyl)-4-(furan-3-yl)-1H-imidazol-1-
yl)-N,N-dimethylacetamide,
2-(2-((1-aminoisoquinolin-6-ylamino)(3-ethoxy-5-ethyl-
2-fluorophenyl)methyl)-4-phenyl-1H-imidazol-1-yl)
ethanol,
$N^6$-((1-ally-4-phenyl-1H-imidazol-2-yl)(3-ethoxy-5-
ethyl-2-fluorophenyl)methyl)isoquinoline-1,6-di-
amine,
$N^6$-((3-ethoxy-5-ethyl)-2-fluorophenyl)(1-(2-methylal-
lyl)4-phenyl-1H-imidazol-2-yl)methyl)isoquinoline-1,
6-diamine,
3-(2-((1-aminoisoquinolin-6-ylamino)(3-ethoxy-5-ethyl-
2-fluorophenyl)methyl)-4-phenyl-1H-imidazol-1-yl)
propanoic acid,
3-(2-((1-aminoisoquinolin-6-ylamino)(3-ethoxy-5-ethyl-
2-fluorophenyl)methyl)-4-phenyl-1H-imidazol-1-yl)-
N,N-dimethylpropanamide, and
2-(2-((1-aminoisoquinolin-6-ylamino)(5-ethyl-2-fluoro-
3-(1-methylpiperidin-4-yloxy)phenyl)methyl)-4-phe-
nyl-1H-imidazol-1-yl)-N,N-dimethylacetamide,
or a stereoisomer, a tautomer, or a pharmaceutically
acceptable salt thereof.

12. A pharmaceutical composition, comprising: a pharmaceutically acceptable carrier and a therapeutically effective amount of a compound of claim 1.

13. A compound according to claim 1, wherein the compound is selected from the group consisting of:
4-((5-ethoxy-2-fluoro-3-isopropoxyphenyl)(4-phenyl-
1H-imidazol-2-yl)methylamino)benzamidine,
4-((5-ethoxy-2-fluoro-3-isopropoxyphenyl)(1H-tetrazol-
5-yl)methylamino)benzamidine,
4-((5-ethoxy-2-fluoro-3-isopropoxyphenyl)(5-phenyl-
2H-1,2,4-triazol-3-yl)methylamino)benzamidine,
4-((5-ethoxy-2-fluoro-3-isopropoxyphenyl)(quinolin-2-
yl)methylamino)benzamidine,
$N^6$-((5-ethoxy-2-fluoro-3-isopropoxyphenyl)(4-phenyl-
1H-imidazol-2-yl)methyl)isoquinoline-1,6-diamine,
4-((5-ethoxy-2-fluoro-3-isopropoxyphenyl)(4-(2-(methylsulfonyl)phenyl)-1H-imidazol-2-yl)methylamino)
benzamidine,
2-(2-((4-carbamimidoylphenylamino)(5-ethoxy-2-fluoro-
3-isopropoxyphenyl)methyl)-1H-imidazol-4-yl)benzoic acid,
4-((5-ethoxy-2-fluoro-3-isopropoxyphenyl)(4-(2-(ethylsulfonyl)phenyl)-1H-imidazol-2-yl)methylamino)benzamidine,
4-((5-ethoxy-2-fluoro-3-((S)-tetrahydrofuran-3-yloxy)
phenyl)(4-phenyl-1H-imidazol-2-yl)methylamino)benzamidine,
4-({(5-Ethoxy-2-fluoro-3-isopropoxy-phenyl)-[4-(2-sulfamoyl-phenyl)-1H-imidazol-2-yl]-methyl}-amino)-
benzamidine,
$N^6$-((5-ethoxy-2-fluoro-3-((S)-tetrahydrofuran-3-yloxy)
phenyl)(4-phenyl-1H-imidazol-2-yl)methyl)isoquinoline-1,6-diamine,
2-(2-((4-carbamimidoylphenylamino)(5-ethoxy-2-fluoro-
3-((S)-tetrahydrofuran-3-yloxy)phenyl)methyl)-1H-
imidazol-4-yl)benzamide,
4-((5-ethoxy-2-fluoro-3-isopropoxyphenyl)(6-methoxy-
pyridin-2-yl)methylamino)benzamidine,
4-((5-ethoxy-2-fluoro-3-isopropoxyphenyl)(6-(methylthio)pyridin-2-yl)methylamino)benzamidine,
4-((5,6-dimethyl-1H-benzo[d]imidazol-2-yl)(5-ethoxy-2-
fluoro-3-isopropoxyphenyl)methylamino)benzamidine,
(Z)-2-(2-((4-(N'-hydroxycarbamimidoyl)phenylamino)
(3-ethylphenyl)methyl)-1H-imidazol-4-yl)benzamide,
4-((5-ethoxy-2-fluoro-3-isopropoxyphenyl)(1-phenyl-
1H-pyrazol-3-yl)methylamino)benzamidine,
2-(2-((4-carbamimidoylphenylamino)(3-ethoxy-5-ethyl-
2-fluorophenyl)methyl)-1H-imidazol- 4-yl)benzamide,
2-(2-((4-carbamimidoylphenylamino)(5-ethyl-2-fluoro-
3-((S)-tetrahydrofuran-3-yloxy)phenyl)methyl)-1H-
imidazol-4-yl)benzamide,
2-(2-((1-aminoisoquinolin-6-ylamino)(3-ethoxy-5-ethyl-
2-fluorophenyl)methyl)-1H-imidazol-4-yl)benzenesulfonamide,
2-(2-((R)-(1-aminoisoquinolin-6-ylamino)(3-ethoxy-5-
ethyl-2-fluorophenyl)methyl)-1H-imidazol-4-yl)benzamide,
2-(2-((1-aminoisoquinolin-6-ylamino)(3-ethoxy-5-ethyl-
2-fluorophenyl)methyl)-1H-imidazol-4-yl)benzamide,
2-(2-((1-aminoisoquinolin-6-ylamino)(5-ethyl-2-fluoro-
3-((S)-tetrahydrofuran-3-yloxy)phenyl)methyl)-1H-
imidazol-4-yl)benzamide,
$N^6$-((5-ethyl-2-fluorophenyl)(5-(2-methoxyphenyl)-2-
methyl-2H-1,2,4-triazol-3-yl)methyl)isoquinoline-1,6-
diamine,
4-((5-ethoxy-2-fluoro-3-isopropoxyphenyl)(5-(2-methoxyphenyl)-2-methyl-2H-1,2,4-triazol-3-yl)methylamino)benzamidine,
2-(2-((1-aminoisoquinolin-6-ylamino)(3-ethoxy-5-ethyl-
2-fluorophenyl)methyl)-4-phenyl-1H-imidazol-1-yl)
acetic acid,
2-(2-((1-aminoisoquinolin-6-ylamino)(3-ethoxy-5-ethyl-
2-fluorophenyl)methyl)-4-phenyl-1H-imidazol-1-yl)-
N,N-dimethylacetamide,
2-(2-((1-aminoisoquinolin-6-ylamino)(3-ethoxy-5-ethyl-
2-fluorophenyl)methyl)-5,6-dimethyl-1H-benzo[d]imidazol-1-yl)acetic acid, and
2-(2-((1-aminoisoquinolin-6-ylamino)(5-ethyl-2-fluoro-
3-((S)-tetrahydrofuran-3-yloxy)phenyl)methyl)-4-phenyl-1H-imidazol-1-yl)acetic acid,
or a stereoisomer, a tautomer, or a pharmaceutically acceptable salt thereof.

14. A pharmaceutical composition, comprising: a pharmaceutically acceptable carrier and a therapeutically effective amount of a compound of claim 2.

15. A pharmaceutical composition, comprising: a pharmaceutically acceptable carrier and a therapeutically effective amount of a compound of claim 3.

16. A pharmaceutical composition, comprising: a pharmaceutically acceptable carrier and a therapeutically effective amount of a compound of claim 4.

17. A pharmaceutical composition, comprising: a pharmaceutically acceptable carrier and a therapeutically effective amount of a compound of claim 5.

18. A pharmaceutical composition, comprising: a pharmaceutically acceptable carrier and a therapeutically effective amount of a compound of claim 6.

19. A pharmaceutical composition, comprising: a pharmaceutically acceptable carrier and a therapeutically effective amount of a compound of claim 7.

20. A pharmaceutical composition, comprising: a pharmaceutically acceptable carrier and a therapeutically effective amount of a compound of claim 8.

21. A pharmaceutical composition, comprising: a pharmaceutically acceptable carrier and a therapeutically effective amount of a compound of claim 9.

22. A pharmaceutical composition, comprising: a pharmaceutically acceptable carrier and a therapeutically effective amount of a compound of claim 10.

23. A pharmaceutical composition, comprising: a pharmaceutically acceptable carrier and a therapeutically effective amount of a compound of claim 11.

24. A pharmaceutical composition, comprising: a pharmaceutically acceptable carrier and a therapeutically effective amount of a compound of claim 13.

* * * * *

UNITED STATES PATENT AND TRADEMARK OFFICE
CERTIFICATE OF CORRECTION

PATENT NO. : 7,576,098 B2
APPLICATION NO. : 11/295961
DATED : August 18, 2009
INVENTOR(S) : Peter W. Glunz, Nicolas Wurtz and Xuhong Cheng It is certified that error appears in the above-identified patent and that said Letters Patent is hereby corrected as shown below:

Column 360
Line 2, "alkyl)" should read -- alkyl --; and
Line 43, "—$SO_2NR^cR_c$," should read -- —$SO_2NR^cR^c$, --.

Column 364
Line 48, "—$(CF_2)_rCF_3$;" should read -- —$(CF_2)_rCF_3$, --.

Column 368

Line 4-12 (Approx.), " 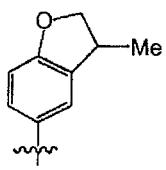 " should read -- 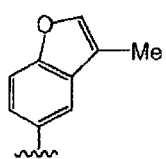 --; and

Line 47-53 (Approx.), " 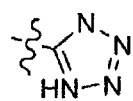 " should read -- 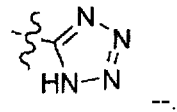 --.

Column 371

Line 4-7 (Approx.), " 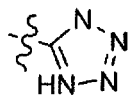 " should read -- 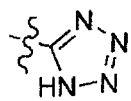 --;

Line 8-12 (Approx.), " 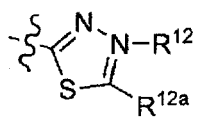 " should read -- 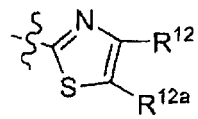 --; and

Signed and Sealed this

Tenth Day of August, 2010

David J. Kappos
*Director of the United States Patent and Trademark Office*

Line 33-36 (Approx.), "  " should read -- --.

Column 373

Line 4-8 (Approx.), " 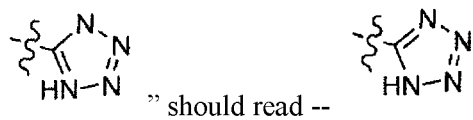 " should read -- --;

Line 18-22 (Approx.), "  " should read -- --; and

Line 33-40 (Approx.), " 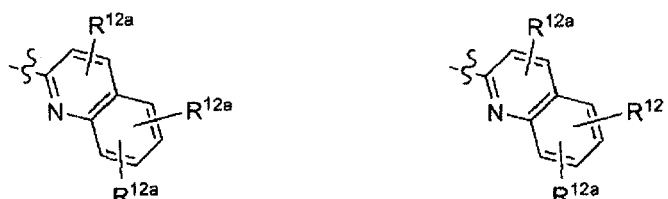 " should read -- --.

Column 375

Line 9-14 (Approx.), "  " should read -- --.

Column 378
Line 22, "(23" should read -- (2,3 --.

Column 380
Line 34, "(1 sL5,6-" should read -- (1,4,5,6- --.

Column 383
Line 44, "ethyl)" should read -- ethyl --;
Line 47, "ethyl)" should read -- ethyl --;
Line 53, "ethyl)" should read -- ethyl --;
Line 62, "ethyl)" should read -- ethyl --; and
Line 65, "ethyl)" should read -- ethyl --.

Column 384
Line 1, "ethyl)" should read -- ethyl --;
Line 4, "ethyl)" should read -- ethyl --;
Line 7, "ethyl)" should read -- ethyl --;
Line 10, "N6" should read -- $N^6$ --;

Column 384 (continued)
Line 14, "ethyl)" should read -- ethyl --;
Line 38, "ethyl)" should read -- ethyl --;
Line 54, "1N$^6$" should read -- N$^6$ --;
Line 54, "ethyl)" should read -- ethyl --;
Line 56, "1N$^6$" should read -- N$^6$ --; and
Line 56, "ethyl)" should read -- ethyl --.

Column 385
Line 11, "-yloxyamino)" should read -- -ylamino) --.

Column 386
Line 9, "hydroxybeuzamidine," should read -- hydroxybenzamidine, --;
Line 10, "ethyl)" should read -- ethyl --;
Line 13, "hydroxybeuzamidine," should read -- hydroxybenzamidine, --;
Line 21, "ethyl)" should read -- ethyl --;
Line 29, "-yloxyamino)" should read -- -ylamino) --;
Line 29, "ethyl)" should read -- ethyl --;
Line 45, "ethyl)" should read -- ethyl --;
Line 48, "ethyl)" should read -- ethyl --;
Line 51, "ethyl)" should read -- ethyl --;
Line 52, "methy1pyridin" should read -- methylpyridin --;
Line 57, "ethyl)" should read -- ethyl --; and
Line 60, "ethyl)" should read -- ethyl --.

Column 387
Line 54, "ethyl)" should read -- ethyl --;
Line 56, "ethyl)" should read -- ethyl --;
Line 58, "ethyl)" should read -- ethyl --;
Line 60, "ethyl)" should read -- ethyl --;
Line 63, "ethyl)" should read -- ethyl --; and
Line 66, "ethyl)" should read -- ethyl --.

Column 388
Line 1, "methyl)" should read -- methyl --;
Line 4, "ethyl)" should read -- ethyl --;
Line 4, "methyl)" should read -- methyl --;
Line 6, "ethyl)" should read -- ethyl --;
Line 7, "methyl)" should read -- methyl --;
Line 9, "ethyl)" should read -- ethyl --;
Line 9, "methyl)" should read -- methyl --;
Line 11, "ethyl)" should read -- ethyl --;
Line 11, "methyl)" should read -- methyl --;
Line 13, "ethyl)" should read -- ethyl --;
Line 13, "methyl)" should read -- methyl --;
Line 16, "ethyl)" should read -- ethyl --;
Line 16, "methyl)" should read -- methyl --;
Line 19, "ethyl)" should read -- ethyl --;

Column 388 (continued)
Line 20, "methyl)" should read -- methyl --;
Line 25, "ethyl)" should read -- ethyl --;
Line 26, "methyl)" should read -- methyl --;
Line 29, "ethyl)" should read -- ethyl --;
Line 29, "methyl)" should read -- methyl --;
Line 32, "ethyl)" should read -- ethyl --;
Line 32, "methyl)" should read -- methyl --;
Line 62, "methyl)" should read -- methyl --;
Line 65, "ethyl)" should read -- ethyl --; and
Line 65-66, "methyl)" should read -- methyl --.

Column 389
Line 1, "ethyl)" should read -- ethyl --;
Line 1-2, "methyl)" should read -- methyl --;
Line 4, "methyl)" should read -- methyl --;
Line 7, "ethyl)" should read -- ethyl --;
Line 7-8, "methyl)" should read -- methyl --;
Line 13, "ethyl)" should read -- ethyl --;
Line 13, "methyl)" should read -- methyl --;
Line 20, "methyl)" should read -- methyl --;
Line 23, "ethyl)" should read -- ethyl --;
Line 23, "methyl)" should read -- methyl --;
Line 29, "ethyl)" should read -- ethyl --;
Line 29, "methyl)" should read -- methyl --;
Line 38, "ethyl)" should read -- ethyl --;
Line 38, "methyl)" should read -- methyl --; and
Line 44, "methyl)" should read -- methyl --.

Column 390
Line 7, "ethyl)" should read -- ethyl --;
Line 7, "methyl)" should read -- methyl --;
Line 9, "ethyl)" should read -- ethyl --;
Line 9, "methyl)" should read -- methyl --;
Line 12, "ethyl)" should read -- ethyl --;
Line 12, "methyl)" should read -- methyl --;
Line 16, "hydroxybeuzamidine," should read -- hydroxybenzamidine, --;
Line 24, "fluorobeuzamidine," should read -- fluorobenzamidine, --;
Line 25, "methyl)" should read -- methyl --;
Line 31, "difluorobeuzamidine," should read -- difluorobenzamidine, --;
Line 33, "hydroxybeuzamidine," should read -- hydroxybenzamidine, --;
Line 37, "fluorobeuzamidine," should read -- fluorobenzamidine, --;
Line 39, "difluorobeuzamidine," should read -- difluorobenzamidine, --;
Line 45, "ethyl)" should read -- ethyl --;
Line 45, "methyl)" should read -- methyl --;
Line 48, "ethyl)" should read -- ethyl --;
Line 48, "methyl)" should read -- methyl --;
Line 54, "yl)2" should read -- yl)(2 --; and
Line 65, "ethyl)" should read -- ethyl --.

Column 391
Line 3, "ethyl)" should read -- ethyl --;
Line 6, "ethyl)" should read -- ethyl --;
Line 9, "ethyl)" should read -- ethyl --; and
Line 36, "ethyl)" should read -- ethyl --.

Column 392
Line 1, "methyl)" should read -- methyl --; and
Line 42, "1-vl)acetic" should read -- 1-yl)acetic --.

Column 393
Line 22, "ally" should read -- allyl --; and
Line 25, "ethyl)" should read -- ethyl --.